United States Patent
Cella

(10) Patent No.: US 11,333,514 B2
(45) Date of Patent: May 17, 2022

(54) INTELLIGENT TRANSPORTATION SYSTEMS

(71) Applicant: STRONG FORCE INTELLECTUAL CAPITAL, LLC, Santa Monica, CA (US)

(72) Inventor: Charles Howard Cella, Pembroke, MA (US)

(73) Assignee: Strong Force Intellectual Capital, LLC, Fort Lauderdale, FL (US)

( * ) Notice: Subject to any disclaimer, the term of this patent is extended or adjusted under 35 U.S.C. 154(b) by 145 days.

(21) Appl. No.: 16/694,733

(22) Filed: Nov. 25, 2019

(65) Prior Publication Data
US 2020/0103244 A1    Apr. 2, 2020

Related U.S. Application Data

(63) Continuation of application No. PCT/US2019/053857, filed on Sep. 30, 2019.
(Continued)

(51) Int. Cl.
*G01C 21/34*        (2006.01)
*B60W 40/08*        (2012.01)
(Continued)

(52) U.S. Cl.
CPC ......... *G01C 21/3469* (2013.01); *B60W 40/08* (2013.01); *G01C 21/3438* (2013.01);
(Continued)

(58) Field of Classification Search
USPC ....................................................... 701/533
See application file for complete search history.

(56) References Cited

U.S. PATENT DOCUMENTS 5,400,734 A    3/1995  Doyon
6,058,352 A    5/2000  Lu et al.
(Continued)

FOREIGN PATENT DOCUMENTS

| KR | 20150050134 | 5/2015 |
|----|----|----|
| WO | WO 2009/061687 | 5/2009 |
| WO | 2018094375 A1 | 5/2018 |

OTHER PUBLICATIONS

"The Difference Between Robotic Process Automation and Artificial Intelligence", CFB Bots, Apr. 20, 2018, retrieved from https://medium.com/@cfb_bots, 7 pages.
(Continued)

*Primary Examiner* — Tyler D Paige
(74) *Attorney, Agent, or Firm* — Dierker & Kavanaugh, P.C.

(57) ABSTRACT

Transportation systems have artificial intelligence including neural networks for recognition and classification of objects and behavior including natural language processing and computer vision systems. The transportation systems involve sets of complex chemical processes, mechanical systems, and interactions with behaviors of operators. System-level interactions and behaviors are classified, predicted and optimized using neural networks and other artificial intelligence systems through selective deployment, as well as hybrids and combinations of the artificial intelligence systems, neural networks, expert systems, cognitive systems, genetic algorithms and deep learning.

12 Claims, 59 Drawing Sheets

Related U.S. Application Data

(60) Provisional application No. 62/739,335, filed on Sep. 30, 2018.

(51) Int. Cl.

| | | |
|---|---|---|
| *G05B 13/02* | (2006.01) | |
| *G05D 1/02* | (2020.01) | |
| *G06F 40/40* | (2020.01) | |
| *G06N 3/04* | (2006.01) | |
| *G06Q 50/18* | (2012.01) | |
| *G07C 5/08* | (2006.01) | |
| *G06N 3/08* | (2006.01) | |
| *G07C 5/00* | (2006.01) | |
| *G05D 1/00* | (2006.01) | |
| *G07C 5/02* | (2006.01) | |
| *G06N 20/00* | (2019.01) | |
| *G06Q 50/30* | (2012.01) | |
| *G06V 20/64* | (2022.01) | |
| *G06N 3/02* | (2006.01) | |
| *G06Q 30/02* | (2012.01) | |
| *G06Q 50/00* | (2012.01) | |

(52) U.S. Cl.
CPC ........ *G05B 13/027* (2013.01); *G05D 1/0088* (2013.01); *G05D 1/0212* (2013.01); *G05D 1/0287* (2013.01); *G06F 40/40* (2020.01); *G06N 3/0418* (2013.01); *G06N 3/0454* (2013.01); *G06N 3/08* (2013.01); *G06N 20/00* (2019.01); *G06Q 50/188* (2013.01); *G06Q 50/30* (2013.01); *G06V 20/64* (2022.01); *G07C 5/006* (2013.01); *G07C 5/008* (2013.01); *G07C 5/02* (2013.01); *G07C 5/08* (2013.01); *G07C 5/0816* (2013.01); *B60W 2040/0881* (2013.01); *G05D 2201/0213* (2013.01); *G06N 3/02* (2013.01); *G06Q 30/0281* (2013.01); *G06Q 50/01* (2013.01)

(56) References Cited

U.S. PATENT DOCUMENTS

| | | |
|---|---|---|
| 6,188,945 B1 | 2/2001 | Graf et al. |
| 6,694,054 B1 | 2/2004 | Gardes et al. |
| 9,451,396 B2 | 9/2016 | Takatsuji |
| 9,493,168 B1 | 11/2016 | Kim et al. |
| 9,744,363 B2 | 8/2017 | Grill, Jr. et al. |
| 9,849,044 B1 | 12/2017 | Groden et al. |
| 10,117,109 B2 | 10/2018 | Madaiah et al. |
| 10,122,692 B2 | 11/2018 | MacCarthaigh |
| 10,126,743 B2 | 11/2018 | Fukumoto |
| 10,152,875 B2 | 12/2018 | Khaligh et al. |
| 10,289,618 B2 | 5/2019 | Fink et al. |
| 10,423,934 B1 | 5/2019 | Zanghi et al. |
| 10,346,415 B1 | 7/2019 | Smith et al. |
| 10,372,130 B1 | 8/2019 | Kaushansky et al. |
| 10,373,522 B2 | 8/2019 | Byron et al. |
| 10,387,205 B2 * | 8/2019 | Boutnaru ............ G06F 9/45516 |
| 10,387,417 B1 | 8/2019 | Hansen et al. |
| 10,387,429 B2 | 8/2019 | Smith-Mikelson et al. |
| 10,620,631 B1 * | 4/2020 | Abeloe ................ G05D 1/0088 |
| 10,696,306 B1 * | 6/2020 | Benisch ............. B60W 60/001 |
| 10,769,525 B2 * | 9/2020 | Redding ................ G06N 3/006 |
| 10,942,520 B1 | 3/2021 | Copeland et al. |
| 2003/0145647 A1 | 8/2003 | Ismail et al. |
| 2005/0143845 A1 * | 6/2005 | Kaji ................... G05B 13/0265 |
| | | 700/28 |
| 2009/0112334 A1 | 4/2009 | Grichnik et al. |
| 2009/0112429 A1 | 4/2009 | Sah et al. |
| 2011/0213511 A1 * | 9/2011 | Visconti ............... B60W 40/09 |
| | | 701/1 |
| 2012/0016551 A1 | 1/2012 | Krause et al. |
| 2015/0298565 A1 | 10/2015 | Iwamura et al. |
| 2015/0317990 A1 | 11/2015 | Fousek et al. |
| 2015/0344036 A1 | 12/2015 | Kristinsson et al. |
| 2016/0098561 A1 | 4/2016 | Keller et al. |
| 2016/0161275 A1 | 6/2016 | Waltermann et al. |
| 2016/0297309 A1 | 10/2016 | Kim |
| 2017/0025983 A1 | 1/2017 | Sills et al. |
| 2017/0299399 A1 | 10/2017 | Yamaguchi et al. |
| 2017/0352267 A1 | 12/2017 | Tzirkel-Hancock et al. |
| 2018/0027215 A1 | 1/2018 | Carlson |
| 2018/0050686 A1 | 2/2018 | Nehl et al. |
| 2018/0053413 A1 | 2/2018 | Patil et al. |
| 2018/0203455 A1 | 7/2018 | Cronin et al. |
| 2018/0208211 A1 | 7/2018 | Chiba |
| 2018/0322112 A1 | 11/2018 | Bellegarda et al. |
| 2019/0033085 A1 | 1/2019 | Ogale et al. |
| 2019/0047584 A1 | 2/2019 | Donnelly |
| 2019/0049267 A1 | 2/2019 | Huang |
| 2019/0079659 A1 * | 3/2019 | Adenwala ............... H04W 4/21 |
| 2019/0113362 A1 | 4/2019 | Kline et al. |
| 2019/0122544 A1 | 4/2019 | Schlesinger et al. |
| 2019/0156596 A1 | 5/2019 | Followell et al. |
| 2019/0178678 A1 * | 6/2019 | Rahbari Asr .......... B60L 58/12 |
| 2019/0225232 A1 | 7/2019 | Blau |
| 2019/0276037 A1 | 9/2019 | Ito et al. |
| 2019/0294159 A1 | 9/2019 | Pedersen et al. |
| 2019/0311614 A1 | 10/2019 | Yang et al. |

OTHER PUBLICATIONS

Villarejo, et al."A Stress Sensor Based on Galvanic Skin Response (GSR) Controlled by ZigBee Sensors", Sensors, 12, 6075-6101, 2012.

Gallego"Stress Level Assessment with Non-Intrusive Sensors, Doctoral Thesis", Universidad Carlos III De Madrid, accessed at http://www.tsc.uc3m.es/~fhernando/ research/ ThesisFHG.pdf on Jun. 21, 2021, Apr. 2018.

Yang, Carl, et al."Did You Enjoy the Ride: Understanding Passenger Experience via Heterogeneous Network Embedding", 2018 IEEE 34th International Conference on Data Engineering, pp. 1392-1403, 2018.

Sekar, M., et al."Carbon fiber based electrochemical sensor for sweat cortisol measurement", Scientific Reports, 9:403-403, 2019.

* cited by examiner

INTELLIGENT TRANSPORTATION SYSTEMS

CROSS-REFERENCE TO RELATED APPLICATIONS

This application is a continuation of International Application S.N. PCT/US2019/053857, filed Sep. 30, 2019, which itself claims priority to U.S. provisional application No. 62/739,335, filed Sep. 30, 2018, which are hereby incorporated by reference as if fully set forth herein in their entirety.

TECHNICAL FIELD

The present disclosure relates to intelligent transportation systems, and in examples, more particularly relates to interconnectivity and optimization of user experiences in transportation systems.

BACKGROUND

As artificial intelligence, cognitive networking, sensor technologies, storage technologies (e.g., blockchain and other distributed ledger technologies) and other technologies progress, opportunities exist for development of systems that enable improved mobility and transportation for passengers and for objects, such as freight, goods, animals and the like. A need exists for improved transportation systems that take advantage of such technologies and their capabilities.

Some applications of artificial intelligence have been, at least to a degree, effective at accomplishing certain tasks, such as tasks involving recognition and classification of objects and behavior, such as in natural language processing (NLP) and computer vision systems. However, in complex, dynamic systems that involve interactions of elements, such as transportation systems that involve sets of complex chemical processes (e.g., involving combustion processes, heating and cooling, battery charging and discharging), mechanical systems, and human systems (involving individual and group behaviors), significant challenges exist in classifying, predicting and optimizing system-level interactions and behaviors. A need exists for systems apply specialized capabilities of different types of neural networks and other artificial intelligence technologies and for systems that enable selective deployment of such technologies, as well as various hybrids and combinations of such technologies.

SUMMARY

Among other things, provided herein are methods, systems, components, processes, modules, blocks, circuits, subsystems, articles, and other elements (collectively referred to in some cases as the "platform" or the "system," which terms should be understood to encompass any of the above except where context indicates otherwise) that individually or collectively enable advances in transportation systems.

An aspect provided herein includes a system for transportation, comprising: a vehicle having a vehicle operating state; an artificial intelligence system to execute a genetic algorithm to generate mutations from an initial vehicle operating state to determine at least one optimized vehicle operating state. In embodiments, the vehicle operating state includes a set of vehicle parameter values and wherein the genetic algorithm is to: vary the set of vehicle parameter values for a set of corresponding time periods such that the vehicle operates according to the set of vehicle parameter values during the corresponding time periods; evaluate the vehicle operating state for each of the corresponding time periods according to a set of measures to generate evaluations; and select, for future operation of the vehicle, an optimized set of vehicle parameter values based on the evaluations.

In embodiments, the vehicle operating state includes a state of a rider of the vehicle, wherein the at least one optimized vehicle operating state includes an optimized state of the rider wherein the genetic algorithm is to optimize the state of the rider, wherein the evaluating according to the set of measures is to determine the state of the rider corresponding to the vehicle parameter values.

In embodiments, the vehicle operating state includes a state of the rider of the vehicle, wherein the set of vehicle parameter values includes a set of vehicle performance control values, wherein the at least one optimized vehicle operating state includes an optimized state of performance of the vehicle wherein the genetic algorithm is to optimize the state of the rider and the state of performance of the vehicle, wherein the evaluating according to the set of measures is to determine the state of the rider and the state of performance of the vehicle corresponding to the vehicle performance control values.

In embodiments, the set of vehicle parameter values includes a set of vehicle performance control values, wherein the at least one optimized vehicle operating state includes an optimized state of performance of the vehicle, wherein the genetic algorithm is to optimize the state of performance of the vehicle, wherein the evaluating according to the set of measures is to determine the state of performance of the vehicle corresponding to the vehicle performance control values.

In embodiments, the set of vehicle parameter values includes a rider-occupied parameter value, and wherein the rider-occupied parameter value affirms a presence of a rider in the vehicle. In embodiments, the vehicle operating state includes a state of a rider of the vehicle, wherein the at least one optimized vehicle operating state includes an optimized state of the rider wherein the genetic algorithm is to optimize the state of the rider, wherein the evaluating according to the set of measures is to determine the state of the rider corresponding to the vehicle parameter values. In embodiments, the state of the rider includes a rider satisfaction parameter. In embodiments, the state of the rider includes an input representative of the rider, wherein the input representative of the rider is selected from the group consisting of: a rider state parameter, a rider comfort parameter, a rider emotional state parameter, a rider satisfaction parameter, a rider goals parameter, a classification of trip, and combinations thereof.

In embodiments, the set of vehicle parameter values includes a set of vehicle performance control values, wherein the at least one optimized vehicle operating state includes an optimized state of performance of the vehicle wherein the genetic algorithm is to optimize the state of the rider and the state of performance of the vehicle, wherein the evaluating according to the set of measures is to determine the state of the rider and the state of performance of the vehicle corresponding to the vehicle performance control values. In embodiments, the set of vehicle parameter values includes a set of vehicle performance control values, wherein the at least one optimized vehicle operating state includes an optimized state of performance of the vehicle, wherein the genetic algorithm is to optimize the state of performance of the vehicle, wherein the evaluating according to the set of measures is to determine the state of performance of the vehicle corresponding to the vehicle performance control values.

In embodiments, the set of vehicle performance control values are selected from the group consisting of: a fuel efficiency; a trip duration; a vehicle wear; a vehicle make; a vehicle model; a vehicle energy consumption profiles; a fuel capacity; a real-time fuel levels; a charge capacity; a recharging capability; a regenerative braking state; and combinations thereof. In embodiments, at least a portion of the set of vehicle performance control values is sourced from at least one of an on-board diagnostic system, a telemetry system, a software system, a vehicle-located sensor, and a system external to the vehicle. In embodiments, the set of measures relates to a set of vehicle operating criteria. In embodiments, the set of measures relates to a set of rider satisfaction criteria. In embodiments, the set of measures relates to a combination of vehicle operating criteria and rider satisfaction criteria. In embodiments, each evaluation uses feedback indicative of an effect on at least one of a state of performance of the vehicle and a state of the rider.

An aspect provided herein includes a system for transportation, comprising: an artificial intelligence system to process inputs representative of a state of a vehicle and inputs representative of a rider state of a rider occupying the vehicle during the state of the vehicle with a genetic algorithm to optimize a set of vehicle parameters that affects the state of the vehicle or the rider state, wherein the genetic algorithm is to perform a series of evaluations using variations of the inputs, wherein each evaluation in the series of evaluations uses feedback indicative of an effect on at least one of a vehicle operating state and the rider state. In embodiments, the inputs representative of the rider state indicate that the rider is absent from the vehicle. In embodiments, the state of the vehicle includes the vehicle operating state. In embodiments, a vehicle parameter in the set of vehicle parameters includes a vehicle performance parameter. In embodiments, the genetic algorithm is to optimize the set of vehicle parameters for the state of the rider.

In embodiments, optimizing the set of vehicle parameters is responsive to an identifying, by the genetic algorithm, of at least one vehicle parameter that produces a favorable rider state. In embodiments, the genetic algorithm is to optimize the set of vehicle parameters for vehicle performance. In embodiments, the genetic algorithm is to optimize the set of vehicle parameters for the state of the rider and is to optimize the set of vehicle parameters for vehicle performance. In embodiments, optimizing the set of vehicle parameters is responsive to the genetic algorithm identifying at least one of a favorable vehicle operating state, and favorable vehicle performance that maintains the rider state. In embodiments, the artificial intelligence system further includes a neural network selected from a plurality of different neural networks, wherein the selection of the neural network involves the genetic algorithm and wherein the selection of the neural network is based on a structured competition among the plurality of different neural networks. In embodiments, the genetic algorithm facilitates training a neural network to process interactions among a plurality of vehicle operating systems and riders to produce the optimized set of vehicle parameters.

In embodiments, a set of inputs relating to at least one vehicle parameter are provided by at least one of an on-board diagnostic system, a telemetry system, a vehicle-located sensor, and a system external to the vehicle. In embodiments, the inputs representative of the rider state comprise at least one of comfort, emotional state, satisfaction, goals, classification of trip, or fatigue. In embodiments, the inputs representative of the rider state reflect a satisfaction parameter of at least one of a driver, a fleet manager, an advertiser, a merchant, an owner, an operator, an insurer, and a regulator. In embodiments, the inputs representative of the rider state comprise inputs relating to a user that, when processed with a cognitive system yield the rider state.

An aspect provided herein includes a system for transportation, comprising: a hybrid neural network for optimizing an operating state of a continuously variable powertrain of a vehicle wherein a portion of the hybrid neural network is to operate to classify a state of the vehicle thereby generating a classified state of the vehicle, and an other portion of the hybrid neural network is to operate to optimize at least one operating parameter of a transmission portion of the continuously variable powertrain.

In embodiments, the system for transportation further comprises: an artificial intelligence system operative on at least one processor, the artificial intelligence system to operate the portion of the hybrid neural network to operate to classify the state of the vehicle and the artificial intelligence system to operate the other portion of the hybrid neural network to optimize the at least one operating parameter of the transmission portion of the continuously variable powertrain based on the classified state of the vehicle. In embodiments, the vehicle comprises a system for automating at least one control parameter of the vehicle. In embodiments, the vehicle is at least a semi-autonomous vehicle. In embodiments, the vehicle is to be automatically routed. In embodiments, the vehicle is a self-driving vehicle. In embodiments, the classified state of the vehicle is a vehicle maintenance state. In embodiments, the classified state of the vehicle is a vehicle health state.

In embodiments, the classified state of the vehicle is a vehicle operating state. In embodiments, the classified state of the vehicle is a vehicle energy utilization state. In embodiments, the classified state of the vehicle is a vehicle charging state. In embodiments, the classified state of the vehicle is a vehicle satisfaction state. In embodiments, the classified state of the vehicle is a vehicle component state. In embodiments, the classified state of the vehicle is a vehicle sub-system state. In embodiments, the classified state of the vehicle is a vehicle powertrain system state. In embodiments, the classified state of the vehicle is a vehicle braking system state. In embodiments, the classified state of the vehicle is a vehicle clutch system state. In embodiments, the classified state of the vehicle is a vehicle lubrication system state. In embodiments, the classified state of the vehicle is a vehicle transportation infrastructure system state. In embodiments, the classified state of the vehicle is a vehicle rider state. In embodiments, at least a portion of the hybrid neural network is a convolutional neural network.

An aspect provided herein includes a method for optimizing operation of a continuously variable vehicle powertrain of a vehicle, the method comprising: executing a first network of a hybrid neural network on at least one processor, the first network classifying a plurality of operational states of the vehicle, wherein at least a portion of the operational states is based on a state of the continuously variable powertrain of the vehicle; and executing a second network of the hybrid neural network on the at least one processor, the second network processing inputs that are descriptive of the vehicle and of at least one detected condition associated with an occupant of the vehicle for at least one of the plurality of classified operational states of the vehicle, wherein the processing the inputs by the second network causes optimization of at least one operating parameter of the continuously variable powertrain of the vehicle for a plurality of the operational states of the vehicle.

In embodiments, the vehicle comprises an artificial intelligence system, the method further comprising automating at least one control parameter of the vehicle by the artificial intelligence system. In embodiments, the vehicle is at least a semi-autonomous vehicle. In embodiments, the vehicle is to be automatically routed. In embodiments, the vehicle is a self-driving vehicle. In embodiments, the method further comprises optimizing, by the artificial intelligence system, an operating state of the continuously variable powertrain of the vehicle based on the optimized at least one operating parameter of the continuously variable powertrain by adjusting at least one other operating parameter of a transmission portion of the continuously variable powertrain.

In embodiments, the method further comprises optimizing, by the artificial intelligence system, the operating state of the continuously variable powertrain by processing social data from a plurality of social data sources. In embodiments, the method further comprises optimizing, by the artificial intelligence system, the operating state of the continuously variable powertrain by processing data sourced from a stream of data from unstructured data sources. In embodiments, the method further comprises optimizing, by the artificial intelligence system, the operating state of the continuously variable powertrain by processing data sourced from wearable devices. In embodiments, the method further comprises optimizing, by the artificial intelligence system, the operating state of the continuously variable powertrain by processing data sourced from in-vehicle sensors. In embodiments, the method further comprises optimizing, by the artificial intelligence system, the operating state of the continuously variable powertrain by processing data sourced from a rider helmet.

In embodiments, the method further comprises optimizing, by the artificial intelligence system, the operating state of the continuously variable powertrain by processing data sourced from rider headgear. In embodiments, the method further comprises optimizing, by the artificial intelligence system, the operating state of the continuously variable powertrain by processing data sourced from a rider voice system. In embodiments, the method further comprises operating, by the artificial intelligence system, a third network of the hybrid neural network to predict a state of the vehicle based at least in part on at least one of the classified plurality of operational states of the vehicle and at least one operating parameter of the transmission. In embodiments, the first network of the hybrid neural network comprises a structure-adaptive network to adapt a structure of the first network responsive to a result of operating the first network of the hybrid neural network. In embodiments, the first network of the hybrid neural network is to process a plurality of social data from social data sources to classify the plurality of operational states of the vehicle.

In embodiments, at least a portion of the hybrid neural network is a convolutional neural network. In embodiments, at least one of the classified plurality of operational states of the vehicle is a vehicle maintenance state. In embodiments, at least one of the classified plurality of operational states of the vehicle is a vehicle health state. In embodiments, at least one of the classified states of the vehicle is a vehicle operating state. In embodiments, at least one of the classified states of the vehicle is a vehicle energy utilization state. In embodiments, at least one of the classified states of the vehicle is a vehicle charging state. In embodiments, at least one of the classified states of the vehicle is a vehicle satisfaction state. In embodiments, at least one of the classified states of the vehicle is a vehicle component state. In embodiments, at least one of the classified states of the vehicle is a vehicle sub-system state. In embodiments, at least one of the classified states of the vehicle is a vehicle powertrain system state. In embodiments, at least one of the classified states of the vehicle is a vehicle braking system state. In embodiments, at least one of the classified states of the vehicle is a vehicle clutch system state.

In embodiments, at least one of the classified states of the vehicle is a vehicle lubrication system state. In embodiments, at least one of the classified states of the vehicle is a vehicle transportation infrastructure system state. In embodiments, the at least one of classified states of the vehicle is a vehicle driver state. In embodiments, the at least one of classified states of the vehicle is a vehicle rider state.

An aspect provided herein includes a system for transportation, comprising: a cognitive system for routing at least one vehicle within a set of vehicles based on a routing parameter determined by facilitating a negotiation among a designated set of vehicles, wherein the negotiation accepts inputs relating to a value attributed by at least one user to at least one parameter of a route.

An aspect provided herein includes a method of negotiation-based vehicle routing comprising: facilitating a negotiation of a route-adjustment value for a plurality of parameters used by a vehicle routing system to route at least one vehicle in a set of vehicles; and determining a parameter in the plurality of parameters for optimizing at least one outcome based on the negotiation. In embodiments, a user is a rider of the at least one vehicle. In embodiments, a user is an administrator for a set of roadways to be used by the at least one vehicle in the set of vehicles. In embodiments, a user is an administrator for a fleet of vehicles including the set of vehicles. In embodiments, the method further comprises offering a set of offered user-indicated values for the plurality of parameters to users with respect to the set of vehicles. In embodiments, the route-adjustment value is based at least in part on the set of offered user-indicated values. In embodiments, the route-adjustment value is further based on at least one user response to the offering. In embodiments, the route-adjustment value is based at least in part on the set of offered user-indicated values and at least one response thereto by at least one user of the set of vehicles. In embodiments, the determined parameter facilitates adjusting a route of at least one of the vehicles in the set of vehicles. In embodiments, adjusting the route includes prioritizing the determined parameter for use by the vehicle routing system.

In embodiments, the facilitating negotiation includes facilitating negotiation of a price of a service. In embodiments, the facilitating negotiation includes facilitating negotiation of a price of fuel. In embodiments, the facilitating negotiation includes facilitating negotiation of a price of recharging. In embodiments, the facilitating negotiation includes facilitating negotiation of a reward for taking a routing action.

An aspect provided herein includes a transportation system for negotiation-based vehicle routing comprising: a route adjustment negotiation system through which users in a set of users negotiate a route-adjustment value for at least one of a plurality of parameters used by a vehicle routing system to route at least one vehicle in a set of vehicles; and a user route optimizing circuit to optimize a portion of a route of at least one user of the set of vehicles based on the route-adjustment value for the at least one of the plurality of parameters. In embodiments, the route-adjustment value is based at least in part on user-indicated values and at least one negotiation response thereto by at least one user of the set of vehicles. In embodiments, the transportation system further comprises a vehicle-based route negotiation interface through which user-indicated values for the plurality of parameters used by the vehicle routing system are captured. In embodiments, a user is a rider of the at least one vehicle. In embodiments, a user is an administrator for a set of roadways to be used by the at least one vehicle in the set of vehicles.

In embodiments, a user is an administrator for a fleet of vehicles including the set of vehicles. In embodiments, the at least one of the plurality of parameters facilitates adjusting a route of the at least one vehicle. In embodiments, adjusting the route includes prioritizing a determined parameter for use by the vehicle routing system. In embodiments, at least one of the user-indicated values is attributed to at least one of the plurality of parameters through an interface to facilitate expression of rating one or more route parameters. In embodiments, the vehicle-based route negotiation interface facilitates expression of rating one or more route parameters. In embodiments, the user-indicated values are derived from a behavior of the user. In embodiments, the vehicle-based route negotiation interface facilitates converting user behavior to the user-indicated values. In embodiments, the user behavior reflects value ascribed to the at least one parameter used by the vehicle routing system to influence a route of at least one vehicle in the set of vehicles. In embodiments, the user-indicated value indicated by at least one user correlates to an item of value provided by the user. In embodiments, the item of value is provided by the user through an offering of the item of value in exchange for a result of routing based on the at least one parameter. In embodiments, the negotiating of the route-adjustment value includes offering an item of value to the users of the set of vehicles.

An aspect provided herein includes a system for transportation, comprising: a cognitive system for routing at least one vehicle within a set of vehicles based on a set of routing parameters determined by facilitating coordination among a designated set of vehicles, wherein the coordination is accomplished by taking at least one input from at least one game-based interface for a user of a vehicle in the designated set of vehicles.

In embodiments, the system for transportation, further comprises: a vehicle routing system to route the at least one vehicle based on the set of routing parameters; and the game-based interface through which the user indicates a routing preference for at least one vehicle within the set of vehicles to undertake a game activity offered in the game-based interface; wherein the game-based interface is to induce the user to undertake a set of favorable routing choices based on the set of routing parameters.

In embodiments, the vehicle routing system accounts for the routing preference of the user when routing the at least one vehicle within the set of vehicles. In embodiments, the game-based interface is disposed for in-vehicle use. In embodiments, the user is a rider of the at least one vehicle. In embodiments, the user is an administrator for a set of roadways to be used by the at least one vehicle in the set of vehicles. In embodiments, the user is an administrator for a fleet of vehicles including the set of vehicles. In embodiments, the set of routing parameters includes at least one of traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, avoidance of driver-operated vehicles. In embodiments, the game activity offered in the game-based interface includes contests. In embodiments, the game activity offered in the game-based interface includes entertainment games.

In embodiments, the game activity offered in the game-based interface includes competitive games. In embodiments, the game activity offered in the game-based interface includes strategy games. In embodiments, the game activity offered in the game-based interface includes scavenger hunts. In embodiments, the set of favorable routing choices is configured so that the vehicle routing system achieves a fuel efficiency objective. In embodiments, the set of favorable routing choices is configured so that the vehicle routing system achieves a reduced traffic objective. In embodiments, the set of favorable routing choices is configured so that the vehicle routing system achieves a reduced pollution objective. In embodiments, the set of favorable routing choices is configured so that the vehicle routing system achieves a reduced carbon footprint objective.

In embodiments, the set of favorable routing choices is configured so that the vehicle routing system achieves a reduced noise in neighborhoods objective. In embodiments, the set of favorable routing choices is configured so that the vehicle routing system achieves a collective satisfaction objective. In embodiments, the set of favorable routing choices is configured so that the vehicle routing system achieves an avoiding accident scenes objective. In embodiments, the set of favorable routing choices is configured so that the vehicle routing system achieves an avoiding high-crime areas objective. In embodiments, the set of favorable routing choices is configured so that the vehicle routing system achieves a reduced traffic congestion objective. In embodiments, the set of favorable routing choices is configured so that the vehicle routing system achieves a bad weather avoidance objective.

In embodiments, the set of favorable routing choices is configured so that the vehicle routing system achieves a maximum travel time objective. In embodiments, the set of favorable routing choices is configured so that the vehicle routing system achieves a maximum speed limit objective. In embodiments, the set of favorable routing choices is configured so that the vehicle routing system achieves an avoidance of toll roads objective. In embodiments, the set of favorable routing choices is configured so that the vehicle routing system achieves an avoidance of city roads objective. In embodiments, the set of favorable routing choices is configured so that the vehicle routing system achieves an avoidance of undivided highways objective. In embodiments, the set of favorable routing choices is configured so that the vehicle routing system achieves an avoidance of left turns objective. In embodiments, the set of favorable routing choices is configured so that the vehicle routing system achieves an avoidance of driver-operated vehicles objective.

An aspect provided herein includes a method of game-based coordinated vehicle routing comprising: presenting, in a game-based interface, a vehicle route preference-affecting game activity; receiving, through the game-based interface, a user response to the presented game activity; adjusting a routing preference for the user responsive to the received response; determining at least one vehicle-routing parameter used to route vehicles to reflect the adjusted routing preference for routing vehicles; and routing, with a vehicle routing system, vehicles in a set of vehicles responsive to the at least one determined vehicle routing parameter adjusted to reflect the adjusted routing preference, wherein routing of the vehicles includes adjusting the determined routing parameter for at least a plurality of vehicles in the set of vehicles.

In embodiments, the method further comprises indicating, by the game-based interface, a reward value for accepting the game activity. In embodiments, the game-based interface further comprises a routing preference negotiation system for a rider to negotiate the reward value for accepting the game activity. In embodiments, the reward value is a result of pooling contributions of value from riders in the set of vehicles. In embodiments, at least one routing parameter used by the vehicle routing system to route the vehicles in the set of vehicles is associated with the game activity and a user acceptance of the game activity adjusts the at least one routing parameter to reflect the routing preference. In embodiments, the user response to the presented game activity is derived from a user interaction with the game-based interface. In embodiments, the at least one routing parameter used by the vehicle routing system to route the vehicles in the set of vehicles includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles.

In embodiments, the game activity presented in the game-based interface includes contests. In embodiments, the game activity presented in the game-based interface includes entertainment games. In embodiments, the game activity presented in the game-based interface includes competitive games. In embodiments, the game activity presented in the game-based interface includes strategy games. In embodiments, the game activity presented in the game-based interface includes scavenger hunts. In embodiments, the routing responsive to the at least one determined vehicle routing parameter achieves a fuel efficiency objective. In embodiments, the routing responsive to the at least one determined vehicle routing parameter achieves a reduced traffic objective.

In embodiments, the routing responsive to the at least one determined vehicle routing parameter achieves a reduced pollution objective. In embodiments, the routing responsive to the at least one determined vehicle routing parameter achieves a reduced carbon footprint objective. In embodiments, the routing responsive to the at least one determined vehicle routing parameter achieves a reduced noise in neighborhoods objective. In embodiments, the routing responsive to the at least one determined vehicle routing parameter achieves a collective satisfaction objective. In embodiments, the routing responsive to the at least one determined vehicle routing parameter achieves an avoiding accident scenes objective. In embodiments, the routing responsive to the at least one determined vehicle routing parameter achieves an avoiding high-crime areas objective.

In embodiments, the routing responsive to the at least one determined vehicle routing parameter achieves a reduced traffic congestion objective.

In embodiments, the routing responsive to the at least one determined vehicle routing parameter achieves a bad weather avoidance objective. In embodiments, the routing responsive to the at least one determined vehicle routing parameter achieves a maximum travel time objective. In embodiments, the routing responsive to the at least one determined vehicle routing parameter achieves a maximum speed limit objective. In embodiments, the routing responsive to the at least one determined vehicle routing parameter achieves an avoidance of toll roads objective. In embodiments, the routing responsive to the at least one determined vehicle routing parameter achieves an avoidance of city roads objective. In embodiments, the routing responsive to the at least one determined vehicle routing parameter achieves an avoidance of undivided highways objective. In embodiments, the routing responsive to the at least one determined vehicle routing parameter achieves an avoidance of left turns objective. In embodiments, the routing responsive to the at least one determined vehicle routing parameter achieves an avoidance of driver-operated vehicles objective.

An aspect provided herein includes a system for transportation, comprising: a cognitive system for routing at least one vehicle, wherein the routing is based, at least in part, by processing at least one input from a rider interface, wherein a reward is made available to a rider in response to the rider undertaking a predetermined action while in the at least one vehicle.

An aspect provided herein includes a transportation system for reward-based coordinated vehicle routing comprising: a reward-based interface to offer a reward and through which a user related to a set of vehicles indicates a routing preference of the user related to the reward by responding to the reward offered in the reward-based interface; a reward offer response processing circuit to determine at least one user action resulting from the user response to the reward and to determine a corresponding effect on at least one routing parameter; and a vehicle routing system to use the routing preference of the user and the corresponding effect on the at least one routing parameter to govern routing of the set of vehicles.

In embodiments, the user is a rider of at least one vehicle in the set of vehicles. In embodiments, the user is an administrator for a set of roadways to be used by at least one vehicle in the set of vehicles. In embodiments, the user is an administrator for a fleet of vehicles including the set of vehicles. In embodiments, the reward-based interface is disposed for in-vehicle use. In embodiments, the at least one routing parameter includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles. In embodiments, the vehicle routing system is to use the routing preference of the user and the corresponding effect on the at least one routing parameter to govern routing of the set of vehicles to achieve a fuel efficiency objective. In embodiments, the vehicle routing system is to use the routing preference of the user and the corresponding effect on the at least one routing parameter to govern routing of the set of vehicles to achieve a reduced traffic objective. In embodiments, the vehicle routing system is to use the routing preference of the user and the corresponding effect on the at least one routing parameter to govern routing of the set of vehicles to achieve a reduced pollution objective. In embodiments, the vehicle routing system is to use the routing preference of the user and the corresponding effect on the at least one routing parameter to govern routing of the set of vehicles to achieve a reduced carbon footprint objective.

In embodiments, the vehicle routing system is to use the routing preference of the user and the corresponding effect on the at least one routing parameter to govern routing of the set of vehicles to achieve a reduced noise in neighborhoods objective. In embodiments, the vehicle routing system is to use the routing preference of the user and the corresponding effect on the at least one routing parameter to govern routing of the set of vehicles to achieve a collective satisfaction objective. In embodiments, the vehicle routing system is to use the routing preference of the user and the corresponding effect on the at least one routing parameter to govern routing of the set of vehicles to achieve an avoiding accident scenes objective. In embodiments, the vehicle routing system is to use the routing preference of the user and the corresponding effect on the at least one routing parameter to govern routing of the set of vehicles to achieve an avoiding high-crime areas objective. In embodiments, the vehicle routing system is to use the routing preference of the user and the corresponding effect on the at least one routing parameter to govern routing of the set of vehicles to achieve a reduced traffic congestion objective.

In embodiments, the vehicle routing system is to use the routing preference of the user and the corresponding effect on the at least one routing parameter to govern routing of the set of vehicles to achieve a bad weather avoidance objective. In embodiments, the vehicle routing system is to use the routing preference of the user and the corresponding effect on the at least one routing parameter to govern routing of the set of vehicles to achieve a maximum travel time objective. In embodiments, the vehicle routing system is to use the routing preference of the user and the corresponding effect on the at least one routing parameter to govern routing of the set of vehicles to achieve a maximum speed limit objective. In embodiments, the vehicle routing system is to use the routing preference of the user and the corresponding effect on the at least one routing parameter to govern routing of the set of vehicles to achieve an avoidance of toll roads objective. In embodiments, the vehicle routing system is to use the routing preference of the user and the corresponding effect on the at least one routing parameter to govern routing of the set of vehicles to achieve an avoidance of city roads objective.

In embodiments, the vehicle routing system is to use the routing preference of the user and the corresponding effect on the at least one routing parameter to govern routing of the set of vehicles to achieve an avoidance of undivided highways objective. In embodiments, the vehicle routing system is to use the routing preference of the user and the corresponding effect on the at least one routing parameter to govern routing of the set of vehicles to achieve an avoidance of left turns objective. In embodiments, the vehicle routing system is to use the routing preference of the user and the corresponding effect on the at least one routing parameter to govern routing of the set of vehicles to achieve an avoidance of driver-operated vehicles objective.

An aspect provided herein includes a method of reward-based coordinated vehicle routing comprising: receiving through a reward-based interface a response of a user related to a set of vehicles to a reward offered in the reward-based interface; determining a routing preference based on the response of the user; determining at least one user action resulting from the response of the user to the reward; determining a corresponding effect of the at least one user action on at least one routing parameter; and governing routing of the set of vehicles responsive to the routing preference and the corresponding effect on the at least one routing parameter.

In embodiments, the user is a rider of at least one vehicle in the set of vehicles. In embodiments, the user is an administrator for a set of roadways to be used by at least one vehicle in the set of vehicles. In embodiments, the user is an administrator for a fleet of vehicles including the set of vehicles.

In embodiments, the reward-based interface is disposed for in-vehicle use. In embodiments, the at least one routing parameter includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles. In embodiments, the user responds to the reward offered in the reward-based interface by accepting the reward offered in the interface, rejecting the reward offered in the reward-based interface, or ignoring the reward offered in the reward-based interface. In embodiments, the user indicates the routing preference by either accepting or rejecting the reward offered in the reward-based interface. In embodiments, the user indicates the routing preference by undertaking an action in at least one vehicle in the set of vehicles that facilitates transferring the reward to the user.

In embodiments, the method further comprises sending, via a reward offer response processing circuit, a signal to the vehicle routing system to select a vehicle route that permits adequate time for the user to perform the at least one user action. In embodiments, the method further comprises: sending, via a reward offer response processing circuit, a signal to a vehicle routing system, the signal indicating a destination of a vehicle associated with the at least one user action; and adjusting, by the vehicle routing system, a route of the vehicle associated with the at least one user action to include the destination. In embodiments, the reward is associated with achieving a vehicle routing fuel efficiency objective.

In embodiments, the reward is associated with achieving a vehicle routing reduced traffic objective. In embodiments, the reward is associated with achieving a vehicle routing reduced pollution objective. In embodiments, the reward is associated with achieving a vehicle routing reduced carbon footprint objective. In embodiments, the reward is associated with achieving a vehicle routing reduced noise in neighborhoods objective. In embodiments, reward is associated with achieving a vehicle routing collective satisfaction objective. In embodiments, the reward is associated with achieving a vehicle routing avoiding accident scenes objective.

In embodiments, the reward is associated with achieving a vehicle routing avoiding high-crime areas objective. In embodiments, the reward is associated with achieving a vehicle routing reduced traffic congestion objective. In embodiments, the reward is associated with achieving a vehicle routing bad weather avoidance objective. In embodiments, the reward is associated with achieving a vehicle routing maximum travel time objective. In embodiments, the reward is associated with achieving a vehicle routing maximum speed limit objective. In embodiments, the reward is associated with achieving a vehicle routing avoidance of toll roads objective. In embodiments, the reward is associated with achieving a vehicle routing avoidance of city roads objective. In embodiments, the reward is associated with achieving a vehicle routing avoidance of undivided highways objective. In embodiments, the reward is associated with achieving a vehicle routing avoidance of left turns objective. In embodiments, the reward is associated with achieving a vehicle routing avoidance of driver-operated vehicles objective.

An aspect provided herein includes a system for transportation, comprising: a data processing system for taking data from a plurality of social data sources and using a neural network to predict an emerging transportation need for a group of individuals.

An aspect provided herein includes a method of predicting a common transportation need for a group, the method comprising: gathering social media-sourced data about a plurality of individuals, the data being sourced from a plurality of social media sources; processing the data to identify a subset of the plurality of individuals who form a social group based on group affiliation references in the data; detecting keywords in the data indicative of a transportation need; and using a neural network trained to predict transportation needs based on the detected keywords to identify the common transportation need for the subset of the plurality of individuals.

In embodiments, the neural network is a convolutional neural network. In embodiments, the neural network is trained based on a model that facilitates matching phrases in social media with transportation activity. In embodiments, the neural network predicts at least one of a destination and an arrival time for the subset of the plurality of individuals sharing the common transportation need. In embodiments, the neural network predicts the common transportation need based on analysis of transportation need-indicative keywords detected in a discussion thread among a portion of individuals in the social group. In embodiments, the method further comprises identifying at least one shared transportation service that facilitates a portion of the social group meeting the predicted common transportation need. In embodiments, the at least one shared transportation service comprises generating a vehicle route that facilitates picking up the portion of the social group.

An aspect provided herein includes a method of predicting a group transportation need for a group, the method comprising: gathering social media-sourced data about a plurality of individuals, the data being sourced from a plurality of social media sources; processing the data to identify a subset of the plurality of individuals who share the group transportation need; detecting keywords in the data indicative of the group transportation need for the subset of the plurality of individuals; predicting the group transportation need using a neural network trained to predict transportation needs based on the detected keywords; and directing a vehicle routing system to meet the group transportation need.

In embodiments, the neural network is a convolutional neural network. In embodiments, directing the vehicle routing system to meet the group transportation need involves routing a plurality of vehicles to a destination derived from the social media-sourced data. In embodiments, the neural network is trained based on a model that facilitates matching phrases in the social media-sourced data with transportation activities. In embodiments, the method further comprises predicting, by the neural network, at least one of a destination and an arrival time for the subset of the plurality of individuals sharing the group transportation need. In embodiments, the method further comprises predicting, by the neural network, the group transportation need based on an analysis of transportation need-indicative keywords detected in a discussion thread in the social media-sourced data. In embodiments, the method further comprises identifying at least one shared transportation service that facilitates meeting the predicted group transportation need for at least a portion of the subset of the plurality of individuals. In embodiments, the at least one shared transportation service comprises generating a vehicle route that facilitates picking up the at least the portion of the subset of the plurality of individuals.

An aspect provided herein includes a method of predicting a group transportation need, the method comprising: gathering social media-sourced data from a plurality of social media sources; processing the data to identify an event; detecting keywords in the data indicative of the event to determine a transportation need associated with the event; and using a neural network trained to predict transportation needs based at least in part on social media-sourced data to direct a vehicle routing system to meet the transportation need. In embodiments, the neural network is a convolutional neural network. In embodiments, the vehicle routing system is directed to meet the transportation need by routing a plurality of vehicles to a location associated with the event. In embodiments, the vehicle routing system is directed to meet the transportation need by routing a plurality of vehicles to avoid a region proximal to a location associated with the event. In embodiments, the vehicle routing system is directed to meet the transportation need by routing vehicles associated with users whose social media-sourced data do not indicate the transportation need to avoid a region proximal to a location associated with the event. In embodiments, the method further comprises presenting at least one transportation service for satisfying the transportation need. In embodiments, the neural network is trained based on a model that facilitates matching phrases in social media-sourced data with transportation activity.

In embodiments, the neural network predicts at least one of a destination and an arrival time for individuals attending the event. In embodiments, the neural network predicts the transportation need based on analysis of transportation need-indicative keywords detected in a discussion thread in the social media-sourced data. In embodiments, the method further comprises identifying at least one shared transportation service that facilitates meeting the predicted transportation need for at least a subset of individuals identified in the social media-sourced data. In embodiments, the at least one shared transportation service comprises generating a vehicle route that facilitates picking up the portion of the subset of individuals identified in the social media-sourced data.

An aspect provided herein includes a system for transportation, comprising: a data processing system for taking data from a plurality of social data sources and using a hybrid neural network to optimize an operating state of a transportation system based on processing the data from the plurality of social data sources with the hybrid neural network.

An aspect provided herein includes a hybrid neural network system for transportation system optimization, the hybrid neural network system comprising a hybrid neural network, including: a first neural network that predicts a localized effect on a transportation system through analysis of social medial data sourced from a plurality of social media data sources; and a second neural network that optimizes an operating state of the transportation system based on the predicted localized effect.

In embodiments, at least one of the first neural network and the second neural network is a convolutional neural network. In embodiments, the second neural network is to optimize an in-vehicle rider experience state. In embodiments, the first neural network identifies a set of vehicles contributing to the localized effect based on correlation of vehicle location and an area of the localized effect. In embodiments, the second neural network is to optimize a routing state of the transportation system for vehicles proximal to a location of the localized effect. In embodiments, the hybrid neural network is trained for at least one of the predicting and optimizing based on keywords in the social media data indicative of an outcome of a transportation system optimization action. In embodiments, the hybrid neural network is trained for at least one of predicting and optimizing based on social media posts.

In embodiments, the hybrid neural network is trained for at least one of predicting and optimizing based on social media feeds. In embodiments, the hybrid neural network is trained for at least one of predicting and optimizing based on ratings derived from the social media data. In embodiments, the hybrid neural network is trained for at least one of predicting and optimizing based on like or dislike activity detected in the social media data. In embodiments, the hybrid neural network is trained for at least one of predicting and optimizing based on indications of relationships in the social media data. In embodiments, the hybrid neural network is trained for at least one of predicting and optimizing based on user behavior detected in the social media data. In embodiments, the hybrid neural network is trained for at least one of predicting and optimizing based on discussion threads in the social media data.

In embodiments, the hybrid neural network is trained for at least one of predicting and optimizing based on chats in the social media data. In embodiments, the hybrid neural network is trained for at least one of predicting and optimizing based on photographs in the social media data. In embodiments, the hybrid neural network is trained for at least one of predicting and optimizing based on traffic-affecting information in the social media data. In embodiments, the hybrid neural network is trained for at least one of predicting and optimizing based on an indication of a specific individual at a location in the social media data. In embodiments, the specific individual is a celebrity. In embodiments, the hybrid neural network is trained for at least one of predicting and optimizing based a presence of a rare or transient phenomena at a location in the social media data.

In embodiments, the hybrid neural network is trained for at least one of predicting and optimizing based a commerce-related event at a location in the social media data. In embodiments, the hybrid neural network is trained for at least one of predicting and optimizing based an entertainment event at a location in the social media data. In embodiments, the social media data analyzed to predict a localized effect on a transportation system includes traffic conditions. In embodiments, the social media data analyzed to predict a localized effect on a transportation system includes weather conditions. In embodiments, the social media data analyzed to predict a localized effect on a transportation system includes entertainment options.

In embodiments, the social media data analyzed to predict a localized effect on a transportation system includes risk-related conditions. In embodiments, the risk-related conditions include crowds gathering for potentially dangerous reasons. In embodiments, the social media data analyzed to predict a localized effect on a transportation system includes commerce-related conditions. In embodiments, the social media data analyzed to predict a localized effect on a transportation system includes goal-related conditions.

In embodiments, the social media data analyzed to predict a localized effect on a transportation system includes estimates of attendance at an event. In embodiments, the social media data analyzed to predict a localized effect on a transportation system includes predictions of attendance at an event. In embodiments, the social media data analyzed to predict a localized effect on a transportation system includes modes of transportation. In embodiments, the modes of transportation include car traffic. In embodiments, the modes of transportation include public transportation options.

In embodiments, the social media data analyzed to predict a localized effect on a transportation system includes hash tags. In embodiments, the social media data analyzed to predict a localized effect on a transportation system includes trending of topics. In embodiments, an outcome of a transportation system optimization action is reducing fuel consumption. In embodiments, an outcome of a transportation system optimization action is reducing traffic congestion. In embodiments, an outcome of a transportation system optimization action is reduced pollution. In embodiments, an outcome of a transportation system optimization action is bad weather avoidance. In embodiments, an operating state of the transportation system being optimized includes an in-vehicle state. In embodiments, an operating state of the transportation system being optimized includes a routing state.

In embodiments, the routing state is for an individual vehicle. In embodiments, the routing state is for a set of vehicles. In embodiments, an operating state of the transportation system being optimized includes a user-experience state.

An aspect provided herein includes a method of optimizing an operating state of a transportation system, the method comprising: gathering social media-sourced data about a plurality of individuals, the data being sourced from a plurality of social media sources; optimizing, using a hybrid neural network, the operating state of the transportation system; predicting, by a first neural network of the hybrid neural network, an effect on the transportation system through an analysis of the social media-sourced data; and optimizing, by a second neural network of the hybrid neural network, at least one operating state of the transportation system responsive to the predicted effect thereon. In embodiments, at least one of the first neural network and the second neural network is a convolutional neural network. In embodiments, the second neural network optimizes an in-vehicle rider experience state. In embodiments, the first neural network identifies a set of vehicles contributing to the effect based on correlation of vehicle location and an effect area. In embodiments, the second neural network optimizes a routing state of the transportation system for vehicles proximal to a location of the effect.

In embodiments, the hybrid neural network is trained for at least one of the predicting and optimizing based on keywords in the social media data indicative of an outcome of a transportation system optimization action. In embodiments, the hybrid neural network is trained for at least one of predicting and optimizing based on social media posts. In embodiments, the hybrid neural network is trained for at least one of predicting and optimizing based on social media feeds. In embodiments, the hybrid neural network is trained for at least one of predicting and optimizing based on ratings derived from the social media data. In embodiments, the hybrid neural network is trained for at least one of predicting and optimizing based on like or dislike activity detected in the social media data. In embodiments, the hybrid neural network is trained for at least one of predicting and optimizing based on indications of relationships in the social media data.

In embodiments, the hybrid neural network is trained for at least one of predicting and optimizing based on user behavior detected in the social media data. In embodiments, the hybrid neural network is trained for at least one of predicting and optimizing based on discussion threads in the social media data. In embodiments, the hybrid neural network is trained for at least one of predicting and optimizing based on chats in the social media data. In embodiments, the hybrid neural network is trained for at least one of predicting and optimizing based on photographs in the social media data. In embodiments, the hybrid neural network is trained for at least one of predicting and optimizing based on traffic-affecting information in the social media data.

In embodiments, the hybrid neural network is trained for at least one of predicting and optimizing based on an indication of a specific individual at a location in the social media data. In embodiments, the specific individual is a celebrity. In embodiments, the hybrid neural network is trained for at least one of predicting and optimizing based a presence of a rare or transient phenomena at a location in the social media data. In embodiments, the hybrid neural network is trained for at least one of predicting and optimizing based a commerce-related event at a location in the social media data. In embodiments, the hybrid neural network is trained for at least one of predicting and optimizing based an entertainment event at a location in the social media data. In embodiments, the social media data analyzed to predict an effect on a transportation system includes traffic conditions.

In embodiments, the social media data analyzed to predict an effect on a transportation system includes weather conditions. In embodiments, the social media data analyzed to predict an effect on a transportation system includes entertainment options. In embodiments, the social media data analyzed to predict an effect on a transportation system includes risk-related conditions. In embodiments, the risk-related conditions include crowds gathering for potentially dangerous reasons. In embodiments, the social media data analyzed to predict an effect on a transportation system includes commerce-related conditions. In embodiments, the social media data analyzed to predict an effect on a transportation system includes goal-related conditions.

In embodiments, the social media data analyzed to predict an effect on a transportation system includes estimates of attendance at an event. In embodiments, the social media data analyzed to predict an effect on a transportation system includes predictions of attendance at an event. In embodiments, the social media data analyzed to predict an effect on a transportation system includes modes of transportation. In embodiments, the modes of transportation include car traffic. In embodiments, the modes of transportation include public transportation options. In embodiments, the social media data analyzed to predict an effect on a transportation system includes hash tags. In embodiments, the social media data analyzed to predict an effect on a transportation system includes trending of topics.

In embodiments, an outcome of a transportation system optimization action is reducing fuel consumption. In embodiments, an outcome of a transportation system optimization action is reducing traffic congestion. In embodiments, an outcome of a transportation system optimization action is reduced pollution. In embodiments, an outcome of a transportation system optimization action is bad weather avoidance. In embodiments, the operating state of the transportation system being optimized includes an in-vehicle state. In embodiments, the operating state of the transportation system being optimized includes a routing state. In embodiments, the routing state is for an individual vehicle. In embodiments, the routing state is for a set of vehicles. In embodiments, the operating state of the transportation system being optimized includes a user-experience state.

An aspect provided herein includes a method of optimizing an operating state of a transportation system, the method comprising: using a first neural network of a hybrid neural network to classify social media data sourced from a plurality of social media sources as affecting a transportation system; using a second network of the hybrid neural network to predict at least one operating objective of the transportation system based on the classified social media data; and using a third network of the hybrid neural network to optimize the operating state of the transportation system to achieve the at least one operating objective of the transportation system. In embodiments, at least one of the neural networks in the hybrid neural network is a convolutional neural network.

An aspect provided herein includes a system for transportation, comprising: a data processing system for taking data from a plurality of social data sources and using a hybrid neural network to optimize an operating state of a vehicle based on processing the data from the plurality of social data sources with the hybrid neural network.

An aspect provided herein includes a method of optimizing an operating state of a vehicle, the method comprising: classifying, using a first neural network of a hybrid neural network, social media data sourced from a plurality of social media sources as affecting a transportation system; predicting, using a second neural network of the hybrid neural network, one or more effects of the classified social media data on the transportation system; and optimizing, using a third neural network of the hybrid neural network, a state of at least one vehicle of the transportation system, wherein the optimizing addresses an influence of the predicted one or more effects on the at least one vehicle. In embodiments, at least one of the neural networks in the hybrid neural network is a convolutional neural network. In embodiments, the social media data includes social media posts. In embodiments, the social media data includes social media feeds. In embodiments, the social media data includes like or dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs.

In embodiments, the social media data includes traffic-affecting information. In embodiments, the social media data includes an indication of a specific individual at a location. In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options.

In embodiments, the social media data includes risk-related conditions. In embodiments, the social media data includes predictions of attendance at an event. In embodiments, the social media data includes estimates of attendance at an event. In embodiments, the social media data includes modes of transportation used with an event. In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution.

In embodiments, the optimized state of the at least one vehicle is an operating state of the vehicle. In embodiments, the optimized state of the at least one vehicle includes an in-vehicle state. In embodiments, the optimized state of the at least one vehicle includes a rider state. In embodiments, the optimized state of the at least one vehicle includes a routing state. In embodiments, the optimized state of the at least one vehicle includes user experience state. In embodiments, a characterization of an outcome of the optimizing in the social media data is used as feedback to improve the optimizing. In embodiments, the feedback includes likes and dislikes of the outcome. In embodiments, the feedback includes social medial activity referencing the outcome.

In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

An aspect provided herein includes a method of optimizing an operating state of a vehicle, the method comprising: classifying, using a first neural network of a hybrid neural network, social media data sourced from a plurality of social media sources as affecting a transportation system; predicting, using a second neural network of the hybrid neural network, at least one vehicle-operating objective of the transportation system based on the classified social media data; and optimizing, using a third neural network of the hybrid neural network, a state of a vehicle in the transportation system to achieve the at least one vehicle-operating objective of the transportation system. In embodiments, at least one of the neural networks in the hybrid neural network is a convolutional neural network. In embodiments, the vehicle-operating objective comprises achieving a rider state of at least one rider in the vehicle. In embodiments, the social media data includes social media posts.

In embodiments, the social media data includes social media feeds. In embodiments, the social media data includes like and dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs. In embodiments, the social media data includes traffic-affecting information.

In embodiments, the social media data includes an indication of a specific individual at a location. In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options.

In embodiments, the social media data includes risk-related conditions. In embodiments, the social media data includes predictions of attendance at an event. In embodiments, the social media data includes estimates of attendance at an event. In embodiments, the social media data includes modes of transportation used with an event. In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized state of the vehicle is an operating state of the vehicle.

In embodiments, the optimized state of the vehicle includes an in-vehicle state. In embodiments, the optimized state of the vehicle includes a rider state. In embodiments, the optimized state of the vehicle includes a routing state. In embodiments, the optimized state of the vehicle includes user experience state. In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome.

In embodiments, the feedback includes hash tags associated with the outcome. In embodiments, the feedback includes ratings of the outcome. In embodiments, the feedback includes requests for the outcome.

An aspect provided herein includes a system for transportation, comprising: a data processing system for taking data from a plurality of social data sources and using a hybrid neural network to optimize satisfaction of at least one rider in a vehicle based on processing the data from the plurality of social data sources with the hybrid neural network.

An aspect provided herein includes a method of optimizing rider satisfaction, the method comprising: classifying, using a first neural network of a hybrid neural network, social media data sourced from a plurality of social media sources as indicative of an effect on a transportation system; predicting, using a second neural network of the hybrid neural network, at least one aspect of rider satisfaction affected by an effect on the transportation system derived from the social media data classified as indicative of an effect on the transportation system; and optimizing, using a third neural network of the hybrid neural network, the at least one aspect of rider satisfaction for at least one rider occupying a vehicle in the transportation system.

In embodiments, at least one of the neural networks in the hybrid neural network is a convolutional neural network. In embodiments, the at least one aspect of rider satisfaction is optimized by predicting an entertainment option for presenting to the rider. In embodiments, the at least one aspect of rider satisfaction is optimized by optimizing route planning for a vehicle occupied by the rider. In embodiments, the at least one aspect of rider satisfaction is a rider state and optimizing the aspects of rider satisfaction comprising optimizing the rider state. In embodiments, social media data specific to the rider is analyzed to determine at least one optimizing action likely to optimize the at least one aspect of rider satisfaction. In embodiments, the optimizing action is selected from the group of actions consisting of adjusting a routing plan to include passing points of interest to the user, avoiding traffic congestion predicted from the social media data, and presenting entertainment options.

In embodiments, the social media data includes social media posts. In embodiments, the social media data includes social media feeds. In embodiments, the social media data includes like or dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs.

In embodiments, the social media data includes traffic-affecting information. In embodiments, the social media data includes an indication of a specific individual at a location. In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options. In embodiments, the social media data includes risk-related conditions. In embodiments, the social media data includes predictions of attendance at an event. In embodiments, the social media data includes estimates of attendance at an event. In embodiments, the social media data includes modes of transportation used with an event. In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized at least one aspect of rider satisfaction is an operating state of the vehicle. In embodiments, the optimized at least one aspect of rider satisfaction includes an in-vehicle state. In embodiments, the optimized at least one aspect of rider satisfaction includes a rider state. In embodiments, the optimized at least one aspect of rider satisfaction includes a routing state. In embodiments, the optimized at least one aspect of rider satisfaction includes user experience state.

In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

An aspect provided herein includes a rider satisfaction system for optimizing rider satisfaction, the system comprising: a first neural network of a hybrid neural network to classify social media data sourced from a plurality of social media sources as indicative of an effect on a transportation system; a second neural network of the hybrid neural network to predict at least one aspect of rider satisfaction affected by an effect on the transportation system derived from the social media data classified as indicative of the effect on the transportation system; and a third network of the hybrid neural network to optimize the at least one aspect of rider satisfaction for at least one rider occupying a vehicle in the transportation system. In embodiments, at least one of the neural networks in the hybrid neural network is a convolutional neural network.

In embodiments, the at least one aspect of rider satisfaction is optimized by predicting an entertainment option for presenting to the rider. In embodiments, the at least one aspect of rider satisfaction is optimized by optimizing route planning for a vehicle occupied by the rider. In embodiments, the at least one aspect of rider satisfaction is a rider state and optimizing the at least one aspect of rider satisfaction comprises optimizing the rider state. In embodiments, social media data specific to the rider is analyzed to determine at least one optimizing action likely to optimize the at least one aspect of rider satisfaction. In embodiments, the at least one optimizing action is selected from the group consisting of: adjusting a routing plan to include passing points of interest to the user, avoiding traffic congestion predicted from the social media data, deriving an economic benefit, deriving an altruistic benefit, and presenting entertainment options.

In embodiments, the economic benefit is saved fuel. In embodiments, the altruistic benefit is reduction of environmental impact. In embodiments, the social media data includes social media posts. In embodiments, the social media data includes social media feeds. In embodiments, the social media data includes like or dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs. In embodiments, the social media data includes traffic-affecting information. In embodiments, the social media data includes an indication of a specific individual at a location.

In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options. In embodiments, the social media data includes risk-related conditions. In embodiments, the social media data includes predictions of attendance at an event. In embodiments, the social media data includes estimates of attendance at an event. In embodiments, the social media data includes modes of transportation used with an event.

In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized at least one aspect of rider satisfaction is an operating state of the vehicle. In embodiments, the optimized at least one aspect of rider satisfaction includes an in-vehicle state. In embodiments, the optimized at least one aspect of rider satisfaction includes a rider state. In embodiments, the optimized at least one aspect of rider satisfaction includes a routing state. In embodiments, the optimized at least one aspect of rider satisfaction includes user experience state. In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

An aspect provided herein includes a system for transportation, comprising: a hybrid neural network wherein one neural network processes a sensor input corresponding to a rider of a vehicle to determine an emotional state of the rider and another neural network optimizes at least one operating parameter of the vehicle to improve the emotional state of the rider.

An aspect provided herein includes a hybrid neural network for rider satisfaction, comprising: a first neural network to detect a detected emotional state of a rider occupying a vehicle through analysis of data gathered from sensors deployed in a vehicle for gathering physiological conditions of the rider; and a second neural network to optimize, for achieving a favorable emotional state of the rider, an operational parameter of the vehicle in response to the detected emotional state of the rider.

In embodiments, the first neural network is a recurrent neural network and the second neural network is a radial basis function neural network. In embodiments, at least one of the neural networks in the hybrid neural network is a convolutional neural network. In embodiments, the second neural network is to optimize the operational parameter based on a correlation between a vehicle operating state and a rider emotional state of the rider. In embodiments, the second neural network optimizes the operational parameter in real time responsive to the detecting of the detected emotional state of the rider by the first neural network. In embodiments, the first neural network comprises a plurality of connected nodes that form a directed cycle, the first neural network further facilitating bi-directional flow of data among the connected nodes. In embodiments, the operational parameter that is optimized affects at least one of: a route of the vehicle, in-vehicle audio contents, a speed of the vehicle, an acceleration of the vehicle, a deceleration of the vehicle, a proximity to objects along the route, and a proximity to other vehicles along the route.

As used herein, "real-time" means pertaining to a data-processing system that controls an ongoing process and delivers its outputs (or controls its inputs) not later than the time when these are needed for effective control. In examples, "real-time" means that an input relating to an event or state is received within 10 seconds of the occurrence of the event, or the existence of the state for use in the ongoing process. In other examples, "real-time" means that an input relating to an event or state is received within 1 second of the occurrence of the event, or the existence of the state for use in the ongoing process. In still other examples, real-time means that an input relating to an event or state is received within 10 milliseconds of the occurrence of the event, or the existence of the state for use in the ongoing process.

An aspect provided herein includes an artificial intelligence system for optimizing rider satisfaction, comprising: a hybrid neural network, including: a recurrent neural network to indicate a change in an emotional state of a rider in a vehicle through recognition of patterns of physiological data of the rider captured by at least one sensor deployed for capturing rider emotional state-indicative data while occupying the vehicle; and a radial basis function neural network to optimize, for achieving a favorable emotional state of the rider, an operational parameter of the vehicle in response to the indication of change in the emotional state of the rider. In embodiments, the operational parameter of the vehicle that is to be optimized is to be determined and adjusted to induce the favorable emotional state of the rider.

An aspect provided herein includes an artificial intelligence system for optimizing rider satisfaction, comprising: a hybrid neural network, including: a convolutional neural network to indicate a change in an emotional state of a rider in a vehicle through recognitions of patterns of visual data of the rider captured by at least one image sensor deployed for capturing images of the rider while occupying the vehicle; and a second neural network to optimize, for achieving a favorable emotional state of the rider, an operational parameter of the vehicle in response to the indication of change in the emotional state of the rider.

In embodiments, the operational parameter of the vehicle that is to be optimized is to be determined and adjusted to induce the favorable emotional state of the rider.

An aspect provided herein includes a transportation system, comprising: an artificial intelligence system for processing feature vectors of an image of a face of a rider in a vehicle to determine an emotional state of the rider and optimizing an operational parameter of the vehicle to improve the emotional state of the rider.

In embodiments, the artificial intelligence system includes: a first neural network to detect the emotional state of the rider through recognition of patterns of the feature vectors of the image of the face of the rider in the vehicle, the feature vectors indicating at least one of a favorable emotional state of the rider and an unfavorable emotional state of the rider; and a second neural network to optimize, for achieving the favorable emotional state of the rider, the operational parameter of the vehicle in response to the detected emotional state of the rider.

In embodiments, the first neural network is a recurrent neural network and the second neural network is a radial basis function neural network. In embodiments, the second neural network optimizes the operational parameter based on a correlation between the vehicle operating state and the emotional state of the rider. In embodiments, the second neural network is to determine an optimum value for the operational parameter of the vehicle, and the transportation system is to adjust the operational parameter of the vehicle to the optimum value to induce the favorable emotional state of the rider. In embodiments, the first neural network further learns to classify the patterns in the feature vectors and associate the patterns with a set of emotional states and changes thereto by processing a training data set, wherein the training data set is sourced from at least one of a stream of data from an unstructured data source, a social media source, a wearable device, an in-vehicle sensor, a rider helmet, a rider headgear, and a rider voice recognition system.

In embodiments, the second neural network optimizes the operational parameter in real time responsive to the detecting of the emotional state of the rider by the first neural network. In embodiments, the first neural network is to detect a pattern of the feature vectors, wherein the pattern is associated with a change in the emotional state of the rider from a first emotional state to a second emotional state, wherein the second neural network optimizes the operational parameter of the vehicle in response to the detection of the pattern associated with the change in the emotional state. In embodiments, the first neural network comprises a plurality of interconnected nodes that form a directed cycle, the first neural network further facilitating bi-directional flow of data among the interconnected nodes. In embodiments, the transportation system further comprises: a feature vector generation system to process a set of images of the face of the rider, the set of images captured over an interval of time from by a plurality of image capture devices while the rider is in the vehicle, wherein the processing of the set of images is to produce the feature vectors of the image of the face of the rider. In embodiments, the transportation system further comprises: image capture devices disposed to capture a set of images of the face of the rider in the vehicle from a plurality of perspectives; and an image processing system to produce the feature vectors from the set of images captured from at least one of the plurality of perspectives.

In embodiments, the transportation system further comprises an interface between the first neural network and the image processing system to communicate a time sequence of the feature vectors, wherein the feature vectors are indicative of the emotional state of the rider. In embodiments, the feature vectors indicate at least one of a changing emotional state of the rider, a stable emotional state of the rider, a rate of change of the emotional state of the rider, a direction of change of the emotional state of the rider, a polarity of a change of the emotional state of the rider; the emotional state of the rider is changing to the unfavorable emotional state; and the emotional state of the rider is changing to the favorable emotional state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the second neural network is to interact with a vehicle control system to adjust the operational parameter. In embodiments, the artificial intelligence system further comprises a neural network that includes one or more perceptrons that mimic human senses that facilitates determining the emotional state of the rider based on an extent to which at least one of the senses of the rider is stimulated. In embodiments, the artificial intelligence system includes: a recurrent neural network to indicate a change in the emotional state of the rider through recognition of patterns of the feature vectors of the image of the face of the rider in the vehicle; and a radial basis function neural network to optimize, for achieving the favorable emotional state of the rider, the operational parameter of the vehicle in response to the indication of the change in the emotional state of the rider.

In embodiments, the radial basis function neural network is to optimize the operational parameter based on a correlation between a vehicle operating state and a rider emotional state. In embodiments, the operational parameter of the vehicle that is optimized is determined and adjusted to induce a favorable rider emotional state. In embodiments, the recurrent neural network further learns to classify the patterns of the feature vectors and associate the patterns of the feature vectors to emotional states and changes thereto from a training data set sourced from at least one of a stream of data from unstructured data sources, social media sources, wearable devices, in-vehicle sensors, a rider helmet, a rider headgear, and a rider voice system. In embodiments, the radial basis function neural network is to optimize the operational parameter in real time responsive to the detecting of the change in the emotional state of the rider by the recurrent neural network. In embodiments, the recurrent neural network detects a pattern of the feature vectors that indicates the emotional state of the rider is changing from a first emotional state to a second emotional state, wherein the radial basis function neural network is to optimize the operational parameter of the vehicle in response to the indicated change in emotional state.

In embodiments, the recurrent neural network comprises a plurality of connected nodes that form a directed cycle, the recurrent neural network further facilitating bi-directional flow of data among the connected nodes. In embodiments, the feature vectors indicate at least one of the emotional state of the rider is changing, the emotional state of the rider is stable, a rate of change of the emotional state of the rider, a direction of change of the emotional state of the rider, and a polarity of a change of the emotional state of the rider; the emotional state of a rider is changing to an unfavorable emotional state; and an emotional state of a rider is changing to a favorable emotional state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route.

In embodiments, the radial basis function neural network is to interact with a vehicle control system to adjust the operational parameter. In embodiments, the artificial intelligence system further comprises a neural network that includes one or more perceptrons that mimic human senses that facilitates determining the emotional state of a rider based on an extent to which at least one of the senses of the rider is stimulated. In embodiments, the artificial intelligence system is to maintain the favorable emotional state of the rider via a modular neural network, the modular neural network comprising: a rider emotional state determining neural network to process the feature vectors of the image of the face of the rider in the vehicle to detect patterns, wherein the patterns in the feature vectors indicate at least one of the favorable emotional state and the unfavorable emotional state; an intermediary circuit to convert data from the rider emotional state determining neural network into vehicle operational state data; and a vehicle operational state optimizing neural network to adjust an operational parameter of the vehicle in response to the vehicle operational state data.

In embodiments, the vehicle operational state optimizing neural network is to adjust the operational parameter of the vehicle for achieving a favorable emotional state of the rider. In embodiments, the vehicle operational state optimizing neural network is to optimize the operational parameter based on a correlation between a vehicle operating state and a rider emotional state. In embodiments, the operational parameter of the vehicle that is optimized is determined and adjusted to induce a favorable rider emotional state. In embodiments, the rider emotional state determining neural network further learns to classify the patterns of the feature vectors and associate the pattern of the feature vectors to emotional states and changes thereto from a training data set sourced from at least one of a stream of data from unstructured data sources, social media sources, wearable devices, in-vehicle sensors, a rider helmet, a rider headgear, and a rider voice system.

In embodiments, the vehicle operational state optimizing neural network is to optimize the operational parameter in real time responsive to the detecting of a change in an emotional state of the rider by the rider emotional state determining neural network. In embodiments, the rider emotional state determining neural network is to detect a pattern of the feature vectors that indicates the emotional state of the rider is changing from a first emotional state to a second emotional state, wherein the vehicle operational state optimizing neural network is to optimize the operational parameter of the vehicle in response to the indicated change in emotional state. In embodiments, the artificial intelligence system comprises a plurality of connected nodes that form a directed cycle, the artificial intelligence system further facilitating bi-directional flow of data among the connected nodes.

In embodiments, the feature vectors indicate at least one of the emotional state of the rider is changing, the emotional state of the rider is stable, a rate of change of the emotional state of the rider, a direction of change of the emotional state of the rider, and a polarity of a change of the emotional state of the rider; the emotional state of a rider is changing to an unfavorable emotional state; and the emotional state of the rider is changing to a favorable emotional state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the vehicle operational state optimizing neural network interacts with a vehicle control system to adjust the operational parameter.

In embodiments, the artificial intelligence system further comprises a neural net that includes one or more perceptrons that mimic human senses that facilitates determining an emotional state of a rider based on an extent to which at least one of the senses of the rider is stimulated. In embodiments, the rider emotional state determining neural network comprises one or more perceptrons that mimic human senses that facilitates determining an emotional state of a rider based on an extent to which at least one of the senses of the rider is stimulated. In embodiments, the artificial intelligence system includes a recurrent neural network to indicate a change in the emotional state of the rider in the vehicle through recognition of patterns of the feature vectors of the image of the face of the rider in the vehicle; the transportation system further comprising: a vehicle control system to control operation of the vehicle by adjusting a plurality of vehicle operational parameters; and a feedback loop to communicate the indicated change in the emotional state of the rider between the vehicle control system and the artificial intelligence system, wherein the vehicle control system is to adjust at least one of the plurality of vehicle operational parameters in response to the indicated change in the emotional state of the rider. In embodiments, the vehicle controls system adjusts the at least one of the plurality of vehicle operational parameters based on a correlation between vehicle operational state and rider emotional state.

In embodiments, the vehicle control system adjusts the at least one of the plurality of vehicle operational parameters that are indicative of a favorable rider emotional state. In embodiments, the vehicle control system selects an adjustment of the at least one of the plurality of vehicle operational parameters that is indicative of producing a favorable rider emotional state. In embodiments, the recurrent neural network further learns to classify the patterns of feature vectors and associate them to emotional states and changes thereto from a training data set sourced from at least one of a stream of data from unstructured data sources, social media sources, wearable devices, in-vehicle sensors, a rider helmet, a rider headgear, and a rider voice system. In embodiments, the vehicle control system adjusts the at least one of the plurality of vehicle operation parameters in real time. In embodiments, the recurrent neural network detects a pattern of the feature vectors that indicates the emotional state of the rider is changing from a first emotional state to a second emotional state, wherein the vehicle operation control system adjusts an operational parameter of the vehicle in response to the indicated change in emotional state. In embodiments, the recurrent neural network comprises a plurality of connected nodes that form a directed cycle, the recurrent neural network further facilitating bi-directional flow of data among the connected nodes.

In embodiments, the feature vectors indicating at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; an emotional state of a rider is changing to a favorable state. In embodiments, the at least one of the plurality of vehicle operational parameters responsively adjusted affects a route of the vehicle, in-vehicle audio content, speed of the vehicle, acceleration of the vehicle, deceleration of the vehicle, proximity to objects along the route, proximity to other vehicles along the route.

In embodiments, the at least one of the plurality of vehicle operation parameters that is responsively adjusted affects operation of a powertrain of the vehicle and a suspension system of the vehicle. In embodiments, the radial basis function neural network interacts with the recurrent neural network via an intermediary component of the artificial intelligence system that produces vehicle control data indicative of an emotional state response of the rider to a current operational state of the vehicle. In embodiments, the recognition of patterns of feature vectors comprises processing the feature vectors of the image of the face of the rider captured during at least two of before the adjusting at least one of the plurality of vehicle operational parameters, during the adjusting at least one of the plurality of vehicle operational parameters, and after adjusting at least one of the plurality of vehicle operational parameters.

In embodiments, the adjusting at least one of the plurality of vehicle operational parameters improves an emotional state of a rider in a vehicle. In embodiments, the adjusting at least one of the plurality of vehicle operational parameters causes an emotional state of the rider to change from an unfavorable emotional state to a favorable emotional state, wherein the change is indicated by the recurrent neural network. In embodiments, the recurrent neural network indicates a change in the emotional state of the rider responsive to a change in an operating parameter of the vehicle by determining a difference between a first set of feature vectors of an image of the face of a rider captured prior to the adjusting at least one of the plurality of operating parameters and a second set of feature vectors of an image of the face of the rider captured during or after the adjusting at least one of the plurality of operating parameters.

In embodiments, the recurrent neural network detects a pattern of the feature vectors that indicates an emotional state of the rider is changing from a first emotional state to a second emotional state, and wherein the vehicle operation control system adjusts an operational parameter of the vehicle in response to the indicated change in emotional state.

An aspect provided herein includes a system for transportation, comprising: an artificial intelligence system for processing a voice of a rider in a vehicle to determine an emotional state of the rider and optimizing at least one operating parameter of the vehicle to improve the emotional state of the rider.

An aspect provided herein includes an artificial intelligence system for voice processing to improve rider satisfaction in a transportation system, comprising: a rider voice capture system deployed to capture voice output of a rider occupying a vehicle; a voice-analysis circuit trained using machine learning that classifies an emotional state of the rider for the captured voice output of the rider; and an expert system trained using machine learning that optimizes at least one operating parameter of the vehicle to change the rider emotional state to an emotional state classified as an improved emotional state.

In embodiments, the rider voice capture system comprises an intelligent agent that engages in a dialog with the rider to obtain rider feedback for use by the voice-analysis circuit for rider emotional state classification. In embodiments, the voice-analysis circuit uses a first machine learning system and the expert system uses a second machine learning system. In embodiments, the expert system is trained to optimize the at least one operating parameter based on feedback of outcomes of the emotional states when adjusting the at least one operating parameter for a set of individuals. In embodiments, the emotional state of the rider is determined by a combination of the captured voice output of the rider and at least one other parameter. In embodiments, the at least one other parameter is a camera-based emotional state determination of the rider. In embodiments, the at least one other parameter is traffic information. In embodiments, the at least one other parameter is weather information. In embodiments, the at least one other parameter is a vehicle state. In embodiments, the at least one other parameter is at least one pattern of physiological data of the rider. In embodiments, the at least one other parameter is a route of the vehicle. In embodiments, the at least one other parameter is in-vehicle audio content. In embodiments, the at least one other parameter is a speed of the vehicle. In embodiments, the at least one other parameter is acceleration of the vehicle. In embodiments, the at least one other parameter is deceleration of the vehicle. In embodiments, the at least one other parameter is proximity to objects along the route. In embodiments, the at least one other parameter is proximity to other vehicles along the route.

An aspect provided herein includes an artificial intelligence system for voice processing to improve rider satisfaction, comprising: a first neural network trained to classify emotional states based on analysis of human voices detects an emotional state of a rider through recognition of aspects of the voice of the rider captured while the rider is occupying the vehicle that correlate to at least one emotional state of the rider; and a second neural network that optimizes, for achieving a favorable emotional state of the rider, an operational parameter of the vehicle in response to the detected emotional state of the rider. In embodiments, at least one of the neural networks is a convolutional neural network. In embodiments, the first neural network is trained through use of a training data set that associates emotional state classes with human voice patterns. In embodiments, the first neural network is trained through the use of a training data set of voice recordings that are tagged with emotional state identifying data. In embodiments, the emotional state of the rider is determined by a combination of the captured voice output of the rider and at least one other parameter. In embodiments, the at least one other parameter is a camera-based emotional state determination of the rider. In embodiments, the at least one other parameter is traffic information. In embodiments, the at least one other parameter is weather information. In embodiments, the at least one other parameter is a vehicle state.

In embodiments, the at least one other parameter is at least one pattern of physiological data of the rider. In embodiments, the at least one other parameter is a route of the vehicle. In embodiments, the at least one other parameter is in-vehicle audio content. In embodiments, the at least one other parameter is a speed of the vehicle. In embodiments, the at least one other parameter is acceleration of the vehicle. In embodiments, the at least one other parameter is deceleration of the vehicle. In embodiments, the at least one other parameter is proximity to objects along the route. In embodiments, the at least one other parameter is proximity to other vehicles along the route.

An aspect provided herein includes a system for transportation, comprising: an artificial intelligence system for processing data from an interaction of a rider with an electronic commerce system of a vehicle to determine a rider state and optimizing at least one operating parameter of the vehicle to improve the rider state.

An aspect provided herein includes a rider satisfaction system for optimizing rider satisfaction, the rider satisfaction system comprising: an electronic commerce interface deployed for access by a rider in a vehicle; a rider interaction circuit that captures rider interactions with the deployed interface; a rider state determination circuit that processes the captured rider interactions to determine a rider state; and an artificial intelligence system trained to optimize, responsive to a rider state, at least one parameter affecting operation of the vehicle to improve the rider state. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the electronic commerce interface is self-adaptive and responsive to at least one of an identity of the rider, a route of the vehicle, a rider mood, rider behavior, vehicle configuration, and vehicle state.

In embodiments, the electronic commerce interface provides in-vehicle-relevant content that is based on at least one of an identity of the rider, a route of the vehicle, a rider mood, rider behavior, vehicle configuration, and vehicle state. In embodiments, the electronic commerce interface executes a user interaction workflow adapted for use by a rider in a vehicle. In embodiments, the electronic commerce interface provides one or more results of a search query that are adapted for presentation in a vehicle. In embodiments, the search query results adapted for presentation in a vehicle are presented in the electronic commerce interface along with advertising adapted for presentation in a vehicle. In embodiments, the rider interaction circuit captures rider interactions with the interface responsive to content presented in the interface.

An aspect provided herein includes a method for optimizing a parameter of a vehicle, comprising: capturing rider interactions with an in-vehicle electronic commerce system; determining a rider state based on the captured rider interactions and a least one operating parameter of the vehicle; processing the rider state with a rider satisfaction model that is adapted to suggest at least one operating parameter of a vehicle the influences the rider state; and optimizing the suggested at least one operating parameter for at least one of maintaining and improving a rider state.

An aspect provided herein includes an artificial intelligence system for improving rider satisfaction, comprising: a first neural network trained to classify rider states based on analysis of rider interactions with an in-vehicle electronic commerce system to detect a rider state through recognition of aspects of the rider interactions captured while the rider is occupying the vehicle that correlate to at least one state of the rider; and a second neural network that optimizes, for achieving a favorable state of the rider, an operational parameter of the vehicle in response to the detected state of the rider.

An aspect provided herein includes a system for transportation, comprising: an artificial intelligence system for processing data from at least one Internet of Things device in an environment of a vehicle to determine a determined state of the vehicle and optimizing at least one operating parameter of the vehicle to improve a state of the rider based on the determined state of the vehicle.

An aspect provided herein includes a method for improving a state of a rider through optimization of operation of a vehicle, the method comprising: capturing vehicle operation-related data with at least one Internet-of-things device; analyzing the captured data with a first neural network that determines a state of the vehicle based at least in part on a portion of the captured vehicle operation-related data; receiving data descriptive of a state of a rider occupying the operating vehicle; using a neural network to determine at least one vehicle operating parameter that affects a state of a rider occupying the operating vehicle; and using an artificial intelligence-based system to optimize the at least one vehicle operating parameter so that a result of the optimizing comprises an improvement in the state of the rider.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the at least one Internet-of-things device is disposed in an operating environment of the vehicle. In embodiments, the at least one Internet-of-things device that captures the data about the vehicle is disposed external to the vehicle. In embodiments, the at least one Internet-of-things device is a dashboard camera. In embodiments, the at least one Internet-of-things device is a mirror camera. In embodiments, the at least one Internet-of-things device is a motion sensor. In embodiments, the at least one Internet-of-things device is a seat-based sensor system. In embodiments, the at least one Internet-of-things device is an IoT enabled lighting system. In embodiments, the lighting system is a vehicle interior lighting system. In embodiments, the lighting system is a headlight lighting system. In embodiments, the at least one Internet-of-things device is a traffic light camera or sensor. In embodiments, the at least one Internet-of-things device is a roadway camera. In embodiments, the roadway camera is disposed on at least one of a telephone phone and a light pole. In embodiments, the at least one Internet-of-things device is an in-road sensor. In embodiments, the at least one Internet-of-things device is an in-vehicle thermostat. In embodiments, the at least one Internet-of-things device is a toll booth. In embodiments, the at least one Internet-of-things device is a street sign. In embodiments, the at least one Internet-of-things device is a traffic control light. In embodiments, the at least one Internet-of-things device is a vehicle mounted sensor. In embodiments, the at least one Internet-of-things device is a refueling system. In embodiments, the at least one Internet-of-things device is a recharging system. In embodiments, the at least one Internet-of-things device is a wireless charging station.

An aspect provided herein includes a rider state modification system for improving a state of a rider in a vehicle, the system comprising: a first neural network that operates to classify a state of the vehicle through analysis of information about the vehicle captured by an Internet-of-things device during operation of the vehicle; and a second neural network that operates to optimize at least one operating parameter of the vehicle based on the classified state of the vehicle, information about a state of a rider occupying the vehicle, and information that correlates vehicle operation with an effect on rider state.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the at least one Internet-of-things device is disposed in an operating environment of the vehicle. In embodiments, the at least one Internet-of-things device that captures the data about the vehicle is disposed external to the vehicle. In embodiments, the at least one Internet-of-things device is a dashboard camera. In embodiments, the at least one Internet-of-things device is a mirror camera. In embodiments, the at least one Internet-of-things device is a motion sensor. In embodiments, the at least one Internet-of-things device is a seat-based sensor system. In embodiments, the at least one Internet-of-things device is an IoT enabled lighting system.

In embodiments, the lighting system is a vehicle interior lighting system. In embodiments, the lighting system is a headlight lighting system. In embodiments, the at least one Internet-of-things device is a traffic light camera or sensor. In embodiments, the at least one Internet-of-things device is a roadway camera. In embodiments, the roadway camera is disposed on at least one of a telephone phone and a light pole. In embodiments, the at least one Internet-of-things device is an in-road sensor. In embodiments, the at least one Internet-of-things device is an in-vehicle thermostat. In embodiments, the at least one Internet-of-things device is a toll booth. In embodiments, the at least one Internet-of-things device is a street sign. In embodiments, the at least one Internet-of-things device is a traffic control light. In embodiments, the at least one Internet-of-things device is a vehicle mounted sensor. In embodiments, the at least one Internet-of-things device is a refueling system. In embodiments, the at least one Internet-of-things device is a recharging system. In embodiments, the at least one Internet-of-things device is a wireless charging station.

An aspect provided herein includes an artificial intelligence system comprising: a first neural network trained to determine an operating state of a vehicle from data about the vehicle captured in an operating environment of the vehicle, wherein the first neural network operates to identify an operating state of a vehicle by processing information about the vehicle that is captured by at least one Internet-of things device while the vehicle is operating; a data structure that facilitates determining operating parameters that influence an operating state of a vehicle; a second neural network that operates to optimize at least one of the determined operating parameters of the vehicle based on the identified operating state by processing information about a state of a rider occupying the vehicle, and information that correlates vehicle operation with an effect on rider state.

In embodiments, the improvement in the state of the rider is reflected in updated data that is descriptive of a state of the rider captured responsive to the vehicle operation based on the optimized at least one vehicle operating parameter. In embodiments, the improvement in the state of the rider is reflected in data captured by at least one Internet-of-things device disposed to capture information about the rider while occupying the vehicle responsive to the optimizing. In embodiments, the vehicle comprises a system for automating at least one control parameter of the vehicle.

In embodiments, the vehicle is at least a semi-autonomous vehicle. In embodiments, the vehicle is automatically routed. In embodiments, the vehicle is a self-driving vehicle. In embodiments, the at least one Internet-of-things device is disposed in an operating environment of the vehicle. In embodiments, the at least one Internet-of-things device that captures the data about the vehicle is disposed external to the vehicle. In embodiments, the at least one Internet-of-things device is a dashboard camera. In embodiments, the at least one Internet-of-things device is a mirror camera. In embodiments, the at least one Internet-of-things device is a motion sensor. In embodiments, the at least one Internet-of-things device is a seat-based sensor system. In embodiments, the at least one Internet-of-things device is an IoT enabled lighting system.

In embodiments, the lighting system is a vehicle interior lighting system. In embodiments, the lighting system is a headlight lighting system. In embodiments, the at least one Internet-of-things device is a traffic light camera or sensor. In embodiments, the at least one Internet-of-things device is a roadway camera. In embodiments, the roadway camera is disposed on at least one of a telephone phone and a light pole. In embodiments, the at least one Internet-of-things device is an in-road sensor. In embodiments, the at least one Internet-of-things device is an in-vehicle thermostat. In embodiments, the at least one Internet-of-things device is a toll booth. In embodiments, the at least one Internet-of-things device is a street sign. In embodiments, the at least one Internet-of-things device is a traffic control light. In embodiments, the at least one Internet-of-things device is a vehicle mounted sensor. In embodiments, the at least one Internet-of-things device is a refueling system. In embodiments, the at least one Internet-of-things device is a recharging system. In embodiments, the at least one Internet-of-things device is a wireless charging station.

An aspect provided herein includes a system for transportation, comprising: an artificial intelligence system for processing a sensory input from a wearable device in a vehicle to determine an emotional state of a rider in the vehicle and optimizing an operating parameter of the vehicle to improve the emotional state of the rider. In embodiments, the vehicle is a self-driving vehicle; wherein the artificial intelligence system is to detect the emotional state of the rider riding in the self-driving vehicle by recognition of patterns of emotional state indicative data from a set of wearable sensors worn by the rider, wherein the patterns are indicative of at least one of a favorable emotional state of the rider and an unfavorable emotional state of the rider; and wherein the artificial intelligence system is to optimize, for achieving at least one of maintaining a detected favorable emotional state of the rider and achieving a favorable emotional state of a rider subsequent to a detection of an unfavorable emotional state, the operating parameter of the vehicle in response to the detected emotional state of the rider. In embodiments, the artificial intelligence system comprises an expert system that detects an emotional state of the rider by processing rider emotional state indicative data received from the set of wearable sensors worn by the rider. In embodiments, the expert system processes the rider emotional state indicative data using at least one of a training set of emotional state indicators of a set of riders and trainer-generated rider emotional state indicators. In embodiments, the artificial intelligence system comprises a recurrent neural network that detects the emotional state of the rider.

In embodiments, recurrent neural network comprises a plurality of connected nodes that form a directed cycle, the recurrent neural network further facilitating bi-directional flow of data among the connected nodes. In embodiments, the artificial intelligence system comprises a radial basis function neural network that optimizes the operational parameter. In embodiments, the artificial intelligence system comprises a radial basis function neural network that optimizes the operational parameter. In embodiments, the optimizing an operational parameter is based on a correlation between a vehicle operating state and a rider emotional state. In embodiments, the correlation is determined using at least one of a training set of emotional state indicators of a set of riders and human trainer-generated rider emotional state indicators. In embodiments, the operational parameter of the vehicle that is optimized is determined and adjusted to induce a favorable rider emotional state.

In embodiments, the artificial intelligence system further learns to classify the patterns of the emotional state indicative data and associate the patterns to emotional states and changes thereto from a training data set sourced from at least one of a stream of data from unstructured data sources, social media sources, wearable devices, in-vehicle sensors, a rider helmet, a rider headgear, and a rider voice system. In embodiments, the artificial intelligence system detects a pattern of the rider emotional state indicative data that indicates the emotional state of the rider is changing from a first emotional state to a second emotional state, the optimizing of the operational parameter of the vehicle being response to the indicated change in emotional state. In embodiments, the patterns of rider emotional state indicative data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the artificial intelligence system interacts with a vehicle control system to optimize the operational parameter. In embodiments, the artificial intelligence system further comprises a neural net that includes one or more perceptrons that mimic human senses that facilitates determining an emotional state of a rider based on an extent to which at least one of the senses of the rider is stimulated. In embodiments, the set of wearable sensors comprises at least two of a watch, a ring, a wrist band, an arm band, an ankle band, a torso band, a skin patch, a head-worn device, eye glasses, foot wear, a glove, an in-ear device, clothing, headphones, a belt, a finger ring, a thumb ring, a toe ring, and a necklace. In embodiments, the artificial intelligence system uses deep learning for determining patterns of wearable sensor-generated emotional state indicative data that indicate an emotional state of the rider as at least one of a favorable emotional state and an unfavorable emotional state. In embodiments, the artificial intelligence system is responsive to a rider indicated emotional state by at least optimizing the operation parameter to at least one of achieve and maintain the rider indicated emotional state.

In embodiments, the artificial intelligence system adapts a characterization of a favorable emotional state of the rider based on context gathered from a plurality of sources including data indicating a purpose of the rider riding in the self-driving vehicle, a time of day, traffic conditions, weather conditions and optimizes the operating parameter to at least one of achieve and maintain the adapted favorable emotional state. In embodiments, the artificial intelligence system optimizes the operational parameter in real time responsive to the detecting of an emotional state of the rider. In embodiments, the vehicle is a self-driving vehicle, wherein the artificial intelligence system comprises: a first neural network to detect the emotional state of the rider through expert system-based processing of rider emotional state indicative wearable sensor data of a plurality of wearable physiological condition sensors worn by the rider in the vehicle, the emotional state indicative wearable sensor data indicative of at least one of a favorable emotional state of the rider and an unfavorable emotional state of the rider; and a second neural network to optimize, for at least one of achieving and maintaining a favorable emotional state of the rider, the operating parameter of the vehicle in response to the detected emotional state of the rider. In embodiments, the first neural network is a recurrent neural network and the second neural network is a radial basis function neural network.

In embodiments, the second neural network optimizes the operational parameter based on a correlation between a vehicle operating state and a rider emotional state. In embodiments, the operational parameter of the vehicle that is optimized is determined and adjusted to induce a favorable rider emotional state. In embodiments, the first neural network further learns to classify patterns of the rider emotional state indicative wearable sensor data and associate the patterns to emotional states and changes thereto from a training data set sourced from at least one of a stream of data from unstructured data sources, social media sources, wearable devices, in-vehicle sensors, a rider helmet, a rider headgear, and a rider voice system. In embodiments, the second neural network optimizes the operational parameter in real time responsive to the detecting of an emotional state of the rider by the first neural network. In embodiments, the first neural network detects a pattern of the rider emotional state indicative wearable sensor data that indicates the emotional state of the rider is changing from a first emotional state to a second emotional state, wherein the second neural network optimizes the operational parameter of the vehicle in response to the indicated change in emotional state.

In embodiments, the first neural network comprises a plurality of connected nodes that form a directed cycle, the first neural network further facilitating bi-directional flow of data among the connected nodes. In embodiments, the first neural net includes one or more perceptrons that mimic human senses that facilitates determining an emotional state of a rider based on an extent to which at least one of the senses of the rider is stimulated. In embodiments, the rider emotional state indicative wearable sensor data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the second neural network interacts with a vehicle control system to adjust the operational parameter. In embodiments, the first neural network includes one or more perceptrons that mimic human senses that facilitates determining an emotional state of a rider based on an extent to which at least one of the senses of the rider is stimulated.

In embodiments, the vehicle is a self-driving vehicle; wherein the artificial intelligence system is to detect a change in the emotional state of the rider riding in the self-driving vehicle at least in part by recognition of patterns of emotional state indicative data from a set of wearable sensors worn by the rider, wherein the patterns are indicative of at least one of a diminishing of a favorable emotional state of the rider and an onset of an unfavorable emotional state of the rider; and wherein the artificial intelligence system is to determine at least one operating parameter of the self-driving vehicle that is indicative of the change in emotional state based on a correlation of the patterns of emotional state indicative data with a set of operating parameters of the vehicle; and wherein the artificial intelligence system is to determine an adjustment of the at least one operating parameter for achieving at least one of restoring the favorable emotional state of the rider and achieving a reduction in the onset of the unfavorable emotional state of a rider.

In embodiments, the correlation of patterns of rider emotional indicative state wearable sensor data is determined using at least one of a training set of emotional state wearable sensor indicators of a set of riders and human trainer-generated rider emotional state wearable sensor indicators. In embodiments, the artificial intelligence system further learns to classify the patterns of the emotional state indicative wearable sensor data and associate the patterns to changes in rider emotional states from a training data set sourced from at least one of a stream of data from unstructured data sources, social media sources, wearable devices, in-vehicle sensors, a rider helmet, a rider headgear, and a rider voice system. In embodiments, the patterns of rider emotional state indicative wearable sensor data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter determined from a result of processing the rider emotional state indicative wearable sensor data affects at least one of a route of the vehicle, in-vehicle audio content, speed of the vehicle, acceleration of the vehicle, deceleration of the vehicle, proximity to objects along the route, and proximity to other vehicles along the route. In embodiments, the artificial intelligence system further interacts with a vehicle control system for adjusting the operational parameter. In embodiments, the artificial intelligence system further comprises a neural net that includes one or more perceptrons that mimic human senses that facilitate determining an emotional state of a rider based on an extent to which at least one of the senses of the rider is stimulated.

In embodiments, the set of wearable sensors comprises at least two of a watch, a ring, a wrist band, an arm band, an ankle band, a torso band, a skin patch, a head-worn device, eye glasses, foot wear, a glove, an in-ear device, clothing, headphones, a belt, a finger ring, a thumb ring, a toe ring, and a necklace. In embodiments, the artificial intelligence system uses deep learning for determining patterns of wearable sensor-generated emotional state indicative data that indicate the change in the emotional state of the rider. In embodiments, the artificial intelligence system further determines the change in emotional state of the rider based on context gathered from a plurality of sources including data indicating a purpose of the rider riding in the self-driving vehicle, a time of day, traffic conditions, weather conditions and optimizes the operating parameter to at least one of achieve and maintain the adapted favorable emotional state. In embodiments, the artificial intelligence system adjusts the operational parameter in real time responsive to the detecting of a change in rider emotional state.

In embodiments, the vehicle is a self-driving vehicle, and wherein the artificial intelligence system includes: a recurrent neural network to indicate a change in the emotional state of a rider in the self-driving vehicle by a recognition of patterns of emotional state indicative wearable sensor data from a set of wearable sensors worn by the rider, wherein the patterns are indicative of at least one of a first degree of a favorable emotional state of the rider and a second degree of an unfavorable emotional state of the rider; and a radial basis function neural network to optimize, for achieving a target emotional state of the rider, the operating parameter of the vehicle in response to the indication of the change in the emotional state of the rider.

In embodiments, the radial basis function neural network optimizes the operational parameter based on a correlation between a vehicle operating state and a rider emotional state. In embodiments, the target emotional state is a favorable rider emotional state and the operational parameter of the vehicle that is optimized is determined and adjusted to induce the favorable rider emotional state. In embodiments, the recurrent neural network further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system. In embodiments, the radial basis function neural network optimizes the operational parameter in real time responsive to the detecting of a change in an emotional state of the rider by the recurrent neural network. In embodiments, the recurrent neural network detects a pattern of the emotional state indicative wearable sensor data that indicates the emotional state of the rider is changing from a first emotional state to a second emotional state, wherein the radial basis function neural network optimizes the operational parameter of the vehicle in response to the indicated change in emotional state. In embodiments, the recurrent neural network comprises a plurality of connected nodes that form a directed cycle, the recurrent neural network further facilitating bi-directional flow of data among the connected nodes.

In embodiments, the patterns of emotional state indicative wearable sensor data indicate at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the radial basis function neural network interacts with a vehicle control system to adjust the operational parameter. In embodiments, the recurrent neural net includes one or more perceptrons that mimic human senses that facilitates determining an emotional state of a rider based on an extent to which at least one of the senses of the rider is stimulated.

In embodiments, the artificial intelligence system is to maintain a favorable emotional state of the rider through use of a modular neural network, the modular neural network comprising: a rider emotional state determining neural network to process emotional state indicative wearable sensor data of a rider in the vehicle to detect patterns, wherein the patterns found in the emotional state indicative wearable sensor data are indicative of at least one of a favorable emotional state of the rider and an unfavorable emotional state of the rider; an intermediary circuit to convert output data from the rider emotional state determining neural network into vehicle operational state data; and a vehicle operational state optimizing neural network to adjust the operating parameter of the vehicle in response to the vehicle operational state data.

In embodiments, the vehicle operational state optimizing neural network adjusts an operational parameter of the vehicle for achieving a favorable emotional state of the rider. In embodiments, the vehicle operational state optimizing neural network optimizes the operational parameter based on a correlation between a vehicle operating state and a rider emotional state. In embodiments, the operational parameter of the vehicle that is optimized is determined and adjusted to induce a favorable rider emotional state. In embodiments, the rider emotional state determining neural network further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system.

In embodiments, the vehicle operational state optimizing neural network optimizes the operational parameter in real time responsive to the detecting of a change in an emotional state of the rider by the rider emotional state determining neural network. In embodiments, the rider emotional state determining neural network detects a pattern of emotional state indicative wearable sensor data that indicates the emotional state of the rider is changing from a first emotional state to a second emotional state, wherein the vehicle operational state optimizing neural network optimizes the operational parameter of the vehicle in response to the indicated change in emotional state. In embodiments, the artificial intelligence system comprises a plurality of connected nodes that form a directed cycle, the artificial intelligence system further facilitating bi-directional flow of data among the connected nodes. In embodiments, the pattern of emotional state indicative wearable sensor data indicate at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the vehicle operational state optimizing neural network interacts with a vehicle control system to adjust the operational parameter. In embodiments, the artificial intelligence system further comprises a neural net that includes one or more perceptrons that mimic human senses that facilitates determining an emotional state of a rider based on an extent to which at least one of the senses of the rider is stimulated. In embodiments, the rider emotional state determining neural network comprises one or more perceptrons that mimic human senses that facilitates determining an emotional state of a rider based on an extent to which at least one of the senses of the rider is stimulated.

In embodiments, the artificial intelligence system is to indicate a change in the emotional state of a rider in the vehicle through recognition of patterns of emotional state indicative wearable sensor data of the rider in the vehicle; the transportation system further comprising: a vehicle control system to control an operation of the vehicle by adjusting a plurality of vehicle operating parameters; and a feedback loop through which the indication of the change in the emotional state of the rider is communicated between the vehicle control system and the artificial intelligence system, wherein the vehicle control system adjusts at least one of the plurality of vehicle operating parameters responsive to the indication of the change. In embodiments, the vehicle controls system adjusts the at least one of the plurality of vehicle operational parameters based on a correlation between vehicle operational state and rider emotional state.

In embodiments, the vehicle control system adjusts the at least one of the plurality of vehicle operational parameters that are indicative of a favorable rider emotional state. In embodiments, the vehicle control system selects an adjustment of the at least one of the plurality of vehicle operational parameters that is indicative of producing a favorable rider emotional state. In embodiments, the artificial intelligence system further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system. In embodiments, the vehicle control system adjusts the at least one of the plurality of vehicle operation parameters in real time.

In embodiments, the artificial intelligence system further detects a pattern of the emotional state indicative wearable sensor data that indicates the emotional state of the rider is changing from a first emotional state to a second emotional state, wherein the vehicle operation control system adjusts an operational parameter of the vehicle in response to the indicated change in emotional state. In embodiments, the artificial intelligence system comprises a plurality of connected nodes that form a directed cycle, the artificial intelligence system further facilitating bi-directional flow of data among the connected nodes. In embodiments, the at least one of the plurality of vehicle operation parameters that is responsively adjusted affects operation of a powertrain of the vehicle and a suspension system of the vehicle.

In embodiments, the radial basis function neural network interacts with the recurrent neural network via an intermediary component of the artificial intelligence system that produces vehicle control data indicative of an emotional state response of the rider to a current operational state of the vehicle. In embodiments, the artificial intelligence system further comprises a modular neural network comprising a rider emotional state recurrent neural network for indicating the change in the emotional state of a rider, a vehicle operational state radial based function neural network, and an intermediary system wherein the intermediary system processes rider emotional state characterization data from the recurrent neural network into vehicle control data that the radial based function neural network uses to interact with the vehicle control system for adjusting the at least one operational parameter.

In embodiments, the artificial intelligence system comprises a neural net that includes one or more perceptrons that mimic human senses that facilitate determining an emotional state of a rider based on an extent to which at least one of the senses of the rider is stimulated. In embodiments, the recognition of patterns of emotional state indicative wearable sensor data comprises processing the emotional state indicative wearable sensor data captured during at least two of before the adjusting at least one of the plurality of vehicle operational parameters, during the adjusting at least one of the plurality of vehicle operational parameters, and after adjusting at least one of the plurality of vehicle operational parameters.

In embodiments, the artificial intelligence system indicates a change in the emotional state of the rider responsive to a change in an operating parameter of the vehicle by determining a difference between a first set of emotional state indicative wearable sensor data of a rider captured prior to the adjusting at least one of the plurality of operating parameters and a second set of emotional state indicative wearable sensor data of the rider captured during or after the adjusting at least one of the plurality of operating parameters.

An aspect provided herein includes a system for transportation, comprising: a cognitive system for managing an advertising market for in-seat advertising for riders of vehicles, wherein the cognitive system takes inputs corresponding to at least one parameter of the vehicle or the rider to determine a characteristic of an advertisement to be delivered within an interface to a rider in a seat of the vehicle, wherein the characteristic of the advertisement is selected from the group consisting of a price, a category, a location and combinations thereof.

An aspect provided herein includes a method of vehicle in-seat advertising, the method comprising: taking inputs relating to at least one parameter of a vehicle; taking inputs relating to at least one parameter of a rider occupying the vehicle; and determining at least one of a price, classification, content, and location of an advertisement to be delivered within an interface of the vehicle to a rider in a seat in the vehicle based on the vehicle-related inputs and the rider-related inputs. In embodiments, the vehicle comprises a system for automating at least one control parameter of the vehicle. In embodiments, the vehicle is at least a semi-autonomous vehicle.

In embodiments, the vehicle is automatically routed. In embodiments, the vehicle is a self-driving vehicle. In embodiments, the cognitive system further determines at least one of a price, classification, content and location of an advertisement placement. In embodiments, an advertisement is delivered from an advertiser who places a winning bid. In embodiments, delivering an advertisement is based on a winning bid. In embodiments, the inputs relating to the at least one parameter of a vehicle include vehicle classification. In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size.

In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes a method of in-vehicle advertising interaction tracking comprising: taking inputs relating to at least one parameter of a vehicle and inputs relating to at least one parameter of a rider occupying the vehicle; aggregating the inputs across a plurality of vehicles; using a cognitive system to determine opportunities for in-vehicle advertisement placement based on the aggregated inputs; offering the placement opportunities in an advertising network that facilitates bidding for the placement opportunities; based on a result of the bidding, delivering an advertisement for placement within a user interface of the vehicle; and monitoring vehicle rider interaction with the advertisement presented in the user interface of the vehicle.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, an advertisement is delivered from an advertiser who places a winning bid. In embodiments, delivering an advertisement is based on a winning bid. In embodiments, the monitored vehicle rider interaction information includes information for resolving click-based payments. In embodiments, the monitored vehicle rider interaction information includes an analytic result of the monitoring. In embodiments, the analytic result is a measure of interest in the advertisement. In embodiments, the inputs relating to the at least one parameter of a vehicle include vehicle classification.

In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes a method of in-vehicle advertising comprising: taking inputs relating to at least one parameter of a vehicle and inputs relating to at least one parameter of a rider occupying the vehicle; aggregating the inputs across a plurality of vehicles; using a cognitive system to determine opportunities for in-vehicle advertisement placement based on the aggregated inputs; offering the placement opportunities in an advertising network that facilitates bidding for the placement opportunities; and based on a result of the bidding, delivering an advertisement for placement within an interface of the vehicle.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the cognitive system further determines at least one of a price, classification, content and location of an advertisement placement. In embodiments, an advertisement is delivered from an advertiser who places a winning bid. In embodiments, delivering an advertisement is based on a winning bid. In embodiments, the inputs relating to the at least one parameter of a vehicle include vehicle classification.

In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes an advertising system of vehicle in-seat advertising, the advertising system comprising: a cognitive system that takes inputs relating to at least one parameter of a vehicle and takes inputs relating to at least one parameter of a rider occupying the vehicle, and determines at least one of a price, classification, content and location of an advertisement to be delivered within an interface of the vehicle to a rider in a seat in the vehicle based on the vehicle-related inputs and the rider-related inputs.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the inputs relating to the at least one parameter of a vehicle include vehicle classification. In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information.

In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

In embodiments, the advertising system is further to determine a vehicle operating state from the inputs related to at least one parameter of the vehicle, wherein the advertisement to be delivered is determined based at least in part on the determined vehicle operating state. In embodiments, the advertising system is further to determine a rider state from the inputs related to at least one parameter of the rider, wherein the advertisement to be delivered is determined based at least in part on the determined rider state.

An aspect provided herein includes a system for transportation, comprising: a hybrid cognitive system for managing an advertising market for in-seat advertising to riders of vehicles, wherein at least one part of the hybrid cognitive system processes inputs corresponding to at least one parameter of the vehicle to determine a vehicle operating state and at least one other part of the cognitive system processes inputs relating to a rider to determine a rider state, wherein the cognitive system determines a characteristic of an advertisement to be delivered within an interface to the rider in a seat of the vehicle, wherein the characteristic of the advertisement is selected from the group consisting of a price, a category, a location and combinations thereof.

An aspect provided herein includes an artificial intelligence system for vehicle in-seat advertising, comprising: a first portion of the artificial intelligence system that determines an operating state of the vehicle by processing inputs relating to at least one parameter of the vehicle; a second portion of the artificial intelligence system that determines a state of the rider of the vehicle by processing inputs relating to at least one parameter of the rider; and a third portion of the artificial intelligence system that determines at least one of a price, classification, content and location of an advertisement to be delivered within an interface of the vehicle to a rider in a seat in the vehicle based on the vehicle state and the rider state.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the cognitive system further determines at least one of a price, classification, content and location of an advertisement placement. In embodiments, an advertisement is delivered from an advertiser who places a winning bid. In embodiments, delivering an advertisement is based on a winning bid. In embodiments, the inputs relating to the at least one parameter of a vehicle include vehicle classification.

In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes a method of in-vehicle advertising interaction tracking comprising: taking inputs relating to at least one parameter of a vehicle and inputs relating to at least one parameter of a rider occupying the vehicle; aggregating the inputs across a plurality of vehicles; using a hybrid cognitive system to determine opportunities for in-vehicle advertisement placement based on the aggregated inputs; offering the placement opportunities in an advertising network that facilitates bidding for the placement opportunities; based on a result of the bidding, delivering an advertisement for placement within a user interface of the vehicle; and monitoring vehicle rider interaction with the advertisement presented in the user interface of the vehicle.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, a first portion of the hybrid cognitive system determines an operating state of the vehicle by processing inputs relating to at least one parameter of the vehicle. In embodiments, a second portion of the hybrid cognitive system determines a state of the rider of the vehicle by processing inputs relating to at least one parameter of the rider. In embodiments, a third portion of the hybrid cognitive system determines at least one of a price, classification, content and location of an advertisement to be delivered within an interface of the vehicle to a rider in a seat in the vehicle based on the vehicle state and the rider state. In embodiments, an advertisement is delivered from an advertiser who places a winning bid. In embodiments, delivering an advertisement is based on a winning bid. In embodiments, the monitored vehicle rider interaction information includes information for resolving click-based payments. In embodiments, the monitored vehicle rider interaction information includes an analytic result of the monitoring. In embodiments, the analytic result is a measure of interest in the advertisement.

In embodiments, the inputs relating to the at least one parameter of a vehicle include vehicle classification. In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes a method of in-vehicle advertising comprising: taking inputs relating to at least one parameter of a vehicle and inputs relating to at least one parameter of a rider occupying the vehicle; aggregating the inputs across a plurality of vehicles; using a hybrid cognitive system to determine opportunities for in-vehicle advertisement placement based on the aggregated inputs; offering the placement opportunities in an advertising network that facilitates bidding for the placement opportunities; and based on a result of the bidding, delivering an advertisement for placement within an interface of the vehicle.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, a first portion of the hybrid cognitive system determines an operating state of the vehicle by processing inputs relating to at least one parameter of the vehicle. In embodiments, a second portion of the hybrid cognitive system determines a state of the rider of the vehicle by processing inputs relating to at least one parameter of the rider. In embodiments, a third portion of the hybrid cognitive system determines at least one of a price, classification, content and location of an advertisement to be delivered within an interface of the vehicle to a rider in a seat in the vehicle based on the vehicle state and the rider state. In embodiments, an advertisement is delivered from an advertiser who places a winning bid. In embodiments, delivering an advertisement is based on a winning bid. In embodiments, the inputs relating to the at least one parameter of a vehicle include vehicle classification. In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

An aspect provided herein includes a system for transportation, comprising: a motorcycle helmet to provide an augmented reality experience based on registration of a location and orientation of a wearer of the helmet in an environment.

An aspect provided herein includes a motorcycle helmet comprising: a data processor configured to facilitate communication between a rider wearing the helmet and a motorcycle, the motorcycle and the helmet communicating location and orientation of the motorcycle; and an augmented reality system with a display disposed to facilitate presenting an augmentation of content in an environment of a rider wearing the helmet, the augmentation responsive to a registration of the communicated location and orientation of the motorcycle, wherein at least one parameter of the augmentation is determined by machine learning on at least one input relating to at least one of the rider and the motorcycle.

In embodiments, the motorcycle comprises a system for automating at least one control parameter of the motorcycle. In embodiments, the motorcycle is at least a semi-autonomous motorcycle. In embodiments, the motorcycle is automatically routed. In embodiments, the motorcycle is a self-driving motorcycle. In embodiments, the content in the environment is content that is visible in a portion of a field of view of the rider wearing the helmet. In embodiments, the machine learning on the input of the rider determines an emotional state of the rider and a value for the at least one parameter is adapted responsive to the rider emotional state. In embodiments, the machine learning on the input of the motorcycle determines an operational state of the motorcycle and a value for the at least one parameter is adapted responsive to the motorcycle operational state. In embodiments, the helmet further comprises a motorcycle configuration expert system for recommending an adjustment of a value of the at least one parameter to the augmented reality system responsive to the at least one input.

An aspect provided herein includes a motorcycle helmet augmented reality system comprising: a display disposed to facilitate presenting an augmentation of content in an environment of a rider wearing the helmet; a circuit for registering at least one of location and orientation of a motorcycle that the rider is riding; a machine learning circuit that determines at least one augmentation parameter by processing at least one input relating to at least one of the rider and the motorcycle; and a reality augmentation circuit that, responsive to the registered at least one of a location and orientation of the motorcycle generates an augmentation element for presenting in the display, the generating based at least in part on the determined at least one augmentation parameter.

In embodiments, the motorcycle comprises a system for automating at least one control parameter of the motorcycle. In embodiments, the motorcycle is at least a semi-autonomous motorcycle. In embodiments, the motorcycle is automatically routed. In embodiments, the motorcycle is a self-driving motorcycle. In embodiments, the content in the environment is content that is visible in a portion of a field of view of the rider wearing the helmet. In embodiments, the machine learning on the input of the rider determines an emotional state of the rider and a value for the at least one parameter is adapted responsive to the rider emotional state. In embodiments, the machine learning on the input of the motorcycle determines an operational state of the motorcycle and a value for the at least one parameter is adapted responsive to the motorcycle operational state.

In embodiments, the helmet further comprises a motorcycle configuration expert system for recommending an adjustment of a value of the at least one parameter to the augmented reality system responsive to the at least one input.

An aspect provided herein includes a vehicle transportation system comprising: a vehicle information ingestion port that provides a network-enabled interface through which inputs comprising operational state and energy consumption information from at least one of a plurality of network-enabled vehicles is gathered in real time; a vehicle charging infrastructure control system that receives operational state and energy consumption information for the plurality of network-enabled vehicles via the ingestion port; an artificial intelligence system functionally connected with the vehicle charging infrastructure control system that, responsive to the receiving of the operational state and energy consumption information, determines at least one charging plan parameter upon which a charging plan for at least a portion of the plurality of network-enabled vehicles, that the vehicle charging control system executes, is dependent.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle.

In embodiments, the artificial intelligence system coordinates a cloud-based system remote from charging infrastructure and a local system positioned with the charging infrastructure. In embodiments, an adjustment to the at least one parameter that when made to the charge infrastructure operation plan ensures that the at least one of the plurality of vehicles has access to energy renewal in a target energy renewal region. In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand.

In embodiments, the recharging plan update facility provides feedback of the applying the adjustment value of the at least one of the plurality of recharging parameters to the artificial intelligence system. In embodiments, the feedback comprises an effect of the adjustment value on recharging infrastructure facilities in the target recharging range. In embodiments, the artificial intelligence system calculates energy parameters, optimizes electricity usage, and optimizes at least one of recharging time, location, and amount. In embodiments, the at least one of the plurality of recharging plan parameters is a routing parameter for the at least one of the plurality of vehicles. In embodiments, the artificial intelligence system provides a recharging plan that accommodates near-term charging needs for the plurality of rechargeable vehicles based on the optimized at least one parameter. In embodiments, the recharging infrastructure comprises at least one of fueling stations and recharging stations. In embodiments, the artificial intelligence system predicts a geolocation of a plurality of vehicles within a geographic region of the at least one of the plurality of vehicles.

In embodiments, the at least one charging plan parameter comprises allocation of vehicles to at least a portion of charging infrastructure within a geographic region of the at least one of the plurality of vehicle. In embodiments, the at least one recharge plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on predicted traffic conditions for the plurality of rechargeable vehicles. In embodiments, the artificial intelligence system executes an optimizing algorithm that calculates energy parameters, optimizes electricity usage, and optimizes at least one of recharging time, location, and amount. In embodiments, the artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure.

An aspect provided herein includes an artificial intelligence vehicle transportation system comprising: a first neural network that processes inputs comprising vehicle route and stored energy state information for a plurality of vehicles and predicts for at least one of the plurality of vehicles a target energy renewal region; a second neural network that processes vehicle energy renewal infrastructure usage and demand information for vehicle energy renewal infrastructure facilities within the target energy renewal region to determine at least one parameter of a charge infrastructure operational plan that facilitates access by the at least one of the plurality vehicles to renewal energy in the target energy renewal region.

In embodiments, the vehicle comprises a system for automating at least one control parameter of the vehicle. In embodiments, the vehicle is at least a semi-autonomous vehicle.

In embodiments, the vehicle is automatically routed. In embodiments, the vehicle is a self-driving vehicle. In embodiments, the artificial intelligence vehicle transportation system coordinates a cloud-based system remote from charging infrastructure and a local system positioned with the charging infrastructure. In embodiments, an adjustment to the at least one parameter that when made to the charge infrastructure operation plan ensures that the at least one of the plurality of vehicles has access to energy renewal in a target energy renewal region. In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the recharging plan update facility provides feedback of the applying the adjustment value of the at least one of the plurality of recharging parameters to the artificial intelligence vehicle transportation system.

In embodiments, the feedback comprises an effect of the adjustment value on recharging infrastructure facilities in the target recharging range. In embodiments, the artificial intelligence vehicle transportation system calculates energy parameters, optimizes electricity usage, and optimizes at least one of recharging time, location, and amount. In embodiments, the at least one of the plurality of recharging plan parameters is a routing parameter for the at least one of the plurality of vehicles. In embodiments, the artificial intelligence vehicle transportation system provides a recharging plan that accommodates near-term charging needs for the plurality of rechargeable vehicles based on the optimized at least one parameter. In embodiments, the recharging infrastructure comprises at least one of fueling stations and recharging stations. In embodiments, the artificial intelligence vehicle transportation system predicts a geolocation of a plurality of vehicles within a geographic region of the at least one of the plurality of vehicles. In embodiments, the at least one charging plan parameter comprises allocation of vehicles to at least a portion of charging infrastructure within a geographic region of the at least one of the plurality of vehicle.

In embodiments, the at least one recharge plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles. In embodiments, the inputs include inputs relating to charging states of a plurality of vehicles within a geolocation range and the artificial intelligence vehicle transportation system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles.

In embodiments, determining the at least one parameter is further based on predicted traffic conditions for the plurality of rechargeable vehicles. In embodiments, the artificial intelligence vehicle transportation system executes an optimizing algorithm that calculates energy parameters, optimizes electricity usage, and optimizes at least one of recharging time, location, and amount. In embodiments, the at least one vehicle comprises a system for automating at least one control parameter of the vehicle. In embodiments, the at least one vehicle is at least a semi-autonomous vehicle. In embodiments, the at least one vehicle is automatically routed. In embodiments, the at least one vehicle is a self-driving vehicle. In embodiments, the artificial intelligence system coordinates a cloud-based system remote from charging infrastructure and a local system positioned with the charging infrastructure. In embodiments, an adjustment to the at least one parameter that when made to the charge infrastructure operation plan ensures that the at least one of the plurality of vehicles has access to energy renewal in a target energy renewal region.

In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the recharging plan update facility provides feedback of the applying the adjustment value of the at least one of the plurality of recharging parameters to the artificial intelligence system. In embodiments, the feedback comprises an effect of the adjustment value on recharging infrastructure facilities in the target recharging range. In embodiments, the artificial intelligence system calculates energy parameters, optimizes electricity usage, and optimizes at least one of recharging time, location, and amount. In embodiments, the at least one of the plurality of recharging plan parameters is a routing parameter for the at least one of the plurality of vehicles.

In embodiments, the artificial intelligence system provides a recharging plan that accommodates near-term charging needs for the plurality of rechargeable vehicles based on the optimized at least one parameter. In embodiments, the recharging infrastructure comprises at least one of fueling stations and recharging stations. In embodiments, the artificial intelligence system predicts a geolocation of a plurality of vehicles within a geographic region of the at least one of the plurality of vehicles. In embodiments, the at least one charging plan parameter comprises allocation of vehicles to at least a portion of charging infrastructure within a geographic region of the at least one of the plurality of vehicle.

In embodiments, the at least one recharge plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on predicted traffic conditions for the plurality of rechargeable vehicles. In embodiments, the artificial intelligence system executes an optimizing algorithm that calculates energy parameters, optimizes electricity usage, and optimizes at least one of recharging time, location, and amount. In embodiments, the artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure.

An aspect provided herein includes a transportation system, comprising: an artificial intelligence system to: apply a vehicle recharging facility utilization optimization algorithm to a plurality of inputs comprising current operating state data that is gathered from a plurality of rechargeable vehicles in a target recharging range of at least one vehicle of the plurality of rechargeable vehicles; evaluate an effect of a plurality of recharging plan parameters on a recharging infrastructure in the target recharging range; select at least one of the plurality of recharging plan parameters that facilitates optimizing energy usage by the plurality of rechargeable vehicles; and generate, based on a result of applying the vehicle recharging optimization algorithm to the plurality of inputs, an adjustment value for the at least one of the plurality of recharging plan parameters. In embodiments, the at least one vehicle comprises a system for automating at least one control parameter of the vehicle. In embodiments, the at least one vehicle is at least a semi-autonomous vehicle. In embodiments, the at least one vehicle is automatically routed. In embodiments, the at least one vehicle is a self-driving vehicle.

An aspect provided herein includes a transportation route planning system comprising: an artificial intelligence system to: predict a near-term need for recharging for a plurality of rechargeable vehicles within a target geographic region based on operational status of the plurality of rechargeable vehicles; gather near-term availability and capacity information for recharging infrastructure within the region; and optimize at least one parameter of a recharging plan for the recharging infrastructure in response to the predicted need for recharging and the near-term availability and capacity information. In embodiments, at least one vehicle of the plurality of rechargeable vehicles comprises a system for automating at least one control parameter of the at least one vehicle. In embodiments, the at least one vehicle is at least a semi-autonomous vehicle. In embodiments, the at least one vehicle is automatically routed. In embodiments, the at least one vehicle is a self-driving vehicle.

An aspect provided herein includes a system for transportation comprising: an artificial intelligence system for determining at least one parameter of a charging plan based on inputs relating to a vehicle, the artificial intelligence system comprising a hybrid neural network for determining the at least one parameter of a charging plan based on inputs relating to a vehicle, where a first portion of the hybrid neural network operates on a first portion of the inputs that relates to route plan for the vehicle and a second distinct portion of the hybrid neural network operates on a second portion of the inputs comprising inputs relating to recharging infrastructure within a recharging range of the vehicle.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the second distinct portion of the hybrid neural net predicts the geolocation of a plurality of vehicles within a geographic region of the vehicle. In embodiments, the at least one parameter of a charging plan comprises allocation of vehicles to at least a portion of recharging infrastructure within the predicted geographic region. In embodiments, the at least one charging plan parameter comprises at least one of vehicle routing, amount of charge or fuel allocated, duration of time for recharging, value of charging, market price, bids for charging, and available supply capacity. In embodiments, the inputs relating to a charging system of the vehicle are determined from a battery charge state a portion of the plurality of vehicles.

An aspect provided herein includes a vehicle transportation system comprising: a vehicle information ingestion port that provides a network-enabled interface through which inputs comprising battery state data from at least one vehicle of a plurality of network-enabled vehicles is gathered in real time; a vehicle charging infrastructure control system that receives battery state data for the plurality of network-enabled vehicles via the ingestion port; and an artificial intelligence system functionally connected with the vehicle charging infrastructure control system that, responsive to the receiving of the battery state data, determines at least one charging plan parameter.

In embodiments, the at least one vehicle comprises a system for automating at least one control parameter of the vehicle. In embodiments, the at least one vehicle is at least a semi-autonomous vehicle. In embodiments, the at least one vehicle is automatically routed. In embodiments, the at least one vehicle is a self-driving vehicle. In embodiments, a charging plan for at least a portion of the plurality of network-enabled vehicles is dependent upon the at least one charging plan parameter. In embodiments, the vehicle charging infrastructure control system executes the charging plan. In embodiments, the artificial intelligence system coordinates a cloud-based system remote from charging infrastructure and a local system positioned with the charging infrastructure. In embodiments, an adjustment to the at least one parameter that when made to the charging plan ensures that the at least one of the plurality of vehicles has access to energy renewal in a target energy renewal region.

In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the charging plan update facility provides feedback of the applying the adjustment value of the at least one of the plurality of recharging parameters to the artificial intelligence system. In embodiments, the feedback comprises an effect of the adjustment value on recharging infrastructure facilities in a target recharging range. In embodiments, the artificial intelligence system calculates energy parameters, optimizes electricity usage, and optimizes at least one of recharging time, location, and amount. In embodiments, the at least one of the plurality of charging plan parameters is a routing parameter for the at least one of the plurality of vehicles.

In embodiments, the artificial intelligence system provides a charging plan that accommodates near-term charging needs for the plurality of rechargeable vehicles based on the at least one parameter. In embodiments, the recharging infrastructure comprises at least one of fueling stations and recharging stations. In embodiments, the artificial intelligence system predicts a geolocation of a plurality of vehicles within a geographic region of the at least one of the plurality of vehicles. In embodiments, the at least one charging plan parameter comprises allocation of vehicles to at least a portion of charging infrastructure within a geographic region of the at least one of the plurality of vehicle.

In embodiments, the at least one charging plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles. In embodiments, the inputs include a route plan for the vehicle. In embodiments, the inputs include at least one indicator of the value of charging.

In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on predicted traffic conditions for the plurality of rechargeable vehicles. In embodiments, the artificial intelligence system executes an optimizing algorithm that calculates energy parameters, optimizes electricity usage, and optimizes at least one of recharging time, location, and amount. In embodiments, the artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure.

In embodiments, a region to which the recharging plan applied is defined by a geofence. In embodiments, the geofence is configurable by an administrator of the region. In embodiments, the artificial intelligence system coordinates a cloud-based system remote from charging infrastructure and a local system positioned with the charging infrastructure. In embodiments, an adjustment to the at least one parameter that when made to the recharging plan ensures that the at least one of the plurality of vehicles has access to energy renewal in a target energy renewal region. In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the recharging plan update facility provides feedback of the applying the adjustment value of the at least one of the plurality of recharging parameters to the artificial intelligence system.

In embodiments, the feedback comprises an effect of the adjustment value on recharging infrastructure facilities in the target recharging range. In embodiments, the artificial intelligence system calculates energy parameters, optimizes electricity usage, and optimizes at least one of recharging time, location, and amount. In embodiments, the at least one of the plurality of recharging plan parameters is a routing parameter for the at least one of the plurality of vehicles. In embodiments, the artificial intelligence system provides a recharging plan that accommodates near-term charging needs for the plurality of rechargeable vehicles based on the at least one parameter. In embodiments, the at least one recharging plan parameter affects recharging infrastructure comprises at least one of fueling stations and recharging stations. In embodiments, the artificial intelligence system predicts a geolocation of a plurality of vehicles within a geographic region of the at least one of the plurality of vehicles. In embodiments, the at least one recharging plan parameter comprises allocation of vehicles to at least a portion of charging infrastructure within a geographic region of the at least one of the plurality of vehicle.

In embodiments, the at least one recharging plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles.

In embodiments, selecting the at least one parameter is further based on predicted traffic conditions for the plurality of rechargeable vehicles. In embodiments, the artificial intelligence system executes an optimizing algorithm that calculates energy parameters, optimizes electricity usage, and optimizes at least one of recharging time, location, and amount. In embodiments, the artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure. In embodiments, the target recharging range is defined by a geofence. In embodiments, the target recharging range is defined by a geofence that is configured by an administrator of the region. In embodiments, the target recharging range is defined by a geofence that is configurable by an administrator of the region to be substantially congruent with a jurisdiction over which the administrator has control or responsibility.

An aspect provided herein includes a transportation system, comprising: an artificial intelligence system that: applies a vehicle recharging optimization algorithm to a plurality of inputs comprising current rechargeable vehicle battery charge state and anticipated usage thereof that is gathered from a plurality of rechargeable vehicles in a target recharging range of one of the plurality of vehicles; evaluates an effect of a plurality of recharging plan parameters on the anticipated battery usage data; selects at least one of the plurality of recharging plan parameters that facilitates optimizing the anticipated battery usage; and generates, based on a result of applying the vehicle recharging optimization algorithm to the plurality of inputs, an adjustment value for the at least one of the plurality of recharging plan parameters.

In embodiments, the at least one charging plan parameter comprises vehicle routing. In embodiments, the at least one charging plan parameter comprises amount of charge or fuel allocated. In embodiments, the at least one charging plan parameter comprises duration of time for recharging. In embodiments, the at least one charging plan parameter comprises value of charging. In embodiments, the at least one charging plan parameter comprises market price. In embodiments, the at least one charging plan parameter comprises bids for charging. In embodiments, the at least one charging plan parameter comprises available supply capacity.

In embodiments, the at least one charging plan parameter comprises allocation of vehicles to at least a portion of charging infrastructure within a geographic region of the at least one of the plurality of vehicle. In embodiments, the at least one charging plan parameter comprises a routing parameter for the at least one of the plurality of vehicles. In embodiments, the target recharging range is defined by a geofence. In embodiments, the target recharging range is defined by a geofence that is configured by an administrator of the region. In embodiments, the target recharging range is defined by a geofence that is configurable by an administrator of the region to be substantially congruent with a jurisdiction over which the administrator has control or responsibility.

An aspect provided herein includes a transportation route planning system comprising: an artificial intelligence system that: predicts a near-term need for recharging for a plurality of rechargeable vehicles within a target geographic region based on a charge status of the plurality of rechargeable vehicles; gathers near-term availability and capacity information for recharging infrastructure within the region; and optimizes at least one parameter of a recharging plan for the recharging infrastructure in response to the predicted recharge need and the near-term availability and capacity information. In embodiments, region is defined by a geofence. In embodiments, the region is defined by a geofence that is configured by an administrator of the region. In embodiments, the region is defined by a geofence that is configurable by an administrator of the region to be substantially congruent with a jurisdiction over which the administrator has control or responsibility. In embodiments, the jurisdiction comprises a government municipality. In embodiments, the at least one parameter of a recharging plan comprises vehicle routing.

In embodiments, the at least one parameter of a recharging plan comprises amount of charge or fuel allocated. In embodiments, the at least one parameter of a recharging plan comprises duration of time for recharging. In embodiments, the at least one parameter of a recharging plan comprises value of charging. In embodiments, the at least one parameter of a recharging plan comprises market price. In embodiments, the at least one parameter of a recharging plan comprises bids for charging. In embodiments, the at least one parameter of a recharging plan comprises available supply capacity. In embodiments, the at least one parameter of a recharging plan comprises allocation of vehicles to at least a portion of charging infrastructure within a geographic region of the at least one of the plurality of vehicle. In embodiments, the at least one parameter of a recharging plan comprises a routing parameter for the at least one of the plurality of vehicles.

An aspect provided herein includes a system for transportation comprising: an artificial intelligence system for determining at least one parameter of a charging plan based on inputs relating to a vehicle, the artificial intelligence system comprising a hybrid neural network for determining the at least one parameter of a charging plan based on inputs relating to a vehicle, where a first portion of the hybrid neural network operates on a first portion of the inputs that relates to the charging system of the vehicle and a second distinct portion of the hybrid neural network operates on a second portion of the inputs comprising inputs relating to the vehicle other than inputs relating to the charging system. In embodiments, the second distinct portion of the hybrid neural net predicts the geolocation of a plurality of vehicles within a geographic region of the vehicle. In embodiments, the at least one parameter of a charging plan comprises allocation of vehicles to at least a portion of recharging infrastructure within the predicted geographic region.

In embodiments, the at least one charging plan parameter comprises at least one of vehicle routing, amount of charge or fuel allocated, duration of time for recharging, value of charging, market price, bids for charging, and available supply capacity. In embodiments, the inputs relating to a charging system of the vehicle are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on a predicted traffic conditions for the plurality of rechargeable vehicles.

In embodiments, the artificial intelligence system executes an optimizing algorithm that calculates energy parameters, optimizes electricity usage, and optimizes at least one of recharging time, location, and amount. In embodiments, the at least one parameter of a charging plan facilitates defining a region of the charging plan. In embodiments, the region is defined by a geofence. In embodiments, the region is defined by a geofence that is configured by an administrator of the region. In embodiments, the region is defined by a geofence that is configurable by an administrator of the region to be substantially congruent with a jurisdiction over which the administrator has control or responsibility.

An aspect provided herein includes a vehicle transportation system comprising: a vehicle information ingestion port that provides a network-enabled interface through which operational state and energy consumption information from at least one of a plurality of network-enabled vehicles is gathered in real time; a vehicle charging infrastructure control system that receives operational state and energy consumption information for the plurality of network-enabled vehicles via the ingestion port; and a cloud-based artificial intelligence system functionally connected with the vehicle charging infrastructure control system that, responsive to the receiving of the operational state and energy consumption information, determines at least one charging plan parameter upon which a charging plan for at least a portion of the plurality of network-enabled vehicles, that the vehicle charging infrastructure control system executes, is dependent.

In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the cloud-based artificial intelligence system coordinates a cloud-based system remote from charging infrastructure and a local system positioned with the charging infrastructure. In embodiments, an adjustment to the at least one parameter that when made to the charge infrastructure operation plan ensures that the at least one of the plurality of vehicles has access to energy renewal in a target energy renewal region. In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the charging plan update facility provides feedback of the applying the adjustment value of the at least one of the plurality of recharging parameters to the cloud-based artificial intelligence system.

In embodiments, the feedback comprises an effect of the adjustment value on recharging infrastructure facilities in the target recharging range. In embodiments, the cloud-based artificial intelligence system calculates energy parameters, optimizes electricity usage, and optimizes at least one of recharging time, location, and amount. In embodiments, the at least one of the plurality of charging plan parameters is a routing parameter for the at least one of the plurality of vehicles. In embodiments, the cloud-based artificial intelligence system provides a charging plan that accommodates near-term charging needs for the plurality of rechargeable vehicles based on the optimized at least one parameter. In embodiments, the charging infrastructure comprises at least one of fueling stations and recharging stations.

In embodiments, the cloud-based artificial intelligence system predicts a geolocation of a plurality of vehicles within a geographic region of the at least one of the plurality of vehicles. In embodiments, the at least one charging plan parameter comprises allocation of vehicles to at least a portion of charging infrastructure within a geographic region of the at least one of the plurality of vehicle. In embodiments, the at least one charging plan parameter comprises at least one of vehicle routing, amount of charge or fuel allocated, duration of time for recharging, value of charging, market price, bids for charging, and available supply capacity. In embodiments, the inputs relating to energy consumption are determined from a battery charge state a portion of the plurality of vehicles.

In embodiments, the inputs include inputs relating to charging states of a plurality of vehicles within a geolocation range and the cloud-based artificial intelligence system optimizes the at least one parameter based on a prediction of geolocations of the plurality of vehicles. In embodiments, the inputs include a route plan for the vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on predicted traffic conditions for the plurality of rechargeable vehicles. In embodiments, the cloud-based artificial intelligence system executes an optimizing algorithm that calculates energy parameters, optimizes electricity usage, and optimizes at least one of recharging time, location, and amount. In embodiments, the cloud-based artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure.

An aspect provided herein includes a cloud-based artificial intelligence vehicle transportation system comprising: a first neural network that processes inputs comprising vehicle route and stored energy state information for a plurality of vehicles and predicts, for at least one vehicle of the plurality of vehicles, a target energy renewal region; a second neural network that processes vehicle energy renewal infrastructure usage and demand information for vehicle energy renewal infrastructure facilities within the target energy renewal region to determine at least one parameter of a charge infrastructure operational plan that facilitates access by the at least one vehicle of the plurality vehicles to renewal energy in the target energy renewal region; wherein at least one of the first neural network and the second neural network executes on servers of a cloud-based computing system.

In embodiments, the at least one vehicle comprises a system for automating at least one control parameter of the vehicle. In embodiments, the at least one vehicle is at least a semi-autonomous vehicle. In embodiments, the at least one vehicle is automatically routed. In embodiments, the at least one vehicle is a self-driving vehicle. In embodiments, the cloud-based artificial intelligence system coordinates a cloud-based system remote from charging infrastructure and a local system positioned with the charging infrastructure. In embodiments, an adjustment to the at least one parameter that when made to the charge infrastructure operation plan ensures that the at least one vehicle of the plurality of vehicles has access to energy renewal in a target energy renewal region.

In embodiments, the at least one parameter comprises at least one of routing to charging infrastructure, amount of charge provided, duration of time for charging, battery state, battery charging profile, time required to charge, value of charging, indicators of value, market price, bids for charging, available supply capacity, and recharge demand. In embodiments, the charge infrastructure operational plan update facility provides feedback of the applying the adjustment value of the at least one of the plurality of recharging parameters to the cloud-based artificial intelligence system. In embodiments, the feedback comprises an effect of the adjustment value on recharging infrastructure facilities in the target recharging range. In embodiments, the cloud-based artificial intelligence system calculates energy parameters, optimizes electricity usage, and optimizes at least one of recharging time, location, and amount.

In embodiments, the at least one of the plurality of charge infrastructure operational plan parameters is a routing parameter for the at least one vehicle of the plurality of vehicles.

In embodiments, the inputs relating to energy consumption are determined from a battery charge state of a portion of the plurality of vehicles. In embodiments, the inputs include inputs relating to charging states of a plurality of vehicles within a geolocation range and the cloud-based artificial intelligence system optimizes the at least one parameter based on a prediction of geolocations of the plurality of vehicles. In embodiments, the inputs include a route plan for the at least one vehicle. In embodiments, the inputs include at least one indicator of the value of charging. In embodiments, the at least one parameter affects automated negotiation of at least one of a duration, a quantity and a price for charging or refueling a vehicle. In embodiments, the at least one parameter comprises a route of a portion of the plurality of rechargeable vehicles. In embodiments, determining the at least one parameter is further based on predicted traffic conditions for the plurality of rechargeable vehicles. In embodiments, the cloud-based artificial intelligence system executes an optimizing algorithm that calculates energy parameters, optimizes electricity usage, and optimizes at least one of recharging time, location, and amount. In embodiments, the cloud-based artificial intelligence system further comprises a hybrid neural network, wherein one neural network of the hybrid neural network is used to process inputs relating to charge or fuel states of the plurality of vehicles and another neural network of the hybrid neural network is used to process inputs relating to charging or refueling infrastructure.

An aspect provided herein includes a transportation system, comprising: a cloud-based artificial intelligence system that: applies a vehicle recharging optimization algorithm to a plurality of inputs comprising current rechargeable vehicle battery charge state and anticipated usage thereof that is gathered into a cloud-based data storage facility from a plurality of rechargeable vehicles in a target recharging range of one of the plurality of vehicles; evaluates an effect of a plurality of recharging plan parameters on the anticipated battery usage data; selects at least one of the plurality of recharging plan parameters that facilitates optimizing the anticipated battery usage; and generates, based on a result of applying the vehicle recharging optimization algorithm to the plurality of inputs, an adjustment value for the at least one of the plurality of recharging plan parameters. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle.

An aspect provided herein includes a cloud-based transportation route planning system comprising: an artificial intelligence system deployed for execution at least in part on cloud-based computing resources, the artificial intelligence system: predicting a near-term need for recharging for a plurality of rechargeable vehicles within a target geographic region based on a charge status of the plurality of rechargeable vehicles; gathering near-term availability and capacity information for recharging infrastructure within the region; and optimizing at least one parameter of a recharging plan for the recharging infrastructure in response to the predicted recharge need and the near-term availability and capacity information. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle.

An aspect provided herein includes a system for transportation comprising: an artificial intelligence system operating on cloud-computing servers, the system for determining at least one parameter of a charging plan based on inputs relating to a vehicle, the artificial intelligence system comprising a hybrid neural network for determining the at least one parameter of the charging plan based on inputs relating to the vehicle, wherein a first portion of the hybrid neural network operates on a first portion of the inputs that relates to the charging system of the vehicle and a second distinct portion of the hybrid neural network operates on a second portion of the inputs comprising inputs relating to the vehicle other than inputs relating to the charging system. In embodiments, the vehicle comprises a system for automating at least one control parameter of the vehicle. In embodiments, the vehicle is at least a semi-autonomous vehicle.

In embodiments, the vehicle is automatically routed. In embodiments, the vehicle is a self-driving vehicle. In embodiments, the second distinct portion of the hybrid neural net predicts the geolocation of a plurality of vehicles within a geographic region of the vehicle. In embodiments, the at least one parameter of a charging plan comprises allocation of vehicles to at least a portion of recharging infrastructure within the predicted geographic region. In embodiments, the at least one charging plan parameter comprises at least one of vehicle routing, amount of charge or fuel allocated, duration of time for recharging, value of charging, market price, bids for charging, and available supply capacity. In embodiments, the inputs relating to a charging system of the vehicle are determined from a battery charge state a portion of the plurality of vehicles. In embodiments, the inputs include inputs relating to charging states of a plurality of vehicles within a geolocation range and the artificial intelligence system optimizes the at least one parameter based on a prediction of geolocations of the plurality of vehicles.

An aspect provided herein includes a distributed transportation system, comprising: an artificial intelligence system for taking inputs relating to a plurality of vehicles and determining at least one parameter of a re-charging and plan for at least one of the plurality of vehicles based on the inputs; a cloud-based system remote from the vehicles; and a local system positioned on at least one of the plurality of vehicles, wherein the cloud-based system gathers inputs relating to a vehicle from the local system and the artificial intelligence system communicates the inputs with at least the cloud-based system. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle.

An aspect provided herein includes a distributed transportation system, comprising: an artificial intelligence system for taking inputs relating to a plurality of vehicle charging infrastructure and determining at least one parameter of a charge infrastructure operational plan for at least one of the plurality of vehicle charging infrastructure based on the inputs; a cloud-based system remote from the vehicle charging infrastructure; and a local system positioned on at least one of a plurality of vehicle charging infrastructure, wherein the cloud-based system gathers inputs relating to a vehicle charging infrastructure from the local system and the artificial intelligence system communicates the inputs with the at least the cloud-based system. In embodiments, the vehicle comprises a system for automating at least one control parameter of the vehicle.

In embodiments, the vehicle is at least a semi-autonomous vehicle. In embodiments, the vehicle is automatically routed. In embodiments, the vehicle is a self-driving vehicle. In embodiments, the cloud-based system provides a charge infrastructure operational plan that accommodates near-term charging needs for a plurality of rechargeable vehicles based on the at least one parameter. In embodiments, the charging infrastructure comprises at least one of fueling stations and recharging stations. In embodiments, the cloud-based system predicts a geolocation of a plurality of rechargeable vehicles within a geographic region of at least one of the plurality of vehicle charging infrastructure. In embodiments, the at least one charge infrastructure operational plan parameter comprises allocation of vehicles to at least a portion of charging infrastructure within a geographic region of the at least one of the plurality of the charging infrastructure. In embodiments, the at least one charge infrastructure operational plan parameter comprises at least one of vehicle routing, amount of charge or fuel allocated, duration of time for recharging, value of charging, market price, bids for charging, and available supply capacity.

An aspect provided herein includes a system for transportation, comprising: a robotic process automation system wherein a set of data is captured for each user in a set of users as each user interacts with a user interface of a vehicle, and wherein an artificial intelligence system is trained using the set of data to interact with the vehicle to automatically undertake actions with the vehicle on behalf of the user.

An aspect provided herein includes a method of robotic process automation to facilitate mimicking human operator operation of a vehicle, comprising: tracking human interactions with a vehicle control-facilitating interface; recording the tracked human interactions in a robotic process automation system training data structure; tracking vehicle operational state information of the vehicle, wherein the vehicle is to be controlled through the vehicle control-facilitating interface; recording the vehicle operational state information in the robotic process automation system training data structure; and training, through the use of at least one neural network, an artificial intelligence system to operate the vehicle in a manner consistent with the human interactions based on the human interactions and the vehicle operational state information in the robotic process automation system training data structure.

In embodiments, the method further comprises controlling at least one aspect of the vehicle with the trained artificial intelligence system. In embodiments, the method further comprises applying deep learning to the controlling the at least one aspect of the vehicle by structured variation in the controlling the at least one aspect of the vehicle to mimic the human interactions and processing feedback from the controlling the at least one aspect of the vehicle with machine learning. In embodiments, the controlling at least one aspect of the vehicle is performed via the vehicle control-facilitating interface.

In embodiments, the controlling at least one aspect of the vehicle is performed by the artificial intelligence system emulating the control-facilitating interface being operated by the human. In embodiments, the vehicle control-facilitating interface comprises at least one of an audio capture system to capture audible expressions of the human, a human-machine interface, a mechanical interface, an optical interface and a sensor-based interface. In embodiments, the tracking vehicle operational state information comprises tracking at least one of a set of vehicle systems and a set of vehicle operational processes affected by the human interactions. In embodiments, the tracking vehicle operational state information comprises tracking at least one vehicle system element, wherein the at least one vehicle system element is controlled via the vehicle control-facilitating interface, and wherein the at least one vehicle system element is affected by the human interactions. In embodiments, the tracking vehicle operational state information comprises tracking the vehicle operational state information before, during, and after the human interaction.

In embodiments, the tracking vehicle operational state information comprises tracking at least one of a plurality of vehicle control system outputs that result from the human interactions and vehicle operational results achieved in response to the human interactions. In embodiments, the vehicle is to be controlled to achieve results that are consistent with results achieved via the human interactions. In embodiments, the method further comprises tracking and recording conditions proximal to the vehicle with a plurality of vehicle mounted sensors, wherein the training of the artificial intelligence system is further responsive to the conditions proximal to the vehicle tracked contemporaneously to the human interactions. In embodiments, the training is further responsive to a plurality of data feeds from remote sensors, the plurality of data feeds comprising data collected by the remove sensors contemporaneous to the human interactions. In embodiments, the artificial intelligence system employs a workflow that involves decision-making and the robotic process automation system facilitates automation of the decision-making. In embodiments, the artificial intelligence system employs a workflow that involves remote control of the vehicle and the robotic process automation system facilitates automation of remotely controlling the vehicle.

An aspect provided herein includes a transportation system for mimicking human operation of a vehicle, comprising: a robotic process automation systems comprising: an operator data collection module to capture human operator interaction with a vehicle control system interface; a vehicle data collection module to capture vehicle response and operating conditions associated at least contemporaneously with the human operator interaction; and an environment data collection module to capture instances of environmental information associated at least contemporaneously with the human operator interaction; and an artificial intelligence system to learn to mimic the human operator to control the vehicle responsive to the robotic process automation system detecting data indicative of at least one of a plurality of the instances of environmental information associated with the contemporaneously captured vehicle response and operating conditions.

In embodiments, the operator data collection module is to capture patterns of data including braking patterns, follow-behind distance, approach to curve acceleration patterns, lane preferences, and passing preferences. In embodiments, vehicle data collection module captures data from a plurality of vehicle data systems that provide data streams indicating states and changes in state in steering, braking, acceleration, forward looking images, and rear-looking images. In embodiments, the artificial intelligence system includes a neural network for training the artificial intelligence system.

An aspect provided herein includes a robotic process automation method of mimicking human operation of a vehicle, comprising: capturing human operator interactions with a vehicle control system interface; capturing vehicle response and operating conditions associated at least contemporaneously with the human operator interaction; capturing instances of environmental information associated at least contemporaneously with the human operator interaction; and training an artificial intelligence system to control the vehicle mimicking the human operator responsive to the environment data collection module detecting data indicative of at least one of a plurality of the instances of environmental information associated with the contemporaneously captured vehicle response and operating conditions.

In embodiments, the method further comprises applying deep learning in the artificial intelligence system to optimize a margin of vehicle operating safety by affecting the controlling of the at least one aspect of the vehicle by structured variation in the controlling of the at least one aspect of the vehicle to mimic the human interactions and processing feedback from the controlling the at least one aspect of the vehicle with machine learning. In embodiments, the robotic process automation system facilitates automation of a decision-making workflow employed by the artificial intelligence system. In embodiments, the robotic process automation system facilitates automation of a remote control workflow that the artificial intelligence system employs to remotely control the vehicle.

An aspect provided herein includes a system for transportation, comprising: an artificial intelligence system to automatically randomize a parameter of an in-vehicle experience to improve a user state wherein the user state benefits from variation of the parameter.

An aspect provided herein includes a system for transportation, comprising: a vehicle interface for gathering physiological sensed data of a rider in the vehicle; and an artificial intelligence-based circuit that is trained on a set of outcomes related to rider in-vehicle experience and that induces, responsive to the sensed rider physiological data, variation in one or more of the user experience parameters to achieve at least one desired outcome in the set of outcomes, the inducing variation including control of timing and extent of the variation.

In embodiments, the induced variation includes random variation. In embodiments, the induced variation includes variation that is according to a prescribed pattern. In embodiments, the prescribed pattern is prescribed according to a regimen. In embodiments, the regimen is developed to provide at least one of physical therapy, chiropractic, and other medical health benefits. In embodiments, the one or more user experience parameters affect at least one of seat position, temperature, humidity, cabin air source, or audio output. In embodiments, the vehicle interface comprises at least one wearable sensor disposed to be worn by the rider. In embodiments, the vehicle interface comprises a vision system disposed to capture and analyze images from a plurality of perspectives of the rider. In embodiments, the variation in one or more of the user experience parameters comprises variation in control of the vehicle.

In embodiments, variation in control of the vehicle includes configuring the vehicle for aggressive driving performance. In embodiments, variation in control of the vehicle includes configuring the vehicle for non-aggressive driving performance. In embodiments, the variation is responsive to the physiological sensed data that includes an indication of a hormonal level of the rider, and the artificial intelligence-based circuit varies the one or more user experience parameters to promote a hormonal state that promotes rider safety.

An aspect provided herein includes a system for transportation, comprising: a system for detecting an indicator of a hormonal system level of a user and automatically varying a user experience in a vehicle to promote a hormonal state that promotes safety.

An aspect provided herein includes a system for transportation comprising: a vehicle interface for gathering hormonal state data of a rider in the vehicle; and an artificial intelligence-based circuit that is trained on a set of outcomes related to rider in-vehicle experience and that induces, responsive to the sensed rider hormonal state data, variation in one or more of the user experience parameters to achieve at least one desired outcome in the set of outcomes, the set of outcomes including a least one outcome that promotes rider safety, the inducing variation including control of timing and extent of the variation.

In embodiments, the variation in the one or more user experience parameters is controlled by the artificial intelligence system to promote a desired hormonal state of the rider. In embodiments, the desired hormonal state of the rider promotes safety. In embodiments, the at least one desired outcome in the set of outcomes is the at least one outcome that promotes rider safety. In embodiments, the variation in the one or more user experience parameters includes varying at least one of a food and a beverage offered to the rider. In embodiments, the one or more user experience parameters affect at least one of seat position, temperature, humidity, cabin air source, or audio output. In embodiments, the vehicle interface comprises at least one wearable sensor disposed to be worn by the rider.

In embodiments, the vehicle interface comprises a vision system disposed to capture and analyze images from a plurality of perspectives of the rider. In embodiments, the variation in one or more of the user experience parameters comprises variation in control of the vehicle. In embodiments, variation in control of the vehicle includes configuring the vehicle for aggressive driving performance. In embodiments, variation in control of the vehicle includes configuring the vehicle for non-aggressive driving performance.

An aspect provided herein includes a system for transportation, comprising: a system for optimizing at least one of a vehicle parameter and a user experience parameter to provide a margin of safety.

An aspect provided herein includes a transportation system for optimizing a margin of safety when mimicking human operation of a vehicle, the transportation system comprising: a set of robotic process automation systems comprising: an operator data collection module to capture human operator interactions with a vehicle control system interface; a vehicle data collection module to capture vehicle response and operating conditions associated at least contemporaneously with the human operator interaction; an environment data collection module to capture instances of environmental information associated at least contemporaneously with the human operator interactions; and an artificial intelligence system to learn to control the vehicle with an optimized margin of safety while mimicking the human operator, wherein the artificial intelligence system is responsive to the robotic process automation system, wherein the artificial intelligence system is to detect data indicative of at least one of a plurality of the instances of environmental information associated with the contemporaneously captured vehicle response and operating conditions, wherein the optimized margin of safety is to be achieved by training the artificial intelligence system to control the vehicle based on a set of human operator interaction data collected from interactions of a set of expert human vehicle operators with the vehicle control system interface.

In embodiments, the operator data collection module captures patterns of data including braking patterns, follow-behind distance, approach to curve acceleration patterns, lane preferences, or passing preferences. In embodiments, vehicle data collection module captures data from a plurality of vehicle data systems that provide data streams indicating states and changes in state in steering, braking, acceleration, forward looking images, or rear-looking images. In embodiments, the artificial intelligence system includes a neural network for training the artificial intelligence system.

An aspect provided herein includes a method of robotic process automation for achieving an optimized margin of vehicle operational safety, comprising: tracking expert vehicle control human interactions with a vehicle control-facilitating interface; recording the tracked expert vehicle control human interactions in a robotic process automation system training data structure; tracking vehicle operational state information of a vehicle; recording vehicle operational state information in the robotic process automation system training data structure; training, via at least one neural network, the vehicle to operate with an optimized margin of vehicle operational safety in a manner consistent with the expert vehicle control human interactions based on the expert vehicle control human interactions and the vehicle operational state information in the robotic process automation system training data structure; and controlling at least one aspect of the vehicle with the trained artificial intelligence system.

In embodiments, the method further comprises applying deep learning to optimize the margin of vehicle operational safety by controlling the at least one aspect of the vehicle through structured variation in the controlling the at least one aspect of the vehicle to mimic the expert vehicle control human interactions and processing feedback from the controlling the at least one aspect of the vehicle with machine learning. In embodiments, the controlling at least one aspect of the vehicle is performed via the vehicle control-facilitating interface. In embodiments, the controlling at least one aspect of the vehicle is performed by the artificial intelligence system emulating the control-facilitating interface being operated by the expert vehicle control human.

In embodiments, the vehicle control-facilitating interface comprises at least one of an audio capture system to capture audible expressions of the expert vehicle control human, a human-machine interface, mechanical interface, an optical interface and a sensor-based interface. In embodiments, the tracking vehicle operational state information comprises tracking at least one of vehicle systems and vehicle operational processes affected by the expert vehicle control human interactions. In embodiments, the tracking vehicle operational state information comprises tracking at least one vehicle system element, wherein the at least one vehicle system element is controlled via the vehicle control-facilitating interface and wherein the at least one vehicle system element is affected by the expert vehicle control human interactions.

In embodiments, the tracking vehicle operational state information comprises tracking the vehicle operational state information before, during, and after the expert vehicle control human interaction. In embodiments, the tracking vehicle operational state information comprises tracking at least one of a plurality of vehicle control system outputs that result from the expert vehicle control human interactions and vehicle operational results achieved responsive to the expert vehicle control human interactions. In embodiments, the vehicle is to be controlled to achieve results that are consistent with results achieved via the expert vehicle control human interactions.

In embodiments, the method further comprises tracking and recording conditions proximal to the vehicle with a plurality of vehicle mounted sensors, wherein the training of the artificial intelligence system is further responsive to the conditions proximal to the vehicle tracked contemporaneously to the expert vehicle control human interactions. In embodiments, the training is further responsive to a plurality of data feeds from remote sensors, the plurality of data feeds comprising data collected by the remote sensors contemporaneous to the expert vehicle control human interactions.

An aspect provided herein includes a method for mimicking human operation of a vehicle by robotic process automation of, comprising: capturing human operator interactions with a vehicle control system interface operatively connected to a vehicle; capturing vehicle response and operating conditions associated at least contemporaneously with the human operator interaction; capturing environmental information associated at least contemporaneously with the human operator interaction; and training an artificial intelligence system to control the vehicle with an optimized margin of safety while mimicking the human operator, the artificial intelligence system taking input from the environment data collection module about the instances of environmental information associated with the contemporaneously collected vehicle response and operating conditions, wherein the optimized margin of safety is achieved by training the artificial intelligence system to control the vehicle based on a set of human operator interaction data collected from interactions of an expert human vehicle operator and a set of outcome data from a set of vehicle safety events.

In embodiments, the method further comprises: applying deep learning of the artificial intelligence system to optimize a margin of vehicle operating safety by affecting a controlling of at least one aspect of the vehicle through structured variation in control of the at least one aspect of the vehicle to mimic the expert vehicle control human interactions and processing feedback from the controlling of the at least one aspect of the vehicle with machine learning. In embodiments, the artificial intelligence system employs a workflow that involves decision-making and the robotic process automation system facilitates automation of the decision-making. In embodiments, the artificial intelligence system employs a workflow that involves remote control of the vehicle and the robotic process automation system facilitates automation of remotely controlling the vehicle.

An aspect provided herein includes a system for transportation, comprising: an interface to configure a set of expert systems to provide respective outputs for managing a set of parameters selected from the group consisting of a set of vehicle parameters, a set of fleet parameters, a set of user experience parameters, and combinations thereof.

An aspect provided herein includes a system for configuration management of components of a transportation system comprising: an interface comprising: a first portion of the interface for configuring a first expert computing system for managing a set of vehicle parameters; a second portion of the interface for configuring a second expert computing system for managing a set of vehicle fleet parameters; and a third portion of the interface for configuring a third expert computing system for managing a set of user experience parameters. In embodiments, the interface is a graphical user interface through which a set of visual elements presented in the graphical user interface, when manipulated in the interface causes at least one of selection and configuration of one or more of the first, second, and third expert systems. In embodiments, the interface is an application programming interface. In embodiments, the interface is an interface to a cloud-based computing platform through which one or more transportation-centric services, programs and modules are configured.

An aspect provided herein includes a transportation system comprising: an interface for configuring a set of expert systems to provide outputs based on which the transportation system manages transportation-related parameters, wherein the parameters facilitate operation of at least one of a set of vehicles, a fleet of vehicles, and a transportation system user experience; and a plurality of visual elements representing a set of attributes and parameters of the set of expert systems that are configurable by the interface and a plurality of the transportation systems, wherein the interface is configured to facilitate manipulating the visual elements thereby causing configuration of the set of expert systems. In embodiments, the plurality of the transportation systems comprise a set of vehicles.

In embodiments, the plurality of the transportation systems comprise a set of infrastructure elements supporting a set of vehicles. In embodiments, the set of infrastructure elements comprises vehicle fueling elements. In embodiments, the set of infrastructure elements comprises vehicle charging elements. In embodiments, the set of infrastructure elements comprises traffic control lights. In embodiments, the set of infrastructure elements comprises a toll booth. In embodiments, the set of infrastructure elements comprises a rail system. In embodiments, the set of infrastructure elements comprises automated parking facilities. In embodiments, the set of infrastructure elements comprises vehicle monitoring sensors. In embodiments, the visual elements display a plurality of models that can be selected for use in the set of expert systems. In embodiments, the visual elements display a plurality of neural network categories that can be selected for use in the set of expert systems.

In embodiments, at least one of the plurality of neural network categories includes a convolutional neural network. In embodiments, the visual elements include one or more indicators of suitability of items represented by the plurality of visual elements for a given purpose. In embodiments, configuring a plurality of expert systems comprises facilitating selection sources of inputs for use by at least a portion of the plurality of expert systems. In embodiments, the interface facilitates selection, for at least a portion of the plurality of expert systems, one or more output types, targets, durations, and purposes.

In embodiments, the interface facilitates selection, for at least a portion of the plurality of expert systems, of one or more weights within a model or an artificial intelligence system. In embodiments, the interface facilitates selection, for at least a portion of the plurality of expert systems, of one or more sets of nodes or interconnections within a model. In embodiments, the interface facilitates selection, for at least a portion of the plurality of expert systems, of a graph structure. In embodiments, the interface facilitates selection, for at least a portion of the plurality of expert systems, of a neural network. In embodiments, the interface facilitates selection, for at least a portion of the plurality of expert systems, of one or more time periods of input, output, or operation.

In embodiments, the interface facilitates selection, for at least a portion of the plurality of expert systems, of one or more frequencies of operation. In embodiments, the interface facilitates selection, for at least a portion of the plurality of expert systems, of frequencies of calculation. In embodiments, the interface facilitates selection, for at least a portion of the plurality of expert systems, of one or more rules for applying to the plurality of parameters. In embodiments, the interface facilitates selection, for at least a portion of the plurality of expert systems, of one or more rules for operating upon any of the inputs or upon the provided outputs.

In embodiments, the plurality of parameters comprise one or more infrastructure parameters selected from the group consisting of storage parameters, network utilization parameters, processing parameters, and processing platform parameters.

In embodiments, the interface facilitates selecting a class of an artificial intelligence computing system, a source of inputs to the selected artificial intelligence computing system, a computing capacity of the selected artificial intelligence computing system, a processor for executing the artificial intelligence computing system, and an outcome objective of executing the artificial intelligence computing system. In embodiments, the interface facilitates selecting one or more operational modes of at least one of the vehicles in the transportation system. In embodiments, the interface facilitates selecting a degree of specificity for outputs produced by at least one of the plurality of expert systems.

An aspect provided herein includes a system for transportation, comprising: an expert system to configure a recommendation for a vehicle configuration, wherein the recommendation includes at least one parameter of configuration for the expert system that controls a parameter selected from the group consisting of a vehicle parameter, a user experience parameter, and combinations thereof.

An aspect provided herein includes a recommendation system for recommending a configuration of a vehicle, the recommendation system comprising an expert system that produces a recommendation of a parameter for configuring a vehicle control system that controls at least one of a vehicle parameter and a vehicle rider experience parameter. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the expert system is a neural network system.

In embodiments, the expert system is a deep learning system. In embodiments, the expert system is a machine learning system. In embodiments, the expert system is a model-based system. In embodiments, the expert system is a rule-based system. In embodiments, the expert system is a random walk-based system. In embodiments, the expert system is a genetic algorithm system. In embodiments, the expert system is a convolutional neural network system. In embodiments, the expert system is a self-organizing system. In embodiments, the expert system is a pattern recognition system. In embodiments, the expert system is a hybrid artificial intelligence-based system. In embodiments, the expert system is an acrylic graph-based system.

In embodiments, the expert system produces a recommendation based on degrees of satisfaction of a plurality of riders of vehicles in the transportation system. In embodiments, the expert system produces a recommendation based on a rider entertainment degree of satisfaction. In embodiments, the expert system produces a recommendation based on a rider safety degree of satisfaction. In embodiments, the expert system produces a recommendation based on a rider comfort degree of satisfaction. In embodiments, the expert system produces a recommendation based on a rider in-vehicle search degree of satisfaction. In embodiments, the at least one rider experience parameter is a parameter of traffic congestion.

In embodiments, the at least one rider experience parameter is a parameter of desired arrival times. In embodiments, the at least one rider experience parameter is a parameter of preferred routes. In embodiments, the at least one rider experience parameter is a parameter of fuel efficiency. In embodiments, the at least one rider experience parameter is a parameter of pollution reduction. In embodiments, the at least one rider experience parameter is a parameter of accident avoidance. In embodiments, the at least one rider experience parameter is a parameter of avoiding bad weather. In embodiments, the at least one rider experience parameter is a parameter of avoiding bad road conditions. In embodiments, the at least one rider experience parameter is a parameter of reduced fuel consumption. In embodiments, the at least one rider experience parameter is a parameter of reduced carbon footprint. In embodiments, the at least one rider experience parameter is a parameter of reduced noise in a region. In embodiments, the at least one rider experience parameter is a parameter of avoiding high-crime regions.

In embodiments, the at least one rider experience parameter is a parameter of collective satisfaction. In embodiments, the at least one rider experience parameter is a parameter of maximum speed limit. In embodiments, the at least one rider experience parameter is a parameter of avoidance of toll roads. In embodiments, the at least one rider experience parameter is a parameter of avoidance of city roads. In embodiments, the at least one rider experience parameter is a parameter of avoidance of undivided highways. In embodiments, the at least one rider experience parameter is a parameter of avoidance of left turns. In embodiments, the at least one rider experience parameter is a parameter of avoidance of driver-operated vehicles. In embodiments, the at least one vehicle parameter is a parameter of fuel consumption. In embodiments, the at least one vehicle parameter is a parameter of carbon footprint. In embodiments, the at least one vehicle parameter is a parameter of vehicle speed.

In embodiments, the at least one vehicle parameter is a parameter of vehicle acceleration. In embodiments, the at least one vehicle parameter is a parameter of travel time. In embodiments, the expert system produces a recommendation based on at least one of user behavior of the rider and rider interactions with content access interfaces of the vehicle. In embodiments, the expert system produces a recommendation based on similarity of a profile of the rider to profiles of other riders. In embodiments, the expert system produces a recommendation based on a result of collaborative filtering determined through querying the rider and taking input that facilitates classifying rider responses thereto on a scale of response classes ranging from favorable to unfavorable. In embodiments, the expert system produces a recommendation based on content relevant to the rider including at least one selected from the group consisting of classification of trip, time of day, classification of road, trip duration, configured route, and number of riders.

An aspect provided herein includes a system for transportation, comprising: a search system to provide network search results for in-vehicle searchers.

An aspect provided herein includes an in-vehicle network search system of a vehicle, the search system comprising: a rider interface through which the rider of the vehicle is enabled to engage with the search system; a search result generating circuit that favors search results based on a set of in-vehicle search criteria that are derived from a plurality of in-vehicle searches previously conducted; and a search result display ranking circuit that orders the favored search results based on a relevance of a location component of the search results with a configured route of the vehicle. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the rider interface comprises at least one of a touch screen, a virtual assistant, an entertainment system interface, a communication interface and a navigation interface. In embodiments, the favored search results are ordered by the search result display ranking circuit so that results that are proximal to the configured route appear before other results. In embodiments, the in-vehicle search criteria are based on ranking parameters of a set of in-vehicle searches. In embodiments, the ranking parameters are observed in connection only with the set of in-vehicle searches. In embodiments, the search system adapts the search result generating circuit to favor search results that correlate to in-vehicle behaviors.

In embodiments, the search results that correlate to in-vehicle behaviors are determined through comparison of rider behavior before and after conducting a search.

In embodiments, the search system further comprises a machine learning circuit that facilitates training the search result generating circuit from a set of search results for a plurality of searchers and a set of search result generating parameters based on an in-vehicle rider behavior model.

An aspect provided herein includes an in-vehicle network search system of a vehicle, the search system comprising: a rider interface through which the rider of the vehicle is enabled to engage with the search system; a search result generating circuit that varies search results based on detection of whether the vehicle is in self-driving or autonomous mode or being driven by an active driver; and a search result display ranking circuit that orders the search results based on a relevance of a location component of the search results with a configured route of the vehicle. In embodiments, the search results vary based on whether the user is a driver of the vehicle or a passenger in the vehicle. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the rider interface comprises at least one of a touch screen, a virtual assistant, an entertainment system interface, a communication interface and a navigation interface. In embodiments, the search results are ordered by the search result display ranking circuit so that results that are proximal to the configured route appear before other results. In embodiments, search criteria used by the search result generating circuit are based on ranking parameters of a set of in-vehicle searches.

In embodiments, the ranking parameters are observed in connection only with the set of in-vehicle searches. In embodiments, the search system adapts the search result generating circuit to favor search results that correlate to in-vehicle behaviors. In embodiments, the search results that correlate to in-vehicle behaviors are determined through comparison of rider behavior before and after conducting a search. In embodiments, the search system further comprises a machine learning circuit that facilitates training the search result generating circuit from a set of search results for a plurality of searchers and a set of search result generating parameters based on an in-vehicle rider behavior model.

An aspect provided herein includes an in-vehicle network search system of a vehicle, the search system comprising: a rider interface through which the rider of the vehicle is enabled to engage with the search system; a search result generating circuit that varies search results based on whether the user is a driver of the vehicle or a passenger in the vehicle; and a search result display ranking circuit that orders the search results based on a relevance of a location component of the search results with a configured route of the vehicle. In embodiments, the vehicle comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the rider interface comprises at least one of a touch screen, a virtual assistant, an entertainment system interface, a communication interface and a navigation interface.

In embodiments, the search results are ordered by the search result display ranking circuit so that results that are proximal to the configured route appear before other results. In embodiments, search criteria used by the search result generating circuit are based on ranking parameters of a set of in-vehicle searches. In embodiments, the ranking parameters are observed in connection only with the set of in-vehicle searches. In embodiments, the search system adapts the search result generating circuit to favor search results that correlate to in-vehicle behaviors.

In embodiments, the search results that correlate to in-vehicle behaviors are determined through comparison of rider behavior before and after conducting a search. In embodiments, the search system, further comprises a machine learning circuit that facilitates training the search result generating circuit from a set of search results for a plurality of searchers and a set of search result generating parameters based on an in-vehicle rider behavior model.

It is to be understood that any combination of features from the methods disclosed herein and/or from the systems disclosed herein may be used together, and/or that any features from any or all of these aspects may be combined with any of the features of the embodiments and/or examples disclosed herein to achieve the benefits as described in this disclosure.

BRIEF DESCRIPTION OF THE FIGURES

In the accompanying figures, like reference numerals refer to identical or functionally similar elements throughout the separate views and together with the detailed description below are incorporated in and form part of the specification, serve to further illustrate various embodiments and to explain various principles and advantages all in accordance with the systems and methods disclosed herein.

Figure 1:
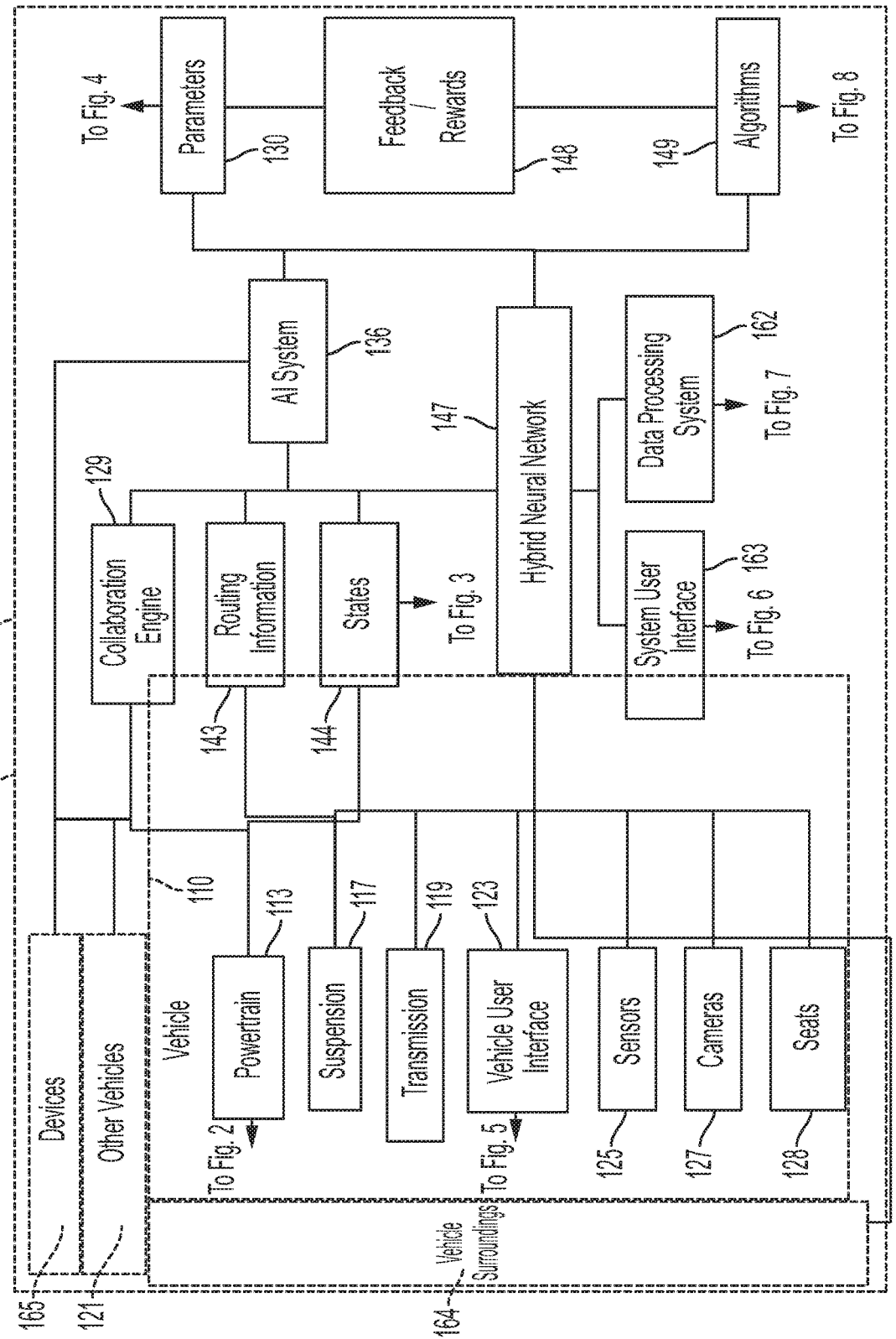
FIG. 1 is a diagrammatic view that illustrates an architecture for a transportation system showing certain illustrative components and arrangements relating to various embodiments of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of the many embodiments of the systems and methods disclosed herein.

DETAILED DESCRIPTION

The present disclosure will now be described in detail by describing various illustrative, non-limiting embodiments thereof with reference to the accompanying drawings and exhibits. The disclosure may, however, be embodied in many different forms and should not be construed as being limited to the illustrative embodiments set forth herein. Rather, the embodiments are provided so that this disclosure will be thorough and will fully convey the concept of the disclosure to those skilled in the art. The claims should be consulted to ascertain the true scope of the disclosure.

Before describing in detail embodiments that are in accordance with the systems and methods disclosed herein, it should be observed that the embodiments reside primarily in combinations of method and/or system components. Accordingly, the system components and methods have been represented where appropriate by conventional symbols in the drawings, showing only those specific details that are pertinent to understanding the embodiments of the systems and methods disclosed herein.

All documents mentioned herein are hereby incorporated by reference in their entirety. References to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth, except where the context clearly indicates otherwise.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one skilled in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the embodiments.

In the following description, it is understood that terms such as "first," "second," "third," "above," "below," and the like, are words of convenience and are not to be construed as implying a chronological order or otherwise limiting any corresponding element unless expressly stated otherwise. The term "set" should be understood to encompass a set with a single member or a plurality of members.

Referring to FIG. 1, an architecture for a transportation system 111 is depicted, showing certain illustrative components and arrangements relating to certain embodiments described herein. The transportation system 111 may include one or more vehicles 110, which may include various mechanical, electrical, and software components and systems, such as a powertrain 113, a suspension system 117, a steering system, a braking system, a fuel system, a charging system, seats 128, a combustion engine, an electric vehicle drive train, a transmission 119, a gear set, and the like. The vehicle may have a vehicle user interface 123, which may include a set of interfaces that include a steering system, buttons, levers, touch screen interfaces, audio interfaces, and the like as described throughout this disclosure. The vehicle may have a set of sensors 125 (including cameras 127), such as for providing input to expert system/artificial intelligence features described throughout this disclosure, such as one or more neural networks (which may include hybrid neural networks 147 as described herein). Sensors 125 and/or external information may be used to inform the expert system/Artificial Intelligence (AI) system 136 and to indicate or track one or more vehicle states 144, such as vehicle operating states 345 (FIG. 3), user experience states 346 (FIG. 3), and others described herein, which also may be as inputs to or taken as outputs from a set of expert system/AI components. Routing information 143 may inform and take input from the expert system/AI system 136, including using in-vehicle navigation capabilities and external navigation capabilities, such as Global Position System (GPS), routing by triangulation (such as cell towers), peer-to-peer routing with other vehicles 121, and the like. A collaboration engine 129 may facilitate collaboration among vehicles and/or among users of vehicles, such as for managing collective experiences, managing fleets and the like. Vehicles 110 may be networked among each other in a peer-to-peer manner, such as using cognitive radio, cellular, wireless or other networking features. An AI system 136 or other expert systems may take as input a wide range of vehicle parameters 130, such as from on board diagnostic systems, telemetry systems, and other software systems, as well as from vehicle-located sensors 125 and from external systems. In embodiments, the system may manage a set of feedback/rewards 148, incentives, or the like, such as to induce certain user behavior and/or to provide feedback to the AI system 136, such as for learning on a set of outcomes to accomplish a given task or objective. The expert system or AI system 136 may inform, use, manage, or take output from a set of algorithms 149, including a wide variety as described herein. In the example of the present disclosure depicted in FIG. 1, a data processing system 162, is connected to the hybrid neural network 147. The data processing system 162 may process data from various sources (see FIG. 7). In the example of the present disclosure depicted in FIG. 1, a system user interface 163, is connected to the hybrid neural network 147. See the disclosure, below, relating to FIG. 6 for further disclosure relating to interfaces. FIG. 1 shows that vehicle surroundings 164 may be part of the transportation system 111. Vehicle surroundings may include roadways, weather conditions, lighting conditions, etc. FIG. 1 shows that devices 165, for example, mobile phones and computer systems, navigation systems, etc., may be connected to various elements of the transportation system 111, and therefore may be part of the transportation system 111 of the present disclosure.

Figure 2:
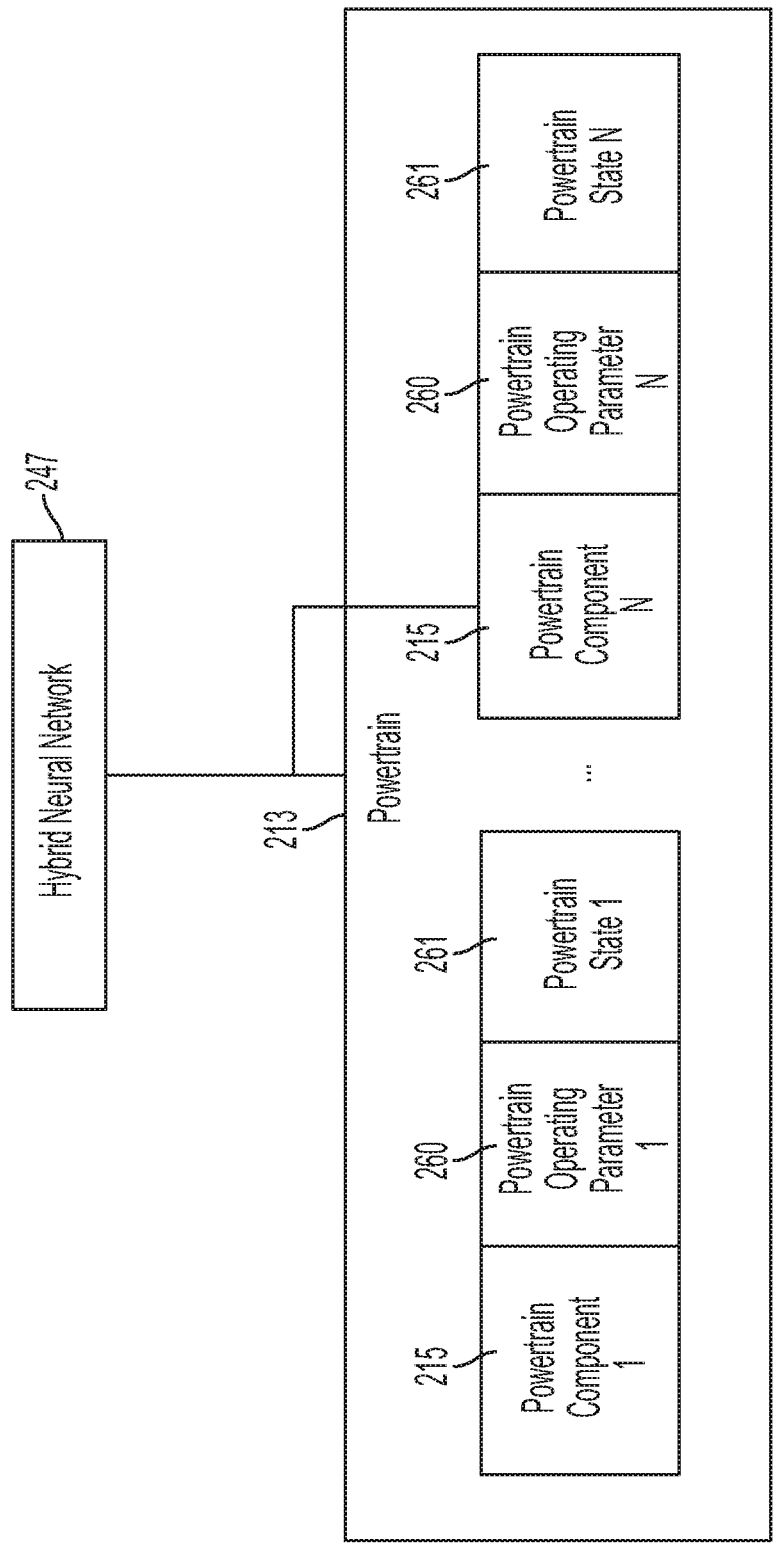
FIG. 2 is a diagrammatic view that illustrates use of a hybrid neural network to optimize a powertrain component of a vehicle relating to various embodiments of the present disclosure.

Referring to FIG. 2, provided herein are transportation systems having a hybrid neural network 247 for optimizing a powertrain 213 of a vehicle, wherein at least two parts of the hybrid neural network 247 optimize distinct parts of the powertrain 213. An artificial intelligence system may control a powertrain component 215 based on an operational model (such as a physics model, an electrodynamic model, a hydrodynamic model, a chemical model, or the like for energy conversion, as well as a mechanical model for operation of various dynamically interacting system components). For example, the AI system may control a powertrain component 215 by manipulating a powertrain operating parameter 260 to achieve a powertrain state 261. The AI system may be trained to operate a powertrain component 215, such as by training on a data set of outcomes (e.g., fuel efficiency, safety, rider satisfaction, or the like) and/or by training on a data set of operator actions (e.g., driver actions sensed by a sensor set, camera or the like or by a vehicle information system). In embodiments, a hybrid approach may be used, where one neural network optimizes one part of a powertrain (e.g., for gear shifting operations), while another neural network optimizes another part (e.g., braking, clutch engagement, or energy discharge and recharging, among others). Any of the powertrain components described throughout this disclosure may be controlled by a set of control instructions that consist of output from at least one component of a hybrid neural network 247.

Figure 3:
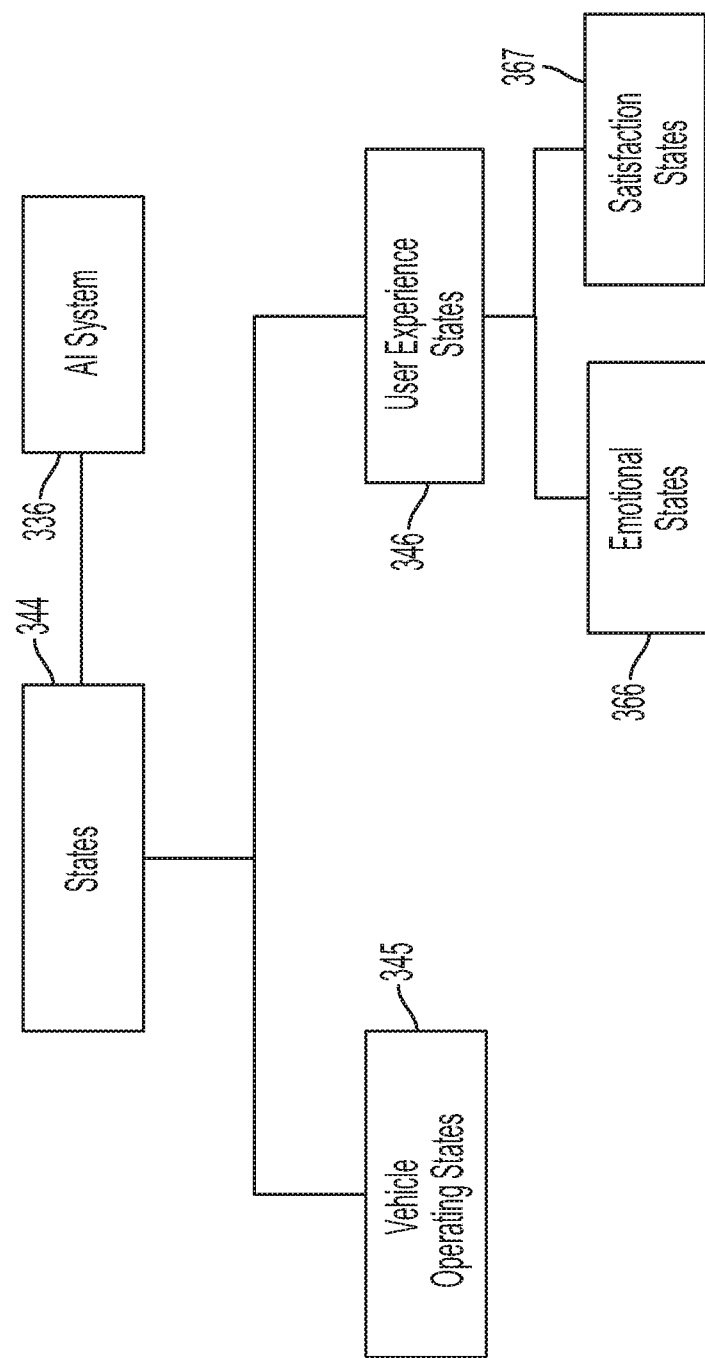
FIG. 3 is a diagrammatic view that illustrates a set of states that may be provided as inputs to and/or be governed by an expert system/Artificial Intelligence (AI) system relating to various embodiments of the present disclosure.

FIG. 3 illustrates a set of states that may be provided as inputs to and/or be governed by an expert system/AI system 336, as well as used in connection with various systems and components in various embodiments described herein. States 344 may include vehicle operating states 345, including vehicle configuration states, component states, diagnostic states, performance states, location states, maintenance states, and many others, as well as user experience states 346, such as experience-specific states, emotional states 366 for users, satisfaction states 367, location states, content/entertainment states and many others.

Figure 4:
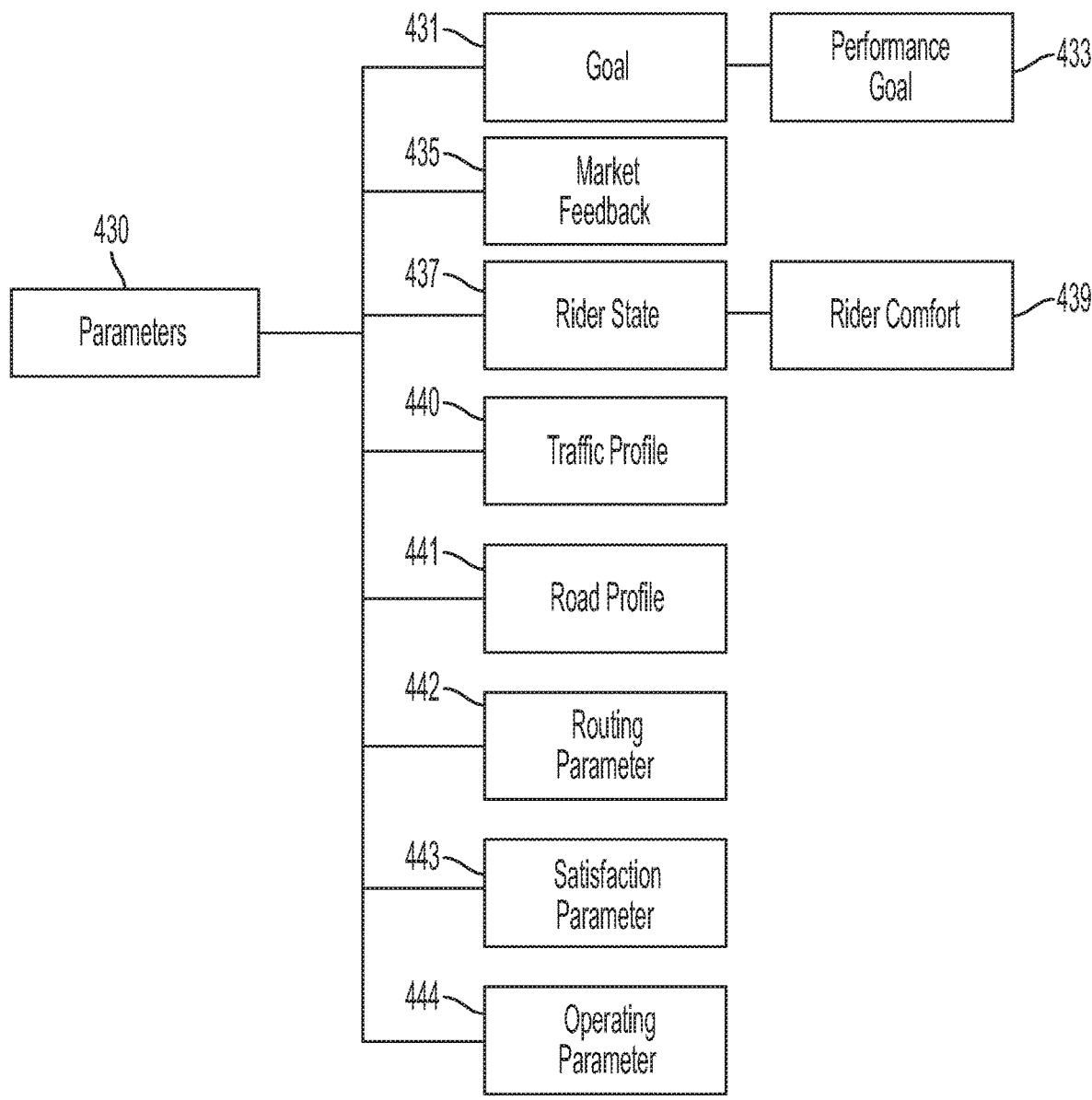
FIG. 4 is a diagrammatic view that illustrates a range of parameters that may be taken as inputs by an expert system or AI system, or component thereof, as described throughout this disclosure, or that may be provided as outputs from such a system and/or one or more sensors, cameras, or external systems relating to various embodiments of the present disclosure.

FIG. 4 illustrates a range of parameters 430 that may be taken as inputs by an expert system or AI system 136 (FIG. 1), or component thereof, as described throughout this disclosure, or that may be provided as outputs from such a system and/or one or more sensors 125 (FIG. 1), cameras 127 (FIG. 1), or external systems. Parameters 430 may include one or more goals 431 or objectives (such as ones that are to be optimized by an expert system/AI system, such as by iteration and/or machine learning), such as a performance goal 433, such as relating to fuel efficiency, trip time, satisfaction, financial efficiency, safety, or the like. Parameters 430 may include market feedback parameters 435, such as relating to pricing, availability, location, or the like of goods, services, fuel, electricity, advertising, content, or the like. Parameters 430 may include rider state parameters 437, such as parameters relating to comfort 439, emotional state, satisfaction, goals, type of trip, fatigue and the like. Parameters 430 may include parameters of various transportation-relevant profiles, such as traffic profiles 440 (location, direction, density and patterns in time, among many others), road profiles 441 (elevation, curvature, direction, road surface conditions and many others), user profiles, and many others. Parameters 430 may include routing parameters 442, such as current vehicle locations, destinations, waypoints, points of interest, type of trip, goal for trip, required arrival time, desired user experience, and many others. Parameters 430 may include satisfaction parameters 443, such as for riders (including drivers), fleet managers, advertisers, merchants, owners, operators, insurers, regulators and others. Parameters 430 may include operating parameters 444, including the wide variety described throughout this disclosure.

Figure 5:
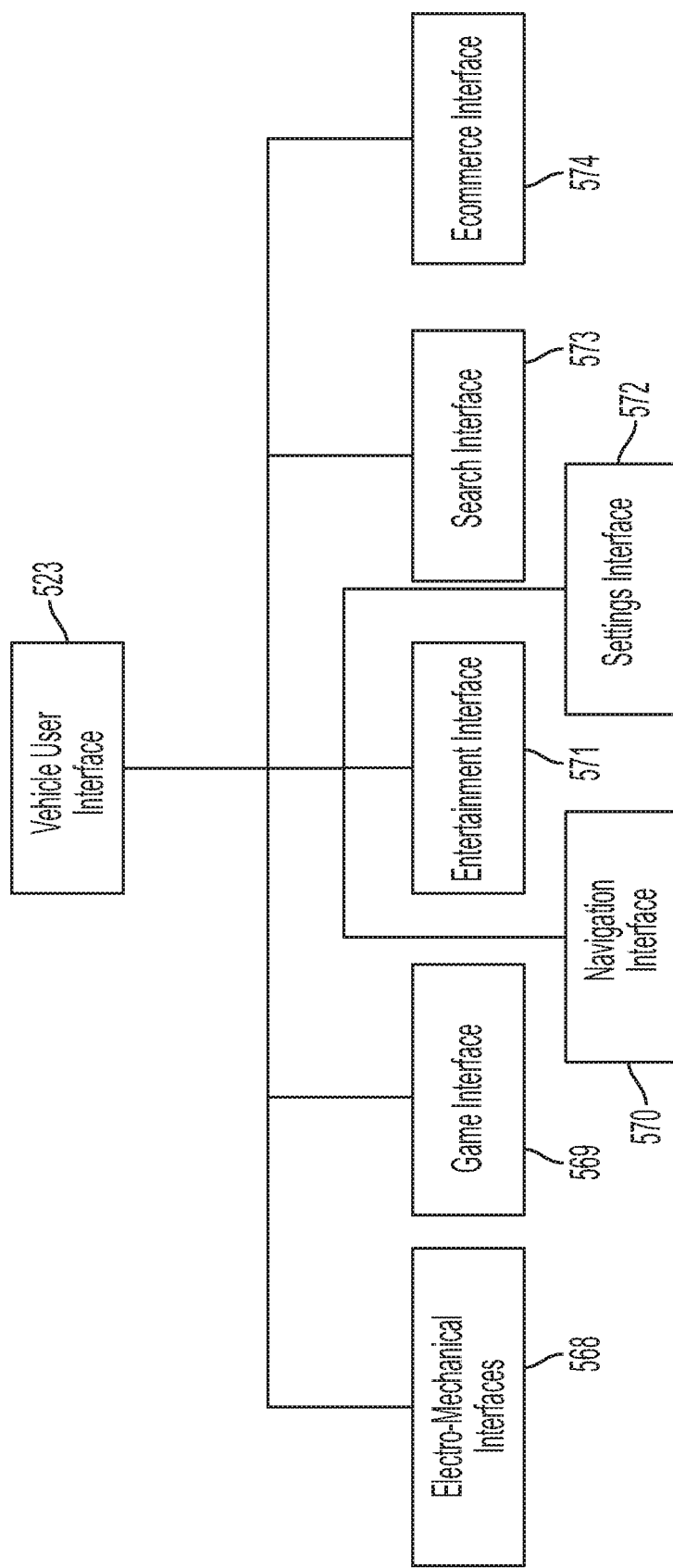
FIG. 5 is a diagrammatic view that illustrates a set of vehicle user interfaces relating to various embodiments of the present disclosure.

FIG. 5 illustrates a set of vehicle user interfaces 523. Vehicle user interfaces 523 may include electromechanical interfaces 568, such as steering interfaces, braking interfaces, interfaces for seats, windows, moonroof, glove box and the like. Interfaces 523 may include various software interfaces (which may have touch screen, dials, knobs, buttons, icons or other features), such as a game interface 569, a navigation interface 570, an entertainment interface 571, a vehicle settings interface 572, a search interface 573, an ecommerce interface 574, and many others. Vehicle interfaces may be used to provide inputs to, and may be governed by, one or more AI systems/expert systems such as described in embodiments throughout this disclosure.

Figure 6:
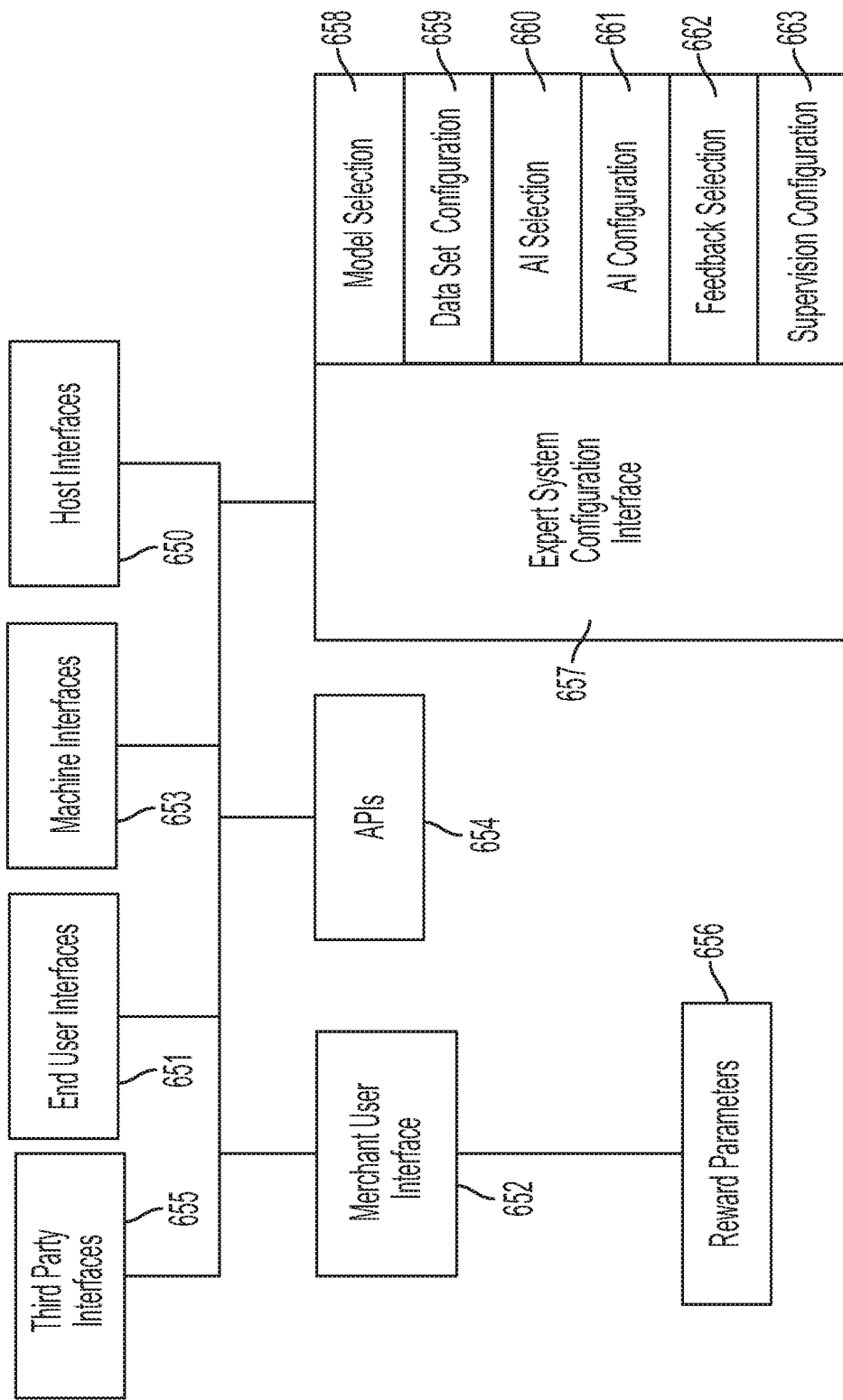
FIG. 6 is a diagrammatic view that illustrates a set of interfaces among transportation system components relating to various embodiments of the present disclosure.

FIG. 6 illustrates a set of interfaces among transportation system components, including interfaces within a host system (such as governing a vehicle or fleet of vehicles) and host interfaces 650 between a host system and one or more third parties and/or external systems. Interfaces include third party interfaces 655 and end user interfaces 651 for users of the host system, including the in-vehicle interfaces that may be used by riders as noted in connection with FIG. 5, as well as user interfaces for others, such as fleet managers, insurers, regulators, police, advertisers, merchants, content providers, and many others. Interfaces may include merchant interfaces 652, such as by which merchants may provide advertisements, content relating to offerings, and one or more rewards, such as to induce routing or other behavior on the part of users. Interfaces may include machine interfaces 653, such as application programming interfaces (API) 654, networking interfaces, peer-to-peer interfaces, connectors, brokers, extract-transform-load (ETL) system, bridges, gateways, ports and the like. Interfaces may include one or more host interfaces by which a host may manage and/or configure one or more of the many embodiments described herein, such as configuring neural network components, setting weight for models, setting one or more goals or objectives, setting reward parameters 656, and many others. Interfaces may include expert system/AI system configuration interfaces 657, such as for selecting one or more models 658, selecting and configuring data sets 659 (such as sensor data, external data and other inputs described herein), AI selection 660 and AI configuration 661 (such as selection of neural network category, parameter weighting and the like), feedback selection 662 for an expert system/AI system, such as for learning, and supervision configuration 663, among many others.

Figure 7:
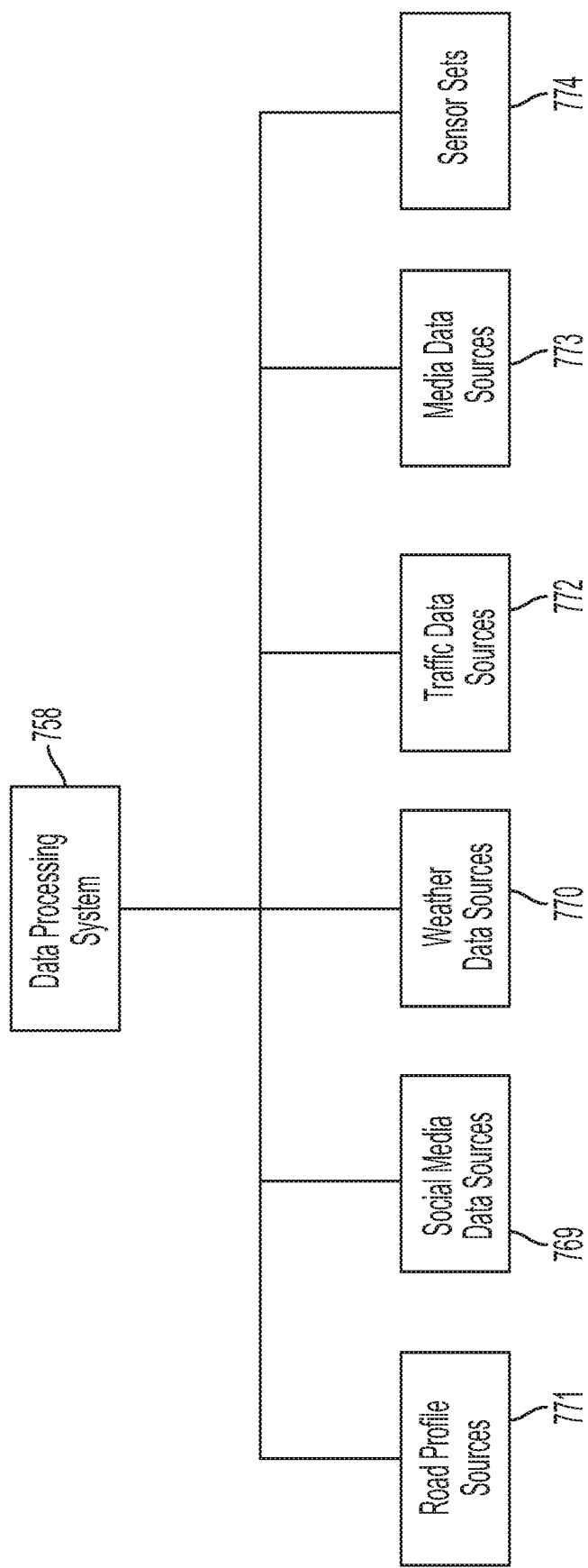
FIG. 7 is a diagrammatic view that illustrates a data processing system, which may process data from various sources relating to various embodiments of the present disclosure.

FIG. 7 illustrates a data processing system 758, which may process data from various sources, including social media data sources 769, weather data sources 770, road profile sources 771, traffic data sources 772, media data sources 773, sensors sets 774, and many others. The data processing system may be configured to extract data, transform data to a suitable format (such as for use by an interface system, an AI system/expert system, or other systems), load it to an appropriate location, normalize data, cleanse data, deduplicate data, store data (such as to enable queries) and perform a wide range of processing tasks as described throughout this disclosure.

Figure 8:
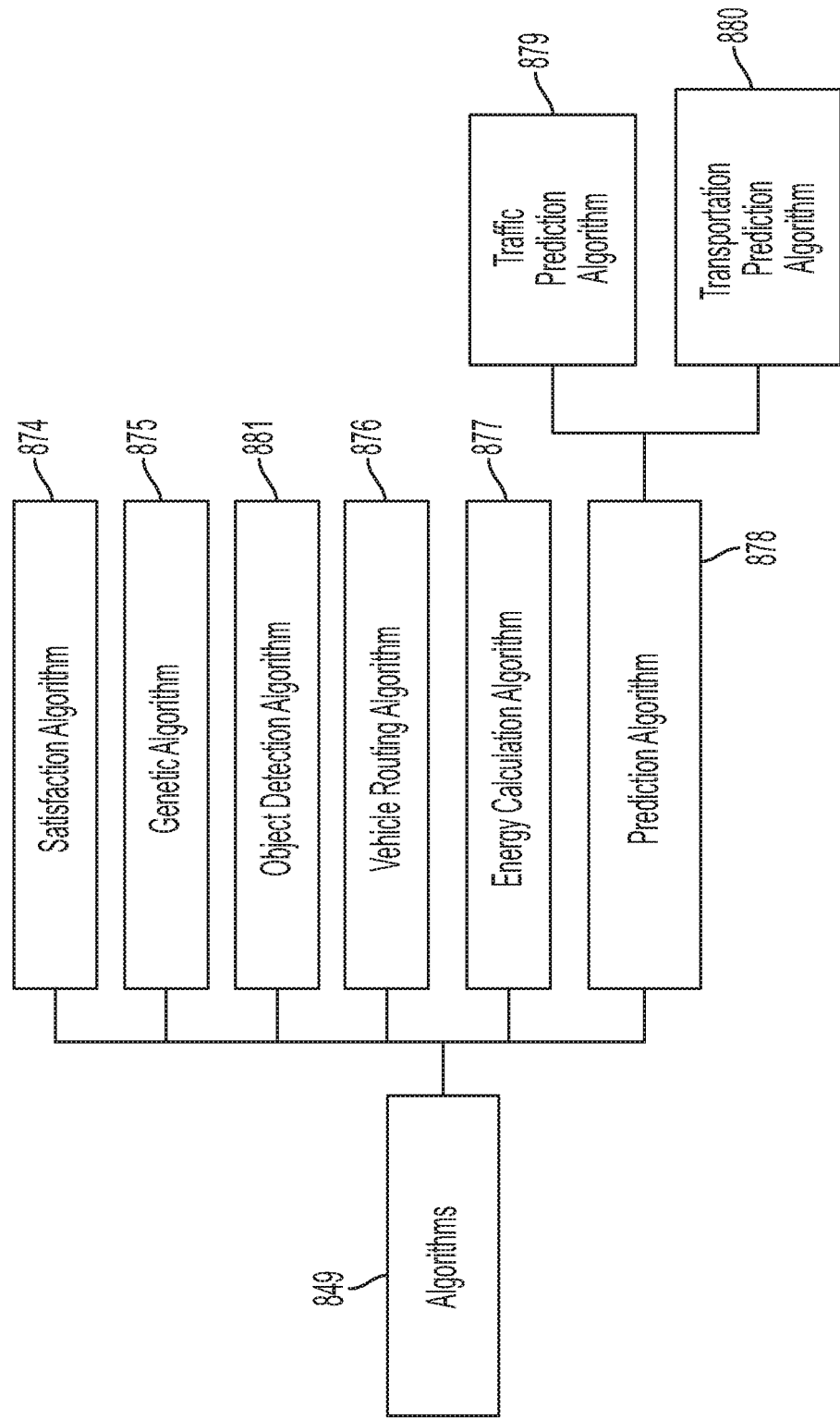
FIG. 8 is a diagrammatic view that illustrates a set of algorithms that may be executed in connection with one or more of the many embodiments of transportation systems described throughout this disclosure relating to various embodiments of the present disclosure.

FIG. 8 illustrates a set of algorithms 849 that may be executed in connection with one or more of the many embodiments of transportation systems described throughout this disclosure. Algorithms 849 may take input from, provide output to, and be managed by a set of AI systems/ expert systems, such as of the many types described herein. Algorithms 849 may include algorithms for providing or managing user satisfaction 874, one or more genetic algorithms 875, such as for seeking favorable states, parameters, or combinations of states/parameters in connection with optimization of one or more of the systems described herein. Algorithms 849 may include vehicle routing algorithms 876, including ones that are sensitive to various vehicle operating parameters, user experience parameters, or other states, parameters, profiles, or the like described herein, as well as to various goals or objectives. Algorithms 849 may include object detection algorithms 876. Algorithms 849 may include energy calculation algorithms 877, such as for calculating energy parameters, for optimizing fuel usage, electricity usage or the like, for optimizing refueling or recharging time, location, amount or the like. Algorithms may include prediction algorithms, such as for a traffic prediction algorithm 879, a transportation prediction algorithm 880, and algorithms for predicting other states or parameters of transportation systems as described throughout this disclosure.

In various embodiments, transportation systems 111 as described herein may include vehicles (including fleets and other sets of vehicles), as well as various infrastructure systems. Infrastructure systems may include Internet of Things systems (such as using cameras and other sensors, such as disposed on or in roadways, on or in traffic lights, utility poles, toll booths, signs and other roadside devices and systems, on or in buildings, and the like), refueling and recharging systems (such as at service stations, charging locations and the like, and including wireless recharging systems that use wireless power transfer), and many others.

Vehicle electrical, mechanical and/or powertrain components as described herein may include a wide range of systems, including transmission, gear system, clutch system, braking system, fuel system, lubrication system, steering system, suspension system, lighting system (including emergency lighting as well as interior and exterior lights), electrical system, and various subsystems and components thereof.

Vehicle operating states and parameters may include route, purpose of trip, geolocation, orientation, vehicle range, powertrain parameters, current gear, speed/acceleration, suspension profile (including various parameters, such as for each wheel), charge state for electric and hybrid vehicles, fuel state for fueled vehicles, and many others as described throughout this disclosure.

Rider and/or user experience states and parameters as described throughout this disclosure may include emotional states, comfort states, psychological states (e.g., anxiety, nervousness, relaxation or the like), awake/asleep states, and/or states related to satisfaction, alertness, health, wellness, one or more goals or objectives, and many others. User experience parameters as described herein may further include ones related to driving, braking, curve approach, seat positioning, window state, ventilation system, climate control, temperature, humidity, sound level, entertainment content type (e.g., news, music, sports, comedy, or the like), route selection (such as for POIs, scenic views, new sites and the like), and many others.

In embodiments, a route may be ascribed various parameters of value, such as parameters of value that may be optimized to improve user experience or other factors, such as under control of an AI system/expert system. Parameters of value of a route may include speed, duration, on time arrival, length (e.g., in miles), goals (e.g., to see a Point of Interest (POI), to complete a task (e.g., complete a shopping list, complete a delivery schedule, complete a meeting, or the like), refueling or recharging parameters, game-based goals, and others. As one of many examples, a route may be attributed value, such as in a model and/or as an input or feedback to an AI system or expert system that is configured to optimize a route, for task completion. A user may, for example, indicate a goal to meet up with at least one of a set of friends during a weekend, such as by interacting with a user interface or menu that allows setting of objectives. A route may be configured (including with inputs that provide awareness of friend locations, such as by interacting with systems that include location information for other vehicles and/or awareness of social relationships, such as through social data feeds) to increase the likelihood of meeting up, such as by intersecting with predicted locations of friends (which may be predicted by a neural network or other AI system/expert system as described throughout this disclosure) and by providing in-vehicle messages (or messages to a mobile device) that indicates possible opportunities for meeting up.

Market feedback factors may be used to optimize various elements of transportation systems as described throughout this disclosure, such as current and predicted pricing and/or cost (e.g., of fuel, electricity and the like, as well as of goods, services, content and the like that may be available along the route and/or in a vehicle), current and predicted capacity, supply and/or demand for one or more transportation related factors (such as fuel, electricity, charging capacity, maintenance, service, replacement parts, new or used vehicles, capacity to provide ride sharing, self-driving vehicle capacity or availability, and the like), and many others.

An interface in or on a vehicle may include a negotiation system, such as a bidding system, a price-negotiating system, a reward-negotiating system, or the like. For example, a user may negotiate for a higher reward in exchange for agreeing to re-route to a merchant location, a user may name a price the user is willing to pay for fuel (which may be provided to nearby refueling stations that may offer to meet the price), or the like. Outputs from negotiation (such as agreed prices, trips and the like) may automatically result in reconfiguration of a route, such as one governed by an AI system/expert system.

Rewards, such as provided by a merchant or a host, among others, as described herein may include one or more coupons, such as redeemable at a location, provision of higher priority (such as in collective routing of multiple vehicles), permission to use a "Fast Lane," priority for charging or refueling capacity, among many others. Actions that can lead to rewards in a vehicle may include playing a game, downloading an app, driving to a location, taking a photograph of a location or object, visiting a website, viewing or listening to an advertisement, watching a video, and many others.

In embodiments an AI system/expert system may use or optimize one or more parameters for a charging plan, such as for charging a battery of an electric or hybrid vehicle. Charging plan parameters may include routing (such as to charging locations), amount of charge or fuel provided, duration of time for charging, battery state, battery charging profile, time required to charge, value of charging, indicators of value, market price, bids for charging, available supply capacity (such as within a geofence or within a range of a set of vehicles), demand (such as based on detected charge/refueling state, based on requested demand, or the like), supply, and others. A neural network or other system (optionally a hybrid system as describe herein), using a model or algorithm (such as a genetic algorithm) may be used (such as by being trained over a set of trials on outcomes, and/or using a training set of human created or human supervised inputs, or the like) may provide a favorable and/or optimized charging plan for a vehicle or a set of vehicles based on the parameters. Other inputs may include priority for certain vehicles (e.g., for emergency responders or for those who have been rewarded priority in connection with various embodiments described herein).

In embodiments a processor, as described herein, may comprise a neural processing chip, such as one employing a fabric, such as a LambdaFabric. Such a chip may have a plurality of cores, such as 256 cores, where each core is configured in a neuron-like arrangement with other cores on the same chip. Each core may comprise a micro-scale digital signal processor, and the fabric may enable the cores to readily connect to the other cores on the chip. In embodiments, the fabric may connect a large number of cores (e.g., more than 500,000 cores) and/or chips, thereby facilitating use in computational environments that require, for example, large scale neural networks, massively parallel computing, and large-scale, complex conditional logic. In embodiments, a low-latency fabric is used, such as one that has latency of 400 nanoseconds, 300 nanoseconds, 200 nanoseconds, 100 nanoseconds, or less from device-to-device, rack-to-rack, or the like. The chip may be a low power chip, such as one that can be powered by energy harvesting from the environment, from an inspection signal, from an onboard antenna, or the like. In embodiments, the cores may be configured to enable application of a set of sparse matrix heterogeneous machine learning algorithms. The chip may run an object-oriented programming language, such as C++, Java, or the like. In embodiments, a chip may be programmed to run each core with a different algorithm, thereby enabling heterogeneity in algorithms, such as to enable one or more of the hybrid neural network embodiments described throughout this disclosure. A chip can thereby take multiple inputs (e.g., one per core) from multiple data sources, undertake massively parallel processing using a large set of distinct algorithms, and provide a plurality of outputs (such as one per core or per set of cores).

In embodiments a chip may contain or enable a security fabric, such as a fabric for performing content inspection, packet inspection (such as against a black list, white list, or the like), and the like, in addition to undertaking processing tasks, such as for a neural network, hybrid AI solution, or the like.

In embodiments, the platform described herein may include, integrate with, or connect with a system for robotic process automation (RPA), whereby an artificial intelligence/machine learning system may be trained on a training set of data that consists of tracking and recording sets of interactions of humans as the humans interact with a set of interfaces, such as graphical user interfaces (e.g., via interactions with mouse, trackpad, keyboard, touch screen, joystick, remote control devices); audio system interfaces (such as by microphones, smart speakers, voice response interfaces, intelligent agent interfaces (e.g., Siri and Alexa) and the like); human-machine interfaces (such as involving robotic systems, prosthetics, cybernetic systems, exoskeleton systems, wearables (including clothing, headgear, headphones, watches, wrist bands, glasses, arm bands, torso bands, belts, rings, necklaces and other accessories); physical or mechanical interfaces (e.g., buttons, dials, toggles, knobs, touch screens, levers, handles, steering systems, wheels, and many others); optical interfaces (including ones triggered by eye tracking, facial recognition, gesture recognition, emotion recognition, and the like); sensor-enabled interfaces (such as ones involving cameras, EEG or other electrical signal sensing (such as for brain-computer interfaces), magnetic sensing, accelerometers, galvanic skin response sensors, optical sensors, IR sensors, LIDAR and other sensor sets that are capable of recognizing thoughts, gestures (facial, hand, posture, or other), utterances, and the like, and others. In addition to tracking and recording human interactions, the RPA system may also track and record a set of states, actions, events and results that occur by, within, from or about the systems and processes with which the humans are engaging. For example, the RPA system may record mouse clicks on a frame of video that appears within a process by which a human review the video, such as where the human highlights points of interest within the video, tags objects in the video, captures parameters (such as sizes, dimensions, or the like), or otherwise operates on the video within a graphical user interface. The RPA system may also record system or process states and events, such as recording what elements were the subject of interaction, what the state of a system was before, during and after interaction, and what outputs were provided by the system or what results were achieved. Through a large training set of observation of human interactions and system states, events, and outcomes, the RPA system may learn to interact with the system in a fashion that mimics that of the human. Learning may be reinforced by training and supervision, such as by having a human correct the RPA system as it attempts in a set of trials to undertake the action that the human would have undertaken (e.g., tagging the right object, labeling an item correctly, selecting the correct button to trigger a next step in a process, or the like), such that over a set of trials the RPA system becomes increasingly effective at replicating the action the human would have taken. Learning may include deep learning, such as by reinforcing learning based on outcomes, such as successful outcomes (such as based on successful process completion, financial yield, and many other outcome measures described throughout this disclosure). In embodiments, an RPA system may be seeded during a learning phase with a set of expert human interactions, such that the RPA system begins to be able to replicate expert interaction with a system. For example, an expert driver's interactions with a robotic system, such as a remote-controlled vehicle or a UAV, may be recorded along with information about the vehicles state (e.g., the surrounding environment, navigation parameters, and purpose), such that the RPA system may learn to drive the vehicle in a way that reflects the same choices as an expert driver. After being taught to replicate the skills or expertise of an expert human, the RPA system may be transitioned to a deep learning mode, where the system further improves based on a set of outcomes, such as by being configured to attempt some level of variation in approach (e.g., trying different navigation paths to optimize time of arrival, or trying different approaches to deceleration and acceleration in curves) and tracking outcomes (with feedback), such that the RPA system can learn, by variation/experimentation (which may be randomized, rule-based, or the like, such as using genetic programming techniques, random-walk techniques, random forest techniques, and others) and selection, to exceed the expertise of the human expert. Thus, the RPA system learns from a human expert, acquires expertise in interacting with a system or process, facilitates automation of the process (such as by taking over some of the more repetitive tasks, including ones that require consistent execution of acquired skills), and provides a very effective seed for artificial intelligence, such as by providing a seed model or system that can be improved by machine learning with feedback on outcomes of a system or process.

RPA systems may have particular value in situations where human expertise or knowledge is acquired with training and experience, as well as in situations where the human brain and sensory systems are particularly adapted and evolved to solve problems that are computationally difficult or highly complex. Thus, in embodiments, RPA systems may be used to learn to undertake, among other things: visual pattern recognition tasks with respect to the various systems, processes, workflows and environments described herein (such as recognizing the meaning of dynamic interactions of objects or entities within a video stream (e.g., to understand what is taking place as humans and objects interact in a video); recognition of the significance of visual patterns (e.g., recognizing objects, structures, defects and conditions in a photograph or radiography image); tagging of relevant objects within a visual pattern (e.g., tagging or labeling objects by type, category, or specific identity (such as person recognition); indication of metrics in a visual pattern (such as dimensions of objects indicated by clicking on dimensions in an x-ray or the like); labeling activities in a visual pattern by category (e.g., what work process is being done); recognizing a pattern that is displayed as a signal (e.g., a wave or similar pattern in a frequency domain, time domain, or other signal processing representation); anticipate a n future state based on a current state (e.g., anticipating motion of a flying or rolling object, anticipating a next action by a human in a process, anticipating a next step by a machine, anticipating a reaction by a person to an event, and many others); recognize and predicting emotional states and reactions (such as based on facial expression, posture, body language or the like); apply a heuristic to achieve a favorable state without deterministic calculation (e.g., selecting a favorable strategy in sport or game, selecting a business strategy, selecting a negotiating strategy, setting a price for a product, developing a message to promote a product or idea, generating creative content, recognizing a favorable style or fashion, and many others); any many others. In embodiments, an RPA system may automate workflows that involve visual inspection of people, systems, and objects (including internal components), workflows that involve performing software tasks, such as involving sequential interactions with a series of screens in a software interface, workflows that involve remote control of robots and other systems and devices, workflows that involve content creation (such as selecting, editing and sequencing content), workflows that involve financial decision-making and negotiation (such as setting prices and other terms and conditions of financial and other transactions), workflows that involve decision-making (such as selecting an optimal configuration for a system or sub-system, selecting an optimal path or sequence of actions in a workflow, process or other activity that involves dynamic decision-making), and many others.

In embodiments, an RPA system may use a set of IoT devices and systems (such as cameras and sensors), to track and record human actions and interactions with respect to various interfaces and systems in an environment. The RPA system may also use data from onboard sensors, telemetry, and event recording systems, such as telemetry systems on vehicles and event logs on computers). The RPA system may thus generate and/or receive a large data set (optionally distributed) for an environment (such as any of the environments described throughout this disclosure) including data recording the various entities (human and non-human), systems, processes, applications (e.g., software applications used to enable workflows), states, events, and outcomes, which can be used to train the RPA system (or a set of RPA systems dedicated to automating various processes and workflows) to accomplish processes and workflows in a way that reflects and mimics accumulated human expertise, and that eventually improves on the results of that human expertise by further machine learning.

Figure 9:
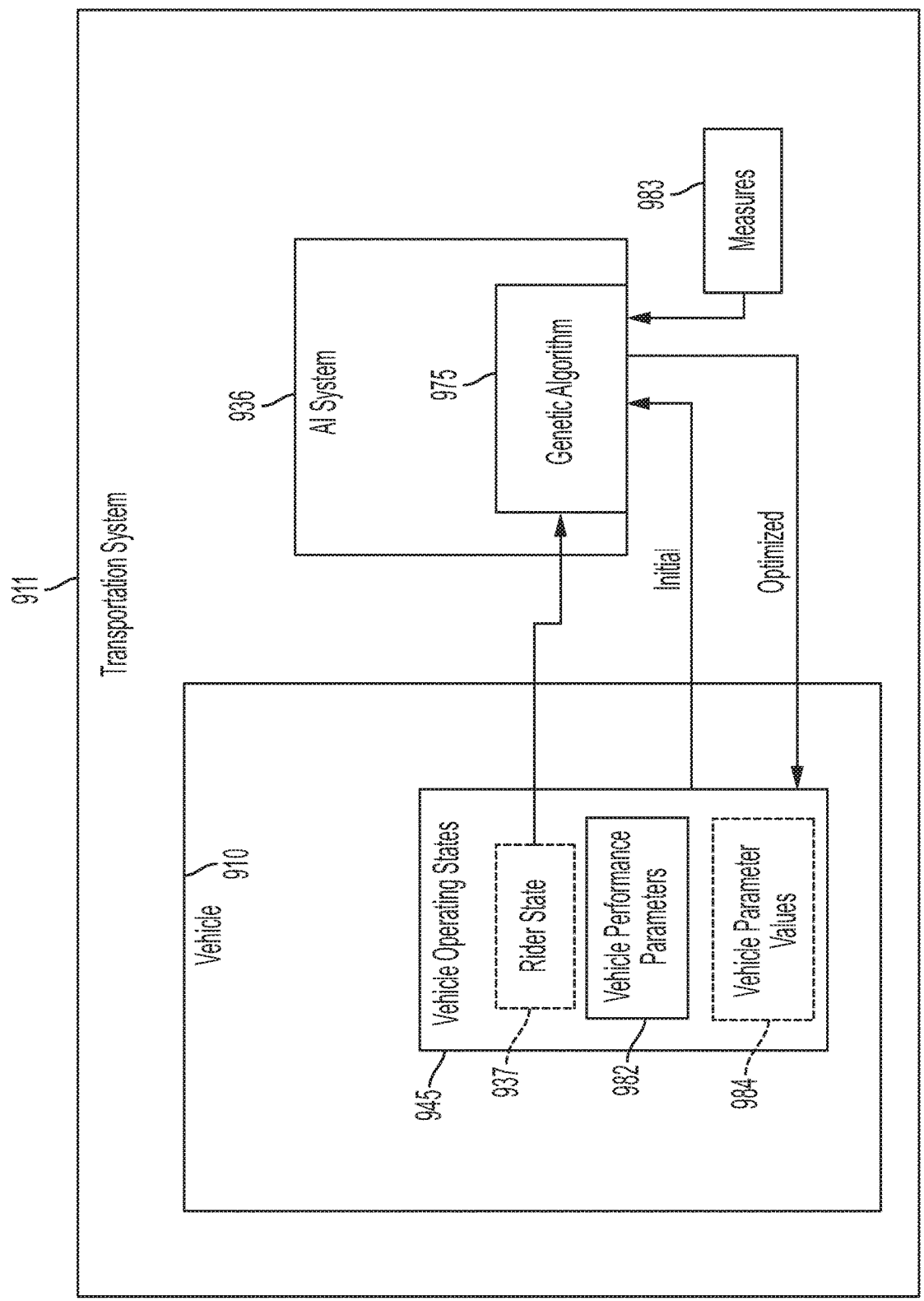
FIG. 9 is a diagrammatic view that illustrates systems described throughout this disclosure relating to various embodiments of the present disclosure.

Referring to FIG. 9, in embodiments provided herein are transportation systems 911 having an artificial intelligence system 936 that uses at least one genetic algorithm 975 to explore a set of possible vehicle operating states 945 to determine at least one optimized operating state. In embodiments, the genetic algorithm 975 takes inputs relating to at least one vehicle performance parameter 982 and at least one rider state 937.

An aspect provided herein includes a system for transportation 911, comprising: a vehicle 910 having a vehicle operating state 945; an artificial intelligence system 936 to execute a genetic algorithm 975 to generate mutations from an initial vehicle operating state to determine at least one optimized vehicle operating state. In embodiments, the vehicle operating state 945 includes a set of vehicle parameter values 984. In embodiments, the genetic algorithm 975 is to: vary the set of vehicle parameter values 984 for a set of corresponding time periods such that the vehicle 910 operates according to the set of vehicle parameter values 984 during the corresponding time periods; evaluate the vehicle operating state 945 for each of the corresponding time periods according to a set of measures 983 to generate evaluations; and select, for future operation of the vehicle 910, an optimized set of vehicle parameter values based on the evaluations.

In embodiments, the vehicle operating state 945 includes the rider state 937 of a rider of the vehicle. In embodiments, the at least one optimized vehicle operating state includes an optimized state of the rider. In embodiments, the genetic algorithm 975 is to optimize the state of the rider. In embodiments, the evaluating according to the set of measures 983 is to determine the state of the rider corresponding to the vehicle parameter values 984.

In embodiments, the vehicle operating state 945 includes a state of the rider of the vehicle. In embodiments, the set of vehicle parameter values 984 includes a set of vehicle performance control values. In embodiments, the at least one optimized vehicle operating state includes an optimized state of performance of the vehicle. In embodiments, the genetic algorithm 975 is to optimize the state of the rider and the state of performance of the vehicle. In embodiments, the evaluating according to the set of measures 983 is to determine the state of the rider and the state of performance of the vehicle corresponding to the vehicle performance control values.

In embodiments, the set of vehicle parameter values 984 includes a set of vehicle performance control values. In embodiments, the at least one optimized vehicle operating state includes an optimized state of performance of the vehicle. In embodiments, the genetic algorithm 975 is to optimize the state of performance of the vehicle. In embodiments, the evaluating according to the set of measures 983 is to determine the state of performance of the vehicle corresponding to the vehicle performance control values.

In embodiments, the set of vehicle parameter values 984 includes a rider-occupied parameter value. In embodiments, the rider-occupied parameter value affirms a presence of a rider in the vehicle 910. In embodiments, the vehicle operating state 945 includes the rider state 937 of a rider of the vehicle. In embodiments, the at least one optimized vehicle operating state includes an optimized state of the rider. In embodiments, the genetic algorithm 975 is to optimize the state of the rider. In embodiments, the evaluating according to the set of measures 983 is to determine the state of the rider corresponding to the vehicle parameter values 984. In embodiments, the state of the rider includes a rider satisfaction parameter. In embodiments, the state of the rider includes an input representative of the rider. In embodiments, the input representative of the rider is selected from the group consisting of: a rider state parameter, a rider comfort parameter, a rider emotional state parameter, a rider satisfaction parameter, a rider goals parameter, a classification of trip, and combinations thereof.

In embodiments, the set of vehicle parameter values 984 includes a set of vehicle performance control values. In embodiments, the at least one optimized vehicle operating state includes an optimized state of performance of the vehicle. In embodiments, the genetic algorithm 975 is to optimize the state of the rider and the state of performance of the vehicle. In embodiments, the evaluating according to the set of measures 983 is to determine the state of the rider and the state of performance of the vehicle corresponding to the vehicle performance control values. In embodiments, the set of vehicle parameter values 984 includes a set of vehicle performance control values. In embodiments, the at least one optimized vehicle operating state includes an optimized state of performance of the vehicle. In embodiments, the genetic algorithm 975 is to optimize the state of performance of the vehicle. In embodiments, the evaluating according to the set of measures 983 is to determine the state of performance of the vehicle corresponding to the vehicle performance control values.

In embodiments, the set of vehicle performance control values are selected from the group consisting of: a fuel efficiency; a trip duration; a vehicle wear; a vehicle make; a vehicle model; a vehicle energy consumption profiles; a fuel capacity; a real-time fuel levels; a charge capacity; a recharging capability; a regenerative braking state; and combinations thereof. In embodiments, at least a portion of the set of vehicle performance control values is sourced from at least one of an on-board diagnostic system, a telemetry system, a software system, a vehicle-located sensor, and a system external to the vehicle 910. In embodiments, the set of measures 983 relates to a set of vehicle operating criteria. In embodiments, the set of measures 983 relates to a set of rider satisfaction criteria. In embodiments, the set of measures 983 relates to a combination of vehicle operating criteria and rider satisfaction criteria. In embodiments, each evaluation uses feedback indicative of an effect on at least one of a state of performance of the vehicle and a state of the rider.

An aspect provided herein includes a system for transportation 911, comprising: an artificial intelligence system 936 to process inputs representative of a state of a vehicle and inputs representative of a rider state 937 of a rider occupying the vehicle during the state of the vehicle with the genetic algorithm 975 to optimize a set of vehicle parameters that affects the state of the vehicle or the rider state 937. In embodiments, the genetic algorithm 975 is to perform a series of evaluations using variations of the inputs. In embodiments, each evaluation in the series of evaluations uses feedback indicative of an effect on at least one of a vehicle operating state 945 and the rider state 937. In embodiments, the inputs representative of the rider state 937 indicate that the rider is absent from the vehicle 910. In embodiments, the state of the vehicle includes the vehicle operating state 945. In embodiments, a vehicle parameter in the set of vehicle parameters includes a vehicle performance parameter 982. In embodiments, the genetic algorithm 975 is to optimize the set of vehicle parameters for the state of the rider.

In embodiments, optimizing the set of vehicle parameters is responsive to an identifying, by the genetic algorithm 975, of at least one vehicle parameter that produces a favorable rider state. In embodiments, the genetic algorithm 975 is to optimize the set of vehicle parameters for vehicle performance. In embodiments, the genetic algorithm 975 is to optimize the set of vehicle parameters for the state of the rider and is to optimize the set of vehicle parameters for vehicle performance. In embodiments, optimizing the set of vehicle parameters is responsive to the genetic algorithm 975 identifying at least one of a favorable vehicle operating state, and favorable vehicle performance that maintains the rider state 937. In embodiments, the artificial intelligence system 936 further includes a neural network selected from a plurality of different neural networks. In embodiments, the selection of the neural network involves the genetic algorithm 975. In embodiments, the selection of the neural network is based on a structured competition among the plurality of different neural networks. In embodiments, the genetic algorithm 975 facilitates training a neural network to process interactions among a plurality of vehicle operating systems and riders to produce the optimized set of vehicle parameters.

In embodiments, a set of inputs relating to at least one vehicle parameter are provided by at least one of an onboard diagnostic system, a telemetry system, a vehicle-located sensor, and a system external to the vehicle. In embodiments, the inputs representative of the rider state 937 comprise at least one of comfort, emotional state, satisfaction, goals, classification of trip, or fatigue. In embodiments, the inputs representative of the rider state 937 reflect a satisfaction parameter of at least one of a driver, a fleet manager, an advertiser, a merchant, an owner, an operator, an insurer, and a regulator. In embodiments, the inputs representative of the rider state 937 comprise inputs relating to a user that, when processed with a cognitive system yield the rider state 937.

Figure 10:
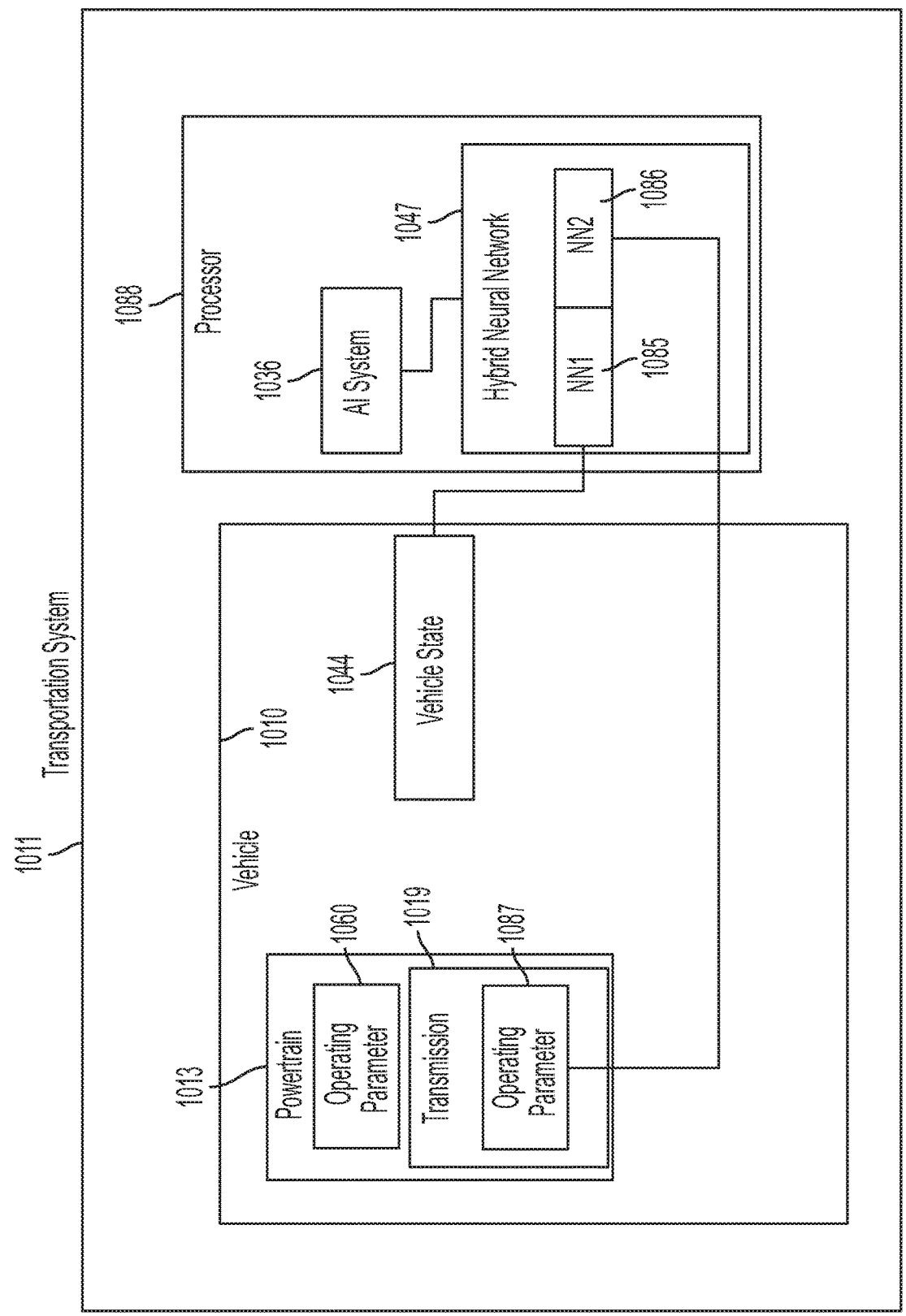
FIG. 10 is a diagrammatic view that illustrates systems described throughout this disclosure relating to various embodiments of the present disclosure.

Referring to FIG. 10, in embodiments provided herein are transportation systems 1011 having a hybrid neural network 1047 for optimizing the operating state of a continuously variable powertrain 1013 of a vehicle 1010. In embodiments, at least one part of the hybrid neural network 1047 operates to classify a state of the vehicle 1010 and another part of the hybrid neural network 1047 operates to optimize at least one operating parameter 1060 of the transmission 1019. In embodiments, the vehicle 1010 may be a self-driving vehicle. In an example, the first portion 1085 of the hybrid neural network may classify the vehicle 1010 as operating in a high-traffic state (such as by use of LIDAR, RADAR, or the like that indicates the presence of other vehicles, or by taking input from a traffic monitoring system, or by detecting the presence of a high density of mobile devices, or the like) and a bad weather state (such as by taking inputs indicating wet roads (such as using vision-based systems), precipitation (such as determined by radar), presence of ice (such as by temperature sensing, vision-based sensing, or the like), hail (such as by impact detection, sound-sensing, or the like), lightning (such as by vision-based systems, sound-based systems, or the like), or the like. Once classified, another neural network 1086 (optionally of another type) may optimize the vehicle operating parameter based on the classified state, such as by putting the vehicle 1010 into a safe-driving mode (e.g., by providing forward-sensing alerts at greater distances and/lower speeds than in good weather, by providing automated braking earlier and more aggressively than in good weather, and the like).

An aspect provided herein includes a system for transportation 1011, comprising: a hybrid neural network 1047 for optimizing an operating state of a continuously variable powertrain 1013 of a vehicle 1010. In embodiments, a portion 1085 of the hybrid neural network 1047 is to operate to classify a state 1044 of the vehicle 1010 thereby generating a classified state of the vehicle, and an other portion 1086 of the hybrid neural network 1047 is to operate to optimize at least one operating parameter 1060 of a transmission 1019 portion of the continuously variable powertrain 1013.

In embodiments, the system for transportation 1011 further comprises: an artificial intelligence system 1036 operative on at least one processor 1088, the artificial intelligence system 1036 to operate the portion 1085 of the hybrid neural network 1047 to operate to classify the state of the vehicle and the artificial intelligence system 1036 to operate the other portion 1086 of the hybrid neural network 1047 to optimize the at least one operating parameter 1087 of the transmission 1019 portion of the continuously variable powertrain 1013 based on the classified state of the vehicle. In embodiments, the vehicle 1010 comprises a system for automating at least one control parameter of the vehicle. In embodiments, the vehicle 1010 is at least a semi-autonomous vehicle. In embodiments, the vehicle 1010 is to be automatically routed. In embodiments, the vehicle 1010 is a self-driving vehicle. In embodiments, the classified state of the vehicle is: a vehicle maintenance state; a vehicle health state; a vehicle operating state; a vehicle energy utilization state; a vehicle charging state; a vehicle satisfaction state; a vehicle component state; a vehicle sub-system state; a vehicle powertrain system state; a vehicle braking system state; a vehicle clutch system state; a vehicle lubrication system state; a vehicle transportation infrastructure system state; or a vehicle rider state. In embodiments, at least a portion of the hybrid neural network 1047 is a convolutional neural network.

Figure 11:
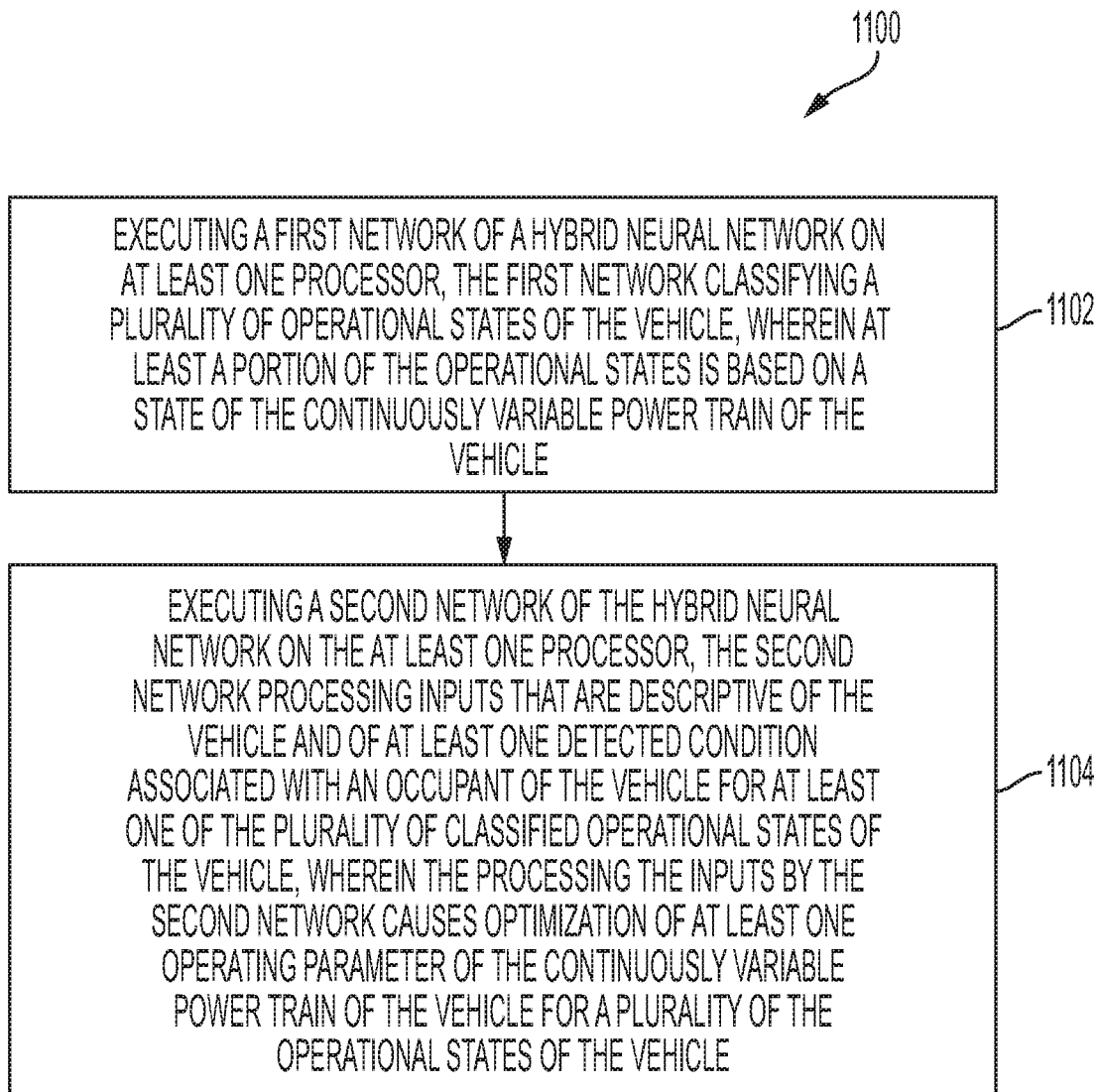
FIG. 11 is a diagrammatic view that illustrates a method described throughout this disclosure relating to various embodiments of the present disclosure.

FIG. 11 illustrates a method 1100 for optimizing operation of a continuously variable vehicle powertrain of a vehicle in accordance with embodiments of the systems and methods disclosed herein. At 1102, the method includes executing a first network of a hybrid neural network on at least one processor, the first network classifying a plurality of operational states of the vehicle. In embodiments, at least a portion of the operational states is based on a state of the continuously variable powertrain of the vehicle. At 1104, the method includes executing a second network of the hybrid neural network on the at least one processor, the second network processing inputs that are descriptive of the vehicle and of at least one detected condition associated with an occupant of the vehicle for at least one of the plurality of classified operational states of the vehicle. In embodiments, the processing the inputs by the second network causes optimization of at least one operating parameter of the continuously variable powertrain of the vehicle for a plurality of the operational states of the vehicle.

Referring to FIG. 10 and FIG. 11 together, in embodiments, the vehicle comprises an artificial intelligence system 1036, the method further comprising automating at least one control parameter of the vehicle by the artificial intelligence system 1036. In embodiments, the vehicle 1010 is at least a semi-autonomous vehicle. In embodiments, the vehicle 1010 is to be automatically routed. In embodiments, the vehicle 1010 is a self-driving vehicle. In embodiments, the method further comprises optimizing, by the artificial intelligence system 1036, an operating state of the continuously variable powertrain 1013 of the vehicle based on the optimized at least one operating parameter 1060 of the continuously variable powertrain 1013 by adjusting at least one other operating parameter 1087 of a transmission 1019 portion of the continuously variable powertrain 1013.

In embodiments, the method further comprises optimizing, by the artificial intelligence system 1036, the operating state of the continuously variable powertrain 1013 by processing social data from a plurality of social data sources. In embodiments, the method further comprises optimizing, by the artificial intelligence system 1036, the operating state of the continuously variable powertrain 1013 by processing data sourced from a stream of data from unstructured data sources. In embodiments, the method further comprises optimizing, by the artificial intelligence system 1036, the operating state of the continuously variable powertrain 1013 by processing data sourced from wearable devices. In embodiments, the method further comprises optimizing, by the artificial intelligence system 1036, the operating state of the continuously variable powertrain 1013 by processing data sourced from in-vehicle sensors. In embodiments, the method further comprises optimizing, by the artificial intelligence system 1036, the operating state of the continuously variable powertrain 1013 by processing data sourced from a rider helmet.

In embodiments, the method further comprises optimizing, by the artificial intelligence system 1036, the operating state of the continuously variable powertrain 1013 by processing data sourced from rider headgear. In embodiments, the method further comprises optimizing, by the artificial intelligence system 1036, the operating state of the continuously variable powertrain 1013 by processing data sourced from a rider voice system. In embodiments, the method further comprises operating, by the artificial intelligence system 1036, a third network of the hybrid neural network 1047 to predict a state of the vehicle based at least in part on at least one of the classified plurality of operational states of the vehicle and at least one operating parameter of the transmission 1019. In embodiments, the first network of the hybrid neural network 1047 comprises a structure-adaptive network to adapt a structure of the first network responsive to a result of operating the first network of the hybrid neural network 1047. In embodiments, the first network of the hybrid neural network 1047 is to process a plurality of social data from social data sources to classify the plurality of operational states of the vehicle.

In embodiments, at least a portion of the hybrid neural network 1047 is a convolutional neural network. In embodiments, at least one of the classified plurality of operational states of the vehicle is: a vehicle maintenance state; or a vehicle health state. In embodiments, at least one of the classified states of the vehicle is: a vehicle operating state; a vehicle energy utilization state; a vehicle charging state; a vehicle satisfaction state; a vehicle component state; a vehicle sub-system state; a vehicle powertrain system state; a vehicle braking system state; a vehicle clutch system state; a vehicle lubrication system state; or a vehicle transportation infrastructure system state. In embodiments, the at least one of classified states of the vehicle is a vehicle driver state. In embodiments, the at least one of classified states of the vehicle is a vehicle rider state.

Figure 12:
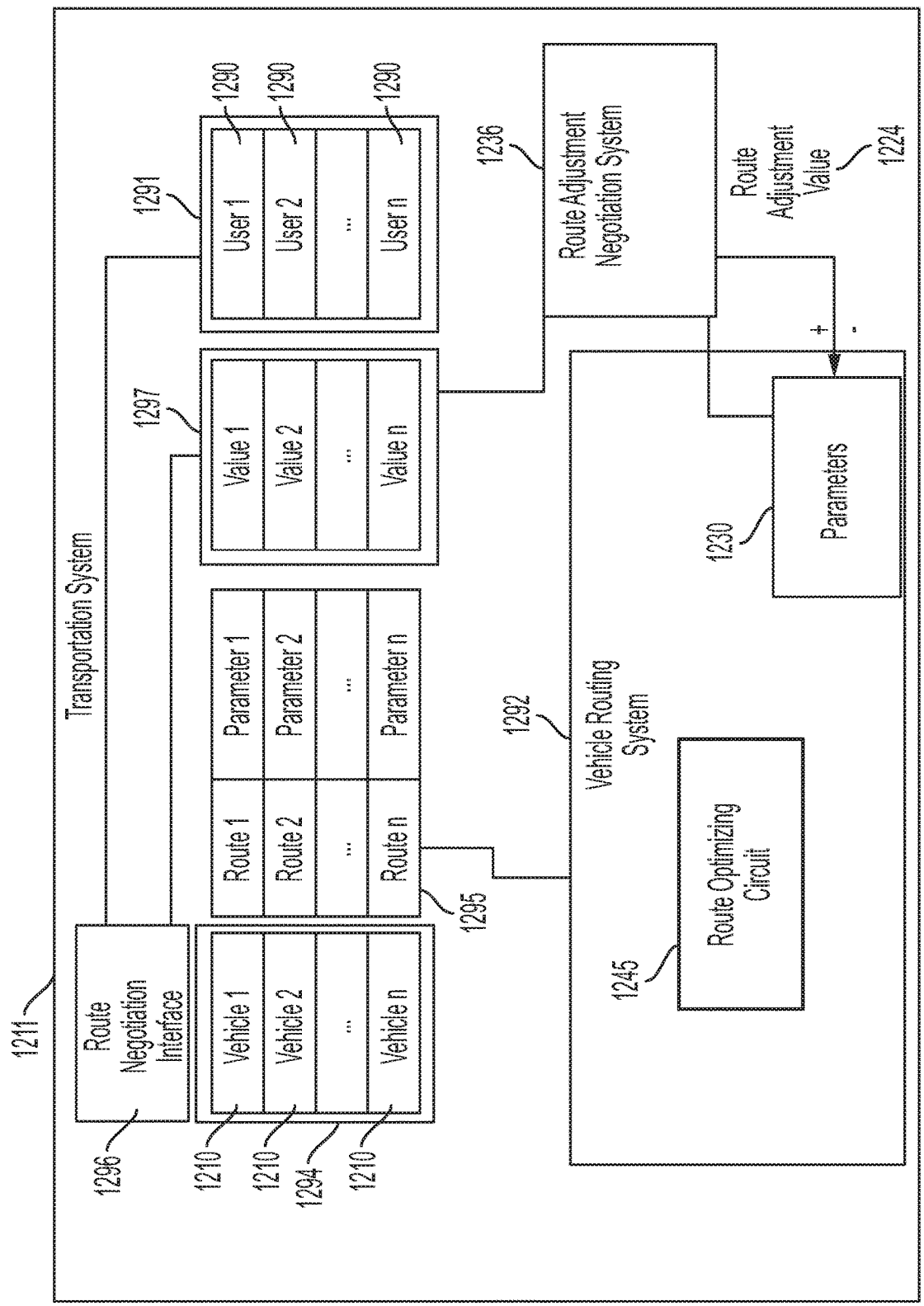
FIG. 12 is a diagrammatic view that illustrates systems described throughout this disclosure relating to various embodiments of the present disclosure.

Referring to FIG. 12, in embodiments, provided herein are transportation systems 1211 having a cognitive system for routing at least one vehicle 1210 within a set of vehicles 1294 based on a routing parameter determined by facilitating negotiation among a designated set of vehicles. In embodiments, negotiation accepts inputs relating to the value attributed by at least one rider to at least one parameter 1230 of a route 1295. A user 1290 may express value by a user interface that rates one or more parameters (e.g., any of the parameters noted throughout), by behavior (e.g., undertaking behavior that reflects or indicates value ascribed to arriving on time, following a given route 1295, or the like), or by providing or offering value (e.g., offering currency, tokens, points, cryptocurrency, rewards, or the like). For example, a user 1290 may negotiate for a preferred route by offering tokens to the system that are awarded if the user 1290 arrives at a designated time, while others may offer to accept tokens in exchange for taking alternative routes (and thereby reducing congestion). Thus, an artificial intelligence system may optimize a combination of offers to provide rewards or to undertake behavior in response to rewards, such that the reward system optimizes a set of outcomes. Negotiation may include explicit negotiation, such as where a driver offers to reward drivers ahead of the driver on the road in exchange for their leaving the route temporarily as the driver passes.

An aspect provided herein includes a system for transportation 1211, comprising: a cognitive system for routing at least one vehicle 1210 within a set of vehicles 1294 based on a routing parameter determined by facilitating a negotiation among a designated set of vehicles, wherein the negotiation accepts inputs relating to a value attributed by at least one user 1290 to at least one parameter of a route 1295.

Figure 13:
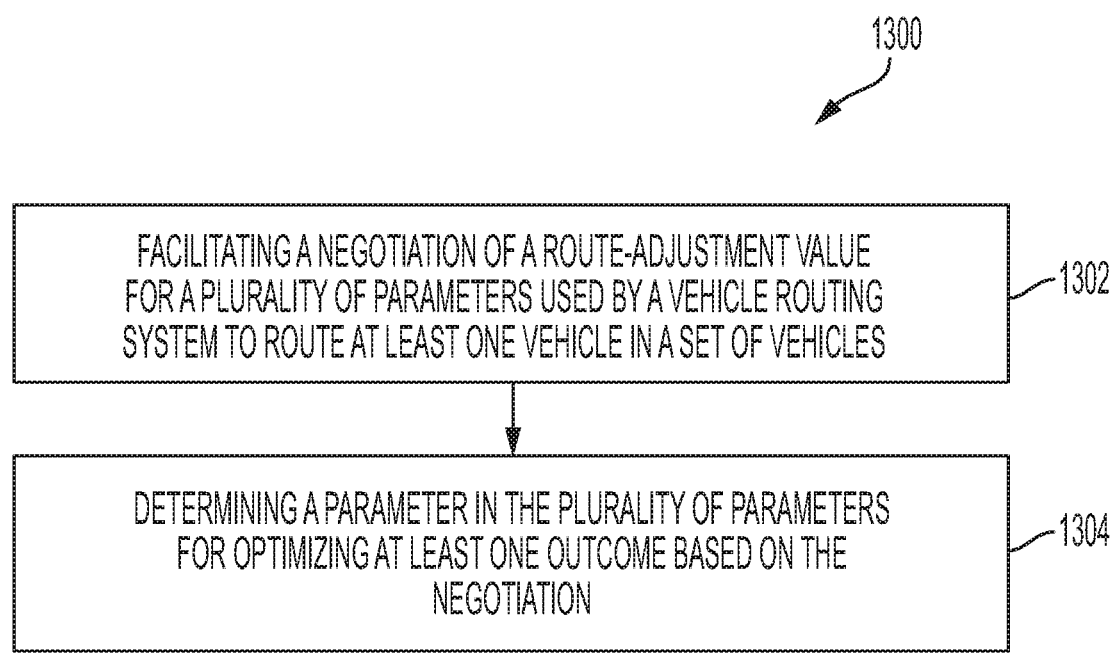
FIG. 13 is a diagrammatic view that illustrates a method described throughout this disclosure relating to various embodiments of the present disclosure.

FIG. 13 illustrates a method 1300 of negotiation-based vehicle routing in accordance with embodiments of the systems and methods disclosed herein. At 1302, the method includes facilitating a negotiation of a route-adjustment value for a plurality of parameters used by a vehicle routing system to route at least one vehicle in a set of vehicles. At 1304, the method includes determining a parameter in the plurality of parameters for optimizing at least one outcome based on the negotiation.

Referring to FIG. 12 and FIG. 13, in embodiments, a user 1290 is an administrator for a set of roadways to be used by the at least one vehicle 1210 in the set of vehicles 1294. In embodiments, a user 1290 is an administrator for a fleet of vehicles including the set of vehicles 1294. In embodiments, the method further comprises offering a set of offered user-indicated values for the plurality of parameters 1230 to users 1290 with respect to the set of vehicles 1294. In embodiments, the route-adjustment value 1224 is based at least in part on the set of offered user-indicated values 1297. In embodiments, the route-adjustment value 1224 is further based on at least one user response to the offering. In embodiments, the route-adjustment value 1224 is based at least in part on the set of offered user-indicated values 1297 and at least one response thereto by at least one user of the set of vehicles 1294. In embodiments, the determined parameter facilitates adjusting a route 1295 of at least one of the vehicles 1210 in the set of vehicles 1294. In embodiments, adjusting the route includes prioritizing the determined parameter for use by the vehicle routing system.

In embodiments, the facilitating negotiation includes facilitating negotiation of a price of a service. In embodiments, the facilitating negotiation includes facilitating negotiation of a price of fuel. In embodiments, the facilitating negotiation includes facilitating negotiation of a price of recharging. In embodiments, the facilitating negotiation includes facilitating negotiation of a reward for taking a routing action.

An aspect provided herein includes a transportation system 1211 for negotiation-based vehicle routing comprising: a route adjustment negotiation system 1289 through which users 1290 in a set of users 1291 negotiate a route-adjustment value 1224 for at least one of a plurality of parameters 1230 used by a vehicle routing system 1292 to route at least one vehicle 1210 in a set of vehicles 1294; and a user route optimizing circuit 1293 to optimize a portion of a route 1295 of at least one user 1290 of the set of vehicles 1294 based on the route-adjustment value 1224 for the at least one of the plurality of parameters 1230. In embodiments, the route-adjustment value 1224 is based at least in part on user-indicated values 1297 and at least one negotiation response thereto by at least one user of the set of vehicles 1294. In embodiments, the transportation system 1211 further comprises a vehicle-based route negotiation interface through which user-indicated values 1297 for the plurality of parameters 1230 used by the vehicle routing system are captured. In embodiments, a user 1290 is a rider of the at least one vehicle 1210. In embodiments, a user 1290 is an administrator for a set of roadways to be used by the at least one vehicle 1210 in the set of vehicles 1294.

In embodiments, a user 1290 is an administrator for a fleet of vehicles including the set of vehicles 1294. In embodiments, the at least one of the plurality of parameters 1230 facilitates adjusting a route 1295 of the at least one vehicle 1210. In embodiments, adjusting the route 1295 includes prioritizing a determined parameter for use by the vehicle routing system. In embodiments, at least one of the user-indicated values 1297 is attributed to at least one of the plurality of parameters 1230 through an interface to facilitate expression of rating one or more route parameters. In embodiments, the vehicle-based route negotiation interface facilitates expression of rating one or more route parameters. In embodiments, the user-indicated values 1297 are derived from a behavior of the user 1290. In embodiments, the vehicle-based route negotiation interface facilitates converting user behavior to the user-indicated values 1297. In embodiments, the user behavior reflects value ascribed to the at least one parameter used by the vehicle routing system to influence a route 1295 of at least one vehicle 1210 in the set of vehicles 1294. In embodiments, the user-indicated value indicated by at least one user 1290 correlates to an item of value provided by the user 1290. In embodiments, the item of value is provided by the user 1290 through an offering of the item of value in exchange for a result of routing based on the at least one parameter. In embodiments, the negotiating of the route-adjustment value 1224 includes offering an item of value to the users of the set of vehicles 1294.

Figure 14:
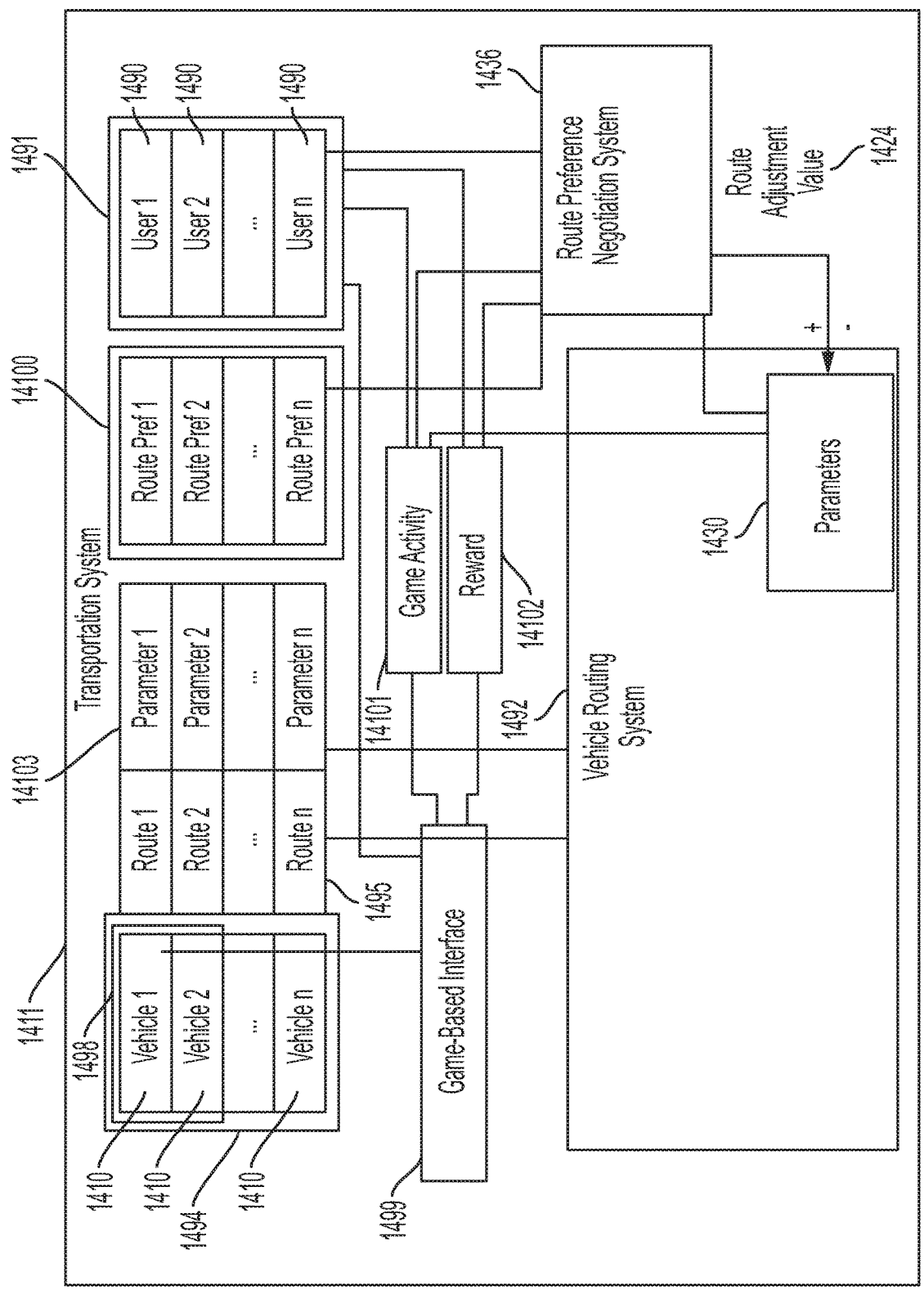
FIG. 14 is a diagrammatic view that illustrates systems described throughout this disclosure relating to various embodiments of the present disclosure.

Referring to FIG. 14, in embodiments provided herein are transportation systems 1411 having a cognitive system for routing at least one vehicle 1410 within a set of vehicles 1494 based on a routing parameter determined by facilitating coordination among a designated set of vehicles 1498. In embodiments, the coordination is accomplished by taking at least one input from at least one game-based interface 1499 for riders of the vehicles. A game-based interface 1499 may include rewards for undertaking game-like actions (i.e., game activities 14101) that provide an ancillary benefit. For example, a rider in a vehicle 1410 may be rewarded for routing the vehicle 1410 to a point of interest off a highway (such as to collect a coin, to capture an item, or the like), while the rider's departure clears space for other vehicles that are seeking to achieve other objectives, such as on-time arrival. For example, a game like Pokemon Go™ may be configured to indicate the presence of rare Pokemon™ creatures in locations that attract traffic away from congested locations. Others may provide rewards (e.g., currency, cryptocurrency or the like) that may be pooled to attract users 1490 away from congested roads.

An aspect provided herein includes a system for transportation 1411, comprising: a cognitive system for routing at least one vehicle 1410 within a set of vehicles 1494 based on a set of routing parameters 1430 determined by facilitating coordination among a designated set of vehicles 1498, wherein the coordination is accomplished by taking at least one input from at least one game-based interface 1499 for a user 1490 of a vehicle 1410 in the designated set of vehicles 1498.

In embodiments, the system for transportation further comprises: a vehicle routing system 1492 to route the at least one vehicle 1410 based on the set of routing parameters 1430; and the game-based interface 1499 through which the user 1490 indicates a routing preference 14100 for at least one vehicle 1410 within the set of vehicles 1494 to undertake a game activity 14101 offered in the game-based interface 1499; wherein the game-based interface 1499 is to induce the user 1490 to undertake a set of favorable routing choices based on the set of routing parameters 1430. As used herein, "to route" means to select a route 1495.

In embodiments, the vehicle routing system 1492 accounts for the routing preference 14100 of the user 1490 when routing the at least one vehicle 1410 within the set of vehicles 1494. In embodiments, the game-based interface 1499 is disposed for in-vehicle use as indicated in FIG. 14 by the line extending from the Game-Based Interface into the box for Vehicle 1. In embodiments, the user 1490 is a rider of the at least one vehicle 1410. In embodiments, the user 1490 is an administrator for a set of roadways to be used by the at least one vehicle 1410 in the set of vehicles 1494. In embodiments, the user 1490 is an administrator for a fleet of vehicles including the set of vehicles 1494. In embodiments, the set of routing parameters 1430 includes at least one of traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, avoidance of driver-operated vehicles. In embodiments, the game activity 14101 offered in the game-based interface 1499 includes contests. In embodiments, the game activity 14101 offered in the game-based interface 1499 includes entertainment games.

In embodiments, the game activity 14101 offered in the game-based interface 1499 includes competitive games. In embodiments, the game activity 14101 offered in the game-based interface 1499 includes strategy games. In embodiments, the game activity 14101 offered in the game-based interface 1499 includes scavenger hunts. In embodiments, the set of favorable routing choices is configured so that the vehicle routing system 1492 achieves a fuel efficiency objective. In embodiments, the set of favorable routing choices is configured so that the vehicle routing system 1492 achieves a reduced traffic objective. In embodiments, the set of favorable routing choices is configured so that the vehicle routing system 1492 achieves a reduced pollution objective. In embodiments, the set of favorable routing choices is configured so that the vehicle routing system 1492 achieves a reduced carbon footprint objective.

In embodiments, the set of favorable routing choices is configured so that the vehicle routing system 1492 achieves a reduced noise in neighborhoods objective. In embodiments, the set of favorable routing choices is configured so that the vehicle routing system 1492 achieves a collective satisfaction objective. In embodiments, the set of favorable routing choices is configured so that the vehicle routing system 1492 achieves an avoiding accident scenes objective. In embodiments, the set of favorable routing choices is configured so that the vehicle routing system 1492 achieves an avoiding high-crime areas objective. In embodiments, the set of favorable routing choices is configured so that the vehicle routing system 1492 achieves a reduced traffic congestion objective. In embodiments, the set of favorable routing choices is configured so that the vehicle routing system 1492 achieves a bad weather avoidance objective.

In embodiments, the set of favorable routing choices is configured so that the vehicle routing system 1492 achieves a maximum travel time objective. In embodiments, the set of favorable routing choices is configured so that the vehicle routing system 1492 achieves a maximum speed limit objective. In embodiments, the set of favorable routing choices is configured so that the vehicle routing system 1492 achieves an avoidance of toll roads objective. In embodiments, the set of favorable routing choices is configured so that the vehicle routing system 1492 achieves an avoidance of city roads objective. In embodiments, the set of favorable routing choices is configured so that the vehicle routing system 1492 achieves an avoidance of undivided highways objective. In embodiments, the set of favorable routing choices is configured so that the vehicle routing system 1492 achieves an avoidance of left turns objective. In embodiments, the set of favorable routing choices is configured so that the vehicle routing system 1492 achieves an avoidance of driver-operated vehicles objective.

Figure 15:
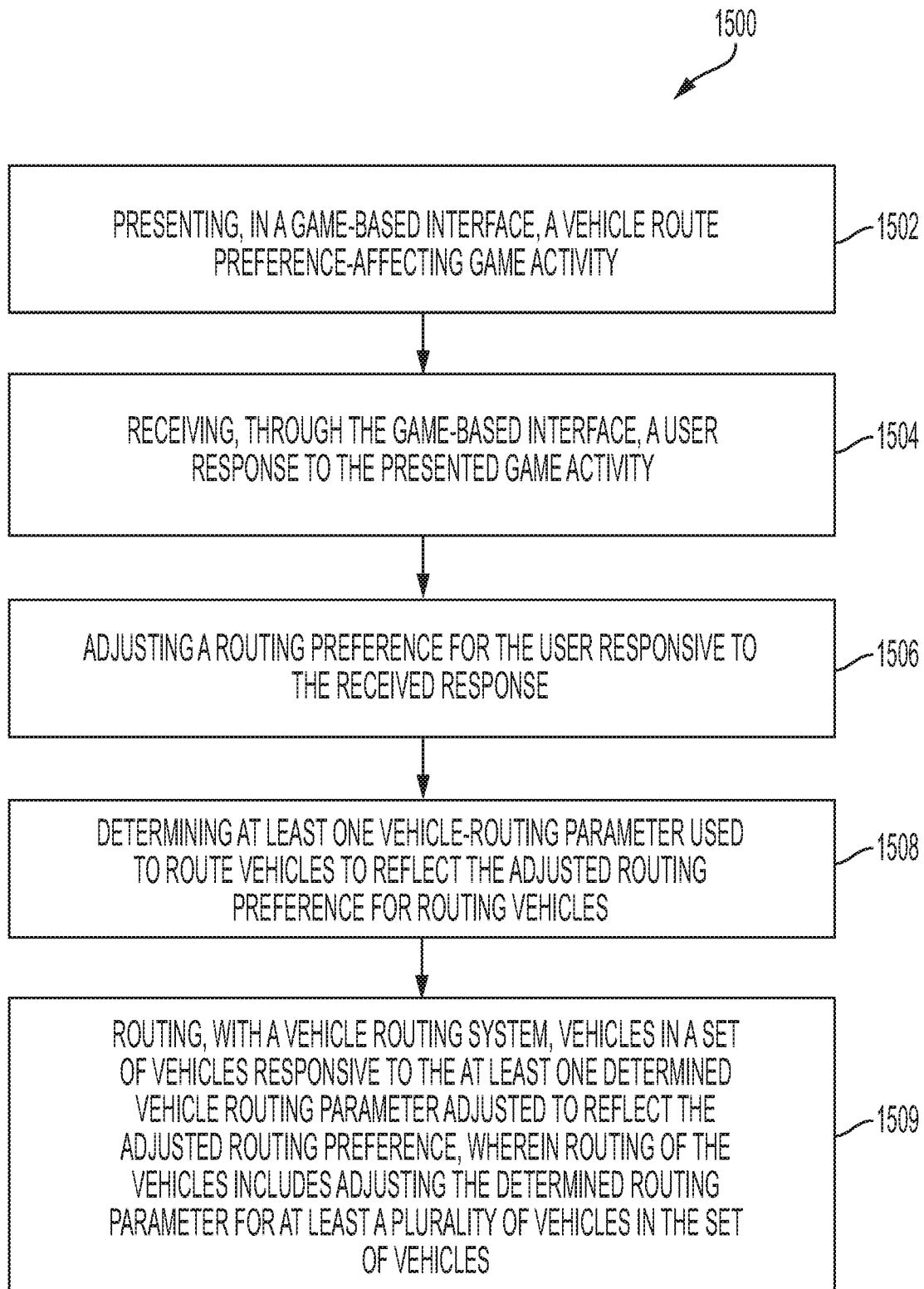
FIG. 15 is a diagrammatic view that illustrates a method described throughout this disclosure relating to various embodiments of the present disclosure.
Figure 16:
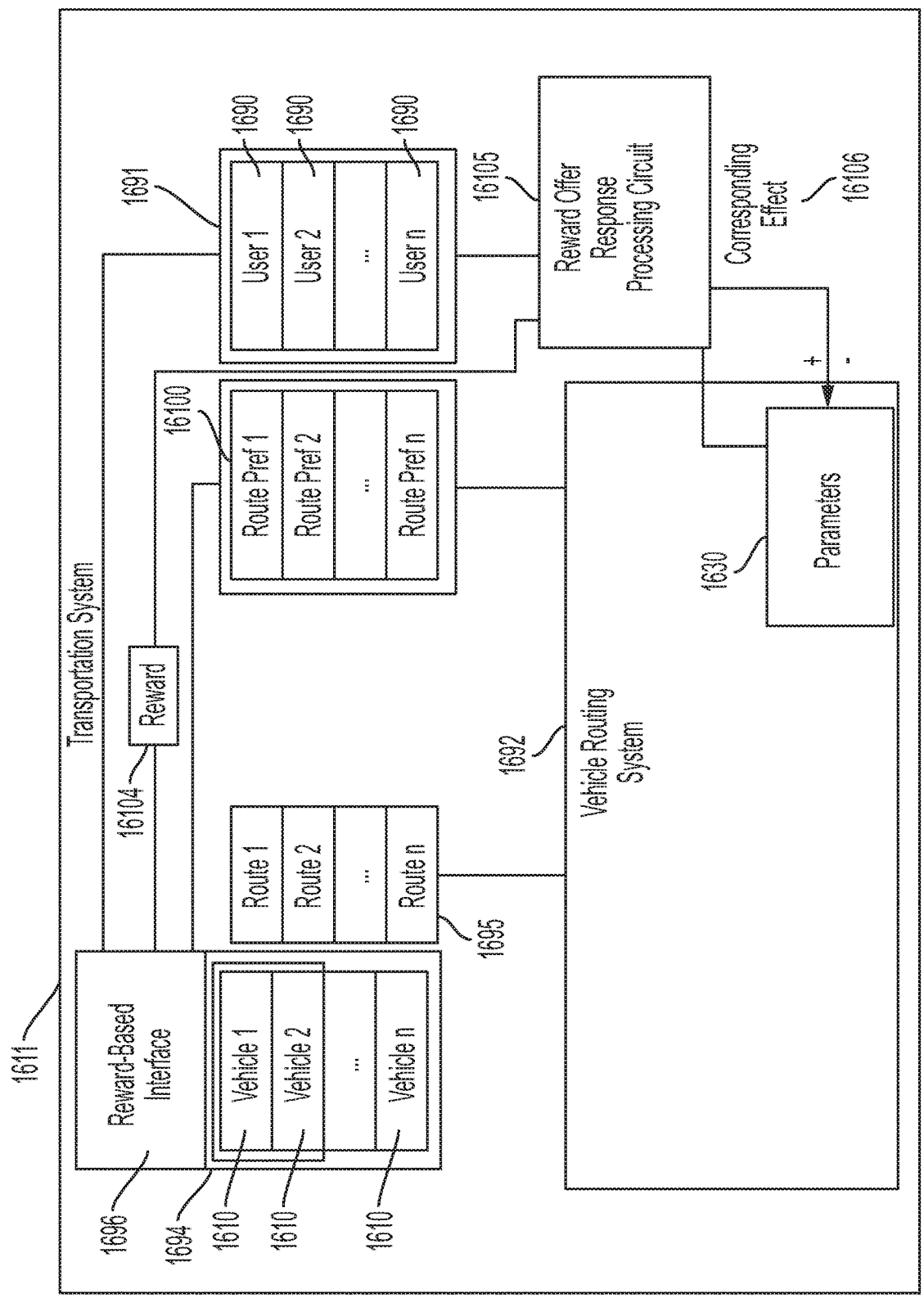
FIG. 16 is a diagrammatic view that illustrates systems described throughout this disclosure relating to various embodiments of the present disclosure.

FIG. 15 illustrates a method 1500 of game-based coordinated vehicle routing in accordance with embodiments of the systems and methods disclosed herein. At 1502, the method includes presenting, in a game-based interface, a vehicle route preference-affecting game activity. At 1504, the method includes receiving, through the game-based interface, a user response to the presented game activity. At 1506, the method includes adjusting a routing preference for the user responsive to the received response. At 1508, the method includes determining at least one vehicle-routing parameter used to route vehicles to reflect the adjusted routing preference for routing vehicles. At 1509, the method includes routing, with a vehicle routing system, vehicles in a set of vehicles responsive to the at least one determined vehicle routing parameter adjusted to reflect the adjusted routing preference, wherein routing of the vehicles includes adjusting the determined routing parameter for at least a plurality of vehicles in the set of vehicles.

Referring to FIG. 14 and FIG. 15, in embodiments, the method further comprises indicating, by the game-based interface 1499, a reward value 14102 for accepting the game activity 14101. In embodiments, the game-based interface 1499 further comprises a routing preference negotiation system 1436 for a rider to negotiate the reward value 14102 for accepting the game activity 14101. In embodiments, the reward value 14102 is a result of pooling contributions of value from riders in the set of vehicles. In embodiments, at least one routing parameter 1430 used by the vehicle routing system 1492 to route the vehicles 1410 in the set of vehicles 1494 is associated with the game activity 14101 and a user acceptance of the game activity 14101 adjusts (e.g., by the routing adjustment value 1424) the at least one routing parameter 1430 to reflect the routing preference. In embodiments, the user response to the presented game activity 14101 is derived from a user interaction with the game-based interface 1499. In embodiments, the at least one routing parameter used by the vehicle routing system 1492 to route the vehicles 1410 in the set of vehicles 1494 includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles.

In embodiments, the game activity 14101 presented in the game-based interface 1499 includes contests. In embodiments, the game activity 14101 presented in the game-based interface 1499 includes entertainment games. In embodiments, the game activity 14101 presented in the game-based interface 1496 includes competitive games. In embodiments, the game activity 14101 presented in the game-based interface 1499 includes strategy games. In embodiments, the game activity 14101 presented in the game-based interface 1499 includes scavenger hunts. In embodiments, the routing responsive to the at least one determined vehicle routing parameter 14103 achieves a fuel efficiency objective. In embodiments, the routing responsive to the at least one determined vehicle routing parameter 14103 achieves a reduced traffic objective.

In embodiments, the routing responsive to the at least one determined vehicle routing parameter 14103 achieves a reduced pollution objective. In embodiments, the routing responsive to the at least one determined vehicle routing parameter 14103 achieves a reduced carbon footprint objective. In embodiments, the routing responsive to the at least one determined vehicle routing parameter 14103 achieves a reduced noise in neighborhoods objective. In embodiments, the routing responsive to the at least one determined vehicle routing parameter 14103 achieves a collective satisfaction objective. In embodiments, the routing responsive to the at least one determined vehicle routing parameter 14103 achieves an avoiding accident scenes objective. In embodiments, the routing responsive to the at least one determined vehicle routing parameter 14103 achieves an avoiding high-crime areas objective. In embodiments, the routing responsive to the at least one determined vehicle routing parameter 14103 achieves a reduced traffic congestion objective.

In embodiments, the routing responsive to the at least one determined vehicle routing parameter 14103 achieves a bad weather avoidance objective. In embodiments, the routing responsive to the at least one determined vehicle routing parameter 14103 achieves a maximum travel time objective. In embodiments, the routing responsive to the at least one determined vehicle routing parameter 14103 achieves a maximum speed limit objective. In embodiments, the routing responsive to the at least one determined vehicle routing parameter 14103 achieves an avoidance of toll roads objective. In embodiments, the routing responsive to the at least one determined vehicle routing parameter 14103 achieves an avoidance of city roads objective. In embodiments, the routing responsive to the at least one determined vehicle routing parameter 14103 achieves an avoidance of undivided highways objective. In embodiments, the routing responsive to the at least one determined vehicle routing parameter 14103 achieves an avoidance of left turns objective. In embodiments, the routing responsive to the at least one determined vehicle routing parameter 14103 achieves an avoidance of driver-operated vehicles objective.

In embodiments, provided herein are transportation systems 1611 having a cognitive system for routing at least one vehicle, wherein the routing is determined at least in part by processing at least one input from a rider interface wherein a rider can obtain a reward 16102 by undertaking an action while in the vehicle. In embodiments, the rider interface may display a set of available rewards for undertaking various actions, such that the rider may select (such as by interacting with a touch screen or audio interface), a set of rewards to pursue, such as by allowing a navigation system of the vehicle (or of a ride-share system of which the user 1690 has at least partial control) or a routing system 1692 of a self-driving vehicle to use the actions that result in rewards to govern routing. For example, selection of a reward for attending a site may result in sending a signal to a navigation or routing system 1692 to set an intermediate destination at the site. As another example, indicating a willingness to watch a piece of content may cause a routing system 1692 to select a route that permits adequate time to view or hear the content.

An aspect provided herein includes a system for transportation 1611, comprising: a cognitive system for routing at least one vehicle 1610, wherein the routing is based, at least in part, by processing at least one input from a rider interface, wherein a reward 16102 is made available to a rider in response to the rider undertaking a predetermined action while in the at least one vehicle 1610.

An aspect provided herein includes a transportation system 1611 for reward-based coordinated vehicle routing comprising: a reward-based interface 16104 to offer a reward 16102 and through which a user 1690 related to a set of vehicles 1694 indicates a routing preference of the user 1690 related to the reward 16102 by responding to the reward 16102 offered in the reward-based interface 16104; a reward offer response processing circuit 16105 to determine at least one user action resulting from the user response to the reward 16102 and to determine a corresponding effect 16106 on at least one routing parameter 1630; and a vehicle routing system 1692 to use the routing preference 16100 of the user 1690 and the corresponding effect on the at least one routing parameter to govern routing of the set of vehicles 1694.

In embodiments, the user 1690 is a rider of at least one vehicle 1610 in the set of vehicles 1694. In embodiments, the user 1690 is an administrator for a set of roadways to be used by at least one vehicle 1610 in the set of vehicles 1694. In embodiments, the user 1690 is an administrator for a fleet of vehicles including the set of vehicles 1694. In embodiments, the reward-based interface 16104 is disposed for in-vehicle use. In embodiments, the at least one routing parameter 1630 includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles. In embodiments, the vehicle routing system 1692 is to use the routing preference of the user 1690 and the corresponding effect on the at least one routing parameter to govern routing of the set of vehicles to achieve a fuel efficiency objective. In embodiments, the vehicle routing system 1692 is to use the routing preference of the user 1690 and the corresponding effect on the at least one routing parameter to govern routing of the set of vehicles to achieve a reduced traffic objective. In embodiments, the vehicle routing system 1692 is to use the routing preference of the user 1690 and the corresponding effect on the at least one routing parameter to govern routing of the set of vehicles to achieve a reduced pollution objective. In embodiments, the vehicle routing system 1692 is to use the routing preference of the user 1690 and the corresponding effect on the at least one routing parameter to govern routing of the set of vehicles to achieve a reduced carbon footprint objective.

In embodiments, the vehicle routing system 1692 is to use the routing preference of the user 1690 and the corresponding effect on the at least one routing parameter to govern routing of the set of vehicles to achieve a reduced noise in neighborhoods objective. In embodiments, the vehicle routing system 1692 is to use the routing preference of the user 1690 and the corresponding effect on the at least one routing parameter to govern routing of the set of vehicles to achieve a collective satisfaction objective. In embodiments, the vehicle routing system 1692 is to use the routing preference of the user 1690 and the corresponding effect on the at least one routing parameter to govern routing of the set of vehicles to achieve an avoiding accident scenes objective. In embodiments, the vehicle routing system 1692 is to use the routing preference of the user 1690 and the corresponding effect on the at least one routing parameter to govern routing of the set of vehicles to achieve an avoiding high-crime areas objective. In embodiments, the vehicle routing system 1692 is to use the routing preference of the user 1690 and the corresponding effect on the at least one routing parameter to govern routing of the set of vehicles to achieve a reduced traffic congestion objective.

In embodiments, the vehicle routing system 1692 is to use the routing preference of the user 1690 and the corresponding effect on the at least one routing parameter to govern routing of the set of vehicles to achieve a bad weather avoidance objective. In embodiments, the vehicle routing system 1692 is to use the routing preference of the user 1690 and the corresponding effect on the at least one routing parameter to govern routing of the set of vehicles to achieve a maximum travel time objective. In embodiments, the vehicle routing system 1692 is to use the routing preference of the user 1690 and the corresponding effect on the at least one routing parameter to govern routing of the set of vehicles to achieve a maximum speed limit objective. In embodiments, the vehicle routing system 1692 is to use the routing preference of the user 1690 and the corresponding effect on the at least one routing parameter to govern routing of the set of vehicles to achieve an avoidance of toll roads objective. In embodiments, the vehicle routing system 1692 is to use the routing preference of the user 1690 and the corresponding effect on the at least one routing parameter to govern routing of the set of vehicles to achieve an avoidance of city roads objective.

In embodiments, the vehicle routing system 1692 is to use the routing preference of the user 1690 and the corresponding effect on the at least one routing parameter to govern routing of the set of vehicles to achieve an avoidance of undivided highways objective. In embodiments, the vehicle routing system 1692 is to use the routing preference of the user 1690 and the corresponding effect on the at least one routing parameter to govern routing of the set of vehicles to achieve an avoidance of left turns objective. In embodiments, the vehicle routing system 1692 is to use the routing preference of the user 1690 and the corresponding effect on the at least one routing parameter to govern routing of the set of vehicles to achieve an avoidance of driver-operated vehicles objective.

Figure 17:
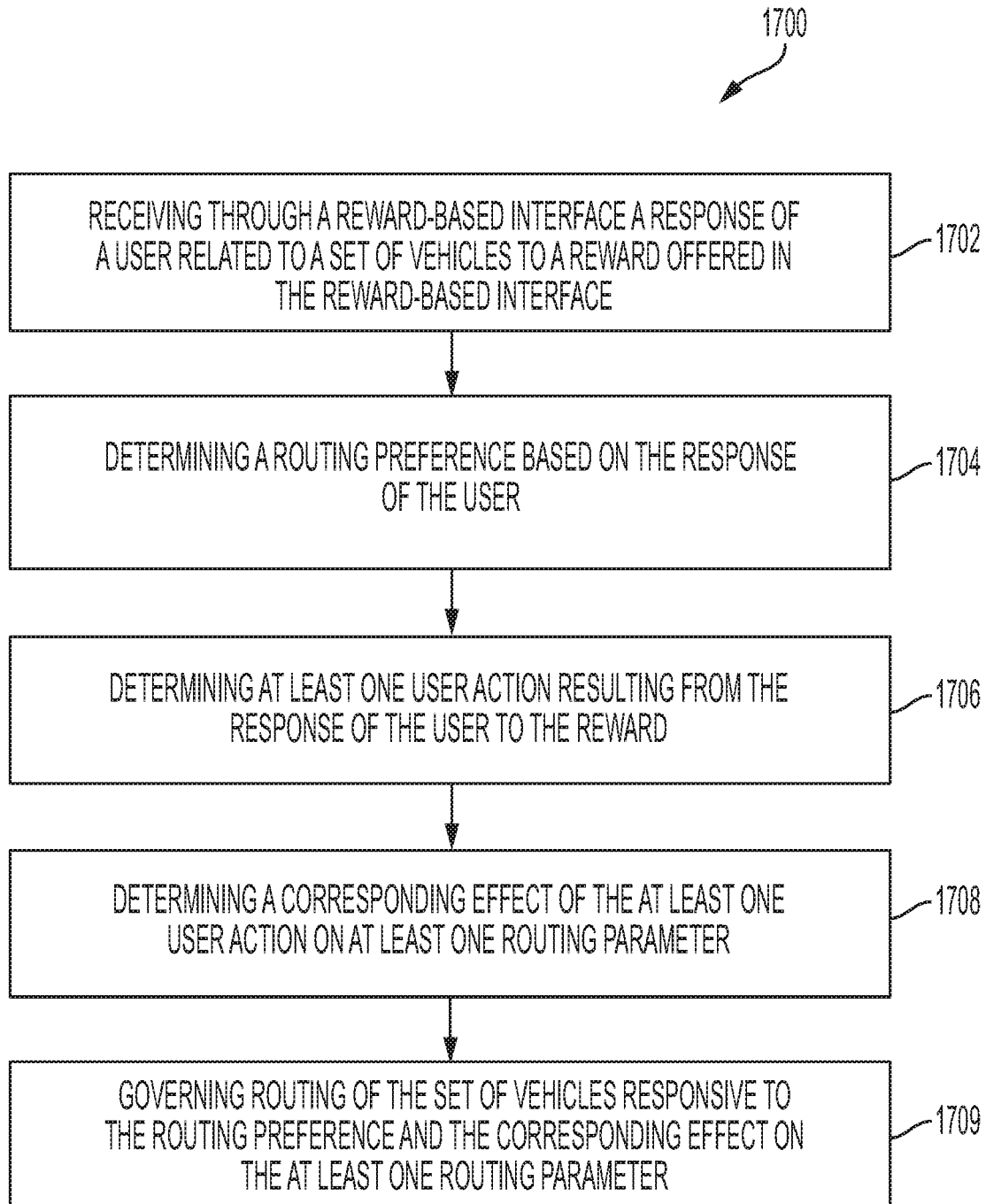
FIG. 17 is a diagrammatic view that illustrates a method described throughout this disclosure relating to various embodiments of the present disclosure.

FIG. 17 illustrates a method 1700 of reward-based coordinated vehicle routing in accordance with embodiments of the systems and methods disclosed herein. At 1702, the method includes receiving through a reward-based interface a response of a user related to a set of vehicles to a reward offered in the reward-based interface. At 1704, the method includes determining a routing preference based on the response of the user. At 1706, the method includes determining at least one user action resulting from the response of the user to the reward. At 1708, the method includes determining a corresponding effect of the at least one user action on at least one routing parameter. At 1709, the method includes governing routing of the set of vehicles responsive to the routing preference and the corresponding effect on the at least one routing parameter.

In embodiments, the user 1690 is a rider of at least one vehicle 1610 in the set of vehicles 1694. In embodiments, the user 1690 is an administrator for a set of roadways to be used by at least one vehicle 1610 in the set of vehicles 1694. In embodiments, the user 1690 is an administrator for a fleet of vehicles including the set of vehicles 1694.

In embodiments, the reward-based interface 16104 is disposed for in-vehicle use. In embodiments, the at least one routing parameter 1630 includes at least one of: traffic congestion, desired arrival times, preferred routes, fuel efficiency, pollution reduction, accident avoidance, avoiding bad weather, avoiding bad road conditions, reduced fuel consumption, reduced carbon footprint, reduced noise in a region, avoiding high-crime regions, collective satisfaction, maximum speed limit, avoidance of toll roads, avoidance of city roads, avoidance of undivided highways, avoidance of left turns, and avoidance of driver-operated vehicles. In embodiments, the user 1690 responds to the reward 16102 offered in the reward-based interface 16104 by accepting the reward 16102 offered in the interface, rejecting the reward 16102 offered in the reward-based interface 16104, or ignoring the reward 16102 offered in the reward-based interface 16104. In embodiments, the user 1690 indicates the routing preference by either accepting or rejecting the reward 16102 offered in the reward-based interface 16104. In embodiments, the user 1690 indicates the routing preference by undertaking an action in at least one vehicle 1610 in the set of vehicles 1694 that facilitates transferring the reward 16102 to the user 1690.

In embodiments, the method further comprises sending, via a reward offer response processing circuit 16105, a signal to the vehicle routing system 1692 to select a vehicle route that permits adequate time for the user 1690 to perform the at least one user action. In embodiments, the method further comprises: sending, via a reward offer response processing circuit 16105, a signal to a vehicle routing system 1692, the signal indicating a destination of a vehicle associated with the at least one user action; and adjusting, by the vehicle routing system 1692, a route of the vehicle 1695 associated with the at least one user action to include the destination. In embodiments, the reward 16102 is associated with achieving a vehicle routing fuel efficiency objective.

In embodiments, the reward 16102 is associated with achieving a vehicle routing reduced traffic objective. In embodiments, the reward 16102 is associated with achieving a vehicle routing reduced pollution objective. In embodiments, the reward 16102 is associated with achieving a vehicle routing reduced carbon footprint objective. In embodiments, the reward 16102 is associated with achieving a vehicle routing reduced noise in neighborhoods objective.

In embodiments, reward 16102 is associated with achieving a vehicle routing collective satisfaction objective. In embodiments, the reward 16102 is associated with achieving a vehicle routing avoiding accident scenes objective.

In embodiments, the reward 16102 is associated with achieving a vehicle routing avoiding high-crime areas objective. In embodiments, the reward 16102 is associated with achieving a vehicle routing reduced traffic congestion objective. In embodiments, the reward 16102 is associated with achieving a vehicle routing bad weather avoidance objective. In embodiments, the reward 16102 is associated with achieving a vehicle routing maximum travel time objective. In embodiments, the reward 16102 is associated with achieving a vehicle routing maximum speed limit objective. In embodiments, the reward 16102 is associated with achieving a vehicle routing avoidance of toll roads objective. In embodiments, the reward 16102 is associated with achieving a vehicle routing avoidance of city roads objective. In embodiments, the reward 16102 is associated with achieving a vehicle routing avoidance of undivided highways objective. In embodiments, the reward 16102 is associated with achieving a vehicle routing avoidance of left turns objective. In embodiments, the reward 16102 is associated with achieving a vehicle routing avoidance of driver-operated vehicles objective.

Figure 18:
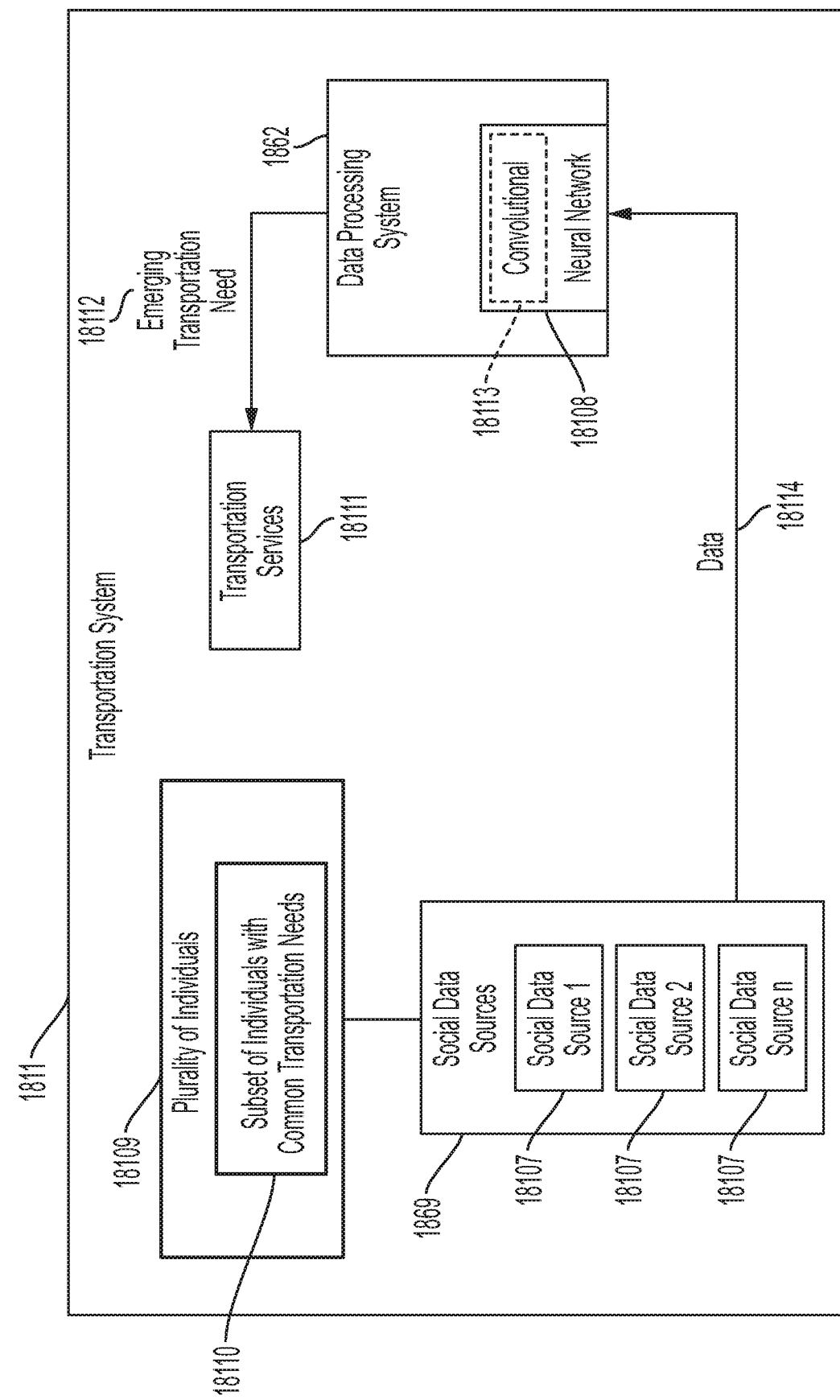
FIG. 18 is a diagrammatic view that illustrates systems described throughout this disclosure relating to various embodiments of the present disclosure.

Referring to FIG. 18, in embodiments provided herein are transportation systems 1811 having a data processing system 1862 for taking data 18114 from a plurality 1869 of social data sources 18107 and using a neural network 18108 to predict an emerging transportation need 18112 for a group of individuals. Among the various social data sources 18107, such as those described above, a large amount of data is available relating to social groups, such as friend groups, families, workplace colleagues, club members, people having shared interests or affiliations, political groups, and others. The expert system described above can be trained, as described throughout, such as using a training data set of human predictions and/or a model, with feedback of outcomes, to predict the transportation needs of a group. For example, based on a discussion thread of a social group as indicated at least in part on a social network feed, it may become evident that a group meeting or trip will take place, and the system may (such as using location information for respective members, as well as indicators of a set of destinations of the trip), predict where and when each member would need to travel in order to participate. Based on such a prediction, the system could automatically identify and show options for travel, such as available public transportation options, flight options, ride share options, and the like. Such options may include ones by which the group may share transportation, such as indicating a route that results in picking up a set of members of the group for travel together. Social media information may include posts, tweets, comments, chats, photographs, and the like and may be processed as noted above.

An aspect provided herein includes a system 1811 for transportation, comprising: a data processing system 1862 for taking data 18114 from a plurality 1869 of social data sources 18107 and using a neural network 18108 to predict an emerging transportation need 18112 for a group of individuals 18110.

Figure 19:
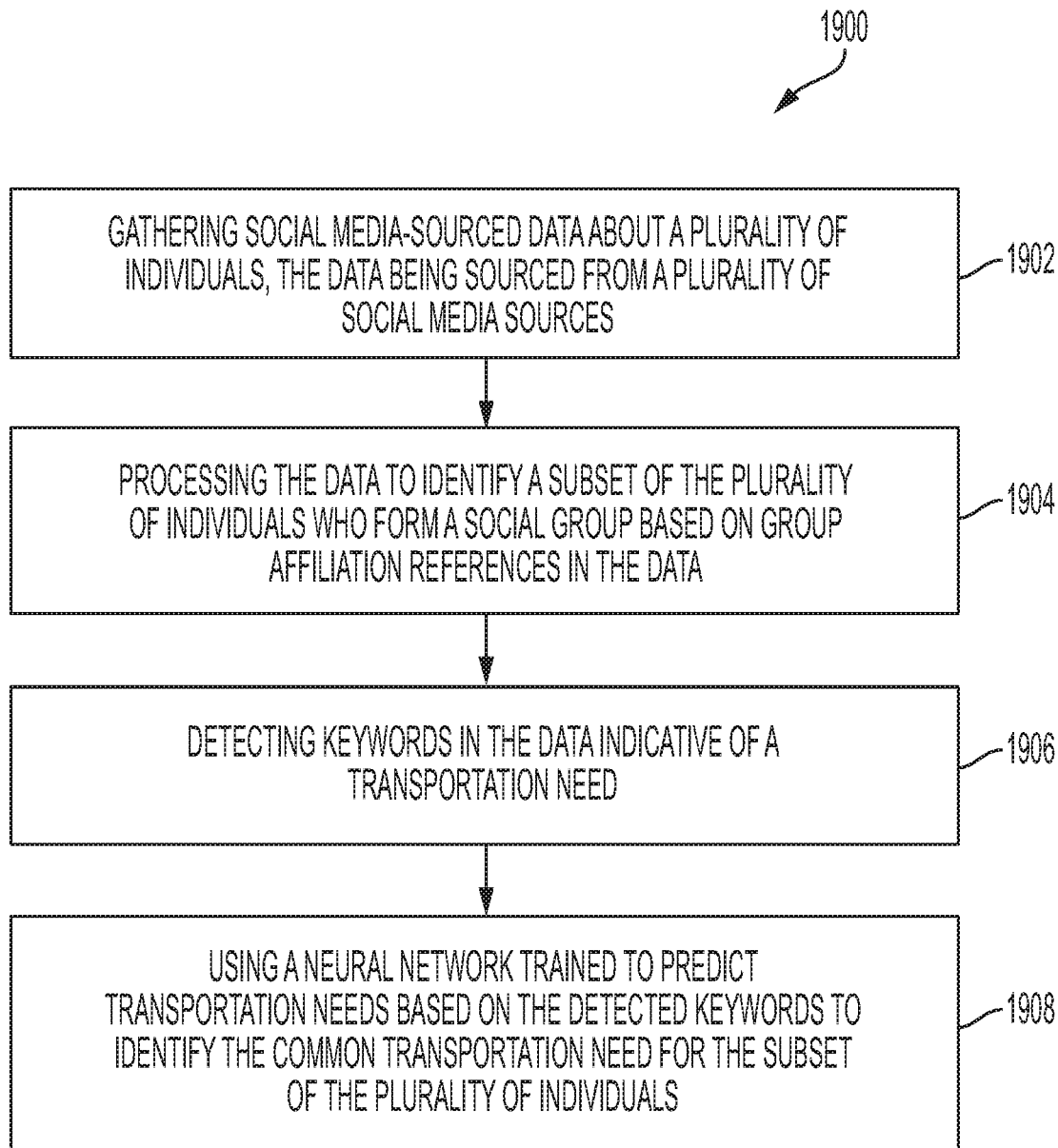
FIG. 19 is a diagrammatic view that illustrates a method described throughout this disclosure relating to various embodiments of the present disclosure.

FIG. 19 illustrates a method 1900 of predicting a common transportation need for a group in accordance with embodiments of the systems and methods disclosed herein. At 1902, the method includes gathering social media-sourced data about a plurality of individuals, the data being sourced from a plurality of social media sources. At 1904, the method includes processing the data to identify a subset of the plurality of individuals who form a social group based on group affiliation references in the data. At 1906, the method includes detecting keywords in the data indicative of a transportation need. At 1908, the method includes using a neural network trained to predict transportation needs based on the detected keywords to identify the common transportation need for the subset of the plurality of individuals.

Referring to FIG. 18 and FIG. 19, in embodiments, the neural network 18108 is a convolutional neural network 18113. In embodiments, the neural network 18108 is trained based on a model that facilitates matching phrases in social media with transportation activity. In embodiments, the neural network 18108 predicts at least one of a destination and an arrival time for the subset 18110 of the plurality of individuals sharing the common transportation need. In embodiments, the neural network 18108 predicts the common transportation need based on analysis of transportation need-indicative keywords detected in a discussion thread among a portion of individuals in the social group. In embodiments, the method further comprises identifying at least one shared transportation service 18111 that facilitates a portion of the social group meeting the predicted common transportation need 18112. In embodiments, the at least one shared transportation service comprises generating a vehicle route that facilitates picking up the portion of the social group.

Figure 20:
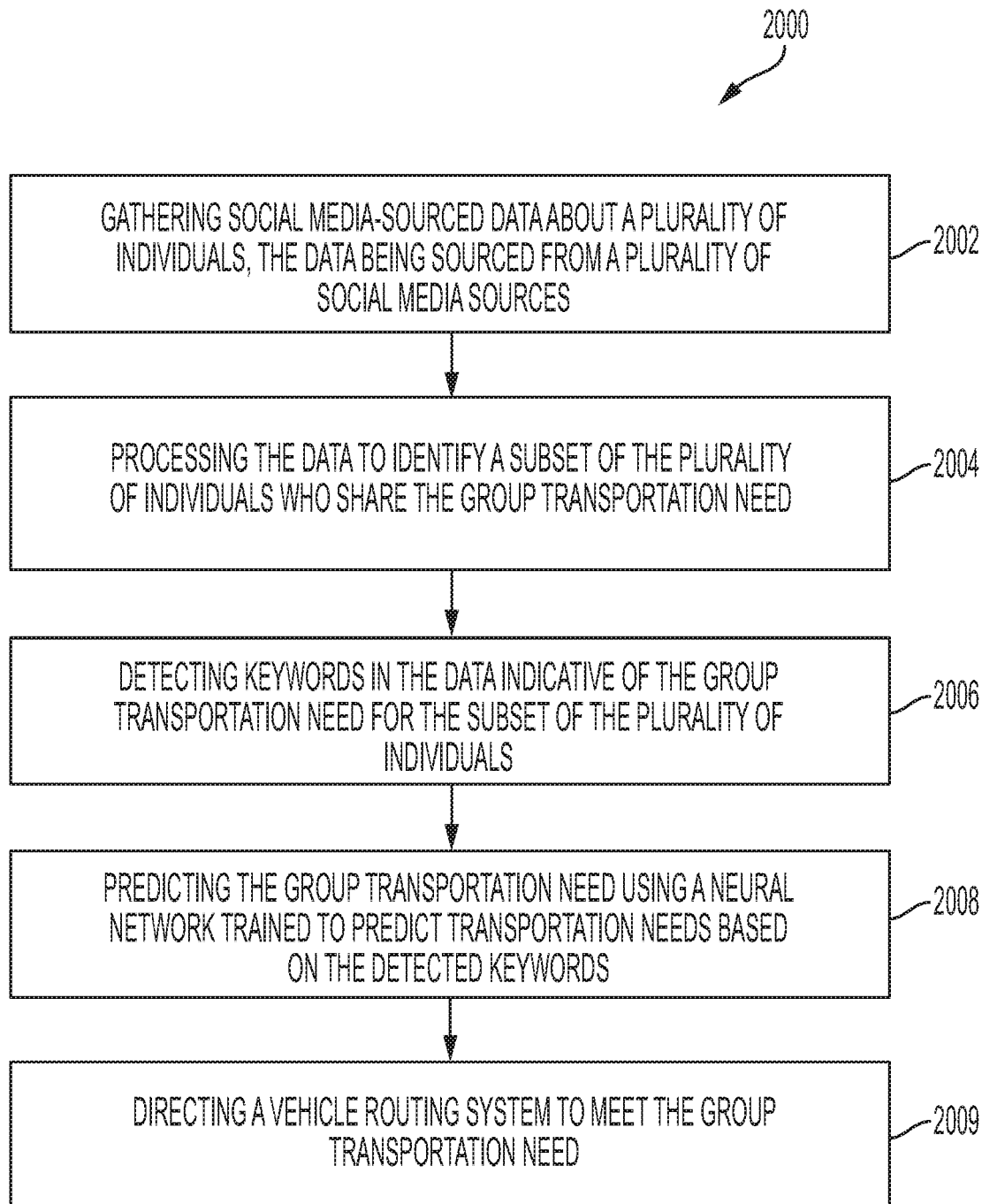
FIG. 20 is a diagrammatic view that illustrates a method described throughout this disclosure relating to various embodiments of the present disclosure.

FIG. 20 illustrates a method 2000 of predicting a group transportation need for a group in accordance with embodiments of the systems and methods disclosed herein. At 2002, the method includes gathering social media-sourced data about a plurality of individuals, the data being sourced from a plurality of social media sources. At 2004, the method includes processing the data to identify a subset of the plurality of individuals who share the group transportation need. At 2006, the method includes detecting keywords in the data indicative of the group transportation need for the subset of the plurality of individuals. At 2008, the method includes predicting the group transportation need using a neural network trained to predict transportation needs based on the detected keywords. At 2009, the method includes directing a vehicle routing system to meet the group transportation need.

Referring to FIG. 18 and FIG. 20, in embodiments, the neural network 18108 is a convolutional neural network 18113. In embodiments, directing the vehicle routing system to meet the group transportation need involves routing a plurality of vehicles to a destination derived from the social media-sourced data 18114. In embodiments, the neural network 18108 is trained based on a model that facilitates matching phrases in the social media-sourced data 18114 with transportation activities. In embodiments, the method further comprises predicting, by the neural network 18108, at least one of a destination and an arrival time for the subset 18110 of the plurality 18109 of individuals sharing the group transportation need. In embodiments, the method further comprises predicting, by the neural network 18108, the group transportation need based on an analysis of transportation need-indicative keywords detected in a discussion thread in the social media-sourced data 18114. In embodiments, the method further comprises identifying at least one shared transportation service 18111 that facilitates meeting the predicted group transportation need for at least a portion of the subset 18110 of the plurality of individuals. In embodiments, the at least one shared transportation service 18111 comprises generating a vehicle route that facilitates picking up the at least the portion of the subset 18110 of the plurality of individuals.

Figure 21:
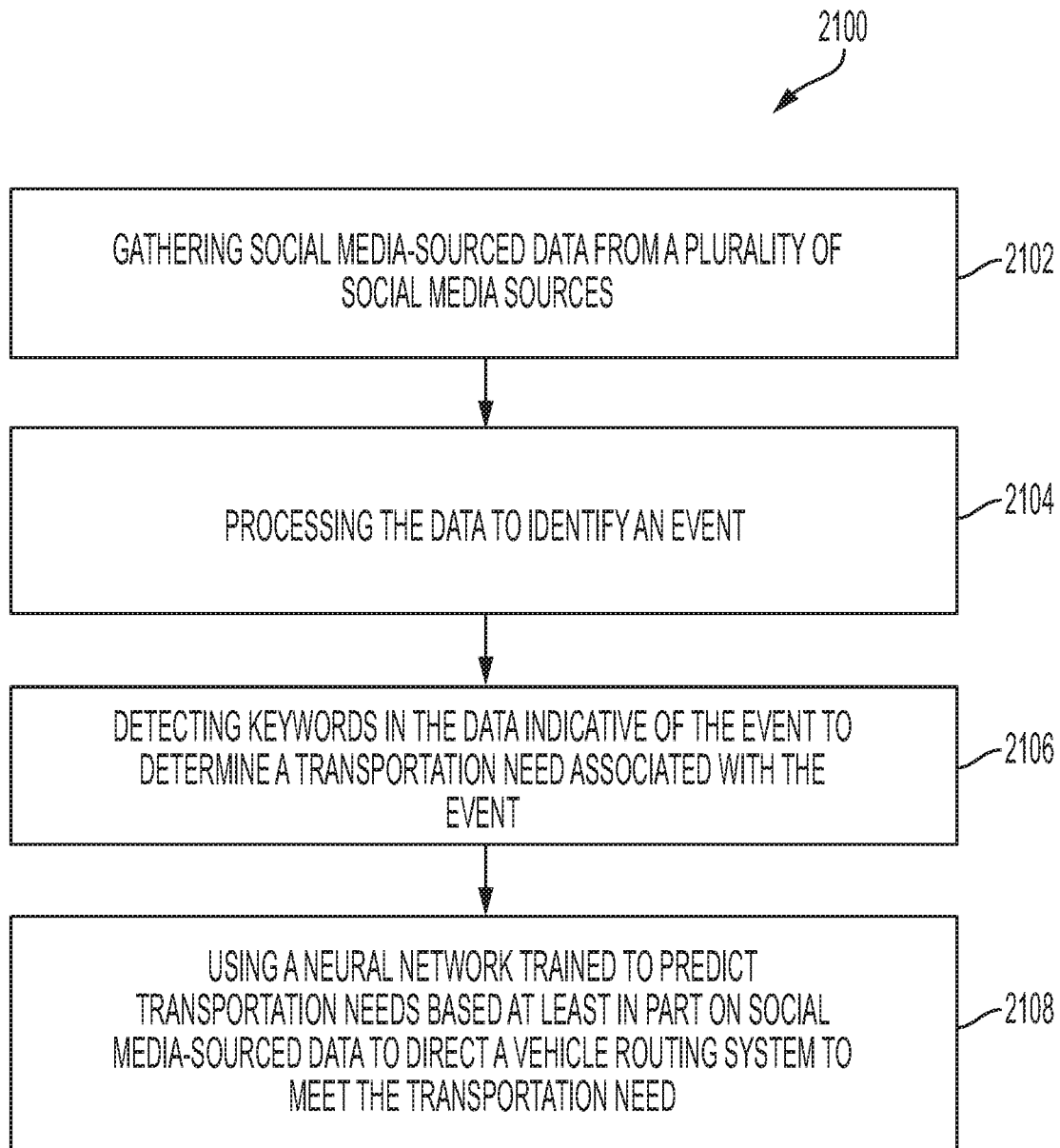
FIG. 21 is a diagrammatic view that illustrates a method described throughout this disclosure relating to various embodiments of the present disclosure.

FIG. 21 illustrates a method 2100 of predicting a group transportation need in accordance with embodiments of the systems and methods disclosed herein. At 2102, the method includes gathering social media-sourced data from a plurality of social media sources. At 2104, the method includes processing the data to identify an event. At 2106, the method includes detecting keywords in the data indicative of the event to determine a transportation need associated with the event. At 2108, the method includes using a neural network trained to predict transportation needs based at least in part on social media-sourced data to direct a vehicle routing system to meet the transportation need.

Referring to FIG. 18 and FIG. 21, in embodiments, the neural network 18108 is a convolutional neural network 18113. In embodiments, the vehicle routing system is directed to meet the transportation need by routing a plurality of vehicles to a location associated with the event. In embodiments, the vehicle routing system is directed to meet the transportation need by routing a plurality of vehicles to avoid a region proximal to a location associated with the event. In embodiments, the vehicle routing system is directed to meet the transportation need by routing vehicles associated with users whose social media-sourced data 18114 do not indicate the transportation need to avoid a region proximal to a location associated with the event. In embodiments, the method further comprises presenting at least one transportation service for satisfying the transportation need. In embodiments, the neural network 18108 is trained based on a model that facilitates matching phrases in social media-sourced data 18114 with transportation activity.

In embodiments, the neural network 18108 predicts at least one of a destination and an arrival time for individuals attending the event. In embodiments, the neural network 18108 predicts the transportation need based on analysis of transportation need-indicative keywords detected in a discussion thread in the social media-sourced data 18114. In embodiments, the method further comprises identifying at least one shared transportation service that facilitates meeting the predicted transportation need for at least a subset of individuals identified in the social media-sourced data 18114. In embodiments, the at least one shared transportation service comprises generating a vehicle route that facilitates picking up the portion of the subset of individuals identified in the social media-sourced data 18114.

Figure 22:
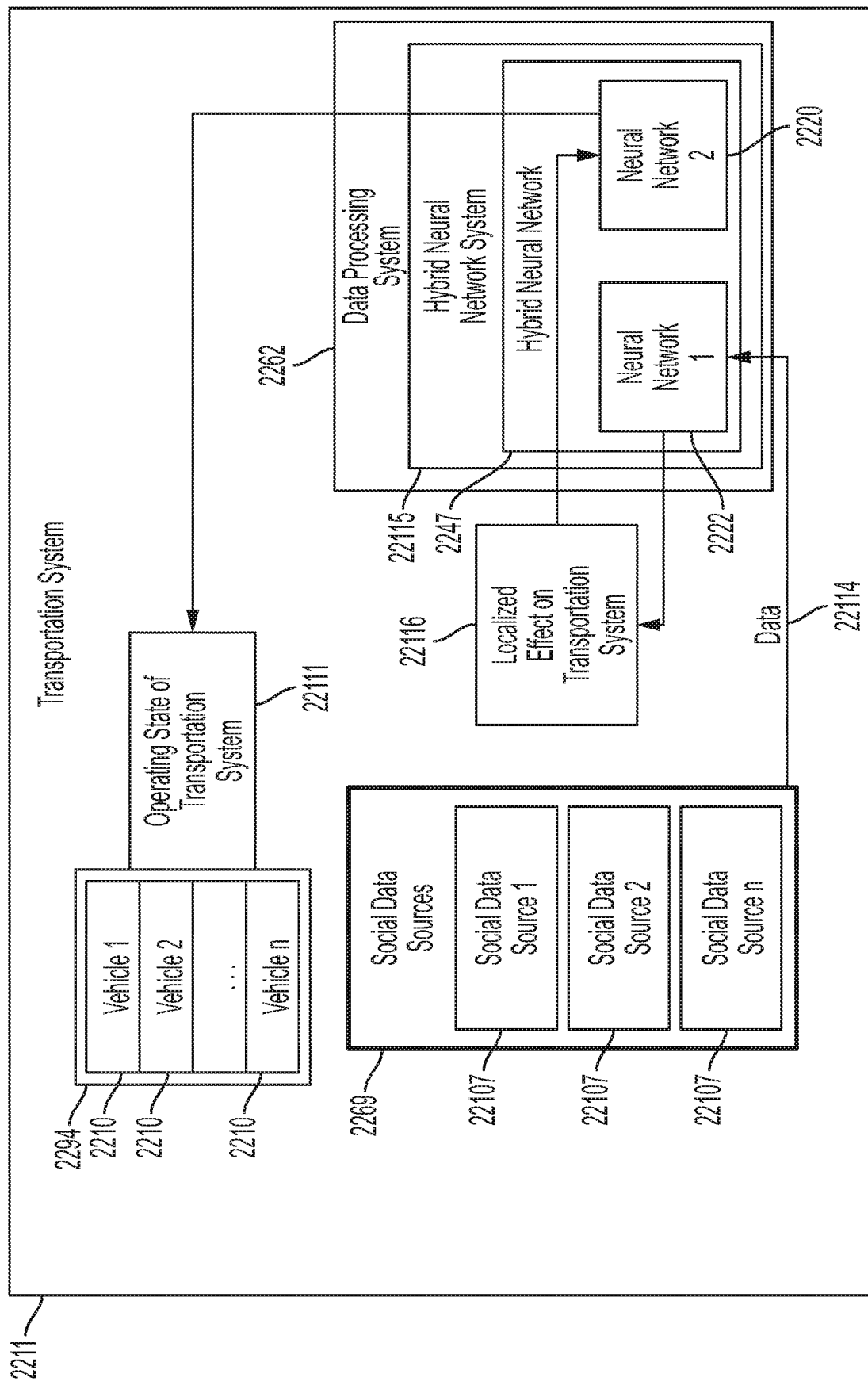
FIG. 22 is a diagrammatic view that illustrates systems described throughout this disclosure relating to various embodiments of the present disclosure.

Referring to FIG. 22, in embodiments provided herein are transportation systems 2211 having a data processing system 2211 for taking social media data 22114 from a plurality 2269 of social data sources 22107 and using a hybrid neural network 2247 to optimize an operating state of a transportation system 22111 based on processing the social data sources 22107 with the hybrid neural network 2247. A hybrid neural network 2247 may have, for example, a neural network component that makes a classification or prediction based on processing social media data 22114 (such as predicting a high level of attendance of an event by processing images on many social media feeds that indicate interest in the event by many people, prediction of traffic, classification of interest by an individual in a topic, and many others) and another component that optimizes an operating state of a transportation system, such as an in-vehicle state, a routing state (for an individual vehicle 2210 or a set of vehicles 2294), a user-experience state, or other state described throughout this disclosure (e.g., routing an individual early to a venue like a music festival where there is likely to be very high attendance, playing music content in a vehicle 2210 for bands who will be at the music festival, or the like).

An aspect provided herein includes a system for transportation, comprising: a data processing system 2211 for taking social media data 22114 from a plurality 2269 of social data sources 22107 and using a hybrid neural network 2247 to optimize an operating state of a transportation system based on processing the data 22114 from the plurality 2269 of social data sources 22107 with the hybrid neural network 2247.

An aspect provided herein includes a hybrid neural network system 22115 for transportation system optimization, the hybrid neural network system 22115 comprising a hybrid neural network 2247, including: a first neural network 2222 that predicts a localized effect 22116 on a transportation system through analysis of social medial data 22114 sourced from a plurality 2269 of social media data sources 22107; and a second neural network 2220 that optimizes an operating state of the transportation system based on the predicted localized effect 22116.

In embodiments, at least one of the first neural network 2222 and the second neural network 2220 is a convolutional neural network. In embodiments, the second neural network 2220 is to optimize an in-vehicle rider experience state. In embodiments, the first neural network 2222 identifies a set of vehicles 2294 contributing to the localized effect 22116 based on correlation of vehicle location and an area of the localized effect 22116. In embodiments, the second neural network 2220 is to optimize a routing state of the transportation system for vehicles proximal to a location of the localized effect 22116. In embodiments, the hybrid neural network 2247 is trained for at least one of the predicting and optimizing based on keywords in the social media data indicative of an outcome of a transportation system optimization action. In embodiments, the hybrid neural network 2247 is trained for at least one of predicting and optimizing based on social media posts.

In embodiments, the hybrid neural network 2247 is trained for at least one of predicting and optimizing based on social media feeds. In embodiments, the hybrid neural network 2247 is trained for at least one of predicting and optimizing based on ratings derived from the social media data 22114. In embodiments, the hybrid neural network 2247 is trained for at least one of predicting and optimizing based on like or dislike activity detected in the social media data 22114. In embodiments, the hybrid neural network 2247 is trained for at least one of predicting and optimizing based on indications of relationships in the social media data 22114. In embodiments, the hybrid neural network 2247 is trained for at least one of predicting and optimizing based on user behavior detected in the social media data 22114. In embodiments, the hybrid neural network 2247 is trained for at least one of predicting and optimizing based on discussion threads in the social media data 22114.

In embodiments, the hybrid neural network 2247 is trained for at least one of predicting and optimizing based on chats in the social media data 22114. In embodiments, the hybrid neural network 2247 is trained for at least one of predicting and optimizing based on photographs in the social media data 22114. In embodiments, the hybrid neural network 2247 is trained for at least one of predicting and optimizing based on traffic-affecting information in the social media data 22114. In embodiments, the hybrid neural network 2247 is trained for at least one of predicting and optimizing based on an indication of a specific individual at a location in the social media data 22114. In embodiments, the specific individual is a celebrity. In embodiments, the hybrid neural network 2247 is trained for at least one of predicting and optimizing based a presence of a rare or transient phenomena at a location in the social media data 22114.

In embodiments, the hybrid neural network 2247 is trained for at least one of predicting and optimizing based a commerce-related event at a location in the social media data 22114. In embodiments, the hybrid neural network 2247 is trained for at least one of predicting and optimizing based an entertainment event at a location in the social media data 22114. In embodiments, the social media data analyzed to predict a localized effect on a transportation system includes traffic conditions. In embodiments, the social media data analyzed to predict a localized effect on a transportation system includes weather conditions. In embodiments, the social media data analyzed to predict a localized effect on a transportation system includes entertainment options.

In embodiments, the social media data analyzed to predict a localized effect on a transportation system includes risk-related conditions. In embodiments, the risk-related conditions include crowds gathering for potentially dangerous reasons. In embodiments, the social media data analyzed to predict a localized effect on a transportation system includes commerce-related conditions. In embodiments, the social media data analyzed to predict a localized effect on a transportation system includes goal-related conditions.

In embodiments, the social media data analyzed to predict a localized effect on a transportation system includes estimates of attendance at an event. In embodiments, the social media data analyzed to predict a localized effect on a transportation system includes predictions of attendance at an event. In embodiments, the social media data analyzed to predict a localized effect on a transportation system includes modes of transportation. In embodiments, the modes of transportation include car traffic. In embodiments, the modes of transportation include public transportation options.

In embodiments, the social media data analyzed to predict a localized effect on a transportation system includes hash tags. In embodiments, the social media data analyzed to predict a localized effect on a transportation system includes trending of topics. In embodiments, an outcome of a transportation system optimization action is reducing fuel consumption. In embodiments, an outcome of a transportation system optimization action is reducing traffic congestion. In embodiments, an outcome of a transportation system optimization action is reduced pollution. In embodiments, an outcome of a transportation system optimization action is bad weather avoidance. In embodiments, an operating state of the transportation system being optimized includes an in-vehicle state. In embodiments, an operating state of the transportation system being optimized includes a routing state.

In embodiments, the routing state is for an individual vehicle 2210. In embodiments, the routing state is for a set of vehicles 2294. In embodiments, an operating state of the transportation system being optimized includes a user-experience state.

Figure 23:
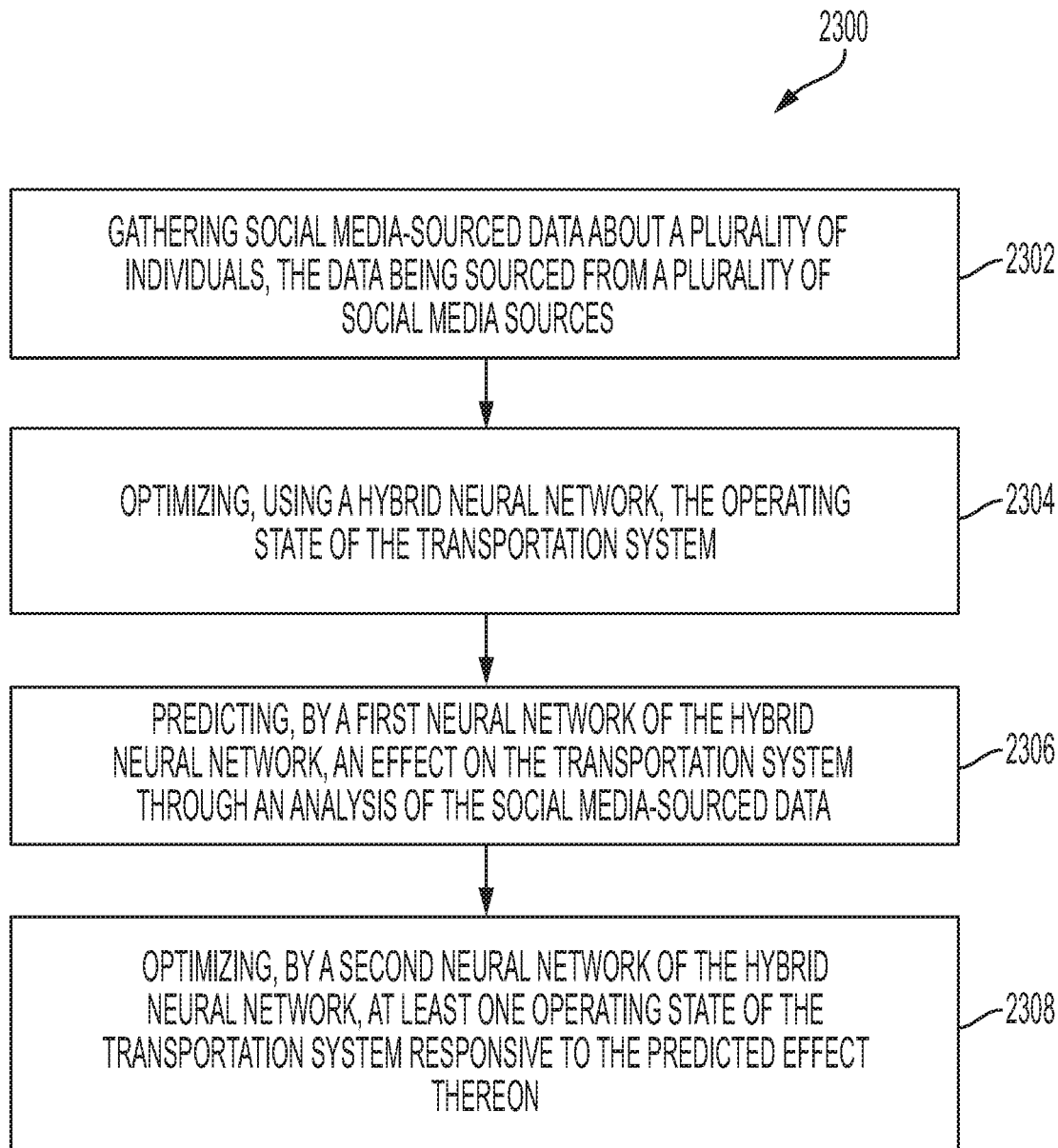
FIG. 23 is a diagrammatic view that illustrates a method described throughout this disclosure relating to various embodiments of the present disclosure.

FIG. 23 illustrates a method 2300 of optimizing an operating state of a transportation system in accordance with embodiments of the systems and methods disclosed herein. At 2302 the method includes gathering social media-sourced data about a plurality of individuals, the data being sourced from a plurality of social media sources. At 2304 the method includes optimizing, using a hybrid neural network, the operating state of the transportation system. At 2306 the method includes predicting, by a first neural network of the hybrid neural network, an effect on the transportation system through an analysis of the social media-sourced data. At 2308 the method includes optimizing, by a second neural network of the hybrid neural network, at least one operating state of the transportation system responsive to the predicted effect thereon.

Referring to FIG. 22 and FIG. 23, in embodiments, at least one of the first neural network 2222 and the second neural network 2220 is a convolutional neural network. In embodiments, the second neural network 2220 optimizes an in-vehicle rider experience state. In embodiments, the first neural network 2222 identifies a set of vehicles contributing to the effect based on correlation of vehicle location and an effect area. In embodiments, the second neural network 2220 optimizes a routing state of the transportation system for vehicles proximal to a location of the effect.

In embodiments, the hybrid neural network 2247 is trained for at least one of the predicting and optimizing based on keywords in the social media data indicative of an outcome of a transportation system optimization action. In embodiments, the hybrid neural network 2247 is trained for at least one of predicting and optimizing based on social media posts. In embodiments, the hybrid neural network 2247 is trained for at least one of predicting and optimizing based on social media feeds. In embodiments, the hybrid neural network 2247 is trained for at least one of predicting and optimizing based on ratings derived from the social media data 22114. In embodiments, the hybrid neural network 2247 is trained for at least one of predicting and optimizing based on like or dislike activity detected in the social media data 22114. In embodiments, the hybrid neural network 2247 is trained for at least one of predicting and optimizing based on indications of relationships in the social media data 22114.

In embodiments, the hybrid neural network 2247 is trained for at least one of predicting and optimizing based on user behavior detected in the social media data 22114. In embodiments, the hybrid neural network 2247 is trained for at least one of predicting and optimizing based on discussion threads in the social media data 22114. In embodiments, the hybrid neural network 2247 is trained for at least one of predicting and optimizing based on chats in the social media data 22114. In embodiments, the hybrid neural network 2247 is trained for at least one of predicting and optimizing based on photographs in the social media data 22114. In embodiments, the hybrid neural network 2247 is trained for at least one of predicting and optimizing based on traffic-affecting information in the social media data 22114.

In embodiments, the hybrid neural network 2247 is trained for at least one of predicting and optimizing based on an indication of a specific individual at a location in the social media data. In embodiments, the specific individual is a celebrity. In embodiments, the hybrid neural network 2247 is trained for at least one of predicting and optimizing based a presence of a rare or transient phenomena at a location in the social media data. In embodiments, the hybrid neural network 2247 is trained for at least one of predicting and optimizing based a commerce-related event at a location in the social media data. In embodiments, the hybrid neural network 2247 is trained for at least one of predicting and optimizing based an entertainment event at a location in the social media data. In embodiments, the social media data analyzed to predict an effect on a transportation system includes traffic conditions.

In embodiments, the social media data analyzed to predict an effect on a transportation system includes weather conditions. In embodiments, the social media data analyzed to predict an effect on a transportation system includes entertainment options. In embodiments, the social media data analyzed to predict an effect on a transportation system includes risk-related conditions. In embodiments, the risk-related conditions include crowds gathering for potentially dangerous reasons. In embodiments, the social media data analyzed to predict an effect on a transportation system includes commerce-related conditions. In embodiments, the social media data analyzed to predict an effect on a transportation system includes goal-related conditions.

In embodiments, the social media data analyzed to predict an effect on a transportation system includes estimates of attendance at an event. In embodiments, the social media data analyzed to predict an effect on a transportation system includes predictions of attendance at an event. In embodiments, the social media data analyzed to predict an effect on a transportation system includes modes of transportation. In embodiments, the modes of transportation include car traffic. In embodiments, the modes of transportation include public transportation options. In embodiments, the social media data analyzed to predict an effect on a transportation system includes hash tags. In embodiments, the social media data analyzed to predict an effect on a transportation system includes trending of topics.

In embodiments, an outcome of a transportation system optimization action is reducing fuel consumption. In embodiments, an outcome of a transportation system optimization action is reducing traffic congestion. In embodiments, an outcome of a transportation system optimization action is reduced pollution. In embodiments, an outcome of a transportation system optimization action is bad weather avoidance. In embodiments, the operating state of the transportation system being optimized includes an in-vehicle state. In embodiments, the operating state of the transportation system being optimized includes a routing state. In embodiments, the routing state is for an individual vehicle. In embodiments, the routing state is for a set of vehicles. In embodiments, the operating state of the transportation system being optimized includes a user-experience state.

Figure 24:
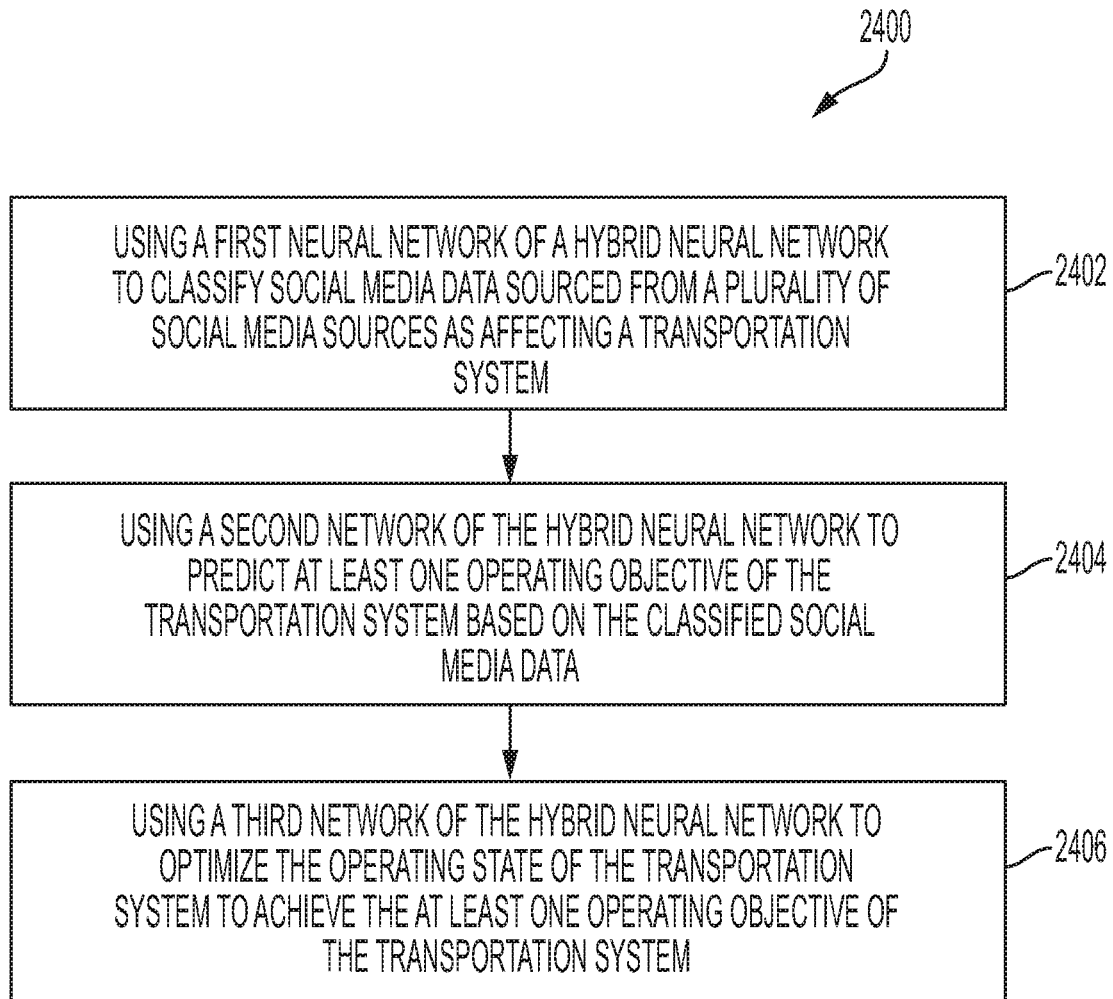
FIG. 24 is a diagrammatic view that illustrates a method described throughout this disclosure relating to various embodiments of the present disclosure.

FIG. 24 illustrates a method 2400 of optimizing an operating state of a transportation system in accordance with embodiments of the systems and methods disclosed herein. At 2402 the method includes using a first neural network of a hybrid neural network to classify social media data sourced from a plurality of social media sources as affecting a transportation system. At 2404 the method includes using a second network of the hybrid neural network to predict at least one operating objective of the transportation system based on the classified social media data. At 2406 the method includes using a third network of the hybrid neural network to optimize the operating state of the transportation system to achieve the at least one operating objective of the transportation system.

Referring to FIG. 22 and FIG. 24, in embodiments, at least one of the neural networks in the hybrid neural network 2247 is a convolutional neural network.

Figure 25:
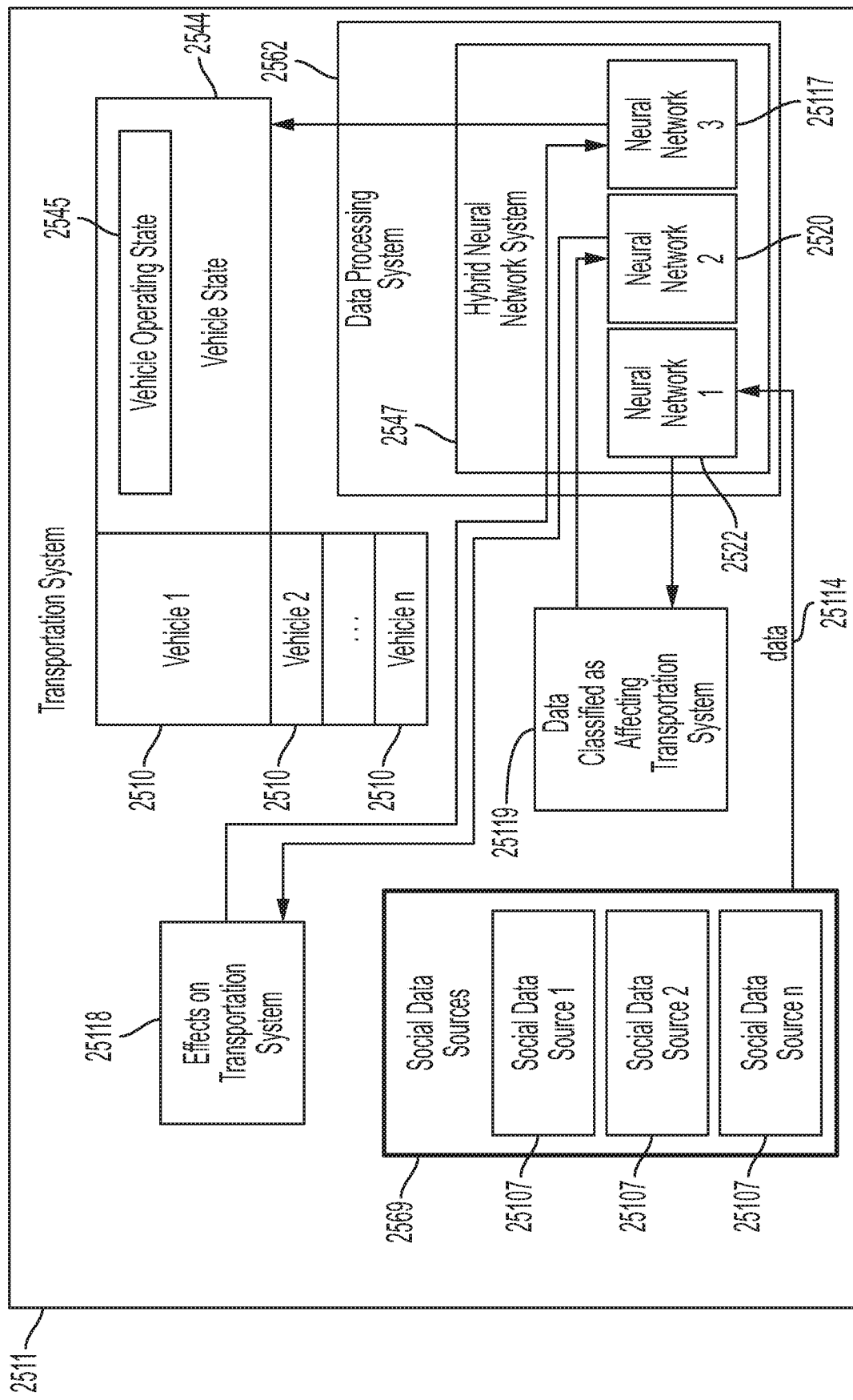
FIG. 25 is a diagrammatic view that illustrates systems described throughout this disclosure relating to various embodiments of the present disclosure.

Referring to FIG. 25, in embodiments provided herein are transportation systems 2511 having a data processing system 2562 for taking social media data 25114 from a plurality of social data sources 25107 and using a hybrid neural network 2547 to optimize an operating state 2545 of a vehicle 2510 based on processing the social data sources with the hybrid neural network 2547. In embodiments, the hybrid neural network 2547 can include one neural network category for prediction, another for classification, and another for optimization of one or more operating states, such as based on optimizing one or more desired outcomes (such a providing efficient travel, highly satisfying rider experiences, comfortable rides, on-time arrival, or the like). Social data sources 2569 may be used by distinct neural network categories (such as any of the types described herein) to predict travel times, to classify content such as for profiling interests of a user, to predict objectives for a transportation plan (such as what will provide overall satisfaction for an individual or a group) and the like. Social data sources 2569 may also inform optimization, such as by providing indications of successful outcomes (e.g., a social data source 25107 like a Facebook feed might indicate that a trip was "amazing" or "horrible," a Yelp review might indicate a restaurant was terrible, or the like). Thus, social data sources 2569, by contributing to outcome tracking, can be used to train a system to optimize transportation plans, such as relating to timing, destinations, trip purposes, what individuals should be invited, what entertainment options should be selected, and many others.

An aspect provided herein includes a system for transportation 2511, comprising: a data processing system 2562 for taking social media data 25114 from a plurality of social data sources 25107 and using a hybrid neural network 2547 to optimize an operating state 2545 of a vehicle 2510 based on processing the data 25114 from the plurality of social data sources 25107 with the hybrid neural network 2547.

Figure 26:
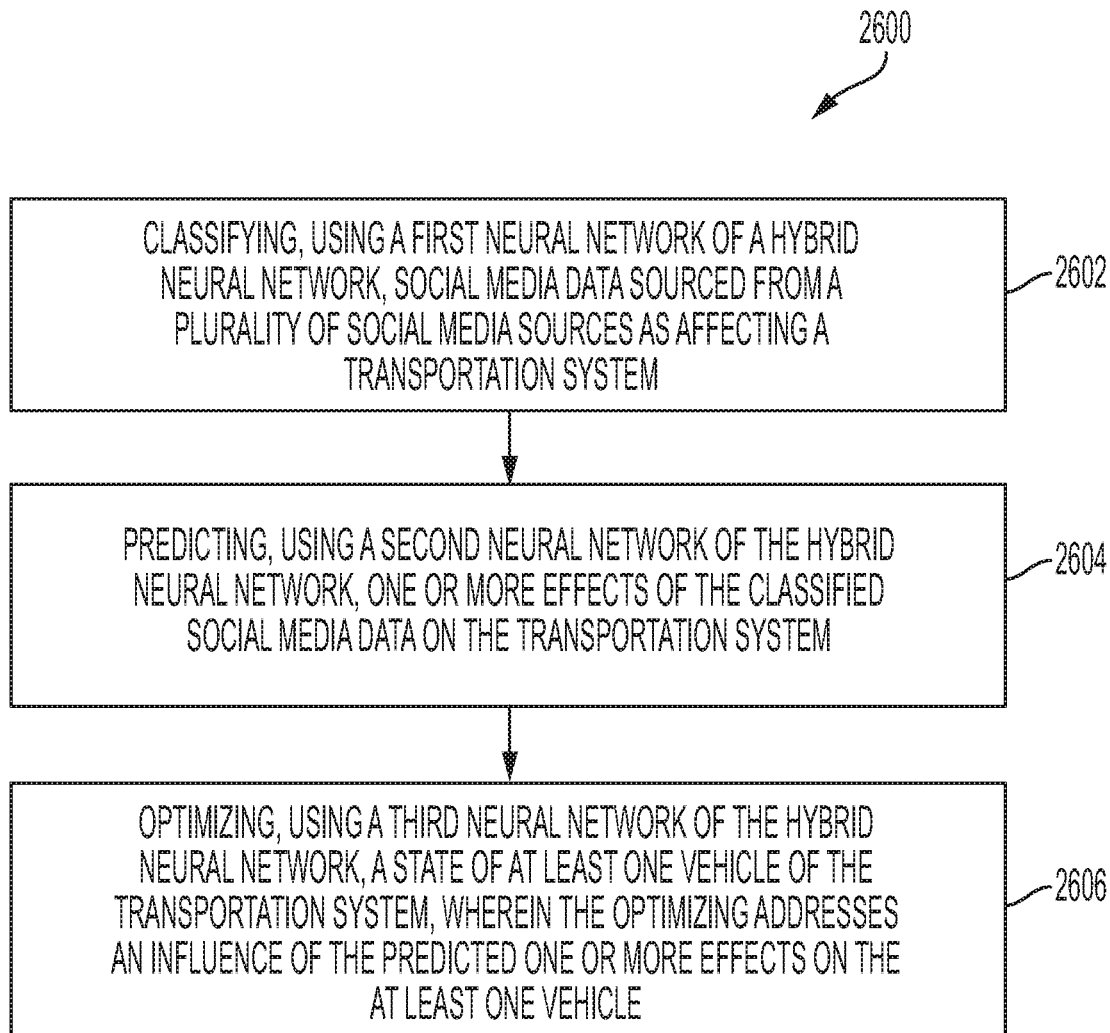
FIG. 26 is a diagrammatic view that illustrates a method described throughout this disclosure relating to various embodiments of the present disclosure.

FIG. 26 illustrates a method 2600 of optimizing an operating state of a vehicle in accordance with embodiments of the systems and methods disclosed herein. At 2602 the method includes classifying, using a first neural network 2522 (FIG. 25) of a hybrid neural network, social media data 25119 (FIG. 25) sourced from a plurality of social media sources as affecting a transportation system. At 2604 the method includes predicting, using a second neural network 2520 (FIG. 25) of the hybrid neural network, one or more effects 25118 (FIG. 25) of the classified social media data on the transportation system. At 2606 the method includes optimizing, using a third neural network 25117 (FIG. 25) of the hybrid neural network, a state of at least one vehicle of the transportation system, wherein the optimizing addresses an influence of the predicted one or more effects on the at least one vehicle.

Referring to FIG. 25 and FIG. 26, in embodiments, at least one of the neural networks in the hybrid neural network 2547 is a convolutional neural network. In embodiments, the social media data 25114 includes social media posts. In embodiments, the social media data 25114 includes social media feeds. In embodiments, the social media data 25114 includes like or dislike activity detected in the social media. In embodiments, the social media data 25114 includes indications of relationships. In embodiments, the social media data 25114 includes user behavior. In embodiments, the social media data 25114 includes discussion threads. In embodiments, the social media data 25114 includes chats. In embodiments, the social media data 25114 includes photographs.

In embodiments, the social media data 25114 includes traffic-affecting information. In embodiments, the social media data 25114 includes an indication of a specific individual at a location. In embodiments, the social media data 25114 includes an indication of a celebrity at a location. In embodiments, the social media data 25114 includes presence of a rare or transient phenomena at a location. In embodiments, the social media data 25114 includes a commerce-related event. In embodiments, the social media data 25114 includes an entertainment event at a location. In embodiments, the social media data 25114 includes traffic conditions. In embodiments, the social media data 25114 includes weather conditions. In embodiments, the social media data 25114 includes entertainment options.

In embodiments, the social media data 25114 includes risk-related conditions. In embodiments, the social media data 25114 includes predictions of attendance at an event. In embodiments, the social media data 25114 includes estimates of attendance at an event. In embodiments, the social media data 25114 includes modes of transportation used with an event. In embodiments, the effect 25118 on the transportation system includes reducing fuel consumption. In embodiments, the effect 25118 on the transportation system includes reducing traffic congestion. In embodiments, the effect 25118 on the transportation system includes reduced carbon footprint. In embodiments, the effect 25118 on the transportation system includes reduced pollution.

In embodiments, the optimized state 2544 of the at least one vehicle 2510 is an operating state of the vehicle 2545. In embodiments, the optimized state of the at least one vehicle includes an in-vehicle state. In embodiments, the optimized state of the at least one vehicle includes a rider state. In embodiments, the optimized state of the at least one vehicle includes a routing state. In embodiments, the optimized state of the at least one vehicle includes user experience state. In embodiments, a characterization of an outcome of the optimizing in the social media data 25114 is used as feedback to improve the optimizing. In embodiments, the feedback includes likes and dislikes of the outcome. In embodiments, the feedback includes social medial activity referencing the outcome.

In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

Figure 26A:
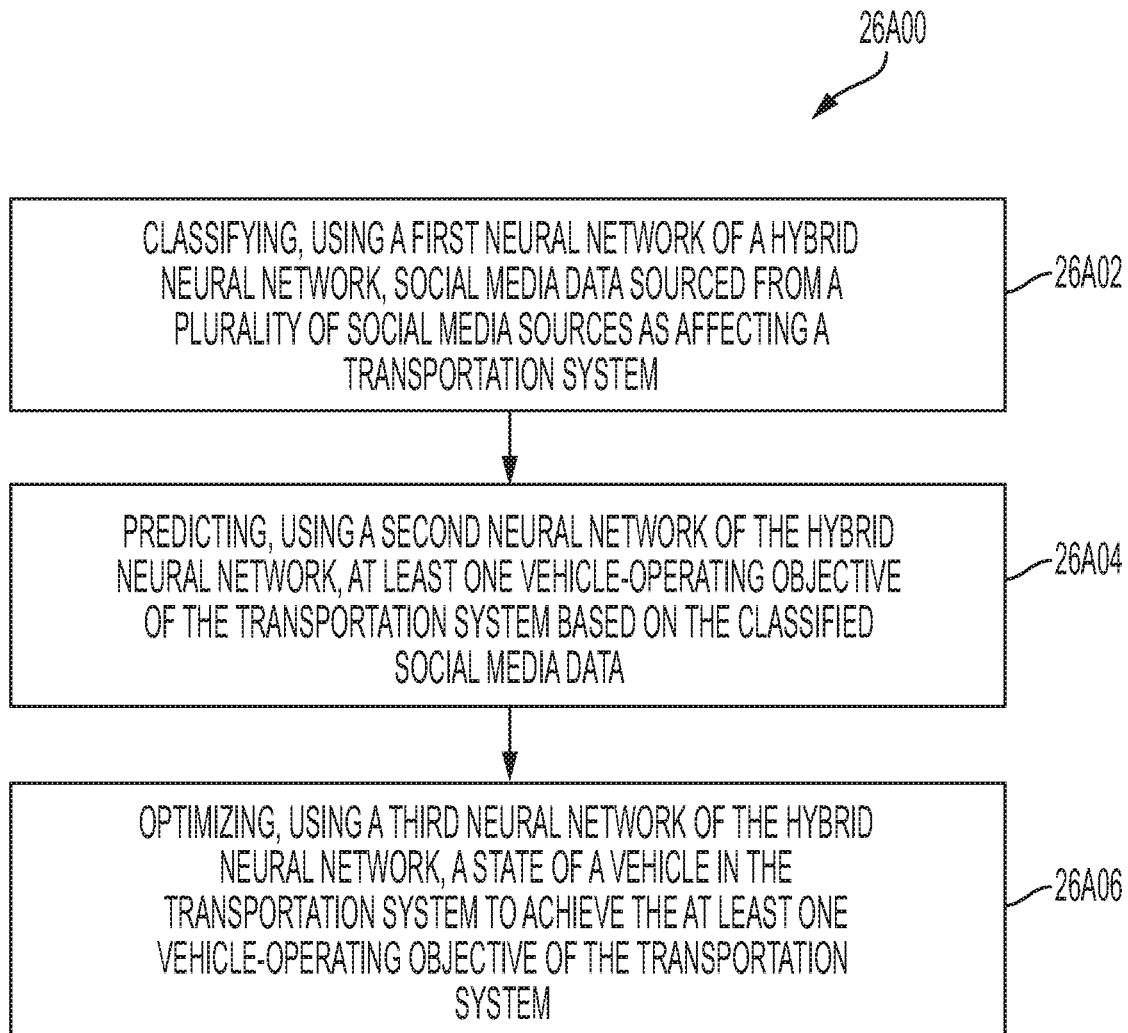
FIG. 26A is a diagrammatic view that illustrates systems described throughout this disclosure relating to various embodiments of the present disclosure.

FIG. 26A illustrates a method 26A00 of optimizing an operating state of a vehicle in accordance with embodiments of the systems and methods disclosed herein. At 26A02 the method includes classifying, using a first neural network of a hybrid neural network, social media data sourced from a plurality of social media sources as affecting a transportation system. At 26A04 the method includes predicting, using a second neural network of the hybrid neural network, at least one vehicle-operating objective of the transportation system based on the classified social media data. At 26A06 the method includes optimizing, using a third neural network of the hybrid neural network, a state of a vehicle in the transportation system to achieve the at least one vehicle-operating objective of the transportation system.

Referring to FIG. 25 and FIG. 26A, in embodiments, at least one of the neural networks in the hybrid neural network 2547 is a convolutional neural network. In embodiments, the vehicle-operating objective comprises achieving a rider state of at least one rider in the vehicle. In embodiments, the social media data 25114 includes social media posts.

In embodiments, the social media data 25114 includes social media feeds. In embodiments, the social media data 25114 includes like and dislike activity detected in the social media. In embodiments, the social media data 25114 includes indications of relationships. In embodiments, the social media data 25114 includes user behavior. In embodiments, the social media data 25114 includes discussion threads. In embodiments, the social media data 25114 includes chats. In embodiments, the social media data 25114 includes photographs. In embodiments, the social media data 25114 includes traffic-affecting information.

In embodiments, the social media data 25114 includes an indication of a specific individual at a location. In embodiments, the social media data 25114 includes an indication of a celebrity at a location. In embodiments, the social media data 25114 includes presence of a rare or transient phenomena at a location. In embodiments, the social media data 25114 includes a commerce-related event. In embodiments, the social media data 25114 includes an entertainment event at a location. In embodiments, the social media data 25114 includes traffic conditions. In embodiments, the social media data 25114 includes weather conditions. In embodiments, the social media data 25114 includes entertainment options.

In embodiments, the social media data 25114 includes risk-related conditions. In embodiments, the social media data 25114 includes predictions of attendance at an event. In embodiments, the social media data 25114 includes estimates of attendance at an event. In embodiments, the social media data 25114 includes modes of transportation used with an event. In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized state of the vehicle is an operating state of the vehicle.

In embodiments, the optimized state of the vehicle includes an in-vehicle state. In embodiments, the optimized state of the vehicle includes a rider state. In embodiments, the optimized state of the vehicle includes a routing state. In embodiments, the optimized state of the vehicle includes user experience state. In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome.

In embodiments, the feedback includes hash tags associated with the outcome. In embodiments, the feedback includes ratings of the outcome. In embodiments, the feedback includes requests for the outcome.

Figure 27:
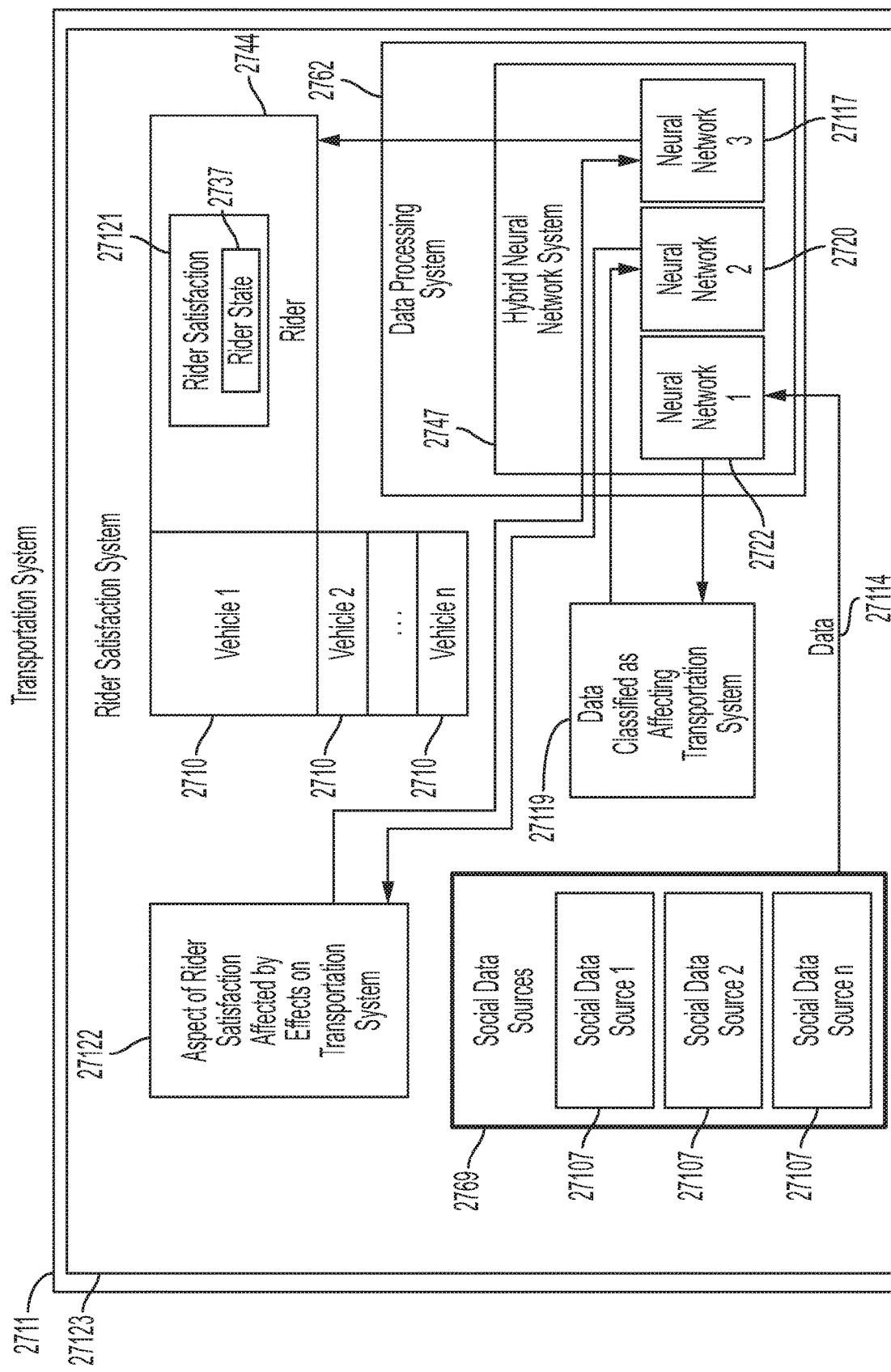
FIG. 27 is a diagrammatic view that illustrates systems described throughout this disclosure relating to various embodiments of the present disclosure.

Referring to FIG. 27, in embodiments provided herein are transportation systems 2711 having a data processing system 2762 for taking data 27114 from a plurality 2769 of social data sources 27107 and using a hybrid neural network 2747 to optimize satisfaction 27121 of at least one rider 27120 in a vehicle 2710 based on processing the social data sources with the hybrid neural network 2747. Social data sources 2769 may be used, for example, to predict what entertainment options are most likely to be effective for a rider 27120 by one neural network category, while another neural network category may be used to optimize a routing plan (such as based on social data that indicates likely traffic, points of interest, or the like). Social data 27114 may also be used for outcome tracking and feedback to optimize the system, both as to entertainment options and as to transportation planning, routing, or the like.

An aspect provided herein includes a system for transportation 2711, comprising: a data processing system 2762 for taking data 27114 from a plurality 2769 of social data sources 27107 and using a hybrid neural network 2747 to optimize satisfaction 27121 of at least one rider 27120 in a vehicle 2710 based on processing the data 27114 from the plurality 2769 of social data sources 27107 with the hybrid neural network 2747.

Figure 28:
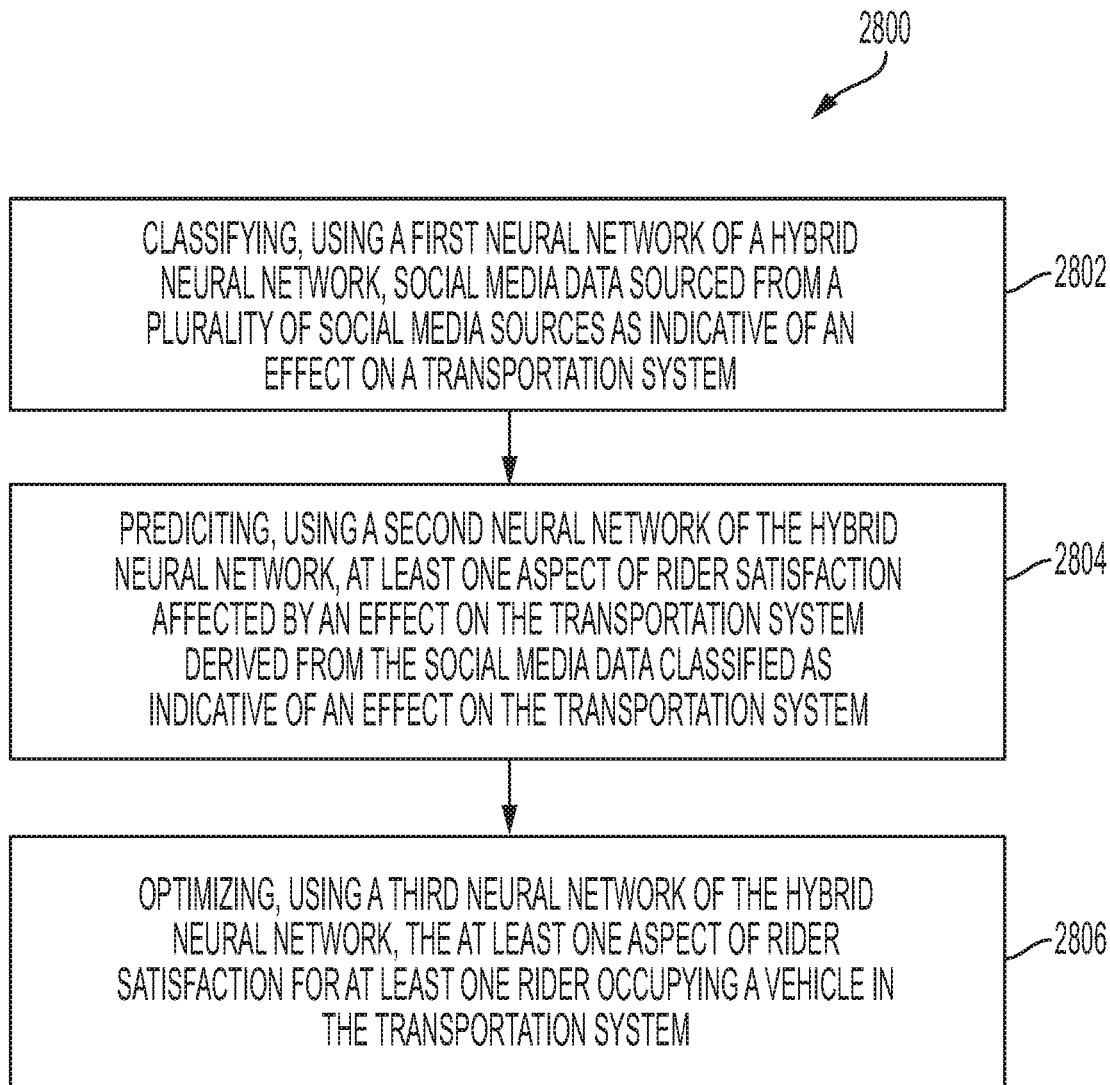
FIG. 28 is a diagrammatic view that illustrates a method described throughout this disclosure relating to various embodiments of the present disclosure.

FIG. 28 illustrates a method 2800 of optimizing rider satisfaction in accordance with embodiments of the systems and methods disclosed herein. At 2802 the method includes classifying, using a first neural network 2722 (FIG. 27) of a hybrid neural network, social media data 27119 (FIG. 27) sourced from a plurality of social media sources as indicative of an effect on a transportation system. At 2804 the method includes predicting, using a second neural network 2720 (FIG. 27) of the hybrid neural network, at least one aspect 27122 (FIG. 27) of rider satisfaction affected by an effect on the transportation system derived from the social media data classified as indicative of an effect on the transportation system. At 2806 the method includes optimizing, using a third neural network 27117 (FIG. 27) of the hybrid neural network, the at least one aspect of rider satisfaction for at least one rider occupying a vehicle in the transportation system.

Referring to FIG. 27 and FIG. 28, in embodiments, at least one of the neural networks in the hybrid neural network 2547 is a convolutional neural network. In embodiments, the at least one aspect of rider satisfaction 27121 is optimized by predicting an entertainment option for presenting to the rider. In embodiments, the at least one aspect of rider satisfaction 27121 is optimized by optimizing route planning for a vehicle occupied by the rider. In embodiments, the at least one aspect of rider satisfaction 27121 is a rider state and optimizing the aspects of rider satisfaction comprising optimizing the rider state. In embodiments, social media data specific to the rider is analyzed to determine at least one optimizing action likely to optimize the at least one aspect of rider satisfaction 27121. In embodiments, the optimizing action is selected from the group of actions consisting of adjusting a routing plan to include passing points of interest to the user, avoiding traffic congestion predicted from the social media data, and presenting entertainment options.

In embodiments, the social media data includes social media posts. In embodiments, the social media data includes social media feeds. In embodiments, the social media data includes like or dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs.

In embodiments, the social media data includes traffic-affecting information. In embodiments, the social media data includes an indication of a specific individual at a location. In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options. In embodiments, the social media data includes risk-related conditions. In embodiments, the social media data includes predictions of attendance at an event. In embodiments, the social media data includes estimates of attendance at an event. In embodiments, the social media data includes modes of transportation used with an event. In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized at least one aspect of rider satisfaction is an operating state of the vehicle. In embodiments, the optimized at least one aspect of rider satisfaction includes an in-vehicle state. In embodiments, the optimized at least one aspect of rider satisfaction includes a rider state. In embodiments, the optimized at least one aspect of rider satisfaction includes a routing state. In embodiments, the optimized at least one aspect of rider satisfaction includes user experience state.

In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

An aspect provided herein includes a rider satisfaction system 27123 for optimizing rider satisfaction 27121, the system comprising: a first neural network 2722 of a hybrid neural network 2747 to classify social media data 27114 sourced from a plurality 2769 of social media sources 27107 as indicative of an effect 27119 on a transportation system 2711; a second neural network 2720 of the hybrid neural network 2747 to predict at least one aspect 27122 of rider satisfaction 27121 affected by an effect on the transportation system derived from the social media data classified as indicative of the effect on the transportation system; and a third network 27117 of the hybrid neural network 2747 to optimize the at least one aspect of rider satisfaction 27121 for at least one rider 2744 occupying a vehicle 2710 in the transportation system 2711. In embodiments, at least one of the neural networks in the hybrid neural network 2747 is a convolutional neural network.

In embodiments, the at least one aspect of rider satisfaction 27121 is optimized by predicting an entertainment option for presenting to the rider 2744. In embodiments, the at least one aspect of rider satisfaction 27121 is optimized by optimizing route planning for a vehicle 2710 occupied by the rider 2744. In embodiments, the at least one aspect of rider satisfaction 27121 is a rider state 2737 and optimizing the at least one aspect of rider satisfaction 27121 comprises optimizing the rider state 2737. In embodiments, social media data specific to the rider 2744 is analyzed to determine at least one optimizing action likely to optimize the at least one aspect of rider satisfaction 27121. In embodiments, the at least one optimizing action is selected from the group consisting of: adjusting a routing plan to include passing points of interest to the user, avoiding traffic congestion predicted from the social media data, deriving an economic benefit, deriving an altruistic benefit, and presenting entertainment options.

In embodiments, the economic benefit is saved fuel. In embodiments, the altruistic benefit is reduction of environmental impact. In embodiments, the social media data includes social media posts. In embodiments, the social media data includes social media feeds. In embodiments, the social media data includes like or dislike activity detected in the social media. In embodiments, the social media data includes indications of relationships. In embodiments, the social media data includes user behavior. In embodiments, the social media data includes discussion threads. In embodiments, the social media data includes chats. In embodiments, the social media data includes photographs. In embodiments, the social media data includes traffic-affecting information. In embodiments, the social media data includes an indication of a specific individual at a location.

In embodiments, the social media data includes an indication of a celebrity at a location. In embodiments, the social media data includes presence of a rare or transient phenomena at a location. In embodiments, the social media data includes a commerce-related event. In embodiments, the social media data includes an entertainment event at a location. In embodiments, the social media data includes traffic conditions. In embodiments, the social media data includes weather conditions. In embodiments, the social media data includes entertainment options. In embodiments, the social media data includes risk-related conditions. In embodiments, the social media data includes predictions of attendance at an event. In embodiments, the social media data includes estimates of attendance at an event. In embodiments, the social media data includes modes of transportation used with an event.

In embodiments, the effect on the transportation system includes reducing fuel consumption. In embodiments, the effect on the transportation system includes reducing traffic congestion. In embodiments, the effect on the transportation system includes reduced carbon footprint. In embodiments, the effect on the transportation system includes reduced pollution. In embodiments, the optimized at least one aspect of rider satisfaction is an operating state of the vehicle. In embodiments, the optimized at least one aspect of rider satisfaction includes an in-vehicle state. In embodiments, the optimized at least one aspect of rider satisfaction includes a rider state. In embodiments, the optimized at least one aspect of rider satisfaction includes a routing state. In embodiments, the optimized at least one aspect of rider satisfaction includes user experience state. In embodiments, a characterization of an outcome of the optimizing in the social media data is used as feedback to improve the optimizing. In embodiments, the feedback includes likes or dislikes of the outcome. In embodiments, the feedback includes social medial activity referencing the outcome. In embodiments, the feedback includes trending of social media activity referencing the outcome. In embodiments, the feedback includes hash tags associated with the outcome. In embodiments, the feedback includes ratings of the outcome. In embodiments, the feedback includes requests for the outcome.

Figure 29:
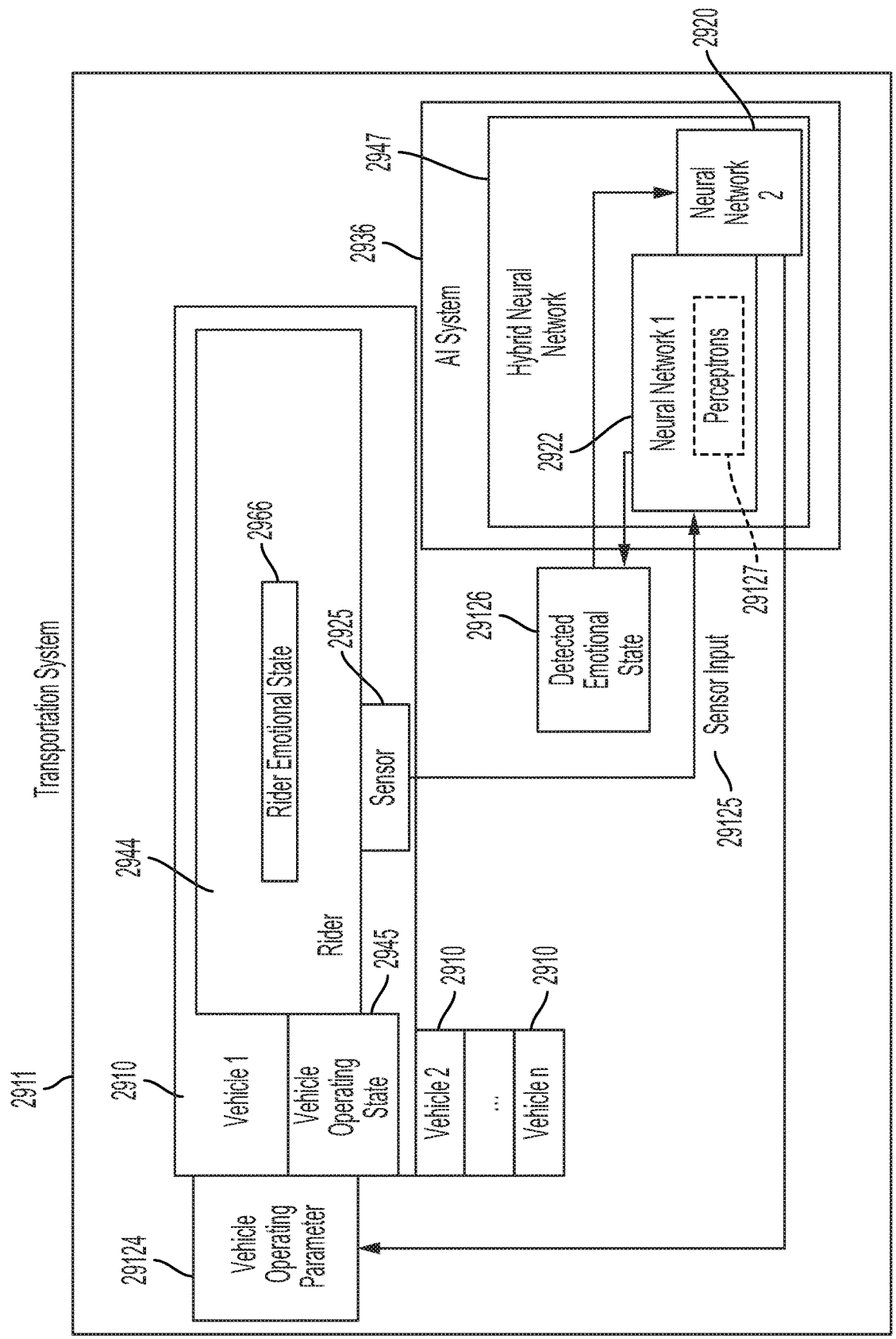
FIG. 29 is a diagrammatic view that illustrates systems described throughout this disclosure relating to various embodiments of the present disclosure.

Referring to FIG. 29, in embodiments provided herein are transportation systems 2911 having a hybrid neural network 2947 wherein one neural network 2922 processes a sensor input 29125 about a rider 2944 of a vehicle 2910 to determine an emotional state 29126 and another neural network optimizes at least one operating parameter 29124 of the vehicle to improve the rider's emotional state 2966. For example, a neural net 2922 that includes one or more perceptrons 29127 that mimic human senses may be used to mimic or assist with determining the likely emotional state of a rider 29126 based on the extent to which various senses have been stimulated, while another neural network 2920 is used in an expert system that performs random and/or systematized variations of various combinations of operating parameters (such as entertainment settings, seat settings, suspension settings, route types and the like) with genetic programming that promotes favorable combinations and eliminates unfavorable ones, optionally based on input from the output of the perceptron-containing neural network 2922 that predict emotional state. These and many other such combinations are encompassed by the present disclosure. In FIG. 29, perceptrons 29127 are depicted as optional.

An aspect provided herein includes a system for transportation 2911, comprising: a hybrid neural network 2947 wherein one neural network 2922 processes a sensor input 29125 corresponding to a rider 2944 of a vehicle 2910 to determine an emotional state 2966 of the rider 2944 and another neural network 2920 optimizes at least one operating parameter 29124 of the vehicle to improve the emotional state 2966 of the rider 2944.

An aspect provided herein includes a hybrid neural network 2947 for rider satisfaction, comprising: a first neural network 2922 to detect a detected emotional state 29126 of a rider 2944 occupying a vehicle 2910 through analysis of data 29125 gathered from sensors 2925 deployed in a vehicle 2910 for gathering physiological conditions of the rider; and a second neural network 2920 to optimize, for achieving a favorable emotional state of the rider, an operational parameter 29124 of the vehicle in response to the detected emotional state 29126 of the rider.

In embodiments, the first neural network 2922 is a recurrent neural network and the second neural network 2920 is a radial basis function neural network. In embodiments, at least one of the neural networks in the hybrid neural network 2947 is a convolutional neural network. In embodiments, the second neural network 2920 is to optimize the operational parameter 29124 based on a correlation between a vehicle operating state 2945 and a rider emotional state 2966 of the rider. In embodiments, the second neural network 2920 optimizes the operational parameter 29124 in real time responsive to the detecting of the detected emotional state 29126 of the rider 2944 by the first neural network 2922. In embodiments, the first neural network 2922 comprises a plurality of connected nodes that form a directed cycle, the first neural network 2922 further facilitating bi-directional flow of data among the connected nodes. In embodiments, the operational parameter 29124 that is optimized affects at least one of: a route of the vehicle, in-vehicle audio contents, a speed of the vehicle, an acceleration of the vehicle, a deceleration of the vehicle, a proximity to objects along the route, and a proximity to other vehicles along the route.

An aspect provided herein includes an artificial intelligence system 2936 for optimizing rider satisfaction, comprising: a hybrid neural network 2947, including: a recurrent neural network (e.g., in FIG. 29, neural network 2922 may be a recurrent neural network) to indicate a change in an emotional state of a rider 2944 in a vehicle 2910 through recognition of patterns of physiological data of the rider captured by at least one sensor 2925 deployed for capturing rider emotional state-indicative data while occupying the vehicle 2910; and a radial basis function neural network (e.g., in FIG. 29, neural network 2920 may be a radial basis function neural network) to optimize, for achieving a favorable emotional state of the rider, an operational parameter 29124 of the vehicle in response to the indication of change in the emotional state of the rider. In embodiments, the operational parameter 29124 of the vehicle that is to be optimized is to be determined and adjusted to induce the favorable emotional state of the rider.

An aspect provided herein includes an artificial intelligence system 2936 for optimizing rider satisfaction, comprising: a hybrid neural network 2947, including: a convolutional neural network (in FIG. 29, neural network 1, depicted at reference numeral 2922, may optionally be a convolutional neural network) to indicate a change in an emotional state of a rider in a vehicle through recognitions of patterns of visual data of the rider captured by at least one image sensor (in FIG. 29, the sensor 2925 may optionally be an image sensor) deployed for capturing images of the rider while occupying the vehicle; and a second neural network 2920 to optimize, for achieving a favorable emotional state of the rider, an operational parameter 29124 of the vehicle in response to the indication of change in the emotional state of the rider.

In embodiments, the operational parameter 19124 of the vehicle that is to be optimized is to be determined and adjusted to induce the favorable emotional state of the rider.

Figure 30:
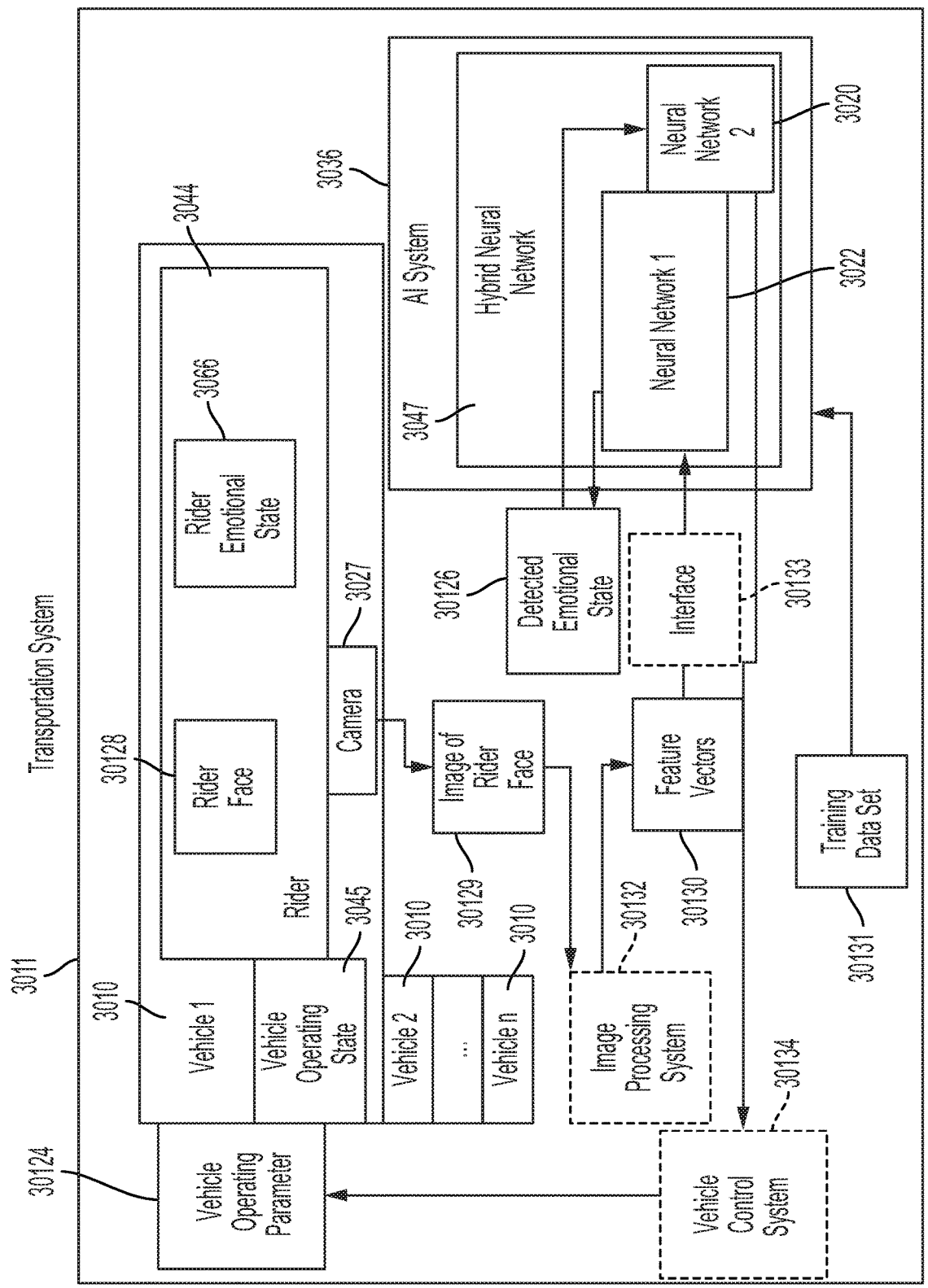
FIG. 30 is a diagrammatic view that illustrates systems described throughout this disclosure relating to various embodiments of the present disclosure.

Referring to FIG. 30, in embodiments provided herein are transportation systems 3011 having an artificial intelligence system 3036 for processing feature vectors of an image of a face of a rider in a vehicle to determine an emotional state and optimizing at least one operating parameter of the vehicle to improve the rider's emotional state. A face may be classified based on images from in-vehicle cameras, available cellphone or other mobile device cameras, or other sources. An expert system, optionally trained based on a training set of data provided by humans or trained by deep learning, may learn to adjust vehicle parameters (such as any described herein) to provide improved emotional states. For example, if a rider's face indicates stress, the vehicle may select a less stressful route, play relaxing music, play humorous content, or the like.

An aspect provided herein includes a transportation system 3011, comprising: an artificial intelligence system 3036 for processing feature vectors 30130 of an image 30129 of a face 30128 of a rider 3044 in a vehicle 3010 to determine an emotional state 3066 of the rider and optimizing an operational parameter 30124 of the vehicle to improve the emotional state 3066 of the rider 3044.

In embodiments, the artificial intelligence system 3036 includes: a first neural network 3022 to detect the emotional state 30126 of the rider through recognition of patterns of the feature vectors 30130 of the image 30129 of the face 30128 of the rider 3044 in the vehicle 3010, the feature vectors 30130 indicating at least one of a favorable emotional state of the rider and an unfavorable emotional state of the rider; and a second neural network 3020 to optimize, for achieving the favorable emotional state of the rider, the operational parameter 30124 of the vehicle in response to the detected emotional state 30126 of the rider.

In embodiments, the first neural network 3022 is a recurrent neural network and the second neural network 3020 is a radial basis function neural network. In embodiments, the second neural network 3020 optimizes the operational parameter 30124 based on a correlation between the vehicle operating state 3045 and the emotional state 3066 of the rider. In embodiments, the second neural network 3020 is to determine an optimum value for the operational parameter of the vehicle, and the transportation system 3011 is to adjust the operational parameter 30124 of the vehicle to the optimum value to induce the favorable emotional state of the rider. In embodiments, the first neural network 3022 further learns to classify the patterns in the feature vectors and associate the patterns with a set of emotional states and changes thereto by processing a training data set 30131. In embodiments, the training data set 30131 is sourced from at least one of a stream of data from an unstructured data source, a social media source, a wearable device, an in-vehicle sensor, a rider helmet, a rider headgear, and a rider voice recognition system.

In embodiments, the second neural network 3020 optimizes the operational parameter 30124 in real time responsive to the detecting of the emotional state of the rider by the first neural network 3022. In embodiments, the first neural network 3022 is to detect a pattern of the feature vectors. In embodiments, the pattern is associated with a change in the emotional state of the rider from a first emotional state to a second emotional state. In embodiments, the second neural network 3020 optimizes the operational parameter of the vehicle in response to the detection of the pattern associated with the change in the emotional state. In embodiments, the first neural network 3022 comprises a plurality of interconnected nodes that form a directed cycle, the first neural network 3022 further facilitating bi-directional flow of data among the interconnected nodes. In embodiments, the transportation system 3011 further comprises: a feature vector generation system to process a set of images of the face of the rider, the set of images captured over an interval of time from by a plurality of image capture devices 3027 while the rider 3044 is in the vehicle 3010, wherein the processing of the set of images is to produce the feature vectors 30130 of the image of the face of the rider. In embodiments, the transportation system further comprises: image capture devices 3027 disposed to capture a set of images of the face of the rider in the vehicle from a plurality of perspectives; and an image processing system to produce the feature vectors from the set of images captured from at least one of the plurality of perspectives.

In embodiments, the transportation system 3011 further comprises an interface 30133 between the first neural network and the image processing system 30132 to communicate a time sequence of the feature vectors, wherein the feature vectors are indicative of the emotional state of the rider. In embodiments, the feature vectors indicate at least one of a changing emotional state of the rider, a stable emotional state of the rider, a rate of change of the emotional state of the rider, a direction of change of the emotional state of the rider, a polarity of a change of the emotional state of the rider; the emotional state of the rider is changing to the unfavorable emotional state; and the emotional state of the rider is changing to the favorable emotional state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the second neural network is to interact with a vehicle control system to adjust the operational parameter. In embodiments, the artificial intelligence system further comprises a neural network that includes one or more perceptrons that mimic human senses that facilitates determining the emotional state of the rider based on an extent to which at least one of the senses of the rider is stimulated. In embodiments, the artificial intelligence system includes: a recurrent neural network to indicate a change in the emotional state of the rider through recognition of patterns of the feature vectors of the image of the face of the rider in the vehicle; and a radial basis function neural network to optimize, for achieving the favorable emotional state of the rider, the operational parameter of the vehicle in response to the indication of the change in the emotional state of the rider.

In embodiments, the radial basis function neural network is to optimize the operational parameter based on a correlation between a vehicle operating state and a rider emotional state. In embodiments, the operational parameter of the vehicle that is optimized is determined and adjusted to induce a favorable rider emotional state. In embodiments, the recurrent neural network further learns to classify the patterns of the feature vectors and associate the patterns of the feature vectors to emotional states and changes thereto from a training data set sourced from at least one of a stream of data from unstructured data sources, social media sources, wearable devices, in-vehicle sensors, a rider helmet, a rider headgear, and a rider voice system. In embodiments, the radial basis function neural network is to optimize the operational parameter in real time responsive to the detecting of the change in the emotional state of the rider by the recurrent neural network. In embodiments, the recurrent neural network detects a pattern of the feature vectors that indicates the emotional state of the rider is changing from a first emotional state to a second emotional state. In embodiments, the radial basis function neural network is to optimize the operational parameter of the vehicle in response to the indicated change in emotional state.

In embodiments, the recurrent neural network comprises a plurality of connected nodes that form a directed cycle, the recurrent neural network further facilitating bi-directional flow of data among the connected nodes. In embodiments, the feature vectors indicate at least one of the emotional state of the rider is changing, the emotional state of the rider is stable, a rate of change of the emotional state of the rider, a direction of change of the emotional state of the rider, and a polarity of a change of the emotional state of the rider; the emotional state of a rider is changing to an unfavorable emotional state; and an emotional state of a rider is changing to a favorable emotional state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route.

In embodiments, the radial basis function neural network is to interact with a vehicle control system 30134 to adjust the operational parameter 30124. In embodiments, the artificial intelligence system 3036 further comprises a neural network that includes one or more perceptrons that mimic human senses that facilitates determining the emotional state of a rider based on an extent to which at least one of the senses of the rider is stimulated. In embodiments, the artificial intelligence system 3036 is to maintain the favorable emotional state of the rider via a modular neural network, the modular neural network comprising: a rider emotional state determining neural network to process the feature vectors of the image of the face of the rider in the vehicle to detect patterns. In embodiments, the patterns in the feature vectors indicate at least one of the favorable emotional state and the unfavorable emotional state; an intermediary circuit to convert data from the rider emotional state determining neural network into vehicle operational state data; and a vehicle operational state optimizing neural network to adjust an operational parameter of the vehicle in response to the vehicle operational state data.

In embodiments, the vehicle operational state optimizing neural network is to adjust the operational parameter 30124 of the vehicle for achieving a favorable emotional state of the rider. In embodiments, the vehicle operational state optimizing neural network is to optimize the operational parameter based on a correlation between a vehicle operating state 3045 and a rider emotional state 3066. In embodiments, the operational parameter of the vehicle that is optimized is determined and adjusted to induce a favorable rider emotional state. In embodiments, the rider emotional state determining neural network further learns to classify the patterns of the feature vectors and associate the pattern of the feature vectors to emotional states and changes thereto from a training data set sourced from at least one of a stream of data from unstructured data sources, social media sources, wearable devices, in-vehicle sensors, a rider helmet, a rider headgear, and a rider voice system.

In embodiments, the vehicle operational state optimizing neural network is to optimize the operational parameter 30124 in real time responsive to the detecting of a change in an emotional state 30126 of the rider by the rider emotional state determining neural network. In embodiments, the rider emotional state determining neural network is to detect a pattern of the feature vectors 30130 that indicates the emotional state of the rider is changing from a first emotional state to a second emotional state. In embodiments, the vehicle operational state optimizing neural network is to optimize the operational parameter of the vehicle in response to the indicated change in emotional state. In embodiments, the artificial intelligence system 3036 comprises a plurality of connected nodes that form a directed cycle, the artificial intelligence system further facilitating bi-directional flow of data among the connected nodes.

In embodiments, the feature vectors 30130 indicate at least one of the emotional state of the rider is changing, the emotional state of the rider is stable, a rate of change of the emotional state of the rider, a direction of change of the emotional state of the rider, and a polarity of a change of the emotional state of the rider; the emotional state of a rider is changing to an unfavorable emotional state; and the emotional state of the rider is changing to a favorable emotional state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the vehicle operational state optimizing neural network interacts with a vehicle control system to adjust the operational parameter.

In embodiments, the artificial intelligence system 3036 further comprises a neural net that includes one or more perceptrons that mimic human senses that facilitates determining an emotional state of a rider based on an extent to which at least one of the senses of the rider is stimulated. It is to be understood that the terms "neural net" and "neural network" are used interchangeably in the present disclosure. In embodiments, the rider emotional state determining neural network comprises one or more perceptrons that mimic human senses that facilitates determining an emotional state of a rider based on an extent to which at least one of the senses of the rider is stimulated. In embodiments, the artificial intelligence system 3036 includes a recurrent neural network to indicate a change in the emotional state of the rider in the vehicle through recognition of patterns of the feature vectors of the image of the face of the rider in the vehicle; the transportation system further comprising: a vehicle control system 30134 to control operation of the vehicle by adjusting a plurality of vehicle operational parameters 30124; and a feedback loop to communicate the indicated change in the emotional state of the rider between the vehicle control system 30134 and the artificial intelligence system 3036. In embodiments, the vehicle control system is to adjust at least one of the plurality of vehicle operational parameters 30124 in response to the indicated change in the emotional state of the rider. In embodiments, the vehicle controls system adjusts the at least one of the plurality of vehicle operational parameters based on a correlation between vehicle operational state and rider emotional state.

In embodiments, the vehicle control system adjusts the at least one of the plurality of vehicle operational parameters 30124 that are indicative of a favorable rider emotional state. In embodiments, the vehicle control system 30134 selects an adjustment of the at least one of the plurality of vehicle operational parameters 30124 that is indicative of producing a favorable rider emotional state. In embodiments, the recurrent neural network further learns to classify the patterns of feature vectors and associate them to emotional states and changes thereto from a training data set 30131 sourced from at least one of a stream of data from unstructured data sources, social media sources, wearable devices, in-vehicle sensors, a rider helmet, a rider headgear, and a rider voice system. In embodiments, the vehicle control system 30134 adjusts the at least one of the plurality of vehicle operation parameters 30124 in real time. In embodiments, the recurrent neural network detects a pattern of the feature vectors that indicates the emotional state of the rider is changing from a first emotional state to a second emotional state. In embodiments, the vehicle operation control system adjusts an operational parameter of the vehicle in response to the indicated change in emotional state. In embodiments, the recurrent neural network comprises a plurality of connected nodes that form a directed cycle, the recurrent neural network further facilitating bi-directional flow of data among the connected nodes.

In embodiments, the feature vectors indicating at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; an emotional state of a rider is changing to a favorable state. In embodiments, the at least one of the plurality of vehicle operational parameters responsively adjusted affects a route of the vehicle, in-vehicle audio content, speed of the vehicle, acceleration of the vehicle, deceleration of the vehicle, proximity to objects along the route, proximity to other vehicles along the route. In embodiments, the at least one of the plurality of vehicle operation parameters that is responsively adjusted affects operation of a powertrain of the vehicle and a suspension system of the vehicle. In embodiments, the radial basis function neural network interacts with the recurrent neural network via an intermediary component of the artificial intelligence system 3036 that produces vehicle control data indicative of an emotional state response of the rider to a current operational state of the vehicle. In embodiments, the recognition of patterns of feature vectors comprises processing the feature vectors of the image of the face of the rider captured during at least two of before the adjusting at least one of the plurality of vehicle operational parameters, during the adjusting at least one of the plurality of vehicle operational parameters, and after adjusting at least one of the plurality of vehicle operational parameters.

In embodiments, the adjusting at least one of the plurality of vehicle operational parameters 30124 improves an emotional state of a rider in a vehicle. In embodiments, the adjusting at least one of the plurality of vehicle operational parameters causes an emotional state of the rider to change from an unfavorable emotional state to a favorable emotional state. In embodiments, the change is indicated by the recurrent neural network. In embodiments, the recurrent neural network indicates a change in the emotional state of the rider responsive to a change in an operating parameter of the vehicle by determining a difference between a first set of feature vectors of an image of the face of a rider captured prior to the adjusting at least one of the plurality of operating parameters and a second set of feature vectors of an image of the face of the rider captured during or after the adjusting at least one of the plurality of operating parameters.

In embodiments, the recurrent neural network detects a pattern of the feature vectors that indicates an emotional state of the rider is changing from a first emotional state to a second emotional state. In embodiments, the vehicle operation control system adjusts an operational parameter of the vehicle in response to the indicated change in emotional state.

Figure 31:
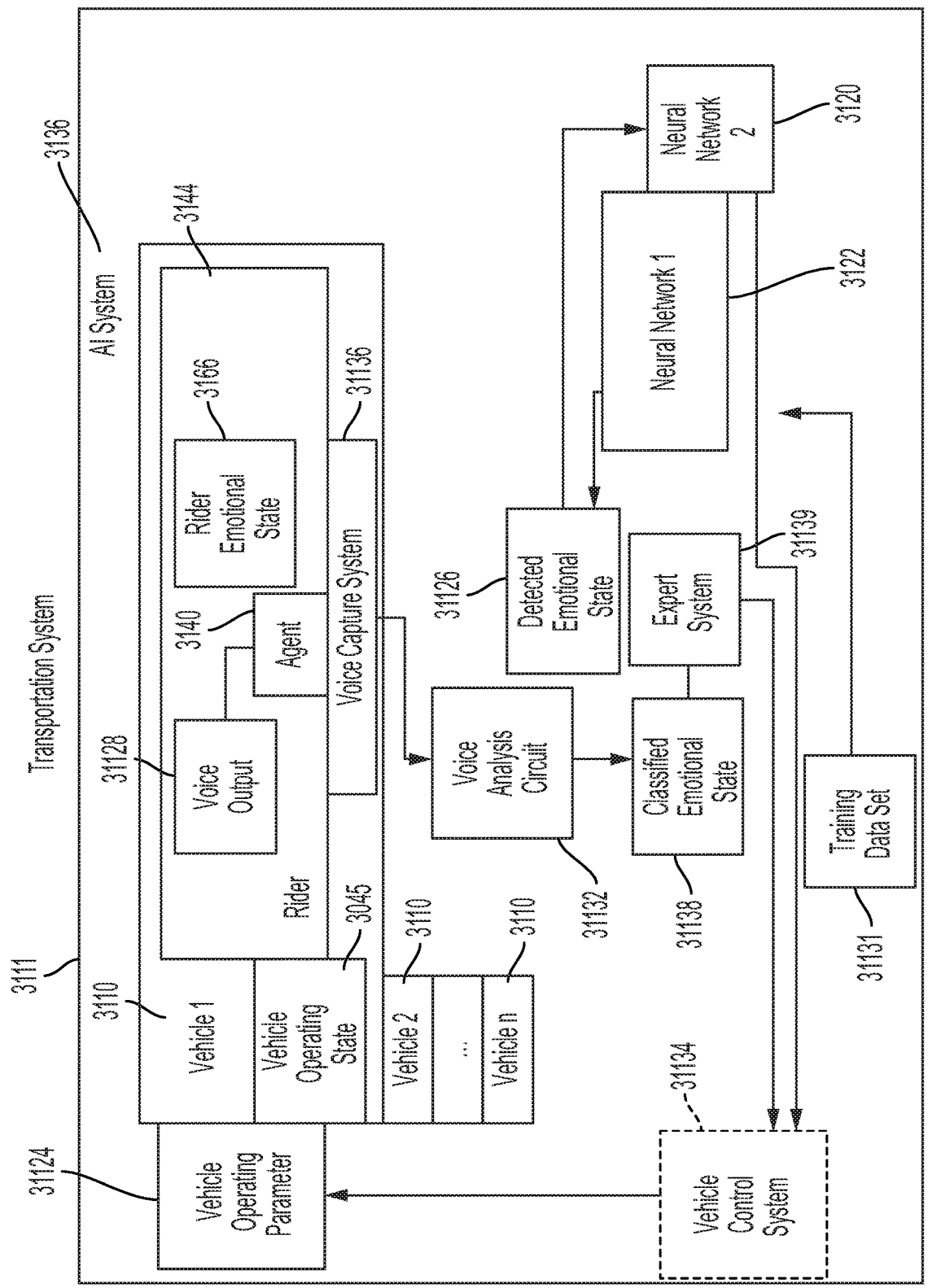
FIG. 31 is a diagrammatic view that illustrates systems described throughout this disclosure relating to various embodiments of the present disclosure.

Referring to FIG. 31, in embodiments, provided herein are transportation systems having an artificial intelligence system for processing a voice of a rider in a vehicle to determine an emotional state and optimizing at least one operating parameter of the vehicle to improve the rider's emotional state. A voice-analysis module may take voice input and, using a training set of labeled data where individuals indicate emotional states while speaking and/or whether others tag the data to indicate perceived emotional states while individuals are talking, a machine learning system (such as any of the types described herein) may be trained (such as using supervised learning, deep learning, or the like) to classify the emotional state of the individual based on the voice. Machine learning may improve classification by using feedback from a large set of trials, where feedback in each instance indicates whether the system has correctly assessed the emotional state of the individual in the case of an instance of speaking. Once trained to classify the emotional state, an expert system (optionally using a different machine learning system or other artificial intelligence system) may, based on feedback of outcomes of the emotional states of a set of individuals, be trained to optimize various vehicle parameters noted throughout this disclosure to maintain or induce more favorable states. For example, among many other indicators, where a voice of an individual indicates happiness, the expert system may select or recommend upbeat music to maintain that state. Where a voice indicates stress, the system may recommend or provide a control signal to change a planned route to one that is less stressful (e.g., has less stop-and-go traffic, or that has a higher probability of an on-time arrival). In embodiments, the system may be configured to engage in a dialog (such as on on-screen dialog or an audio dialog), such as using an intelligent agent module of the system, that is configured to use a series of questions to help obtain feedback from a user about the user's emotional state, such as asking the rider about whether the rider is experiencing stress, what the source of the stress may be (e.g., traffic conditions, potential for late arrival, behavior of other drivers, or other sources unrelated to the nature of the ride), what might mitigate the stress (route options, communication options (such as offering to send a note that arrival may be delayed), entertainment options, ride configuration options, and the like), and the like. Driver responses may be fed as inputs to the expert system as indicators of emotional state, as well as to constrain efforts to optimize one or more vehicle parameters, such as by eliminating options for configuration that are not related to a driver's source of stress from a set of available configurations.

An aspect provided herein includes a system for transportation 3111, comprising: an artificial intelligence system 3136 for processing a voice 31135 of a rider 3144 in a vehicle 3110 to determine an emotional state 3166 of the rider 3144 and optimizing at least one operating parameter 31124 of the vehicle 3110 to improve the emotional state 3166 of the rider 3144.

An aspect provided herein includes an artificial intelligence system 3136 for voice processing to improve rider satisfaction in a transportation system 3111, comprising: a rider voice capture system 30136 deployed to capture voice output 31128 of a rider 3144 occupying a vehicle 3110; a voice-analysis circuit 31132 trained using machine learning that classifies an emotional state 31138 of the rider for the captured voice output of the rider; and an expert system 31139 trained using machine learning that optimizes at least one operating parameter 31124 of the vehicle to change the rider emotional state to an emotional state classified as an improved emotional state.

In embodiments, the rider voice capture system 31136 comprises an intelligent agent 31140 that engages in a dialog with the rider to obtain rider feedback for use by the voice-analysis circuit 31132 for rider emotional state classification. In embodiments, the voice-analysis circuit 31132 uses a first machine learning system and the expert system 31139 uses a second machine learning system. In embodiments, the expert system 31139 is trained to optimize the at least one operating parameter 31124 based on feedback of outcomes of the emotional states when adjusting the at least one operating parameter 31124 for a set of individuals. In embodiments, the emotional state 3166 of the rider is determined by a combination of the captured voice output 31128 of the rider and at least one other parameter. In embodiments, the at least one other parameter is a camera-based emotional state determination of the rider. In embodiments, the at least one other parameter is traffic information. In embodiments, the at least one other parameter is weather information. In embodiments, the at least one other parameter is a vehicle state. In embodiments, the at least one other parameter is at least one pattern of physiological data of the rider. In embodiments, the at least one other parameter is a route of the vehicle. In embodiments, the at least one other parameter is in-vehicle audio content. In embodiments, the at least one other parameter is a speed of the vehicle. In embodiments, the at least one other parameter is acceleration of the vehicle. In embodiments, the at least one other parameter is deceleration of the vehicle. In embodiments, the at least one other parameter is proximity to objects along the route. In embodiments, the at least one other parameter is proximity to other vehicles along the route.

An aspect provided herein includes an artificial intelligence system 3136 for voice processing to improve rider satisfaction, comprising: a first neural network 3122 trained to classify emotional states based on analysis of human voices detects an emotional state of a rider through recognition of aspects of the voice 31128 of the rider captured while the rider is occupying the vehicle 3110 that correlate to at least one emotional state 3166 of the rider; and a second neural network 3120 that optimizes, for achieving a favorable emotional state of the rider, an operational parameter 31124 of the vehicle in response to the detected emotional state 31126 of the rider 3144. In embodiments, at least one of the neural networks is a convolutional neural network. In embodiments, the first neural network 3122 is trained through use of a training data set that associates emotional state classes with human voice patterns. In embodiments, the first neural network 3122 is trained through the use of a training data set of voice recordings that are tagged with emotional state identifying data. In embodiments, the emotional state of the rider is determined by a combination of the captured voice output of the rider and at least one other parameter. In embodiments, the at least one other parameter is a camera-based emotional state determination of the rider. In embodiments, the at least one other parameter is traffic information. In embodiments, the at least one other parameter is weather information. In embodiments, the at least one other parameter is a vehicle state.

In embodiments, the at least one other parameter is at least one pattern of physiological data of the rider. In embodiments, the at least one other parameter is a route of the vehicle. In embodiments, the at least one other parameter is in-vehicle audio content. In embodiments, the at least one other parameter is a speed of the vehicle. In embodiments, the at least one other parameter is acceleration of the vehicle. In embodiments, the at least one other parameter is deceleration of the vehicle. In embodiments, the at least one other parameter is proximity to objects along the route. In embodiments, the at least one other parameter is proximity to other vehicles along the route.

Figure 32:
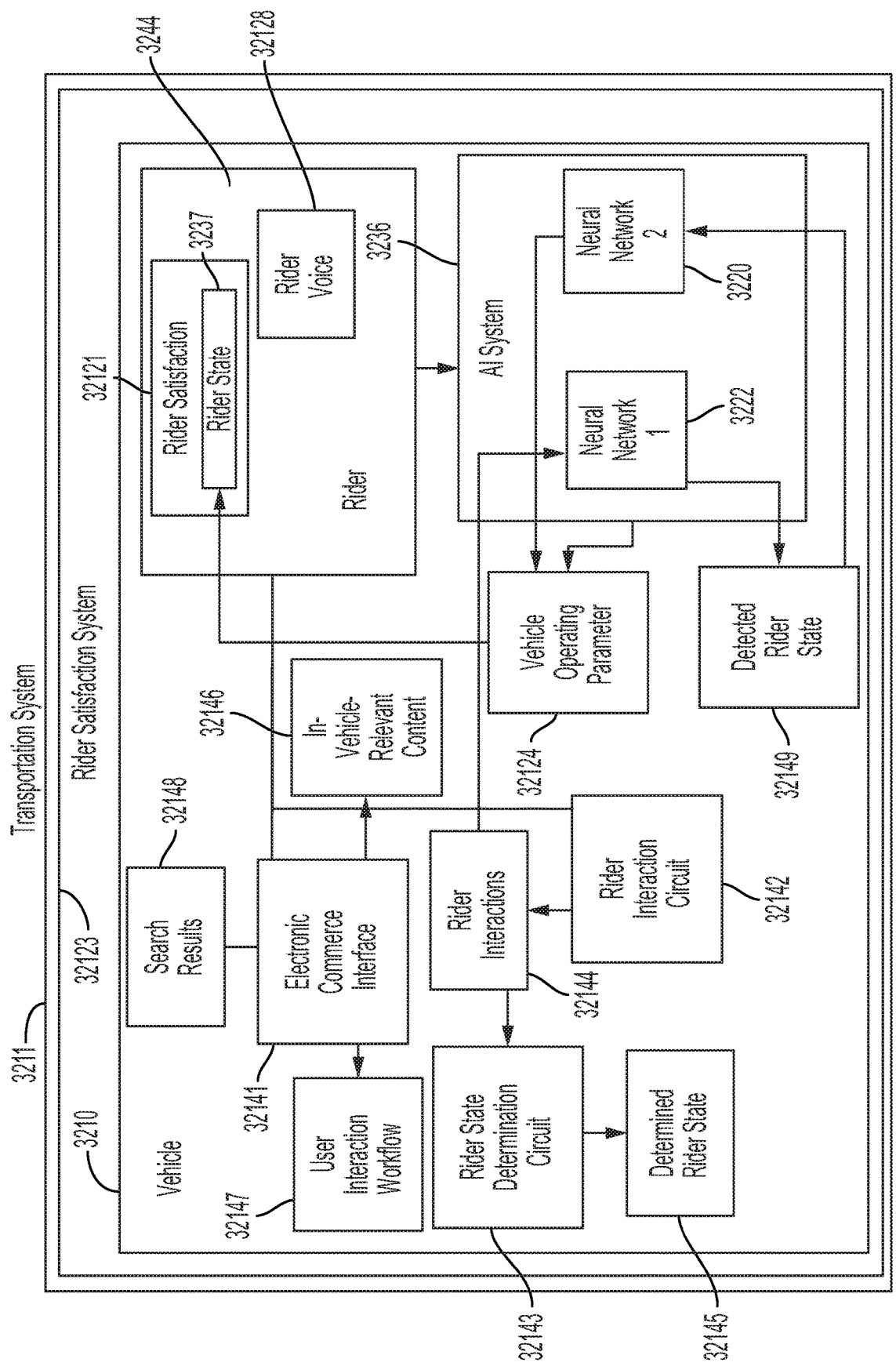
FIG. 32 is a diagrammatic view that illustrates systems described throughout this disclosure relating to various embodiments of the present disclosure.

Referring now to FIG. 32, in embodiments provided herein are transportation systems 3211 having an artificial intelligence system 3236 for processing data from an interaction of a rider with an electronic commerce system of a vehicle to determine a rider state and optimizing at least one operating parameter of the vehicle to improve the rider's state. Another common activity for users of device interfaces is e-commerce, such as shopping, bidding in auctions, selling items and the like. E-commerce systems use search functions, undertake advertising and engage users with various work flows that may eventually result in an order, a purchase, a bid, or the like. As described herein with search, a set of in-vehicle-relevant search results may be provided for e-commerce, as well as in-vehicle relevant advertising. In addition, in-vehicle-relevant interfaces and workflows may be configured based on detection of an in-vehicle rider, which may be quite different than workflows that are provided for e-commerce interfaces that are configured for smart phones or for desktop systems. Among other factors, an in-vehicle system may have access to information that is unavailable to conventional e-commerce systems, including route information (including direction, planned stops, planned duration and the like), rider mood and behavior information (such as from past routes, as well as detected from in-vehicle sensor sets), vehicle configuration and state information (such as make and model), and any of the other vehicle-related parameters described throughout this disclosure. As one example, a rider who is bored (as detected by an in-vehicle sensor set, such as using an expert system that is trained to detect boredom) and is on a long trip (as indicated by a route that is being undertaken by a car) may be far more patient, and likely to engage in deeper, richer content, and longer workflows, than a typical mobile user. As another example, an in-vehicle rider may be far more likely to engage in free trials, surveys, or other behaviors that promote brand engagement. Also, an in-vehicle user may be motivated to use otherwise down time to accomplish specific goals, such as shopping for needed items. Presenting the same interfaces, content, and workflows to in-vehicle users may miss excellent opportunities for deeper engagement that would be highly unlikely in other settings where many more things may compete for a user's attention. In embodiments, an e-commerce system interface may be provided for in-vehicle users, where at least one of interface displays, content, search results, advertising, and one or more associated workflows (such as for shopping, bidding, searching, purchasing, providing feedback, viewing products, entering ratings or reviews, or the like) is configured based on the detection of the use of an in-vehicle interface. Displays and interactions may be further configured (optionally based on a set of rules or based on machine learning), such as based on detection of display types (e.g., allowing richer or larger images for large, HD displays), network capabilities (e.g., enabling faster loading and lower latency by caching low-resolution images that initially render), audio system capabilities (such as using audio for dialog management and intelligence assistant interactions) and the like for the vehicle. Display elements, content, and workflows may be configured by machine learning, such as by A/B testing and/or using genetic programming techniques, such as configuring alternative interaction types and tracking outcomes. Outcomes used to train automatic configuration of workflows for in-vehicle e-commerce interfaces may include extent of engagement, yield, purchases, rider satisfaction, ratings, and others. In-vehicle users may be profiled and clustered, such as by behavioral profiling, demographic profiling, psychographic profiling, location-based profiling, collaborative filtering, similarity-based clustering, or the like, as with conventional e-commerce, but profiles may be enhanced with route information, vehicle information, vehicle configuration information, vehicle state information, rider information and the like. A set of in-vehicle user profiles, groups and clusters may be maintained separately from conventional user profiles, such that learning on what content to present, and how to present it, is accomplished with increased likelihood that the differences in in-vehicle shopping area accounted for when targeting search results, advertisements, product offers, discounts, and the like.

An aspect provided herein includes a system for transportation 3211, comprising: an artificial intelligence system 3236 for processing data from an interaction of a rider 3244 with an electronic commerce system of a vehicle to determine a rider state and optimizing at least one operating parameter of the vehicle to improve the rider state.

An aspect provided herein includes a rider satisfaction system 32123 for optimizing rider satisfaction 32121, the rider satisfaction system comprising: an electronic commerce interface 32141 deployed for access by a rider in a vehicle 3210; a rider interaction circuit that captures rider interactions with the deployed interface 32141; a rider state determination circuit 32143 that processes the captured rider interactions 32144 to determine a rider state 32145; and an artificial intelligence system 3236 trained to optimize, responsive to a rider state 3237, at least one parameter 32124 affecting operation of the vehicle to improve the rider state 3237. In embodiments, the vehicle 3210 comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the electronic commerce interface is self-adaptive and responsive to at least one of an identity of the rider, a route of the vehicle, a rider mood, rider behavior, vehicle configuration, and vehicle state.

In embodiments, the electronic commerce interface 32141 provides in-vehicle-relevant content 32146 that is based on at least one of an identity of the rider, a route of the vehicle, a rider mood, rider behavior, vehicle configuration, and vehicle state. In embodiments, the electronic commerce interface executes a user interaction workflow 32147 adapted for use by a rider 3244 in a vehicle 3210. In embodiments, the electronic commerce interface provides one or more results of a search query 32148 that are adapted for presentation in a vehicle. In embodiments, the search query results adapted for presentation in a vehicle are presented in the electronic commerce interface along with advertising adapted for presentation in a vehicle. In embodiments, the rider interaction circuit 32142 captures rider interactions 32144 with the interface responsive to content 32146 presented in the interface.

Figure 33:
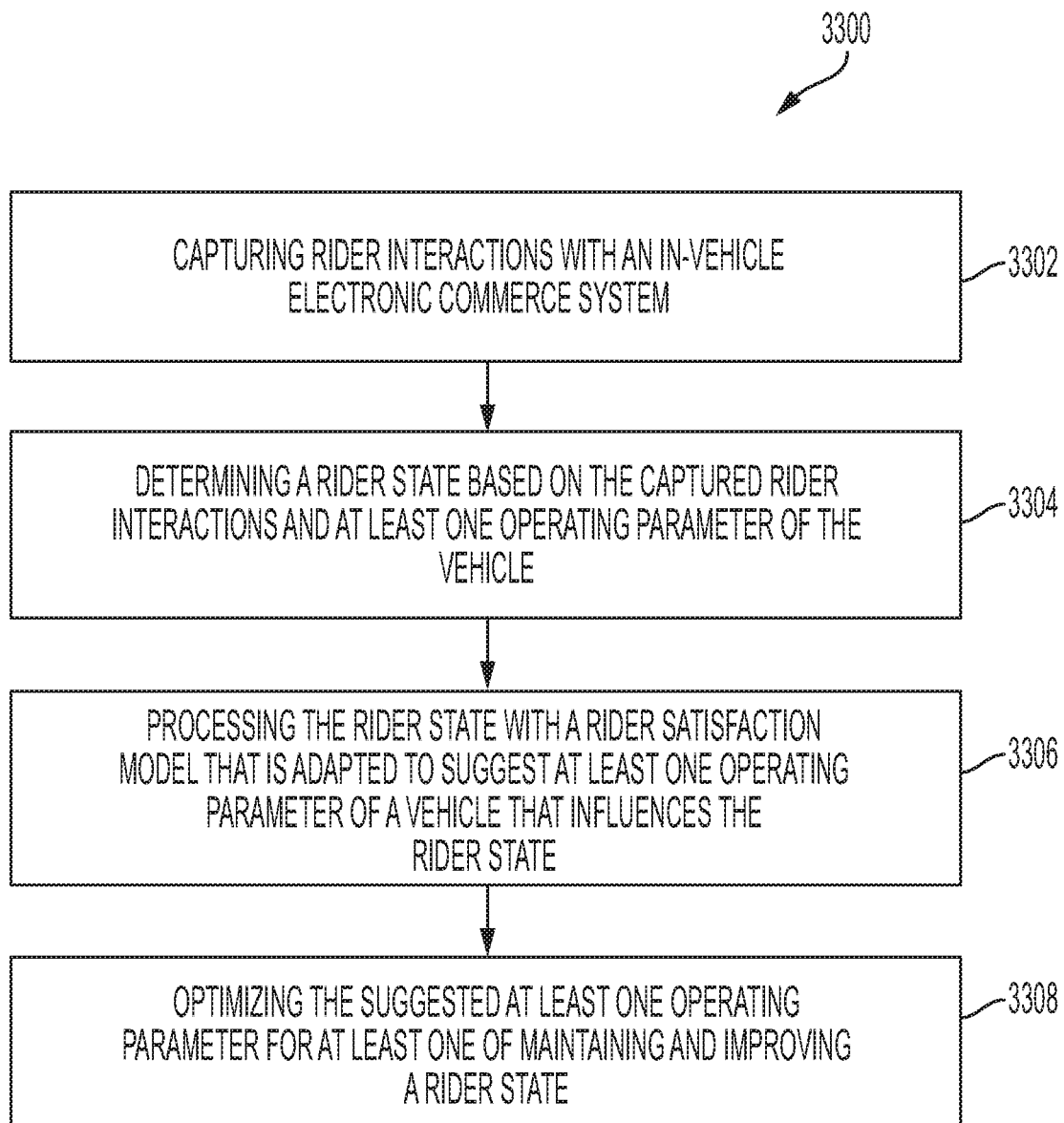
FIG. 33 is a diagrammatic view that illustrates a method described throughout this disclosure relating to various embodiments of the present disclosure.

FIG. 33 illustrates a method 3300 for optimizing a parameter of a vehicle in accordance with embodiments of the systems and methods disclosed herein. At 3302 the method includes capturing rider interactions with an in-vehicle electronic commerce system. At 3304 the method includes determining a rider state based on the captured rider interactions and a least one operating parameter of the vehicle. At 3306 the method includes processing the rider state with a rider satisfaction model that is adapted to suggest at least one operating parameter of a vehicle the influences the rider state. At 3308 the method includes optimizing the suggested at least one operating parameter for at least one of maintaining and improving a rider state.

Referring to FIG. 32 and FIG. 33, an aspect provided herein includes an artificial intelligence system 3236 for improving rider satisfaction, comprising: a first neural network 3222 trained to classify rider states based on analysis of rider interactions 32144 with an in-vehicle electronic commerce system to detect a rider state 32149 through recognition of aspects of the rider interactions 32144 captured while the rider is occupying the vehicle that correlate to at least one state 3237 of the rider; and a second neural network 3220 that optimizes, for achieving a favorable state of the rider, an operational parameter of the vehicle in response to the detected state of the rider.

Figure 34:
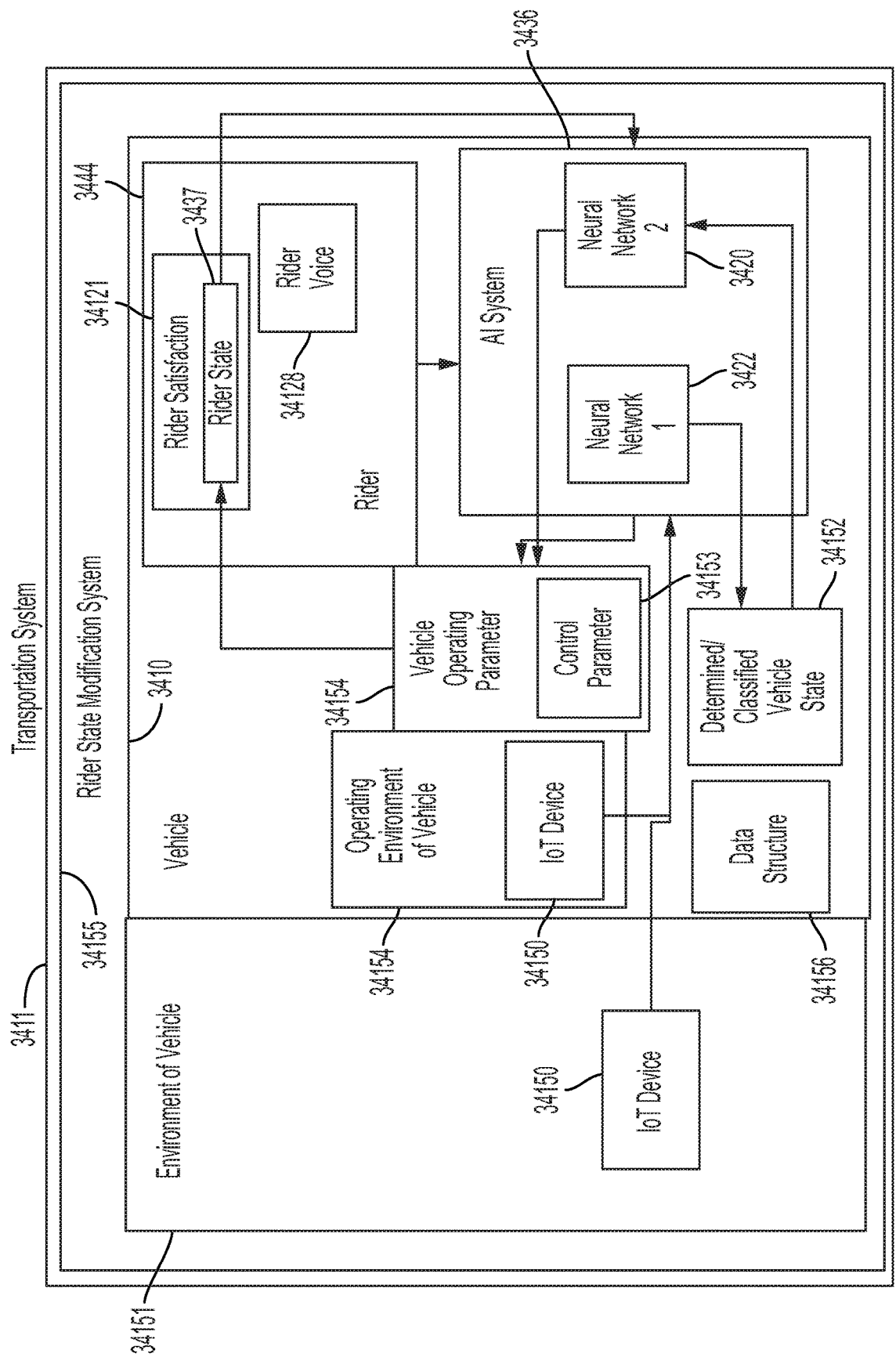
FIG. 34 is a diagrammatic view that illustrates systems described throughout this disclosure relating to various embodiments of the present disclosure.

Referring to FIG. 34, in embodiments provided herein are transportation systems 3411 having an artificial intelligence system 3436 for processing data from at least one Internet of Things (IoT) device 34150 in the environment 34151 of a vehicle 3410 to determine a state 34152 of the vehicle and optimizing at least one operating parameter 34124 of the vehicle to improve a rider's state 3437 based on the determined state 34152 of the vehicle.

An aspect provided herein includes a system for transportation 3411, comprising: an artificial intelligence system 3436 for processing data from at least one Internet of Things device 34150 in an environment 34151 of a vehicle 3410 to determine a determined state 34152 of the vehicle and optimizing at least one operating parameter 34124 of the vehicle to improve a state 3437 of the rider based on the determined state 34152 of the vehicle 3410.

Figure 35:
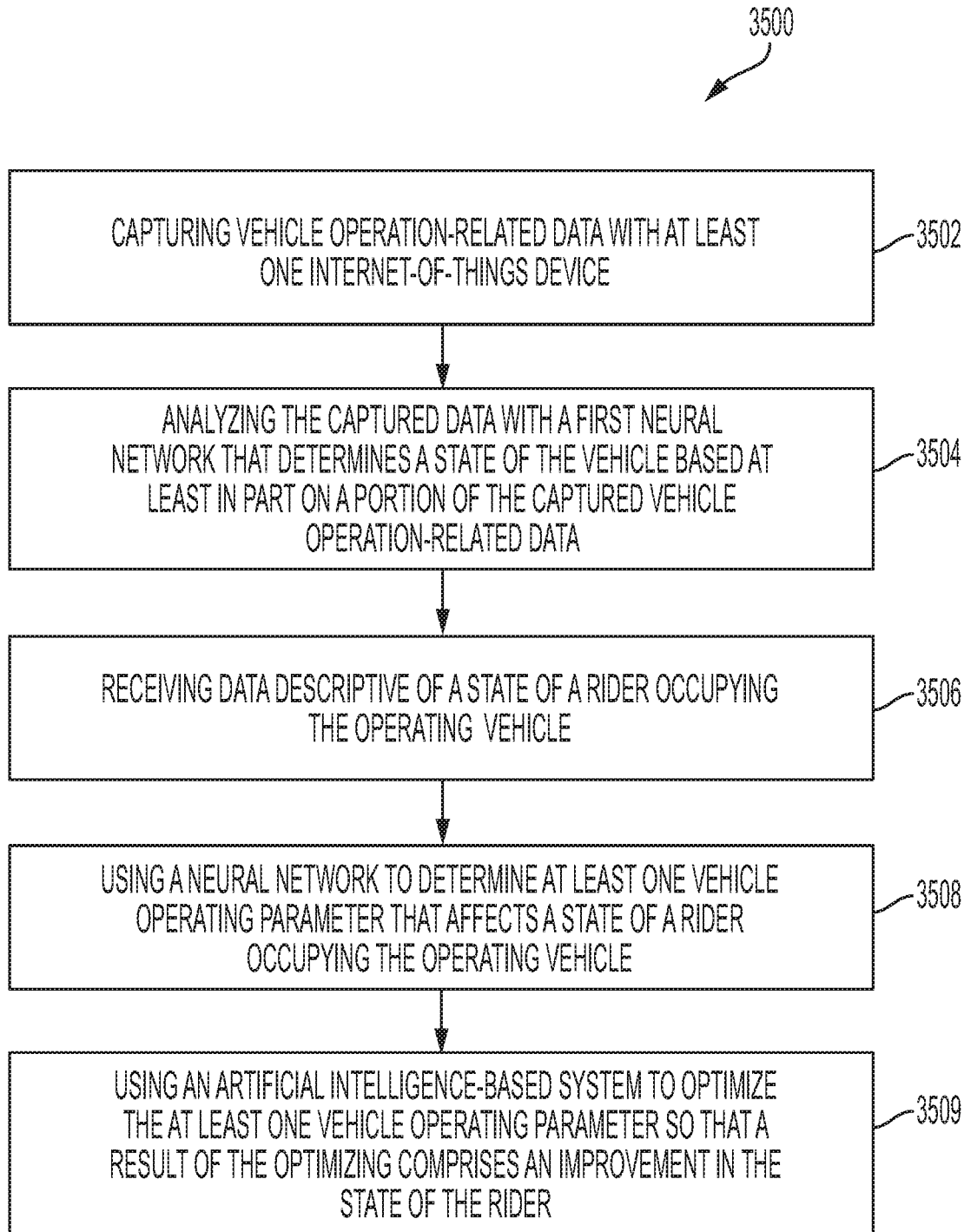
FIG. 35 is a diagrammatic view that illustrates a method described throughout this disclosure relating to various embodiments of the present disclosure.

FIG. 35 illustrates a method 3500 for improving a state of a rider through optimization of operation of a vehicle in accordance with embodiments of the systems and methods disclosed herein. At 3502 the method includes capturing vehicle operation-related data with at least one Internet-of-things device. At 3504 the method includes analyzing the captured data with a first neural network that determines a state of the vehicle based at least in part on a portion of the captured vehicle operation-related data. At 3506 the method includes receiving data descriptive of a state of a rider occupying the operating vehicle. At 3508 the method includes using a neural network to determine at least one vehicle operating parameter that affects a state of a rider occupying the operating vehicle. At 3509 the method includes using an artificial intelligence-based system to optimize the at least one vehicle operating parameter so that a result of the optimizing comprises an improvement in the state of the rider.

Referring to FIG. 34 and FIG. 35, in embodiments, the vehicle 3410 comprises a system for automating at least one control parameter 34153 of the vehicle 3410. In embodiments, the vehicle 3410 is at least a semi-autonomous vehicle. In embodiments, the vehicle 3410 is automatically routed. In embodiments, the vehicle 3410 is a self-driving vehicle. In embodiments, the at least one Internet-of-things device 34150 is disposed in an operating environment 34154 of the vehicle. In embodiments, the at least one Internet-of-things device 34150 that captures the data about the vehicle 3410 is disposed external to the vehicle 3410. In embodiments, the at least one Internet-of-things device is a dashboard camera. In embodiments, the at least one Internet-of-things device is a mirror camera. In embodiments, the at least one Internet-of-things device is a motion sensor. In embodiments, the at least one Internet-of-things device is a seat-based sensor system. In embodiments, the at least one Internet-of-things device is an IoT enabled lighting system. In embodiments, the lighting system is a vehicle interior lighting system. In embodiments, the lighting system is a headlight lighting system. In embodiments, the at least one Internet-of-things device is a traffic light camera or sensor. In embodiments, the at least one Internet-of-things device is a roadway camera. In embodiments, the roadway camera is disposed on at least one of a telephone phone and a light pole. In embodiments, the at least one Internet-of-things device is an in-road sensor. In embodiments, the at least one Internet-of-things device is an in-vehicle thermostat. In embodiments, the at least one Internet-of-things device is a toll booth. In embodiments, the at least one Internet-of-things device is a street sign. In embodiments, the at least one Internet-of-things device is a traffic control light. In embodiments, the at least one Internet-of-things device is a vehicle mounted sensor. In embodiments, the at least one Internet-of-things device is a refueling system. In embodiments, the at least one Internet-of-things device is a recharging system. In embodiments, the at least one Internet-of-things device is a wireless charging station.

An aspect provided herein includes a rider state modification system 34155 for improving a state 3437 of a rider 3444 in a vehicle 3410, the system comprising: a first neural network 3422 that operates to classify a state of the vehicle through analysis of information about the vehicle captured by an Internet-of-things device 34150 during operation of the vehicle 3410; and a second neural network 3420 that operates to optimize at least one operating parameter 34124 of the vehicle based on the classified state 34152 of the vehicle, information about a state of a rider occupying the vehicle, and information that correlates vehicle operation with an effect on rider state.

In embodiments, the vehicle comprises a system for automating at least one control parameter 34153 of the vehicle 3410. In embodiments, the vehicle 3410 is at least a semi-autonomous vehicle. In embodiments, the vehicle 3410 is automatically routed. In embodiments, the vehicle 3410 is a self-driving vehicle. In embodiments, the at least one Internet-of-things device 34150 is disposed in an operating environment of the vehicle 3410. In embodiments, the at least one Internet-of-things device 34150 that captures the data about the vehicle 3410 is disposed external to the vehicle 3410. In embodiments, the at least one Internet-of-things device is a dashboard camera. In embodiments, the at least one Internet-of-things device is a mirror camera. In embodiments, the at least one Internet-of-things device is a motion sensor. In embodiments, the at least one Internet-of-things device is a seat-based sensor system. In embodiments, the at least one Internet-of-things device is an IoT enabled lighting system. In embodiments, the lighting system is a vehicle interior lighting system. In embodiments, the lighting system is a headlight lighting system. In embodiments, the at least one Internet-of-things device is a traffic light camera or sensor. In embodiments, the at least one Internet-of-things device is a roadway camera. In embodiments, the roadway camera is disposed on at least one of a telephone phone and a light pole. In embodiments, the at least one Internet-of-things device is an in-road sensor. In embodiments, the at least one Internet-of-things device is an in-vehicle thermostat. In embodiments, the at least one Internet-of-things device is a toll booth. In embodiments, the at least one Internet-of-things device is a street sign. In embodiments, the at least one Internet-of-things device is a traffic control light. In embodiments, the at least one Internet-of-things device is a vehicle mounted sensor. In embodiments, the at least one Internet-of-things device is a refueling system. In embodiments, the at least one Internet-of-things device is a recharging system. In embodiments, the at least one Internet-of-things device is a wireless charging station.

An aspect provided herein includes an artificial intelligence system 3436 comprising: a first neural network 3422 trained to determine an operating state 34152 of a vehicle 3410 from data about the vehicle captured in an operating environment 34154 of the vehicle, wherein the first neural network 3422 operates to identify an operating state 34152 of the vehicle by processing information about the vehicle 3410 that is captured by at least one Internet-of things device 34150 while the vehicle is operating; a data structure 34156 that facilitates determining operating parameters that influence an operating state of a vehicle; a second neural network 3420 that operates to optimize at least one of the determined operating parameters 34124 of the vehicle based on the identified operating state 34152 by processing information about a state of a rider 3444 occupying the vehicle 3410, and information that correlates vehicle operation with an effect on rider state.

In embodiments, the improvement in the state of the rider is reflected in updated data that is descriptive of a state of the rider captured responsive to the vehicle operation based on the optimized at least one vehicle operating parameter. In embodiments, the improvement in the state of the rider is reflected in data captured by at least one Internet-of-things device 34150 disposed to capture information about the rider 3444 while occupying the vehicle 3410 responsive to the optimizing. In embodiments, the vehicle 3410 comprises a system for automating at least one control parameter 34153 of the vehicle. In embodiments, the vehicle 3410 is at least a semi-autonomous vehicle. In embodiments, the vehicle 3410 is automatically routed. In embodiments, the vehicle 3410 is a self-driving vehicle. In embodiments, the at least one Internet-of-things device 34150 is disposed in an operating environment 34154 of the vehicle. In embodiments, the at least one Internet-of-things device 34150 that captures the data about the vehicle is disposed external to the vehicle. In embodiments, the at least one Internet-of-things device 34150 is a dashboard camera. In embodiments, the at least one Internet-of-things device 34150 is a mirror camera. In embodiments, the at least one Internet-of-things device 34150 is a motion sensor. In embodiments, the at least one Internet-of-things device 34150 is a seat-based sensor system. In embodiments, the at least one Internet-of-things device 34150 is an IoT enabled lighting system.

In embodiments, the lighting system is a vehicle interior lighting system. In embodiments, the lighting system is a headlight lighting system. In embodiments, the at least one Internet-of-things device 34150 is a traffic light camera or sensor. In embodiments, the at least one Internet-of-things device 34150 is a roadway camera. In embodiments, the roadway camera is disposed on at least one of a telephone phone and a light pole. In embodiments, the at least one Internet-of-things device 34150 is an in-road sensor. In embodiments, the at least one Internet-of-things device 34150 is an in-vehicle thermostat. In embodiments, the at least one Internet-of-things device 34150 is a toll booth. In embodiments, the at least one Internet-of-things device 34150 is a street sign. In embodiments, the at least one Internet-of-things device 34150 is a traffic control light. In embodiments, the at least one Internet-of-things device 34150 is a vehicle mounted sensor. In embodiments, the at least one Internet-of-things device 34150 is a refueling system. In embodiments, the at least one Internet-of-things device 34150 is a recharging system. In embodiments, the at least one Internet-of-things device 34150 is a wireless charging station.

Figure 36:
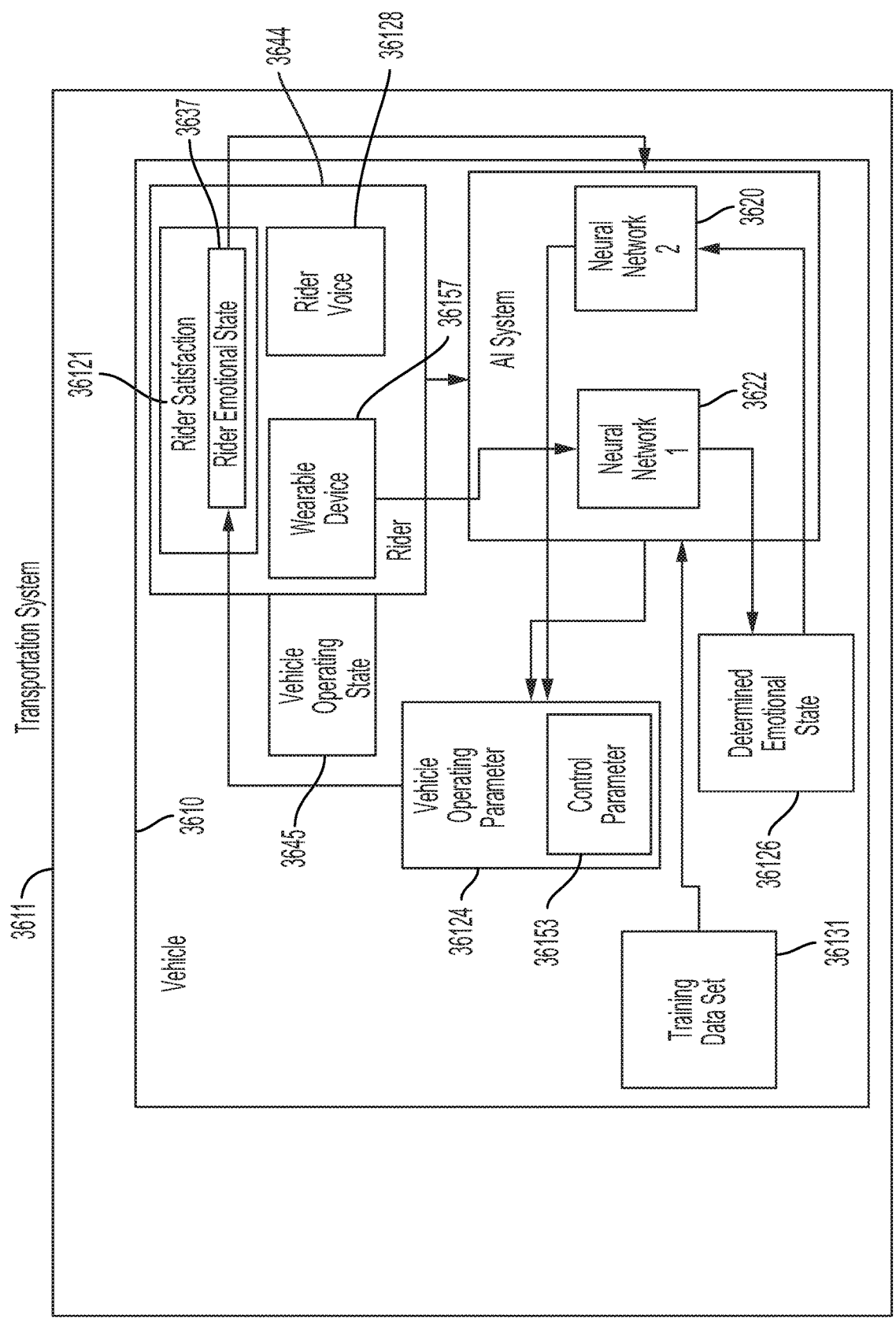
FIG. 36 is a diagrammatic view that illustrates systems described throughout this disclosure relating to various embodiments of the present disclosure.

Referring to FIG. 36, in embodiments provided herein are transportation systems 3611 having an artificial intelligence system 3636 for processing a sensory input from a wearable device 36157 in a vehicle 3610 to determine an emotional state 36126 and optimizing at least one operating parameter 36124 of the vehicle 3610 to improve the rider's emotional state 3637. A wearable device 36150, such as any described throughout this disclosure, may be used to detect any of the emotional states described herein (favorable or unfavorable) and used both as an input to a real-time control system (such as a model-based, rule-based, or artificial intelligence system of any of the types described herein), such as to indicate an objective to improve an unfavorable state or maintain a favorable state, as well as a feedback mechanism to train an artificial intelligence system 3636 to configure sets of operating parameters 36124 to promote or maintain favorable states.

An aspect provided herein includes a system for transportation 3611, comprising: an artificial intelligence system 3636 for processing a sensory input from a wearable device 36157 in a vehicle 3610 to determine an emotional state 36126 of a rider 3644 in the vehicle 3610 and optimizing an operating parameter 36124 of the vehicle to improve the emotional state 3637 of the rider 3644. In embodiments, the vehicle is a self-driving vehicle. In embodiments, the artificial intelligence system 3636 is to detect the emotional state 36126 of the rider riding in the self-driving vehicle by recognition of patterns of emotional state indicative data from a set of wearable sensors 36157 worn by the rider 3644. In embodiments, the patterns are indicative of at least one of a favorable emotional state of the rider and an unfavorable emotional state of the rider. In embodiments, the artificial intelligence system 3636 is to optimize, for achieving at least one of maintaining a detected favorable emotional state of the rider and achieving a favorable emotional state of a rider subsequent to a detection of an unfavorable emotional state, the operating parameter 36124 of the vehicle in response to the detected emotional state of the rider. In embodiments, the artificial intelligence system 3636 comprises an expert system that detects an emotional state of the rider by processing rider emotional state indicative data received from the set of wearable sensors 36157 worn by the rider. In embodiments, the expert system processes the rider emotional state indicative data using at least one of a training set of emotional state indicators of a set of riders and trainer-generated rider emotional state indicators. In embodiments, the artificial intelligence system comprises a recurrent neural network 3622 that detects the emotional state of the rider.

In embodiments, the recurrent neural network comprises a plurality of connected nodes that form a directed cycle, the recurrent neural network further facilitating bi-directional flow of data among the connected nodes. In embodiments, the artificial intelligence system 3636 comprises a radial basis function neural network 3620 that optimizes the operational parameter 36124. In embodiments, the optimizing an operational parameter 36124 is based on a correlation between a vehicle operating state 3645 and a rider emotional state 3637. In embodiments, the correlation is determined using at least one of a training set of emotional state indicators of a set of riders and human trainer-generated rider emotional state indicators. In embodiments, the operational parameter of the vehicle that is optimized is determined and adjusted to induce a favorable rider emotional state.

In embodiments, the artificial intelligence system 3636 further learns to classify the patterns of the emotional state indicative data and associate the patterns to emotional states and changes thereto from a training data set 36131 sourced from at least one of a stream of data from unstructured data sources, social media sources, wearable devices, in-vehicle sensors, a rider helmet, a rider headgear, and a rider voice system. In embodiments, the artificial intelligence system 3636 detects a pattern of the rider emotional state indicative data that indicates the emotional state of the rider is changing from a first emotional state to a second emotional state, the optimizing of the operational parameter of the vehicle being response to the indicated change in emotional state. In embodiments, the patterns of rider emotional state indicative data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter 36124 that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the artificial intelligence system 3636 interacts with a vehicle control system to optimize the operational parameter. In embodiments, the artificial intelligence system 3636 further comprises a neural net 3622 that includes one or more perceptrons that mimic human senses that facilitates determining an emotional state of a rider based on an extent to which at least one of the senses of the rider is stimulated. In embodiments, the set of wearable sensors 36157 comprises at least two of a watch, a ring, a wrist band, an arm band, an ankle band, a torso band, a skin patch, a head-worn device, eye glasses, foot wear, a glove, an in-ear device, clothing, headphones, a belt, a finger ring, a thumb ring, a toe ring, and a necklace. In embodiments, the artificial intelligence system 3636 uses deep learning for determining patterns of wearable sensor-generated emotional state indicative data that indicate an emotional state of the rider as at least one of a favorable emotional state and an unfavorable emotional state. In embodiments, the artificial intelligence system 3636 is responsive to a rider indicated emotional state by at least optimizing the operation parameter to at least one of achieve and maintain the rider indicated emotional state.

In embodiments, the artificial intelligence system 3636 adapts a characterization of a favorable emotional state of the rider based on context gathered from a plurality of sources including data indicating a purpose of the rider riding in the self-driving vehicle, a time of day, traffic conditions, weather conditions and optimizes the operating parameter 36124 to at least one of achieve and maintain the adapted favorable emotional state. In embodiments, the artificial intelligence system 3636 optimizes the operational parameter in real time responsive to the detecting of an emotional state of the rider. In embodiments, the vehicle is a self-driving vehicle. In embodiments, the artificial intelligence system comprises: a first neural network 3622 to detect the emotional state of the rider through expert system-based processing of rider emotional state indicative wearable sensor data of a plurality of wearable physiological condition sensors worn by the rider in the vehicle, the emotional state indicative wearable sensor data indicative of at least one of a favorable emotional state of the rider and an unfavorable emotional state of the rider; and a second neural network 3620 to optimize, for at least one of achieving and maintaining a favorable emotional state of the rider, the operating parameter 36124 of the vehicle in response to the detected emotional state of the rider. In embodiments, the first neural network 3622 is a recurrent neural network and the second neural network 3620 is a radial basis function neural network.

In embodiments, the second neural network 3620 optimizes the operational parameter 36124 based on a correlation between a vehicle operating state 3645 and a rider emotional state 3637. In embodiments, the operational parameter of the vehicle that is optimized is determined and adjusted to induce a favorable rider emotional state. In embodiments, the first neural network 3622 further learns to classify patterns of the rider emotional state indicative wearable sensor data and associate the patterns to emotional states and changes thereto from a training data set sourced from at least one of a stream of data from unstructured data sources, social media sources, wearable devices, in-vehicle sensors, a rider helmet, a rider headgear, and a rider voice system. In embodiments, the second neural network 3620 optimizes the operational parameter in real time responsive to the detecting of an emotional state of the rider by the first neural network 3622. In embodiments, the first neural network 3622 detects a pattern of the rider emotional state indicative wearable sensor data that indicates the emotional state of the rider is changing from a first emotional state to a second emotional state. In embodiments, the second neural network 3620 optimizes the operational parameter of the vehicle in response to the indicated change in emotional state.

In embodiments, the first neural network 3622 comprises a plurality of connected nodes that form a directed cycle, the first neural network 3622 further facilitating bi-directional flow of data among the connected nodes. In embodiments, the first neural network 3622 includes one or more perceptrons that mimic human senses that facilitates determining an emotional state of a rider based on an extent to which at least one of the senses of the rider is stimulated. In embodiments, the rider emotional state indicative wearable sensor data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the second neural network 3620 interacts with a vehicle control system to adjust the operational parameter. In embodiments, the first neural network 3622 includes one or more perceptrons that mimic human senses that facilitates determining an emotional state of a rider based on an extent to which at least one of the senses of the rider is stimulated.

In embodiments, the vehicle is a self-driving vehicle. In embodiments, the artificial intelligence system 3636 is to detect a change in the emotional state of the rider riding in the self-driving vehicle at least in part by recognition of patterns of emotional state indicative data from a set of wearable sensors worn by the rider. In embodiments, the patterns are indicative of at least one of a diminishing of a favorable emotional state of the rider and an onset of an unfavorable emotional state of the rider. In embodiments, the artificial intelligence system 3636 is to determine at least one operating parameter 36124 of the self-driving vehicle that is indicative of the change in emotional state based on a correlation of the patterns of emotional state indicative data with a set of operating parameters of the vehicle. In embodiments, the artificial intelligence system 3636 is to determine an adjustment of the at least one operating parameter 36124 for achieving at least one of restoring the favorable emotional state of the rider and achieving a reduction in the onset of the unfavorable emotional state of a rider.

In embodiments, the correlation of patterns of rider emotional indicative state wearable sensor data is determined using at least one of a training set of emotional state wearable sensor indicators of a set of riders and human trainer-generated rider emotional state wearable sensor indicators. In embodiments, the artificial intelligence system 3636 further learns to classify the patterns of the emotional state indicative wearable sensor data and associate the patterns to changes in rider emotional states from a training data set sourced from at least one of a stream of data from unstructured data sources, social media sources, wearable devices, in-vehicle sensors, a rider helmet, a rider headgear, and a rider voice system. In embodiments, the patterns of rider emotional state indicative wearable sensor data indicates at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter determined from a result of processing the rider emotional state indicative wearable sensor data affects at least one of a route of the vehicle, in-vehicle audio content, speed of the vehicle, acceleration of the vehicle, deceleration of the vehicle, proximity to objects along the route, and proximity to other vehicles along the route. In embodiments, the artificial intelligence system 3636 further interacts with a vehicle control system for adjusting the operational parameter. In embodiments, the artificial intelligence system 3636 further comprises a neural net that includes one or more perceptrons that mimic human senses that facilitate determining an emotional state of a rider based on an extent to which at least one of the senses of the rider is stimulated.

In embodiments, the set of wearable sensors comprises at least two of a watch, a ring, a wrist band, an arm band, an ankle band, a torso band, a skin patch, a head-worn device, eye glasses, foot wear, a glove, an in-ear device, clothing, headphones, a belt, a finger ring, a thumb ring, a toe ring, and a necklace. In embodiments, the artificial intelligence system 3636 uses deep learning for determining patterns of wearable sensor-generated emotional state indicative data that indicate the change in the emotional state of the rider. In embodiments, the artificial intelligence system 3636 further determines the change in emotional state of the rider based on context gathered from a plurality of sources including data indicating a purpose of the rider riding in the self-driving vehicle, a time of day, traffic conditions, weather conditions and optimizes the operating parameter 36124 to at least one of achieve and maintain the adapted favorable emotional state. In embodiments, the artificial intelligence system 3636 adjusts the operational parameter in real time responsive to the detecting of a change in rider emotional state.

In embodiments, the vehicle is a self-driving vehicle. In embodiments, the artificial intelligence system 3636 includes: a recurrent neural network to indicate a change in the emotional state of a rider in the self-driving vehicle by a recognition of patterns of emotional state indicative wearable sensor data from a set of wearable sensors worn by the rider. In embodiments, the patterns are indicative of at least one of a first degree of an favorable emotional state of the rider and a second degree of an unfavorable emotional state of the rider; and a radial basis function neural network to optimize, for achieving a target emotional state of the rider, the operating parameter 36124 of the vehicle in response to the indication of the change in the emotional state of the rider.

In embodiments, the radial basis function neural network optimizes the operational parameter based on a correlation between a vehicle operating state and a rider emotional state. In embodiments, the target emotional state is a favorable rider emotional state and the operational parameter of the vehicle that is optimized is determined and adjusted to induce the favorable rider emotional state. In embodiments, the recurrent neural network further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system. In embodiments, the radial basis function neural network optimizes the operational parameter in real time responsive to the detecting of a change in an emotional state of the rider by the recurrent neural network. In embodiments, the recurrent neural network detects a pattern of the emotional state indicative wearable sensor data that indicates the emotional state of the rider is changing from a first emotional state to a second emotional state. In embodiments, the radial basis function neural network optimizes the operational parameter of the vehicle in response to the indicated change in emotional state. In embodiments, the recurrent neural network comprises a plurality of connected nodes that form a directed cycle, the recurrent neural network further facilitating bi-directional flow of data among the connected nodes.

In embodiments, the patterns of emotional state indicative wearable sensor data indicate at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state. In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the radial basis function neural network interacts with a vehicle control system to adjust the operational parameter. In embodiments, the recurrent neural net includes one or more perceptrons that mimic human senses that facilitates determining an emotional state of a rider based on an extent to which at least one of the senses of the rider is stimulated.

In embodiments, the artificial intelligence system 3636 is to maintain a favorable emotional state of the rider through use of a modular neural network, the modular neural network comprising: a rider emotional state determining neural network to process emotional state indicative wearable sensor data of a rider in the vehicle to detect patterns. In embodiments, the patterns found in the emotional state indicative wearable sensor data are indicative of at least one of a favorable emotional state of the rider and an unfavorable emotional state of the rider; an intermediary circuit to convert output data from the rider emotional state determining neural network into vehicle operational state data; and a vehicle operational state optimizing neural network to adjust the operating parameter 36124 of the vehicle in response to the vehicle operational state data.

In embodiments, the vehicle operational state optimizing neural network adjusts an operational parameter of the vehicle for achieving a favorable emotional state of the rider. In embodiments, the vehicle operational state optimizing neural network optimizes the operational parameter based on a correlation between a vehicle operating state and a rider emotional state. In embodiments, the operational parameter of the vehicle that is optimized is determined and adjusted to induce a favorable rider emotional state. In embodiments, the rider emotional state determining neural network further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system.

In embodiments, the vehicle operational state optimizing neural network optimizes the operational parameter in real time responsive to the detecting of a change in an emotional state of the rider by the rider emotional state determining neural network. In embodiments, the rider emotional state determining neural network detects a pattern of emotional state indicative wearable sensor data that indicates the emotional state of the rider is changing from a first emotional state to a second emotional state. In embodiments, the vehicle operational state optimizing neural network optimizes the operational parameter of the vehicle in response to the indicated change in emotional state. In embodiments, the artificial intelligence system 3636 comprises a plurality of connected nodes that forms a directed cycle, the artificial intelligence system 3636 further facilitating bi-directional flow of data among the connected nodes. In embodiments, the pattern of emotional state indicative wearable sensor data indicate at least one of an emotional state of the rider is changing, an emotional state of the rider is stable, a rate of change of an emotional state of the rider, a direction of change of an emotional state of the rider, and a polarity of a change of an emotional state of the rider; an emotional state of a rider is changing to an unfavorable state; and an emotional state of a rider is changing to a favorable state.

In embodiments, the operational parameter that is optimized affects at least one of a route of the vehicle, in-vehicle audio content, speed of the vehicle, acceleration of the vehicle, deceleration of the vehicle, proximity to objects along the route, and proximity to other vehicles along the route. In embodiments, the vehicle operational state optimizing neural network interacts with a vehicle control system to adjust the operational parameter. In embodiments, the artificial intelligence system 3636 further comprises a neural net that includes one or more perceptrons that mimic human senses that facilitates determining an emotional state of a rider based on an extent to which at least one of the senses of the rider is stimulated. In embodiments, the rider emotional state determining neural network comprises one or more perceptrons that mimic human senses that facilitates determining an emotional state of a rider based on an extent to which at least one of the senses of the rider is stimulated.

In embodiments, the artificial intelligence system 3636 is to indicate a change in the emotional state of a rider in the vehicle through recognition of patterns of emotional state indicative wearable sensor data of the rider in the vehicle; the transportation system further comprising: a vehicle control system to control an operation of the vehicle by adjusting a plurality of vehicle operating parameters; and a feedback loop through which the indication of the change in the emotional state of the rider is communicated between the vehicle control system and the artificial intelligence system 3636. In embodiments, the vehicle control system adjusts at least one of the plurality of vehicle operating parameters responsive to the indication of the change. In embodiments, the vehicle controls system adjusts the at least one of the plurality of vehicle operational parameters based on a correlation between vehicle operational state and rider emotional state.

In embodiments, the vehicle control system adjusts the at least one of the plurality of vehicle operational parameters that are indicative of a favorable rider emotional state. In embodiments, the vehicle control system selects an adjustment of the at least one of the plurality of vehicle operational parameters that is indicative of producing a favorable rider emotional state. In embodiments, the artificial intelligence system 3636 further learns to classify the patterns of emotional state indicative wearable sensor data and associate them to emotional states and changes thereto from a training data set sourced from at least one of a stream of data from unstructured data sources, social media sources, wearable devices, in-vehicle sensors, a rider helmet, a rider headgear, and a rider voice system. In embodiments, the vehicle control system adjusts the at least one of the plurality of vehicle operation parameters in real time.

In embodiments, the artificial intelligence system 3636 further detects a pattern of the emotional state indicative wearable sensor data that indicates the emotional state of the rider is changing from a first emotional state to a second emotional state. In embodiments, the vehicle operation control system adjusts an operational parameter of the vehicle in response to the indicated change in emotional state. In embodiments, the artificial intelligence system 3636 comprises a plurality of connected nodes that form a directed cycle, the artificial intelligence system 3636 further facilitating bi-directional flow of data among the connected nodes. In embodiments, the at least one of the plurality of vehicle operation parameters that is responsively adjusted affects operation of a powertrain of the vehicle and a suspension system of the vehicle.

In embodiments, the radial basis function neural network interacts with the recurrent neural network via an intermediary component of the artificial intelligence system 3636 that produces vehicle control data indicative of an emotional state response of the rider to a current operational state of the vehicle. In embodiments, the artificial intelligence system 3636 further comprises a modular neural network comprising a rider emotional state recurrent neural network for indicating the change in the emotional state of a rider, a vehicle operational state radial based function neural network, and an intermediary system. In embodiments, the intermediary system processes rider emotional state characterization data from the recurrent neural network into vehicle control data that the radial based function neural network uses to interact with the vehicle control system for adjusting the at least one operational parameter.

In embodiments, the artificial intelligence system 3636 comprises a neural net that includes one or more perceptrons that mimic human senses that facilitate determining an emotional state of a rider based on an extent to which at least one of the senses of the rider is stimulated. In embodiments, the recognition of patterns of emotional state indicative wearable sensor data comprises processing the emotional state indicative wearable sensor data captured during at least two of before the adjusting at least one of the plurality of vehicle operational parameters, during the adjusting at least one of the plurality of vehicle operational parameters, and after adjusting at least one of the plurality of vehicle operational parameters.

In embodiments, the artificial intelligence system 3636 indicates a change in the emotional state of the rider responsive to a change in an operating parameter 36124 of the vehicle by determining a difference between a first set of emotional state indicative wearable sensor data of a rider captured prior to the adjusting at least one of the plurality of operating parameters and a second set of emotional state indicative wearable sensor data of the rider captured during or after the adjusting at least one of the plurality of operating parameters.

Figure 37:
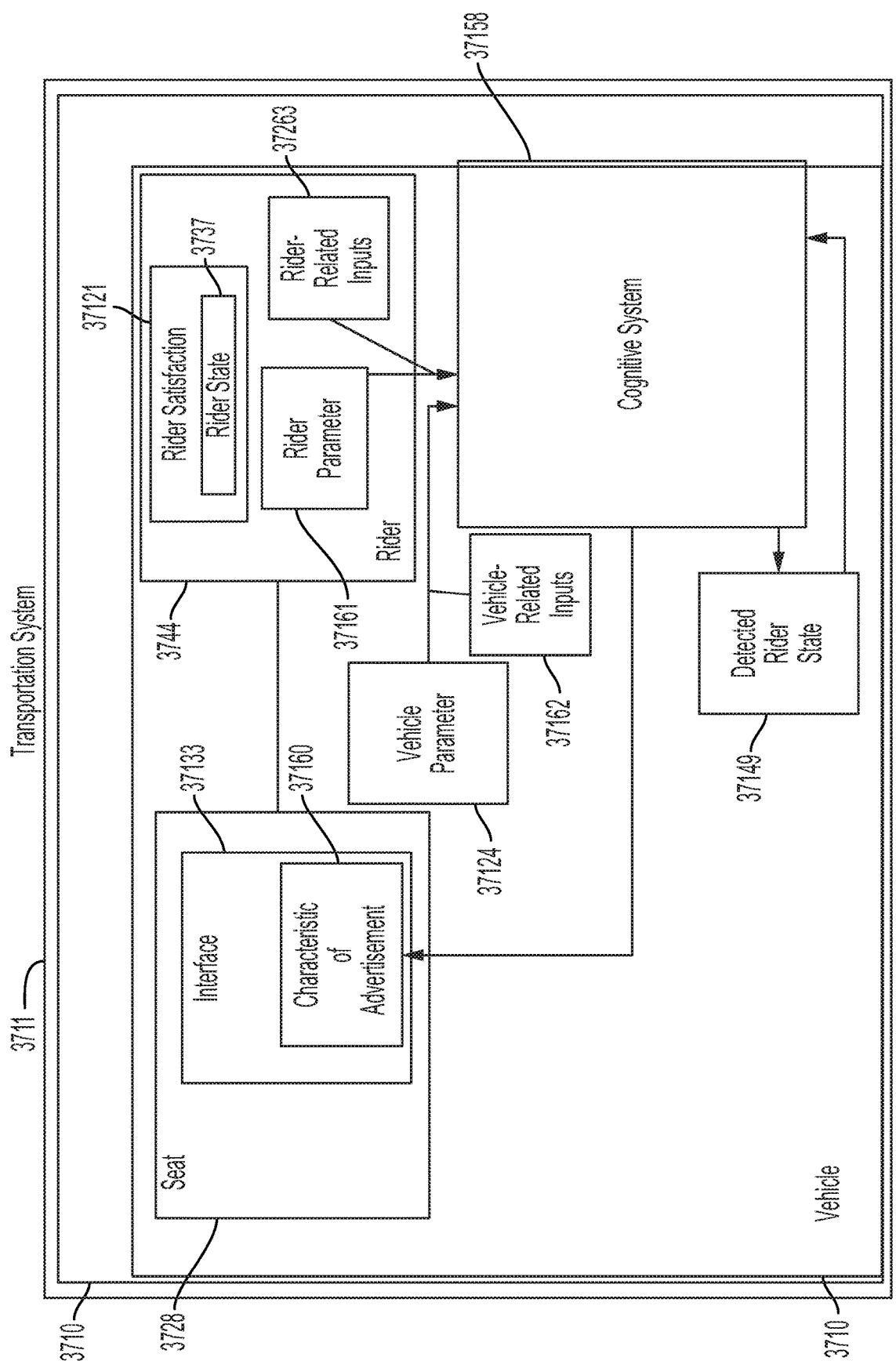
FIG. 37 is a diagrammatic view that illustrates systems described throughout this disclosure relating to various embodiments of the present disclosure.

Referring to FIG. 37, in embodiments provided herein are transportation systems 3711 having a cognitive system 37158 for managing an advertising market for in-seat advertising for riders 3744 of self-driving vehicles. In embodiments, the cognitive system 37158 takes inputs relating to at least one parameter 37124 of the vehicle and/or the rider 3744 to determine at least one of a price, a type and a location of an advertisement to be delivered within an interface 37133 to a rider 3744 in a seat 3728 of the vehicle. As described above in connection with search, in-vehicle riders, particularly in self-driving vehicles, may be situationally disposed quite differently toward advertising when riding in a vehicle than at other times. Bored riders may be more willing to watch advertising content, click on offers or promotions, engage in surveys, or the like. In embodiments, an advertising marketplace platform may segment and separately handle advertising placements (including handling bids and asks for advertising placement and the like) for in-vehicle ads. Such an advertising marketplace platform may use information that is unique to a vehicle, such as vehicle type, display type, audio system capabilities, screen size, rider demographic information, route information, location information, and the like when characterizing advertising placement opportunities, such that bids for in-vehicle advertising placement reflect such vehicle, rider and other transportation-related parameters. For example, an advertiser may bid for placement of advertising on in-vehicle display systems of self-driving vehicles that are worth more than $50,000 and that are routed north on highway 101 during the morning commute. The advertising marketplace platform may be used to configure many such vehicle-related placement opportunities, to handle bidding for such opportunities, to place advertisements (such as by load-balanced servers that cache the ads) and to resolve outcomes. Yield metrics may be tracked and used to optimize configuration of the marketplace.

An aspect provided herein includes a system for transportation, comprising: a cognitive system 37158 for managing an advertising market for in-seat advertising for riders of self-driving vehicles, wherein the cognitive system 37158 takes inputs corresponding to at least one parameter 37159 of the vehicle or the rider 3744 to determine a characteristic 37160 of an advertisement to be delivered within an interface 37133 to a rider 3744 in a seat 3728 of the vehicle, wherein the characteristic 37160 of the advertisement is selected from the group consisting of a price, a category, a location and combinations thereof.

Figure 38:
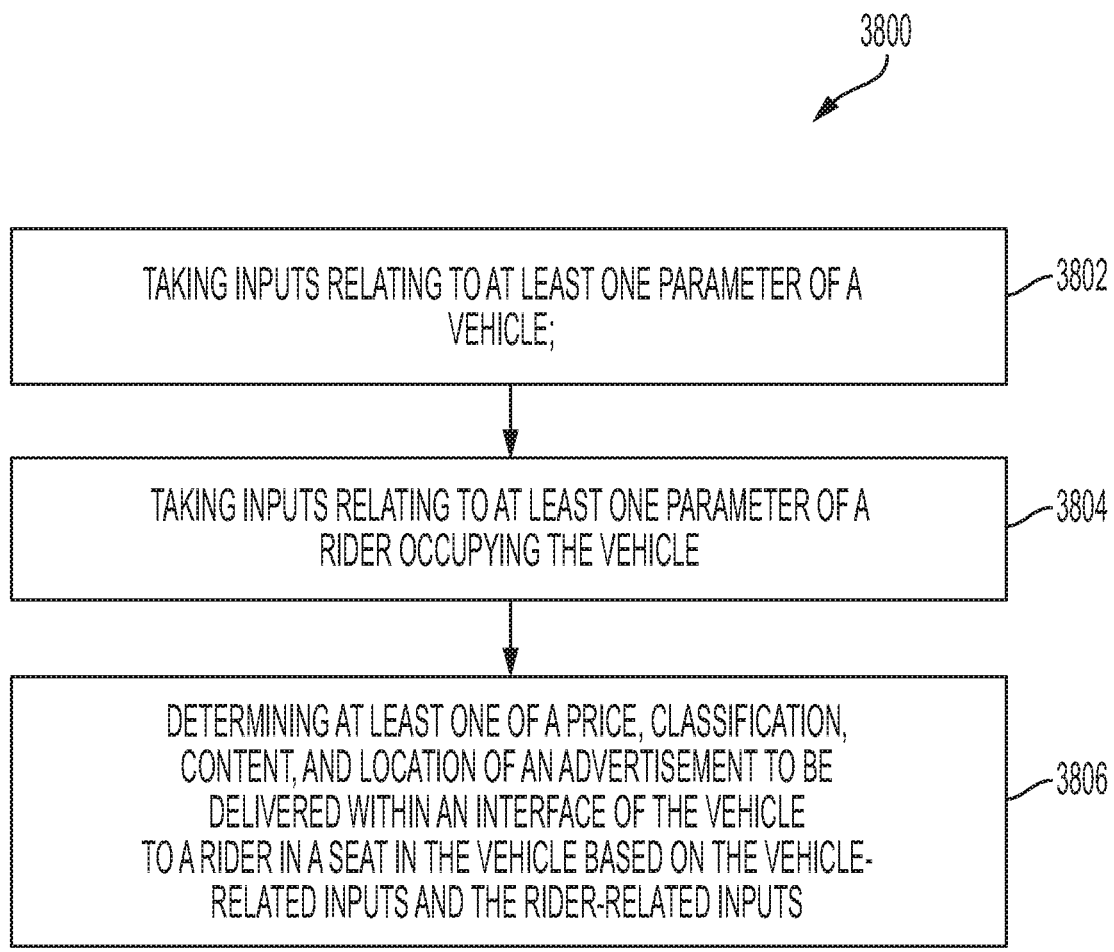
FIG. 38 is a diagrammatic view that illustrates a method described throughout this disclosure relating to various embodiments of the present disclosure.

FIG. 38 illustrates a method 3800 of vehicle in-seat advertising in accordance with embodiments of the systems and methods disclosed herein. At 3802 the method includes taking inputs relating to at least one parameter of a vehicle. At 3804 the method includes taking inputs relating to at least one parameter of a rider occupying the vehicle. At 3806 the method includes determining at least one of a price, classification, content, and location of an advertisement to be delivered within an interface of the vehicle to a rider in a seat in the vehicle based on the vehicle-related inputs and the rider-related inputs.

Referring to FIG. 37 and FIG. 38, in embodiments, the vehicle 3710 is automatically routed. In embodiments, the vehicle 3710 is a self-driving vehicle. In embodiments, the cognitive system 37158 further determines at least one of a price, classification, content and location of an advertisement placement. In embodiments, an advertisement is delivered from an advertiser who places a winning bid. In embodiments, delivering an advertisement is based on a winning bid. In embodiments, the inputs 37162 relating to the at least one parameter of a vehicle include vehicle classification. In embodiments, the inputs 37162 relating to the at least one parameter of a vehicle include display classification. In embodiments, the inputs 37162 relating to the at least one parameter of a vehicle include audio system capability. In embodiments, the inputs 37162 relating to the at least one parameter of a vehicle include screen size.

In embodiments, the inputs 37162 relating to the at least one parameter of a vehicle include route information. In embodiments, the inputs 37162 relating to the at least one parameter of a vehicle include location information. In embodiments, the inputs 37163 relating to the at least one parameter of a rider include rider demographic information. In embodiments, the inputs 37163 relating to the at least one parameter of a rider include rider emotional state. In embodiments, the inputs 37163 relating to the at least one parameter of a rider include rider response to prior in-seat advertising. In embodiments, the inputs 37163 relating to the at least one parameter of a rider include rider social media activity.

Figure 39:
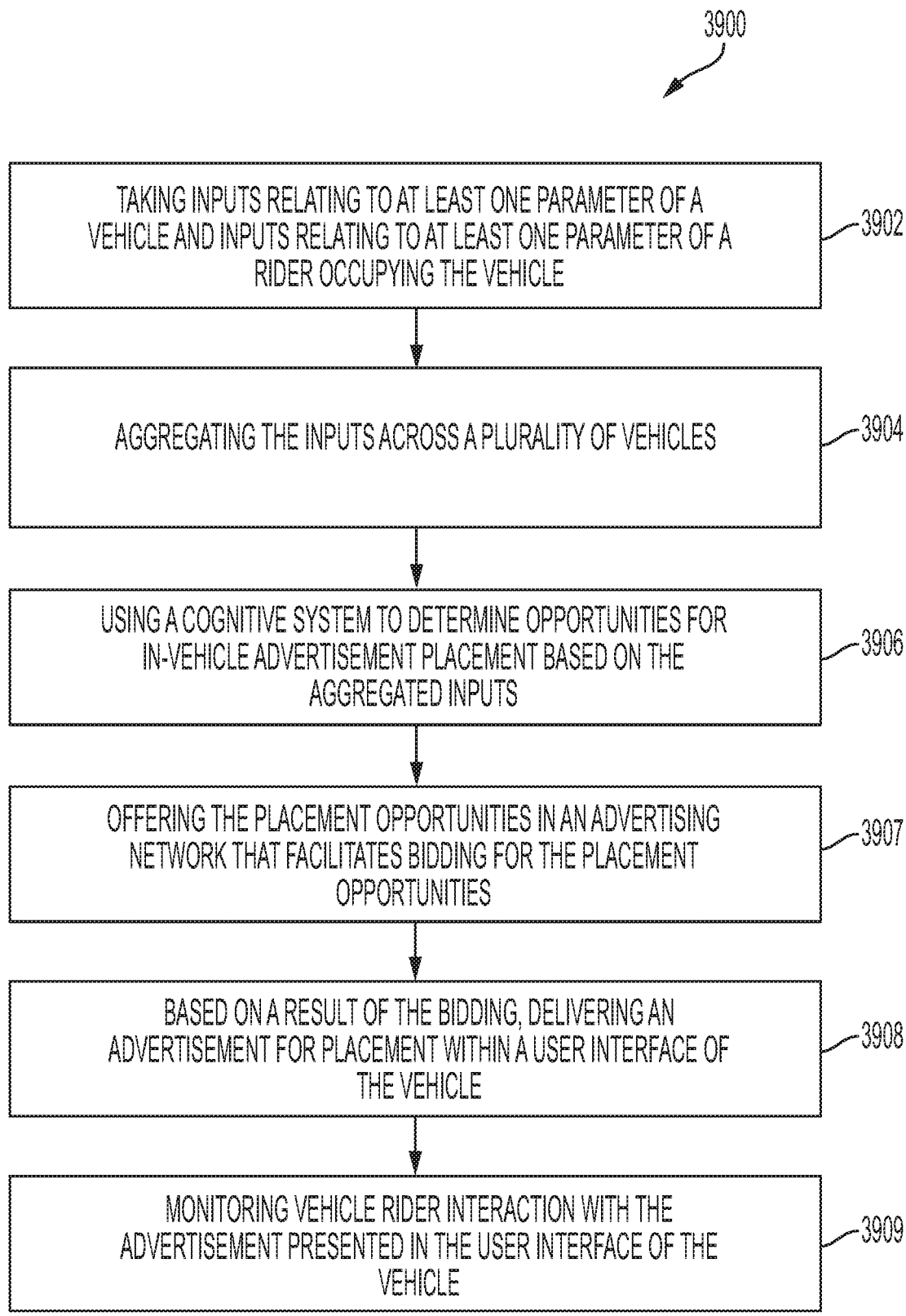
FIG. 39 is a diagrammatic view that illustrates a method described throughout this disclosure relating to various embodiments of the present disclosure.

FIG. 39 illustrates a method 3900 of in-vehicle advertising interaction tracking in accordance with embodiments of the systems and methods disclosed herein. At 3902 the method includes taking inputs relating to at least one parameter of a vehicle and inputs relating to at least one parameter of a rider occupying the vehicle. At 3904 the method includes aggregating the inputs across a plurality of vehicles. At 3906 the method includes using a cognitive system to determine opportunities for in-vehicle advertisement placement based on the aggregated inputs. At 3907 the method includes offering the placement opportunities in an advertising network that facilitates bidding for the placement opportunities. At 3908 the method includes based on a result of the bidding, delivering an advertisement for placement within a user interface of the vehicle. At 3909 the method includes monitoring vehicle rider interaction with the advertisement presented in the user interface of the vehicle.

Referring to FIGS. 37 and 39, in embodiments, the vehicle 3710 comprises a system for automating at least one control parameter of the vehicle. In embodiments, the vehicle 3710 is at least a semi-autonomous vehicle. In embodiments, the vehicle 3710 is automatically routed. In embodiments, the vehicle 3710 is a self-driving vehicle. In embodiments, an advertisement is delivered from an advertiser who places a winning bid. In embodiments, delivering an advertisement is based on a winning bid. In embodiments, the monitored vehicle rider interaction information includes information for resolving click-based payments. In embodiments, the monitored vehicle rider interaction information includes an analytic result of the monitoring. In embodiments, the analytic result is a measure of interest in the advertisement. In embodiments, the inputs 37162 relating to the at least one parameter of a vehicle include vehicle classification.

In embodiments, the inputs 37162 relating to the at least one parameter of a vehicle include display classification. In embodiments, the inputs 37162 relating to the at least one parameter of a vehicle include audio system capability. In embodiments, the inputs 37162 relating to the at least one parameter of a vehicle include screen size. In embodiments, the inputs 37162 relating to the at least one parameter of a vehicle include route information. In embodiments, the inputs 37162 relating to the at least one parameter of a vehicle include location information. In embodiments, the inputs 37163 relating to the at least one parameter of a rider include rider demographic information. In embodiments, the inputs 37163 relating to the at least one parameter of a rider include rider emotional state. In embodiments, the inputs 37163 relating to the at least one parameter of a rider include rider response to prior in-seat advertising. In embodiments, the inputs 37163 relating to the at least one parameter of a rider include rider social media activity.

Figure 40:
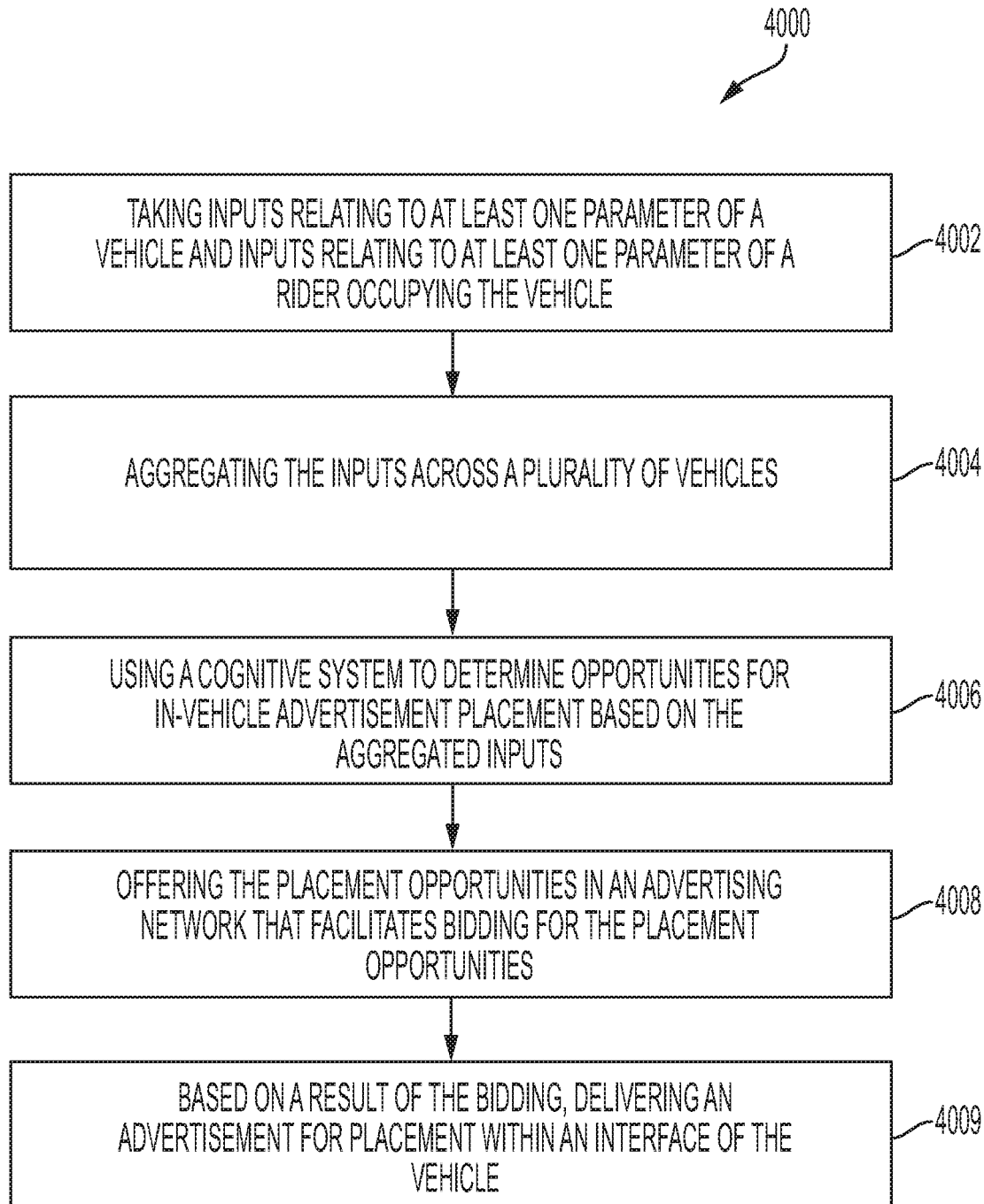
FIG. 40 is a diagrammatic view that illustrates a method described throughout this disclosure relating to various embodiments of the present disclosure.

FIG. 40 illustrates a method 4000 of in-vehicle advertising in accordance with embodiments of the systems and methods disclosed herein. At 4002 the method includes taking inputs relating to at least one parameter of a vehicle and inputs relating to at least one parameter of a rider occupying the vehicle. At 4004 the method includes aggregating the inputs across a plurality of vehicles. At 4006 the method includes using a cognitive system to determine opportunities for in-vehicle advertisement placement based on the aggregated inputs. At 4008 the method includes offering the placement opportunities in an advertising network that facilitates bidding for the placement opportunities. At 4009 the method includes based on a result of the bidding, delivering an advertisement for placement within an interface of the vehicle.

Referring to FIG. 37 and FIG. 40, in embodiments, the vehicle 3710 comprises a system for automating at least one control parameter of the vehicle. In embodiments, the vehicle 3710 is at least a semi-autonomous vehicle. In embodiments, the vehicle 3710 is automatically routed. In embodiments, the vehicle 3710 is a self-driving vehicle. In embodiments, the cognitive system 37158 further determines at least one of a price, classification, content and location of an advertisement placement. In embodiments, an advertisement is delivered from an advertiser who places a winning bid. In embodiments, delivering an advertisement is based on a winning bid. In embodiments, the inputs 37162 relating to the at least one parameter of a vehicle include vehicle classification.

In embodiments, the inputs 37162 relating to the at least one parameter of a vehicle include display classification. In embodiments, the inputs 37162 relating to the at least one parameter of a vehicle include audio system capability. In embodiments, the inputs 37162 relating to the at least one parameter of a vehicle include screen size. In embodiments, the inputs 37162 relating to the at least one parameter of a vehicle include route information. In embodiments, the inputs 37162 relating to the at least one parameter of a vehicle include location information. In embodiments, the inputs 37163 relating to the at least one parameter of a rider include rider demographic information. In embodiments, the inputs 37163 relating to the at least one parameter of a rider include rider emotional state. In embodiments, the inputs 37163 relating to the at least one parameter of a rider include rider response to prior in-seat advertising. In embodiments, the inputs 37163 relating to the at least one parameter of a rider include rider social media activity.

An aspect provided herein includes an advertising system of vehicle in-seat advertising, the advertising system comprising: a cognitive system 37158 that takes inputs 37162 relating to at least one parameter 37124 of a vehicle 3710 and takes inputs relating to at least one parameter 37161 of a rider occupying the vehicle, and determines at least one of a price, classification, content and location of an advertisement to be delivered within an interface 37133 of the vehicle 3710 to a rider 3744 in a seat 3728 in the vehicle 3710 based on the vehicle-related inputs 37162 and the rider-related inputs 37163.

In embodiments, the vehicle 4110 comprises a system for automating at least one control parameter of the vehicle. In embodiments, the vehicle 4110 is at least a semi-autonomous vehicle. In embodiments, the vehicle 4110 is automatically routed. In embodiments, the vehicle 4110 is a self-driving vehicle. In embodiments, the inputs 37162 relating to the at least one parameter of a vehicle include vehicle classification. In embodiments, the inputs 37162 relating to the at least one parameter of a vehicle include display classification. In embodiments, the inputs 37162 relating to the at least one parameter of a vehicle include audio system capability. In embodiments, the inputs 37162 relating to the at least one parameter of a vehicle include screen size. In embodiments, the inputs 37162 relating to the at least one parameter of a vehicle include route information. In embodiments, the inputs 37162 relating to the at least one parameter of a vehicle include location information. In embodiments, the inputs 37163 relating to the at least one parameter of a rider include rider demographic information. In embodiments, the inputs 37163 relating to the at least one parameter of a rider include rider emotional state. In embodiments, the inputs 37163 relating to the at least one parameter of a rider include rider response to prior in-seat advertising. In embodiments, the inputs 37163 relating to the at least one parameter of a rider include rider social media activity.

In embodiments, the advertising system is further to determine a vehicle operating state from the inputs 37162 related to at least one parameter of the vehicle. In embodiments, the advertisement to be delivered is determined based at least in part on the determined vehicle operating state. In embodiments, the advertising system is further to determine a rider state 37149 from the inputs 37163 related to at least one parameter of the rider. In embodiments, the advertisement to be delivered is determined based at least in part on the determined rider state 37149.

Figure 41:
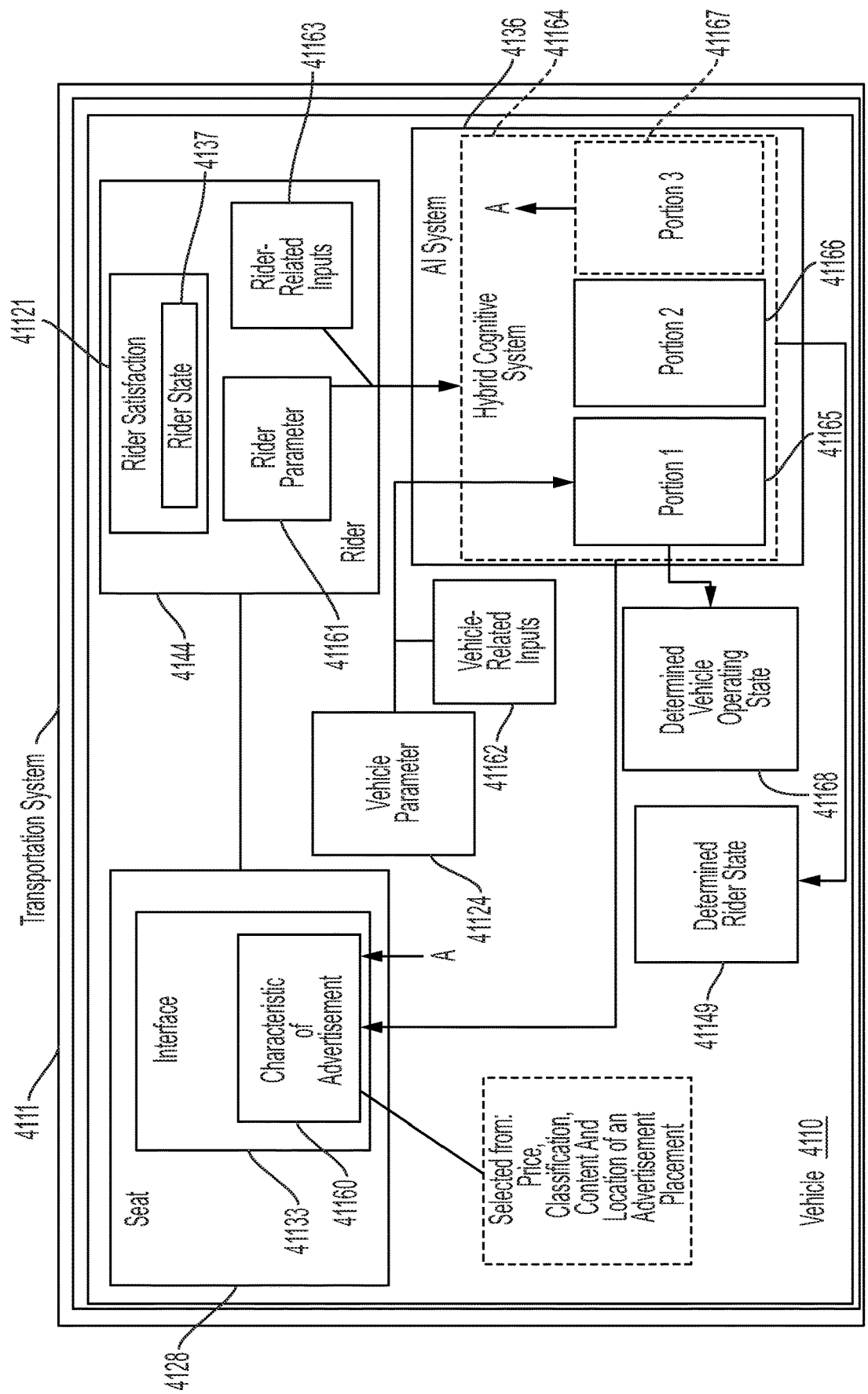
FIG. 41 is a diagrammatic view that illustrates systems described throughout this disclosure relating to various embodiments of the present disclosure.

Referring to FIG. 41, in embodiments provided herein are transportation systems 4111 having a hybrid cognitive system 41164 for managing an advertising market for in-seat advertising to riders of vehicles 4110. In embodiments, at least one part of the hybrid cognitive system 41164 processes inputs 41162 relating to at least one parameter 41124 of the vehicle to determine a vehicle operating state and at least one other part of the cognitive system processes inputs relating to a rider to determine a rider state. In embodiments, the cognitive system determines at least one of a price, a type and a location of an advertisement to be delivered within an interface to a rider in a seat of the vehicle.

An aspect provided herein includes a system for transportation 4111, comprising: a hybrid cognitive system 41164 for managing an advertising market for in-seat advertising to riders 4144 of vehicles 4110. In embodiments, at least one part 41165 of the hybrid cognitive system processes inputs 41162 corresponding to at least one parameter of the vehicle to determine a vehicle operating state 41168 and at least one other part 41166 of the cognitive system 41164 processes inputs 41163 relating to a rider to determine a rider state 41149. In embodiments, the cognitive system 41164 determines a characteristic 41160 of an advertisement to be delivered within an interface 41133 to the rider 4144 in a seat 4128 of the vehicle 4110. In embodiments, the characteristic 41160 of the advertisement is selected from the group consisting of a price, a category, a location and combinations thereof.

An aspect provided herein includes an artificial intelligence system 4136 for vehicle in-seat advertising, comprising: a first portion 41165 of the artificial intelligence system 4136 that determines a vehicle operating state 41168 of the vehicle by processing inputs 41162 relating to at least one parameter of the vehicle; a second portion 41166 of the artificial intelligence system 4136 that determines a state 41149 of the rider of the vehicle by processing inputs 41163 relating to at least one parameter of the rider; and a third portion 41167 of the artificial intelligence system 4136 that determines at least one of a price, classification, content and location of an advertisement to be delivered within an interface 41133 of the vehicle to a rider 4144 in a seat in the vehicle 4110 based on the vehicle (operating) state 41168 and the rider state 41149.

In embodiments, the vehicle 4110 comprises a system for automating at least one control parameter of the vehicle. In embodiments, the vehicle is at least a semi-autonomous vehicle. In embodiments, the vehicle is automatically routed. In embodiments, the vehicle is a self-driving vehicle. In embodiments, the cognitive system 41164 further determines at least one of a price, classification, content and location of an advertisement placement. In embodiments, an advertisement is delivered from an advertiser who places a winning bid. In embodiments, delivering an advertisement is based on a winning bid. In embodiments, the inputs relating to the at least one parameter of a vehicle include vehicle classification.

In embodiments, the inputs relating to the at least one parameter of a vehicle include display classification. In embodiments, the inputs relating to the at least one parameter of a vehicle include audio system capability. In embodiments, the inputs relating to the at least one parameter of a vehicle include screen size. In embodiments, the inputs relating to the at least one parameter of a vehicle include route information. In embodiments, the inputs relating to the at least one parameter of a vehicle include location information. In embodiments, the inputs relating to the at least one parameter of a rider include rider demographic information. In embodiments, the inputs relating to the at least one parameter of a rider include rider emotional state. In embodiments, the inputs relating to the at least one parameter of a rider include rider response to prior in-seat advertising. In embodiments, the inputs relating to the at least one parameter of a rider include rider social media activity.

Figure 42:
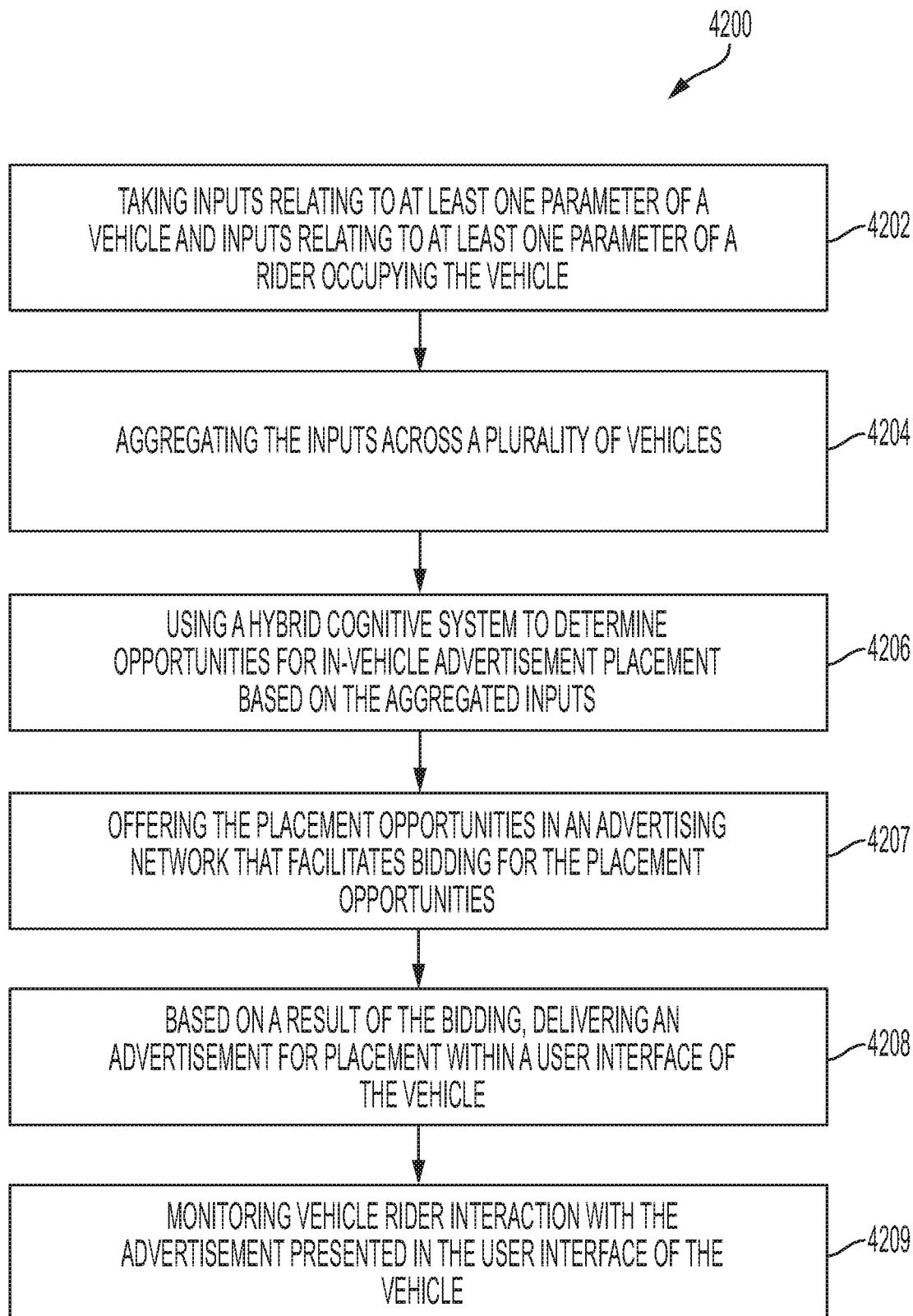
FIG. 42 is a diagrammatic view that illustrates a method described throughout this disclosure relating to various embodiments of the present disclosure.

FIG. 42 illustrates a method 4200 of in-vehicle advertising interaction tracking in accordance with embodiments of the systems and methods disclosed herein. At 4202 the method includes taking inputs relating to at least one parameter of a vehicle and inputs relating to at least one parameter of a rider occupying the vehicle. At 4204 the method includes aggregating the inputs across a plurality of vehicles. At 4206 the method includes using a hybrid cognitive system to determine opportunities for in-vehicle advertisement placement based on the aggregated inputs. At 4207 the method includes offering the placement opportunities in an advertising network that facilitates bidding for the placement opportunities. At 4208 the method includes based on a result of the bidding, delivering an advertisement for placement within a user interface of the vehicle. At 4209 the method includes monitoring vehicle rider interaction with the advertisement presented in the user interface of the vehicle.

Referring to FIG. 41 and FIG. 42, in embodiments, the vehicle 4110 comprises a system for automating at least one control parameter of the vehicle. In embodiments, the vehicle 4110 is at least a semi-autonomous vehicle. In embodiments, the vehicle 4110 is automatically routed. In embodiments, the vehicle 4110 is a self-driving vehicle. In embodiments, a first portion 41165 of the hybrid cognitive system 41164 determines an operating state of the vehicle by processing inputs relating to at least one parameter of the vehicle. In embodiments, a second portion 41166 of the hybrid cognitive system 41164 determines a state 41149 of the rider of the vehicle by processing inputs relating to at least one parameter of the rider. In embodiments, a third portion 41167 of the hybrid cognitive system 41164 determines at least one of a price, classification, content and location of an advertisement to be delivered within an interface of the vehicle to a rider in a seat in the vehicle based on the vehicle state and the rider state. In embodiments, an advertisement is delivered from an advertiser who places a winning bid. In embodiments, delivering an advertisement is based on a winning bid. In embodiments, the monitored vehicle rider interaction information includes information for resolving click-based payments. In embodiments, the monitored vehicle rider interaction information includes an analytic result of the monitoring. In embodiments, the analytic result is a measure of interest in the advertisement. In embodiments, the inputs 41162 relating to the at least one parameter of a vehicle include vehicle classification. In embodiments, the inputs 41162 relating to the at least one parameter of a vehicle include display classification. In embodiments, the inputs 41162 relating to the at least one parameter of a vehicle include audio system capability. In embodiments, the inputs 41162 relating to the at least one parameter of a vehicle include screen size. In embodiments, the inputs 41162 relating to the at least one parameter of a vehicle include route information. In embodiments, the inputs 41162 relating to the at least one parameter of a vehicle include location information. In embodiments, the inputs 41163 relating to the at least one parameter of a rider include rider demographic information. In embodiments, the inputs 41163 relating to the at least one parameter of a rider include rider emotional state. In embodiments, the inputs 41163 relating to the at least one parameter of a rider include rider response to prior in-seat advertising. In embodiments, the inputs 41163 relating to the at least one parameter of a rider include rider social media activity.

Figure 43:
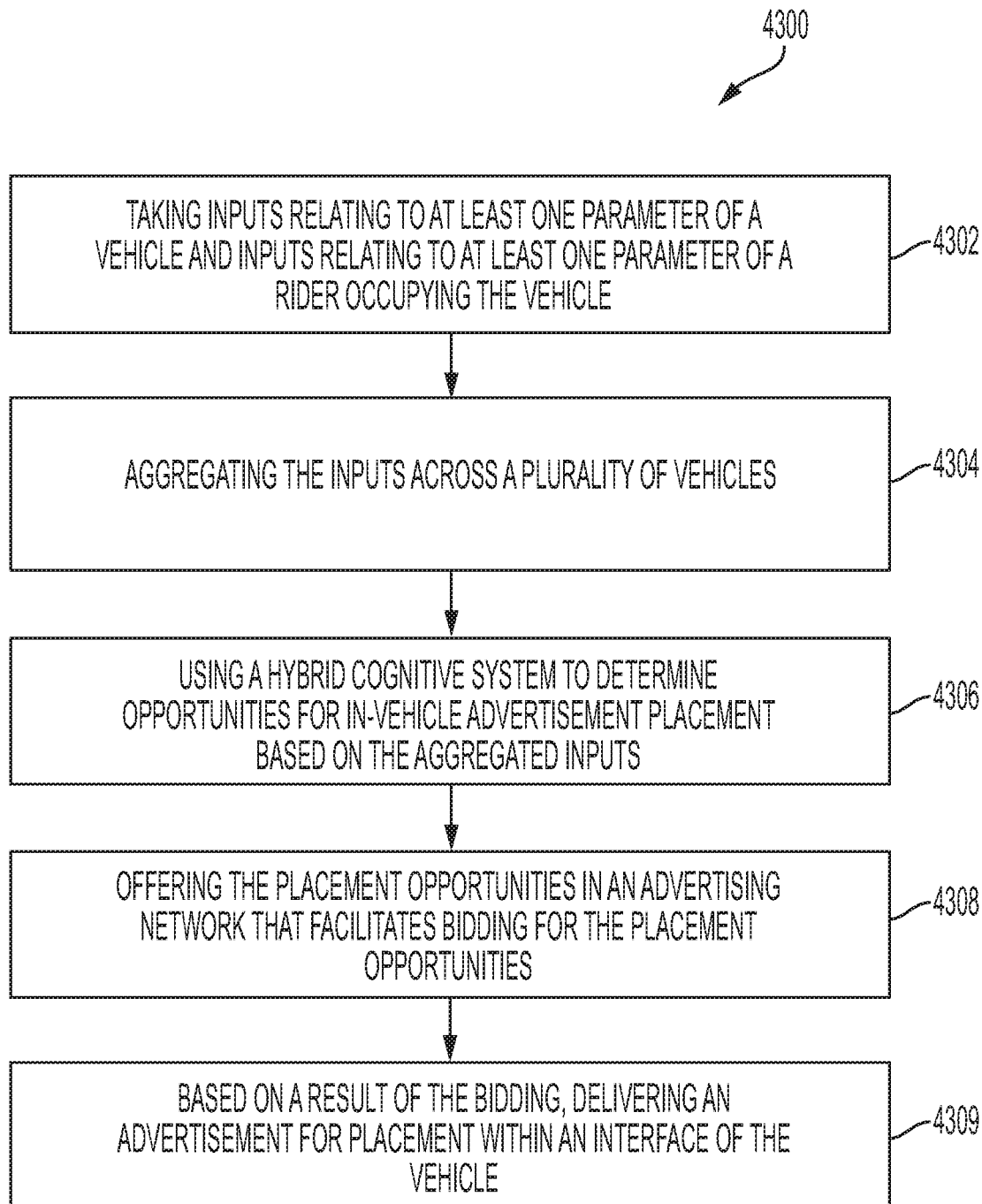
FIG. 43 is a diagrammatic view that illustrates a method described throughout this disclosure relating to various embodiments of the present disclosure.

FIG. 43 illustrates a method 4300 of in-vehicle advertising in accordance with embodiments of the systems and methods disclosed herein. At 4302 the method includes taking inputs relating to at least one parameter of a vehicle and inputs relating to at least one parameter of a rider occupying the vehicle. At 4304 the method includes aggregating the inputs across a plurality of vehicles. At 4306 the method includes using a hybrid cognitive system to determine opportunities for in-vehicle advertisement placement based on the aggregated inputs. At 4308 the method includes offering the placement opportunities in an advertising network that facilitates bidding for the placement opportunities. At 4309 the method includes based on a result of the bidding, delivering an advertisement for placement within an interface of the vehicle.

Referring to FIG. 41 and FIG. 43, in embodiments, the vehicle 4110 comprises a system for automating at least one control parameter of the vehicle. In embodiments, the vehicle 4110 is at least a semi-autonomous vehicle. In embodiments, the vehicle 4110 is automatically routed. In embodiments, the vehicle 4110 is a self-driving vehicle. In embodiments, a first portion 41165 of the hybrid cognitive system 41164 determines an operating state 41168 of the vehicle by processing inputs 41162 relating to at least one parameter of the vehicle. In embodiments, a second portion 41166 of the hybrid cognitive system 41164 determines a state 41149 of the rider of the vehicle by processing inputs 41163 relating to at least one parameter of the rider. In embodiments, a third portion 41167 of the hybrid cognitive system 41164 determines at least one of a price, classification, content and location of an advertisement to be delivered within an interface 41133 of the vehicle 4110 to a rider 4144 in a seat 4128 in the vehicle 4110 based on the vehicle (operating) state 41168 and the rider state 41149. In embodiments, an advertisement is delivered from an advertiser who places a winning bid. In embodiments, delivering an advertisement is based on a winning bid. In embodiments, the inputs 41162 relating to the at least one parameter of a vehicle include vehicle classification. In embodiments, the inputs 41162 relating to the at least one parameter of a vehicle include display classification. In embodiments, the inputs 41162 relating to the at least one parameter of a vehicle include audio system capability. In embodiments, the inputs 41162 relating to the at least one parameter of a vehicle include screen size. In embodiments, the inputs 41162 relating to the at least one parameter of a vehicle include route information. In embodiments, the inputs 41162 relating to the at least one parameter of a vehicle include location information. In embodiments, the inputs 41163 relating to the at least one parameter of a rider include rider demographic information. In embodiments, the inputs 41163 relating to the at least one parameter of a rider include rider emotional state. In embodiments, the inputs 41163 relating to the at least one parameter of a rider include rider response to prior in-seat advertising. In embodiments, the inputs 41163 relating to the at least one parameter of a rider include rider social media activity.

Figure 44:
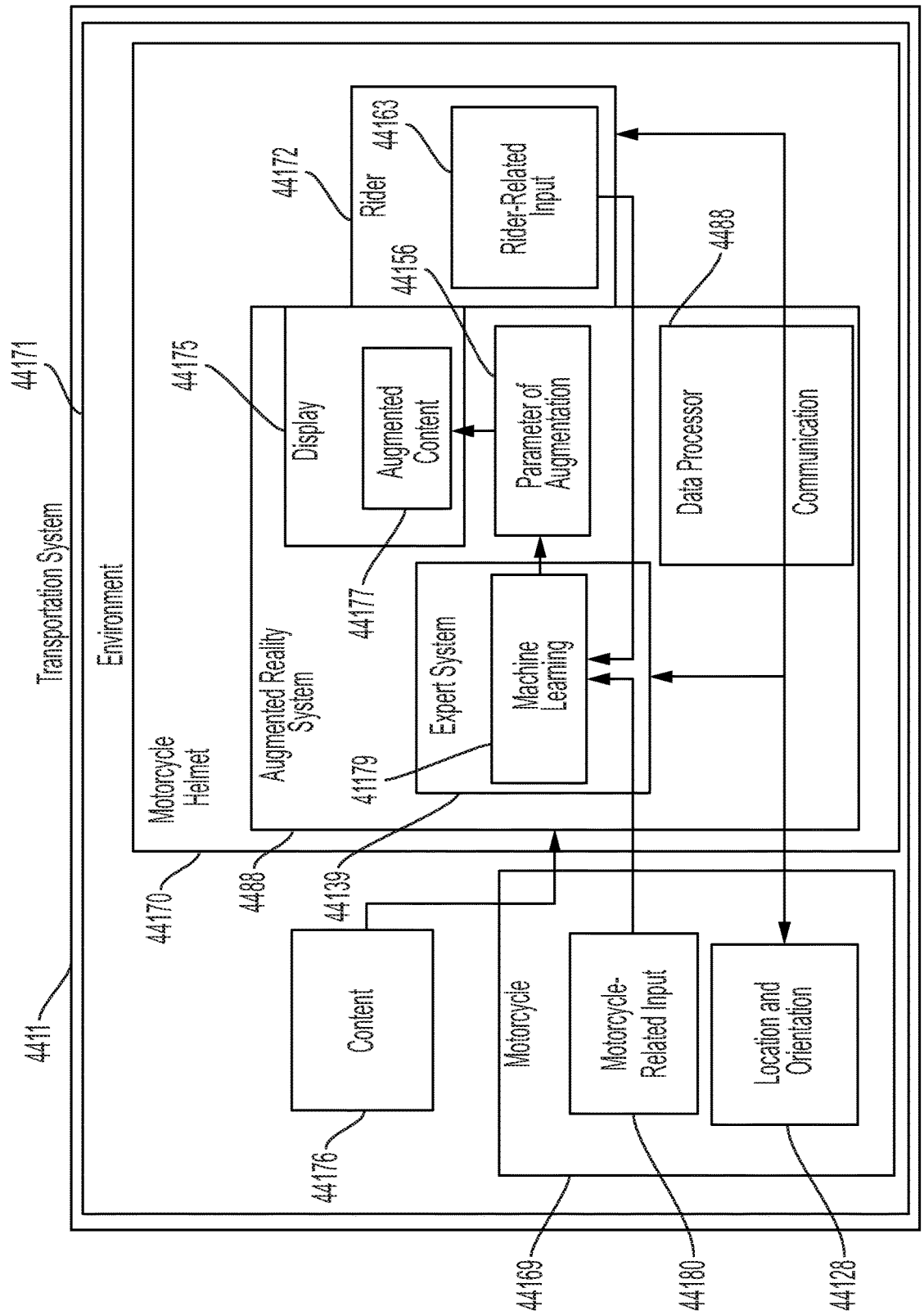
FIG. 44 is a diagrammatic view that illustrates systems described throughout this disclosure relating to various embodiments of the present disclosure.
Figure 45:
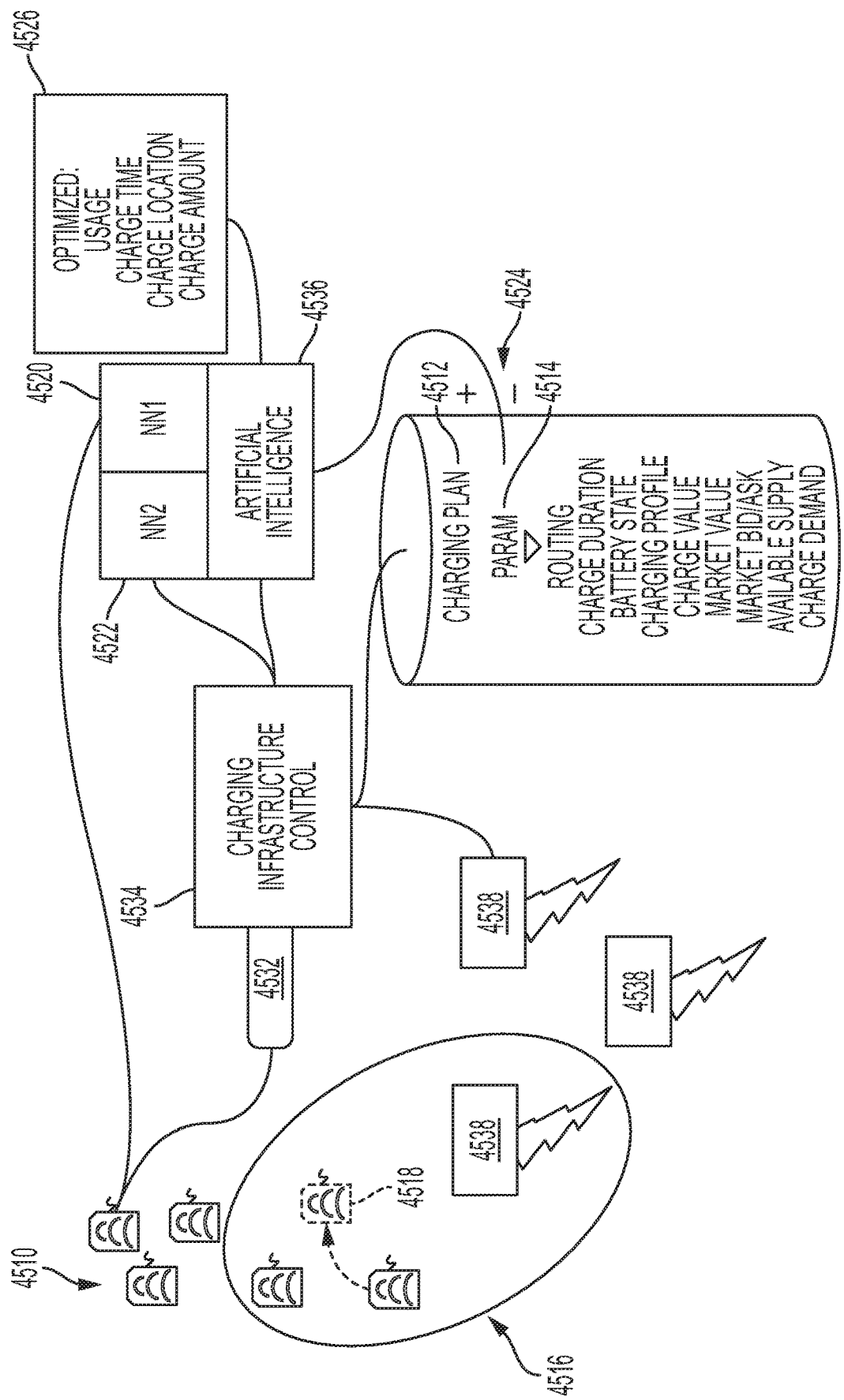
FIG. 45 is a diagrammatic view that illustrates systems and methods described throughout this disclosure relating to various embodiments of the present disclosure.
Figure 46:
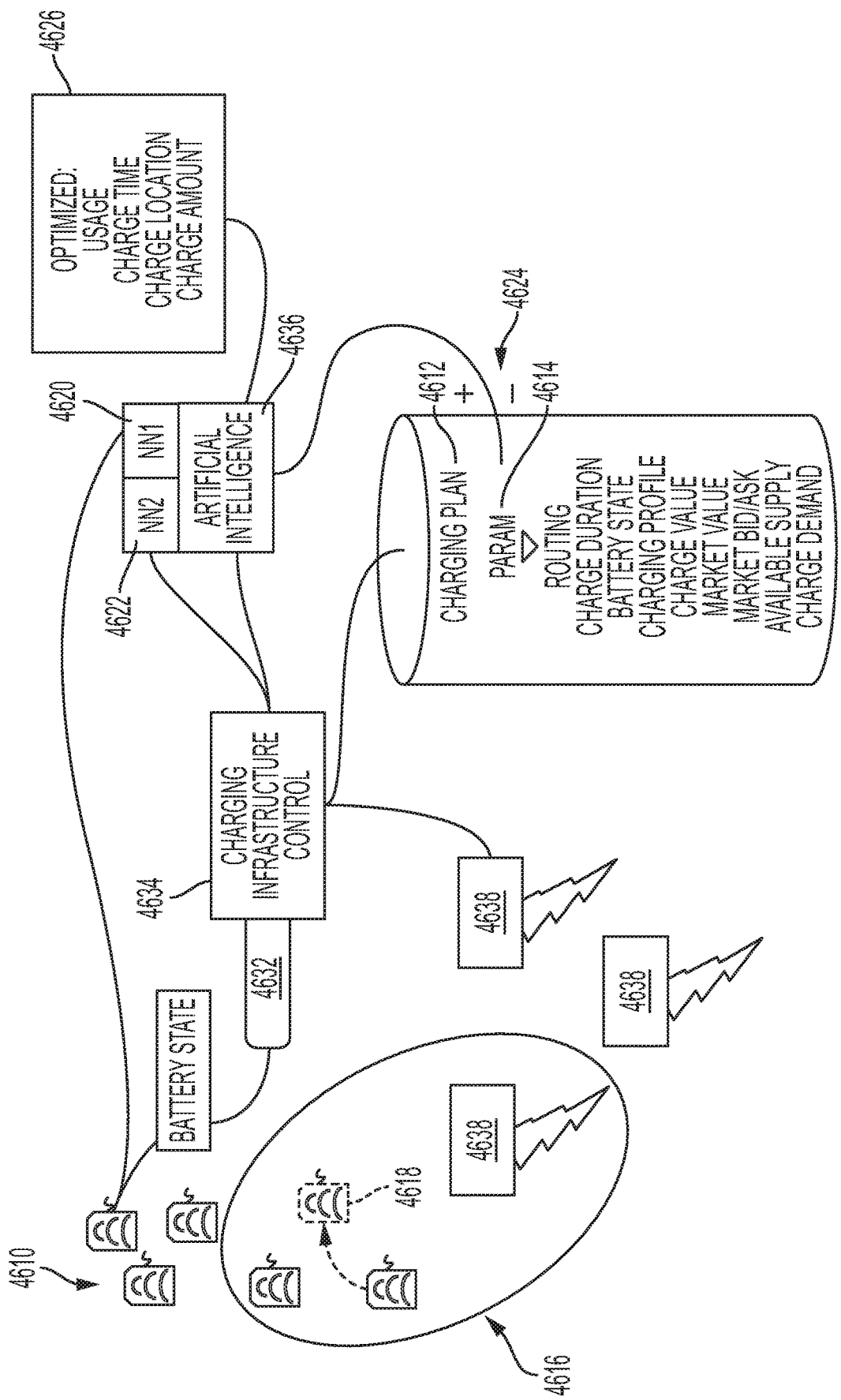
FIG. 46 is a diagrammatic view that illustrates systems and methods described throughout this disclosure relating to various embodiments of the present disclosure.
Figure 47:
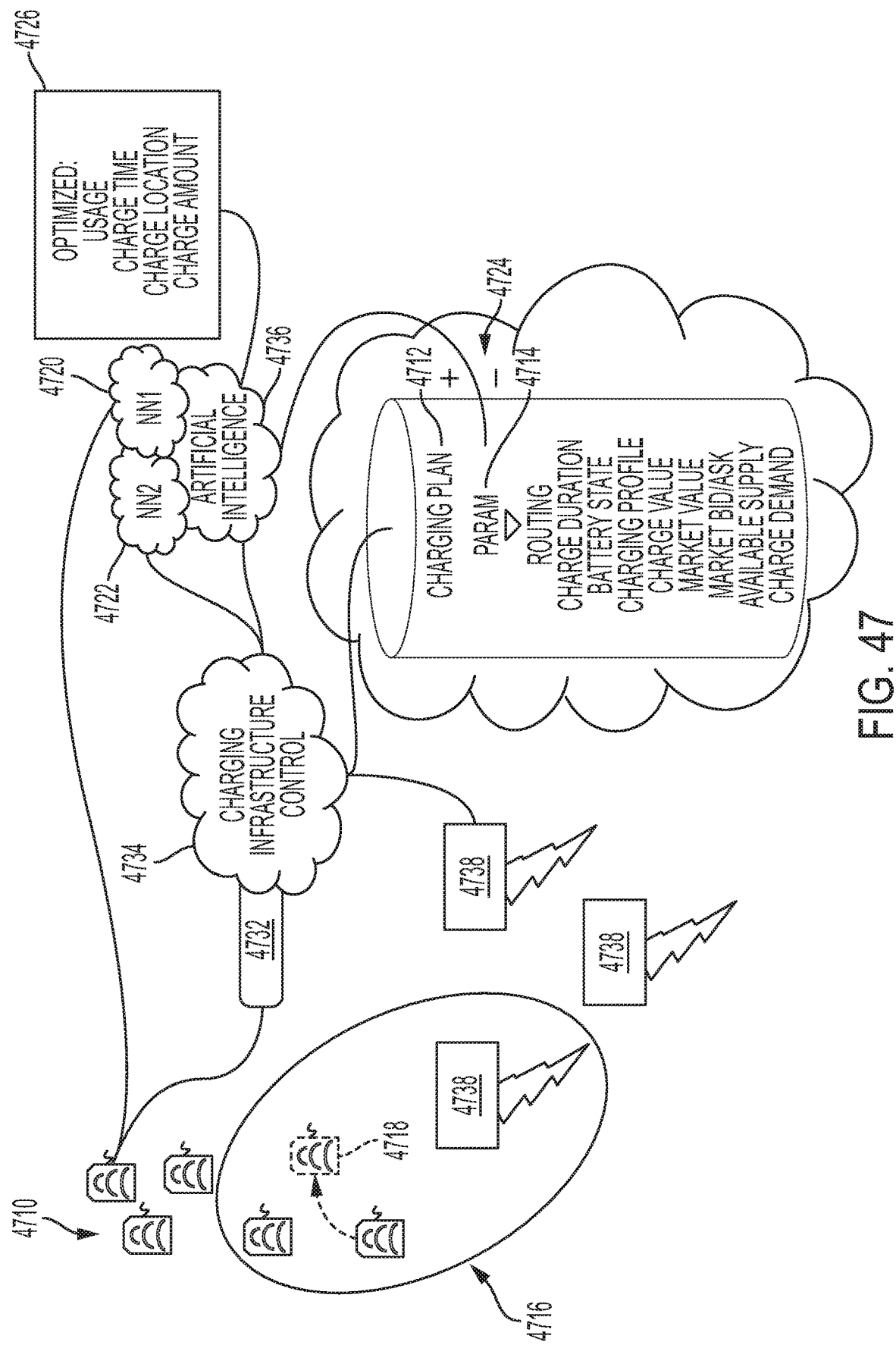
FIG. 47 is a diagrammatic view that illustrates systems and methods described throughout this disclosure relating to various embodiments of the present disclosure.

Referring to FIG. 44, in embodiments provided herein are transportation systems 4411 having a motorcycle helmet 44170 that is configured to provide an augmented reality experience based on registration of the location and orientation of the wearer 44172 in an environment 44171.

An aspect provided herein includes a system for transportation 4411, comprising: a motorcycle helmet 44170 to provide an augmented reality experience based on registration of a location and orientation of a wearer 44172 of the helmet 44170 in an environment 44171.

An aspect provided herein includes a motorcycle helmet 44170 comprising: a data processor 4488 configured to facilitate data communication between a rider 44172 wearing the helmet 44170 and a motorcycle 44169, the motorcycle 44169 and the helmet 44170 communicating location and orientation 44173 of the motorcycle 44169; and an augmented reality system 44174 with a display 44175 disposed to facilitate presenting an augmentation of content in an environment 44171 of a rider wearing the helmet, the augmentation responsive to a registration of the communicated location and orientation 44128 of the motorcycle 44169. In embodiments, at least one parameter of the augmentation is determined by machine learning on at least one input relating to at least one of the rider 44172 and the motorcycle 44180.

In embodiments, the motorcycle 44169 comprises a system for automating at least one control parameter of the motorcycle. In embodiments, the motorcycle 44169 is at least a semi-autonomous motorcycle. In embodiments, the motorcycle 44169 is automatically routed. In embodiments, the motorcycle 44169 is a self-driving motorcycle. In embodiments, the content in the environment is content that is visible in a portion of a field of view of the rider wearing the helmet. In embodiments, the machine learning on the input of the rider determines an emotional state of the rider and a value for the at least one parameter is adapted responsive to the rider emotional state. In embodiments, the machine learning on the input of the motorcycle determines an operational state of the motorcycle and a value for the at least one parameter is adapted responsive to the motorcycle operational state. In embodiments, the helmet 44170 further comprises a motorcycle configuration expert system 44139 for recommending an adjustment of a value of the at least one parameter 44156 to the augmented reality system responsive to the at least one input.

An aspect provided herein includes a motorcycle helmet augmented reality system comprising: a display 44175 disposed to facilitate presenting an augmentation of content in an environment of a rider wearing the helmet; a circuit 4488 for registering at least one of location and orientation of a motorcycle that the rider is riding; a machine learning circuit 44179 that determines at least one augmentation parameter 44156 by processing at least one input relating to at least one of the rider 44163 and the motorcycle 44180; and a reality augmentation circuit 4488 that, responsive to the registered at least one of a location and orientation of the motorcycle generates an augmentation element 44177 for presenting in the display 44175, the generating based at least in part on the determined at least one augmentation parameter 44156.

In embodiments, the motorcycle 44169 comprises a system for automating at least one control parameter of the motorcycle. In embodiments, the motorcycle 44169 is at least a semi-autonomous motorcycle. In embodiments, the motorcycle 44169 is automatically routed. In embodiments, the motorcycle 44169 is a self-driving motorcycle. In embodiments, the content 44176 in the environment is content that is visible in a portion of a field of view of the rider 44172 wearing the helmet. In embodiments, the machine learning on the input of the rider determines an emotional state of the rider and a value for the at least one parameter is adapted responsive to the rider emotional state. In embodiments, the machine learning on the input of the motorcycle determines an operational state of the motorcycle and a value for the at least one parameter is adapted responsive to the motorcycle operational state.

In embodiments, the helmet further comprises a motorcycle configuration expert system 44139 for recommending an adjustment of a value of the at least one parameter 44156 to the augmented reality system 4488 responsive to the at least one input.

In embodiments, leveraging network technologies for a transportation system may support a cognitive collective charging or refueling plan for vehicles in the transportation system. Such a transportation system may include an artificial intelligence system for taking inputs relating to a plurality of vehicles, such as self-driving vehicles, and determining at least one parameter of a re-charging or refueling plan for at least one of the plurality of vehicles based on the inputs.

In embodiments, the transportation system may be a vehicle transportation system. Such a vehicle transportation system may include a network-enabled vehicle information ingestion port 4532 that may provide a network (e.g., Internet and the like) interface through which inputs, such as inputs comprising operational state and energy consumption information from at least one of a plurality of network-enabled vehicles 4510 may be gathered. In embodiments, such inputs may be gathered in real time as the plurality of network-enabled vehicles 4510 connect to and deliver vehicle operational state, energy consumption and other related information. In embodiments, the inputs may relate to vehicle energy consumption and may be determined from a battery charge state of a portion of the plurality of vehicles. The inputs may include a route plan for the vehicle, an indicator of the value of charging of the vehicle, and the like. The inputs may include predicted traffic conditions for the plurality of vehicles. The transportation system may also include vehicle charging or refueling infrastructure that may include one or more vehicle charging infrastructure control system(s) 4534. These control system(s) 4534 may receive the operational state and energy consumption information for the plurality of network-enabled vehicles 4510 via the ingestion port 4532 or directly through a common or set of connected networks, such as the Internet and the like. Such a transportation system may further include an artificial intelligence system 4536 that may be functionally connected with the vehicle charging infrastructure control system(s) 4534 that, for example, responsive to the receiving of the operational state and energy consumption information, may determine, provide, adjust or create at least one charging plan parameter 4514 upon which a charging plan 4512 for at least a portion of the plurality of network-enabled vehicles 4510 is dependent. This dependency may yield changes in the application of the charging plan 4512 by the control system(s) 4534, such as when a processor of the control system(s) 4534 executes a program derived from or based on the charging plan 4512. The charging infrastructure control system(s) 4534 may include a cloud-based computing system remote from charging infrastructure systems (e.g., remote from an electric vehicle charging kiosk and the like); it may also include a local charging infrastructure system 4538 that may be disposed with and/or integrated with an infrastructure element, such as a fuel station, a charging kiosk and the like. In embodiments, the artificial intelligence system 4536 may interface and coordinate with the cloud-based system 4534, the local charging infrastructure system 4538 or both. In embodiments, coordination of the cloud-based system may take on a different form of interfacing, such as providing parameters that affect more than one charging kiosk and the like than may coordination with the local charging infrastructure system 4538, which may provide information that the local system could use to adapt charging system control commands and the like that may be provided from, for example, a cloud-based control system 4534. In an example, a cloud-based control system (that may control only a portion, such as a localized set, of available charging/refueling infrastructure devices) may respond to the charging plan parameter 4514 of the artificial intelligence system 4536 by setting a charging rate that facilitates highly parallel vehicle charging. However, the local charging infrastructure system 4538 may adapt this control plan, such as based on a control plan parameter provided to it by the artificial intelligence system 4536, to permit a different charging rate (e.g., a faster charging rate), such as for a brief period to accommodate an accumulation of vehicles queued up or estimated to use a local charging kiosk in the period. In this way, an adjustment to the at least one parameter 4514 that when made to the charge infrastructure operation plan 4512 ensures that the at least one of the plurality of vehicles 4510 has access to energy renewal in a target energy renewal geographic region 4516.

In embodiments, a charging or refueling plan may have a plurality of parameters that may impact a wide range of transportation aspects ranging from vehicle-specific to vehicle group-specific to vehicle location-specific and infrastructure impacting aspects. Therefore, a parameter of the plan may impact or relate to any of vehicle routing to charging infrastructure, amount of charge permitted to be provided, duration of time or rate for charging, battery conditions or state, battery charging profile, time required to charge to a minimum value that may be based on consumption needs of the vehicle(s), market value of charging, indicators of market value, market price, infrastructure provider profit, bids or offers for providing fuel or electricity to one or more charging or refueling infrastructure kiosks, available supply capacity, recharge demand (local, regional, system wide), and the like.

In embodiments, to facilitate a cognitive charging or refueling plan, the transportation system may include a recharging plan update facility that interacts with the artificial intelligence system 4536 to apply an adjustment value 4524 to the at least one of the plurality of recharging plan parameters 4514. An adjustment value 4524 may be further adjusted based on feedback of applying the adjustment value. In embodiments, the feedback may be used by the artificial intelligence system 4534 to further adjust the adjustment value. In an example, feedback may impact the adjustment value applied to charging or refueling infrastructure facilities in a localized way, such as for a target recharging geographic region 4516 or geographic range relative to one or more vehicles. In embodiments, providing a parameter adjustment value may facilitate optimizing consumption of a remaining battery charge state of at least one of the plurality of vehicles.

By processing energy-related consumption, demand, availability, and access information and the like, the artificial intelligence system 4536 may optimize aspects of the transportation system, such as vehicle electricity usage as shown in the box at 4526. The artificial intelligence system 4536 may further optimize at least one of recharging time, location, and amount. In an example, a recharging plan parameter that may be configured and updated based on feedback may be a routing parameter for the at least one of the plurality of vehicles as shown in the box at 4526.

The artificial intelligence system 4536 may further optimize a transportation system charging or refueling control plan parameter 4514 to, for example, accommodate near-term charging needs for the plurality of rechargeable vehicles 4510 based on the optimized at least one parameter. The artificial intelligence system 4536 may execute an optimizing algorithm that may calculate energy parameters (including vehicle and non-vehicle energy), optimizes electricity usage for at least vehicles and/or charging or refueling infrastructure, and optimizes at least one charging or refueling infrastructure-specific recharging time, location, and amount.

In embodiments, the artificial intelligence system 4534 may predict a geolocation 4518 of one or more vehicles within a geographic region 4516. The geographic region 4516 may include vehicles that are currently located in or predicted to be in the region and optionally may require or prefer recharging or refueling. As an example of predicting geolocation and its impact on a charging plan, a charging plan parameter may include allocation of vehicles currently in or predicted to be in the region to charging or refueling infrastructure in the geographic region 4516. In embodiments, geolocation prediction may include receiving inputs relating to charging states of a plurality of vehicles within or predicted to be within a geolocation range so that the artificial intelligence system can optimize at least one charging plan parameter 4514 based on a prediction of geolocations of the plurality of vehicles.

There are many aspects of a charging plan that may be impacted. Some aspects may be financial related, such as automated negotiation of at least one of a duration, a quantity and a price for charging or refueling a vehicle.

The transportation system cognitive charging plan system may include the artificial intelligence system being configured with a hybrid neural network. A first neural network 4522 of the hybrid neural network may be used to process inputs relating to charge or fuel states of the plurality of vehicles (directly received from the vehicles or through the vehicle information port 4532) and a second neural network 4520 of the hybrid neural network is used to process inputs relating to charging or refueling infrastructure and the like. In embodiments, the first neural network 4522 may process inputs comprising vehicle route and stored energy state information for a plurality of vehicles to predict for at least one of the plurality of vehicles a target energy renewal region. The second neural network 4520 may process vehicle energy renewal infrastructure usage and demand information for vehicle energy renewal infrastructure facilities within the target energy renewal region to determine at least one parameter 4514 of a charge infrastructure operational plan 4512 that facilitates access by the at least one of the plurality vehicles to renewal energy in the target energy renewal region 4516. In embodiments, the first and/or second neural networks may be configured as any of the neural networks described herein including without limitation convolutional type networks.

In embodiments, a transportation system may be distributed and may include an artificial intelligence system 4536 for taking inputs relating to a plurality of vehicles 4510 and determining at least one parameter 4514 of a re-charging and refueling plan 4512 for at least one of the plurality of vehicles based on the inputs. In embodiments, such inputs may be gathered in real time as plurality of vehicles 4510 connect to and deliver vehicle operational state, energy consumption and other related information. In embodiments, the inputs may relate to vehicle energy consumption and may be determined from a battery charge state of a portion of the plurality of vehicles. The inputs may include a route plan for the vehicle, an indicator of the value of charging of the vehicle, and the like. The inputs may include predicted traffic conditions for the plurality of vehicles. The distributed transportation system may also include cloud-based and vehicle-based systems that exchange information about the vehicle, such as energy consumption and operational information and information about the transportation system, such as recharging or refueling infrastructure. The artificial intelligence system may respond to transportation system and vehicle information shared by the cloud and vehicle-based system with control parameters that facilitate executing a cognitive charging plan for at least a portion of charging or refueling infrastructure of the transportation system. The artificial intelligence system 4536 may determine, provide, adjust or create at least one charging plan parameter 4514 upon which a charging plan 4512 for at least a portion of the plurality of vehicles 4510 is dependent. This dependency may yield changes in the execution of the charging plan 4512 by at least one the cloud-based and vehicle-based systems, such as when a processor executes a program derived from or based on the charging plan 4512.

In embodiments, an artificial intelligence system of a transportation system may facilitate execution of a cognitive charging plan by applying a vehicle recharging facility utilization optimization algorithm to a plurality of rechargeable vehicle-specific inputs, e.g., current operating state data for rechargeable vehicles present in a target recharging range of one of the plurality of rechargeable vehicles. The artificial intelligence system may also evaluate an impact of a plurality of recharging plan parameters on recharging infrastructure of the transportation system in the target recharging range. The artificial intelligence system may select at least one of the plurality of recharging plan parameters that facilitates, for example optimizing energy usage by the plurality of rechargeable vehicles and generate an adjustment value for the at least one of the plurality of recharging plan parameters. The artificial intelligence system may further predict a near-term need for recharging for a portion of the plurality of rechargeable vehicles within the target region based on, for example, operational status of the plurality of rechargeable vehicles that may be determined from the rechargeable vehicle-specific inputs. Based on this prediction and near-term recharging infrastructure availability and capacity information, the artificial intelligence system may optimize at least one parameter of the recharging plan. In embodiments, the artificial intelligence system may operate a hybrid neural network for the predicting and parameter selection or adjustment. In an example, a first portion of the hybrid neural network may process inputs that relates to route plans for one more rechargeable vehicles. In the example, a second portion of the hybrid neural network that is distinct from the first portion may process inputs relating to recharging infrastructure within a recharging range of at least one of the rechargeable vehicles. In this example, the second distinct portion of the hybrid neural net predicts the geolocation of a plurality of vehicles within the target region. To facilitate execution of the recharging plan, the parameter may impact an allocation of vehicles to at least a portion of recharging infrastructure within the predicted geographic region.

In embodiments, vehicles described herein may comprise a system for automating at least one control parameter of the vehicle. The vehicles may further at least operate as a semi-autonomous vehicle. The vehicles may be automatically routed. Also, the vehicles, recharging and otherwise may be self-driving vehicles.

In embodiments, leveraging network technologies for a transportation system may support a cognitive collective charging or refueling plan for vehicles in the transportation system. Such a transportation system may include an artificial intelligence system for taking inputs relating to battery status of a plurality of vehicles, such as self-driving vehicles and determining at least one parameter of a re-charging and/or refueling plan for optimizing battery operation of at least one of the plurality of vehicles based on the inputs.

In embodiments, such a vehicle transportation system may include a network-enabled vehicle information ingestion port 4632 that may provide a network (e.g., Internet and the like) interface through which inputs, such as inputs comprising operational state and energy consumption information and battery state from at least one of a plurality of network-enabled vehicles 4610 may be gathered. In embodiments, such inputs may be gathered in real time as a plurality of vehicles 4610 connect to a network and deliver vehicle operational state, energy consumption, battery state and other related information. In embodiments, the inputs may relate to vehicle energy consumption and may include a battery charge state of a portion of the plurality of vehicles. The inputs may include a route plan for the vehicle, an indicator of the value of charging of the vehicle, and the like. The inputs may include predicted traffic conditions for the plurality of vehicles. The transportation system may also include vehicle charging or refueling infrastructure that may include one or more vehicle charging infrastructure control systems 4634. These control systems may receive the battery status information and the like for the plurality of network-enabled vehicles 4610 via the ingestion port 4632 and/or directly through a common or set of connected networks, such as an Internet infrastructure including wireless networks and the like. Such a transportation system may further include an artificial intelligence system 4636 that may be functionally connected with the vehicle charging infrastructure control systems that may, based on at least the battery status information from the portion of the plurality of vehicles determine, provide, adjust or create at least one charging plan parameter 4614 upon which a charging plan 4612 for at least a portion of the plurality of network-enabled vehicles 4610 is dependent. This parameter dependency may yield changes in the application of the charging plan 4612 by the control system(s) 4634, such as when a processor of the control system(s) 4634 executes a program derived from or based on the charging plan 4612. These changes may be applied to optimize anticipated battery usage of one or more of the vehicles. The optimizing may be vehicle-specific, aggregated across a set of vehicles, and the like. The charging infrastructure control system(s) 4634 may include a cloud-based computing system remote from charging infrastructure systems (e.g., remote from an electric vehicle charging kiosk and the like); it may also include a local charging infrastructure system 4638 that may be disposed with and/or integrated into an infrastructure element, such as a fuel station, a charging kiosk and the like. In embodiments, the artificial intelligence system 4636 may interface with the cloud-based system 4634, the local charging infrastructure system 4638 or both. In embodiments, the artificial intelligence system may interface with individual vehicles to facilitate optimizing anticipated battery usage. In embodiments, interfacing with the cloud-based system may affect infrastructure-wide impact of a charging plan, such as providing parameters that affect more than one charging kiosk. Interfacing with the local charging infrastructure system 4638 may include providing information that the local system could use to adapt charging system control commands and the like that may be provided from, for example, a regional or broader control system, such as a cloud-based control system 4634. In an example, a cloud-based control system (that may control only a target or geographic region, such as a localized set, a town, a county, a city, a ward, county and the like of available charging or refueling infrastructure devices) may respond to the charging plan parameter 4614 of the artificial intelligence system 4636 by setting a charging rate that facilitates highly parallel vehicle charging so that vehicle battery usage can be optimized. However, the local charging infrastructure system 4638 may adapt this control plan, such as based on a control plan parameter provided to it by the artificial intelligence system 4636, to permit a different charging rate (e.g., a faster charging rate), such as for a brief period to accommodate an accumulation of vehicles for which anticipated battery usage is not yet optimized. In this way, an adjustment to the at least one parameter 4614 that when made to the charge infrastructure operation plan 4612 ensures that the at least one of the plurality of vehicles 4610 has access to energy renewal in a target energy renewal region 4616. In embodiments, a target energy renewal region may be defined by a geofence that may be configured by an administrator of the region. In an example an administrator may have control or responsibility for a jurisdiction (e.g., a township, and the like). In the example, the administrator may configure a geofence for a region that is substantially congruent with the jurisdiction.

In embodiments, a charging or refueling plan may have a plurality of parameters that may impact a wide range of transportation aspects ranging from vehicle-specific to vehicle group-specific to vehicle location-specific and infrastructure impacting aspects. Therefore, a parameter of the plan may impact or relate to any of vehicle routing to charging infrastructure, amount of charge permitted to be provided, duration of time or rate for charging, battery conditions or state, battery charging profile, time required to charge to a minimum value that may be based on consumption needs of the vehicle(s), market value of charging, indicators of market value, market price, infrastructure provider profit, bids or offers for providing fuel or electricity to one or more charging or refueling infrastructure kiosks, available supply capacity, recharge demand (local, regional, system wide), maximum energy usage rate, time between battery charging, and the like.

In embodiments, to facilitate a cognitive charging or refueling plan, the transportation system may include a recharging plan update facility that interacts with the artificial intelligence system 4636 to apply an adjustment value 4624 to the at least one of the plurality of recharging plan parameters 4614. An adjustment value 4624 may be further adjusted based on feedback of applying the adjustment value. In embodiments, the feedback may be used by the artificial intelligence system 4634 to further adjust the adjustment value. In an example, feedback may impact the adjustment value applied to charging or refueling infrastructure facilities in a localized way, such as impacting only a set of vehicles that are impacted by or projected to be impacted by a traffic jam so that their battery operation is optimized, so as to, for example, ensure that they have sufficient battery power throughout the duration of the traffic jam. In embodiments, providing a parameter adjustment value may facilitate optimizing consumption of a remaining battery charge state of at least one of the plurality of vehicles.

By processing energy-related consumption, demand, availability, and access information and the like, the artificial intelligence system 4636 may optimize aspects of the transportation system, such as vehicle electricity usage as shown in the box at 4626. The artificial intelligence system 4636 may further optimize at least one of recharging time, location, and amount as shown in the box at 4626. In an example a recharging plan parameter that may be configured and updated based on feedback may be a routing parameter for the at least one of the plurality of vehicles.

The artificial intelligence system 4636 may further optimize a transportation system charging or refueling control plan parameter 4614 to, for example accommodate near-term charging needs for the plurality of rechargeable vehicles 4610 based on the optimized at least one parameter. The artificial intelligence system 4636 may execute a vehicle recharging optimizing algorithm that may calculate energy parameters (including vehicle and non-vehicle energy) that may impact an anticipated battery usage, optimizes electricity usage for at least vehicles and/or charging or refueling infrastructure, and optimizes at least one charging or refueling infrastructure-specific recharging time, location, and amount.

In embodiments, the artificial intelligence system 4634 may predict a geolocation 4618 of one or more vehicles within a geographic region 4616. The geographic region 4616 may include vehicles that are currently located in or predicted to be in the region and optionally may require or prefer recharging or refueling. As an example of predicting geolocation and its impact on a charging plan, a charging plan parameter may include allocation of vehicles currently in or predicted to be in the region to charging or refueling infrastructure in the geographic region 4616. In embodiments, geolocation prediction may include receiving inputs relating to battery and battery charging states and recharging needs of a plurality of vehicles within or predicted to be within a geolocation range so that the artificial intelligence system can optimize at least one charging plan parameter 4614 based on a prediction of geolocations of the plurality of vehicles.

There are many aspects of a charging plan that may be impacted. Some aspects may be financial related, such as automated negotiation of at least one of a duration, a quantity and a price for charging or refueling a vehicle.

The transportation system cognitive charging plan system may include the artificial intelligence system being configured with a hybrid neural network. A first neural network 4622 of the hybrid neural network may be used to process inputs relating to battery charge or fuel states of the plurality of vehicles (directly received from the vehicles or through the vehicle information port 4632) and a second neural network 4620 of the hybrid neural network is used to process inputs relating to charging or refueling infrastructure and the like. In embodiments, the first neural network 4622 may process inputs comprising information about a charging system of the vehicle and vehicle route and stored energy state information for a plurality of vehicles to predict for at least one of the plurality of vehicles a target energy renewal region. The second neural network 4620 may further predict a geolocation of a portion of the plurality of vehicles relative to another vehicle or set of vehicles. The second neural network 4620 may process vehicle energy renewal infrastructure usage and demand information for vehicle energy renewal infrastructure facilities within the target energy renewal region to determine at least one parameter 4614 of a charge infrastructure operational plan 4612 that facilitates access by the at least one of the plurality vehicles to renewal energy in the target energy renewal region 4616. In embodiments, the first and/or second neural networks may be configured as any of the neural networks described herein including without limitation convolutional type networks.

In embodiments, a transportation system may be distributed and may include an artificial intelligence system 4636 for taking inputs relating to a plurality of vehicles 4610 and determining at least one parameter 4614 of a re-charging and refueling plan 4612 for at least one of the plurality of vehicles based on the inputs. In embodiments, such inputs may be gathered in real time as plurality of vehicles 4610 connect to a network and deliver vehicle operational state, energy consumption and other related information. In embodiments, the inputs may relate to vehicle energy consumption and may be determined from a battery charge state of a portion of the plurality of vehicles. The inputs may include a route plan for the vehicle, an indicator of the value of charging of the vehicle, and the like. The inputs may include predicted traffic conditions for the plurality of vehicles. The distributed transportation system may also include cloud-based and vehicle-based systems that exchange information about the vehicle, such as energy consumption and operational information and information about the transportation system, such as recharging or refueling infrastructure. The artificial intelligence system may respond to transportation system and vehicle information shared by the cloud and vehicle-based system with control parameters that facilitate executing a cognitive charging plan for at least a portion of charging or refueling infrastructure of the transportation system. The artificial intelligence system 4636 may determine, provide, adjust or create at least one charging plan parameter 4614 upon which a charging plan 4612 for at least a portion of the plurality of vehicles 4610 is dependent. This dependency may yield changes in the execution of the charging plan 4612 by at least one the cloud-based and vehicle-based systems, such as when a processor executes a program derived from or based on the charging plan 4612.

In embodiments, an artificial intelligence system of a transportation system may facilitate execution of a cognitive charging plan by applying a vehicle recharging facility utilization of a vehicle battery operation optimization algorithm to a plurality of rechargeable vehicle-specific inputs, e.g., current operating state data for rechargeable vehicles present in a target recharging range of one of the plurality of rechargeable vehicles. The artificial intelligence system may also evaluate an impact of a plurality of recharging plan parameters on recharging infrastructure of the transportation system in the target recharging range. The artificial intelligence system may select at least one of the plurality of recharging plan parameters that facilitates, for example optimizing energy usage by the plurality of rechargeable vehicles and generate an adjustment value for the at least one of the plurality of recharging plan parameters. The artificial intelligence system may further predict a near-term need for recharging for a portion of the plurality of rechargeable vehicles within the target region based on, for example, operational status of the plurality of rechargeable vehicles that may be determined from the rechargeable vehicle-specific inputs. Based on this prediction and near-term recharging infrastructure availability and capacity information, the artificial intelligence system may optimize at least one parameter of the recharging plan. In embodiments, the artificial intelligence system may operate a hybrid neural network for the predicting and parameter selection or adjustment. In an example, a first portion of the hybrid neural network may process inputs that relates to route plans for one more rechargeable vehicles. In the example, a second portion of the hybrid neural network that is distinct from the first portion may process inputs relating to recharging infrastructure within a recharging range of at least one of the rechargeable vehicles. In this example, the second distinct portion of the hybrid neural net predicts the geolocation of a plurality of vehicles within the target region. To facilitate execution of the recharging plan, the parameter may impact an allocation of vehicles to at least a portion of recharging infrastructure within the predicted geographic region.

In embodiments, vehicles described herein may comprise a system for automating at least one control parameter of the vehicle. The vehicles may further at least operate as a semi-autonomous vehicle. The vehicles may be automatically routed. Also, the vehicles, recharging and otherwise may be self-driving vehicles.

In embodiments, leveraging network technologies for a transportation system may support a cognitive collective charging or refueling plan for vehicles in the transportation system. Such a transportation system may include a cloud-based artificial intelligence system for taking inputs relating to a plurality of vehicles, such as self-driving vehicles and determining at least one parameter of a re-charging and/or refueling plan for at least one of the plurality of vehicles based on the inputs.

In embodiments, such a vehicle transportation system may include a cloud-enabled vehicle information ingestion port 4732 that may provide a network (e.g., Internet and the like) interface through which inputs, such as inputs comprising operational state and energy consumption information from at least one of a plurality of network-enabled vehicles 4710 may be gathered and provided into cloud resources, such as the cloud-based control and artificial intelligence systems described herein. In embodiments, such inputs may be gathered in real time as a plurality of vehicles 4710 connect to the cloud and deliver vehicle operational state, energy consumption and other related information through at least the port 4732. In embodiments, the inputs may relate to vehicle energy consumption and may be determined from a battery charge state of a portion of the plurality of vehicles. The inputs may include a route plan for the vehicle, an indicator of the value of charging of the vehicle, and the like. The inputs may include predicted traffic conditions for the plurality of vehicles. The transportation system may also include vehicle charging or refueling infrastructure that may include one or more vehicle charging infrastructure cloud-based control system(s) 4734. These cloud-based control system(s) 4734 may receive the operational state and energy consumption information for the plurality of network-enabled vehicles 4710 via the cloud-enabled ingestion port 4732 and/or directly through a common or set of connected networks, such as the Internet and the like. Such a transportation system may further include a cloud-based artificial intelligence system 4736 that may be functionally connected with the vehicle charging infrastructure cloud-based control system(s) 4734 that, for example may determine, provide, adjust or create at least one charging plan parameter 4714 upon which a charging plan 4712 for at least a portion of the plurality of network-enabled vehicles 4710 is dependent. This dependency may yield changes in the application of the charging plan 4712 by the cloud-based control system(s) 4734, such as when a processor of the cloud-based control system(s) 4734 executes a program derived from or based on the charging plan 4712. The charging infrastructure cloud-based control system(s) 4734 may include a cloud-based computing system remote from charging infrastructure systems (e.g., remote from an electric vehicle charging kiosk and the like); it may also include a local charging infrastructure system 4738 that may be disposed with and/or integrated into an infrastructure element, such as a fuel station, a charging kiosk and the like. In embodiments, the cloud-based artificial intelligence system 4736 may interface and coordinate with the cloud-based charging infrastructure control system 4734, the local charging infrastructure system 4738 or both. In embodiments, coordination of the cloud-based system may take on a form of interfacing, such as providing parameters that affect more than one charging kiosk and the like than may be different from coordination with the local charging infrastructure system 4738, which may provide information that the local system could use to adapt cloud-based charging system control commands and the like that may be provided from, for example, a cloud-based control system 4734. In an example, a cloud-based control system (that may control only a portion, such as a localized set, of available charging or refueling infrastructure devices) may respond to the charging plan parameter 4714 of the cloud-based artificial intelligence system 4736 by setting a charging rate that facilitates highly parallel vehicle charging. However, the local charging infrastructure system 4738 may adapt this control plan, such as based on a control plan parameter provided to it by the cloud-based artificial intelligence system 4736, to permit a different charging rate (e.g., a faster charging rate), such as for a brief period to accommodate an accumulation of vehicles queued up or estimated to use a local charging kiosk in the period. In this way, an adjustment to the at least one parameter 4714 that when made to the charge infrastructure operation plan 4712 ensures that the at least one of the plurality of vehicles 4710 has access to energy renewal in a target energy renewal region 4716.

In embodiments, a charging or refueling plan may have a plurality of parameters that may impact a wide range of transportation aspects ranging from vehicle-specific to vehicle group-specific to vehicle location-specific and infrastructure impacting aspects. Therefore, a parameter of the plan may impact or relate to any of vehicle routing to charging infrastructure, amount of charge permitted to be provided, duration of time or rate for charging, battery conditions or state, battery charging profile, time required to charge to a minimum value that may be based on consumption needs of the vehicle(s), market value of charging, indicators of market value, market price, infrastructure provider profit, bids or offers for providing fuel or electricity to one or more charging or refueling infrastructure kiosks, available supply capacity, recharge demand (local, regional, system wide), and the like.

In embodiments, to facilitate a cognitive charging or refueling plan, the transportation system may include a recharging plan update facility that interacts with the cloud-based artificial intelligence system 4736 to apply an adjustment value 4724 to the at least one of the plurality of recharging plan parameters 4714. An adjustment value 4724 may be further adjusted based on feedback of applying the adjustment value. In embodiments, the feedback may be used by the cloud-based artificial intelligence system 4734 to further adjust the adjustment value. In an example, feedback may impact the adjustment value applied to charging or refueling infrastructure facilities in a localized way, such as for a target recharging area 4716 or geographic range relative to one or more vehicles. In embodiments, providing a parameter adjustment value may facilitate optimizing consumption of a remaining battery charge state of at least one of the plurality of vehicles.

By processing energy-related consumption, demand, availability, and access information and the like, the cloud-based artificial intelligence system 4736 may optimize aspects of the transportation system, such as vehicle electricity usage. The cloud-based artificial intelligence system 4736 may further optimize at least one of recharging time, location, and amount. In an example, a recharging plan parameter that may be configured and updated based on feedback may be a routing parameter for the at least one of the plurality of vehicles.

The cloud-based artificial intelligence system 4736 may further optimize a transportation system charging or refueling control plan parameter 4714 to, for example, accommodate near-term charging needs for the plurality of rechargeable vehicles 4710 based on the optimized at least one parameter. The cloud-based artificial intelligence system 4736 may execute an optimizing algorithm that may calculate energy parameters (including vehicle and non-vehicle energy), optimizes electricity usage for at least vehicles and/or charging or refueling infrastructure, and optimizes at least one charging or refueling infrastructure-specific recharging time, location, and amount.

In embodiments, the cloud-based artificial intelligence system 4734 may predict a geolocation 4718 of one or more vehicles within a geographic region 4716. The geographic region 4716 may include vehicles that are currently located in or predicted to be in the region and optionally may require or prefer recharging or refueling. As an example of predicting geolocation and its impact on a charging plan, a charging plan parameter may include allocation of vehicles currently in or predicted to be in the region to charging or refueling infrastructure in the geographic region 4716. In embodiments, geolocation prediction may include receiving inputs relating to charging states of a plurality of vehicles within or predicted to be within a geolocation range so that the cloud-based artificial intelligence system can optimize at least one charging plan parameter 4714 based on a prediction of geolocations of the plurality of vehicles.

There are many aspects of a charging plan that may be impacted. Some aspects may be financial related, such as automated negotiation of at least one of a duration, a quantity and a price for charging or refueling a vehicle.

The transportation system cognitive charging plan system may include the cloud-based artificial intelligence system being configured with a hybrid neural network. A first neural network 4722 of the hybrid neural network may be used to process inputs relating to charge or fuel states of the plurality of vehicles (directly received from the vehicles or through the vehicle information port 4732) and a second neural network 4720 of the hybrid neural network is used to process inputs relating to charging or refueling infrastructure and the like. In embodiments, the first neural network 4722 may process inputs comprising vehicle route and stored energy state information for a plurality of vehicles to predict for at least one of the plurality of vehicles a target energy renewal region. The second neural network 4720 may process vehicle energy renewal infrastructure usage and demand information for vehicle energy renewal infrastructure facilities within the target energy renewal region to determine at least one parameter 4714 of a charge infrastructure operational plan 4712 that facilitates access by the at least one of the plurality vehicles to renewal energy in the target energy renewal region 4716. In embodiments, the first and/or second neural networks may be configured as any of the neural networks described herein including without limitation convolutional type networks.

In embodiments, a transportation system may be distributed and may include a cloud-based artificial intelligence system 4736 for taking inputs relating to a plurality of vehicles 4710 and determining at least one parameter 4714 of a re-charging and refueling plan 4712 for at least one of the plurality of vehicles based on the inputs. In embodiments, such inputs may be gathered in real time as plurality of vehicles 4710 connect to and deliver vehicle operational state, energy consumption and other related information. In embodiments, the inputs may relate to vehicle energy consumption and may be determined from a battery charge state of a portion of the plurality of vehicles. The inputs may include a route plan for the vehicle, an indicator of the value of charging of the vehicle, and the like. The inputs may include predicted traffic conditions for the plurality of vehicles. The distributed transportation system may also include cloud-based and vehicle-based systems that exchange information about the vehicle, such as energy consumption and operational information and information about the transportation system, such as recharging or refueling infrastructure. The cloud-based artificial intelligence system may respond to transportation system and vehicle information shared by the cloud and vehicle-based system with control parameters that facilitate executing a cognitive charging plan for at least a portion of charging or refueling infrastructure of the transportation system. The cloud-based artificial intelligence system 4736 may determine, provide, adjust or create at least one charging plan parameter 4714 upon which a charging plan 4712 for at least a portion of the plurality of vehicles 4710 is dependent. This dependency may yield changes in the execution of the charging plan 4712 by at least one the cloud-based and vehicle-based systems, such as when a processor executes a program derived from or based on the charging plan 4712.

In embodiments, a cloud-based artificial intelligence system of a transportation system may facilitate execution of a cognitive charging plan by applying a vehicle recharging facility utilization optimization algorithm to a plurality of rechargeable vehicle-specific inputs, e.g., current operating state data for rechargeable vehicles present in a target recharging range of one of the plurality of rechargeable vehicles. The cloud-based artificial intelligence system may also evaluate an impact of a plurality of recharging plan parameters on recharging infrastructure of the transportation system in the target recharging range. The cloud-based artificial intelligence system may select at least one of the plurality of recharging plan parameters that facilitates, for example optimizing energy usage by the plurality of rechargeable vehicles and generate an adjustment value for the at least one of the plurality of recharging plan parameters. The cloud-based artificial intelligence system may further predict a near-term need for recharging for a portion of the plurality of rechargeable vehicles within the target region based on, for example operational status of the plurality of rechargeable vehicles that may be determined from the rechargeable vehicle-specific inputs. Based on this prediction and near-term recharging infrastructure availability and capacity information, the cloud-based artificial intelligence system may optimize at least one parameter of the recharging plan. In embodiments, the cloud-based artificial intelligence system may operate a hybrid neural network for the predicting and parameter selection or adjustment. In an example, a first portion of the hybrid neural network may process inputs that relates to route plans for one more rechargeable vehicles. In the example, a second portion of the hybrid neural network that is distinct from the first portion may process inputs relating to recharging infrastructure within a recharging range of at least one of the rechargeable vehicles. In this example, the second distinct portion of the hybrid neural net predicts the geolocation of a plurality of vehicles within the target region. To facilitate execution of the recharging plan, the parameter may impact an allocation of vehicles to at least a portion of recharging infrastructure within the predicted geographic region.

In embodiments, vehicles described herein may comprise a system for automating at least one control parameter of the vehicle. The vehicles may further at least operate as a semi-autonomous vehicle. The vehicles may be automatically routed. Also, the vehicles, recharging and otherwise may be self-driving vehicles.

Figure 48:
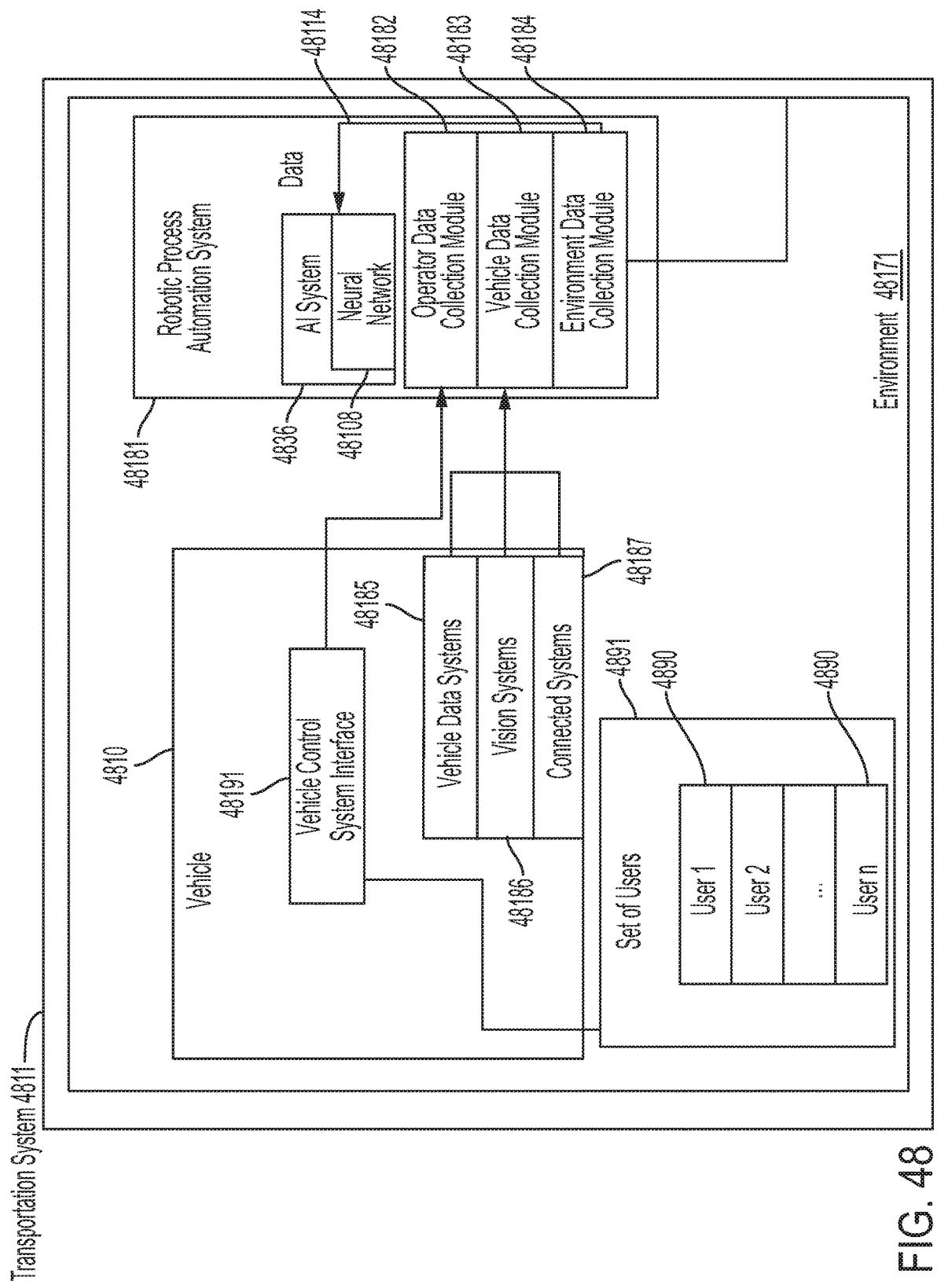
FIG. 48 is a diagrammatic view that illustrates systems described throughout this disclosure relating to various embodiments of the present disclosure.

Referring to FIG. 48, provided herein are transportation systems 4811 having a robotic process automation system 48181 (RPA system). In embodiments, data is captured for each of a set of individuals/users 4891 as the individuals/users 4890 interact with a user interface 4823 of a vehicle 4811, and an artificial intelligence system 4836 is trained using the data and interacts with the vehicle 4810 to automatically undertake actions with the vehicle 4810 on behalf of the user 4890. Data 48114 collected for the RPA system 48181 may include a sequence of images, sensor data, telemetry data, or the like, among many other types of data described throughout this disclosure. Interactions of an individual/user 4890 with a vehicle 4810 may include interactions with various vehicle interfaces as described throughout this disclosure. For example, a robotic process automation (RPA) system 4810 may observe patterns of a driver, such as braking patterns, typical following distance behind other vehicles, approach to curves (e.g., entry angle, entry speed, exit angle, exit speed and the like), acceleration patterns, lane preferences, passing preferences, and the like. Such patterns may be obtained through vision systems 48186 (e.g., ones observing the driver, the steering wheel, the brake, the surrounding environment 48171, and the like), through vehicle data systems 48185 (e.g., data streams indicating states and changes in state in steering, braking and the like, as well as forward and rear-facing cameras and sensors), through connected systems 48187 (e.g., GPS, cellular systems, and other network systems, as well as peer-to-peer, vehicle-to-vehicle, mesh and cognitive networks, among others), and other sources. Using a training data set, the RPA system 48181, such as via a neural network 48108 of any of the types described herein, may learn to drive in the same style as a driver. In embodiments, the RPA system 48181 may learn changes in style, such as varying levels of aggressiveness in different situations, such as based on time of day, length of trip, type of trip, or the like. Thus, a self-driving car may learn to drive like its typical driver. Similarly, an RPA system 48181 may be used to observe driver, passenger, or other individual interactions with a navigation system, an audio entertainment system, a video entertainment system, a climate control system, a seat warming and/or cooling system, a steering system, a braking system, a mirror system, a window system, a door system, a trunk system, a fueling system, a moonroof system, a ventilation system, a lumbar support system, a seat positioning system, a GPS system, a WIFI system, a glovebox system, or other system.

An aspect provided herein includes a system 4811 for transportation, comprising: a robotic process automation system 48181. In embodiments, a set of data is captured for each user 4890 in a set of users 4891 as each user 4890 interacts with a user interface 4823 of a vehicle 4810. In embodiments, an artificial intelligence system 4836 is trained using the set of data 48114 to interact with the vehicle 4810 to automatically undertake actions with the vehicle 4810 on behalf of the user 4890.

Figure 49:
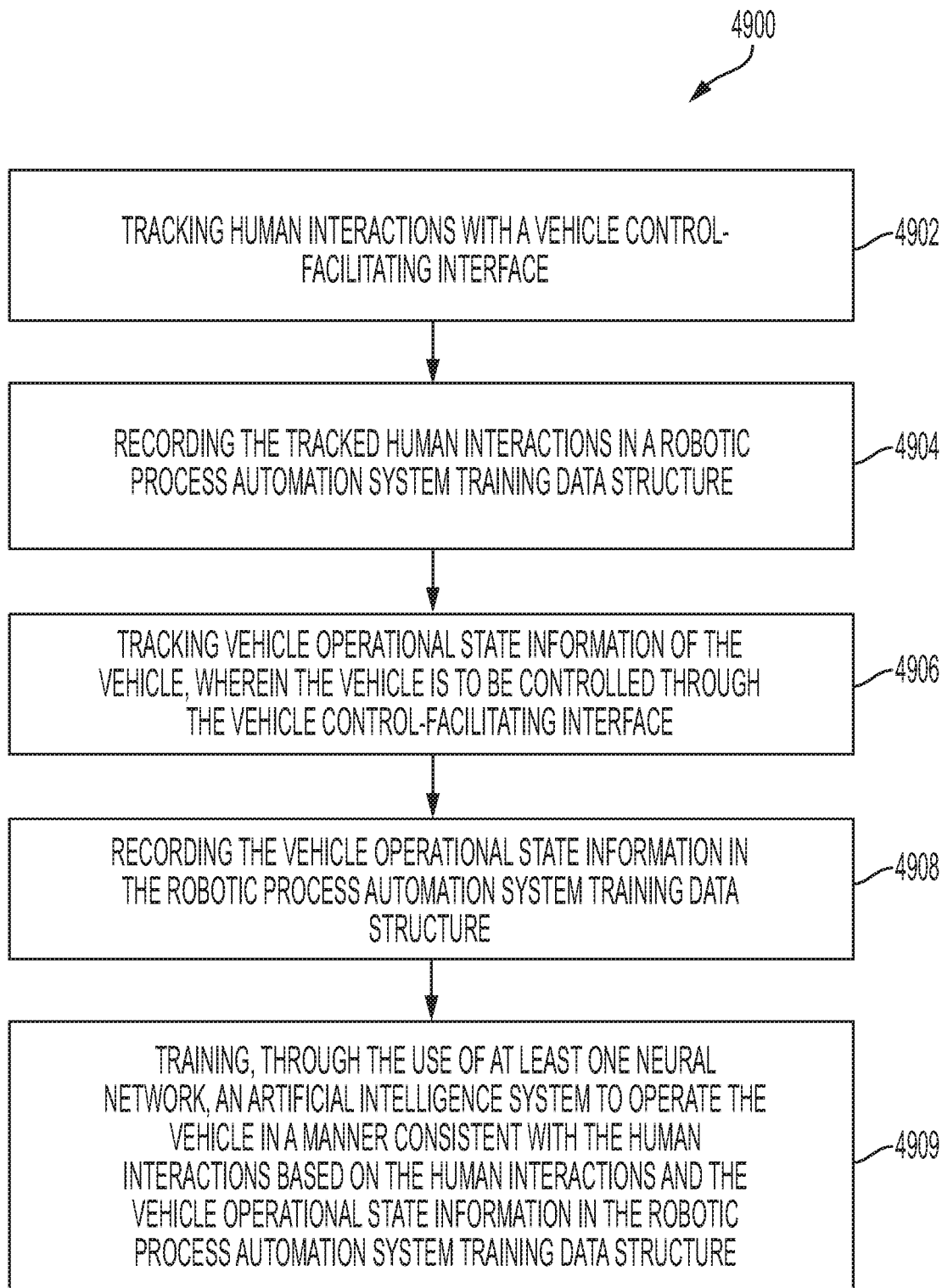
FIG. 49 is a diagrammatic view that illustrates a method described throughout this disclosure relating to various embodiments of the present disclosure.

FIG. 49 illustrates a method 4900 of robotic process automation to facilitate mimicking human operator operation of a vehicle in accordance with embodiments of the systems and methods disclosed herein. At 4902 the method includes tracking human interactions with a vehicle control-facilitating interface. At 4904 the method includes recording the tracked human interactions in a robotic process automation system training data structure. At 4906 the method includes tracking vehicle operational state information of the vehicle. In embodiments, the vehicle is to be controlled through the vehicle control-facilitating interface. At 4908 the method includes recording the vehicle operational state information in the robotic process automation system training data structure. At 4909 the method includes training, through the use of at least one neural network, an artificial intelligence system to operate the vehicle in a manner consistent with the human interactions based on the human interactions and the vehicle operational state information in the robotic process automation system training data structure.

In embodiments, the method further comprises controlling at least one aspect of the vehicle with the trained artificial intelligence system. In embodiments, the method further comprises applying deep learning to the controlling the at least one aspect of the vehicle by structured variation in the controlling the at least one aspect of the vehicle to mimic the human interactions and processing feedback from the controlling the at least one aspect of the vehicle with machine learning. In embodiments, the controlling at least one aspect of the vehicle is performed via the vehicle control-facilitating interface.

In embodiments, the controlling at least one aspect of the vehicle is performed by the artificial intelligence system emulating the control-facilitating interface being operated by the human. In embodiments, the vehicle control-facilitating interface comprises at least one of an audio capture system to capture audible expressions of the human, a human-machine interface, a mechanical interface, an optical interface and a sensor-based interface. In embodiments, the tracking vehicle operational state information comprises tracking at least one of a set of vehicle systems and a set of vehicle operational processes affected by the human interactions. In embodiments, the tracking vehicle operational state information comprises tracking at least one vehicle system element. In embodiments, the at least one vehicle system element is controlled via the vehicle control-facilitating interface. In embodiments, the at least one vehicle system element is affected by the human interactions. In embodiments, the tracking vehicle operational state information comprises tracking the vehicle operational state information before, during, and after the human interaction.

In embodiments, the tracking vehicle operational state information comprises tracking at least one of a plurality of vehicle control system outputs that result from the human interactions and vehicle operational results achieved in response to the human interactions. In embodiments, the vehicle is to be controlled to achieve results that are consistent with results achieved via the human interactions. In embodiments, the method further comprises tracking and recording conditions proximal to the vehicle with a plurality of vehicle mounted sensors. In embodiments, the training of the artificial intelligence system is further responsive to the conditions proximal to the vehicle tracked contemporaneously to the human interactions. In embodiments, the training is further responsive to a plurality of data feeds from remote sensors, the plurality of data feeds comprising data collected by the remove sensors contemporaneous to the human interactions. In embodiments, the artificial intelligence system employs a workflow that involves decision-making and the robotic process automation system facilitates automation of the decision-making. In embodiments, the artificial intelligence system employs a workflow that involves remote control of the vehicle and the robotic process automation system facilitates automation of remotely controlling the vehicle.

An aspect provided herein includes a transportation system 4811 for mimicking human operation of a vehicle 4810, comprising: a robotic process automation system 48181 comprising: an operator data collection module 48182 to capture human operator interaction with a vehicle control system interface 48191; a vehicle data collection module 48183 to capture vehicle response and operating conditions associated at least contemporaneously with the human operator interaction; and an environment data collection module 48184 to capture instances of environmental information associated at least contemporaneously with the human operator interaction; and an artificial intelligence system 4836 to learn to mimic the human operator (e.g., user 4890) to control the vehicle 4810 responsive to the robotic process automation system 48181 detecting data 48114 indicative of at least one of a plurality of the instances of environmental information associated with the contemporaneously captured vehicle response and operating conditions.

In embodiments, the operator data collection module 48182 is to capture patterns of data including braking patterns, follow-behind distance, approach to curve acceleration patterns, lane preferences, and passing preferences. In embodiments, vehicle data collection module 48183 captures data from a plurality of vehicle data systems 48185 that provide data streams indicating states and changes in state in steering, braking, acceleration, forward looking images, and rear-looking images. In embodiments, the artificial intelligence system 4836 includes a neural network 48108 for training the artificial intelligence system 4836.

Figure 50:
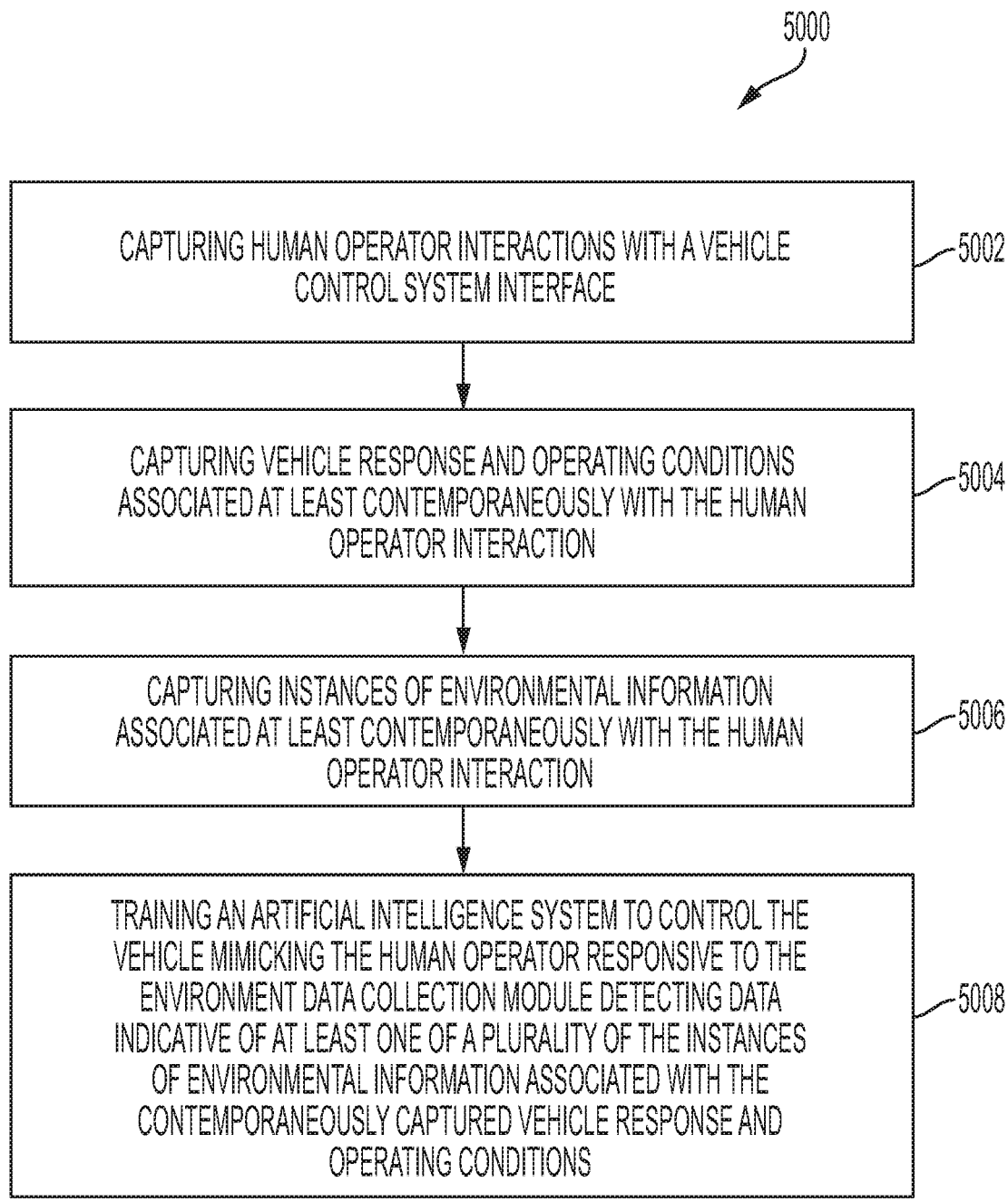
FIG. 50 is a diagrammatic view that illustrates a method described throughout this disclosure relating to various embodiments of the present disclosure.

FIG. 50 illustrates a robotic process automation method 5000 of mimicking human operation of a vehicle in accordance with embodiments of the systems and methods disclosed herein. At 5002 the method includes capturing human operator interactions with a vehicle control system interface. At 5004 the method includes capturing vehicle response and operating conditions associated at least contemporaneously with the human operator interaction. At 5006 the method includes capturing instances of environmental information associated at least contemporaneously with the human operator interaction. At 5008 the method includes training an artificial intelligence system to control the vehicle mimicking the human operator responsive to the environment data collection module detecting data indicative of at least one of a plurality of the instances of environmental information associated with the contemporaneously captured vehicle response and operating conditions.

In embodiments, the method further comprises applying deep learning in the artificial intelligence system to optimize a margin of vehicle operating safety by affecting the controlling of the at least one aspect of the vehicle by structured variation in the controlling of the at least one aspect of the vehicle to mimic the human interactions and processing feedback from the controlling the at least one aspect of the vehicle with machine learning. In embodiments, the robotic process automation system facilitates automation of a decision-making workflow employed by the artificial intelligence system. In embodiments, the robotic process automation system facilitates automation of a remote control workflow that the artificial intelligence system employs to remotely control the vehicle.

Figure 51:
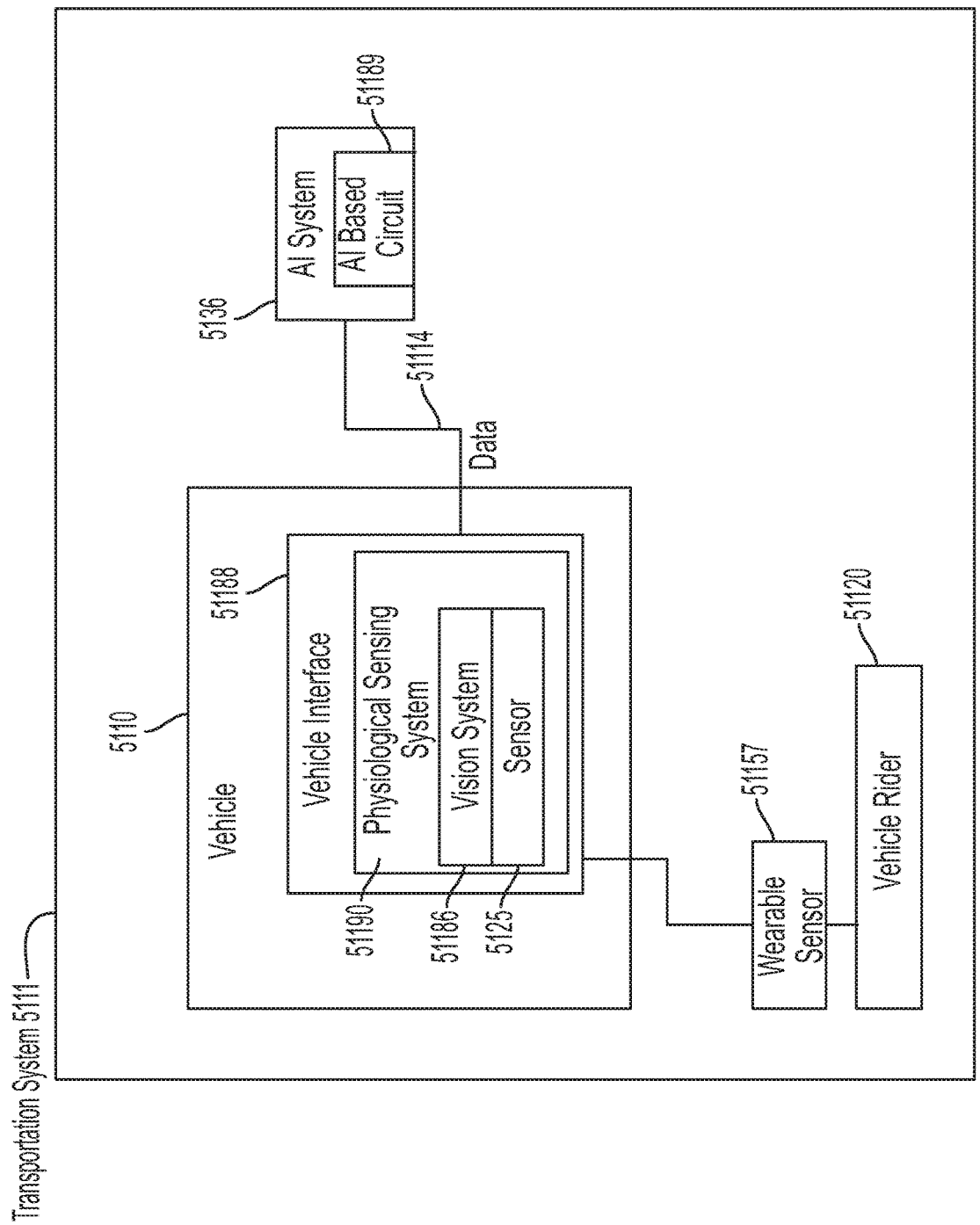
FIG. 51 is a diagrammatic view that illustrates systems described throughout this disclosure relating to various embodiments of the present disclosure.

Referring to FIG. 51, a transportation system 5111 is provided having an artificial intelligence system 5136 that automatically randomizes a parameter of an in-vehicle experience in order to improve a user state that benefits from variation. In embodiments, a system used to control a driver or passenger experience (such as in a self-driving car, assisted car, or conventional vehicle) may be configured to automatically undertake actions based on an objective or feedback function, such as where an artificial intelligence system 5136 is trained on outcomes from a training data set to provide outputs to one or more vehicle systems to improve health, satisfaction, mood, safety, one or more financial metrics, efficiency, or the like.

Such systems may involve a wide range of in-vehicle experience parameters (including any of the experience parameters described herein, such as driving experience (including assisted and self-driving, as well as vehicle responsiveness to inputs, such as in controlled suspension performance, approaches to curves, braking and the like), seat positioning (including lumbar support, leg room, seatback angle, seat height and angle, etc.), climate control (including ventilation, window or moonroof state (e.g., open or closed), temperature, humidity, fan speed, air motion and the like), sound (e.g., volume, bass, treble, individual speaker control, focus area of sound, etc.), content (audio, video and other types, including music, news, advertising and the like), route selection (e.g., for speed, for road experience (e.g., smooth or rough, flat or hilly, straight or curving), for points of interest (POIs), for view (e.g., scenic routes), for novelty (e.g., to see different locations), and/or for defined purposes (e.g., shopping opportunities, saving fuel, refueling opportunities, recharging opportunities, or the like).

In many situations, variation of one or more vehicle experience parameters may provide or result in a preferred state for a vehicle 5110 (or set of vehicles), a user (such as vehicle rider 51120), or both, as compared to seeking to find a single optimized state of such a parameter. For example, while a user may have a preferred seat position, sitting in the same position every day, or during an extended period on the same day, may have adverse effects, such as placing undue pressure on certain joints, promoting atrophy of certain muscles, diminishing flexibility of soft tissue, or the like. In such a situation, an automated control system (including one that is configured to use artificial intelligence of any of the types described herein) may be configured to induce variation in one or more of the user experience parameters described herein, optionally with random variation or with variation that is according to a prescribed pattern, such as one that may be prescribed according to a regimen, such as one developed to provide physical therapy, chiropractic, or other medical or health benefits. As one example, seat positioning may be varied over time to promote health of joints, muscles, ligaments, cartilage or the like. As another example, consistent with evidence that human health is improved when an individual experiences significant variations in temperature, humidity, and other climate factors, a climate control system may be varied (randomly or according to a defined regimen) to provide varying temperature, humidity, fresh air (including by opening windows or ventilation) or the like in order to improve the health, mood, or alertness of a user.

An artificial intelligence-based control system 5136 may be trained on a set of outcomes (of various types described herein) to provide a level of variation of a user experience that achieves desired outcomes, including selection of the timing and extent of such variations. As another example, an audio system may be varied to preserve hearing (such as based on tracking accumulated sound pressure levels, accumulated dosage, or the like), to promote alertness (such as by varying the type of content), and/or to improve health (such as by providing a mix of stimulating and relaxing content). In embodiments, such an artificial intelligence system 5136 may be fed sensor data 51444, such as from a wearable device 51157 (including a sensor set) or a physiological sensing system 51190, which includes a set of systems and/or sensors capable of providing physiological monitoring within a vehicle 5110 (e.g., a vison-based system 51186 that observes a user, a sensor 5125 embedded in a seat, a steering wheel, or the like that can measure a physiological parameter, or the like). For example, a vehicle interface 51188 (such as a steering wheel or any other interface described herein) can measure a physiological parameter (e.g., galvanic skin response, such as to indicate a stress level, cortisol level, or the like of a driver or other user), which can be used to indicate a current state for purposes of control or can be used as part of a training data set to optimize one or more parameters that may benefit from control, including control of variation of user experience to achieve desired outcomes. In one such example, an artificial intelligence system 5136 may vary parameters, such as driving experience, music and the like, to account for changes in hormonal systems of the user (such as cortisol and other adrenal system hormones), such as to induce healthy changes in state (consistent with evidence that varying cortisol levels over the course of a day are typical in healthy individuals, but excessively high or low levels at certain times of day may be unhealthy or unsafe). Such a system may, for example, "amp up" the experience with more aggressive settings (e.g., more acceleration into curves, tighter suspension, and/or louder music) in the morning when rising cortisol levels are healthy and "mellow out" the experience (such as by softer suspension, relaxing music and/or gentle driving motion) in the afternoon when cortisol levels should be dropping to lower levels to promote health. Experiences may consider both health of the user and safety, such as by ensuring that levels vary over time, but are sufficiently high to assure alertness (and hence safety) in situations where high alertness is required. While cortisol (an important hormone) is provided as an example, user experience parameters may be controlled (optionally with random or configured variation) with respect to other hormonal or biological systems, including insulin-related systems, cardiovascular systems (e.g., relating to pulse and blood pressure), gastrointestinal systems, and many others.

An aspect provided herein includes a system for transportation 5111, comprising: an artificial intelligence system 5136 to automatically randomize a parameter of an in-vehicle experience to improve a user state. In embodiments, the user state benefits from variation of the parameter.

An aspect provided herein includes a system for transportation 5111, comprising: a vehicle interface 51188 for gathering physiological sensed data of a rider 51120 in the vehicle 5110; and an artificial intelligence-based circuit 51189 that is trained on a set of outcomes related to rider in-vehicle experience and that induces, responsive to the sensed rider physiological data, variation in one or more of the user experience parameters to achieve at least one desired outcome in the set of outcomes, the inducing variation including control of timing and extent of the variation. In embodiments, the induced variation includes random variation. In embodiments, the induced variation includes variation that is according to a prescribed pattern. In embodiments, the prescribed pattern is prescribed according to a regimen. In embodiments, the regimen is developed to provide at least one of physical therapy, chiropractic, and other medical health benefits. In embodiments, the one or more user experience parameters affect at least one of seat position, temperature, humidity, cabin air source, or audio output. In embodiments, the vehicle interface 51188 comprises at least one wearable sensor 51157 disposed to be worn by the rider 51120. In embodiments, the vehicle interface 51188 comprises a vision system 51186 disposed to capture and analyze images from a plurality of perspectives of the rider 51120. In embodiments, the variation in one or more of the user experience parameters comprises variation in control of the vehicle 5110.

In embodiments, variation in control of the vehicle 5110 includes configuring the vehicle 5110 for aggressive driving performance. In embodiments, variation in control of the vehicle 5110 includes configuring the vehicle 5110 for non-aggressive driving performance. In embodiments, the variation is responsive to the physiological sensed data that includes an indication of a hormonal level of the rider 51120, and the artificial intelligence-based circuit 51189 varies the one or more user experience parameters to promote a hormonal state that promotes rider safety.

Figure 52:
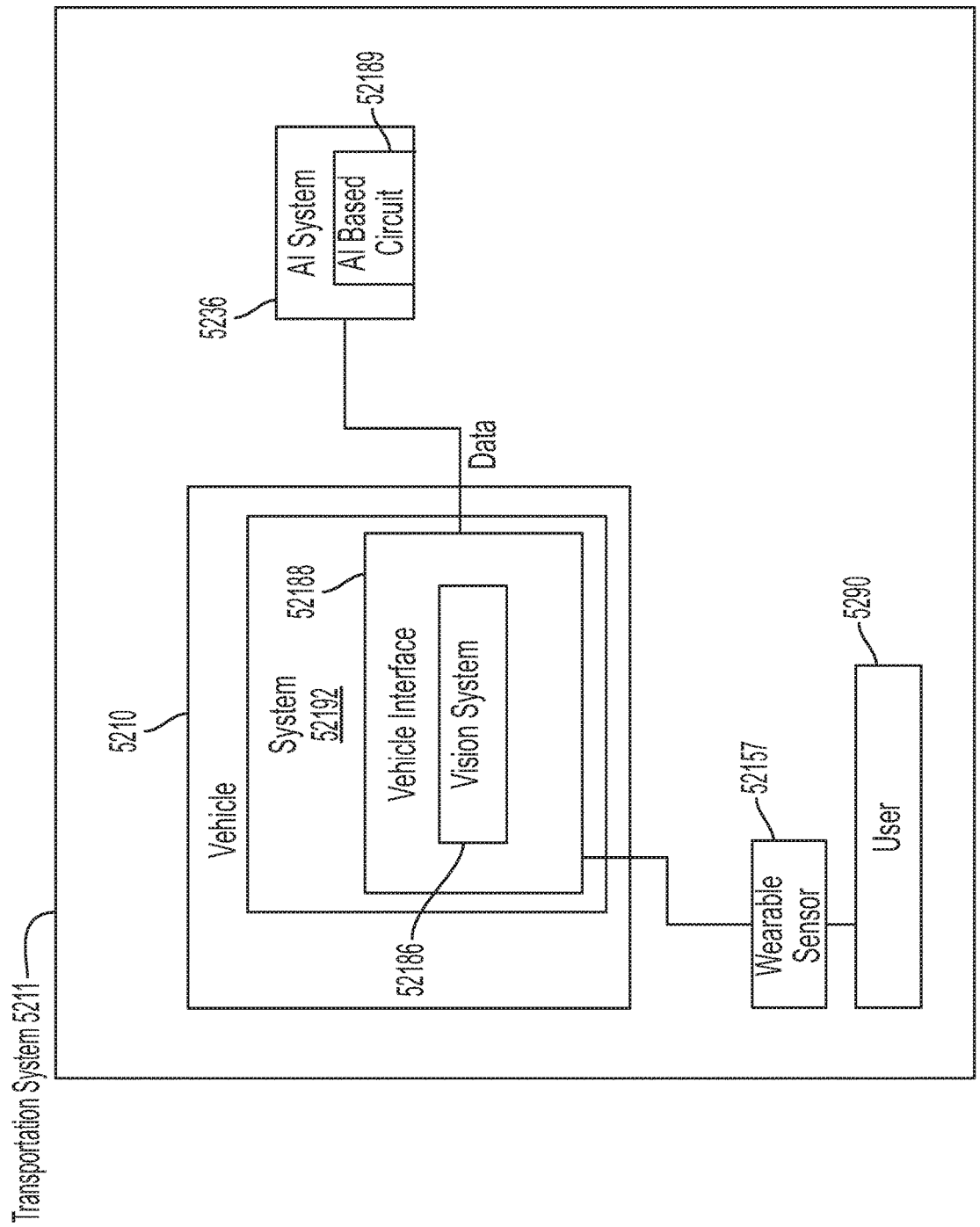
FIG. 52 is a diagrammatic view that illustrates systems described throughout this disclosure relating to various embodiments of the present disclosure.

Referring now to FIG. 52, also provided herein are transportation systems 5211 having a system 52192 for taking an indicator of a hormonal system level of a user 5290 and automatically varying a user experience in the vehicle 5210 to promote a hormonal state that promotes safety.

An aspect provided herein includes a system for transportation 5211, comprising: a system 52192 for detecting an indicator of a hormonal system level of a user 5290 and automatically varying a user experience in a vehicle 5210 to promote a hormonal state that promotes safety.

An aspect provided herein includes a system for transportation 5211 comprising: a vehicle interface 52188 for gathering hormonal state data of a rider (e.g., user 5290) in the vehicle 5210; and an artificial intelligence-based circuit 52189 that is trained on a set of outcomes related to rider in-vehicle experience and that induces, responsive to the sensed rider hormonal state data, variation in one or more of the user experience parameters to achieve at least one desired outcome in the set of outcomes, the set of outcomes including a least one outcome that promotes rider safety, the inducing variation including control of timing and extent of the variation.

In embodiments, the variation in the one or more user experience parameters is controlled by the artificial intelligence system 5236 to promote a desired hormonal state of the rider (e.g., user 5290). In embodiments, the desired hormonal state of the rider promotes safety. In embodiments, the at least one desired outcome in the set of outcomes is the at least one outcome that promotes rider safety. In embodiments, the variation in the one or more user experience parameters includes varying at least one of a food and a beverage offered to the rider (e.g., user 5290). In embodiments, the one or more user experience parameters affect at least one of seat position, temperature, humidity, cabin air source, or audio output. In embodiments, the vehicle interface 52188 comprises at least one wearable sensor 52157 disposed to be worn by the rider (e.g., user 5290).

In embodiments, the vehicle interface 52188 comprises a vision system 52186 disposed to capture and analyze images from a plurality of perspectives of the rider (e.g., user 5290). In embodiments, the variation in one or more of the user experience parameters comprises variation in control of the vehicle 5210. In embodiments, variation in control of the vehicle 5210 includes configuring the vehicle 5210 for aggressive driving performance. In embodiments, variation in control of the vehicle 5210 includes configuring the vehicle 5210 for non-aggressive driving performance.

Figure 53:
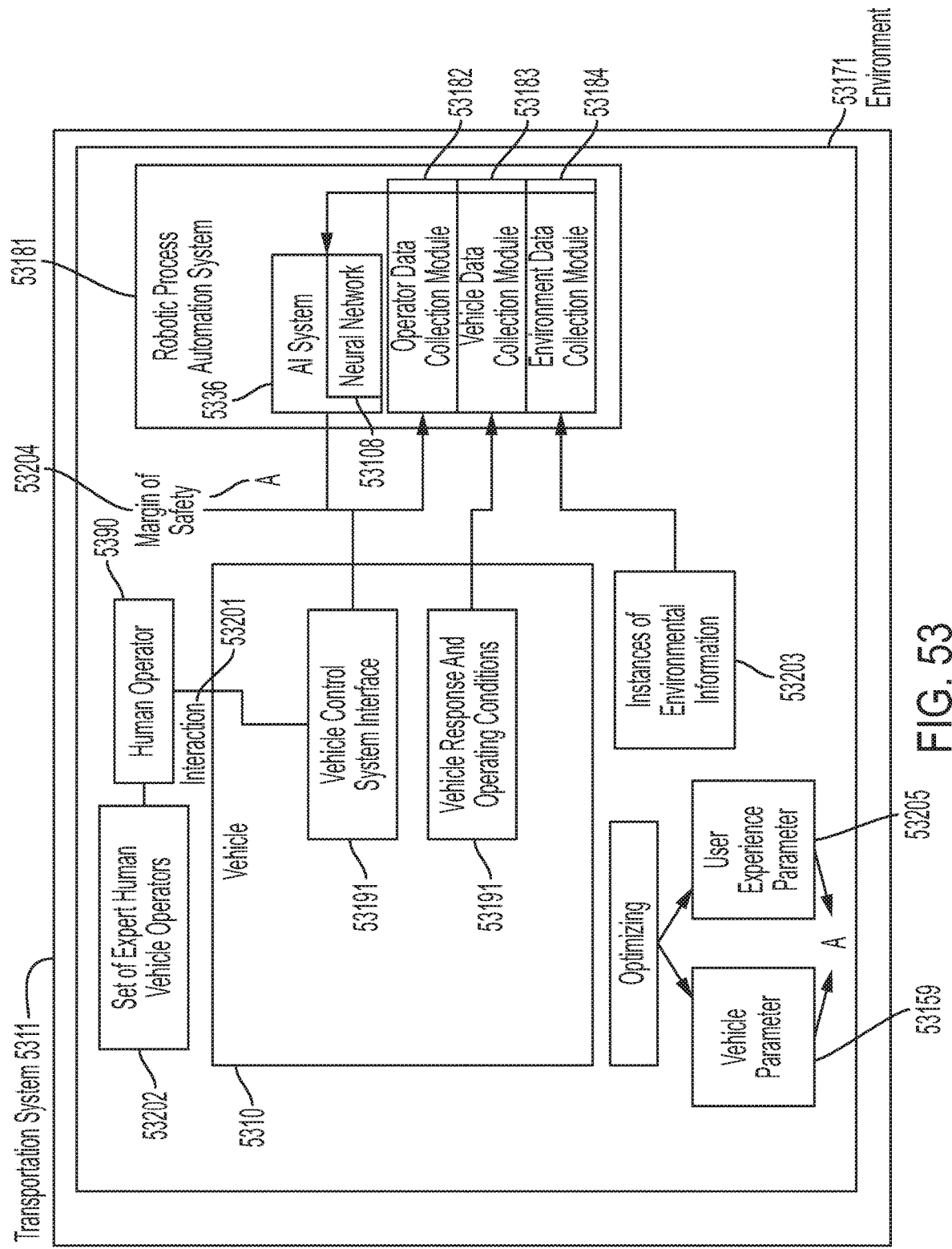
FIG. 53 is a diagrammatic view that illustrates systems described throughout this disclosure relating to various embodiments of the present disclosure.

Referring to FIG. 53, provided herein are transportation systems 5311 having a system for optimizing at least one of a vehicle parameter 53159 and a user experience parameter 53205 to provide a margin of safety 53204. In embodiments, the margin of safety 53204 may be a user-selected margin of safety or user-based margin of safety, such as selected based on a profile of a user or actively selected by a user, such as by interaction with a user interface, or selected based on a profile developed by tracking user behavior, including behavior in a vehicle 5310 and in other contexts, such as on social media, in e-commerce, in consuming content, in moving from place-to-place, or the like. In many situations, there is a tradeoff between optimizing the performance of a dynamic system (such as to achieve some objective function, like fuel efficiency) and one or more risks that are present in the system. This is particularly true in situations where there is some asymmetry between the benefits of optimizing one or more parameters and the risks that are present in the dynamic systems in which the parameter plays a role. As an example, seeking to minimize travel time (such as for a daily commute), leads to an increased likelihood of arriving late, because a wide range of effects in dynamic systems, such as ones involving vehicle traffic, tend to cascade and periodically produce travel times that vary widely (and quite often adversely). Variances in many systems are not symmetrical; for example, unusually uncrowded roads may improve a 30-mile commute time by a few minutes, but an accident, or high congestion, can increase the same commute by an hour or more. Thus, to avoid risks that have high adverse consequences, a wide margin of safety may be required. In embodiments, systems are provided herein for using an expert system (which may be model-based, rule-based, deep learning, a hybrid, or other intelligent systems as described herein) to provide a desired margin of safety with respect to adverse events that are present in transportation-related dynamic systems. The margin of safety 53204 may be provided via an output of the expert system 5336, such as an instruction, a control parameter for a vehicle 5310 or an in-vehicle user experience, or the like. An artificial intelligence system 5336 may be trained to provide the margin of safety 53204 based on a training set of data based on outcomes of transportation systems, such as traffic data, weather data, accident data, vehicle maintenance data, fueling and charging system data (including in-vehicle data and data from infrastructure systems, such as charging stations, fueling stations, and energy production, transportation, and storage systems), user behavior data, user health data, user satisfaction data, financial information (e.g., user financial information, pricing information (e.g., for fuel, for food, for accommodations along a route, and the like), vehicle safety data, failure mode data, vehicle information system data, and the like), and many other types of data as described herein and in the documents incorporated by reference herein.

An aspect provided herein includes a system for transportation 5311, comprising: a system for optimizing at least one of a vehicle parameter 53159 and a user experience parameter 53205 to provide a margin of safety 53204.

An aspect provided herein includes a transportation system 5311 for optimizing a margin of safety when mimicking human operation of a vehicle 5310, the transportation system 5311 comprising: a set of robotic process automation systems 53181 comprising: an operator data collection module 53182 to capture human operator 5390 interactions 53201 with a vehicle control system interface 53191; a vehicle data collection module 53183 to capture vehicle response and operating conditions associated at least contemporaneously with the human operator interaction 53201; an environment data collection module 53184 to capture instances of environmental information 53203 associated at least contemporaneously with the human operator interactions 53201; and an artificial intelligence system 5336 to learn to control the vehicle 5310 with an optimized margin of safety while mimicking the human operator. In embodiments, the artificial intelligence system 5336 is responsive to the robotic process automation system 53181. In embodiments, the artificial intelligence system 5336 is to detect data indicative of at least one of a plurality of the instances of environmental information associated with the contemporaneously captured vehicle response and operating conditions. In embodiments, the optimized margin of safety is to be achieved by training the artificial intelligence system 5336 to control the vehicle 5310 based on a set of human operator interaction data collected from interactions of a set of expert human vehicle operators with the vehicle control system interface 53191.

In embodiments, the operator data collection module 53182 captures patterns of data including braking patterns, follow-behind distance, approach to curve acceleration patterns, lane preferences, or passing preferences. In embodiments, the vehicle data collection module 53183 captures data from a plurality of vehicle data systems that provide data streams indicating states and changes in state in steering, braking, acceleration, forward looking images, or rear-looking images. In embodiments, the artificial intelligence system includes a neural network 53108 for training the artificial intelligence system 53114.

Figure 54:
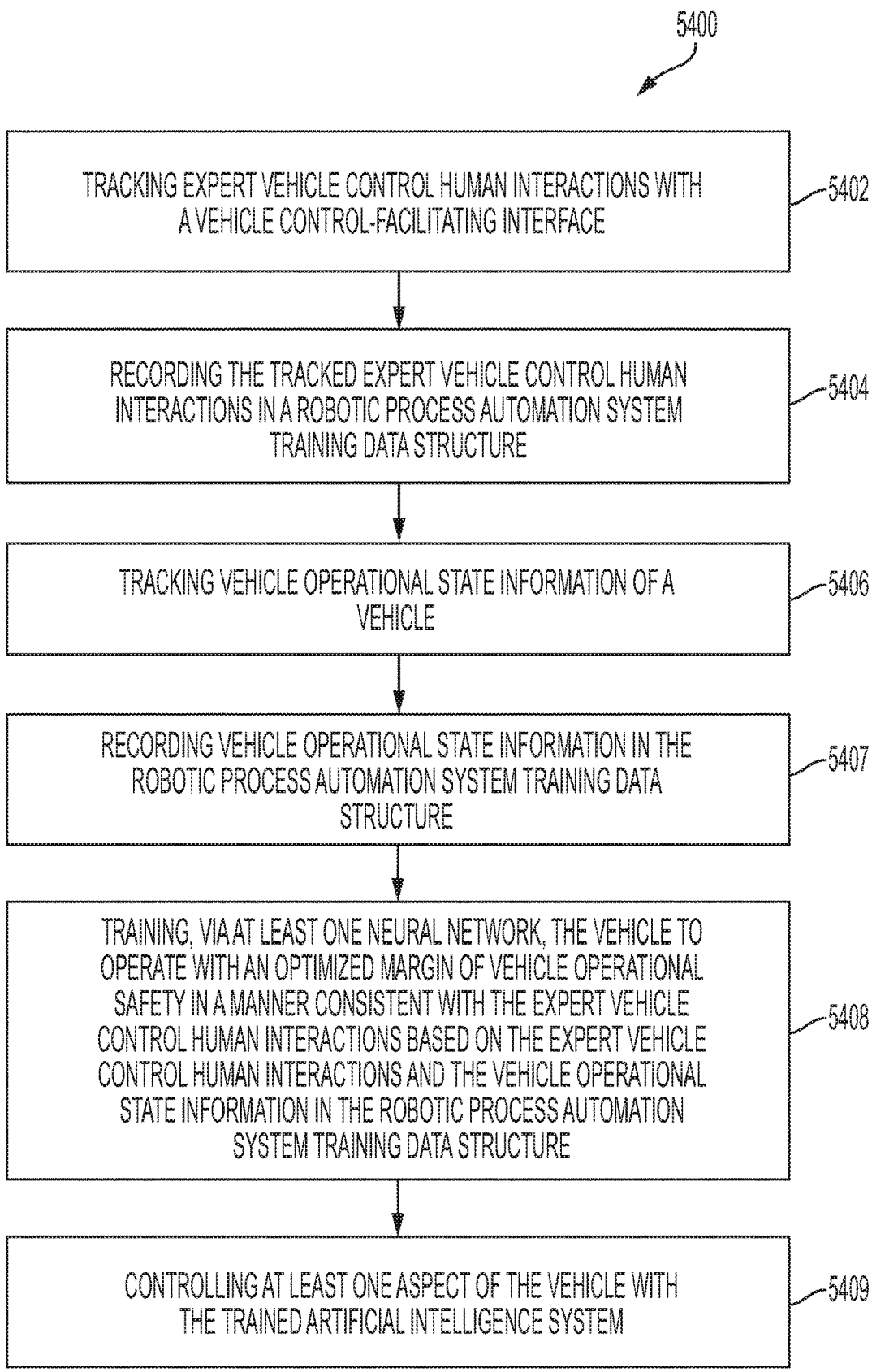
FIG. 54 is a diagrammatic view that illustrates a method described throughout this disclosure relating to various embodiments of the present disclosure.

FIG. 54 illustrates a method 5400 of robotic process automation for achieving an optimized margin of vehicle operational safety in accordance with embodiments of the systems and methods disclosed herein. At 5402 the method includes tracking expert vehicle control human interactions with a vehicle control-facilitating interface. At 5404 the method includes recording the tracked expert vehicle control human interactions in a robotic process automation system training data structure. At 5406 the method includes tracking vehicle operational state information of a vehicle. At 5407 the method includes recording vehicle operational state information in the robotic process automation system training data structure. At 5408 the method includes training, via at least one neural network, the vehicle to operate with an optimized margin of vehicle operational safety in a manner consistent with the expert vehicle control human interactions based on the expert vehicle control human interactions and the vehicle operational state information in the robotic process automation system training data structure. At 5409 the method includes controlling at least one aspect of the vehicle with the trained artificial intelligence system.

Referring to FIG. 53 and FIG. 54, in embodiments, the method further comprises applying deep learning to optimize the margin of vehicle operational safety by controlling the at least one aspect of the vehicle through structured variation in the controlling the at least one aspect of the vehicle to mimic the expert vehicle control human interactions 53201 and processing feedback from the controlling the at least one aspect of the vehicle with machine learning. In embodiments, the controlling at least one aspect of the vehicle is performed via the vehicle control-facilitating interface 53191. In embodiments, the controlling at least one aspect of the vehicle is performed by the artificial intelligence system emulating the control-facilitating interface being operated by the expert vehicle control human 53202. In embodiments, the vehicle control-facilitating interface 53191 comprises at least one of an audio capture system to capture audible expressions of the expert vehicle control human, a human-machine interface, mechanical interface, an optical interface and a sensor-based interface. In embodiments, the tracking vehicle operational state information comprises tracking at least one of vehicle systems and vehicle operational processes affected by the expert vehicle control human interactions. In embodiments, the tracking vehicle operational state information comprises tracking at least one vehicle system element. In embodiments, the at least one vehicle system element is controlled via the vehicle control-facilitating interface. In embodiments, the at least one vehicle system element is affected by the expert vehicle control human interactions.

In embodiments, the tracking vehicle operational state information comprises tracking the vehicle operational state information before, during, and after the expert vehicle control human interaction. In embodiments, the tracking vehicle operational state information comprises tracking at least one of a plurality of vehicle control system outputs that result from the expert vehicle control human interactions and vehicle operational results achieved responsive to the expert vehicle control human interactions. In embodiments, the vehicle is to be controlled to achieve results that are consistent with results achieved via the expert vehicle control human interactions.

In embodiments, the method further comprises tracking and recording conditions proximal to the vehicle with a plurality of vehicle mounted sensors. In embodiments, the training of the artificial intelligence system is further responsive to the conditions proximal to the vehicle tracked contemporaneously to the expert vehicle control human interactions. In embodiments, the training is further responsive to a plurality of data feeds from remote sensors, the plurality of data feeds comprising data collected by the remote sensors contemporaneous to the expert vehicle control human interactions.

Figure 55:
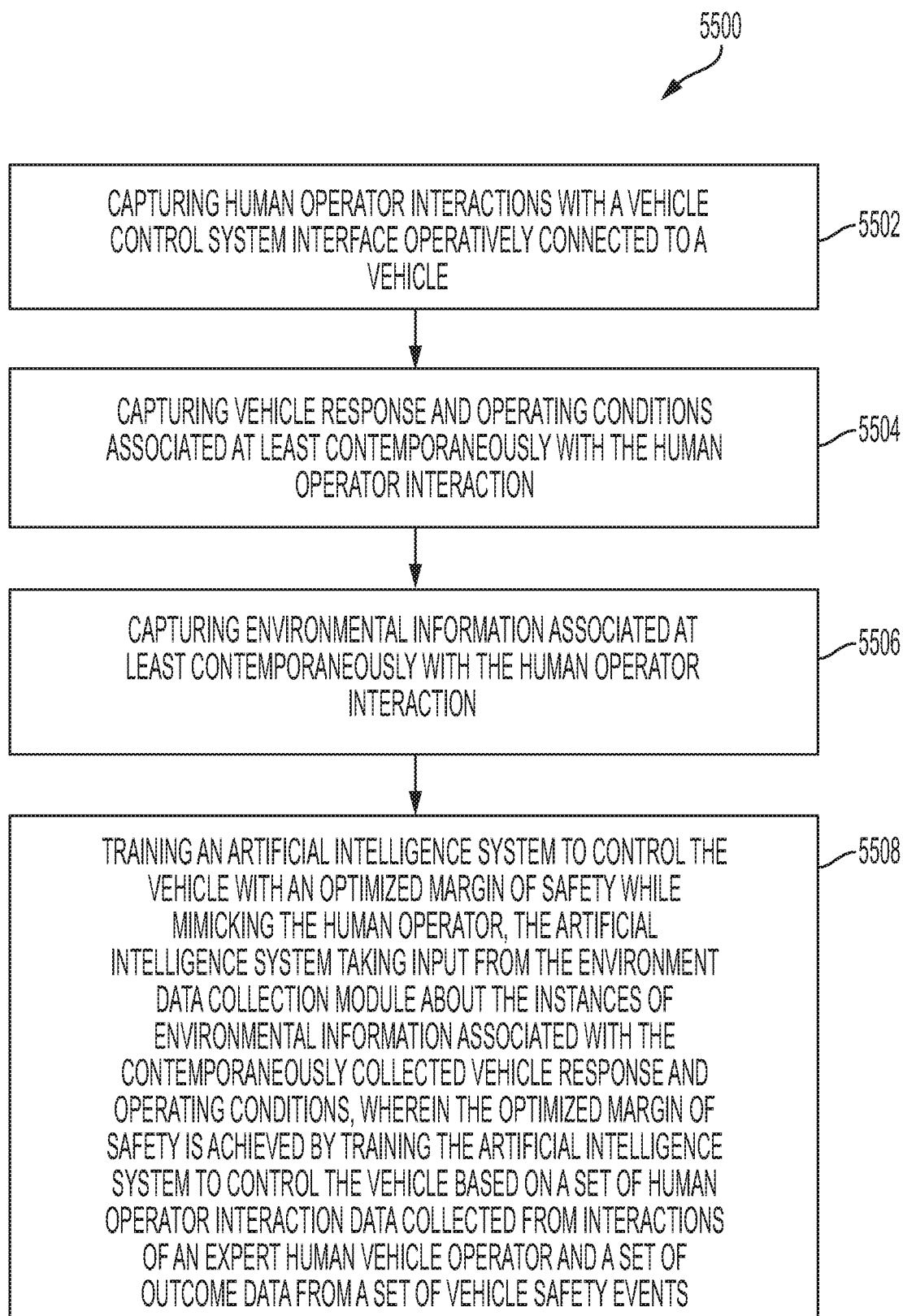
FIG. 55 is a diagrammatic view that illustrates a method described throughout this disclosure relating to various embodiments of the present disclosure.

FIG. 55 illustrates a method 5500 for mimicking human operation of a vehicle by robotic process automation of in accordance with embodiments of the systems and methods disclosed herein. At 5502 the method includes capturing human operator interactions with a vehicle control system interface operatively connected to a vehicle. At 5504 the method includes capturing vehicle response and operating conditions associated at least contemporaneously with the human operator interaction. At 5506 the method includes capturing environmental information associated at least contemporaneously with the human operator interaction. At 5508 the method includes training an artificial intelligence system to control the vehicle with an optimized margin of safety while mimicking the human operator, the artificial intelligence system taking input from the environment data collection module about the instances of environmental information associated with the contemporaneously collected vehicle response and operating conditions. In embodiments, the optimized margin of safety is achieved by training the artificial intelligence system to control the vehicle based on a set of human operator interaction data collected from interactions of an expert human vehicle operator and a set of outcome data from a set of vehicle safety events.

Referring to FIGS. 53 and 55 in embodiments, the method further comprises: applying deep learning of the artificial intelligence system 53114 to optimize a margin of vehicle operating safety 53204 by affecting a controlling of at least one aspect of the vehicle through structured variation in control of the at least one aspect of the vehicle to mimic the expert vehicle control human interactions 53201 and processing feedback from the controlling of the at least one aspect of the vehicle with machine learning. In embodiments, the artificial intelligence system employs a workflow that involves decision-making and the robotic process automation system 53181 facilitates automation of the decision-making. In embodiments, the artificial intelligence system employs a workflow that involves remote control of the vehicle and the robotic process automation system facilitates automation of remotely controlling the vehicle 5310.

Figure 56:
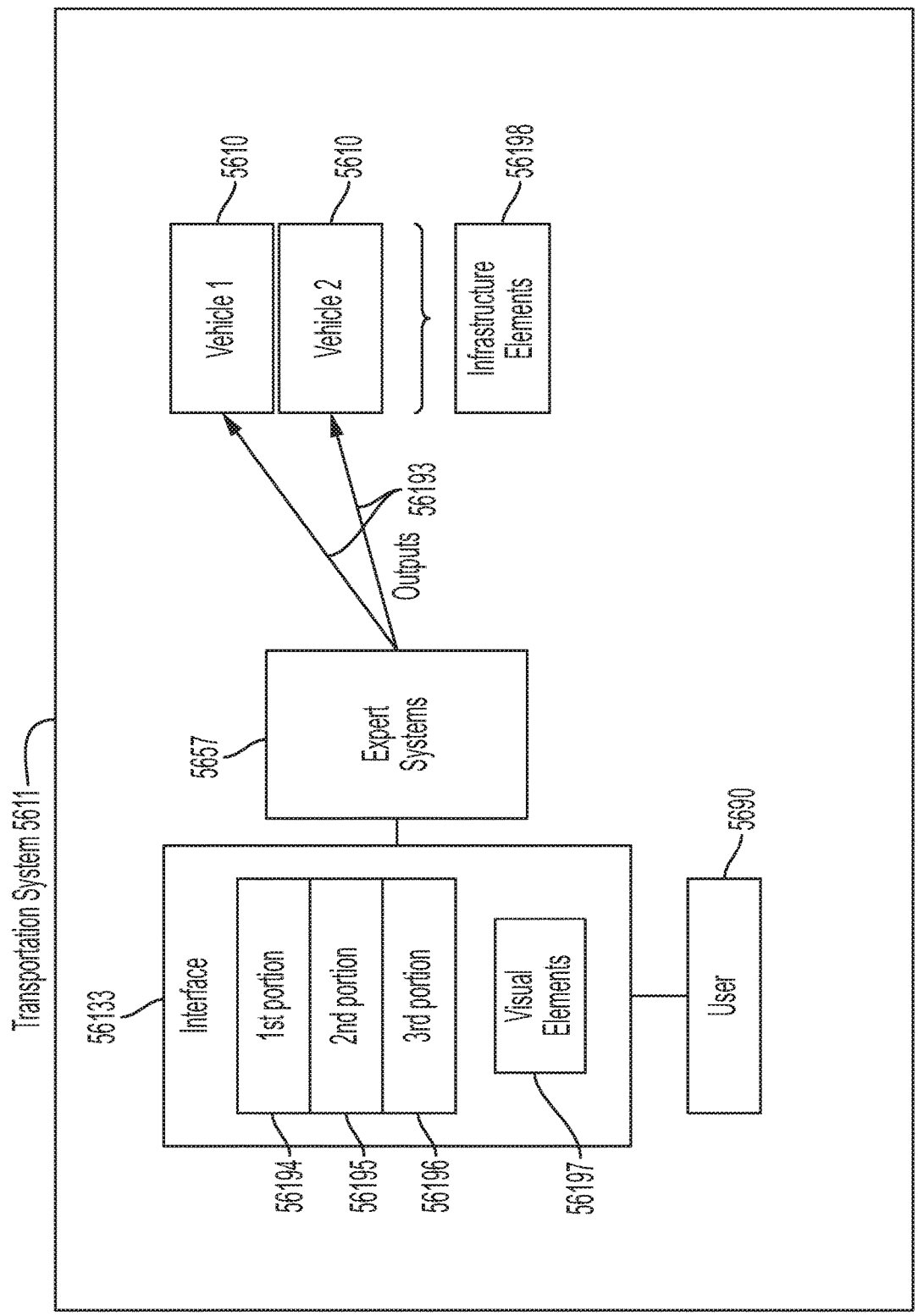
FIG. 56 is a diagrammatic view that illustrates systems described throughout this disclosure relating to various embodiments of the present disclosure.

Referring now to FIG. 56, a transportation system 5611 is depicted which includes an interface 56133 by which a set of expert systems 5657 may be configured to provide respective outputs 56193 for managing at least one of a set of vehicle parameters, a set of fleet parameters and a set of user experience parameters.

Such an interface 56133 may include a graphical user interface (such as having a set of visual elements, menu items, forms, and the like that can be manipulated to enable selection and/or configuration of an expert system 5657), an application programming interface, an interface to a computing platform (e.g., a cloud-computing platform, such as to configure parameters of one or more services, programs, modules, or the like), and others. For example, an interface 56133 may be used to select a type of expert system 5657, such as a model (e.g., a selected model for representing behavior of a vehicle, a fleet or a user, or a model representing an aspect of an environment relevant to transportation, such as a weather model, a traffic model, a fuel consumption model, an energy distribution model, a pricing model or the like), an artificial intelligence system (such as selecting a type of neural network, deep learning system, or the like, of any type described herein), or a combination or hybrid thereof. For example, a user may, in an interface 56133, elect to use the European Center for Medium-Range Weather Forecast (ECMWF) to forecast weather events that may impact a transportation environment, along with a recurrent neural network for forecasting user shopping behavior (such as to indicate likely preferences of a user along a traffic route).

Thus, an interface 56133 may be configured to provide a host, manager, operator, service provider, vendor, or other entity interacting within or with a transportation system 5611 with the ability to review a range of models, expert systems 5657, neural network categories, and the like. The interface 56133 may optionally be provided with one or more indicators of suitability for a given purpose, such as one or more ratings, statistical measures of validity, or the like. The interface 56133 may also be configured to select a set (e.g., a model, expert system, neural network, etc.) that is well adapted for purposes of a given transportation system, environment, and purpose. In embodiments, such an interface 56133 may allow a user 5690 to configure one or more parameters of an expert system 5657, such as one or more input data sources to which a model is to be applied and/or one or more inputs to a neural network, one or more output types, targets, durations, or purposes, one or more weights within a model or an artificial intelligence system, one or more sets of nodes and/or interconnections within a model, graph structure, neural network, or the like, one or more time periods of input, output, or operation, one or more frequencies of operation, calculation, or the like, one or more rules (such as rules applying to any of the parameters configured as described herein or operating upon any of the inputs or outputs noted herein), one or more infrastructure parameters (such as storage parameters, network utilization parameters, processing parameters, processing platform parameters, or the like). As one example among many other possible example, a user 5690 may configure a selected neural network to take inputs from a weather model, a traffic model, and a real-time traffic reporting system in order to provide a real-time output 56193 to a routing system for a vehicle 5610, where the neural network is configured to have ten million nodes and to undertake processing on a selected cloud platform.

In embodiments, the interface 56133 may include elements for selection and/or configuration of a purpose, an objective or a desired outcome of a system and/or subsystem, such as one that provides input, feedback, or supervision to a model, to a machine learning system, or the like. For example, a user 5690 may be allowed, in an interface 56133, to select among modes (e.g., comfort mode, sports mode, high-efficiency mode, work mode, entertainment mode, sleep mode, relaxation mode, long-distance trip mode, or the like) that correspond to desired outcomes, which may include emotional outcomes, financial outcomes, performance outcomes, trip duration outcomes, energy utilization outcomes, environmental impact outcomes, traffic avoidance outcomes, or the like. Outcomes may be declared with varying levels of specificity. Outcomes may be defined by or for a given user 5690 (such as based on a user profile or behavior) or for a group of users (such as by one or more functions that harmonizes outcomes according to multiple user profiles, such as by selecting a desired configuration that is consistent with an acceptable state for each of a set of riders). As an example, a rider may indicate a preferred outcome of active entertainment, while another rider may indicate a preferred outcome of maximum safety. In such a case, the interface 56133 may provide a reward parameter to a model or expert system 5657 for actions that reduce risk and for actions that increase entertainment, resulting in outcomes that are consistent with objectives of both riders. Rewards may be weighted, such as to optimize a set of outcomes. Competition among potentially conflicting outcomes may be resolved by a model, by rule (e.g., a vehicle owner's objectives may be weighted higher than other riders, a parent's over a child, or the like), or by machine learning, such as by using genetic programming techniques (such as by varying combinations of weights and/or outcomes randomly or systematically and determining overall satisfaction of a rider or set of riders).

An aspect provided herein includes a system for transportation 5611, comprising: an interface 56133 to configure a set of expert systems 5657 to provide respective outputs 56193 for managing a set of parameters selected from the group consisting of a set of vehicle parameters, a set of fleet parameters, a set of user experience parameters, and combinations thereof.

An aspect provided herein includes a system for configuration management of components of a transportation system 5611 comprising: an interface 56133 comprising: a first portion 56194 of the interface 56133 for configuring a first expert computing system of the expert computing systems 5657 for managing a set of vehicle parameters; a second portion 56195 of the interface 56133 for configuring a second expert computing system of the expert computing systems 5657 for managing a set of vehicle fleet parameters; and a third portion 56196 of the interface 56133 for configuring a third expert computing system for managing a set of user experience parameters. In embodiments, the interface 56133 is a graphical user interface through which a set of visual elements 56197 presented in the graphical user interface, when manipulated in the interface 56133 causes at least one of selection and configuration of one or more of the first, second, and third expert systems 5657. In embodiments, the interface 56133 is an application programming interface. In embodiments, the interface 56133 is an interface to a cloud-based computing platform through which one or more transportation-centric services, programs and modules are configured.

An aspect provided herein includes a transportation system 5611 comprising: an interface 56133 for configuring a set of expert systems 5657 to provide outputs 56193 based on which the transportation system 5611 manages transportation-related parameters. In embodiments, the parameters facilitate operation of at least one of a set of vehicles, a fleet of vehicles, and a transportation system user experience; and a plurality of visual elements 56197 representing a set of attributes and parameters of the set of expert systems 5657 that are configurable by the interface 56133 and a plurality of the transportation systems 5611. In embodiments, the interface 56133 is configured to facilitate manipulating the visual elements 56197 thereby causing configuration of the set of expert systems 5657. In embodiments, the plurality of the transportation systems comprise a set of vehicles 5610.

In embodiments, the plurality of the transportation systems comprise a set of infrastructure elements 56198 supporting a set of vehicles 5610. In embodiments, the set of infrastructure elements 56198 comprises vehicle fueling elements. In embodiments, the set of infrastructure elements 56198 comprises vehicle charging elements. In embodiments, the set of infrastructure elements 56198 comprises traffic control lights. In embodiments, the set of infrastructure elements 56198 comprises a toll booth. In embodiments, the set of infrastructure elements 56198 comprises a rail system. In embodiments, the set of infrastructure elements 56198 comprises automated parking facilities. In embodiments, the set of infrastructure elements 56198 comprises vehicle monitoring sensors.

In embodiments, the visual elements 56197 display a plurality of models that can be selected for use in the set of expert systems 5657. In embodiments, the visual elements 56197 display a plurality of neural network categories that can be selected for use in the set of expert systems 5657. In embodiments, at least one of the plurality of neural network categories includes a convolutional neural network. In embodiments, the visual elements 56197 include one or more indicators of suitability of items represented by the plurality of visual elements 56197 for a given purpose. In embodiments, configuring a plurality of expert systems 5657 comprises facilitating selection sources of inputs for use by at least a portion of the plurality of expert systems 5657. In embodiments, the interface 56133 facilitates selection, for at least a portion of the plurality of expert systems 5657, one or more output types, targets, durations, and purposes.

In embodiments, the interface 56133 facilitates selection, for at least a portion of the plurality of expert systems 5657, of one or more weights within a model or an artificial intelligence system. In embodiments, the interface 56133 facilitates selection, for at least a portion of the plurality of expert systems 5657, of one or more sets of nodes or interconnections within a model. In embodiments, the interface 56133 facilitates selection, for at least a portion of the plurality of expert systems 5657, of a graph structure. In embodiments, the interface 56133 facilitates selection, for at least a portion of the plurality of expert systems 5657, of a neural network. In embodiments, the interface facilitates selection, for at least a portion of the plurality of expert systems, of one or more time periods of input, output, or operation.

In embodiments, the interface 56133 facilitates selection, for at least a portion of the plurality of expert systems 5657, of one or more frequencies of operation. In embodiments, the interface 56133 facilitates selection, for at least a portion of the plurality of expert systems 5657, of frequencies of calculation. In embodiments, the interface 56133 facilitates selection, for at least a portion of the plurality of expert systems 5657, of one or more rules for applying to the plurality of parameters. In embodiments, the interface 56133 facilitates selection, for at least a portion of the plurality of expert systems 5657, of one or more rules for operating upon any of the inputs or upon the provided outputs. In embodiments, the plurality of parameters comprise one or more infrastructure parameters selected from the group consisting of storage parameters, network utilization parameters, processing parameters, and processing platform parameters.

In embodiments, the interface 56133 facilitates selecting a class of an artificial intelligence computing system, a source of inputs to the selected artificial intelligence computing system, a computing capacity of the selected artificial intelligence computing system, a processor for executing the artificial intelligence computing system, and an outcome objective of executing the artificial intelligence computing system. In embodiments, the interface 56133 facilitates selecting one or more operational modes of at least one of the vehicles 5610 in the transportation system 5611. In embodiments, the interface 56133 facilitates selecting a degree of specificity for outputs 56193 produced by at least one of the plurality of expert systems 5657.

Figure 57:
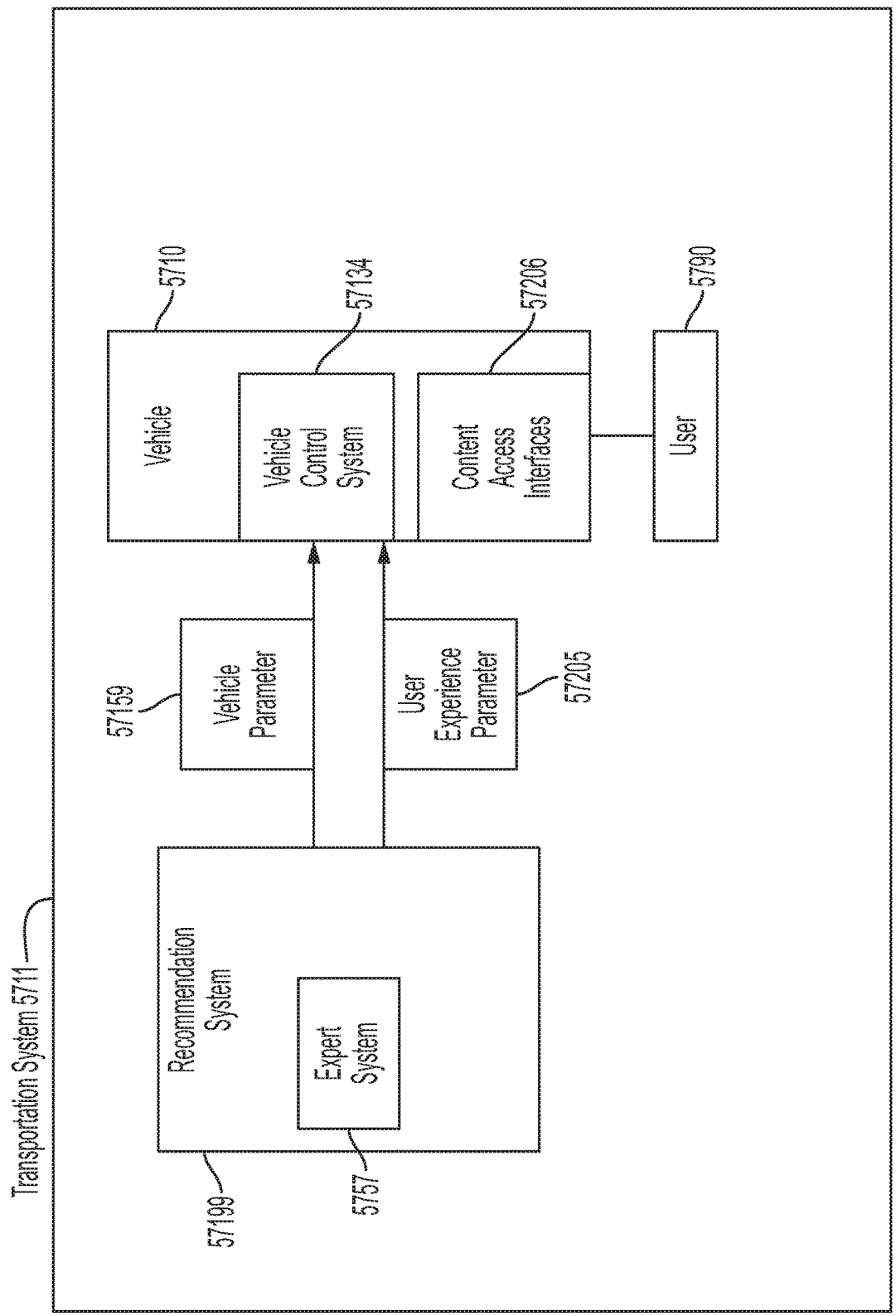
FIG. 57 is a diagrammatic view that illustrates systems described throughout this disclosure relating to various embodiments of the present disclosure.

Referring now to FIG. 57, an example of a transportation system 5711 is depicted having an expert system 5757 for configuring a recommendation for a configuration of a vehicle 5710. In embodiments, the recommendation includes at least one parameter of configuration for the expert system 5757 that controls a parameter of at least one of a vehicle parameter 57159 and a user experience parameter 57205. Such a recommendation system may recommend a configuration for a user based on a wide range of information, including data sets indicating degrees of satisfaction of other users, such as user profiles, user behavior tracking (within a vehicle and outside), content recommendation systems (such as collaborative filtering systems used to recommend music, movies, video and other content), content search systems (e.g., such as used to provide relevant search results to queries), e-commerce tracking systems (such as to indicate user preferences, interests, and intents), and many others. The recommendation system 57199 may use the foregoing to profile a rider and, based on indicators of satisfaction by other riders, determine a configuration of a vehicle 5710, or an experience within the vehicle 5710, for the rider.

The configuration may use similarity (such as by similarity matrix approaches, attribute-based clustering approaches (e.g., k-means clustering) or other techniques to group a rider with other similar riders. Configuration may use collaborative filtering, such as by querying a rider about particular content, experiences, and the like and taking input as to whether they are favorable or unfavorable (optionally with a degree of favorability, such as a rating system (e.g., 5 stars for a great item of content). The recommendation system 57199 may use genetic programming, such as by configuring (with random and/or systematic variation) combinations of vehicle parameters and/or user experience parameters and taking inputs from a rider or a set of riders (e.g., a large survey group) to determine a set of favorable configurations. This may occur with machine learning over a large set of outcomes, where outcomes may include various reward functions of the type described herein, including indicators of overall satisfaction and/or indicators of specific objectives. Thus, a machine learning system or other expert systems 5757 may learn to configure the overall ride for a rider or set of riders and to recommend such a configuration for a rider. Recommendations may be based on context, such as whether a rider is alone or in a group, the time of day (or week, month or year), the type of trip, the objective of the trip, the type or road, the duration of a trip, the route, and the like.

An aspect provided herein includes a system for transportation 5711, comprising: an expert system 5757 to configure a recommendation for a vehicle configuration. In embodiments, the recommendation includes at least one parameter of configuration for the expert system 5757 that controls a parameter selected from the group consisting of a vehicle parameter 57159, a user experience parameter 57205, and combinations thereof.

An aspect provided herein includes a recommendation system 57199 for recommending a configuration of a vehicle 5710, the recommendation system 57199 comprising an expert system 5757 that produces a recommendation of a parameter for configuring a vehicle control system 57134 that controls at least one of a vehicle parameter 57159 and a vehicle rider experience parameter 57205.

In embodiments, the vehicle 5710 comprises a system for automating at least one control parameter of the vehicle 5710. In embodiments, the vehicle is at least a semi-autonomous vehicle. In embodiments, the vehicle is automatically routed. In embodiments, the vehicle is a self-driving vehicle.

In embodiments, the expert system 5757 is a neural network system. In embodiments, the expert system 5757 is a deep learning system. In embodiments, the expert system 5757 is a machine learning system. In embodiments, the expert system 5757 is a model-based system. In embodiments, the expert system 5757 is a rule-based system. In embodiments, the expert system 5757 is a random walk-based system. In embodiments, the expert system 5757 is a genetic algorithm system. In embodiments, the expert system 5757 is a convolutional neural network system. In embodiments, the expert system 5757 is a self-organizing system. In embodiments, the expert system 5757 is a pattern recognition system. In embodiments, the expert system 5757 is a hybrid artificial intelligence-based system. In embodiments, the expert system 5757 is an acrylic graph-based system.

In embodiments, the expert system 5757 produces a recommendation based on degrees of satisfaction of a plurality of riders of vehicles 5710 in the transportation system 5711. In embodiments, the expert system 5757 produces a recommendation based on a rider entertainment degree of satisfaction. In embodiments, the expert system 5757 produces a recommendation based on a rider safety degree of satisfaction. In embodiments, the expert system 5757 produces a recommendation based on a rider comfort degree of satisfaction. In embodiments, the expert system 5757 produces a recommendation based on a rider in-vehicle search degree of satisfaction.

In embodiments, the at least one rider (or user) experience parameter 57205 is a parameter of traffic congestion. In embodiments, the at least one rider experience parameter 57205 is a parameter of desired arrival times. In embodiments, the at least one rider experience parameter 57205 is a parameter of preferred routes. In embodiments, the at least one rider experience parameter 57205 is a parameter of fuel efficiency. In embodiments, the at least one rider experience parameter 57205 is a parameter of pollution reduction. In embodiments, the at least one rider experience parameter 57205 is a parameter of accident avoidance. In embodiments, the at least one rider experience parameter 57205 is a parameter of avoiding bad weather. In embodiments, the at least one rider experience parameter 57205 is a parameter of avoiding bad road conditions. In embodiments, the at least one rider experience parameter 57205 is a parameter of reduced fuel consumption. In embodiments, the at least one rider experience parameter 57205 is a parameter of reduced carbon footprint. In embodiments, the at least one rider experience parameter 57205 is a parameter of reduced noise in a region. In embodiments, the at least one rider experience parameter 57205 is a parameter of avoiding high-crime regions.

In embodiments, the at least one rider experience parameter 57205 is a parameter of collective satisfaction. In embodiments, the at least one rider experience parameter 57205 is a parameter of maximum speed limit. In embodiments, the at least one rider experience parameter 57205 is a parameter of avoidance of toll roads. In embodiments, the at least one rider experience parameter 57205 is a parameter of avoidance of city roads. In embodiments, the at least one rider experience parameter 57205 is a parameter of avoidance of undivided highways. In embodiments, the at least one rider experience parameter 57205 is a parameter of avoidance of left turns. In embodiments, the at least one rider experience parameter 57205 is a parameter of avoidance of driver-operated vehicles.

In embodiments, the at least one vehicle parameter 57159 is a parameter of fuel consumption. In embodiments, the at least one vehicle parameter 57159 is a parameter of carbon footprint. In embodiments, the at least one vehicle parameter 57159 is a parameter of vehicle speed. In embodiments, the at least one vehicle parameter 57159 is a parameter of vehicle acceleration. In embodiments, the at least one vehicle parameter 57159 is a parameter of travel time.

In embodiments, the expert system 5757 produces a recommendation based on at least one of user behavior of the rider (e.g., user 5790) and rider interactions with content access interfaces 57206 of the vehicle 5710. In embodiments, the expert system 5757 produces a recommendation based on similarity of a profile of the rider (e.g., user 5790) to profiles of other riders. In embodiments, the expert system 5757 produces a recommendation based on a result of collaborative filtering determined through querying the rider (e.g., user 5790) and taking input that facilitates classifying rider responses thereto on a scale of response classes ranging from favorable to unfavorable. In embodiments, the expert system 5757 produces a recommendation based on content relevant to the rider (e.g., user 5790) including at least one selected from the group consisting of classification of trip, time of day, classification of road, trip duration, configured route, and number of riders.

Figure 58:
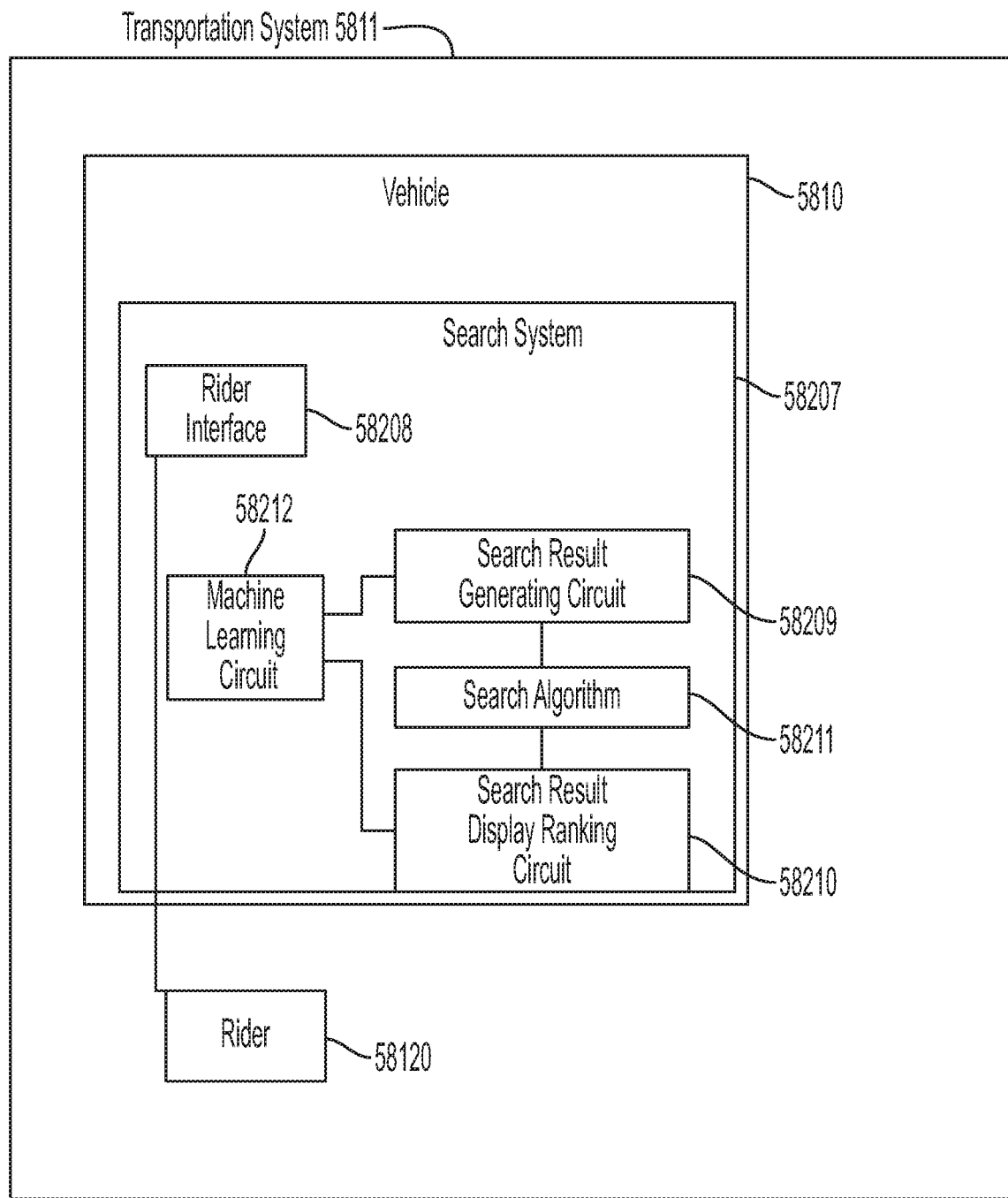
FIG. 58 is a diagrammatic view that illustrates systems described throughout this disclosure relating to various embodiments of the present disclosure.

Referring now to FIG. 58, an example transportation system 5811 is depicted having a search system 58207 that is configured to provide network search results for in-vehicle searchers.

Self-driving vehicles offer their riders greatly increased opportunity to engage with in-vehicle interfaces, such as touch screens, virtual assistants, entertainment system interfaces, communication interfaces, navigation interfaces, and the like. While systems exist to display the interface of a rider's mobile device on an in-vehicle interface, the content displayed on a mobile device screen is not necessarily tuned to the unique situation of a rider in a vehicle. In fact, riders in vehicles may be collectively quite different in their immediate needs from other individuals who engage with the interfaces, as the presence in the vehicle itself tends to indicate a number of things that are different from a user sitting at home, sitting at a desk, or walking around. One activity that engages almost all device users is searching, which is undertaken on many types of devices (desktops, mobile devices, wearable devices, and others). Searches typically include keyword entry, which may include natural language text entry or spoken queries. Queries are processed to provide search results, in one or more lists or menu elements, often involving delineation between sponsored results and non-sponsored results. Ranking algorithms typically factor in a wide range of inputs, in particular the extent of utility (such as indicated by engagement, clicking, attention, navigation, purchasing, viewing, listening, or the like) of a given search result to other users, such that more useful items are promoted higher in lists.

However, the usefulness of a search result may be very different for a rider in a self-driving vehicle than for more general searchers. For example, a rider who is being driven on a defined route (as the route is a necessary input to the self-driving vehicle) may be far more likely to value search results that are relevant to locations that are ahead of the rider on the route than the same individual would be sitting at the individual's desk at work or on a computer at home. Accordingly, conventional search engines may fail to deliver the most relevant results, deliver results that crowd out more relevant results, and the like, when considering the situation of a rider in a self-driving vehicle.

In embodiments of the system 5811 of FIG. 58, a search result ranking system (search system 58207) may be configured to provide in-vehicle-relevant search results. In embodiments, such a configuration may be accomplished by segmenting a search result ranking algorithm to include ranking parameters that are observed in connection only with a set of in-vehicle searches, so that in-vehicle results are ranked based on outcomes with respect to in-vehicle searches by other users. In embodiments, such a configuration may be accomplished by adjusting the weighting parameters applied to one or more weights in a conventional search algorithm when an in-vehicle search is detected (such as by detecting an indicator of an in-vehicle system, such as by communication protocol type, IP address, presence of cookies stored on a vehicle, detection of mobility, or the like). For example, local search results may be weighted more heavily in a ranking algorithm.

In embodiments, routing information from a vehicle 5810 may be used as an input to a ranking algorithm, such as allowing favorable weighting of results that are relevant to local points of interest ahead on a route.

In embodiments, content types may be weighted more heavily in search results based on detection of an in-vehicle query, such as weather information, traffic information, event information and the like. In embodiments, outcomes tracked may be adjusted for in-vehicle search rankings, such as by including route changes as a factor in rankings (e.g., where a search result appears to be associated in time with a route change to a location that was the subject of a search result), by including rider feedback on search results (such as satisfaction indicators for a ride), by detecting in-vehicle behaviors that appear to derive from search results (such as playing music that appeared in a search result), and the like.

In embodiments, a set of in-vehicle-relevant search results may be provided in a separate portion of a search result interface (e.g., a rider interface 58208), such as in a portion of a window that allows a rider 57120 to see conventional search engine results, sponsored search results and in-vehicle relevant search results. In embodiments, both general search results and sponsored search results may be configured using any of the techniques described herein or other techniques that would be understood by skilled in the art to provide in-vehicle-relevant search results.

In embodiments where in-vehicle-relevant search results and conventional search results are presented in the same interface (e.g., the rider interface 58208), selection and engagement with in-vehicle-relevant search results can be used as a success metric to train or reinforce one or more search algorithms 58211. In embodiments, in-vehicle search algorithms 58211 may be trained using machine learning, optionally seeded by one or more conventional search models, which may optionally be provided with adjusted initial parameters based on one or more models of user behavior that may contemplate differences between in-vehicle behavior and other behavior. Machine learning may include use of neural networks, deep learning systems, model-based systems, and others. Feedback to machine learning may include conventional engagement metrics used for search, as well as metrics of rider satisfaction, emotional state, yield metrics (e.g., for sponsored search results, banner ads, and the like), and the like.

An aspect provided herein includes a system for transportation 5811, comprising: a search system 58207 to provide network search results for in-vehicle searchers.

An aspect provided herein includes an in-vehicle network search system 58207 of a vehicle 5810, the search system comprising: a rider interface 58208 through which the rider 58120 of the vehicle 5810 is enabled to engage with the search system 58207; a search result generating circuit 58209 that favors search results based on a set of in-vehicle search criteria that are derived from a plurality of in-vehicle searches previously conducted; and a search result display ranking circuit 58210 that orders the favored search results based on a relevance of a location component of the search results with a configured route of the vehicle 5810.

In embodiments, the vehicle 5810 comprises a system for automating at least one control parameter of the vehicle 5810. In embodiments, the vehicle 5810 is at least a semi-autonomous vehicle. In embodiments, the vehicle 5810 is automatically routed. In embodiments, the vehicle 5810 is a self-driving vehicle.

In embodiments, the rider interface 58208 comprises at least one of a touch screen, a virtual assistant, an entertainment system interface, a communication interface and a navigation interface.

In embodiments, the favored search results are ordered by the search result display ranking circuit 58210 so that results that are proximal to the configured route appear before other results. In embodiments, the in-vehicle search criteria are based on ranking parameters of a set of in-vehicle searches. In embodiments, the ranking parameters are observed in connection only with the set of in-vehicle searches. In embodiments, the search system 58207 adapts the search result generating circuit 58209 to favor search results that correlate to in-vehicle behaviors. In embodiments, the search results that correlate to in-vehicle behaviors are determined through comparison of rider behavior before and after conducting a search. In embodiments, the search system further comprises a machine learning circuit 58212 that facilitates training the search result generating circuit 58209 from a set of search results for a plurality of searchers and a set of search result generating parameters based on an in-vehicle rider behavior model.

An aspect provided herein includes an in-vehicle network search system 58207 of a vehicle 5810, the search system 58207 comprising: a rider interface 58208 through which the rider 58120 of the vehicle 5810 is enabled to engage with the search system 5810; a search result generating circuit 58209 that varies search results based on detection of whether the vehicle 5810 is in self-driving or autonomous mode or being driven by an active driver; and a search result display ranking circuit 58210 that orders the search results based on a relevance of a location component of the search results with a configured route of the vehicle 5810. In embodiments, the search results vary based on whether the user (e.g., the rider 58120) is a driver of the vehicle 5810 or a passenger in the vehicle 5810.

In embodiments, the vehicle 5810 comprises a system for automating at least one control parameter of the vehicle 5810. In embodiments, the vehicle 5810 is at least a semi-autonomous vehicle. In embodiments, the vehicle 5810 is automatically routed. In embodiments, the vehicle 5810 is a self-driving vehicle.

In embodiments, the rider interface 58208 comprises at least one of a touch screen, a virtual assistant, an entertainment system interface, a communication interface and a navigation interface.

In embodiments, the search results are ordered by the search result display ranking circuit 58210 so that results that are proximal to the configured route appear before other results.

In embodiments, search criteria used by the search result generating circuit 58209 are based on ranking parameters of a set of in-vehicle searches. In embodiments, the ranking parameters are observed in connection only with the set of in-vehicle searches. In embodiments, the search system 58207 adapts the search result generating circuit 58209 to favor search results that correlate to in-vehicle behaviors. In embodiments, the search results that correlate to in-vehicle behaviors are determined through comparison of rider behavior before and after conducting a search. In embodiments, the search system 58207 further comprises a machine learning circuit 58212 that facilitates training the search result generating circuit 58209 from a set of search results for a plurality of searchers and a set of search result generating parameters based on an in-vehicle rider behavior model.

An aspect provided herein includes an in-vehicle network search system 58207 of a vehicle 5810, the search system 58207 comprising: a rider interface 58208 through which the rider 58120 of the vehicle 5810 is enabled to engage with the search system 58207; a search result generating circuit 58209 that varies search results based on whether the user (e.g., the rider 58120) is a driver of the vehicle or a passenger in the vehicle; and a search result display ranking circuit 58210 that orders the search results based on a relevance of a location component of the search results with a configured route of the vehicle 5810.

In embodiments, the vehicle 5810 comprises a system for automating at least one control parameter of the vehicle 5810. In embodiments, the vehicle 5810 is at least a semi-autonomous vehicle. In embodiments, the vehicle 5810 is automatically routed. In embodiments, the vehicle 5810 is a self-driving vehicle.

In embodiments, the rider interface 58208 comprises at least one of a touch screen, a virtual assistant, an entertainment system interface, a communication interface and a navigation interface.

In embodiments, the search results are ordered by the search result display ranking circuit 58210 so that results that are proximal to the configured route appear before other results. In embodiments, search criteria used by the search result generating circuit 58209 are based on ranking parameters of a set of in-vehicle searches. In embodiments, the ranking parameters are observed in connection only with the set of in-vehicle searches.

In embodiments, the search system 58204 adapts the search result generating circuit 58209 to favor search results that correlate to in-vehicle behaviors. In embodiments, the search results that correlate to in-vehicle behaviors are determined through comparison of rider behavior before and after conducting a search. In embodiments, the search system 58207, further comprises a machine learning circuit 58212 that facilitates training the search result generating circuit 58209 from a set of search results for a plurality of searchers and a set of search result generating parameters based on an in-vehicle rider behavior model.

In embodiments, provided herein is a system for transportation having a hybrid neural network for optimizing a power train of a vehicle, wherein at least two parts of the hybrid neural network optimize distinct parts of the power train. In embodiments, provided herein is a system for transportation having a hybrid neural network for optimizing a power train of a vehicle, wherein at least two parts of the hybrid neural network optimize distinct parts of the power train and having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle. In embodiments, provided herein is a system for transportation having a hybrid neural network for optimizing a power train of a vehicle, wherein at least two parts of the hybrid neural network optimize distinct parts of the power train and having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter. In embodiments, provided herein is a system for transportation having a hybrid neural network for optimizing a power train of a vehicle, wherein at least two parts of the hybrid neural network optimize distinct parts of the power train and having an artificial intelligence system that uses at least one genetic algorithm to explore a set of possible vehicle operating states to determine at least one optimized operating state, wherein the genetic algorithm takes inputs relating to at least one vehicle performance parameter and at least one rider state. In embodiments, provided herein is a system for transportation having a hybrid neural network for optimizing a power train of a vehicle, wherein at least two parts of the hybrid neural network optimize distinct parts of the power train and having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission. In embodiments, provided herein is a system for transportation having a hybrid neural network for optimizing a power train of a vehicle, wherein at least two parts of the hybrid neural network optimize distinct parts of the power train and having a hybrid neural network where one neural network type is used for classifying a type of object in the surroundings of the vehicle and another neural network type is used for routing the vehicle. In embodiments, provided herein is a system for transportation having a hybrid neural network for optimizing a power train of a vehicle, wherein at least two parts of the hybrid neural network optimize distinct parts of the power train and having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid neural network for optimizing a power train of a vehicle, wherein at least two parts of the hybrid neural network optimize distinct parts of the power train and having an artificial intelligence system that simultaneously optimizes vehicle routing based on traffic and a road profile. In embodiments, provided herein is a system for transportation having a hybrid neural network for optimizing a power train of a vehicle, wherein at least two parts of the hybrid neural network optimize distinct parts of the power train and having a hybrid neural network where one neural network is used to optimize a route based on traffic and another neural network is used to optimize energy consumption based on a road profile of a route. In embodiments, provided herein is a system for transportation having a hybrid neural network for optimizing a power train of a vehicle, wherein at least two parts of the hybrid neural network optimize distinct parts of the power train and having a cognitive system for routing at least one vehicle within a set of peers based on a goal determined by automatically facilitating collaboration among a designated set of peers. In embodiments, provided herein is a system for transportation having a hybrid neural network for optimizing a power train of a vehicle, wherein at least two parts of the hybrid neural network optimize distinct parts of the power train and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network for optimizing a power train of a vehicle, wherein at least two parts of the hybrid neural network optimize distinct parts of the power train and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network for optimizing a power train of a vehicle, wherein at least two parts of the hybrid neural network optimize distinct parts of the power train and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network for optimizing a power train of a vehicle, wherein at least two parts of the hybrid neural network optimize distinct parts of the power train and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network for optimizing a power train of a vehicle, wherein at least two parts of the hybrid neural network optimize distinct parts of the power train and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network for optimizing a power train of a vehicle, wherein at least two parts of the hybrid neural network optimize distinct parts of the power train and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a neural network to predict a transportation need of at least one individual. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a neural network to predict an emerging transportation need for a group of individuals. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a neural network to predict an emerging condition relevant to a transportation plan of at least one individual. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a neural network to predict traffic congestion relating to a route for a vehicle. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network for optimizing a power train of a vehicle, wherein at least two parts of the hybrid neural network optimize distinct parts of the power train and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network for optimizing a power train of a vehicle, wherein at least two parts of the hybrid neural network optimize distinct parts of the power train and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having a two-person automobile seating system with dual, lay-flat seats that are configured to move between a flat configuration to facilitate sleep and a seated configuration to facilitate waking activity. In embodiments, provided herein is a system for transportation having a hybrid neural network for optimizing a power train of a vehicle, wherein at least two parts of the hybrid neural network optimize distinct parts of the power train and having an entertainment system configured to provide entertainment to an automobile rider while maintaining the rider's orientation to the environment of the vehicle. In embodiments, provided herein is a system for transportation having a hybrid neural network for optimizing a power train of a vehicle, wherein at least two parts of the hybrid neural network optimize distinct parts of the power train and having an automobile seating system with at least one rear-facing lay-flat seat that is configured to move between a flat configuration and an upright configuration. In embodiments, provided herein is a system for transportation having a hybrid neural network for optimizing a power train of a vehicle, wherein at least two parts of the hybrid neural network optimize distinct parts of the power train and having an automobile seating system with at least one rear-facing seat that is configured with at least one visual orientation system to maintain a rider's orientation to the surrounding environment. In embodiments, provided herein is a system for transportation having a hybrid neural network for optimizing a power train of a vehicle, wherein at least two parts of the hybrid neural network optimize distinct parts of the power train and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network for optimizing a power train of a vehicle, wherein at least two parts of the hybrid neural network optimize distinct parts of the power train and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network for optimizing a power train of a vehicle, wherein at least two parts of the hybrid neural network optimize distinct parts of the power train and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network for optimizing a power train of a vehicle, wherein at least two parts of the hybrid neural network optimize distinct parts of the power train and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network for optimizing a power train of a vehicle, wherein at least two parts of the hybrid neural network optimize distinct parts of the power train and having an artificial intelligence system for processing an input from at least one sensor to determine a comfort state and optimizing at least one configuration parameter of the seat to improve the rider's comfort. In embodiments, provided herein is a system for transportation having a hybrid neural network for optimizing a power train of a vehicle, wherein at least two parts of the hybrid neural network optimize distinct parts of the power train and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network for optimizing a power train of a vehicle, wherein at least two parts of the hybrid neural network optimize distinct parts of the power train and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network for optimizing a power train of a vehicle, wherein at least two parts of the hybrid neural network optimize distinct parts of the power train and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing a power train of a vehicle, wherein at least two parts of the hybrid neural network optimize distinct parts of the power train and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network for optimizing a power train of a vehicle, wherein at least two parts of the hybrid neural network optimize distinct parts of the power train and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network for optimizing a power train of a vehicle, wherein at least two parts of the hybrid neural network optimize distinct parts of the power train and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network for optimizing a power train of a vehicle, wherein at least two parts of the hybrid neural network optimize distinct parts of the power train and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network for optimizing a power train of a vehicle, wherein at least two parts of the hybrid neural network optimize distinct parts of the power train and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing a power train of a vehicle, wherein at least two parts of the hybrid neural network optimize distinct parts of the power train and having a self-driving motorcycle. In embodiments, provided herein is a system for transportation having a hybrid neural network for optimizing a power train of a vehicle, wherein at least two parts of the hybrid neural network optimize distinct parts of the power train and having a motorcycle helmet that is configured to provide an augmented reality experience based on registration of the location and orientation of the wearer in an environment. In embodiments, provided herein is a system for transportation having a hybrid neural network for optimizing a power train of a vehicle, wherein at least two parts of the hybrid neural network optimize distinct parts of the power train and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network for optimizing a power train of a vehicle, wherein at least two parts of the hybrid neural network optimize distinct parts of the power train and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network for optimizing a power train of a vehicle, wherein at least two parts of the hybrid neural network optimize distinct parts of the power train and having a motorcycle helmet configured with a data processor and configured to communicate with a self-driving motorcycle for coordinated control of the helmet and the motorcycle. In embodiments, provided herein is a system for transportation having a hybrid neural network for optimizing a power train of a vehicle, wherein at least two parts of the hybrid neural network optimize distinct parts of the power train and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network for optimizing a power train of a vehicle, wherein at least two parts of the hybrid neural network optimize distinct parts of the power train and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network for optimizing a power train of a vehicle, wherein at least two parts of the hybrid neural network optimize distinct parts of the power train and having a cognitive radio system for managing peer-to-peer communications within a mobile ad hoc network of self-driving vehicles. In embodiments, provided herein is a system for transportation having a hybrid neural network for optimizing a power train of a vehicle, wherein at least two parts of the hybrid neural network optimize distinct parts of the power train and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network for optimizing a power train of a vehicle, wherein at least two parts of the hybrid neural network optimize distinct parts of the power train and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network for optimizing a power train of a vehicle, wherein at least two parts of the hybrid neural network optimize distinct parts of the power train and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network for optimizing a power train of a vehicle, wherein at least two parts of the hybrid neural network optimize distinct parts of the power train and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network for optimizing a power train of a vehicle, wherein at least two parts of the hybrid neural network optimize distinct parts of the power train and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network for optimizing a power train of a vehicle, wherein at least two parts of the hybrid neural network optimize distinct parts of the power train and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network for optimizing a power train of a vehicle, wherein at least two parts of the hybrid neural network optimize distinct parts of the power train and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network for optimizing a power train of a vehicle, wherein at least two parts of the hybrid neural network optimize distinct parts of the power train and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan based on inputs relating to a self-driving vehicle. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network for optimizing a power train of a vehicle, wherein at least two parts of the hybrid neural network optimize distinct parts of the power train and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network for optimizing a power train of a vehicle, wherein at least two parts of the hybrid neural network optimize distinct parts of the power train and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for optimizing a power train of a vehicle, wherein at least two parts of the hybrid neural network optimize distinct parts of the power train and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for optimizing a power train of a vehicle, wherein at least two parts of the hybrid neural network optimize distinct parts of the power train and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for optimizing a power train of a vehicle, wherein at least two parts of the hybrid neural network optimize distinct parts of the power train and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for optimizing a power train of a vehicle, wherein at least two parts of the hybrid neural network optimize distinct parts of the power train and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for optimizing a power train of a vehicle, wherein at least two parts of the hybrid neural network optimize distinct parts of the power train and having an artificial intelligence system that automatically randomizes a parameter of an in-vehicle experience in order to improve a user state that benefits from variation. In embodiments, provided herein is a system for transportation having a hybrid neural network for optimizing a power train of a vehicle, wherein at least two parts of the hybrid neural network optimize distinct parts of the power train and having a system for taking an indicator of a hormonal system level of a user and automatically varying a user experience in the vehicle to promote a healthy hormonal state. In embodiments, provided herein is a system for transportation having a hybrid neural network for optimizing a power train of a vehicle, wherein at least two parts of the hybrid neural network optimize distinct parts of the power train and having a system for taking an indicator of a hormonal system level of a user and automatically varying a user experience in the vehicle to promote a hormonal state that promotes safety. In embodiments, provided herein is a system for transportation having a hybrid neural network for optimizing a power train of a vehicle, wherein at least two parts of the hybrid neural network optimize distinct parts of the power train and having a dietary control system wherein at least one of a food or a beverage is made available under control of an automated control system. In embodiments, provided herein is a system for transportation having a hybrid neural network for optimizing a power train of a vehicle, wherein at least two parts of the hybrid neural network optimize distinct parts of the power train and having an automated restocking system for an in-vehicle dietary system. In embodiments, provided herein is a system for transportation having a hybrid neural network for optimizing a power train of a vehicle, wherein at least two parts of the hybrid neural network optimize distinct parts of the power train and having a system for optimizing at least one of a vehicle parameter and a user experience parameter to provide a margin of safety. In embodiments, provided herein is a system for transportation having a hybrid neural network for optimizing a power train of a vehicle, wherein at least two parts of the hybrid neural network optimize distinct parts of the power train and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for optimizing a power train of a vehicle, wherein at least two parts of the hybrid neural network optimize distinct parts of the power train and having an expert system for allocating rewards across one or more different types of objectives within a transportation system. In embodiments, provided herein is a system for transportation having a hybrid neural network for optimizing a power train of a vehicle, wherein at least two parts of the hybrid neural network optimize distinct parts of the power train and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for optimizing a power train of a vehicle, wherein at least two parts of the hybrid neural network optimize distinct parts of the power train and having a search system that is configured to provide network search results for in-vehicle searchers.

In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system that uses at least one genetic algorithm to explore a set of possible vehicle operating states to determine at least one optimized operating state, wherein the genetic algorithm takes inputs relating to at least one vehicle performance parameter and at least one rider state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network where one neural network type is used for classifying a type of object in the surroundings of the vehicle and another network type is used for routing the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system that simultaneously optimizes vehicle routing based on traffic and a road profile. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network where one neural network is used to optimize a route based on traffic and another neural network is used to optimize energy consumption based on a road profile of a route. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for routing at least one vehicle within a set of peers based on a goal determined by automatically facilitating collaboration among a designated set of peers. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a neural network to predict a transportation need of at least one individual. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a neural network to predict an emerging transportation need for a group of individuals. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a neural network to predict an emerging condition relevant to a transportation plan of at least one individual. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a neural network to predict traffic congestion relating to a route for a vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a two-person automobile seating system with dual, lay-flat seats that are configured to move between a flat configuration to facilitate sleep and a seated configuration to facilitate waking activity. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an entertainment system configured to provide entertainment to an automobile rider while maintaining the rider's orientation to the environment of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an automobile seating system with at least one rear-facing lay-flat seat that is configured to move between a flat configuration and an upright configuration. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an automobile seating system with at least one rear-facing seat that is configured with at least one visual orientation system to maintain a rider's orientation to the surrounding environment. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing an input from at least one sensor to determine a comfort state and optimizing at least one configuration parameter of the seat to improve the rider's comfort. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a self-driving motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet that is configured to provide an augmented reality experience based on registration of the location and orientation of the wearer in an environment. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet configured with a data processor and configured to communicate with a self-driving motorcycle for coordinated control of the helmet and the motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive radio system for managing peer-to-peer communications within a mobile ad hoc network of self-driving vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan based on inputs relating to a self-driving vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an artificial intelligence system that automatically randomizes a parameter of an in-vehicle experience in order to improve a user state that benefits from variation. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a system for taking an indicator of a hormonal system level of a user and automatically varying a user experience in the vehicle to promote a healthy hormonal state. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a system for taking an indicator of a hormonal system level of a user and automatically varying a user experience in the vehicle to promote a hormonal state that promotes safety. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a dietary control system wherein at least one of a food or a beverage is made available under control of an automated control system. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an automated restocking system for an in-vehicle dietary system. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a system for optimizing at least one of a vehicle parameter and a user experience parameter to provide a margin of safety. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an expert system for allocating rewards across one or more different types of objectives within a transportation system. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for optimizing the power train and suspension of a vehicle, wherein at least one part of the neural network optimizes at least one parameter of the power train of the vehicle and at least one part of the neural network optimizes at least one parameter of the suspension of the vehicle and having a search system that is configured to provide network search results for in-vehicle searchers.

In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system that uses at least one genetic algorithm to explore a set of possible vehicle operating states to determine at least one optimized operating state, wherein the genetic algorithm takes inputs relating to at least one vehicle performance parameter and at least one rider state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network where one neural network type is used for classifying a type of object in the surroundings of the vehicle and another neural network type is used for routing the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system that simultaneously optimizes vehicle routing based on traffic and a road profile. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network where one neural network is used to optimize a route based on traffic and another neural network is used to optimize energy consumption based on a road profile of a route. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for routing at least one vehicle within a set of peers based on a goal determined by automatically facilitating collaboration among a designated set of peers. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a neural network to predict a transportation need of at least one individual. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a neural network to predict an emerging transportation need for a group of individuals. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a neural network to predict an emerging condition relevant to a transportation plan of at least one individual. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a neural network to predict traffic congestion relating to a route for a vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a hybrid neural network to optimize an operating state of a transportation system based on processing the social data sources with the hybrid neural network. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a hybrid neural network to optimize an operating state of a vehicle based on processing the social data sources with the hybrid neural network. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a two-person automobile seating system with dual, lay-flat seats that are configured to move between a flat configuration to facilitate sleep and a seated configuration to facilitate waking activity. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an entertainment system configured to provide entertainment to an automobile rider while maintaining the rider's orientation to the environment of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an automobile seating system with at least one rear-facing lay-flat seat that is configured to move between a flat configuration and an upright configuration. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an automobile seating system with at least one rear-facing seat that is configured with at least one visual orientation system to maintain a rider's orientation to the surrounding environment. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing a voice of a rider in a vehicle to determine an emotional state and optimizing at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing an input from at least one sensor to determine a comfort state and optimizing at least one configuration parameter of the seat to improve the rider's comfort. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a helmet configured for use with a self-driving vehicle, wherein the helmet is configured to provide an augmented reality experience based on registration of the location and orientation of the self-driving vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a self-driving motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet that is configured to provide an augmented reality experience based on registration of the location and orientation of the wearer in an environment. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet configured with a data processor and configured to communicate with a self-driving motorcycle for coordinated control of the helmet and the motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive radio system for managing peer-to-peer communications within a mobile ad hoc network of self-driving vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan based on inputs relating to a self-driving vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an artificial intelligence system that automatically randomizes a parameter of an in-vehicle experience in order to improve a user state that benefits from variation. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a system for taking an indicator of a hormonal system level of a user and automatically varying a user experience in the vehicle to promote a healthy hormonal state. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a system for taking an indicator of a hormonal system level of a user and automatically varying a user experience in the vehicle to promote a hormonal state that promotes safety. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a dietary control system wherein at least one of a food or a beverage is made available under control of an automated control system. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an automated restocking system for an in-vehicle dietary system. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a system for optimizing at least one of a vehicle parameter and a user experience parameter to provide a margin of safety. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an interface by which a set of expert systems may be configured to provide respective outputs for managing at least one of a set of vehicle parameters, a set of fleet parameters and a set of user experience parameters. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an expert system for allocating rewards across one or more different types of objectives within a transportation system. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid cognitive system for optimizing the power train and suspension of a vehicle, wherein at least one part of the cognitive system optimizes at least one parameter of the power train of the vehicle based on a performance goal and at least one part of the neural network optimizes at least one parameter of the suspension of the vehicle based on a rider comfort parameter and having a search system that is configured to provide network search results for in-vehicle searchers.

In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network where one neural network type is used for classifying a type of object in the surroundings of the vehicle and another neural network type is used for routing the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network where one neural network is used to optimize production based on at least one market feedback factor and another neural network is used to optimize scheduling of at least one robotic manufacturing component for a vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system that simultaneously optimizes vehicle routing based on traffic and a road profile. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network where one neural network is used to optimize a route based on traffic and another neural network is used to optimize energy consumption based on a road profile of a route. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for routing at least one vehicle within a set of peers based on a goal determined by automatically facilitating collaboration among a designated set of peers. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for managing the offering and/or fulfillment of rewards to riders of vehicles by a plurality of merchants, wherein a reward is earned by a rider undertaking an action while in the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a neural network to predict a transportation need of at least one individual. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a neural network to predict an emerging transportation need for a group of individuals. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a neural network to predict an emerging condition relevant to a transportation plan of at least one individual. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a neural network to predict traffic congestion relating to a route for a vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a hybrid neural network to optimize an operating state of a transportation system based on processing the social data sources with the hybrid neural network. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a hybrid neural network to optimize an operating state of a vehicle based on processing the social data sources with the hybrid neural network. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a data processing system for taking data from a plurality of social data sources and using a hybrid neural network to optimize satisfaction of at least one rider in a vehicle based on processing the social data sources with the hybrid neural network. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing a sensor input about a rider of a vehicle to determine an emotional state and optimizing at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a two-person automobile seating system with dual, lay-flat seats that are configured to move between a flat configuration to facilitate sleep and a seated configuration to facilitate waking activity. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an entertainment system configured to provide entertainment to an automobile rider while maintaining the rider's orientation to the environment of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an automobile seating system with at least one rear-facing lay-flat seat that is configured to move between a flat configuration and an upright configuration. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an automobile seating system with at least one rear-facing seat that is configured with at least one visual orientation system to maintain a rider's orientation to the surrounding environment. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing a voice of a rider in a vehicle to determine an emotional state and optimizing at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing an input from at least one sensor to determine a comfort state and optimizing at least one configuration parameter of the seat to improve the rider's comfort. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a self-driving motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet that is configured to provide an augmented reality experience based on registration of the location and orientation of the wearer in an environment. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet configured with a data processor and configured to communicate with a self-driving motorcycle for coordinated control of the helmet and the motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive radio system for managing peer-to-peer communications within a mobile ad hoc network of self-driving vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan based on inputs relating to a self-driving vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an artificial intelligence system that automatically randomizes a parameter of an in-vehicle experience in order to improve a user state that benefits from variation. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a system for taking an indicator of a hormonal system level of a user and automatically varying a user experience in the vehicle to promote a healthy hormonal state. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a system for taking an indicator of a hormonal system level of a user and automatically varying a user experience in the vehicle to promote a hormonal state that promotes safety. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a dietary control system wherein at least one of a food or a beverage is made available under control of an automated control system. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an automated restocking system for an in-vehicle dietary system. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a system for optimizing at least one of a vehicle parameter and a user experience parameter to provide a margin of safety. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an expert system for allocating rewards across one or more different types of objectives within a transportation system. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system that uses at least one genetic algorithm to explore a set of possible vehicle operating states to determine at least one optimized operating state, wherein the genetic algorithm takes inputs relating to at least one vehicle performance parameter and at least one rider state and having a search system that is configured to provide network search results for in-vehicle searchers.

In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network where one neural network type is used for classifying a type of object in the surroundings of the vehicle and another neural network type is used for routing the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system that simultaneously optimizes vehicle routing based on traffic and a road profile. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network where one neural network is used to optimize a route based on traffic and another neural network is used to optimize energy consumption based on a road profile of a route. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for routing at least one vehicle within a set of peers based on a goal determined by automatically facilitating collaboration among a designated set of peers. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a neural network to predict a transportation need of at least one individual. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a neural network to predict an emerging transportation need for a group of individuals. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a neural network to predict an emerging condition relevant to a transportation plan of at least one individual. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a neural network to predict traffic congestion relating to a route for a vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a two-person automobile seating system with dual, lay-flat seats that are configured to move between a flat configuration to facilitate sleep and a seated configuration to facilitate waking activity. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an entertainment system configured to provide entertainment to an automobile rider while maintaining the rider's orientation to the environment of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an automobile seating system with at least one rear-facing lay-flat seat that is configured to move between a flat configuration and an upright configuration. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an automobile seating system with at least one rear-facing seat that is configured with at least one visual orientation system to maintain a rider's orientation to the surrounding environment. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing an input from at least one sensor to determine a comfort state and optimizing at least one configuration parameter of the seat to improve the rider's comfort. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a self-driving motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet that is configured to provide an augmented reality experience based on registration of the location and orientation of the wearer in an environment. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet configured with a data processor and configured to communicate with a self-driving motorcycle for coordinated control of the helmet and the motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive radio system for managing peer-to-peer communications within a mobile ad hoc network of self-driving vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan based on inputs relating to a self-driving vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an artificial intelligence system that automatically randomizes a parameter of an in-vehicle experience in order to improve a user state that benefits from variation. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a system for taking an indicator of a hormonal system level of a user and automatically varying a user experience in the vehicle to promote a healthy hormonal state. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a system for taking an indicator of a hormonal system level of a user and automatically varying a user experience in the vehicle to promote a hormonal state that promotes safety. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a dietary control system wherein at least one of a food or a beverage is made available under control of an automated control system. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an automated restocking system for an in-vehicle dietary system. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a system for optimizing at least one of a vehicle parameter and a user experience parameter to provide a margin of safety. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an expert system for allocating rewards across one or more different types of objectives within a transportation system. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for optimizing the operating state of a continuously variable power train of a self-driving vehicle wherein at least one part of the hybrid neural network operates to classify a state of the self-driving vehicle and another part of the hybrid neural network operates to optimize at least one operating parameter of the transmission and having a search system that is configured to provide network search results for in-vehicle searchers.

In embodiments, provided herein is a system for transportation having a hybrid neural network where one neural network type is used for classifying a type of object in the surroundings of the vehicle and another neural network type is used for routing the vehicle. In embodiments, provided herein is a system for transportation having a hybrid neural network where one neural network type is used for classifying a type of object in the surroundings of the vehicle and another neural network type is used for routing the vehicle and having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid neural network where one neural network type is used for classifying a type of object in the surroundings of the vehicle and another neural network type is used for routing the vehicle and having an artificial intelligence system that simultaneously optimizes vehicle routing based on traffic and a road profile. In embodiments, provided herein is a system for transportation having a hybrid neural network where one neural network type is used for classifying a type of object in the surroundings of the vehicle and another neural network type is used for routing the vehicle and having a hybrid neural network where one neural network is used to optimize a route based on traffic and another neural network is used to optimize energy consumption based on a road profile of a route. In embodiments, provided herein is a system for transportation having a hybrid neural network where one neural network type is used for classifying a type of object in the surroundings of the vehicle and another neural network type is used for routing the vehicle and having a cognitive system for routing at least one vehicle within a set of peers based on a goal determined by automatically facilitating collaboration among a designated set of peers. In embodiments, provided herein is a system for transportation having a hybrid neural network where one neural network type is used for classifying a type of object in the surroundings of the vehicle and another neural network type is used for routing the vehicle and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network where one neural network type is used for classifying a type of object in the surroundings of the vehicle and another neural network type is used for routing the vehicle and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network where one neural network type is used for classifying a type of object in the surroundings of the vehicle and another neural network type is used for routing the vehicle and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network where one neural network type is used for classifying a type of object in the surroundings of the vehicle and another neural network type is used for routing the vehicle and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network where one neural network type is used for classifying a type of object in the surroundings of the vehicle and another neural network type is used for routing the vehicle and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network where one neural network type is used for classifying a type of object in the surroundings of the vehicle and another neural network type is used for routing the vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a neural network to predict a transportation need of at least one individual. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a neural network to predict an emerging transportation need for a group of individuals. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a neural network to predict an emerging condition relevant to a transportation plan of at least one individual. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a neural network to predict traffic congestion relating to a route for a vehicle. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network where one neural network type is used for classifying a type of object in the surroundings of the vehicle and another neural network type is used for routing the vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network where one neural network type is used for classifying a type of object in the surroundings of the vehicle and another neural network type is used for routing the vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having a two-person automobile seating system with dual, lay-flat seats that are configured to move between a flat configuration to facilitate sleep and a seated configuration to facilitate waking activity. In embodiments, provided herein is a system for transportation having a hybrid neural network where one neural network type is used for classifying a type of object in the surroundings of the vehicle and another neural network type is used for routing the vehicle and having an entertainment system configured to provide entertainment to an automobile rider while maintaining the rider's orientation to the environment of the vehicle. In embodiments, provided herein is a system for transportation having a hybrid neural network where one neural network type is used for classifying a type of object in the surroundings of the vehicle and another neural network type is used for routing the vehicle and having an automobile seating system with at least one rear-facing lay-flat seat that is configured to move between a flat configuration and an upright configuration. In embodiments, provided herein is a system for transportation having a hybrid neural network where one neural network type is used for classifying a type of object in the surroundings of the vehicle and another neural network type is used for routing the vehicle and having an automobile seating system with at least one rear-facing seat that is configured with at least one visual orientation system to maintain a rider's orientation to the surrounding environment. In embodiments, provided herein is a system for transportation having a hybrid neural network where one neural network type is used for classifying a type of object in the surroundings of the vehicle and another neural network type is used for routing the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network where one neural network type is used for classifying a type of object in the surroundings of the vehicle and another neural network type is used for routing the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network where one neural network type is used for classifying a type of object in the surroundings of the vehicle and another neural network type is used for routing the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network where one neural network type is used for classifying a type of object in the surroundings of the vehicle and another neural network type is used for routing the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network where one neural network type is used for classifying a type of object in the surroundings of the vehicle and another neural network type is used for routing the vehicle and having an artificial intelligence system for processing an input from at least one sensor to determine a comfort state and optimizing at least one configuration parameter of the seat to improve the rider's comfort. In embodiments, provided herein is a system for transportation having a hybrid neural network where one neural network type is used for classifying a type of object in the surroundings of the vehicle and another neural network type is used for routing the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network where one neural network type is used for classifying a type of object in the surroundings of the vehicle and another neural network type is used for routing the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network where one neural network type is used for classifying a type of object in the surroundings of the vehicle and another neural network type is used for routing the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network type is used for classifying a type of object in the surroundings of the vehicle and another neural network type is used for routing the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network where one neural network type is used for classifying a type of object in the surroundings of the vehicle and another neural network type is used for routing the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network where one neural network type is used for classifying a type of object in the surroundings of the vehicle and another neural network type is used for routing the vehicle and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network where one neural network type is used for classifying a type of object in the surroundings of the vehicle and another neural network type is used for routing the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network where one neural network type is used for classifying a type of object in the surroundings of the vehicle and another neural network type is used for routing the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network type is used for classifying a type of object in the surroundings of the vehicle and another neural network type is used for routing the vehicle and having a self-driving motorcycle. In embodiments, provided herein is a system for transportation having a hybrid neural network where one neural network type is used for classifying a type of object in the surroundings of the vehicle and another neural network type is used for routing the vehicle and having a motorcycle helmet that is configured to provide an augmented reality experience based on registration of the location and orientation of the wearer in an environment. In embodiments, provided herein is a system for transportation having a hybrid neural network where one neural network type is used for classifying a type of object in the surroundings of the vehicle and another neural network type is used for routing the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network where one neural network type is used for classifying a type of object in the surroundings of the vehicle and another neural network type is used for routing the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network where one neural network type is used for classifying a type of object in the surroundings of the vehicle and another neural network type is used for routing the vehicle and having a motorcycle helmet configured with a data processor and configured to communicate with a self-driving motorcycle for coordinated control of the helmet and the motorcycle. In embodiments, provided herein is a system for transportation having a hybrid neural network where one neural network type is used for classifying a type of object in the surroundings of the vehicle and another neural network type is used for routing the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network where one neural network type is used for classifying a type of object in the surroundings of the vehicle and another neural network type is used for routing the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network where one neural network type is used for classifying a type of object in the surroundings of the vehicle and another neural network type is used for routing the vehicle and having a cognitive radio system for managing peer-to-peer communications within a mobile ad hoc network of self-driving vehicles. In embodiments, provided herein is a system for transportation having a hybrid neural network where one neural network type is used for classifying a type of object in the surroundings of the vehicle and another neural network type is used for routing the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network where one neural network type is used for classifying a type of object in the surroundings of the vehicle and another neural network type is used for routing the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network where one neural network type is used for classifying a type of object in the surroundings of the vehicle and another neural network type is used for routing the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network where one neural network type is used for classifying a type of object in the surroundings of the vehicle and another neural network type is used for routing the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network where one neural network type is used for classifying a type of object in the surroundings of the vehicle and another neural network type is used for routing the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network where one neural network type is used for classifying a type of object in the surroundings of the vehicle and another neural network type is used for routing the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network where one neural network type is used for classifying a type of object in the surroundings of the vehicle and another neural network type is used for routing the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network where one neural network type is used for classifying a type of object in the surroundings of the vehicle and another neural network type is used for routing the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan based on inputs relating to a self-driving vehicle. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network where one neural network type is used for classifying a type of object in the surroundings of the vehicle and another neural network type is used for routing the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network where one neural network type is used for classifying a type of object in the surroundings of the vehicle and another neural network type is used for routing the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network where one neural network type is used for classifying a type of object in the surroundings of the vehicle and another neural network type is used for routing the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network where one neural network type is used for classifying a type of object in the surroundings of the vehicle and another neural network type is used for routing the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network where one neural network type is used for classifying a type of object in the surroundings of the vehicle and another neural network type is used for routing the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network where one neural network type is used for classifying a type of object in the surroundings of the vehicle and another neural network type is used for routing the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network where one neural network type is used for classifying a type of object in the surroundings of the vehicle and another neural network type is used for routing the vehicle and having an artificial intelligence system that automatically randomizes a parameter of an in-vehicle experience in order to improve a user state that benefits from variation. In embodiments, provided herein is a system for transportation having a hybrid neural network where one neural network type is used for classifying a type of object in the surroundings of the vehicle and another neural network type is used for routing the vehicle and having a system for taking an indicator of a hormonal system level of a user and automatically varying a user experience in the vehicle to promote a healthy hormonal state. In embodiments, provided herein is a system for transportation having a hybrid neural network where one neural network type is used for classifying a type of object in the surroundings of the vehicle and another neural network type is used for routing the vehicle and having a system for taking an indicator of a hormonal system level of a user and automatically varying a user experience in the vehicle to promote a hormonal state that promotes safety. In embodiments, provided herein is a system for transportation having a hybrid neural network where one neural network type is used for classifying a type of object in the surroundings of the vehicle and another neural network type is used for routing the vehicle and having a dietary control system wherein at least one of a food or a beverage is made available under control of an automated control system. In embodiments, provided herein is a system for transportation having a hybrid neural network where one neural network type is used for classifying a type of object in the surroundings of the vehicle and another neural network type is used for routing the vehicle and having an automated restocking system for an in-vehicle dietary system. In embodiments, provided herein is a system for transportation having a hybrid neural network where one neural network type is used for classifying a type of object in the surroundings of the vehicle and another neural network type is used for routing the vehicle and having a system for optimizing at least one of a vehicle parameter and a user experience parameter to provide a margin of safety. In embodiments, provided herein is a system for transportation having a hybrid neural network where one neural network type is used for classifying a type of object in the surroundings of the vehicle and another neural network type is used for routing the vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network where one neural network type is used for classifying a type of object in the surroundings of the vehicle and another neural network type is used for routing the vehicle and having an expert system for allocating rewards across one or more different types of objectives within a transportation system. In embodiments, provided herein is a system for transportation having a hybrid neural network where one neural network type is used for classifying a type of object in the surroundings of the vehicle and another neural network type is used for routing the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network where one neural network type is used for classifying a type of object in the surroundings of the vehicle and another neural network type is used for routing the vehicle and having a search system that is configured to provide network search results for in-vehicle searchers.

In embodiments, provided herein is a system for transportation having a hybrid neural network where one neural network is used to optimize production based on at least one market feedback factor and another neural network is used to optimize scheduling of at least one robotic manufacturing component for a vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system that simultaneously optimizes vehicle routing based on traffic and a road profile. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid neural network where one neural network is used to optimize a route based on traffic and another neural network is used to optimize energy consumption based on a road profile of a route. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for routing at least one vehicle within a set of peers based on a goal determined by automatically facilitating collaboration among a designated set of peers. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a neural network to predict a transportation need of at least one individual. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a neural network to predict an emerging transportation need for a group of individuals. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a neural network to predict an emerging condition relevant to a transportation plan of at least one individual. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a neural network to predict traffic congestion relating to a route for a vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network where one neural network is used to optimize production based on at least one market feedback factor and another neural network is used to optimize scheduling of at least one robotic manufacturing component for a vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having a two-person automobile seating system with dual, lay-flat seats that are configured to move between a flat configuration to facilitate sleep and a seated configuration to facilitate waking activity. In embodiments, provided herein is a system for transportation having a hybrid neural network where one neural network is used to optimize production based on at least one market feedback factor and another neural network is used to optimize scheduling of at least one robotic manufacturing component for a vehicle and having an entertainment system configured to provide entertainment to an automobile rider while maintaining the rider's orientation to the environment of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an automobile seating system with at least one rear-facing lay-flat seat that is configured to move between a flat configuration and an upright configuration. In embodiments, provided herein is a system for transportation having a hybrid neural network where one neural network is used to optimize production based on at least one market feedback factor and another neural network is used to optimize scheduling of at least one robotic manufacturing component for a vehicle and having an automobile seating system with at least one rear-facing seat that is configured with at least one visual orientation system to maintain a rider's orientation to the surrounding environment. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing an input from at least one sensor to determine a comfort state and optimizing at least one configuration parameter of the seat to improve the rider's comfort. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network where one neural network is used to optimize production based on at least one market feedback factor and another neural network is used to optimize scheduling of at least one robotic manufacturing component for a vehicle and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a self-driving motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet that is configured to provide an augmented reality experience based on registration of the location and orientation of the wearer in an environment. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet configured with a data processor and configured to communicate with a self-driving motorcycle for coordinated control of the helmet and the motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive radio system for managing peer-to-peer communications within a mobile ad hoc network of self-driving vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network where one neural network is used to optimize production based on at least one market feedback factor and another neural network is used to optimize scheduling of at least one robotic manufacturing component for a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan based on inputs relating to a self-driving vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network where one neural network is used to optimize production based on at least one market feedback factor and another neural network is used to optimize scheduling of at least one robotic manufacturing component for a vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network where one neural network is used to optimize production based on at least one market feedback factor and another neural network is used to optimize scheduling of at least one robotic manufacturing component for a vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network where one neural network is used to optimize production based on at least one market feedback factor and another neural network is used to optimize scheduling of at least one robotic manufacturing component for a vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network where one neural network is used to optimize production based on at least one market feedback factor and another neural network is used to optimize scheduling of at least one robotic manufacturing component for a vehicle and having an artificial intelligence system that automatically randomizes a parameter of an in-vehicle experience in order to improve a user state that benefits from variation. In embodiments, provided herein is a system for transportation having a hybrid neural network where one neural network is used to optimize production based on at least one market feedback factor and another neural network is used to optimize scheduling of at least one robotic manufacturing component for a vehicle and having a system for taking an indicator of a hormonal system level of a user and automatically varying a user experience in the vehicle to promote a healthy hormonal state. In embodiments, provided herein is a system for transportation having a hybrid neural network where one neural network is used to optimize production based on at least one market feedback factor and another neural network is used to optimize scheduling of at least one robotic manufacturing component for a vehicle and having a system for taking an indicator of a hormonal system level of a user and automatically varying a user experience in the vehicle to promote a hormonal state that promotes safety. In embodiments, provided herein is a system for transportation having a hybrid neural network where one neural network is used to optimize production based on at least one market feedback factor and another neural network is used to optimize scheduling of at least one robotic manufacturing component for a vehicle and having a dietary control system wherein at least one of a food or a beverage is made available under control of an automated control system. In embodiments, provided herein is a system for transportation having a hybrid neural network where one neural network is used to optimize production based on at least one market feedback factor and another neural network is used to optimize scheduling of at least one robotic manufacturing component for a vehicle and having an automated restocking system for an in-vehicle dietary system. In embodiments, provided herein is a system for transportation having a hybrid neural network where one neural network is used to optimize production based on at least one market feedback factor and another neural network is used to optimize scheduling of at least one robotic manufacturing component for a vehicle and having a system for optimizing at least one of a vehicle parameter and a user experience parameter to provide a margin of safety. In embodiments, provided herein is a system for transportation having a hybrid neural network where one neural network is used to optimize production based on at least one market feedback factor and another neural network is used to optimize scheduling of at least one robotic manufacturing component for a vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network where one neural network is used to optimize production based on at least one market feedback factor and another neural network is used to optimize scheduling of at least one robotic manufacturing component for a vehicle and having an expert system for allocating rewards across one or more different types of objectives within a transportation system. In embodiments, provided herein is a system for transportation having a hybrid neural network where one neural network is used to optimize production based on at least one market feedback factor and another neural network is used to optimize scheduling of at least one robotic manufacturing component for a vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network where one neural network is used to optimize production based on at least one market feedback factor and another neural network is used to optimize scheduling of at least one robotic manufacturing component for a vehicle and having a search system that is configured to provide network search results for in-vehicle searchers.

In embodiments, provided herein is a system for transportation having an artificial intelligence system that simultaneously optimizes vehicle routing based on traffic and a road profile. In embodiments, provided herein is a system for transportation having an artificial intelligence system that simultaneously optimizes vehicle routing based on traffic and a road profile and having a hybrid neural network where one neural network is used to optimize a route based on traffic and another neural network is used to optimize energy consumption based on a road profile of a route. In embodiments, provided herein is a system for transportation having an artificial intelligence system that simultaneously optimizes vehicle routing based on traffic and a road profile and having a cognitive system for routing at least one vehicle within a set of peers based on a goal determined by automatically facilitating collaboration among a designated set of peers. In embodiments, provided herein is a system for transportation having an artificial intelligence system that simultaneously optimizes vehicle routing based on traffic and a road profile and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having an artificial intelligence system that simultaneously optimizes vehicle routing based on traffic and a road profile and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having an artificial intelligence system that simultaneously optimizes vehicle routing based on traffic and a road profile and having a cognitive system for managing the offering and/or fulfillment of rewards to riders of vehicles by a plurality of merchants, wherein a reward is earned by a rider undertaking an action while in the vehicle. In embodiments, provided herein is a system for transportation having an artificial intelligence system that simultaneously optimizes vehicle routing based on traffic and a road profile and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having an artificial intelligence system that simultaneously optimizes vehicle routing based on traffic and a road profile and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having an artificial intelligence system that simultaneously optimizes vehicle routing based on traffic and a road profile and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having an artificial intelligence system that simultaneously optimizes vehicle routing based on traffic and a road profile and having a data processing system for taking data from a plurality of social data sources and using a neural network to predict a transportation need of at least one individual. In embodiments, provided herein is a system for transportation having an artificial intelligence system that simultaneously optimizes vehicle routing based on traffic and a road profile and having a data processing system for taking data from a plurality of social data sources and using a neural network to predict an emerging transportation need for a group of individuals. In embodiments, provided herein is a system for transportation having an artificial intelligence system that simultaneously optimizes vehicle routing based on traffic and a road profile and having a data processing system for taking data from a plurality of social data sources and using a neural network to predict an emerging condition relevant to a transportation plan of at least one individual. In embodiments, provided herein is a system for transportation having an artificial intelligence system that simultaneously optimizes vehicle routing based on traffic and a road profile and having a data processing system for taking data from a plurality of social data sources and using a neural network to predict traffic congestion relating to a route for a vehicle. In embodiments, provided herein is a system for transportation having an artificial intelligence system that simultaneously optimizes vehicle routing based on traffic and a road profile and having a data processing system for taking data from a plurality of social data sources and using a hybrid neural network to optimize an operating state of a transportation system based on processing the social data sources with the hybrid neural network. In embodiments, provided herein is a system for transportation having an artificial intelligence system that simultaneously optimizes vehicle routing based on traffic and a road profile and having a data processing system for taking data from a plurality of social data sources and using a hybrid neural network to optimize an operating state of a vehicle based on processing the social data sources with the hybrid neural network. In embodiments, provided herein is a system for transportation having an artificial intelligence system that simultaneously optimizes vehicle routing based on traffic and a road profile and having a data processing system for taking data from a plurality of social data sources and using a hybrid neural network to optimize satisfaction of at least one rider in a vehicle based on processing the social data sources with the hybrid neural network. In embodiments, provided herein is a system for transportation having an artificial intelligence system that simultaneously optimizes vehicle routing based on traffic and a road profile and having an artificial intelligence system for processing a sensor input about a rider of a vehicle to determine an emotional state and optimizing at least one operating parameter of the vehicle to improve the rider's emotional state. In embodiments, provided herein is a system for transportation having an artificial intelligence system that simultaneously optimizes vehicle routing based on traffic and a road profile and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having an artificial intelligence system that simultaneously optimizes vehicle routing based on traffic and a road profile and having a two-person automobile seating system with dual, lay-flat seats that are configured to move between a flat configuration to facilitate sleep and a seated configuration to facilitate waking activity. In embodiments, provided herein is a system for transportation having an artificial intelligence system that simultaneously optimizes vehicle routing based on traffic and a road profile and having an entertainment system configured to provide entertainment to an automobile rider while maintaining the rider's orientation to the environment of the vehicle. In embodiments, provided herein is a system for transportation having an artificial intelligence system that simultaneously optimizes vehicle routing based on traffic and a road profile and having an automobile seating system with at least one rear-facing lay-flat seat that is configured to move between a flat configuration and an upright configuration. In embodiments, provided herein is a system for transportation having an artificial intelligence system that simultaneously optimizes vehicle routing based on traffic and a road profile and having an automobile seating system with at least one rear-facing seat that is configured with at least one visual orientation system to maintain a rider's orientation to the surrounding environment. In embodiments, provided herein is a system for transportation having an artificial intelligence system that simultaneously optimizes vehicle routing based on traffic and a road profile and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an artificial intelligence system that simultaneously optimizes vehicle routing based on traffic and a road profile and having an artificial intelligence system for processing a voice of a rider in a vehicle to determine an emotional state and optimizing at least one operating parameter of the vehicle to improve the rider's emotional state. In embodiments, provided herein is a system for transportation having an artificial intelligence system that simultaneously optimizes vehicle routing based on traffic and a road profile and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system that simultaneously optimizes vehicle routing based on traffic and a road profile and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system that simultaneously optimizes vehicle routing based on traffic and a road profile and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system that simultaneously optimizes vehicle routing based on traffic and a road profile and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system that simultaneously optimizes vehicle routing based on traffic and a road profile and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system that simultaneously optimizes vehicle routing based on traffic and a road profile and having an artificial intelligence system for processing an input from at least one sensor to determine a comfort state and optimizing at least one configuration parameter of the seat to improve the rider's comfort. In embodiments, provided herein is a system for transportation having an artificial intelligence system that simultaneously optimizes vehicle routing based on traffic and a road profile and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system that simultaneously optimizes vehicle routing based on traffic and a road profile and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system that simultaneously optimizes vehicle routing based on traffic and a road profile and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system that simultaneously optimizes vehicle routing based on traffic and a road profile and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system that simultaneously optimizes vehicle routing based on traffic and a road profile and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system that simultaneously optimizes vehicle routing based on traffic and a road profile and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system that simultaneously optimizes vehicle routing based on traffic and a road profile and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system that simultaneously optimizes vehicle routing based on traffic and a road profile and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system that simultaneously optimizes vehicle routing based on traffic and a road profile and having a self-driving motorcycle. In embodiments, provided herein is a system for transportation having an artificial intelligence system that simultaneously optimizes vehicle routing based on traffic and a road profile and having a motorcycle helmet that is configured to provide an augmented reality experience based on registration of the location and orientation of the wearer in an environment. In embodiments, provided herein is a system for transportation having an artificial intelligence system that simultaneously optimizes vehicle routing based on traffic and a road profile and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system that simultaneously optimizes vehicle routing based on traffic and a road profile and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system that simultaneously optimizes vehicle routing based on traffic and a road profile and having a motorcycle helmet configured with a data processor and configured to communicate with a self-driving motorcycle for coordinated control of the helmet and the motorcycle. In embodiments, provided herein is a system for transportation having an artificial intelligence system that simultaneously optimizes vehicle routing based on traffic and a road profile and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system that simultaneously optimizes vehicle routing based on traffic and a road profile and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system that simultaneously optimizes vehicle routing based on traffic and a road profile and having a cognitive radio system for managing peer-to-peer communications within a mobile ad hoc network of self-driving vehicles. In embodiments, provided herein is a system for transportation having an artificial intelligence system that simultaneously optimizes vehicle routing based on traffic and a road profile and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system that simultaneously optimizes vehicle routing based on traffic and a road profile and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system that simultaneously optimizes vehicle routing based on traffic and a road profile and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system that simultaneously optimizes vehicle routing based on traffic and a road profile and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system that simultaneously optimizes vehicle routing based on traffic and a road profile and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system that simultaneously optimizes vehicle routing based on traffic and a road profile and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system that simultaneously optimizes vehicle routing based on traffic and a road profile and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system that simultaneously optimizes vehicle routing based on traffic and a road profile and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system that simultaneously optimizes vehicle routing based on traffic and a road profile and having an artificial intelligence system for determining at least one parameter of a charging plan based on inputs relating to a self-driving vehicle. In embodiments, provided herein is a system for transportation having an artificial intelligence system that simultaneously optimizes vehicle routing based on traffic and a road profile and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system that simultaneously optimizes vehicle routing based on traffic and a road profile and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system that simultaneously optimizes vehicle routing based on traffic and a road profile and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system that simultaneously optimizes vehicle routing based on traffic and a road profile and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system that simultaneously optimizes vehicle routing based on traffic and a road profile and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system that simultaneously optimizes vehicle routing based on traffic and a road profile and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system that simultaneously optimizes vehicle routing based on traffic and a road profile and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system that simultaneously optimizes vehicle routing based on traffic and a road profile and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system that simultaneously optimizes vehicle routing based on traffic and a road profile and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system that simultaneously optimizes vehicle routing based on traffic and a road profile and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system that simultaneously optimizes vehicle routing based on traffic and a road profile and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system that simultaneously optimizes vehicle routing based on traffic and a road profile and having an artificial intelligence system that automatically randomizes a parameter of an in-vehicle experience in order to improve a user state that benefits from variation. In embodiments, provided herein is a system for transportation having an artificial intelligence system that simultaneously optimizes vehicle routing based on traffic and a road profile and having a system for taking an indicator of a hormonal system level of a user and automatically varying a user experience in the vehicle to promote a healthy hormonal state. In embodiments, provided herein is a system for transportation having an artificial intelligence system that simultaneously optimizes vehicle routing based on traffic and a road profile and having a system for taking an indicator of a hormonal system level of a user and automatically varying a user experience in the vehicle to promote a hormonal state that promotes safety. In embodiments, provided herein is a system for transportation having an artificial intelligence system that simultaneously optimizes vehicle routing based on traffic and a road profile and having a dietary control system wherein at least one of a food or a beverage is made available under control of an automated control system. In embodiments, provided herein is a system for transportation having an artificial intelligence system that simultaneously optimizes vehicle routing based on traffic and a road profile and having an automated restocking system for an in-vehicle dietary system. In embodiments, provided herein is a system for transportation having an artificial intelligence system that simultaneously optimizes vehicle routing based on traffic and a road profile and having a system for optimizing at least one of a vehicle parameter and a user experience parameter to provide a margin of safety. In embodiments, provided herein is a system for transportation having an artificial intelligence system that simultaneously optimizes vehicle routing based on traffic and a road profile and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system that simultaneously optimizes vehicle routing based on traffic and a road profile and having an expert system for allocating rewards across one or more different types of objectives within a transportation system. In embodiments, provided herein is a system for transportation having an artificial intelligence system that simultaneously optimizes vehicle routing based on traffic and a road profile and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system that simultaneously optimizes vehicle routing based on traffic and a road profile and having a search system that is configured to provide network search results for in-vehicle searchers.

In embodiments, provided herein is a system for transportation having a hybrid neural network where one neural network is used to optimize a route based on traffic and another neural network is used to optimize energy consumption based on a road profile of a route. In embodiments, provided herein is a system for transportation having a hybrid neural network where one neural network is used to optimize a route based on traffic and another neural network is used to optimize energy consumption based on a road profile of a route and having a cognitive system for routing at least one vehicle within a set of peers based on a goal determined by automatically facilitating collaboration among a designated set of peers. In embodiments, provided herein is a system for transportation having a hybrid neural network where one neural network is used to optimize a route based on traffic and another neural network is used to optimize energy consumption based on a road profile of a route and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a hybrid neural network where one neural network is used to optimize a route based on traffic and another neural network is used to optimize energy consumption based on a road profile of a route and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a hybrid neural network where one neural network is used to optimize a route based on traffic and another neural network is used to optimize energy consumption based on a road profile of a route and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a hybrid neural network where one neural network is used to optimize a route based on traffic and another neural network is used to optimize energy consumption based on a road profile of a route and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a hybrid neural network where one neural network is used to optimize a route based on traffic and another neural network is used to optimize energy consumption based on a road profile of a route and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a hybrid neural network where one neural network is used to optimize a route based on traffic and another neural network is used to optimize energy consumption based on a road profile of a route and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a neural network to predict a transportation need of at least one individual. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a neural network to predict an emerging transportation need for a group of individuals. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a neural network to predict an emerging condition relevant to a transportation plan of at least one individual. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a neural network to predict traffic congestion relating to a route for a vehicle. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a hybrid neural network to optimize an operating state of a transportation system based on processing the social data sources with the hybrid neural network. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a hybrid neural network to optimize an operating state of a vehicle based on processing the social data sources with the hybrid neural network. In embodiments, provided herein is a system for transportation having a hybrid neural network where one neural network is used to optimize a route based on traffic and another neural network is used to optimize energy consumption based on a road profile of a route and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a hybrid neural network where one neural network is used to optimize a route based on traffic and another neural network is used to optimize energy consumption based on a road profile of a route and having an artificial intelligence system for processing a sensor input about a rider of a vehicle to determine an emotional state and optimizing at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having a two-person automobile seating system with dual, lay-flat seats that are configured to move between a flat configuration to facilitate sleep and a seated configuration to facilitate waking activity. In embodiments, provided herein is a system for transportation having a hybrid neural network where one neural network is used to optimize a route based on traffic and another neural network is used to optimize energy consumption based on a road profile of a route and having an entertainment system configured to provide entertainment to an automobile rider while maintaining the rider's orientation to the environment of the vehicle. In embodiments, provided herein is a system for transportation having a hybrid neural network where one neural network is used to optimize a route based on traffic and another neural network is used to optimize energy consumption based on a road profile of a route and having an automobile seating system with at least one rear-facing lay-flat seat that is configured to move between a flat configuration and an upright configuration. In embodiments, provided herein is a system for transportation having a hybrid neural network where one neural network is used to optimize a route based on traffic and another neural network is used to optimize energy consumption based on a road profile of a route and having an automobile seating system with at least one rear-facing seat that is configured with at least one visual orientation system to maintain a rider's orientation to the surrounding environment. In embodiments, provided herein is a system for transportation having a hybrid neural network where one neural network is used to optimize a route based on traffic and another neural network is used to optimize energy consumption based on a road profile of a route and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network where one neural network is used to optimize a route based on traffic and another neural network is used to optimize energy consumption based on a road profile of a route and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network where one neural network is used to optimize a route based on traffic and another neural network is used to optimize energy consumption based on a road profile of a route and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network where one neural network is used to optimize a route based on traffic and another neural network is used to optimize energy consumption based on a road profile of a route and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network where one neural network is used to optimize a route based on traffic and another neural network is used to optimize energy consumption based on a road profile of a route and having an artificial intelligence system for processing an input from at least one sensor to determine a comfort state and optimizing at least one configuration parameter of the seat to improve the rider's comfort. In embodiments, provided herein is a system for transportation having a hybrid neural network where one neural network is used to optimize a route based on traffic and another neural network is used to optimize energy consumption based on a road profile of a route and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network where one neural network is used to optimize a route based on traffic and another neural network is used to optimize energy consumption based on a road profile of a route and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network where one neural network is used to optimize a route based on traffic and another neural network is used to optimize energy consumption based on a road profile of a route and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network is used to optimize a route based on traffic and another neural network is used to optimize energy consumption based on a road profile of a route and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network where one neural network is used to optimize a route based on traffic and another neural network is used to optimize energy consumption based on a road profile of a route and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network where one neural network is used to optimize a route based on traffic and another neural network is used to optimize energy consumption based on a road profile of a route and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network where one neural network is used to optimize a route based on traffic and another neural network is used to optimize energy consumption based on a road profile of a route and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network where one neural network is used to optimize a route based on traffic and another neural network is used to optimize energy consumption based on a road profile of a route and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network where one neural network is used to optimize a route based on traffic and another neural network is used to optimize energy consumption based on a road profile of a route and having a self-driving motorcycle. In embodiments, provided herein is a system for transportation having a hybrid neural network where one neural network is used to optimize a route based on traffic and another neural network is used to optimize energy consumption based on a road profile of a route and having a motorcycle helmet that is configured to provide an augmented reality experience based on registration of the location and orientation of the wearer in an environment. In embodiments, provided herein is a system for transportation having a hybrid neural network where one neural network is used to optimize a route based on traffic and another neural network is used to optimize energy consumption based on a road profile of a route and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network where one neural network is used to optimize a route based on traffic and another neural network is used to optimize energy consumption based on a road profile of a route and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network where one neural network is used to optimize a route based on traffic and another neural network is used to optimize energy consumption based on a road profile of a route and having a motorcycle helmet configured with a data processor and configured to communicate with a self-driving motorcycle for coordinated control of the helmet and the motorcycle. In embodiments, provided herein is a system for transportation having a hybrid neural network where one neural network is used to optimize a route based on traffic and another neural network is used to optimize energy consumption based on a road profile of a route and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network where one neural network is used to optimize a route based on traffic and another neural network is used to optimize energy consumption based on a road profile of a route and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network where one neural network is used to optimize a route based on traffic and another neural network is used to optimize energy consumption based on a road profile of a route and having a cognitive radio system for managing peer-to-peer communications within a mobile ad hoc network of self-driving vehicles. In embodiments, provided herein is a system for transportation having a hybrid neural network where one neural network is used to optimize a route based on traffic and another neural network is used to optimize energy consumption based on a road profile of a route and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network where one neural network is used to optimize a route based on traffic and another neural network is used to optimize energy consumption based on a road profile of a route and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network where one neural network is used to optimize a route based on traffic and another neural network is used to optimize energy consumption based on a road profile of a route and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network where one neural network is used to optimize a route based on traffic and another neural network is used to optimize energy consumption based on a road profile of a route and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network where one neural network is used to optimize a route based on traffic and another neural network is used to optimize energy consumption based on a road profile of a route and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network where one neural network is used to optimize a route based on traffic and another neural network is used to optimize energy consumption based on a road profile of a route and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network where one neural network is used to optimize a route based on traffic and another neural network is used to optimize energy consumption based on a road profile of a route and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network where one neural network is used to optimize a route based on traffic and another neural network is used to optimize energy consumption based on a road profile of a route and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan based on inputs relating to a self-driving vehicle. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network where one neural network is used to optimize a route based on traffic and another neural network is used to optimize energy consumption based on a road profile of a route and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network where one neural network is used to optimize a route based on traffic and another neural network is used to optimize energy consumption based on a road profile of a route and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network where one neural network is used to optimize a route based on traffic and another neural network is used to optimize energy consumption based on a road profile of a route and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network where one neural network is used to optimize a route based on traffic and another neural network is used to optimize energy consumption based on a road profile of a route and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network where one neural network is used to optimize a route based on traffic and another neural network is used to optimize energy consumption based on a road profile of a route and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network where one neural network is used to optimize a route based on traffic and another neural network is used to optimize energy consumption based on a road profile of a route and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network where one neural network is used to optimize a route based on traffic and another neural network is used to optimize energy consumption based on a road profile of a route and having an artificial intelligence system that automatically randomizes a parameter of an in-vehicle experience in order to improve a user state that benefits from variation. In embodiments, provided herein is a system for transportation having a hybrid neural network where one neural network is used to optimize a route based on traffic and another neural network is used to optimize energy consumption based on a road profile of a route and having a system for taking an indicator of a hormonal system level of a user and automatically varying a user experience in the vehicle to promote a healthy hormonal state. In embodiments, provided herein is a system for transportation having a hybrid neural network where one neural network is used to optimize a route based on traffic and another neural network is used to optimize energy consumption based on a road profile of a route and having a system for taking an indicator of a hormonal system level of a user and automatically varying a user experience in the vehicle to promote a hormonal state that promotes safety. In embodiments, provided herein is a system for transportation having a hybrid neural network where one neural network is used to optimize a route based on traffic and another neural network is used to optimize energy consumption based on a road profile of a route and having a dietary control system wherein at least one of a food or a beverage is made available under control of an automated control system. In embodiments, provided herein is a system for transportation having a hybrid neural network where one neural network is used to optimize a route based on traffic and another neural network is used to optimize energy consumption based on a road profile of a route and having an automated restocking system for an in-vehicle dietary system. In embodiments, provided herein is a system for transportation having a hybrid neural network where one neural network is used to optimize a route based on traffic and another neural network is used to optimize energy consumption based on a road profile of a route and having a system for optimizing at least one of a vehicle parameter and a user experience parameter to provide a margin of safety. In embodiments, provided herein is a system for transportation having a hybrid neural network where one neural network is used to optimize a route based on traffic and another neural network is used to optimize energy consumption based on a road profile of a route and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network where one neural network is used to optimize a route based on traffic and another neural network is used to optimize energy consumption based on a road profile of a route and having an expert system for allocating rewards across one or more different types of objectives within a transportation system. In embodiments, provided herein is a system for transportation having a hybrid neural network where one neural network is used to optimize a route based on traffic and another neural network is used to optimize energy consumption based on a road profile of a route and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network where one neural network is used to optimize a route based on traffic and another neural network is used to optimize energy consumption based on a road profile of a route and having a search system that is configured to provide network search results for in-vehicle searchers.

In embodiments, provided herein is a system for transportation having a cognitive system for routing at least one vehicle within a set of peers based on a goal determined by automatically facilitating collaboration among a designated set of peers. In embodiments, provided herein is a system for transportation having a cognitive system for routing at least one vehicle within a set of peers based on a goal determined by automatically facilitating collaboration among a designated set of peers and having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a cognitive system for routing at least one vehicle within a set of peers based on a goal determined by automatically facilitating collaboration among a designated set of peers and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a cognitive system for routing at least one vehicle within a set of peers based on a goal determined by automatically facilitating collaboration among a designated set of peers and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a cognitive system for routing at least one vehicle within a set of peers based on a goal determined by automatically facilitating collaboration among a designated set of peers and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a cognitive system for routing at least one vehicle within a set of peers based on a goal determined by automatically facilitating collaboration among a designated set of peers and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a cognitive system for routing at least one vehicle within a set of peers based on a goal determined by automatically facilitating collaboration among a designated set of peers and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a neural network to predict a transportation need of at least one individual. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a neural network to predict an emerging transportation need for a group of individuals. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a neural network to predict an emerging condition relevant to a transportation plan of at least one individual. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a neural network to predict traffic congestion relating to a route for a vehicle. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a hybrid neural network to optimize an operating state of a transportation system based on processing the social data sources with the hybrid neural network. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a hybrid neural network to optimize an operating state of a vehicle based on processing the social data sources with the hybrid neural network. In embodiments, provided herein is a system for transportation having a cognitive system for routing at least one vehicle within a set of peers based on a goal determined by automatically facilitating collaboration among a designated set of peers and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a cognitive system for routing at least one vehicle within a set of peers based on a goal determined by automatically facilitating collaboration among a designated set of peers and having an artificial intelligence system for processing a sensor input about a rider of a vehicle to determine an emotional state and optimizing at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having a two-person automobile seating system with dual, lay-flat seats that are configured to move between a flat configuration to facilitate sleep and a seated configuration to facilitate waking activity. In embodiments, provided herein is a system for transportation having a cognitive system for routing at least one vehicle within a set of peers based on a goal determined by automatically facilitating collaboration among a designated set of peers and having an entertainment system configured to provide entertainment to an automobile rider while maintaining the rider's orientation to the environment of the vehicle. In embodiments, provided herein is a system for transportation having a cognitive system for routing at least one vehicle within a set of peers based on a goal determined by automatically facilitating collaboration among a designated set of peers and having an automobile seating system with at least one rear-facing lay-flat seat that is configured to move between a flat configuration and an upright configuration. In embodiments, provided herein is a system for transportation having a cognitive system for routing at least one vehicle within a set of peers based on a goal determined by automatically facilitating collaboration among a designated set of peers and having an automobile seating system with at least one rear-facing seat that is configured with at least one visual orientation system to maintain a rider's orientation to the surrounding environment. In embodiments, provided herein is a system for transportation having a cognitive system for routing at least one vehicle within a set of peers based on a goal determined by automatically facilitating collaboration among a designated set of peers and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having an artificial intelligence system for processing a voice of a rider in a vehicle to determine an emotional state and optimizing at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a cognitive system for routing at least one vehicle within a set of peers based on a goal determined by automatically facilitating collaboration among a designated set of peers and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a cognitive system for routing at least one vehicle within a set of peers based on a goal determined by automatically facilitating collaboration among a designated set of peers and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a cognitive system for routing at least one vehicle within a set of peers based on a goal determined by automatically facilitating collaboration among a designated set of peers and having an artificial intelligence system for processing a sensory input from a wearable device in a vehicle to determine an emotional state and optimizing at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having an artificial intelligence system for processing an input from at least one seat sensor to determine an emotional state of a rider and optimizing at least one operating parameter of the vehicle to improve the rider's emotional state. In embodiments, provided herein is a system for transportation having a cognitive system for routing at least one vehicle within a set of peers based on a goal determined by automatically facilitating collaboration among a designated set of peers and having an artificial intelligence system for processing an input from at least one sensor to determine a comfort state and optimizing at least one configuration parameter of the seat to improve the rider's comfort. In embodiments, provided herein is a system for transportation having a cognitive system for routing at least one vehicle within a set of peers based on a goal determined by automatically facilitating collaboration among a designated set of peers and having an artificial intelligence system for processing an input from at least one sensor that indicates a rider's posture to determine a comfort state and optimizing at least one configuration parameter of the seat to improve the rider's comfort. In embodiments, provided herein is a system for transportation having a cognitive system for routing at least one vehicle within a set of peers based on a goal determined by automatically facilitating collaboration among a designated set of peers and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for routing at least one vehicle within a set of peers based on a goal determined by automatically facilitating collaboration among a designated set of peers and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of peers based on a goal determined by automatically facilitating collaboration among a designated set of peers and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for routing at least one vehicle within a set of peers based on a goal determined by automatically facilitating collaboration among a designated set of peers and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for routing at least one vehicle within a set of peers based on a goal determined by automatically facilitating collaboration among a designated set of peers and having a helmet configured for use with a self-driving vehicle, wherein the helmet is configured to provide an augmented reality experience based on registration of the location and orientation of the self-driving vehicle. In embodiments, provided herein is a system for transportation having a cognitive system for routing at least one vehicle within a set of peers based on a goal determined by automatically facilitating collaboration among a designated set of peers and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for routing at least one vehicle within a set of peers based on a goal determined by automatically facilitating collaboration among a designated set of peers and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of peers based on a goal determined by automatically facilitating collaboration among a designated set of peers and having a self-driving motorcycle. In embodiments, provided herein is a system for transportation having a cognitive system for routing at least one vehicle within a set of peers based on a goal determined by automatically facilitating collaboration among a designated set of peers and having a motorcycle helmet that is configured to provide an augmented reality experience based on registration of the location and orientation of the wearer in an environment. In embodiments, provided herein is a system for transportation having a cognitive system for routing at least one vehicle within a set of peers based on a goal determined by automatically facilitating collaboration among a designated set of peers and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for routing at least one vehicle within a set of peers based on a goal determined by automatically facilitating collaboration among a designated set of peers and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for routing at least one vehicle within a set of peers based on a goal determined by automatically facilitating collaboration among a designated set of peers and having a motorcycle helmet configured with a data processor and configured to communicate with a self-driving motorcycle for coordinated control of the helmet and the motorcycle. In embodiments, provided herein is a system for transportation having a cognitive system for routing at least one vehicle within a set of peers based on a goal determined by automatically facilitating collaboration among a designated set of peers and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for routing at least one vehicle within a set of peers based on a goal determined by automatically facilitating collaboration among a designated set of peers and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for routing at least one vehicle within a set of peers based on a goal determined by automatically facilitating collaboration among a designated set of peers and having a cognitive radio system for managing peer-to-peer communications within a mobile ad hoc network of self-driving vehicles. In embodiments, provided herein is a system for transportation having a cognitive system for routing at least one vehicle within a set of peers based on a goal determined by automatically facilitating collaboration among a designated set of peers and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for routing at least one vehicle within a set of peers based on a goal determined by automatically facilitating collaboration among a designated set of peers and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for routing at least one vehicle within a set of peers based on a goal determined by automatically facilitating collaboration among a designated set of peers and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for routing at least one vehicle within a set of peers based on a goal determined by automatically facilitating collaboration among a designated set of peers and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for routing at least one vehicle within a set of peers based on a goal determined by automatically facilitating collaboration among a designated set of peers and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for routing at least one vehicle within a set of peers based on a goal determined by automatically facilitating collaboration among a designated set of peers and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for routing at least one vehicle within a set of peers based on a goal determined by automatically facilitating collaboration among a designated set of peers and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for routing at least one vehicle within a set of peers based on a goal determined by automatically facilitating collaboration among a designated set of peers and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan based on inputs relating to a self-driving vehicle. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for routing at least one vehicle within a set of peers based on a goal determined by automatically facilitating collaboration among a designated set of peers and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for routing at least one vehicle within a set of peers based on a goal determined by automatically facilitating collaboration among a designated set of peers and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for routing at least one vehicle within a set of peers based on a goal determined by automatically facilitating collaboration among a designated set of peers and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for routing at least one vehicle within a set of peers based on a goal determined by automatically facilitating collaboration among a designated set of peers and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for routing at least one vehicle within a set of peers based on a goal determined by automatically facilitating collaboration among a designated set of peers and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for routing at least one vehicle within a set of peers based on a goal determined by automatically facilitating collaboration among a designated set of peers and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for routing at least one vehicle within a set of peers based on a goal determined by automatically facilitating collaboration among a designated set of peers and having an artificial intelligence system that automatically randomizes a parameter of an in-vehicle experience in order to improve a user state that benefits from variation. In embodiments, provided herein is a system for transportation having a cognitive system for routing at least one vehicle within a set of peers based on a goal determined by automatically facilitating collaboration among a designated set of peers and having a system for taking an indicator of a hormonal system level of a user and automatically varying a user experience in the vehicle to promote a healthy hormonal state. In embodiments, provided herein is a system for transportation having a cognitive system for routing at least one vehicle within a set of peers based on a goal determined by automatically facilitating collaboration among a designated set of peers and having a system for taking an indicator of a hormonal system level of a user and automatically varying a user experience in the vehicle to promote a hormonal state that promotes safety. In embodiments, provided herein is a system for transportation having a cognitive system for routing at least one vehicle within a set of peers based on a goal determined by automatically facilitating collaboration among a designated set of peers and having a dietary control system wherein at least one of a food or a beverage is made available under control of an automated control system. In embodiments, provided herein is a system for transportation having a cognitive system for routing at least one vehicle within a set of peers based on a goal determined by automatically facilitating collaboration among a designated set of peers and having an automated restocking system for an in-vehicle dietary system. In embodiments, provided herein is a system for transportation having a cognitive system for routing at least one vehicle within a set of peers based on a goal determined by automatically facilitating collaboration among a designated set of peers and having a system for optimizing at least one of a vehicle parameter and a user experience parameter to provide a margin of safety. In embodiments, provided herein is a system for transportation having a cognitive system for routing at least one vehicle within a set of peers based on a goal determined by automatically facilitating collaboration among a designated set of peers and having an interface by which a set of expert systems may be configured to provide respective outputs for managing at least one of a set of vehicle parameters, a set of fleet parameters and a set of user experience parameters. In embodiments, provided herein is a system for transportation having a cognitive system for routing at least one vehicle within a set of peers based on a goal determined by automatically facilitating collaboration among a designated set of peers and having an expert system for allocating rewards across one or more different types of objectives within a transportation system. In embodiments, provided herein is a system for transportation having a cognitive system for routing at least one vehicle within a set of peers based on a goal determined by automatically facilitating collaboration among a designated set of peers and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for routing at least one vehicle within a set of peers based on a goal determined by automatically facilitating collaboration among a designated set of peers and having a search system that is configured to provide network search results for in-vehicle searchers.

In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a neural network to predict a transportation need of at least one individual. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a neural network to predict an emerging transportation need for a group of individuals. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a neural network to predict an emerging condition relevant to a transportation plan of at least one individual. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a neural network to predict traffic congestion relating to a route for a vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a hybrid neural network to optimize an operating state of a transportation system based on processing the social data sources with the hybrid neural network. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a hybrid neural network to optimize an operating state of a vehicle based on processing the social data sources with the hybrid neural network. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing a sensor input about a rider of a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a two-person automobile seating system with dual, lay-flat seats that are configured to move between a flat configuration to facilitate sleep and a seated configuration to facilitate waking activity. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an entertainment system configured to provide entertainment to an automobile rider while maintaining the rider's orientation to the environment of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an automobile seating system with at least one rear-facing lay-flat seat that is configured to move between a flat configuration and an upright configuration. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an automobile seating system with at least one rear-facing seat that is configured with at least one visual orientation system to maintain a rider's orientation to the surrounding environment. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing a voice of a rider in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing a sensory input from a wearable device in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing an input from at least one seat sensor to determine an emotional state of a rider and optimizing at least one operating parameter of the vehicle to improve the rider's emotional state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing an input from at least one sensor to determine a comfort state and optimizing at least one configuration parameter of the seat to improve the rider's comfort. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for processing an input from at least one sensor that indicates a rider's posture to determine a comfort state and optimizing at least one configuration parameter of the seat to improve the rider's comfort. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a helmet configured for use with a self-driving vehicle, wherein the helmet is configured to provide an augmented reality experience based on registration of the location and orientation of the self-driving vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a self-driving motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet that is configured to provide an augmented reality experience based on registration of the location and orientation of the wearer in an environment. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet configured with a data processor and configured to communicate with a self-driving motorcycle for coordinated control of the helmet and the motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive radio system for managing peer-to-peer communications within a mobile ad hoc network of self-driving vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan based on inputs relating to a self-driving vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an artificial intelligence system that automatically randomizes a parameter of an in-vehicle experience in order to improve a user state that benefits from variation. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a system for taking an indicator of a hormonal system level of a user and automatically varying a user experience in the vehicle to promote a healthy hormonal state. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a system for taking an indicator of a hormonal system level of a user and automatically varying a user experience in the vehicle to promote a hormonal state that promotes safety. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a dietary control system wherein at least one of a food or a beverage is made available under control of an automated control system. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an automated restocking system for an in-vehicle dietary system. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a system for optimizing at least one of a vehicle parameter and a user experience parameter to provide a margin of safety. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an interface by which a set of expert systems may be configured to provide respective outputs for managing at least one of a set of vehicle parameters, a set of fleet parameters and a set of user experience parameters. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an expert system for allocating rewards across one or more different types of objectives within a transportation system. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for routing at least one vehicle within a set of vehicles based on a routing parameter determined by facilitating negotiation among a designated set of vehicles, wherein negotiation accepts inputs relating to the value attributed by at least one rider to at least one parameter of a route and having a search system that is configured to provide network search results for in-vehicle searchers.

In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for managing the offering and/or fulfillment of rewards to riders of vehicles by a plurality of merchants, wherein a reward is earned by a rider undertaking an action while in the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a neural network to predict a transportation need of at least one individual. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a neural network to predict an emerging transportation need for a group of individuals. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a neural network to predict an emerging condition relevant to a transportation plan of at least one individual. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a neural network to predict traffic congestion relating to a route for a vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a hybrid neural network to optimize an operating state of a transportation system based on processing the social data sources with the hybrid neural network. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a hybrid neural network to optimize an operating state of a vehicle based on processing the social data sources with the hybrid neural network. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing a sensor input about a rider of a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a two-person automobile seating system with dual, lay-flat seats that are configured to move between a flat configuration to facilitate sleep and a seated configuration to facilitate waking activity. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an entertainment system configured to provide entertainment to an automobile rider while maintaining the rider's orientation to the environment of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an automobile seating system with at least one rear-facing lay-flat seat that is configured to move between a flat configuration and an upright configuration. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an automobile seating system with at least one rear-facing seat that is configured with at least one visual orientation system to maintain a rider's orientation to the surrounding environment. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing a voice of a rider in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing a sensory input from a wearable device in a vehicle to determine an emotional state and optimizing at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing an input from at least one seat sensor to determine an emotional state of a rider and optimizing at least one operating parameter of the vehicle to improve the rider's emotional state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing an input from at least one sensor to determine a comfort state and optimizing at least one configuration parameter of the seat to improve the rider's comfort. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for processing an input from at least one sensor that indicates a rider's posture to determine a comfort state and optimizing at least one configuration parameter of the seat to improve the rider's comfort. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a helmet configured for use with a self-driving vehicle, wherein the helmet is configured to provide an augmented reality experience based on registration of the location and orientation of the self-driving vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a self-driving motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet that is configured to provide an augmented reality experience based on registration of the location and orientation of the wearer in an environment. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet configured with a data processor and configured to communicate with a self-driving motorcycle for coordinated control of the helmet and the motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive radio system for managing peer-to-peer communications within a mobile ad hoc network of self-driving vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan based on inputs relating to a self-driving vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an artificial intelligence system that automatically randomizes a parameter of an in-vehicle experience in order to improve a user state that benefits from variation. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a system for taking an indicator of a hormonal system level of a user and automatically varying a user experience in the vehicle to promote a healthy hormonal state. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a system for taking an indicator of a hormonal system level of a user and automatically varying a user experience in the vehicle to promote a hormonal state that promotes safety. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a dietary control system wherein at least one of a food or a beverage is made available under control of an automated control system. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an automated restocking system for an in-vehicle dietary system. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a system for optimizing at least one of a vehicle parameter and a user experience parameter to provide a margin of safety. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an interface by which a set of expert systems may be configured to provide respective outputs for managing at least one of a set of vehicle parameters, a set of fleet parameters and a set of user experience parameters. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an expert system for allocating rewards across one or more different types of objectives within a transportation system. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for routing at least one vehicle within a set of vehicles based on a routing parameter determined by facilitating coordination among a designated set of vehicles, wherein the coordination is accomplished by taking at least one input from at least one game-based interface for riders of the vehicles and having a search system that is configured to provide network search results for in-vehicle searchers.

In embodiments, provided herein is a system for transportation having a cognitive system for managing the offering and/or fulfillment of rewards to riders of vehicles by a plurality of merchants, wherein a reward is earned by a rider undertaking an action while in the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a neural network to predict a transportation need of at least one individual. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a neural network to predict an emerging transportation need for a group of individuals. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a neural network to predict an emerging condition relevant to a transportation plan of at least one individual. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a neural network to predict traffic congestion relating to a route for a vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a hybrid neural network to optimize an operating state of a transportation system based on processing the social data sources with the hybrid neural network. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a hybrid neural network to optimize an operating state of a vehicle based on processing the social data sources with the hybrid neural network. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a two-person automobile seating system with dual, lay-flat seats that are configured to move between a flat configuration to facilitate sleep and a seated configuration to facilitate waking activity. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an entertainment system configured to provide entertainment to an automobile rider while maintaining the rider's orientation to the environment of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an automobile seating system with at least one rear-facing lay-flat seat that is configured to move between a flat configuration and an upright configuration. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an automobile seating system with at least one rear-facing seat that is configured with at least one visual orientation system to maintain a rider's orientation to the surrounding environment. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing a voice of a rider in a vehicle to determine an emotional state and optimizing at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing an input from at least one sensor to determine a comfort state and optimizing at least one configuration parameter of the seat to improve the rider's comfort. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a helmet configured for use with a self-driving vehicle, wherein the helmet is configured to provide an augmented reality experience based on registration of the location and orientation of the self-driving vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a self-driving motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet that is configured to provide an augmented reality experience based on registration of the location and orientation of the wearer in an environment. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet configured with a data processor and configured to communicate with a self-driving motorcycle for coordinated control of the helmet and the motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive radio system for managing peer-to-peer communications within a mobile ad hoc network of self-driving vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan based on inputs relating to a self-driving vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an artificial intelligence system that automatically randomizes a parameter of an in-vehicle experience in order to improve a user state that benefits from variation. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a system for taking an indicator of a hormonal system level of a user and automatically varying a user experience in the vehicle to promote a healthy hormonal state. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a system for taking an indicator of a hormonal system level of a user and automatically varying a user experience in the vehicle to promote a hormonal state that promotes safety. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a dietary control system wherein at least one of a food or a beverage is made available under control of an automated control system. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an automated restocking system for an in-vehicle dietary system. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a system for optimizing at least one of a vehicle parameter and a user experience parameter to provide a margin of safety. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an interface by which a set of expert systems may be configured to provide respective outputs for managing at least one of a set of vehicle parameters, a set of fleet parameters and a set of user experience parameters. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an expert system for allocating rewards across one or more different types of objectives within a transportation system. In embodiments, provided herein is a system for transportation having a cognitive system for managing the offering and/or fulfillment of rewards to riders of vehicles by a plurality of merchants, wherein a reward is earned by a rider undertaking an action while in the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for managing the offering and/or fulfillment of rewards to riders of vehicles by a plurality of merchants, wherein a reward is earned by a rider undertaking an action while in the vehicle and having a search system that is configured to provide network search results for in-vehicle searchers.

In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a neural network to predict a transportation need of at least one individual. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a neural network to predict an emerging transportation need for a group of individuals. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a neural network to predict an emerging condition relevant to a transportation plan of at least one individual. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a neural network to predict traffic congestion relating to a route for a vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a hybrid neural network to optimize an operating state of a transportation system based on processing the social data sources with the hybrid neural network. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a hybrid neural network to optimize an operating state of a vehicle based on processing the social data sources with the hybrid neural network. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a two-person automobile seating system with dual, lay-flat seats that are configured to move between a flat configuration to facilitate sleep and a seated configuration to facilitate waking activity. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an entertainment system configured to provide entertainment to an automobile rider while maintaining the rider's orientation to the environment of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an automobile seating system with at least one rear-facing lay-flat seat that is configured to move between a flat configuration and an upright configuration. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an automobile seating system with at least one rear-facing seat that is configured with at least one visual orientation system to maintain a rider's orientation to the surrounding environment. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing a voice of a rider in a vehicle to determine an emotional state and optimizing at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing an input from at least one sensor to determine a comfort state and optimizing at least one configuration parameter of the seat to improve the rider's comfort. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a helmet configured for use with a self-driving vehicle, wherein the helmet is configured to provide an augmented reality experience based on registration of the location and orientation of the self-driving vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a self-driving motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet that is configured to provide an augmented reality experience based on registration of the location and orientation of the wearer in an environment. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet configured with a data processor and configured to communicate with a self-driving motorcycle for coordinated control of the helmet and the motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive radio system for managing peer-to-peer communications within a mobile ad hoc network of self-driving vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan based on inputs relating to a self-driving vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an artificial intelligence system that automatically randomizes a parameter of an in-vehicle experience in order to improve a user state that benefits from variation. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a system for taking an indicator of a hormonal system level of a user and automatically varying a user experience in the vehicle to promote a healthy hormonal state. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a system for taking an indicator of a hormonal system level of a user and automatically varying a user experience in the vehicle to promote a hormonal state that promotes safety. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a dietary control system wherein at least one of a food or a beverage is made available under control of an automated control system. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an automated restocking system for an in-vehicle dietary system. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a system for optimizing at least one of a vehicle parameter and a user experience parameter to provide a margin of safety. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an interface by which a set of expert systems may be configured to provide respective outputs for managing at least one of a set of vehicle parameters, a set of fleet parameters and a set of user experience parameters. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an expert system for allocating rewards across one or more different types of objectives within a transportation system. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a merchant interface to a cognitive system for managing the offering and/or fulfillment of rewards to riders of vehicles by a plurality of merchants, wherein a merchant may specify parameters of a reward that can be earned by a rider undertaking an action while in a vehicle and having a search system that is configured to provide network search results for in-vehicle searchers.

In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a neural network to predict a transportation need of at least one individual. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a neural network to predict an emerging transportation need for a group of individuals. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a neural network to predict an emerging condition relevant to a transportation plan of at least one individual. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a neural network to predict traffic congestion relating to a route for a vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a hybrid neural network to optimize an operating state of a transportation system based on processing the social data sources with the hybrid neural network. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a hybrid neural network to optimize an operating state of a vehicle based on processing the social data sources with the hybrid neural network. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a two-person automobile seating system with dual, lay-flat seats that are configured to move between a flat configuration to facilitate sleep and a seated configuration to facilitate waking activity. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an entertainment system configured to provide entertainment to an automobile rider while maintaining the rider's orientation to the environment of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an automobile seating system with at least one rear-facing lay-flat seat that is configured to move between a flat configuration and an upright configuration. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an automobile seating system with at least one rear-facing seat that is configured with at least one visual orientation system to maintain a rider's orientation to the surrounding environment. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing a voice of a rider in a vehicle to determine an emotional state and optimizing at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing an input from at least one sensor to determine a comfort state and optimizing at least one configuration parameter of the seat to improve the rider's comfort. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a helmet configured for use with a self-driving vehicle, wherein the helmet is configured to provide an augmented reality experience based on registration of the location and orientation of the self-driving vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a self-driving motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet that is configured to provide an augmented reality experience based on registration of the location and orientation of the wearer in an environment. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet configured with a data processor and configured to communicate with a self-driving motorcycle for coordinated control of the helmet and the motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive radio system for managing peer-to-peer communications within a mobile ad hoc network of self-driving vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan based on inputs relating to a self-driving vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an artificial intelligence system that automatically randomizes a parameter of an in-vehicle experience in order to improve a user state that benefits from variation. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a system for taking an indicator of a hormonal system level of a user and automatically varying a user experience in the vehicle to promote a healthy hormonal state. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a system for taking an indicator of a hormonal system level of a user and automatically varying a user experience in the vehicle to promote a hormonal state that promotes safety. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a dietary control system wherein at least one of a food or a beverage is made available under control of an automated control system. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an automated restocking system for an in-vehicle dietary system. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a system for optimizing at least one of a vehicle parameter and a user experience parameter to provide a margin of safety. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an interface by which a set of expert systems may be configured to provide respective outputs for managing at least one of a set of vehicle parameters, a set of fleet parameters and a set of user experience parameters. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an expert system for allocating rewards across one or more different types of objectives within a transportation system. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a rider interface to a cognitive system for managing the offering and/or fulfillment of rewards to riders of vehicles by a plurality of merchants, wherein a reward is offered to a rider for undertaking an action while in the vehicle and having a search system that is configured to provide network search results for in-vehicle searchers.

In embodiments, provided herein is a system for transportation having a cognitive system for routing at least one vehicle, wherein the routing is determined at least in part by processing at least one input from a rider interface wherein a rider can obtain a reward by undertaking an action while in the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a neural network to predict a transportation need of at least one individual. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a neural network to predict an emerging transportation need for a group of individuals. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a neural network to predict an emerging condition relevant to a transportation plan of at least one individual. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a neural network to predict traffic congestion relating to a route for a vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a hybrid neural network to optimize an operating state of a transportation system based on processing the social data sources with the hybrid neural network. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a hybrid neural network to optimize an operating state of a vehicle based on processing the social data sources with the hybrid neural network. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a two-person automobile seating system with dual, lay-flat seats that are configured to move between a flat configuration to facilitate sleep and a seated configuration to facilitate waking activity. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an entertainment system configured to provide entertainment to an automobile rider while maintaining the rider's orientation to the environment of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an automobile seating system with at least one rear-facing lay-flat seat that is configured to move between a flat configuration and an upright configuration. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an automobile seating system with at least one rear-facing seat that is configured with at least one visual orientation system to maintain a rider's orientation to the surrounding environment. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing a voice of a rider in a vehicle to determine an emotional state and optimizing at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing an input from at least one sensor to determine a comfort state and optimizing at least one configuration parameter of the seat to improve the rider's comfort. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a helmet configured for use with a self-driving vehicle, wherein the helmet is configured to provide an augmented reality experience based on registration of the location and orientation of the self-driving vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a self-driving motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet that is configured to provide an augmented reality experience based on registration of the location and orientation of the wearer in an environment. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet configured with a data processor and configured to communicate with a self-driving motorcycle for coordinated control of the helmet and the motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cognitive radio system for managing peer-to-peer communications within a mobile ad hoc network of self-driving vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan based on inputs relating to a self-driving vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an artificial intelligence system that automatically randomizes a parameter of an in-vehicle experience in order to improve a user state that benefits from variation. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a system for taking an indicator of a hormonal system level of a user and automatically varying a user experience in the vehicle to promote a healthy hormonal state. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a system for taking an indicator of a hormonal system level of a user and automatically varying a user experience in the vehicle to promote a hormonal state that promotes safety. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a dietary control system wherein at least one of a food or a beverage is made available under control of an automated control system. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an automated restocking system for an in-vehicle dietary system. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a system for optimizing at least one of a vehicle parameter and a user experience parameter to provide a margin of safety. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an interface by which a set of expert systems may be configured to provide respective outputs for managing at least one of a set of vehicle parameters, a set of fleet parameters and a set of user experience parameters. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an expert system for allocating rewards across one or more different types of objectives within a transportation system. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for routing at least one vehicle, wherein the routing is determined at least in part by processing at least one input from a rider interface wherein a rider can obtain a reward by undertaking an action while in the vehicle and having a search system that is configured to provide network search results for in-vehicle searchers.

In embodiments, provided herein is a system for transportation having a data processing system for taking data from a plurality of social data sources and using a neural network to predict a transportation need of at least one individual. In embodiments, provided herein is a system for transportation having a data processing system for taking data from a plurality of social data sources and using a neural network to predict a transportation need of at least one individual and having a data processing system for taking data from a plurality of social data sources and using a neural network to predict an emerging transportation need for a group of individuals. In embodiments, provided herein is a system for transportation having a data processing system for taking data from a plurality of social data sources and using a neural network to predict a transportation need of at least one individual and having a data processing system for taking data from a plurality of social data sources and using a neural network to predict an emerging condition relevant to a transportation plan of at least one individual. In embodiments, provided herein is a system for transportation having a data processing system for taking data from a plurality of social data sources and using a neural network to predict a transportation need of at least one individual and having a data processing system for taking data from a plurality of social data sources and using a neural network to predict traffic congestion relating to a route for a vehicle. In embodiments, provided herein is a system for transportation having a data processing system for taking data from a plurality of social data sources and using a neural network to predict a transportation need of at least one individual and having a data processing system for taking data from a plurality of social data sources and using a hybrid neural network to optimize an operating state of a transportation system based on processing the social data sources with the hybrid neural network. In embodiments, provided herein is a system for transportation having a data processing system for taking data from a plurality of social data sources and using a neural network to predict a transportation need of at least one individual and having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a neural network to predict a transportation need of at least one individual and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a neural network to predict a transportation need of at least one individual and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict a transportation need of at least one individual and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a neural network to predict a transportation need of at least one individual and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a neural network to predict a transportation need of at least one individual and having an entertainment system configured to provide entertainment to an automobile rider while maintaining the rider's orientation to the environment of the vehicle. In embodiments, provided herein is a system for transportation having a data processing system for taking data from a plurality of social data sources and using a neural network to predict a transportation need of at least one individual and having an automobile seating system with at least one rear-facing lay-flat seat that is configured to move between a flat configuration and an upright configuration. In embodiments, provided herein is a system for transportation having a data processing system for taking data from a plurality of social data sources and using a neural network to predict a transportation need of at least one individual and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a neural network to predict a transportation need of at least one individual and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict a transportation need of at least one individual and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict a transportation need of at least one individual and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a neural network to predict a transportation need of at least one individual and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a neural network to predict a transportation need of at least one individual and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a neural network to predict a transportation need of at least one individual and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict a transportation need of at least one individual and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a neural network to predict a transportation need of at least one individual and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a neural network to predict a transportation need of at least one individual and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a neural network to predict a transportation need of at least one individual and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a neural network to predict a transportation need of at least one individual and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict a transportation need of at least one individual and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a neural network to predict a transportation need of at least one individual and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a neural network to predict a transportation need of at least one individual and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a neural network to predict a transportation need of at least one individual and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a neural network to predict a transportation need of at least one individual and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict a transportation need of at least one individual and having a self-driving motorcycle. In embodiments, provided herein is a system for transportation having a data processing system for taking data from a plurality of social data sources and using a neural network to predict a transportation need of at least one individual and having a motorcycle helmet that is configured to provide an augmented reality experience based on registration of the location and orientation of the wearer in an environment. In embodiments, provided herein is a system for transportation having a data processing system for taking data from a plurality of social data sources and using a neural network to predict a transportation need of at least one individual and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a neural network to predict a transportation need of at least one individual and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a neural network to predict a transportation need of at least one individual and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a neural network to predict a transportation need of at least one individual and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a neural network to predict a transportation need of at least one individual and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a neural network to predict a transportation need of at least one individual and having a cognitive radio system for managing peer-to-peer communications within a mobile ad hoc network of self-driving vehicles. In embodiments, provided herein is a system for transportation having a data processing system for taking data from a plurality of social data sources and using a neural network to predict a transportation need of at least one individual and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a neural network to predict a transportation need of at least one individual and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a neural network to predict a transportation need of at least one individual and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a neural network to predict a transportation need of at least one individual and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a neural network to predict a transportation need of at least one individual and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a neural network to predict a transportation need of at least one individual and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a neural network to predict a transportation need of at least one individual and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a neural network to predict a transportation need of at least one individual and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a neural network to predict a transportation need of at least one individual and having an artificial intelligence system for determining at least one parameter of a charging plan based on inputs relating to a self-driving vehicle. In embodiments, provided herein is a system for transportation having a data processing system for taking data from a plurality of social data sources and using a neural network to predict a transportation need of at least one individual and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a neural network to predict a transportation need of at least one individual and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a neural network to predict a transportation need of at least one individual and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a neural network to predict a transportation need of at least one individual and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a neural network to predict a transportation need of at least one individual and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a neural network to predict a transportation need of at least one individual and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a neural network to predict a transportation need of at least one individual and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a neural network to predict a transportation need of at least one individual and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a neural network to predict a transportation need of at least one individual and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a neural network to predict a transportation need of at least one individual and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a neural network to predict a transportation need of at least one individual and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a neural network to predict a transportation need of at least one individual and having an artificial intelligence system that automatically randomizes a parameter of an in-vehicle experience in order to improve a user state that benefits from variation. In embodiments, provided herein is a system for transportation having a data processing system for taking data from a plurality of social data sources and using a neural network to predict a transportation need of at least one individual and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a neural network to predict a transportation need of at least one individual and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a neural network to predict a transportation need of at least one individual and having a dietary control system wherein at least one of a food or a beverage is made available under control of an automated control system. In embodiments, provided herein is a system for transportation having a data processing system for taking data from a plurality of social data sources and using a neural network to predict a transportation need of at least one individual and having an automated restocking system for an in-vehicle dietary system. In embodiments, provided herein is a system for transportation having a data processing system for taking data from a plurality of social data sources and using a neural network to predict a transportation need of at least one individual and having a system for optimizing at least one of a vehicle parameter and a user experience parameter to provide a margin of safety. In embodiments, provided herein is a system for transportation having a data processing system for taking data from a plurality of social data sources and using a neural network to predict a transportation need of at least one individual and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a neural network to predict a transportation need of at least one individual and having an expert system for allocating rewards across one or more different types of objectives within a transportation system. In embodiments, provided herein is a system for transportation having a data processing system for taking data from a plurality of social data sources and using a neural network to predict a transportation need of at least one individual and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a neural network to predict a transportation need of at least one individual and having a search system that is configured to provide network search results for in-vehicle searchers.

In embodiments, provided herein is a system for transportation having a data processing system for taking data from a plurality of social data sources and using a neural network to predict an emerging transportation need for a group of individuals. In embodiments, provided herein is a system for transportation having a data processing system for taking data from a plurality of social data sources and using a neural network to predict an emerging transportation need for a group of individuals and having a data processing system for taking data from a plurality of social data sources and using a neural network to predict an emerging condition relevant to a transportation plan of at least one individual. In embodiments, provided herein is a system for transportation having a data processing system for taking data from a plurality of social data sources and using a neural network to predict an emerging transportation need for a group of individuals and having a data processing system for taking data from a plurality of social data sources and using a neural network to predict traffic congestion relating to a route for a vehicle. In embodiments, provided herein is a system for transportation having a data processing system for taking data from a plurality of social data sources and using a neural network to predict an emerging transportation need for a group of individuals and having a data processing system for taking data from a plurality of social data sources and using a hybrid neural network to optimize an operating state of a transportation system based on processing the social data sources with the hybrid neural network. In embodiments, provided herein is a system for transportation having a data processing system for taking data from a plurality of social data sources and using a neural network to predict an emerging transportation need for a group of individuals and having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a neural network to predict an emerging transportation need for a group of individuals and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a neural network to predict an emerging transportation need for a group of individuals and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging transportation need for a group of individuals and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a neural network to predict an emerging transportation need for a group of individuals and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a neural network to predict an emerging transportation need for a group of individuals and having an entertainment system configured to provide entertainment to an automobile rider while maintaining the rider's orientation to the environment of the vehicle. In embodiments, provided herein is a system for transportation having a data processing system for taking data from a plurality of social data sources and using a neural network to predict an emerging transportation need for a group of individuals and having an automobile seating system with at least one rear-facing lay-flat seat that is configured to move between a flat configuration and an upright configuration. In embodiments, provided herein is a system for transportation having a data processing system for taking data from a plurality of social data sources and using a neural network to predict an emerging transportation need for a group of individuals and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a neural network to predict an emerging transportation need for a group of individuals and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging transportation need for a group of individuals and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging transportation need for a group of individuals and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a neural network to predict an emerging transportation need for a group of individuals and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a neural network to predict an emerging transportation need for a group of individuals and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a neural network to predict an emerging transportation need for a group of individuals and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging transportation need for a group of individuals and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a neural network to predict an emerging transportation need for a group of individuals and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a neural network to predict an emerging transportation need for a group of individuals and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a neural network to predict an emerging transportation need for a group of individuals and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging transportation need for a group of individuals and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging transportation need for a group of individuals and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a neural network to predict an emerging transportation need for a group of individuals and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a neural network to predict an emerging transportation need for a group of individuals and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a neural network to predict an emerging transportation need for a group of individuals and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a neural network to predict an emerging transportation need for a group of individuals and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging transportation need for a group of individuals and having a self-driving motorcycle. In embodiments, provided herein is a system for transportation having a data processing system for taking data from a plurality of social data sources and using a neural network to predict an emerging transportation need for a group of individuals and having a motorcycle helmet that is configured to provide an augmented reality experience based on registration of the location and orientation of the wearer in an environment. In embodiments, provided herein is a system for transportation having a data processing system for taking data from a plurality of social data sources and using a neural network to predict an emerging transportation need for a group of individuals and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a neural network to predict an emerging transportation need for a group of individuals and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a neural network to predict an emerging transportation need for a group of individuals and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a neural network to predict an emerging transportation need for a group of individuals and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a neural network to predict an emerging transportation need for a group of individuals and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a neural network to predict an emerging transportation need for a group of individuals and having a cognitive radio system for managing peer-to-peer communications within a mobile ad hoc network of self-driving vehicles. In embodiments, provided herein is a system for transportation having a data processing system for taking data from a plurality of social data sources and using a neural network to predict an emerging transportation need for a group of individuals and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a neural network to predict an emerging transportation need for a group of individuals and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a neural network to predict an emerging transportation need for a group of individuals and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a neural network to predict an emerging transportation need for a group of individuals and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a neural network to predict an emerging transportation need for a group of individuals and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a neural network to predict an emerging transportation need for a group of individuals and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a neural network to predict an emerging transportation need for a group of individuals and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a neural network to predict an emerging transportation need for a group of individuals and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a neural network to predict an emerging transportation need for a group of individuals and having an artificial intelligence system for determining at least one parameter of a charging plan based on inputs relating to a self-driving vehicle. In embodiments, provided herein is a system for transportation having a data processing system for taking data from a plurality of social data sources and using a neural network to predict an emerging transportation need for a group of individuals and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a neural network to predict an emerging transportation need for a group of individuals and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a neural network to predict an emerging transportation need for a group of individuals and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a neural network to predict an emerging transportation need for a group of individuals and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a neural network to predict an emerging transportation need for a group of individuals and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a neural network to predict an emerging transportation need for a group of individuals and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a neural network to predict an emerging transportation need for a group of individuals and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a neural network to predict an emerging transportation need for a group of individuals and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a neural network to predict an emerging transportation need for a group of individuals and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a neural network to predict an emerging transportation need for a group of individuals and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a neural network to predict an emerging transportation need for a group of individuals and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a neural network to predict an emerging transportation need for a group of individuals and having an artificial intelligence system that automatically randomizes a parameter of an in-vehicle experience in order to improve a user state that benefits from variation. In embodiments, provided herein is a system for transportation having a data processing system for taking data from a plurality of social data sources and using a neural network to predict an emerging transportation need for a group of individuals and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a neural network to predict an emerging transportation need for a group of individuals and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a neural network to predict an emerging transportation need for a group of individuals and having a dietary control system wherein at least one of a food or a beverage is made available under control of an automated control system. In embodiments, provided herein is a system for transportation having a data processing system for taking data from a plurality of social data sources and using a neural network to predict an emerging transportation need for a group of individuals and having an automated restocking system for an in-vehicle dietary system. In embodiments, provided herein is a system for transportation having a data processing system for taking data from a plurality of social data sources and using a neural network to predict an emerging transportation need for a group of individuals and having a system for optimizing at least one of a vehicle parameter and a user experience parameter to provide a margin of safety. In embodiments, provided herein is a system for transportation having a data processing system for taking data from a plurality of social data sources and using a neural network to predict an emerging transportation need for a group of individuals and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a neural network to predict an emerging transportation need for a group of individuals and having an expert system for allocating rewards across one or more different types of objectives within a transportation system. In embodiments, provided herein is a system for transportation having a data processing system for taking data from a plurality of social data sources and using a neural network to predict an emerging transportation need for a group of individuals and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a neural network to predict an emerging transportation need for a group of individuals and having a search system that is configured to provide network search results for in-vehicle searchers.

In embodiments, provided herein is a system for transportation having a data processing system for taking data from a plurality of social data sources and using a neural network to predict an emerging condition relevant to a transportation plan of at least one individual. In embodiments, provided herein is a system for transportation having a data processing system for taking data from a plurality of social data sources and using a neural network to predict an emerging condition relevant to a transportation plan of at least one individual and having a data processing system for taking data from a plurality of social data sources and using a neural network to predict traffic congestion relating to a route for a vehicle. In embodiments, provided herein is a system for transportation having a data processing system for taking data from a plurality of social data sources and using a neural network to predict an emerging condition relevant to a transportation plan of at least one individual and having a data processing system for taking data from a plurality of social data sources and using a hybrid neural network to optimize an operating state of a transportation system based on processing the social data sources with the hybrid neural network. In embodiments, provided herein is a system for transportation having a data processing system for taking data from a plurality of social data sources and using a neural network to predict an emerging condition relevant to a transportation plan of at least one individual and having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a neural network to predict an emerging condition relevant to a transportation plan of at least one individual and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a neural network to predict an emerging condition relevant to a transportation plan of at least one individual and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a neural network to predict an emerging condition relevant to a transportation plan of at least one individual and having an entertainment system configured to provide entertainment to an automobile rider while maintaining the rider's orientation to the environment of the vehicle. In embodiments, provided herein is a system for transportation having a data processing system for taking data from a plurality of social data sources and using a neural network to predict an emerging condition relevant to a transportation plan of at least one individual and having an automobile seating system with at least one rear-facing lay-flat seat that is configured to move between a flat configuration and an upright configuration. In embodiments, provided herein is a system for transportation having a data processing system for taking data from a plurality of social data sources and using a neural network to predict an emerging condition relevant to a transportation plan of at least one individual and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a neural network to predict an emerging condition relevant to a transportation plan of at least one individual and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a neural network to predict an emerging condition relevant to a transportation plan of at least one individual and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a neural network to predict an emerging condition relevant to a transportation plan of at least one individual and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a neural network to predict an emerging condition relevant to a transportation plan of at least one individual and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a neural network to predict an emerging condition relevant to a transportation plan of at least one individual and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a neural network to predict an emerging condition relevant to a transportation plan of at least one individual and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a neural network to predict an emerging condition relevant to a transportation plan of at least one individual and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging condition relevant to a transportation plan of at least one individual and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging condition relevant to a transportation plan of at least one individual and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a neural network to predict an emerging condition relevant to a transportation plan of at least one individual and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a neural network to predict an emerging condition relevant to a transportation plan of at least one individual and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a neural network to predict an emerging condition relevant to a transportation plan of at least one individual and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a neural network to predict an emerging condition relevant to a transportation plan of at least one individual and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict an emerging condition relevant to a transportation plan of at least one individual and having a self-driving motorcycle. In embodiments, provided herein is a system for transportation having a data processing system for taking data from a plurality of social data sources and using a neural network to predict an emerging condition relevant to a transportation plan of at least one individual and having a motorcycle helmet that is configured to provide an augmented reality experience based on registration of the location and orientation of the wearer in an environment. In embodiments, provided herein is a system for transportation having a data processing system for taking data from a plurality of social data sources and using a neural network to predict an emerging condition relevant to a transportation plan of at least one individual and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a neural network to predict an emerging condition relevant to a transportation plan of at least one individual and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a neural network to predict an emerging condition relevant to a transportation plan of at least one individual and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a neural network to predict an emerging condition relevant to a transportation plan of at least one individual and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a neural network to predict an emerging condition relevant to a transportation plan of at least one individual and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a neural network to predict an emerging condition relevant to a transportation plan of at least one individual and having a cognitive radio system for managing peer-to-peer communications within a mobile ad hoc network of self-driving vehicles. In embodiments, provided herein is a system for transportation having a data processing system for taking data from a plurality of social data sources and using a neural network to predict an emerging condition relevant to a transportation plan of at least one individual and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a neural network to predict an emerging condition relevant to a transportation plan of at least one individual and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a neural network to predict an emerging condition relevant to a transportation plan of at least one individual and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a neural network to predict an emerging condition relevant to a transportation plan of at least one individual and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a neural network to predict an emerging condition relevant to a transportation plan of at least one individual and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a neural network to predict an emerging condition relevant to a transportation plan of at least one individual and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a neural network to predict an emerging condition relevant to a transportation plan of at least one individual and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a neural network to predict an emerging condition relevant to a transportation plan of at least one individual and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan based on inputs relating to a self-driving vehicle. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a neural network to predict an emerging condition relevant to a transportation plan of at least one individual and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a neural network to predict an emerging condition relevant to a transportation plan of at least one individual and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a neural network to predict an emerging condition relevant to a transportation plan of at least one individual and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a neural network to predict an emerging condition relevant to a transportation plan of at least one individual and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a neural network to predict an emerging condition relevant to a transportation plan of at least one individual and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a neural network to predict an emerging condition relevant to a transportation plan of at least one individual and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a neural network to predict an emerging condition relevant to a transportation plan of at least one individual and having an artificial intelligence system that automatically randomizes a parameter of an in-vehicle experience in order to improve a user state that benefits from variation. In embodiments, provided herein is a system for transportation having a data processing system for taking data from a plurality of social data sources and using a neural network to predict an emerging condition relevant to a transportation plan of at least one individual and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a neural network to predict an emerging condition relevant to a transportation plan of at least one individual and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a neural network to predict an emerging condition relevant to a transportation plan of at least one individual and having a dietary control system wherein at least one of a food or a beverage is made available under control of an automated control system. In embodiments, provided herein is a system for transportation having a data processing system for taking data from a plurality of social data sources and using a neural network to predict an emerging condition relevant to a transportation plan of at least one individual and having an automated restocking system for an in-vehicle dietary system. In embodiments, provided herein is a system for transportation having a data processing system for taking data from a plurality of social data sources and using a neural network to predict an emerging condition relevant to a transportation plan of at least one individual and having a system for optimizing at least one of a vehicle parameter and a user experience parameter to provide a margin of safety. In embodiments, provided herein is a system for transportation having a data processing system for taking data from a plurality of social data sources and using a neural network to predict an emerging condition relevant to a transportation plan of at least one individual and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a neural network to predict an emerging condition relevant to a transportation plan of at least one individual and having an expert system for allocating rewards across one or more different types of objectives within a transportation system. In embodiments, provided herein is a system for transportation having a data processing system for taking data from a plurality of social data sources and using a neural network to predict an emerging condition relevant to a transportation plan of at least one individual and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a neural network to predict an emerging condition relevant to a transportation plan of at least one individual and having a search system that is configured to provide network search results for in-vehicle searchers.

In embodiments, provided herein is a system for transportation having a data processing system for taking data from a plurality of social data sources and using a neural network to predict traffic congestion relating to a route for a vehicle. In embodiments, provided herein is a system for transportation having a data processing system for taking data from a plurality of social data sources and using a neural network to predict traffic congestion relating to a route for a vehicle and having a data processing system for taking data from a plurality of social data sources and using a hybrid neural network to optimize an operating state of a transportation system based on processing the social data sources with the hybrid neural network. In embodiments, provided herein is a system for transportation having a data processing system for taking data from a plurality of social data sources and using a neural network to predict traffic congestion relating to a route for a vehicle and having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a neural network to predict traffic congestion relating to a route for a vehicle and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a neural network to predict traffic congestion relating to a route for a vehicle and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a neural network to predict traffic congestion relating to a route for a vehicle and having an entertainment system configured to provide entertainment to an automobile rider while maintaining the rider's orientation to the environment of the vehicle. In embodiments, provided herein is a system for transportation having a data processing system for taking data from a plurality of social data sources and using a neural network to predict traffic congestion relating to a route for a vehicle and having an automobile seating system with at least one rear-facing lay-flat seat that is configured to move between a flat configuration and an upright configuration. In embodiments, provided herein is a system for transportation having a data processing system for taking data from a plurality of social data sources and using a neural network to predict traffic congestion relating to a route for a vehicle and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a neural network to predict traffic congestion relating to a route for a vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a neural network to predict traffic congestion relating to a route for a vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a neural network to predict traffic congestion relating to a route for a vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a neural network to predict traffic congestion relating to a route for a vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a neural network to predict traffic congestion relating to a route for a vehicle and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a neural network to predict traffic congestion relating to a route for a vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a neural network to predict traffic congestion relating to a route for a vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a neural network to predict traffic congestion relating to a route for a vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict traffic congestion relating to a route for a vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a neural network to predict traffic congestion relating to a route for a vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a neural network to predict traffic congestion relating to a route for a vehicle and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a neural network to predict traffic congestion relating to a route for a vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a neural network to predict traffic congestion relating to a route for a vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a neural network to predict traffic congestion relating to a route for a vehicle and having a self-driving motorcycle. In embodiments, provided herein is a system for transportation having a data processing system for taking data from a plurality of social data sources and using a neural network to predict traffic congestion relating to a route for a vehicle and having a motorcycle helmet that is configured to provide an augmented reality experience based on registration of the location and orientation of the wearer in an environment. In embodiments, provided herein is a system for transportation having a data processing system for taking data from a plurality of social data sources and using a neural network to predict traffic congestion relating to a route for a vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a neural network to predict traffic congestion relating to a route for a vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a neural network to predict traffic congestion relating to a route for a vehicle and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a neural network to predict traffic congestion relating to a route for a vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a neural network to predict traffic congestion relating to a route for a vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a neural network to predict traffic congestion relating to a route for a vehicle and having a cognitive radio system for managing peer-to-peer communications within a mobile ad hoc network of self-driving vehicles. In embodiments, provided herein is a system for transportation having a data processing system for taking data from a plurality of social data sources and using a neural network to predict traffic congestion relating to a route for a vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a neural network to predict traffic congestion relating to a route for a vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a neural network to predict traffic congestion relating to a route for a vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a neural network to predict traffic congestion relating to a route for a vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a neural network to predict traffic congestion relating to a route for a vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a neural network to predict traffic congestion relating to a route for a vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a neural network to predict traffic congestion relating to a route for a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a neural network to predict traffic congestion relating to a route for a vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan based on inputs relating to a self-driving vehicle. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a neural network to predict traffic congestion relating to a route for a vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a neural network to predict traffic congestion relating to a route for a vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a neural network to predict traffic congestion relating to a route for a vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a neural network to predict traffic congestion relating to a route for a vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a neural network to predict traffic congestion relating to a route for a vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a neural network to predict traffic congestion relating to a route for a vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a neural network to predict traffic congestion relating to a route for a vehicle and having an artificial intelligence system that automatically randomizes a parameter of an in-vehicle experience in order to improve a user state that benefits from variation. In embodiments, provided herein is a system for transportation having a data processing system for taking data from a plurality of social data sources and using a neural network to predict traffic congestion relating to a route for a vehicle and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a neural network to predict traffic congestion relating to a route for a vehicle and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a neural network to predict traffic congestion relating to a route for a vehicle and having a dietary control system wherein at least one of a food or a beverage is made available under control of an automated control system. In embodiments, provided herein is a system for transportation having a data processing system for taking data from a plurality of social data sources and using a neural network to predict traffic congestion relating to a route for a vehicle and having an automated restocking system for an in-vehicle dietary system. In embodiments, provided herein is a system for transportation having a data processing system for taking data from a plurality of social data sources and using a neural network to predict traffic congestion relating to a route for a vehicle and having a system for optimizing at least one of a vehicle parameter and a user experience parameter to provide a margin of safety. In embodiments, provided herein is a system for transportation having a data processing system for taking data from a plurality of social data sources and using a neural network to predict traffic congestion relating to a route for a vehicle and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a neural network to predict traffic congestion relating to a route for a vehicle and having an expert system for allocating rewards across one or more different types of objectives within a transportation system. In embodiments, provided herein is a system for transportation having a data processing system for taking data from a plurality of social data sources and using a neural network to predict traffic congestion relating to a route for a vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a neural network to predict traffic congestion relating to a route for a vehicle and having a search system that is configured to provide network search results for in-vehicle searchers.

In embodiments, provided herein is a system for transportation having a data processing system for taking data from a plurality of social data sources and using a hybrid neural network to optimize an operating state of a transportation system based on processing the social data sources with the hybrid neural network. In embodiments, provided herein is a system for transportation having a data processing system for taking data from a plurality of social data sources and using a hybrid neural network to optimize an operating state of a transportation system based on processing the social data sources with the hybrid neural network and having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a hybrid neural network to optimize an operating state of a transportation system based on processing the social data sources with the hybrid neural network and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a hybrid neural network to optimize an operating state of a transportation system based on processing the social data sources with the hybrid neural network and having an entertainment system configured to provide entertainment to an automobile rider while maintaining the rider's orientation to the environment of the vehicle. In embodiments, provided herein is a system for transportation having a data processing system for taking data from a plurality of social data sources and using a hybrid neural network to optimize an operating state of a transportation system based on processing the social data sources with the hybrid neural network and having an automobile seating system with at least one rear-facing lay-flat seat that is configured to move between a flat configuration and an upright configuration. In embodiments, provided herein is a system for transportation having a data processing system for taking data from a plurality of social data sources and using a hybrid neural network to optimize an operating state of a transportation system based on processing the social data sources with the hybrid neural network and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a hybrid neural network to optimize an operating state of a transportation system based on processing the social data sources with the hybrid neural network and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a transportation system based on processing the social data sources with the hybrid neural network and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a transportation system based on processing the social data sources with the hybrid neural network and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a hybrid neural network to optimize an operating state of a transportation system based on processing the social data sources with the hybrid neural network and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a hybrid neural network to optimize an operating state of a transportation system based on processing the social data sources with the hybrid neural network and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a hybrid neural network to optimize an operating state of a transportation system based on processing the social data sources with the hybrid neural network and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a hybrid neural network to optimize an operating state of a transportation system based on processing the social data sources with the hybrid neural network and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a transportation system based on processing the social data sources with the hybrid neural network and having a self-driving motorcycle. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet that is configured to provide an augmented reality experience based on registration of the location and orientation of the wearer in an environment. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a hybrid neural network to optimize an operating state of a transportation system based on processing the social data sources with the hybrid neural network and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a hybrid neural network to optimize an operating state of a transportation system based on processing the social data sources with the hybrid neural network and having a cognitive radio system for managing peer-to-peer communications within a mobile ad hoc network of self-driving vehicles. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a hybrid neural network to optimize an operating state of a transportation system based on processing the social data sources with the hybrid neural network and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a hybrid neural network to optimize an operating state of a transportation system based on processing the social data sources with the hybrid neural network and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a hybrid neural network to optimize an operating state of a transportation system based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a hybrid neural network to optimize an operating state of a transportation system based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan based on inputs relating to a self-driving vehicle. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a hybrid neural network to optimize an operating state of a transportation system based on processing the social data sources with the hybrid neural network and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a hybrid neural network to optimize an operating state of a transportation system based on processing the social data sources with the hybrid neural network and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a hybrid neural network to optimize an operating state of a transportation system based on processing the social data sources with the hybrid neural network and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a hybrid neural network to optimize an operating state of a transportation system based on processing the social data sources with the hybrid neural network and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a hybrid neural network to optimize an operating state of a transportation system based on processing the social data sources with the hybrid neural network and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a hybrid neural network to optimize an operating state of a transportation system based on processing the social data sources with the hybrid neural network and having an artificial intelligence system that automatically randomizes a parameter of an in-vehicle experience in order to improve a user state that benefits from variation. In embodiments, provided herein is a system for transportation having a data processing system for taking data from a plurality of social data sources and using a hybrid neural network to optimize an operating state of a transportation system based on processing the social data sources with the hybrid neural network and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a hybrid neural network to optimize an operating state of a transportation system based on processing the social data sources with the hybrid neural network and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a hybrid neural network to optimize an operating state of a transportation system based on processing the social data sources with the hybrid neural network and having a dietary control system wherein at least one of a food or a beverage is made available under control of an automated control system. In embodiments, provided herein is a system for transportation having a data processing system for taking data from a plurality of social data sources and using a hybrid neural network to optimize an operating state of a transportation system based on processing the social data sources with the hybrid neural network and having an automated restocking system for an in-vehicle dietary system. In embodiments, provided herein is a system for transportation having a data processing system for taking data from a plurality of social data sources and using a hybrid neural network to optimize an operating state of a transportation system based on processing the social data sources with the hybrid neural network and having a system for optimizing at least one of a vehicle parameter and a user experience parameter to provide a margin of safety. In embodiments, provided herein is a system for transportation having a data processing system for taking data from a plurality of social data sources and using a hybrid neural network to optimize an operating state of a transportation system based on processing the social data sources with the hybrid neural network and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a hybrid neural network to optimize an operating state of a transportation system based on processing the social data sources with the hybrid neural network and having an expert system for allocating rewards across one or more different types of objectives within a transportation system. In embodiments, provided herein is a system for transportation having a data processing system for taking data from a plurality of social data sources and using a hybrid neural network to optimize an operating state of a transportation system based on processing the social data sources with the hybrid neural network and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a hybrid neural network to optimize an operating state of a transportation system based on processing the social data sources with the hybrid neural network and having a search system that is configured to provide network search results for in-vehicle searchers.

In embodiments, provided herein is a system for transportation having a data processing system for taking data from a plurality of social data sources and using a hybrid neural network to optimize an operating state of a vehicle based on processing the social data sources with the hybrid neural network. In embodiments, provided herein is a system for transportation having a data processing system for taking data from a plurality of social data sources and using a hybrid neural network to optimize an operating state of a vehicle based on processing the social data sources with the hybrid neural network and having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a hybrid neural network to optimize an operating state of a vehicle based on processing the social data sources with the hybrid neural network and having an entertainment system configured to provide entertainment to an automobile rider while maintaining the rider's orientation to the environment of the vehicle. In embodiments, provided herein is a system for transportation having a data processing system for taking data from a plurality of social data sources and using a hybrid neural network to optimize an operating state of a vehicle based on processing the social data sources with the hybrid neural network and having an automobile seating system with at least one rear-facing lay-flat seat that is configured to move between a flat configuration and an upright configuration. In embodiments, provided herein is a system for transportation having a data processing system for taking data from a plurality of social data sources and using a hybrid neural network to optimize an operating state of a vehicle based on processing the social data sources with the hybrid neural network and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a hybrid neural network to optimize an operating state of a vehicle based on processing the social data sources with the hybrid neural network and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a vehicle based on processing the social data sources with the hybrid neural network and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a vehicle based on processing the social data sources with the hybrid neural network and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a hybrid neural network to optimize an operating state of a vehicle based on processing the social data sources with the hybrid neural network and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a hybrid neural network to optimize an operating state of a vehicle based on processing the social data sources with the hybrid neural network and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a hybrid neural network to optimize an operating state of a vehicle based on processing the social data sources with the hybrid neural network and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a hybrid neural network to optimize an operating state of a vehicle based on processing the social data sources with the hybrid neural network and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize an operating state of a vehicle based on processing the social data sources with the hybrid neural network and having a self-driving motorcycle. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet that is configured to provide an augmented reality experience based on registration of the location and orientation of the wearer in an environment. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a hybrid neural network to optimize an operating state of a vehicle based on processing the social data sources with the hybrid neural network and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a hybrid neural network to optimize an operating state of a vehicle based on processing the social data sources with the hybrid neural network and having a cognitive radio system for managing peer-to-peer communications within a mobile ad hoc network of self-driving vehicles. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a hybrid neural network to optimize an operating state of a vehicle based on processing the social data sources with the hybrid neural network and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a hybrid neural network to optimize an operating state of a vehicle based on processing the social data sources with the hybrid neural network and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a hybrid neural network to optimize an operating state of a vehicle based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a hybrid neural network to optimize an operating state of a vehicle based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan based on inputs relating to a self-driving vehicle. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a hybrid neural network to optimize an operating state of a vehicle based on processing the social data sources with the hybrid neural network and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a hybrid neural network to optimize an operating state of a vehicle based on processing the social data sources with the hybrid neural network and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a hybrid neural network to optimize an operating state of a vehicle based on processing the social data sources with the hybrid neural network and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a hybrid neural network to optimize an operating state of a vehicle based on processing the social data sources with the hybrid neural network and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a hybrid neural network to optimize an operating state of a vehicle based on processing the social data sources with the hybrid neural network and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a hybrid neural network to optimize an operating state of a vehicle based on processing the social data sources with the hybrid neural network and having an artificial intelligence system that automatically randomizes a parameter of an in-vehicle experience in order to improve a user state that benefits from variation. In embodiments, provided herein is a system for transportation having a data processing system for taking data from a plurality of social data sources and using a hybrid neural network to optimize an operating state of a vehicle based on processing the social data sources with the hybrid neural network and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a hybrid neural network to optimize an operating state of a vehicle based on processing the social data sources with the hybrid neural network and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a hybrid neural network to optimize an operating state of a vehicle based on processing the social data sources with the hybrid neural network and having a dietary control system wherein at least one of a food or a beverage is made available under control of an automated control system. In embodiments, provided herein is a system for transportation having a data processing system for taking data from a plurality of social data sources and using a hybrid neural network to optimize an operating state of a vehicle based on processing the social data sources with the hybrid neural network and having an automated restocking system for an in-vehicle dietary system. In embodiments, provided herein is a system for transportation having a data processing system for taking data from a plurality of social data sources and using a hybrid neural network to optimize an operating state of a vehicle based on processing the social data sources with the hybrid neural network and having a system for optimizing at least one of a vehicle parameter and a user experience parameter to provide a margin of safety. In embodiments, provided herein is a system for transportation having a data processing system for taking data from a plurality of social data sources and using a hybrid neural network to optimize an operating state of a vehicle based on processing the social data sources with the hybrid neural network and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a hybrid neural network to optimize an operating state of a vehicle based on processing the social data sources with the hybrid neural network and having an expert system for allocating rewards across one or more different types of objectives within a transportation system. In embodiments, provided herein is a system for transportation having a data processing system for taking data from a plurality of social data sources and using a hybrid neural network to optimize an operating state of a vehicle based on processing the social data sources with the hybrid neural network and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a hybrid neural network to optimize an operating state of a vehicle based on processing the social data sources with the hybrid neural network and having a search system that is configured to provide network search results for in-vehicle searchers.

In embodiments, provided herein is a system for transportation having a data processing system for taking data from a plurality of social data sources and using a hybrid neural network to optimize satisfaction of at least one rider in a vehicle based on processing the social data sources with the hybrid neural network. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing a sensor input about a rider of a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a two-person automobile seating system with dual, lay-flat seats that are configured to move between a flat configuration to facilitate sleep and a seated configuration to facilitate waking activity. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an entertainment system configured to provide entertainment to an automobile rider while maintaining the rider's orientation to the environment of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an automobile seating system with at least one rear-facing lay-flat seat that is configured to move between a flat configuration and an upright configuration. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an automobile seating system with at least one rear-facing seat that is configured with at least one visual orientation system to maintain a rider's orientation to the surrounding environment. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing a voice of a rider in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing a sensory input from a wearable device in a vehicle to determine an emotional state and optimizing at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing an input from at least one seat sensor to determine an emotional state of a rider and optimizing at least one operating parameter of the vehicle to improve the rider's emotional state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing an input from at least one sensor to determine a comfort state and optimizing at least one configuration parameter of the seat to improve the rider's comfort. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for processing an input from at least one sensor that indicates a rider's posture to determine a comfort state and optimizing at least one configuration parameter of the seat to improve the rider's comfort. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a helmet configured for use with a self-driving vehicle, wherein the helmet is configured to provide an augmented reality experience based on registration of the location and orientation of the self-driving vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a self-driving motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet that is configured to provide an augmented reality experience based on registration of the location and orientation of the wearer in an environment. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet configured with a data processor and configured to communicate with a self-driving motorcycle for coordinated control of the helmet and the motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cognitive radio system for managing peer-to-peer communications within a mobile ad hoc network of self-driving vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan based on inputs relating to a self-driving vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan for a vehicle based on inputs relating to a self-driving vehicle, wherein the inputs include a route plan for the vehicle. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an artificial intelligence system that automatically randomizes a parameter of an in-vehicle experience in order to improve a user state that benefits from variation. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a system for taking an indicator of a hormonal system level of a user and automatically varying a user experience in the vehicle to promote a healthy hormonal state. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a system for taking an indicator of a hormonal system level of a user and automatically varying a user experience in the vehicle to promote a hormonal state that promotes safety. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a dietary control system wherein at least one of a food or a beverage is made available under control of an automated control system. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an automated restocking system for an in-vehicle dietary system. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a system for optimizing at least one of a vehicle parameter and a user experience parameter to provide a margin of safety. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an interface by which a set of expert systems may be configured to provide respective outputs for managing at least one of a set of vehicle parameters, a set of fleet parameters and a set of user experience parameters. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an expert system for allocating rewards across one or more different types of objectives within a transportation system. In embodiments, provided herein is a system for transportation having a data processing system for taking data from a plurality of social data sources and using a hybrid neural network to optimize satisfaction of at least one rider in a vehicle based on processing the social data sources with the hybrid neural network and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a data processing system for taking data from a plurality of social data sources and using a hybrid neural network to optimize satisfaction of at least one rider in a vehicle based on processing the social data sources with the hybrid neural network and having a search system that is configured to provide network search results for in-vehicle searchers.

In embodiments, provided herein is a system for transportation having an artificial intelligence system for processing a sensor input about a rider of a vehicle to determine an emotional state and optimizing at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having a two-person automobile seating system with dual, lay-flat seats that are configured to move between a flat configuration to facilitate sleep and a seated configuration to facilitate waking activity. In embodiments, provided herein is a system for transportation having an artificial intelligence system for processing a sensor input about a rider of a vehicle to determine an emotional state and optimizing at least one operating parameter of the vehicle to improve the rider's emotional state and having an entertainment system configured to provide entertainment to an automobile rider while maintaining the rider's orientation to the environment of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an automobile seating system with at least one rear-facing lay-flat seat that is configured to move between a flat configuration and an upright configuration. In embodiments, provided herein is a system for transportation having an artificial intelligence system for processing a sensor input about a rider of a vehicle to determine an emotional state and optimizing at least one operating parameter of the vehicle to improve the rider's emotional state and having an automobile seating system with at least one rear-facing seat that is configured with at least one visual orientation system to maintain a rider's orientation to the surrounding environment. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing a voice of a rider in a vehicle to determine an emotional state and optimizing at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing a sensor input about a rider of a vehicle to determine an emotional state and optimizing at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing a sensor input about a rider of a vehicle to determine an emotional state and optimizing at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a self-driving motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing a sensor input about a rider of a vehicle to determine an emotional state and optimizing at least one operating parameter of the vehicle to improve the rider's emotional state and having a cognitive radio system for managing peer-to-peer communications within a mobile ad hoc network of self-driving vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing a sensor input about a rider of a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan based on inputs relating to a self-driving vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing a sensor input about a rider of a vehicle to determine an emotional state and optimizing at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing a sensor input about a rider of a vehicle to determine an emotional state and optimizing at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing a sensor input about a rider of a vehicle to determine an emotional state and optimizing at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing a sensor input about a rider of a vehicle to determine an emotional state and optimizing at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing a sensor input about a rider of a vehicle to determine an emotional state and optimizing at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having an artificial intelligence system for processing a sensor input about a rider of a vehicle to determine an emotional state and optimizing at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having an artificial intelligence system for processing a sensor input about a rider of a vehicle to determine an emotional state and optimizing at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having an artificial intelligence system for processing a sensor input about a rider of a vehicle to determine an emotional state and optimizing at least one operating parameter of the vehicle to improve the rider's emotional state and having a dietary control system wherein at least one of a food or a beverage is made available under control of an automated control system. In embodiments, provided herein is a system for transportation having an artificial intelligence system for processing a sensor input about a rider of a vehicle to determine an emotional state and optimizing at least one operating parameter of the vehicle to improve the rider's emotional state and having an automated restocking system for an in-vehicle dietary system. In embodiments, provided herein is a system for transportation having an artificial intelligence system for processing a sensor input about a rider of a vehicle to determine an emotional state and optimizing at least one operating parameter of the vehicle to improve the rider's emotional state and having a system for optimizing at least one of a vehicle parameter and a user experience parameter to provide a margin of safety. In embodiments, provided herein is a system for transportation having an artificial intelligence system for processing a sensor input about a rider of a vehicle to determine an emotional state and optimizing at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing a sensor input about a rider of a vehicle to determine an emotional state and optimizing at least one operating parameter of the vehicle to improve the rider's emotional state and having an expert system for allocating rewards across one or more different types of objectives within a transportation system. In embodiments, provided herein is a system for transportation having an artificial intelligence system for processing a sensor input about a rider of a vehicle to determine an emotional state and optimizing at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing a sensor input about a rider of a vehicle to determine an emotional state and optimizing at least one operating parameter of the vehicle to improve the rider's emotional state and having a search system that is configured to provide network search results for in-vehicle searchers.

In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a two-person automobile seating system with dual, lay-flat seats that are configured to move between a flat configuration to facilitate sleep and a seated configuration to facilitate waking activity. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an entertainment system configured to provide entertainment to an automobile rider while maintaining the rider's orientation to the environment of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an automobile seating system with at least one rear-facing lay-flat seat that is configured to move between a flat configuration and an upright configuration. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an automobile seating system with at least one rear-facing seat that is configured with at least one visual orientation system to maintain a rider's orientation to the surrounding environment. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing a voice of a rider in a vehicle to determine an emotional state and optimizing at least one operating parameter of the vehicle to improve the rider's emotional state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing a sensory input from a wearable device in a vehicle to determine an emotional state and optimizing at least one operating parameter of the vehicle to improve the rider's emotional state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing an input from at least one seat sensor to determine an emotional state of a rider and optimizing at least one operating parameter of the vehicle to improve the rider's emotional state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a self-driving motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cognitive radio system for managing peer-to-peer communications within a mobile ad hoc network of self-driving vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan based on inputs relating to a self-driving vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a dietary control system wherein at least one of a food or a beverage is made available under control of an automated control system. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an automated restocking system for an in-vehicle dietary system. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a system for optimizing at least one of a vehicle parameter and a user experience parameter to provide a margin of safety. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an expert system for allocating rewards across one or more different types of objectives within a transportation system. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network wherein one neural network processes a sensor input about a rider of a vehicle to determine an emotional state and another neural network optimizes at least one operating parameter of the vehicle to improve the rider's emotional state and having a search system that is configured to provide network search results for in-vehicle searchers.

In embodiments, provided herein is a system for transportation having a two-person automobile seating system with dual, lay-flat seats that are configured to move between a flat configuration to facilitate sleep and a seated configuration to facilitate waking activity. In embodiments, provided herein is a system for transportation having a two-person automobile seating system with dual, lay-flat seats that are configured to move between a flat configuration to facilitate sleep and a seated configuration to facilitate waking activity and having an entertainment system configured to provide entertainment to an automobile rider while maintaining the rider's orientation to the environment of the vehicle. In embodiments, provided herein is a system for transportation having a two-person automobile seating system with dual, lay-flat seats that are configured to move between a flat configuration to facilitate sleep and a seated configuration to facilitate waking activity and having an automobile seating system with at least one rear-facing lay-flat seat that is configured to move between a flat configuration and an upright configuration. In embodiments, provided herein is a system for transportation having a two-person automobile seating system with dual, lay-flat seats that are configured to move between a flat configuration to facilitate sleep and a seated configuration to facilitate waking activity and having an automobile seating system with at least one rear-facing seat that is configured with at least one visual orientation system to maintain a rider's orientation to the surrounding environment. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing a voice of a rider in a vehicle to determine an emotional state and optimizing at least one operating parameter of the vehicle to improve the rider's emotional state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing a sensory input from a wearable device in a vehicle to determine an emotional state and optimizing at least one operating parameter of the vehicle to improve the rider's emotional state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing an input from at least one seat sensor to determine an emotional state of a rider and optimizing at least one operating parameter of the vehicle to improve the rider's emotional state. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing an input from at least one sensor to determine a comfort state and optimizing at least one configuration parameter of the seat to improve the rider's comfort. In embodiments, provided herein is a system for transportation having a two-person automobile seating system with dual, lay-flat seats that are configured to move between a flat configuration to facilitate sleep and a seated configuration to facilitate waking activity and having an artificial intelligence system for processing an input from at least one sensor that indicates a rider's posture to determine a comfort state and optimizing at least one configuration parameter of the seat to improve the rider's comfort. In embodiments, provided herein is a system for transportation having a two-person automobile seating system with dual, lay-flat seats that are configured to move between a flat configuration to facilitate sleep and a seated configuration to facilitate waking activity and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a two-person automobile seating system with dual, lay-flat seats that are configured to move between a flat configuration to facilitate sleep and a seated configuration to facilitate waking activity and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a two-person automobile seating system with dual, lay-flat seats that are configured to move between a flat configuration to facilitate sleep and a seated configuration to facilitate waking activity and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a two-person automobile seating system with dual, lay-flat seats that are configured to move between a flat configuration to facilitate sleep and a seated configuration to facilitate waking activity and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a two-person automobile seating system with dual, lay-flat seats that are configured to move between a flat configuration to facilitate sleep and a seated configuration to facilitate waking activity and having a helmet configured for use with a self-driving vehicle, wherein the helmet is configured to provide an augmented reality experience based on registration of the location and orientation of the self-driving vehicle. In embodiments, provided herein is a system for transportation having a two-person automobile seating system with dual, lay-flat seats that are configured to move between a flat configuration to facilitate sleep and a seated configuration to facilitate waking activity and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a two-person automobile seating system with dual, lay-flat seats that are configured to move between a flat configuration to facilitate sleep and a seated configuration to facilitate waking activity and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a two-person automobile seating system with dual, lay-flat seats that are configured to move between a flat configuration to facilitate sleep and a seated configuration to facilitate waking activity and having a self-driving motorcycle. In embodiments, provided herein is a system for transportation having a two-person automobile seating system with dual, lay-flat seats that are configured to move between a flat configuration to facilitate sleep and a seated configuration to facilitate waking activity and having a motorcycle helmet that is configured to provide an augmented reality experience based on registration of the location and orientation of the wearer in an environment. In embodiments, provided herein is a system for transportation having a two-person automobile seating system with dual, lay-flat seats that are configured to move between a flat configuration to facilitate sleep and a seated configuration to facilitate waking activity and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a two-person automobile seating system with dual, lay-flat seats that are configured to move between a flat configuration to facilitate sleep and a seated configuration to facilitate waking activity and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a two-person automobile seating system with dual, lay-flat seats that are configured to move between a flat configuration to facilitate sleep and a seated configuration to facilitate waking activity and having a motorcycle helmet configured with a data processor and configured to communicate with a self-driving motorcycle for coordinated control of the helmet and the motorcycle. In embodiments, provided herein is a system for transportation having a two-person automobile seating system with dual, lay-flat seats that are configured to move between a flat configuration to facilitate sleep and a seated configuration to facilitate waking activity and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a two-person automobile seating system with dual, lay-flat seats that are configured to move between a flat configuration to facilitate sleep and a seated configuration to facilitate waking activity and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a two-person automobile seating system with dual, lay-flat seats that are configured to move between a flat configuration to facilitate sleep and a seated configuration to facilitate waking activity and having a cognitive radio system for managing peer-to-peer communications within a mobile ad hoc network of self-driving vehicles. In embodiments, provided herein is a system for transportation having a two-person automobile seating system with dual, lay-flat seats that are configured to move between a flat configuration to facilitate sleep and a seated configuration to facilitate waking activity and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a two-person automobile seating system with dual, lay-flat seats that are configured to move between a flat configuration to facilitate sleep and a seated configuration to facilitate waking activity and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a two-person automobile seating system with dual, lay-flat seats that are configured to move between a flat configuration to facilitate sleep and a seated configuration to facilitate waking activity and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a two-person automobile seating system with dual, lay-flat seats that are configured to move between a flat configuration to facilitate sleep and a seated configuration to facilitate waking activity and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a two-person automobile seating system with dual, lay-flat seats that are configured to move between a flat configuration to facilitate sleep and a seated configuration to facilitate waking activity and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a two-person automobile seating system with dual, lay-flat seats that are configured to move between a flat configuration to facilitate sleep and a seated configuration to facilitate waking activity and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a two-person automobile seating system with dual, lay-flat seats that are configured to move between a flat configuration to facilitate sleep and a seated configuration to facilitate waking activity and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a two-person automobile seating system with dual, lay-flat seats that are configured to move between a flat configuration to facilitate sleep and a seated configuration to facilitate waking activity and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan based on inputs relating to a self-driving vehicle. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a two-person automobile seating system with dual, lay-flat seats that are configured to move between a flat configuration to facilitate sleep and a seated configuration to facilitate waking activity and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a two-person automobile seating system with dual, lay-flat seats that are configured to move between a flat configuration to facilitate sleep and a seated configuration to facilitate waking activity and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan for a vehicle based on inputs relating to a self-driving vehicle, wherein the inputs include a route plan for the vehicle. In embodiments, provided herein is a system for transportation having a two-person automobile seating system with dual, lay-flat seats that are configured to move between a flat configuration to facilitate sleep and a seated configuration to facilitate waking activity and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a two-person automobile seating system with dual, lay-flat seats that are configured to move between a flat configuration to facilitate sleep and a seated configuration to facilitate waking activity and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a two-person automobile seating system with dual, lay-flat seats that are configured to move between a flat configuration to facilitate sleep and a seated configuration to facilitate waking activity and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a two-person automobile seating system with dual, lay-flat seats that are configured to move between a flat configuration to facilitate sleep and a seated configuration to facilitate waking activity and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a two-person automobile seating system with dual, lay-flat seats that are configured to move between a flat configuration to facilitate sleep and a seated configuration to facilitate waking activity and having an artificial intelligence system that automatically randomizes a parameter of an in-vehicle experience in order to improve a user state that benefits from variation. In embodiments, provided herein is a system for transportation having a two-person automobile seating system with dual, lay-flat seats that are configured to move between a flat configuration to facilitate sleep and a seated configuration to facilitate waking activity and having a system for taking an indicator of a hormonal system level of a user and automatically varying a user experience in the vehicle to promote a healthy hormonal state. In embodiments, provided herein is a system for transportation having a two-person automobile seating system with dual, lay-flat seats that are configured to move between a flat configuration to facilitate sleep and a seated configuration to facilitate waking activity and having a system for taking an indicator of a hormonal system level of a user and automatically varying a user experience in the vehicle to promote a hormonal state that promotes safety. In embodiments, provided herein is a system for transportation having a two-person automobile seating system with dual, lay-flat seats that are configured to move between a flat configuration to facilitate sleep and a seated configuration to facilitate waking activity and having a dietary control system wherein at least one of a food or a beverage is made available under control of an automated control system. In embodiments, provided herein is a system for transportation having a two-person automobile seating system with dual, lay-flat seats that are configured to move between a flat configuration to facilitate sleep and a seated configuration to facilitate waking activity and having an automated restocking system for an in-vehicle dietary system. In embodiments, provided herein is a system for transportation having a two-person automobile seating system with dual, lay-flat seats that are configured to move between a flat configuration to facilitate sleep and a seated configuration to facilitate waking activity and having a system for optimizing at least one of a vehicle parameter and a user experience parameter to provide a margin of safety. In embodiments, provided herein is a system for transportation having a two-person automobile seating system with dual, lay-flat seats that are configured to move between a flat configuration to facilitate sleep and a seated configuration to facilitate waking activity and having an interface by which a set of expert systems may be configured to provide respective outputs for managing at least one of a set of vehicle parameters, a set of fleet parameters and a set of user experience parameters. In embodiments, provided herein is a system for transportation having a two-person automobile seating system with dual, lay-flat seats that are configured to move between a flat configuration to facilitate sleep and a seated configuration to facilitate waking activity and having an expert system for allocating rewards across one or more different types of objectives within a transportation system. In embodiments, provided herein is a system for transportation having a two-person automobile seating system with dual, lay-flat seats that are configured to move between a flat configuration to facilitate sleep and a seated configuration to facilitate waking activity and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a two-person automobile seating system with dual, lay-flat seats that are configured to move between a flat configuration to facilitate sleep and a seated configuration to facilitate waking activity and having a search system that is configured to provide network search results for in-vehicle searchers.

In embodiments, provided herein is a system for transportation having an entertainment system configured to provide entertainment to an automobile rider while maintaining the rider's orientation to the environment of the vehicle. In embodiments, provided herein is a system for transportation having an entertainment system configured to provide entertainment to an automobile rider while maintaining the rider's orientation to the environment of the vehicle and having an automobile seating system with at least one rear-facing lay-flat seat that is configured to move between a flat configuration and an upright configuration. In embodiments, provided herein is a system for transportation having an entertainment system configured to provide entertainment to an automobile rider while maintaining the rider's orientation to the environment of the vehicle and having an automobile seating system with at least one rear-facing seat that is configured with at least one visual orientation system to maintain a rider's orientation to the surrounding environment. In embodiments, provided herein is a system for transportation having an entertainment system configured to provide entertainment to an automobile rider while maintaining the rider's orientation to the environment of the vehicle and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an entertainment system configured to provide entertainment to an automobile rider while maintaining the rider's orientation to the environment of the vehicle and having an artificial intelligence system for processing a voice of a rider in a vehicle to determine an emotional state and optimizing at least one operating parameter of the vehicle to improve the rider's emotional state. In embodiments, provided herein is a system for transportation having an entertainment system configured to provide entertainment to an automobile rider while maintaining the rider's orientation to the environment of the vehicle and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an entertainment system configured to provide entertainment to an automobile rider while maintaining the rider's orientation to the environment of the vehicle and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an entertainment system configured to provide entertainment to an automobile rider while maintaining the rider's orientation to the environment of the vehicle and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an entertainment system configured to provide entertainment to an automobile rider while maintaining the rider's orientation to the environment of the vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having an entertainment system configured to provide entertainment to an automobile rider while maintaining the rider's orientation to the environment of the vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having an entertainment system configured to provide entertainment to an automobile rider while maintaining the rider's orientation to the environment of the vehicle and having an artificial intelligence system for processing an input from at least one sensor to determine a comfort state and optimizing at least one configuration parameter of the seat to improve the rider's comfort. In embodiments, provided herein is a system for transportation having an entertainment system configured to provide entertainment to an automobile rider while maintaining the rider's orientation to the environment of the vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having an entertainment system configured to provide entertainment to an automobile rider while maintaining the rider's orientation to the environment of the vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an entertainment system configured to provide entertainment to an automobile rider while maintaining the rider's orientation to the environment of the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an entertainment system configured to provide entertainment to an automobile rider while maintaining the rider's orientation to the environment of the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an entertainment system configured to provide entertainment to an automobile rider while maintaining the rider's orientation to the environment of the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an entertainment system configured to provide entertainment to an automobile rider while maintaining the rider's orientation to the environment of the vehicle and having a helmet configured for use with a self-driving vehicle, wherein the helmet is configured to provide an augmented reality experience based on registration of the location and orientation of the self-driving vehicle. In embodiments, provided herein is a system for transportation having an entertainment system configured to provide entertainment to an automobile rider while maintaining the rider's orientation to the environment of the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an entertainment system configured to provide entertainment to an automobile rider while maintaining the rider's orientation to the environment of the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an entertainment system configured to provide entertainment to an automobile rider while maintaining the rider's orientation to the environment of the vehicle and having a self-driving motorcycle. In embodiments, provided herein is a system for transportation having an entertainment system configured to provide entertainment to an automobile rider while maintaining the rider's orientation to the environment of the vehicle and having a motorcycle helmet that is configured to provide an augmented reality experience based on registration of the location and orientation of the wearer in an environment. In embodiments, provided herein is a system for transportation having an entertainment system configured to provide entertainment to an automobile rider while maintaining the rider's orientation to the environment of the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an entertainment system configured to provide entertainment to an automobile rider while maintaining the rider's orientation to the environment of the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an entertainment system configured to provide entertainment to an automobile rider while maintaining the rider's orientation to the environment of the vehicle and having a motorcycle helmet configured with a data processor and configured to communicate with a self-driving motorcycle for coordinated control of the helmet and the motorcycle. In embodiments, provided herein is a system for transportation having an entertainment system configured to provide entertainment to an automobile rider while maintaining the rider's orientation to the environment of the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an entertainment system configured to provide entertainment to an automobile rider while maintaining the rider's orientation to the environment of the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an entertainment system configured to provide entertainment to an automobile rider while maintaining the rider's orientation to the environment of the vehicle and having a cognitive radio system for managing peer-to-peer communications within a mobile ad hoc network of self-driving vehicles. In embodiments, provided herein is a system for transportation having an entertainment system configured to provide entertainment to an automobile rider while maintaining the rider's orientation to the environment of the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an entertainment system configured to provide entertainment to an automobile rider while maintaining the rider's orientation to the environment of the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an entertainment system configured to provide entertainment to an automobile rider while maintaining the rider's orientation to the environment of the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an entertainment system configured to provide entertainment to an automobile rider while maintaining the rider's orientation to the environment of the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an entertainment system configured to provide entertainment to an automobile rider while maintaining the rider's orientation to the environment of the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an entertainment system configured to provide entertainment to an automobile rider while maintaining the rider's orientation to the environment of the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an entertainment system configured to provide entertainment to an automobile rider while maintaining the rider's orientation to the environment of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an entertainment system configured to provide entertainment to an automobile rider while maintaining the rider's orientation to the environment of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an entertainment system configured to provide entertainment to an automobile rider while maintaining the rider's orientation to the environment of the vehicle and having an artificial intelligence system for determining at least one parameter of a charging plan based on inputs relating to a self-driving vehicle. In embodiments, provided herein is a system for transportation having an entertainment system configured to provide entertainment to an automobile rider while maintaining the rider's orientation to the environment of the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an entertainment system configured to provide entertainment to an automobile rider while maintaining the rider's orientation to the environment of the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an entertainment system configured to provide entertainment to an automobile rider while maintaining the rider's orientation to the environment of the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an entertainment system configured to provide entertainment to an automobile rider while maintaining the rider's orientation to the environment of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an entertainment system configured to provide entertainment to an automobile rider while maintaining the rider's orientation to the environment of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an entertainment system configured to provide entertainment to an automobile rider while maintaining the rider's orientation to the environment of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an entertainment system configured to provide entertainment to an automobile rider while maintaining the rider's orientation to the environment of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having an entertainment system configured to provide entertainment to an automobile rider while maintaining the rider's orientation to the environment of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an entertainment system configured to provide entertainment to an automobile rider while maintaining the rider's orientation to the environment of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an entertainment system configured to provide entertainment to an automobile rider while maintaining the rider's orientation to the environment of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an entertainment system configured to provide entertainment to an automobile rider while maintaining the rider's orientation to the environment of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an entertainment system configured to provide entertainment to an automobile rider while maintaining the rider's orientation to the environment of the vehicle and having an artificial intelligence system that automatically randomizes a parameter of an in-vehicle experience in order to improve a user state that benefits from variation. In embodiments, provided herein is a system for transportation having an entertainment system configured to provide entertainment to an automobile rider while maintaining the rider's orientation to the environment of the vehicle and having a system for taking an indicator of a hormonal system level of a user and automatically varying a user experience in the vehicle to promote a healthy hormonal state. In embodiments, provided herein is a system for transportation having an entertainment system configured to provide entertainment to an automobile rider while maintaining the rider's orientation to the environment of the vehicle and having a system for taking an indicator of a hormonal system level of a user and automatically varying a user experience in the vehicle to promote a hormonal state that promotes safety. In embodiments, provided herein is a system for transportation having an entertainment system configured to provide entertainment to an automobile rider while maintaining the rider's orientation to the environment of the vehicle and having a dietary control system wherein at least one of a food or a beverage is made available under control of an automated control system. In embodiments, provided herein is a system for transportation having an entertainment system configured to provide entertainment to an automobile rider while maintaining the rider's orientation to the environment of the vehicle and having an automated restocking system for an in-vehicle dietary system. In embodiments, provided herein is a system for transportation having an entertainment system configured to provide entertainment to an automobile rider while maintaining the rider's orientation to the environment of the vehicle and having a system for optimizing at least one of a vehicle parameter and a user experience parameter to provide a margin of safety. In embodiments, provided herein is a system for transportation having an entertainment system configured to provide entertainment to an automobile rider while maintaining the rider's orientation to the environment of the vehicle and having an interface by which a set of expert systems may be configured to provide respective outputs for managing at least one of a set of vehicle parameters, a set of fleet parameters and a set of user experience parameters. In embodiments, provided herein is a system for transportation having an entertainment system configured to provide entertainment to an automobile rider while maintaining the rider's orientation to the environment of the vehicle and having an expert system for allocating rewards across one or more different types of objectives within a transportation system. In embodiments, provided herein is a system for transportation having an entertainment system configured to provide entertainment to an automobile rider while maintaining the rider's orientation to the environment of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an entertainment system configured to provide entertainment to an automobile rider while maintaining the rider's orientation to the environment of the vehicle and having a search system that is configured to provide network search results for in-vehicle searchers.

In embodiments, provided herein is a system for transportation having an automobile seating system with at least one rear-facing lay-flat seat that is configured to move between a flat configuration and an upright configuration. In embodiments, provided herein is a system for transportation having an automobile seating system with at least one rear-facing lay-flat seat that is configured to move between a flat configuration and an upright configuration and having an automobile seating system with at least one rear-facing seat that is configured with at least one visual orientation system to maintain a rider's orientation to the surrounding environment. In embodiments, provided herein is a system for transportation having an automobile seating system with at least one rear-facing lay-flat seat that is configured to move between a flat configuration and an upright configuration and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an automobile seating system with at least one rear-facing lay-flat seat that is configured to move between a flat configuration and an upright configuration and having an artificial intelligence system for processing a voice of a rider in a vehicle to determine an emotional state and optimizing at least one operating parameter of the vehicle to improve the rider's emotional state. In embodiments, provided herein is a system for transportation having an automobile seating system with at least one rear-facing lay-flat seat that is configured to move between a flat configuration and an upright configuration and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an automobile seating system with at least one rear-facing lay-flat seat that is configured to move between a flat configuration and an upright configuration and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an automobile seating system with at least one rear-facing lay-flat seat that is configured to move between a flat configuration and an upright configuration and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an automobile seating system with at least one rear-facing lay-flat seat that is configured to move between a flat configuration and an upright configuration and having an artificial intelligence system for processing a sensory input from a wearable device in a vehicle to determine an emotional state and optimizing at least one operating parameter of the vehicle to improve the rider's emotional state. In embodiments, provided herein is a system for transportation having an automobile seating system with at least one rear-facing lay-flat seat that is configured to move between a flat configuration and an upright configuration and having an artificial intelligence system for processing an input from at least one seat sensor to determine an emotional state of a rider and optimizing at least one operating parameter of the vehicle to improve the rider's emotional state. In embodiments, provided herein is a system for transportation having an automobile seating system with at least one rear-facing lay-flat seat that is configured to move between a flat configuration and an upright configuration and having an artificial intelligence system for processing an input from at least one sensor to determine a comfort state and optimizing at least one configuration parameter of the seat to improve the rider's comfort. In embodiments, provided herein is a system for transportation having an automobile seating system with at least one rear-facing lay-flat seat that is configured to move between a flat configuration and an upright configuration and having an artificial intelligence system for processing an input from at least one sensor that indicates a rider's posture to determine a comfort state and optimizing at least one configuration parameter of the seat to improve the rider's comfort. In embodiments, provided herein is a system for transportation having an automobile seating system with at least one rear-facing lay-flat seat that is configured to move between a flat configuration and an upright configuration and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an automobile seating system with at least one rear-facing lay-flat seat that is configured to move between a flat configuration and an upright configuration and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an automobile seating system with at least one rear-facing lay-flat seat that is configured to move between a flat configuration and an upright configuration and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an automobile seating system with at least one rear-facing lay-flat seat that is configured to move between a flat configuration and an upright configuration and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an automobile seating system with at least one rear-facing lay-flat seat that is configured to move between a flat configuration and an upright configuration and having a helmet configured for use with a self-driving vehicle, wherein the helmet is configured to provide an augmented reality experience based on registration of the location and orientation of the self-driving vehicle. In embodiments, provided herein is a system for transportation having an automobile seating system with at least one rear-facing lay-flat seat that is configured to move between a flat configuration and an upright configuration and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an automobile seating system with at least one rear-facing lay-flat seat that is configured to move between a flat configuration and an upright configuration and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an automobile seating system with at least one rear-facing lay-flat seat that is configured to move between a flat configuration and an upright configuration and having a self-driving motorcycle. In embodiments, provided herein is a system for transportation having an automobile seating system with at least one rear-facing lay-flat seat that is configured to move between a flat configuration and an upright configuration and having a motorcycle helmet that is configured to provide an augmented reality experience based on registration of the location and orientation of the wearer in an environment. In embodiments, provided herein is a system for transportation having an automobile seating system with at least one rear-facing lay-flat seat that is configured to move between a flat configuration and an upright configuration and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an automobile seating system with at least one rear-facing lay-flat seat that is configured to move between a flat configuration and an upright configuration and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an automobile seating system with at least one rear-facing lay-flat seat that is configured to move between a flat configuration and an upright configuration and having a motorcycle helmet configured with a data processor and configured to communicate with a self-driving motorcycle for coordinated control of the helmet and the motorcycle. In embodiments, provided herein is a system for transportation having an automobile seating system with at least one rear-facing lay-flat seat that is configured to move between a flat configuration and an upright configuration and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an automobile seating system with at least one rear-facing lay-flat seat that is configured to move between a flat configuration and an upright configuration and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an automobile seating system with at least one rear-facing lay-flat seat that is configured to move between a flat configuration and an upright configuration and having a cognitive radio system for managing peer-to-peer communications within a mobile ad hoc network of self-driving vehicles. In embodiments, provided herein is a system for transportation having an automobile seating system with at least one rear-facing lay-flat seat that is configured to move between a flat configuration and an upright configuration and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an automobile seating system with at least one rear-facing lay-flat seat that is configured to move between a flat configuration and an upright configuration and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an automobile seating system with at least one rear-facing lay-flat seat that is configured to move between a flat configuration and an upright configuration and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an automobile seating system with at least one rear-facing lay-flat seat that is configured to move between a flat configuration and an upright configuration and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an automobile seating system with at least one rear-facing lay-flat seat that is configured to move between a flat configuration and an upright configuration and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an automobile seating system with at least one rear-facing lay-flat seat that is configured to move between a flat configuration and an upright configuration and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an automobile seating system with at least one rear-facing lay-flat seat that is configured to move between a flat configuration and an upright configuration and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an automobile seating system with at least one rear-facing lay-flat seat that is configured to move between a flat configuration and an upright configuration and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an automobile seating system with at least one rear-facing lay-flat seat that is configured to move between a flat configuration and an upright configuration and having an artificial intelligence system for determining at least one parameter of a charging plan based on inputs relating to a self-driving vehicle. In embodiments, provided herein is a system for transportation having an automobile seating system with at least one rear-facing lay-flat seat that is configured to move between a flat configuration and an upright configuration and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an automobile seating system with at least one rear-facing lay-flat seat that is configured to move between a flat configuration and an upright configuration and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an automobile seating system with at least one rear-facing lay-flat seat that is configured to move between a flat configuration and an upright configuration and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an automobile seating system with at least one rear-facing lay-flat seat that is configured to move between a flat configuration and an upright configuration and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an automobile seating system with at least one rear-facing lay-flat seat that is configured to move between a flat configuration and an upright configuration and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an automobile seating system with at least one rear-facing lay-flat seat that is configured to move between a flat configuration and an upright configuration and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an automobile seating system with at least one rear-facing lay-flat seat that is configured to move between a flat configuration and an upright configuration and having an artificial intelligence system for determining at least one parameter of a charging plan for a vehicle based on inputs relating to a self-driving vehicle, wherein the inputs include a route plan for the vehicle. In embodiments, provided herein is a system for transportation having an automobile seating system with at least one rear-facing lay-flat seat that is configured to move between a flat configuration and an upright configuration and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an automobile seating system with at least one rear-facing lay-flat seat that is configured to move between a flat configuration and an upright configuration and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an automobile seating system with at least one rear-facing lay-flat seat that is configured to move between a flat configuration and an upright configuration and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an automobile seating system with at least one rear-facing lay-flat seat that is configured to move between a flat configuration and an upright configuration and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an automobile seating system with at least one rear-facing lay-flat seat that is configured to move between a flat configuration and an upright configuration and having an artificial intelligence system that automatically randomizes a parameter of an in-vehicle experience in order to improve a user state that benefits from variation. In embodiments, provided herein is a system for transportation having an automobile seating system with at least one rear-facing lay-flat seat that is configured to move between a flat configuration and an upright configuration and having a system for taking an indicator of a hormonal system level of a user and automatically varying a user experience in the vehicle to promote a healthy hormonal state. In embodiments, provided herein is a system for transportation having an automobile seating system with at least one rear-facing lay-flat seat that is configured to move between a flat configuration and an upright configuration and having a system for taking an indicator of a hormonal system level of a user and automatically varying a user experience in the vehicle to promote a hormonal state that promotes safety. In embodiments, provided herein is a system for transportation having an automobile seating system with at least one rear-facing lay-flat seat that is configured to move between a flat configuration and an upright configuration and having a dietary control system wherein at least one of a food or a beverage is made available under control of an automated control system. In embodiments, provided herein is a system for transportation having an automobile seating system with at least one rear-facing lay-flat seat that is configured to move between a flat configuration and an upright configuration and having an automated restocking system for an in-vehicle dietary system. In embodiments, provided herein is a system for transportation having an automobile seating system with at least one rear-facing lay-flat seat that is configured to move between a flat configuration and an upright configuration and having a system for optimizing at least one of a vehicle parameter and a user experience parameter to provide a margin of safety. In embodiments, provided herein is a system for transportation having an automobile seating system with at least one rear-facing lay-flat seat that is configured to move between a flat configuration and an upright configuration and having an interface by which a set of expert systems may be configured to provide respective outputs for managing at least one of a set of vehicle parameters, a set of fleet parameters and a set of user experience parameters. In embodiments, provided herein is a system for transportation having an automobile seating system with at least one rear-facing lay-flat seat that is configured to move between a flat configuration and an upright configuration and having an expert system for allocating rewards across one or more different types of objectives within a transportation system. In embodiments, provided herein is a system for transportation having an automobile seating system with at least one rear-facing lay-flat seat that is configured to move between a flat configuration and an upright configuration and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an automobile seating system with at least one rear-facing lay-flat seat that is configured to move between a flat configuration and an upright configuration and having a search system that is configured to provide network search results for in-vehicle searchers.

In embodiments, provided herein is a system for transportation having an automobile seating system with at least one rear-facing seat that is configured with at least one visual orientation system to maintain a rider's orientation to the surrounding environment. In embodiments, provided herein is a system for transportation having an automobile seating system with at least one rear-facing seat that is configured with at least one visual orientation system to maintain a rider's orientation to the surrounding environment and having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an automobile seating system with at least one rear-facing seat that is configured with at least one visual orientation system to maintain a rider's orientation to the surrounding environment and having an artificial intelligence system for processing a voice of a rider in a vehicle to determine an emotional state and optimizing at least one operating parameter of the vehicle to improve the rider's emotional state. In embodiments, provided herein is a system for transportation having an automobile seating system with at least one rear-facing seat that is configured with at least one visual orientation system to maintain a rider's orientation to the surrounding environment and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an automobile seating system with at least one rear-facing seat that is configured with at least one visual orientation system to maintain a rider's orientation to the surrounding environment and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an automobile seating system with at least one rear-facing seat that is configured with at least one visual orientation system to maintain a rider's orientation to the surrounding environment and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an automobile seating system with at least one rear-facing seat that is configured with at least one visual orientation system to maintain a rider's orientation to the surrounding environment and having an artificial intelligence system for processing a sensory input from a wearable device in a vehicle to determine an emotional state and optimizing at least one operating parameter of the vehicle to improve the rider's emotional state. In embodiments, provided herein is a system for transportation having an automobile seating system with at least one rear-facing seat that is configured with at least one visual orientation system to maintain a rider's orientation to the surrounding environment and having an artificial intelligence system for processing an input from at least one seat sensor to determine an emotional state of a rider and optimizing at least one operating parameter of the vehicle to improve the rider's emotional state. In embodiments, provided herein is a system for transportation having an automobile seating system with at least one rear-facing seat that is configured with at least one visual orientation system to maintain a rider's orientation to the surrounding environment and having an artificial intelligence system for processing an input from at least one sensor to determine a comfort state and optimizing at least one configuration parameter of the seat to improve the rider's comfort. In embodiments, provided herein is a system for transportation having an automobile seating system with at least one rear-facing seat that is configured with at least one visual orientation system to maintain a rider's orientation to the surrounding environment and having an artificial intelligence system for processing an input from at least one sensor that indicates a rider's posture to determine a comfort state and optimizing at least one configuration parameter of the seat to improve the rider's comfort. In embodiments, provided herein is a system for transportation having an automobile seating system with at least one rear-facing seat that is configured with at least one visual orientation system to maintain a rider's orientation to the surrounding environment and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an automobile seating system with at least one rear-facing seat that is configured with at least one visual orientation system to maintain a rider's orientation to the surrounding environment and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an automobile seating system with at least one rear-facing seat that is configured with at least one visual orientation system to maintain a rider's orientation to the surrounding environment and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an automobile seating system with at least one rear-facing seat that is configured with at least one visual orientation system to maintain a rider's orientation to the surrounding environment and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an automobile seating system with at least one rear-facing seat that is configured with at least one visual orientation system to maintain a rider's orientation to the surrounding environment and having a helmet configured for use with a self-driving vehicle, wherein the helmet is configured to provide an augmented reality experience based on registration of the location and orientation of the self-driving vehicle. In embodiments, provided herein is a system for transportation having an automobile seating system with at least one rear-facing seat that is configured with at least one visual orientation system to maintain a rider's orientation to the surrounding environment and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an automobile seating system with at least one rear-facing seat that is configured with at least one visual orientation system to maintain a rider's orientation to the surrounding environment and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an automobile seating system with at least one rear-facing seat that is configured with at least one visual orientation system to maintain a rider's orientation to the surrounding environment and having a self-driving motorcycle. In embodiments, provided herein is a system for transportation having an automobile seating system with at least one rear-facing seat that is configured with at least one visual orientation system to maintain a rider's orientation to the surrounding environment and having a motorcycle helmet that is configured to provide an augmented reality experience based on registration of the location and orientation of the wearer in an environment. In embodiments, provided herein is a system for transportation having an automobile seating system with at least one rear-facing seat that is configured with at least one visual orientation system to maintain a rider's orientation to the surrounding environment and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an automobile seating system with at least one rear-facing seat that is configured with at least one visual orientation system to maintain a rider's orientation to the surrounding environment and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an automobile seating system with at least one rear-facing seat that is configured with at least one visual orientation system to maintain a rider's orientation to the surrounding environment and having a motorcycle helmet configured with a data processor and configured to communicate with a self-driving motorcycle for coordinated control of the helmet and the motorcycle. In embodiments, provided herein is a system for transportation having an automobile seating system with at least one rear-facing seat that is configured with at least one visual orientation system to maintain a rider's orientation to the surrounding environment and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an automobile seating system with at least one rear-facing seat that is configured with at least one visual orientation system to maintain a rider's orientation to the surrounding environment and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an automobile seating system with at least one rear-facing seat that is configured with at least one visual orientation system to maintain a rider's orientation to the surrounding environment and having a cognitive radio system for managing peer-to-peer communications within a mobile ad hoc network of self-driving vehicles. In embodiments, provided herein is a system for transportation having an automobile seating system with at least one rear-facing seat that is configured with at least one visual orientation system to maintain a rider's orientation to the surrounding environment and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an automobile seating system with at least one rear-facing seat that is configured with at least one visual orientation system to maintain a rider's orientation to the surrounding environment and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an automobile seating system with at least one rear-facing seat that is configured with at least one visual orientation system to maintain a rider's orientation to the surrounding environment and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an automobile seating system with at least one rear-facing seat that is configured with at least one visual orientation system to maintain a rider's orientation to the surrounding environment and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an automobile seating system with at least one rear-facing seat that is configured with at least one visual orientation system to maintain a rider's orientation to the surrounding environment and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an automobile seating system with at least one rear-facing seat that is configured with at least one visual orientation system to maintain a rider's orientation to the surrounding environment and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an automobile seating system with at least one rear-facing seat that is configured with at least one visual orientation system to maintain a rider's orientation to the surrounding environment and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an automobile seating system with at least one rear-facing seat that is configured with at least one visual orientation system to maintain a rider's orientation to the surrounding environment and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan based on inputs relating to a self-driving vehicle. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an automobile seating system with at least one rear-facing seat that is configured with at least one visual orientation system to maintain a rider's orientation to the surrounding environment and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an automobile seating system with at least one rear-facing seat that is configured with at least one visual orientation system to maintain a rider's orientation to the surrounding environment and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan for a vehicle based on inputs relating to a self-driving vehicle, wherein the inputs include a route plan for the vehicle. In embodiments, provided herein is a system for transportation having an automobile seating system with at least one rear-facing seat that is configured with at least one visual orientation system to maintain a rider's orientation to the surrounding environment and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an automobile seating system with at least one rear-facing seat that is configured with at least one visual orientation system to maintain a rider's orientation to the surrounding environment and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an automobile seating system with at least one rear-facing seat that is configured with at least one visual orientation system to maintain a rider's orientation to the surrounding environment and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an automobile seating system with at least one rear-facing seat that is configured with at least one visual orientation system to maintain a rider's orientation to the surrounding environment and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an automobile seating system with at least one rear-facing seat that is configured with at least one visual orientation system to maintain a rider's orientation to the surrounding environment and having an artificial intelligence system that automatically randomizes a parameter of an in-vehicle experience in order to improve a user state that benefits from variation. In embodiments, provided herein is a system for transportation having an automobile seating system with at least one rear-facing seat that is configured with at least one visual orientation system to maintain a rider's orientation to the surrounding environment and having a system for taking an indicator of a hormonal system level of a user and automatically varying a user experience in the vehicle to promote a healthy hormonal state. In embodiments, provided herein is a system for transportation having an automobile seating system with at least one rear-facing seat that is configured with at least one visual orientation system to maintain a rider's orientation to the surrounding environment and having a system for taking an indicator of a hormonal system level of a user and automatically varying a user experience in the vehicle to promote a hormonal state that promotes safety. In embodiments, provided herein is a system for transportation having an automobile seating system with at least one rear-facing seat that is configured with at least one visual orientation system to maintain a rider's orientation to the surrounding environment and having a dietary control system wherein at least one of a food or a beverage is made available under control of an automated control system. In embodiments, provided herein is a system for transportation having an automobile seating system with at least one rear-facing seat that is configured with at least one visual orientation system to maintain a rider's orientation to the surrounding environment and having an automated restocking system for an in-vehicle dietary system. In embodiments, provided herein is a system for transportation having an automobile seating system with at least one rear-facing seat that is configured with at least one visual orientation system to maintain a rider's orientation to the surrounding environment and having a system for optimizing at least one of a vehicle parameter and a user experience parameter to provide a margin of safety. In embodiments, provided herein is a system for transportation having an automobile seating system with at least one rear-facing seat that is configured with at least one visual orientation system to maintain a rider's orientation to the surrounding environment and having an interface by which a set of expert systems may be configured to provide respective outputs for managing at least one of a set of vehicle parameters, a set of fleet parameters and a set of user experience parameters. In embodiments, provided herein is a system for transportation having an automobile seating system with at least one rear-facing seat that is configured with at least one visual orientation system to maintain a rider's orientation to the surrounding environment and having an expert system for allocating rewards across one or more different types of objectives within a transportation system. In embodiments, provided herein is a system for transportation having an automobile seating system with at least one rear-facing seat that is configured with at least one visual orientation system to maintain a rider's orientation to the surrounding environment and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an automobile seating system with at least one rear-facing seat that is configured with at least one visual orientation system to maintain a rider's orientation to the surrounding environment and having a search system that is configured to provide network search results for in-vehicle searchers.

In embodiments, provided herein is a system for transportation having an artificial intelligence system for processing feature vectors of an image of a face of a rider in a vehicle to determine an emotional state and optimizing at least one operating parameter of the vehicle to improve the rider's emotional state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing a voice of a rider in a vehicle to determine an emotional state and optimizing at least one operating parameter of the vehicle to improve the rider's emotional state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a self-driving motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cognitive radio system for managing peer-to-peer communications within a mobile ad hoc network of self-driving vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling.

In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a dietary control system wherein at least one of a food or a beverage is made available under control of an automated control system. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an automated restocking system for an in-vehicle dietary system. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a system for optimizing at least one of a vehicle parameter and a user experience parameter to provide a margin of safety. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an expert system for allocating rewards across one or more different types of objectives within a transportation system. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing feature vectors of an image of a face of a rider in a vehicle to determine an emotional state and optimizing at least one operating parameter of the vehicle to improve the rider's emotional state and having a search system that is configured to provide network search results for in-vehicle searchers.

In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing a voice of a rider in a vehicle to determine an emotional state and optimizing at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing a voice of a rider in a vehicle to determine an emotional state and optimizing at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a voice of a rider in a vehicle to determine an emotional state and optimizing at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing a voice of a rider in a vehicle to determine an emotional state and optimizing at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing a voice of a rider in a vehicle to determine an emotional state and optimizing at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing a voice of a rider in a vehicle to determine an emotional state and optimizing at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing a voice of a rider in a vehicle to determine an emotional state and optimizing at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a voice of a rider in a vehicle to determine an emotional state and optimizing at least one operating parameter of the vehicle to improve the rider's emotional state and having a self-driving motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing a voice of a rider in a vehicle to determine an emotional state and optimizing at least one operating parameter of the vehicle to improve the rider's emotional state and having a cognitive radio system for managing peer-to-peer communications within a mobile ad hoc network of self-driving vehicles. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing a voice of a rider in a vehicle to determine an emotional state and optimizing at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing a voice of a rider in a vehicle to determine an emotional state and optimizing at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing a voice of a rider in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing a voice of a rider in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing a voice of a rider in a vehicle to determine an emotional state and optimizing at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing a voice of a rider in a vehicle to determine an emotional state and optimizing at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing a voice of a rider in a vehicle to determine an emotional state and optimizing at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing a voice of a rider in a vehicle to determine an emotional state and optimizing at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing a voice of a rider in a vehicle to determine an emotional state and optimizing at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing a voice of a rider in a vehicle to determine an emotional state and optimizing at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having an artificial intelligence system for processing a voice of a rider in a vehicle to determine an emotional state and optimizing at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having an artificial intelligence system for processing a voice of a rider in a vehicle to determine an emotional state and optimizing at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having an artificial intelligence system for processing a voice of a rider in a vehicle to determine an emotional state and optimizing at least one operating parameter of the vehicle to improve the rider's emotional state and having a dietary control system wherein at least one of a food or a beverage is made available under control of an automated control system. In embodiments, provided herein is a system for transportation having an artificial intelligence system for processing a voice of a rider in a vehicle to determine an emotional state and optimizing at least one operating parameter of the vehicle to improve the rider's emotional state and having an automated restocking system for an in-vehicle dietary system. In embodiments, provided herein is a system for transportation having an artificial intelligence system for processing a voice of a rider in a vehicle to determine an emotional state and optimizing at least one operating parameter of the vehicle to improve the rider's emotional state and having a system for optimizing at least one of a vehicle parameter and a user experience parameter to provide a margin of safety. In embodiments, provided herein is a system for transportation having an artificial intelligence system for processing a voice of a rider in a vehicle to determine an emotional state and optimizing at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing a voice of a rider in a vehicle to determine an emotional state and optimizing at least one operating parameter of the vehicle to improve the rider's emotional state and having an expert system for allocating rewards across one or more different types of objectives within a transportation system. In embodiments, provided herein is a system for transportation having an artificial intelligence system for processing a voice of a rider in a vehicle to determine an emotional state and optimizing at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing a voice of a rider in a vehicle to determine an emotional state and optimizing at least one operating parameter of the vehicle to improve the rider's emotional state and having a search system that is configured to provide network search results for in-vehicle searchers.

In embodiments, provided herein is a system for transportation having an artificial intelligence system for processing at least one input from a rider to a search interface of a self-driving vehicle to determine a state and optimizing at least one operating parameter of the self-driving vehicle to improve the rider's state. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a self-driving motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet that is configured to provide an augmented reality experience based on registration of the location and orientation of the wearer in an environment. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet configured with a data processor and configured to communicate with a self-driving motorcycle for coordinated control of the helmet and the motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cognitive radio system for managing peer-to-peer communications within a mobile ad hoc network of self-driving vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan based on inputs relating to a self-driving vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an artificial intelligence system that automatically randomizes a parameter of an in-vehicle experience in order to improve a user state that benefits from variation. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a system for taking an indicator of a hormonal system level of a user and automatically varying a user experience in the vehicle to promote a healthy hormonal state. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a system for taking an indicator of a hormonal system level of a user and automatically varying a user experience in the vehicle to promote a hormonal state that promotes safety. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a dietary control system wherein at least one of a food or a beverage is made available under control of an automated control system. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an automated restocking system for an in-vehicle dietary system. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a system for optimizing at least one of a vehicle parameter and a user experience parameter to provide a margin of safety. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an expert system for allocating rewards across one or more different types of objectives within a transportation system. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing at least one input from a rider to a search interface of a self-driving vehicle to determine a state and optimizing at least one operating parameter of the self-driving vehicle to improve the rider's state and having a search system that is configured to provide network search results for in-vehicle searchers.

In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a self-driving motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet that is configured to provide an augmented reality experience based on registration of the location and orientation of the wearer in an environment. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet configured with a data processor and configured to communicate with a self-driving motorcycle for coordinated control of the helmet and the motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cognitive radio system for managing peer-to-peer communications within a mobile ad hoc network of self-driving vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan based on inputs relating to a self-driving vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an artificial intelligence system that automatically randomizes a parameter of an in-vehicle experience in order to improve a user state that benefits from variation. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a system for taking an indicator of a hormonal system level of a user and automatically varying a user experience in the vehicle to promote a healthy hormonal state. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a system for taking an indicator of a hormonal system level of a user and automatically varying a user experience in the vehicle to promote a hormonal state that promotes safety. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a dietary control system wherein at least one of a food or a beverage is made available under control of an automated control system. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an automated restocking system for an in-vehicle dietary system. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a system for optimizing at least one of a vehicle parameter and a user experience parameter to provide a margin of safety. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an expert system for allocating rewards across one or more different types of objectives within a transportation system. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing data from an interaction of a rider with an electronic commerce system of a self-driving vehicle to determine a rider state and optimizing at least one operating parameter of the self-driving vehicle to improve the rider's state and having a search system that is configured to provide network search results for in-vehicle searchers.

In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a self-driving motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet that is configured to provide an augmented reality experience based on registration of the location and orientation of the wearer in an environment. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet configured with a data processor and configured to communicate with a self-driving motorcycle for coordinated control of the helmet and the motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cognitive radio system for managing peer-to-peer communications within a mobile ad hoc network of self-driving vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan based on inputs relating to a self-driving vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an artificial intelligence system that automatically randomizes a parameter of an in-vehicle experience in order to improve a user state that benefits from variation. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a system for taking an indicator of a hormonal system level of a user and automatically varying a user experience in the vehicle to promote a healthy hormonal state. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a system for taking an indicator of a hormonal system level of a user and automatically varying a user experience in the vehicle to promote a hormonal state that promotes safety. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a dietary control system wherein at least one of a food or a beverage is made available under control of an automated control system. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an automated restocking system for an in-vehicle dietary system. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a system for optimizing at least one of a vehicle parameter and a user experience parameter to provide a margin of safety. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an expert system for allocating rewards across one or more different types of objectives within a transportation system. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing data from at least one Internet of Things device in the environment of a self-driving vehicle to determine a state of the self-driving vehicle and optimizing at least one operating parameter of the self-driving vehicle to improve a rider's state based on the determined state of the self-driving vehicle and having a search system that is configured to provide network search results for in-vehicle searchers.

In embodiments, provided herein is a system for transportation having an artificial intelligence system for processing a sensory input from a wearable device in a vehicle to determine an emotional state and optimizing at least one operating parameter of the vehicle to improve the rider's emotional state. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing a sensory input from a wearable device in a vehicle to determine an emotional state and optimizing at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing a sensory input from a wearable device in a vehicle to determine an emotional state and optimizing at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a self-driving motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cognitive radio system for managing peer-to-peer communications within a mobile ad hoc network of self-driving vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing a sensory input from a wearable device in a vehicle to determine an emotional state and optimizing at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing a sensory input from a wearable device in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan based on inputs relating to a self-driving vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing a sensory input from a wearable device in a vehicle to determine an emotional state and optimizing at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing a sensory input from a wearable device in a vehicle to determine an emotional state and optimizing at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing a sensory input from a wearable device in a vehicle to determine an emotional state and optimizing at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing a sensory input from a wearable device in a vehicle to determine an emotional state and optimizing at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having an artificial intelligence system for processing a sensory input from a wearable device in a vehicle to determine an emotional state and optimizing at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having an artificial intelligence system for processing a sensory input from a wearable device in a vehicle to determine an emotional state and optimizing at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having an artificial intelligence system for processing a sensory input from a wearable device in a vehicle to determine an emotional state and optimizing at least one operating parameter of the vehicle to improve the rider's emotional state and having a dietary control system wherein at least one of a food or a beverage is made available under control of an automated control system. In embodiments, provided herein is a system for transportation having an artificial intelligence system for processing a sensory input from a wearable device in a vehicle to determine an emotional state and optimizing at least one operating parameter of the vehicle to improve the rider's emotional state and having an automated restocking system for an in-vehicle dietary system. In embodiments, provided herein is a system for transportation having an artificial intelligence system for processing a sensory input from a wearable device in a vehicle to determine an emotional state and optimizing at least one operating parameter of the vehicle to improve the rider's emotional state and having a system for optimizing at least one of a vehicle parameter and a user experience parameter to provide a margin of safety. In embodiments, provided herein is a system for transportation having an artificial intelligence system for processing a sensory input from a wearable device in a vehicle to determine an emotional state and optimizing at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing a sensory input from a wearable device in a vehicle to determine an emotional state and optimizing at least one operating parameter of the vehicle to improve the rider's emotional state and having an expert system for allocating rewards across one or more different types of objectives within a transportation system. In embodiments, provided herein is a system for transportation having an artificial intelligence system for processing a sensory input from a wearable device in a vehicle to determine an emotional state and optimizing at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing a sensory input from a wearable device in a vehicle to determine an emotional state and optimizing at least one operating parameter of the vehicle to improve the rider's emotional state and having a search system that is configured to provide network search results for in-vehicle searchers.

In embodiments, provided herein is a system for transportation having an artificial intelligence system for processing an input from at least one seat sensor to determine an emotional state of a rider and optimizing at least one operating parameter of the vehicle to improve the rider's emotional state. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for processing an input from at least one sensor to determine a comfort state and optimizing at least one configuration parameter of the seat to improve the rider's comfort. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing an input from at least one seat sensor to determine an emotional state of a rider and optimizing at least one operating parameter of the vehicle to improve the rider's emotional state and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing an input from at least one seat sensor to determine an emotional state of a rider and optimizing at least one operating parameter of the vehicle to improve the rider's emotional state and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing an input from at least one seat sensor to determine an emotional state of a rider and optimizing at least one operating parameter of the vehicle to improve the rider's emotional state and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a self-driving motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet that is configured to provide an augmented reality experience based on registration of the location and orientation of the wearer in an environment. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet configured with a data processor and configured to communicate with a self-driving motorcycle for coordinated control of the helmet and the motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing an input from at least one seat sensor to determine an emotional state of a rider and optimizing at least one operating parameter of the vehicle to improve the rider's emotional state and having a cognitive radio system for managing peer-to-peer communications within a mobile ad hoc network of self-driving vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing an input from at least one seat sensor to determine an emotional state of a rider and optimizing at least one operating parameter of the vehicle to improve the rider's emotional state and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing an input from at least one seat sensor to determine an emotional state of a rider and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan based on inputs relating to a self-driving vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing an input from at least one seat sensor to determine an emotional state of a rider and optimizing at least one operating parameter of the vehicle to improve the rider's emotional state and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing an input from at least one seat sensor to determine an emotional state of a rider and optimizing at least one operating parameter of the vehicle to improve the rider's emotional state and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing an input from at least one seat sensor to determine an emotional state of a rider and optimizing at least one operating parameter of the vehicle to improve the rider's emotional state and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing an input from at least one seat sensor to determine an emotional state of a rider and optimizing at least one operating parameter of the vehicle to improve the rider's emotional state and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing an input from at least one seat sensor to determine an emotional state of a rider and optimizing at least one operating parameter of the vehicle to improve the rider's emotional state and having an artificial intelligence system that automatically randomizes a parameter of an in-vehicle experience in order to improve a user state that benefits from variation. In embodiments, provided herein is a system for transportation having an artificial intelligence system for processing an input from at least one seat sensor to determine an emotional state of a rider and optimizing at least one operating parameter of the vehicle to improve the rider's emotional state and having a system for taking an indicator of a hormonal system level of a user and automatically varying a user experience in the vehicle to promote a healthy hormonal state. In embodiments, provided herein is a system for transportation having an artificial intelligence system for processing an input from at least one seat sensor to determine an emotional state of a rider and optimizing at least one operating parameter of the vehicle to improve the rider's emotional state and having a system for taking an indicator of a hormonal system level of a user and automatically varying a user experience in the vehicle to promote a hormonal state that promotes safety. In embodiments, provided herein is a system for transportation having an artificial intelligence system for processing an input from at least one seat sensor to determine an emotional state of a rider and optimizing at least one operating parameter of the vehicle to improve the rider's emotional state and having a dietary control system wherein at least one of a food or a beverage is made available under control of an automated control system. In embodiments, provided herein is a system for transportation having an artificial intelligence system for processing an input from at least one seat sensor to determine an emotional state of a rider and optimizing at least one operating parameter of the vehicle to improve the rider's emotional state and having an automated restocking system for an in-vehicle dietary system. In embodiments, provided herein is a system for transportation having an artificial intelligence system for processing an input from at least one seat sensor to determine an emotional state of a rider and optimizing at least one operating parameter of the vehicle to improve the rider's emotional state and having a system for optimizing at least one of a vehicle parameter and a user experience parameter to provide a margin of safety. In embodiments, provided herein is a system for transportation having an artificial intelligence system for processing an input from at least one seat sensor to determine an emotional state of a rider and optimizing at least one operating parameter of the vehicle to improve the rider's emotional state and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing an input from at least one seat sensor to determine an emotional state of a rider and optimizing at least one operating parameter of the vehicle to improve the rider's emotional state and having an expert system for allocating rewards across one or more different types of objectives within a transportation system. In embodiments, provided herein is a system for transportation having an artificial intelligence system for processing an input from at least one seat sensor to determine an emotional state of a rider and optimizing at least one operating parameter of the vehicle to improve the rider's emotional state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing an input from at least one seat sensor to determine an emotional state of a rider and optimizing at least one operating parameter of the vehicle to improve the rider's emotional state and having a search system that is configured to provide network search results for in-vehicle searchers.

In embodiments, provided herein is a system for transportation having an artificial intelligence system for processing an input from at least one sensor to determine a comfort state and optimizing at least one configuration parameter of the seat to improve the rider's comfort. In embodiments, provided herein is a system for transportation having an artificial intelligence system for processing an input from at least one sensor to determine a comfort state and optimizing at least one configuration parameter of the seat to improve the rider's comfort and having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing an input from at least one sensor to determine a comfort state and optimizing at least one configuration parameter of the seat to improve the rider's comfort and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing an input from at least one sensor to determine a comfort state and optimizing at least one configuration parameter of the seat to improve the rider's comfort and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one sensor to determine a comfort state and optimizing at least one configuration parameter of the seat to improve the rider's comfort and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing an input from at least one sensor to determine a comfort state and optimizing at least one configuration parameter of the seat to improve the rider's comfort and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing an input from at least one sensor to determine a comfort state and optimizing at least one configuration parameter of the seat to improve the rider's comfort and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing an input from at least one sensor to determine a comfort state and optimizing at least one configuration parameter of the seat to improve the rider's comfort and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing an input from at least one sensor to determine a comfort state and optimizing at least one configuration parameter of the seat to improve the rider's comfort and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one sensor to determine a comfort state and optimizing at least one configuration parameter of the seat to improve the rider's comfort and having a self-driving motorcycle. In embodiments, provided herein is a system for transportation having an artificial intelligence system for processing an input from at least one sensor to determine a comfort state and optimizing at least one configuration parameter of the seat to improve the rider's comfort and having a motorcycle helmet that is configured to provide an augmented reality experience based on registration of the location and orientation of the wearer in an environment. In embodiments, provided herein is a system for transportation having an artificial intelligence system for processing an input from at least one sensor to determine a comfort state and optimizing at least one configuration parameter of the seat to improve the rider's comfort and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing an input from at least one sensor to determine a comfort state and optimizing at least one configuration parameter of the seat to improve the rider's comfort and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing an input from at least one sensor to determine a comfort state and optimizing at least one configuration parameter of the seat to improve the rider's comfort and having a motorcycle helmet configured with a data processor and configured to communicate with a self-driving motorcycle for coordinated control of the helmet and the motorcycle. In embodiments, provided herein is a system for transportation having an artificial intelligence system for processing an input from at least one sensor to determine a comfort state and optimizing at least one configuration parameter of the seat to improve the rider's comfort and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing an input from at least one sensor to determine a comfort state and optimizing at least one configuration parameter of the seat to improve the rider's comfort and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing an input from at least one sensor to determine a comfort state and optimizing at least one configuration parameter of the seat to improve the rider's comfort and having a cognitive radio system for managing peer-to-peer communications within a mobile ad hoc network of self-driving vehicles. In embodiments, provided herein is a system for transportation having an artificial intelligence system for processing an input from at least one sensor to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing an input from at least one sensor to determine a comfort state and optimizing at least one configuration parameter of the seat to improve the rider's comfort and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing an input from at least one sensor to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing an input from at least one sensor to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing an input from at least one sensor to determine a comfort state and optimizing at least one configuration parameter of the seat to improve the rider's comfort and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing an input from at least one sensor to determine a comfort state and optimizing at least one configuration parameter of the seat to improve the rider's comfort and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing an input from at least one sensor to determine a comfort state and optimizing at least one configuration parameter of the seat to improve the rider's comfort and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing an input from at least one sensor to determine a comfort state and optimizing at least one configuration parameter of the seat to improve the rider's comfort and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan based on inputs relating to a self-driving vehicle. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing an input from at least one sensor to determine a comfort state and optimizing at least one configuration parameter of the seat to improve the rider's comfort and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing an input from at least one sensor to determine a comfort state and optimizing at least one configuration parameter of the seat to improve the rider's comfort and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing an input from at least one sensor to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing an input from at least one sensor to determine a comfort state and optimizing at least one configuration parameter of the seat to improve the rider's comfort and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing an input from at least one sensor to determine a comfort state and optimizing at least one configuration parameter of the seat to improve the rider's comfort and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing an input from at least one sensor to determine a comfort state and optimizing at least one configuration parameter of the seat to improve the rider's comfort and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing an input from at least one sensor to determine a comfort state and optimizing at least one configuration parameter of the seat to improve the rider's comfort and having an artificial intelligence system that automatically randomizes a parameter of an in-vehicle experience in order to improve a user state that benefits from variation. In embodiments, provided herein is a system for transportation having an artificial intelligence system for processing an input from at least one sensor to determine a comfort state and optimizing at least one configuration parameter of the seat to improve the rider's comfort and having a system for taking an indicator of a hormonal system level of a user and automatically varying a user experience in the vehicle to promote a healthy hormonal state. In embodiments, provided herein is a system for transportation having an artificial intelligence system for processing an input from at least one sensor to determine a comfort state and optimizing at least one configuration parameter of the seat to improve the rider's comfort and having a system for taking an indicator of a hormonal system level of a user and automatically varying a user experience in the vehicle to promote a hormonal state that promotes safety. In embodiments, provided herein is a system for transportation having an artificial intelligence system for processing an input from at least one sensor to determine a comfort state and optimizing at least one configuration parameter of the seat to improve the rider's comfort and having a dietary control system wherein at least one of a food or a beverage is made available under control of an automated control system. In embodiments, provided herein is a system for transportation having an artificial intelligence system for processing an input from at least one sensor to determine a comfort state and optimizing at least one configuration parameter of the seat to improve the rider's comfort and having an automated restocking system for an in-vehicle dietary system. In embodiments, provided herein is a system for transportation having an artificial intelligence system for processing an input from at least one sensor to determine a comfort state and optimizing at least one configuration parameter of the seat to improve the rider's comfort and having a system for optimizing at least one of a vehicle parameter and a user experience parameter to provide a margin of safety. In embodiments, provided herein is a system for transportation having an artificial intelligence system for processing an input from at least one sensor to determine a comfort state and optimizing at least one configuration parameter of the seat to improve the rider's comfort and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing an input from at least one sensor to determine a comfort state and optimizing at least one configuration parameter of the seat to improve the rider's comfort and having an expert system for allocating rewards across one or more different types of objectives within a transportation system. In embodiments, provided herein is a system for transportation having an artificial intelligence system for processing an input from at least one sensor to determine a comfort state and optimizing at least one configuration parameter of the seat to improve the rider's comfort and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing an input from at least one sensor to determine a comfort state and optimizing at least one configuration parameter of the seat to improve the rider's comfort and having a search system that is configured to provide network search results for in-vehicle searchers.

In embodiments, provided herein is a system for transportation having an artificial intelligence system for processing an input from at least one sensor that indicates a rider's posture to determine a comfort state and optimizing at least one configuration parameter of the seat to improve the rider's comfort. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having an artificial intelligence system for processing an input from at least one sensor that indicates a rider's posture to determine a comfort state and optimizing at least one configuration parameter of the seat to improve the rider's comfort and having a helmet configured for use with a self-driving vehicle, wherein the helmet is configured to provide an augmented reality experience based on registration of the location and orientation of the self-driving vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having an artificial intelligence system for processing an input from at least one sensor that indicates a rider's posture to determine a comfort state and optimizing at least one configuration parameter of the seat to improve the rider's comfort and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a self-driving motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet that is configured to provide an augmented reality experience based on registration of the location and orientation of the wearer in an environment. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet configured with a data processor and configured to communicate with a self-driving motorcycle for coordinated control of the helmet and the motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cognitive radio system for managing peer-to-peer communications within a mobile ad hoc network of self-driving vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for processing an input from at least one sensor that indicates a rider's posture to determine a comfort state and optimizing at least one configuration parameter of the seat to improve the rider's comfort and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for processing an input from at least one sensor that indicates a rider's posture to determine a comfort state and optimizing at least one configuration parameter of the seat to improve the rider's comfort and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan based on inputs relating to a self-driving vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for processing an input from at least one sensor that indicates a rider's posture to determine a comfort state and optimizing at least one configuration parameter of the seat to improve the rider's comfort and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for processing an input from at least one sensor that indicates a rider's posture to determine a comfort state and optimizing at least one configuration parameter of the seat to improve the rider's comfort and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for processing an input from at least one sensor that indicates a rider's posture to determine a comfort state and optimizing at least one configuration parameter of the seat to improve the rider's comfort and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for processing an input from at least one sensor that indicates a rider's posture to determine a comfort state and optimizing at least one configuration parameter of the seat to improve the rider's comfort and having an artificial intelligence system that automatically randomizes a parameter of an in-vehicle experience in order to improve a user state that benefits from variation. In embodiments, provided herein is a system for transportation having an artificial intelligence system for processing an input from at least one sensor that indicates a rider's posture to determine a comfort state and optimizing at least one configuration parameter of the seat to improve the rider's comfort and having a system for taking an indicator of a hormonal system level of a user and automatically varying a user experience in the vehicle to promote a healthy hormonal state. In embodiments, provided herein is a system for transportation having an artificial intelligence system for processing an input from at least one sensor that indicates a rider's posture to determine a comfort state and optimizing at least one configuration parameter of the seat to improve the rider's comfort and having a system for taking an indicator of a hormonal system level of a user and automatically varying a user experience in the vehicle to promote a hormonal state that promotes safety. In embodiments, provided herein is a system for transportation having an artificial intelligence system for processing an input from at least one sensor that indicates a rider's posture to determine a comfort state and optimizing at least one configuration parameter of the seat to improve the rider's comfort and having a dietary control system wherein at least one of a food or a beverage is made available under control of an automated control system. In embodiments, provided herein is a system for transportation having an artificial intelligence system for processing an input from at least one sensor that indicates a rider's posture to determine a comfort state and optimizing at least one configuration parameter of the seat to improve the rider's comfort and having an automated restocking system for an in-vehicle dietary system. In embodiments, provided herein is a system for transportation having an artificial intelligence system for processing an input from at least one sensor that indicates a rider's posture to determine a comfort state and optimizing at least one configuration parameter of the seat to improve the rider's comfort and having a system for optimizing at least one of a vehicle parameter and a user experience parameter to provide a margin of safety. In embodiments, provided herein is a system for transportation having an artificial intelligence system for processing an input from at least one sensor that indicates a rider's posture to determine a comfort state and optimizing at least one configuration parameter of the seat to improve the rider's comfort and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for processing an input from at least one sensor that indicates a rider's posture to determine a comfort state and optimizing at least one configuration parameter of the seat to improve the rider's comfort and having an expert system for allocating rewards across one or more different types of objectives within a transportation system. In embodiments, provided herein is a system for transportation having an artificial intelligence system for processing an input from at least one sensor that indicates a rider's posture to determine a comfort state and optimizing at least one configuration parameter of the seat to improve the rider's comfort and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for processing an input from at least one sensor that indicates a rider's posture to determine a comfort state and optimizing at least one configuration parameter of the seat to improve the rider's comfort and having a search system that is configured to provide network search results for in-vehicle searchers.

In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a helmet configured for use with a self-driving vehicle, wherein the helmet is configured to provide an augmented reality experience based on registration of the location and orientation of the self-driving vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a self-driving motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet that is configured to provide an augmented reality experience based on registration of the location and orientation of the wearer in an environment. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet configured with a data processor and configured to communicate with a self-driving motorcycle for coordinated control of the helmet and the motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a cognitive radio system for managing peer-to-peer communications within a mobile ad hoc network of self-driving vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan based on inputs relating to a self-driving vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an artificial intelligence system that automatically randomizes a parameter of an in-vehicle experience in order to improve a user state that benefits from variation. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a system for taking an indicator of a hormonal system level of a user and automatically varying a user experience in the vehicle to promote a healthy hormonal state. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a system for taking an indicator of a hormonal system level of a user and automatically varying a user experience in the vehicle to promote a hormonal state that promotes safety. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a dietary control system wherein at least one of a food or a beverage is made available under control of an automated control system. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an automated restocking system for an in-vehicle dietary system. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a system for optimizing at least one of a vehicle parameter and a user experience parameter to provide a margin of safety. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an interface by which a set of expert systems may be configured to provide respective outputs for managing at least one of a set of vehicle parameters, a set of fleet parameters and a set of user experience parameters. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an expert system for allocating rewards across one or more different types of objectives within a transportation system. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for managing an advertising market for in-seat advertising for riders of self-driving vehicles, wherein the cognitive system takes inputs relating to at least one parameter of the self-driving vehicle and/or the rider to determine at least one of a price, a type and a location of an advertisement to be delivered within an interface to a rider in a set of the vehicle and having a search system that is configured to provide network search results for in-vehicle searchers.

In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a helmet configured for use with a self-driving vehicle, wherein the helmet is configured to provide an augmented reality experience based on registration of the location and orientation of the self-driving vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a self-driving motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet that is configured to provide an augmented reality experience based on registration of the location and orientation of the wearer in an environment. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control of the helmet and the motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive radio system for managing peer-to-peer communications within a mobile ad hoc network of self-driving vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system that automatically randomizes a parameter of an in-vehicle experience in order to improve a user state that benefits from variation. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for taking an indicator of a hormonal system level of a user and automatically varying a user experience in the vehicle to promote a healthy hormonal state. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for taking an indicator of a hormonal system level of a user and automatically varying a user experience in the vehicle to promote a hormonal state that promotes safety. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a dietary control system wherein at least one of a food or a beverage is made available under control of an automated control system. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an automated restocking system for an in-vehicle dietary system. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for optimizing at least one of a vehicle parameter and a user experience parameter to provide a margin of safety. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an expert system for allocating rewards across one or more different types of objectives within a transportation system. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid cognitive system for managing an advertising market for in-seat advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a search system that is configured to provide network search results for in-vehicle searchers.

In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a helmet configured for use with a self-driving vehicle, wherein the helmet is configured to provide an augmented reality experience based on registration of the location and orientation of the self-driving vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a self-driving motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet that is configured to provide an augmented reality experience based on registration of the location and orientation of the wearer in an environment. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet configured with a data processor and configured to communicate with a self-driving motorcycle for coordinated control between the helmet and the motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a cognitive radio system for managing peer-to-peer communications within a mobile ad hoc network of self-driving vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan based on inputs relating to a self-driving vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an artificial intelligence system that automatically randomizes a parameter of an in-vehicle experience in order to improve a user state that benefits from variation. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a system for taking an indicator of a hormonal system level of a user and automatically varying a user experience in the vehicle to promote a healthy hormonal state. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a system for taking an indicator of a hormonal system level of a user and automatically varying a user experience in the vehicle to promote a hormonal state that promotes safety. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a dietary control system wherein at least one of a food or a beverage is made available under control of an automated control system. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an automated restocking system for an in-vehicle dietary system. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a system for optimizing at least one of a vehicle parameter and a user experience parameter to provide a margin of safety. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an interface by which a set of expert systems may be configured to provide respective outputs for managing at least one of a set of vehicle parameters, a set of fleet parameters and a set of user experience parameters. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an expert system for allocating rewards across one or more different types of objectives within a transportation system. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a helmet configured with a data processor and configured to communicate with a self-driving vehicle for coordinated control between the helmet and the self-driving vehicle, such that at least one parameter of the helmet is optimized based on machine learning on at least one input from the self-driving vehicle and having a search system that is configured to provide network search results for in-vehicle searchers.

In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a helmet configured for use with a self-driving vehicle, wherein the helmet is configured to provide an augmented reality experience based on registration of the location and orientation of the self-driving vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a self-driving motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet that is configured to provide an augmented reality experience based on registration of the location and orientation of the wearer in an environment. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet configured with a data processor and configured to communicate with a self-driving motorcycle for coordinated control of the helmet and the motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a cognitive radio system for managing peer-to-peer communications within a mobile ad hoc network of self-driving vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan based on inputs relating to a self-driving vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan for a vehicle based on inputs relating to a self-driving vehicle, wherein the inputs include a route plan for the vehicle. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an artificial intelligence system that automatically randomizes a parameter of an in-vehicle experience in order to improve a user state that benefits from variation. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a system for taking an indicator of a hormonal system level of a user and automatically varying a user experience in the vehicle to promote a healthy hormonal state. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a system for taking an indicator of a hormonal system level of a user and automatically varying a user experience in the vehicle to promote a hormonal state that promotes safety. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a dietary control system wherein at least one of a food or a beverage is made available under control of an automated control system. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an automated restocking system for an in-vehicle dietary system. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a system for optimizing at least one of a vehicle parameter and a user experience parameter to provide a margin of safety. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an interface by which a set of expert systems may be configured to provide respective outputs for managing at least one of a set of vehicle parameters, a set of fleet parameters and a set of user experience parameters. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an expert system for allocating rewards across one or more different types of objectives within a transportation system. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a helmet configured with a data processor and configured to communicate with a self-driving vehicle for coordinated control between the helmet and the vehicle, such that at least one parameter of the vehicle helmet is optimized based on machine learning on at least one input from the helmet and having a search system that is configured to provide network search results for in-vehicle searchers.

In embodiments, provided herein is a system for transportation having a helmet configured for use with a self-driving vehicle, wherein the helmet is configured to provide an augmented reality experience based on registration of the location and orientation of the self-driving vehicle. In embodiments, provided herein is a system for transportation having a helmet configured for use with a self-driving vehicle, wherein the helmet is configured to provide an augmented reality experience based on registration of the location and orientation of the self-driving vehicle and having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a helmet configured for use with a self-driving vehicle, wherein the helmet is configured to provide an augmented reality experience based on registration of the location and orientation of the self-driving vehicle and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a helmet configured for use with a self-driving vehicle, wherein the helmet is configured to provide an augmented reality experience based on registration of the location and orientation of the self-driving vehicle and having a self-driving motorcycle. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet that is configured to provide an augmented reality experience based on registration of the location and orientation of the wearer in an environment. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet configured with a data processor and configured to communicate with a self-driving motorcycle for coordinated control of the helmet and the motorcycle. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a helmet configured for use with a self-driving vehicle, wherein the helmet is configured to provide an augmented reality experience based on registration of the location and orientation of the self-driving vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a helmet configured for use with a self-driving vehicle, wherein the helmet is configured to provide an augmented reality experience based on registration of the location and orientation of the self-driving vehicle and having a cognitive radio system for managing peer-to-peer communications within a mobile ad hoc network of self-driving vehicles. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a helmet configured for use with a self-driving vehicle, wherein the helmet is configured to provide an augmented reality experience based on registration of the location and orientation of the self-driving vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another network is used to process inputs relating to charging or refueling infrastructure. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a helmet configured for use with a self-driving vehicle, wherein the helmet is configured to provide an augmented reality experience based on registration of the location and orientation of the self-driving vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a helmet configured for use with a self-driving vehicle, wherein the helmet is configured to provide an augmented reality experience based on registration of the location and orientation of the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a helmet configured for use with a self-driving vehicle, wherein the helmet is configured to provide an augmented reality experience based on registration of the location and orientation of the self-driving vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan based on inputs relating to a self-driving vehicle. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a helmet configured for use with a self-driving vehicle, wherein the helmet is configured to provide an augmented reality experience based on registration of the location and orientation of the self-driving vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a helmet configured for use with a self-driving vehicle, wherein the helmet is configured to provide an augmented reality experience based on registration of the location and orientation of the self-driving vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a helmet configured for use with a self-driving vehicle, wherein the helmet is configured to provide an augmented reality experience based on registration of the location and orientation of the self-driving vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a helmet configured for use with a self-driving vehicle, wherein the helmet is configured to provide an augmented reality experience based on registration of the location and orientation of the self-driving vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a helmet configured for use with a self-driving vehicle, wherein the helmet is configured to provide an augmented reality experience based on registration of the location and orientation of the self-driving vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a helmet configured for use with a self-driving vehicle, wherein the helmet is configured to provide an augmented reality experience based on registration of the location and orientation of the self-driving vehicle and having an artificial intelligence system that automatically randomizes a parameter of an in-vehicle experience in order to improve a user state that benefits from variation. In embodiments, provided herein is a system for transportation having a helmet configured for use with a self-driving vehicle, wherein the helmet is configured to provide an augmented reality experience based on registration of the location and orientation of the self-driving vehicle and having a system for taking an indicator of a hormonal system level of a user and automatically varying a user experience in the vehicle to promote a healthy hormonal state. In embodiments, provided herein is a system for transportation having a helmet configured for use with a self-driving vehicle, wherein the helmet is configured to provide an augmented reality experience based on registration of the location and orientation of the self-driving vehicle and having a system for taking an indicator of a hormonal system level of a user and automatically varying a user experience in the vehicle to promote a hormonal state that promotes safety. In embodiments, provided herein is a system for transportation having a helmet configured for use with a self-driving vehicle, wherein the helmet is configured to provide an augmented reality experience based on registration of the location and orientation of the self-driving vehicle and having a dietary control system wherein at least one of a food or a beverage is made available under control of an automated control system. In embodiments, provided herein is a system for transportation having a helmet configured for use with a self-driving vehicle, wherein the helmet is configured to provide an augmented reality experience based on registration of the location and orientation of the self-driving vehicle and having an automated restocking system for an in-vehicle dietary system. In embodiments, provided herein is a system for transportation having a helmet configured for use with a self-driving vehicle, wherein the helmet is configured to provide an augmented reality experience based on registration of the location and orientation of the self-driving vehicle and having a system for optimizing at least one of a vehicle parameter and a user experience parameter to provide a margin of safety. In embodiments, provided herein is a system for transportation having a helmet configured for use with a self-driving vehicle, wherein the helmet is configured to provide an augmented reality experience based on registration of the location and orientation of the self-driving vehicle and having an interface by which a set of expert systems may be configured to provide respective outputs for managing at least one of a set of vehicle parameters, a set of fleet parameters and a set of user experience parameters. In embodiments, provided herein is a system for transportation having a helmet configured for use with a self-driving vehicle, wherein the helmet is configured to provide an augmented reality experience based on registration of the location and orientation of the self-driving vehicle and having an expert system for allocating rewards across one or more different types of objectives within a transportation system. In embodiments, provided herein is a system for transportation having a helmet configured for use with a self-driving vehicle, wherein the helmet is configured to provide an augmented reality experience based on registration of the location and orientation of the self-driving vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a helmet configured for use with a self-driving vehicle, wherein the helmet is configured to provide an augmented reality experience based on registration of the location and orientation of the self-driving vehicle and having a search system that is configured to provide network search results for in-vehicle searchers.

In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a self-driving motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet that is configured to provide an augmented reality experience based on registration of the location and orientation of the wearer in an environment. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet configured with a data processor and configured to communicate with a self-driving motorcycle for coordinated control of the helmet and the motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a cognitive radio system for managing peer-to-peer communications within a mobile ad hoc network of self-driving vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan based on inputs relating to a self-driving vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an artificial intelligence system that automatically randomizes a parameter of an in-vehicle experience in order to improve a user state that benefits from variation. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a system for taking an indicator of a hormonal system level of a user and automatically varying a user experience in the vehicle to promote a healthy hormonal state. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a system for taking an indicator of a hormonal system level of a user and automatically varying a user experience in the vehicle to promote a hormonal state that promotes safety. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a dietary control system wherein at least one of a food or a beverage is made available under control of an automated control system. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an automated restocking system for an in-vehicle dietary system. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a system for optimizing at least one of a vehicle parameter and a user experience parameter to provide a margin of safety. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an interface by which a set of expert systems may be configured to provide respective outputs for managing at least one of a set of vehicle parameters, a set of fleet parameters and a set of user experience parameters. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an expert system for allocating rewards across one or more different types of objectives within a transportation system. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for managing an advertising market for in-helmet advertising for riders of self-driving vehicles, wherein the cognitive system takes inputs relating to at least one parameter of the self-driving vehicle and/or the rider to determine at least one of a price, a type and a location of an advertisement to be delivered within an interface of the helmet and having a search system that is configured to provide network search results for in-vehicle searchers.

In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a self-driving motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet that is configured to provide an augmented reality experience based on registration of the location and orientation of the wearer in an environment. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control of the helmet and the motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive radio system for managing peer-to-peer communications within a mobile ad hoc network of self-driving vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an artificial intelligence system that automatically randomizes a parameter of an in-vehicle experience in order to improve a user state that benefits from variation. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for taking an indicator of a hormonal system level of a user and automatically varying a user experience in the vehicle to promote a healthy hormonal state. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for taking an indicator of a hormonal system level of a user and automatically varying a user experience in the vehicle to promote a hormonal state that promotes safety. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a dietary control system wherein at least one of a food or a beverage is made available under control of an automated control system. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an automated restocking system for an in-vehicle dietary system. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a system for optimizing at least one of a vehicle parameter and a user experience parameter to provide a margin of safety. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an expert system for allocating rewards across one or more different types of objectives within a transportation system. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid cognitive system for managing an advertising market for in-helmet advertising to riders of self-driving vehicles, wherein at least one part of the hybrid cognitive system processes inputs relating to at least one parameter of the self-driving vehicle to determine a vehicle operating state and at least one other part of the cognitive system processes inputs relating to a rider to determine a rider state, wherein the cognitive system determines at least one of a price, a type and a location of an advertisement to be delivered within an interface to a rider in a set of the vehicle and having a search system that is configured to provide network search results for in-vehicle searchers.

In embodiments, provided herein is a system for transportation having a self-driving motorcycle. In embodiments, provided herein is a system for transportation having a self-driving motorcycle and having a motorcycle helmet that is configured to provide an augmented reality experience based on registration of the location and orientation of the wearer in an environment. In embodiments, provided herein is a system for transportation having a self-driving motorcycle and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a self-driving motorcycle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a self-driving motorcycle and having a motorcycle helmet configured with a data processor and configured to communicate with a self-driving motorcycle for coordinated control of the helmet and the motorcycle. In embodiments, provided herein is a system for transportation having a self-driving motorcycle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a self-driving motorcycle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a self-driving motorcycle and having a cognitive radio system for managing peer-to-peer communications within a mobile ad hoc network of self-driving vehicles. In embodiments, provided herein is a system for transportation having a self-driving motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a self-driving motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a self-driving motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a self-driving motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a self-driving motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a self-driving motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a self-driving motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a self-driving motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a self-driving motorcycle and having an artificial intelligence system for determining at least one parameter of a charging plan based on inputs relating to a self-driving vehicle. In embodiments, provided herein is a system for transportation having a self-driving motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a self-driving motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a self-driving motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a self-driving motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a self-driving motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a self-driving motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a self-driving motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a self-driving motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a self-driving motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a self-driving motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a self-driving motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a self-driving motorcycle and having an artificial intelligence system that automatically randomizes a parameter of an in-vehicle experience in order to improve a user state that benefits from variation. In embodiments, provided herein is a system for transportation having a self-driving motorcycle and having a system for taking an indicator of a hormonal system level of a user and automatically varying a user experience in the vehicle to promote a healthy hormonal state. In embodiments, provided herein is a system for transportation having a self-driving motorcycle and having a system for taking an indicator of a hormonal system level of a user and automatically varying a user experience in the vehicle to promote a hormonal state that promotes safety. In embodiments, provided herein is a system for transportation having a self-driving motorcycle and having a dietary control system wherein at least one of a food or a beverage is made available under control of an automated control system. In embodiments, provided herein is a system for transportation having a self-driving motorcycle and having an automated restocking system for an in-vehicle dietary system. In embodiments, provided herein is a system for transportation having a self-driving motorcycle and having a system for optimizing at least one of a vehicle parameter and a user experience parameter to provide a margin of safety. In embodiments, provided herein is a system for transportation having a self-driving motorcycle and having an interface by which a set of expert systems may be configured to provide respective outputs for managing at least one of a set of vehicle parameters, a set of fleet parameters and a set of user experience parameters. In embodiments, provided herein is a system for transportation having a self-driving motorcycle and having an expert system for allocating rewards across one or more different types of objectives within a transportation system. In embodiments, provided herein is a system for transportation having a self-driving motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a self-driving motorcycle and having a search system that is configured to provide network search results for in-vehicle searchers.

In embodiments, provided herein is a system for transportation having a motorcycle helmet that is configured to provide an augmented reality experience based on registration of the location and orientation of the wearer in an environment. In embodiments, provided herein is a system for transportation having a motorcycle helmet that is configured to provide an augmented reality experience based on registration of the location and orientation of the wearer in an environment and having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a motorcycle helmet that is configured to provide an augmented reality experience based on registration of the location and orientation of the wearer in an environment and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a motorcycle helmet that is configured to provide an augmented reality experience based on registration of the location and orientation of the wearer in an environment and having a motorcycle helmet configured with a data processor and configured to communicate with a self-driving motorcycle for coordinated control of the helmet and the motorcycle. In embodiments, provided herein is a system for transportation having a motorcycle helmet that is configured to provide an augmented reality experience based on registration of the location and orientation of the wearer in an environment and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a motorcycle helmet that is configured to provide an augmented reality experience based on registration of the location and orientation of the wearer in an environment and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet that is configured to provide an augmented reality experience based on registration of the location and orientation of the wearer in an environment and having a cognitive radio system for managing peer-to-peer communications within a mobile ad hoc network of self-driving vehicles. In embodiments, provided herein is a system for transportation having a motorcycle helmet that is configured to provide an augmented reality experience based on registration of the location and orientation of the wearer in an environment and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet that is configured to provide an augmented reality experience based on registration of the location and orientation of the wearer in an environment and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet that is configured to provide an augmented reality experience based on registration of the location and orientation of the wearer in an environment and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet that is configured to provide an augmented reality experience based on registration of the location and orientation of the wearer in an environment and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet that is configured to provide an augmented reality experience based on registration of the location and orientation of the wearer in an environment and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet that is configured to provide an augmented reality experience based on registration of the location and orientation of the wearer in an environment and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet that is configured to provide an augmented reality experience based on registration of the location and orientation of the wearer in an environment and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet that is configured to provide an augmented reality experience based on registration of the location and orientation of the wearer in an environment and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet that is configured to provide an augmented reality experience based on registration of the location and orientation of the wearer in an environment and having an artificial intelligence system for determining at least one parameter of a charging plan based on inputs relating to a self-driving vehicle. In embodiments, provided herein is a system for transportation having a motorcycle helmet that is configured to provide an augmented reality experience based on registration of the location and orientation of the wearer in an environment and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet that is configured to provide an augmented reality experience based on registration of the location and orientation of the wearer in an environment and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet that is configured to provide an augmented reality experience based on registration of the location and orientation of the wearer in an environment and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet that is configured to provide an augmented reality experience based on registration of the location and orientation of the wearer in an environment and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet that is configured to provide an augmented reality experience based on registration of the location and orientation of the wearer in an environment and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet that is configured to provide an augmented reality experience based on registration of the location and orientation of the wearer in an environment and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet that is configured to provide an augmented reality experience based on registration of the location and orientation of the wearer in an environment and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet that is configured to provide an augmented reality experience based on registration of the location and orientation of the wearer in an environment and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet that is configured to provide an augmented reality experience based on registration of the location and orientation of the wearer in an environment and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet that is configured to provide an augmented reality experience based on registration of the location and orientation of the wearer in an environment and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet that is configured to provide an augmented reality experience based on registration of the location and orientation of the wearer in an environment and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet that is configured to provide an augmented reality experience based on registration of the location and orientation of the wearer in an environment and having an artificial intelligence system that automatically randomizes a parameter of an in-vehicle experience in order to improve a user state that benefits from variation. In embodiments, provided herein is a system for transportation having a motorcycle helmet that is configured to provide an augmented reality experience based on registration of the location and orientation of the wearer in an environment and having a system for taking an indicator of a hormonal system level of a user and automatically varying a user experience in the vehicle to promote a healthy hormonal state. In embodiments, provided herein is a system for transportation having a motorcycle helmet that is configured to provide an augmented reality experience based on registration of the location and orientation of the wearer in an environment and having a system for taking an indicator of a hormonal system level of a user and automatically varying a user experience in the vehicle to promote a hormonal state that promotes safety. In embodiments, provided herein is a system for transportation having a motorcycle helmet that is configured to provide an augmented reality experience based on registration of the location and orientation of the wearer in an environment and having a dietary control system wherein at least one of a food or a beverage is made available under control of an automated control system. In embodiments, provided herein is a system for transportation having a motorcycle helmet that is configured to provide an augmented reality experience based on registration of the location and orientation of the wearer in an environment and having an automated restocking system for an in-vehicle dietary system. In embodiments, provided herein is a system for transportation having a motorcycle helmet that is configured to provide an augmented reality experience based on registration of the location and orientation of the wearer in an environment and having a system for optimizing at least one of a vehicle parameter and a user experience parameter to provide a margin of safety. In embodiments, provided herein is a system for transportation having a motorcycle helmet that is configured to provide an augmented reality experience based on registration of the location and orientation of the wearer in an environment and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet that is configured to provide an augmented reality experience based on registration of the location and orientation of the wearer in an environment and having an expert system for allocating rewards across one or more different types of objectives within a transportation system. In embodiments, provided herein is a system for transportation having a motorcycle helmet that is configured to provide an augmented reality experience based on registration of the location and orientation of the wearer in an environment and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet that is configured to provide an augmented reality experience based on registration of the location and orientation of the wearer in an environment and having a search system that is configured to provide network search results for in-vehicle searchers.

In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a motorcycle helmet configured with a data processor and configured to communicate with a self-driving motorcycle for coordinated control of the helmet and the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a cognitive radio system for managing peer-to-peer communications within a mobile ad hoc network of self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan based on inputs relating to a self-driving vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an artificial intelligence system that automatically randomizes a parameter of an in-vehicle experience in order to improve a user state that benefits from variation. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a system for taking an indicator of a hormonal system level of a user and automatically varying a user experience in the vehicle to promote a healthy hormonal state. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a system for taking an indicator of a hormonal system level of a user and automatically varying a user experience in the vehicle to promote a hormonal state that promotes safety. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a dietary control system wherein at least one of a food or a beverage is made available under control of an automated control system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an automated restocking system for an in-vehicle dietary system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a system for optimizing at least one of a vehicle parameter and a user experience parameter to provide a margin of safety. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an expert system for allocating rewards across one or more different types of objectives within a transportation system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle and having a search system that is configured to provide network search results for in-vehicle searchers.

In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a motorcycle helmet configured with a data processor and configured to communicate with a self-driving motorcycle for coordinated control of the helmet and the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a cognitive radio system for managing peer-to-peer communications within a mobile ad hoc network of self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one input relating to at least one of the rider and the motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan based on inputs relating to a self-driving vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an artificial intelligence system that automatically randomizes a parameter of an in-vehicle experience in order to improve a user state that benefits from variation. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a system for taking an indicator of a hormonal system level of a user and automatically varying a user experience in the vehicle to promote a healthy hormonal state. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a system for taking an indicator of a hormonal system level of a user and automatically varying a user experience in the vehicle to promote a hormonal state that promotes safety. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a dietary control system wherein at least one of a food or a beverage is made available under control of an automated control system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an automated restocking system for an in-vehicle dietary system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a system for optimizing at least one of a vehicle parameter and a user experience parameter to provide a margin of safety. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an expert system for allocating rewards across one or more different types of objectives within a transportation system. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet configured for use with a self-driving motorcycle, wherein the motorcycle helmet is configured to provide an augmented reality experience based on registration of the location and orientation of the self-driving motorcycle, wherein at least one parameter of the augmented reality experience is determined by machine learning on at least one input relating to at least one of the rider and the motorcycle and having a search system that is configured to provide network search results for in-vehicle searchers.

In embodiments, provided herein is a system for transportation having a motorcycle helmet configured with a data processor and configured to communicate with a self-driving motorcycle for coordinated control of the helmet and the motorcycle. In embodiments, provided herein is a system for transportation having a motorcycle helmet configured with a data processor and configured to communicate with a self-driving motorcycle for coordinated control of the helmet and the motorcycle and having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a motorcycle helmet configured with a data processor and configured to communicate with a self-driving motorcycle for coordinated control of the helmet and the motorcycle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet configured with a data processor and configured to communicate with a self-driving motorcycle for coordinated control of the helmet and the motorcycle and having a cognitive radio system for managing peer-to-peer communications within a mobile ad hoc network of self-driving vehicles. In embodiments, provided herein is a system for transportation having a motorcycle helmet configured with a data processor and configured to communicate with a self-driving motorcycle for coordinated control of the helmet and the motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet configured with a data processor and configured to communicate with a self-driving motorcycle for coordinated control of the helmet and the motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet configured with a data processor and configured to communicate with a self-driving motorcycle for coordinated control of the helmet and the motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet configured with a data processor and configured to communicate with a self-driving motorcycle for coordinated control of the helmet and the motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet configured with a data processor and configured to communicate with a self-driving motorcycle for coordinated control of the helmet and the motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet configured with a data processor and configured to communicate with a self-driving motorcycle for coordinated control of the helmet and the motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet configured with a data processor and configured to communicate with a self-driving motorcycle for coordinated control of the helmet and the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet configured with a data processor and configured to communicate with a self-driving motorcycle for coordinated control of the helmet and the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan based on inputs relating to a self-driving vehicle. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet configured with a data processor and configured to communicate with a self-driving motorcycle for coordinated control of the helmet and the motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet configured with a data processor and configured to communicate with a self-driving motorcycle for coordinated control of the helmet and the motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet configured with a data processor and configured to communicate with a self-driving motorcycle for coordinated control of the helmet and the motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet configured with a data processor and configured to communicate with a self-driving motorcycle for coordinated control of the helmet and the motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet configured with a data processor and configured to communicate with a self-driving motorcycle for coordinated control of the helmet and the motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet configured with a data processor and configured to communicate with a self-driving motorcycle for coordinated control of the helmet and the motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet configured with a data processor and configured to communicate with a self-driving motorcycle for coordinated control of the helmet and the motorcycle and having an artificial intelligence system that automatically randomizes a parameter of an in-vehicle experience in order to improve a user state that benefits from variation. In embodiments, provided herein is a system for transportation having a motorcycle helmet configured with a data processor and configured to communicate with a self-driving motorcycle for coordinated control of the helmet and the motorcycle and having a system for taking an indicator of a hormonal system level of a user and automatically varying a user experience in the vehicle to promote a healthy hormonal state. In embodiments, provided herein is a system for transportation having a motorcycle helmet configured with a data processor and configured to communicate with a self-driving motorcycle for coordinated control of the helmet and the motorcycle and having a system for taking an indicator of a hormonal system level of a user and automatically varying a user experience in the vehicle to promote a hormonal state that promotes safety. In embodiments, provided herein is a system for transportation having a motorcycle helmet configured with a data processor and configured to communicate with a self-driving motorcycle for coordinated control of the helmet and the motorcycle and having a dietary control system wherein at least one of a food or a beverage is made available under control of an automated control system. In embodiments, provided herein is a system for transportation having a motorcycle helmet configured with a data processor and configured to communicate with a self-driving motorcycle for coordinated control of the helmet and the motorcycle and having an automated restocking system for an in-vehicle dietary system. In embodiments, provided herein is a system for transportation having a motorcycle helmet configured with a data processor and configured to communicate with a self-driving motorcycle for coordinated control of the helmet and the motorcycle and having a system for optimizing at least one of a vehicle parameter and a user experience parameter to provide a margin of safety. In embodiments, provided herein is a system for transportation having a motorcycle helmet configured with a data processor and configured to communicate with a self-driving motorcycle for coordinated control of the helmet and the motorcycle and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet configured with a data processor and configured to communicate with a self-driving motorcycle for coordinated control of the helmet and the motorcycle and having an expert system for allocating rewards across one or more different types of objectives within a transportation system. In embodiments, provided herein is a system for transportation having a motorcycle helmet configured with a data processor and configured to communicate with a self-driving motorcycle for coordinated control of the helmet and the motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet configured with a data processor and configured to communicate with a self-driving motorcycle for coordinated control of the helmet and the motorcycle and having a search system that is configured to provide network search results for in-vehicle searchers.

In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a cognitive radio system for managing peer-to-peer communications within a mobile ad hoc network of self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan based on inputs relating to a self-driving vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an artificial intelligence system that automatically randomizes a parameter of an in-vehicle experience in order to improve a user state that benefits from variation. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a system for taking an indicator of a hormonal system level of a user and automatically varying a user experience in the vehicle to promote a healthy hormonal state. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a system for taking an indicator of a hormonal system level of a user and automatically varying a user experience in the vehicle to promote a hormonal state that promotes safety. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a dietary control system wherein at least one of a food or a beverage is made available under control of an automated control system. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an automated restocking system for an in-vehicle dietary system. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a system for optimizing at least one of a vehicle parameter and a user experience parameter to provide a margin of safety. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an expert system for allocating rewards across one or more different types of objectives within a transportation system. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet configured with a data processor and configured to communicate with a self-driving motorcycle for coordinated control between the helmet and the motorcycle, wherein an input from the helmet provides at least one routing instruction to the motorcycle and having a search system that is configured to provide network search results for in-vehicle searchers.

In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a cognitive radio system for managing peer-to-peer communications within a mobile ad hoc network of self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan based on inputs relating to a self-driving vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan for a vehicle based on inputs relating to a self-driving vehicle, wherein the inputs include a route plan for the vehicle. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an artificial intelligence system that automatically randomizes a parameter of an in-vehicle experience in order to improve a user state that benefits from variation. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a system for taking an indicator of a hormonal system level of a user and automatically varying a user experience in the vehicle to promote a healthy hormonal state. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a system for taking an indicator of a hormonal system level of a user and automatically varying a user experience in the vehicle to promote a hormonal state that promotes safety. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a dietary control system wherein at least one of a food or a beverage is made available under control of an automated control system. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an automated restocking system for an in-vehicle dietary system. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a system for optimizing at least one of a vehicle parameter and a user experience parameter to provide a margin of safety. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an interface by which a set of expert systems may be configured to provide respective outputs for managing at least one of a set of vehicle parameters, a set of fleet parameters and a set of user experience parameters. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an expert system for allocating rewards across one or more different types of objectives within a transportation system. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a motorcycle helmet configured with a data processor and configured to communicate with a self-driving motorcycle for coordinated control between the helmet and the motorcycle, wherein an input from the helmet provides at least one driving instruction to the motorcycle and having a search system that is configured to provide network search results for in-vehicle searchers.

In embodiments, provided herein is a system for transportation having a cognitive radio system for managing peer-to-peer communications within a mobile ad hoc network of self-driving vehicles. In embodiments, provided herein is a system for transportation having a cognitive radio system for managing peer-to-peer communications within a mobile ad hoc network of self-driving vehicles and having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having a cognitive radio system for managing peer-to-peer communications within a mobile ad hoc network of self-driving vehicles and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a cognitive radio system for managing peer-to-peer communications within a mobile ad hoc network of self-driving vehicles and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a cognitive radio system for managing peer-to-peer communications within a mobile ad hoc network of self-driving vehicles and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a cognitive radio system for managing peer-to-peer communications within a mobile ad hoc network of self-driving vehicles and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a cognitive radio system for managing peer-to-peer communications within a mobile ad hoc network of self-driving vehicles and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cognitive radio system for managing peer-to-peer communications within a mobile ad hoc network of self-driving vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cognitive radio system for managing peer-to-peer communications within a mobile ad hoc network of self-driving vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cognitive radio system for managing peer-to-peer communications within a mobile ad hoc network of self-driving vehicles and having an artificial intelligence system for determining at least one parameter of a charging plan based on inputs relating to a self-driving vehicle. In embodiments, provided herein is a system for transportation having a cognitive radio system for managing peer-to-peer communications within a mobile ad hoc network of self-driving vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cognitive radio system for managing peer-to-peer communications within a mobile ad hoc network of self-driving vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cognitive radio system for managing peer-to-peer communications within a mobile ad hoc network of self-driving vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cognitive radio system for managing peer-to-peer communications within a mobile ad hoc network of self-driving vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cognitive radio system for managing peer-to-peer communications within a mobile ad hoc network of self-driving vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cognitive radio system for managing peer-to-peer communications within a mobile ad hoc network of self-driving vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cognitive radio system for managing peer-to-peer communications within a mobile ad hoc network of self-driving vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having a cognitive radio system for managing peer-to-peer communications within a mobile ad hoc network of self-driving vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cognitive radio system for managing peer-to-peer communications within a mobile ad hoc network of self-driving vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive radio system for managing peer-to-peer communications within a mobile ad hoc network of self-driving vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive radio system for managing peer-to-peer communications within a mobile ad hoc network of self-driving vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive radio system for managing peer-to-peer communications within a mobile ad hoc network of self-driving vehicles and having an artificial intelligence system that automatically randomizes a parameter of an in-vehicle experience in order to improve a user state that benefits from variation. In embodiments, provided herein is a system for transportation having a cognitive radio system for managing peer-to-peer communications within a mobile ad hoc network of self-driving vehicles and having a system for taking an indicator of a hormonal system level of a user and automatically varying a user experience in the vehicle to promote a healthy hormonal state. In embodiments, provided herein is a system for transportation having a cognitive radio system for managing peer-to-peer communications within a mobile ad hoc network of self-driving vehicles and having a system for taking an indicator of a hormonal system level of a user and automatically varying a user experience in the vehicle to promote a hormonal state that promotes safety. In embodiments, provided herein is a system for transportation having a cognitive radio system for managing peer-to-peer communications within a mobile ad hoc network of self-driving vehicles and having a dietary control system wherein at least one of a food or a beverage is made available under control of an automated control system. In embodiments, provided herein is a system for transportation having a cognitive radio system for managing peer-to-peer communications within a mobile ad hoc network of self-driving vehicles and having an automated restocking system for an in-vehicle dietary system. In embodiments, provided herein is a system for transportation having a cognitive radio system for managing peer-to-peer communications within a mobile ad hoc network of self-driving vehicles and having a system for optimizing at least one of a vehicle parameter and a user experience parameter to provide a margin of safety. In embodiments, provided herein is a system for transportation having a cognitive radio system for managing peer-to-peer communications within a mobile ad hoc network of self-driving vehicles and having an interface by which a set of expert systems may be configured to provide respective outputs for managing at least one of a set of vehicle parameters, a set of fleet parameters and a set of user experience parameters. In embodiments, provided herein is a system for transportation having a cognitive radio system for managing peer-to-peer communications within a mobile ad hoc network of self-driving vehicles and having an expert system for allocating rewards across one or more different types of objectives within a transportation system. In embodiments, provided herein is a system for transportation having a cognitive radio system for managing peer-to-peer communications within a mobile ad hoc network of self-driving vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive radio system for managing peer-to-peer communications within a mobile ad hoc network of self-driving vehicles and having a search system that is configured to provide network search results for in-vehicle searchers.

In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan based on inputs relating to a self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a cognitive system for facilitating automated negotiation of at least one of a duration, a quantity and a price for charging or refueling a vehicle, wherein the cognitive system manages a bidding marketplace for charging and/or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an artificial intelligence system that automatically randomizes a parameter of an in-vehicle experience in order to improve a user state that benefits from variation. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a system for taking an indicator of a hormonal system level of a user and automatically varying a user experience in the vehicle to promote a healthy hormonal state. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a system for taking an indicator of a hormonal system level of a user and automatically varying a user experience in the vehicle to promote a hormonal state that promotes safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a dietary control system wherein at least one of a food or a beverage is made available under control of an automated control system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an automated restocking system for an in-vehicle dietary system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a system for optimizing at least one of a vehicle parameter and a user experience parameter to provide a margin of safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an expert system for allocating rewards across one or more different types of objectives within a transportation system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for taking inputs relating to a plurality of self-driving vehicles and determining at least one parameter of a re-charging and/or refueling plan for at least one of the plurality of vehicles based on the inputs and having a search system that is configured to provide network search results for in-vehicle searchers.

In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan based on inputs relating to a self-driving vehicle. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an artificial intelligence system that automatically randomizes a parameter of an in-vehicle experience in order to improve a user state that benefits from variation. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a system for taking an indicator of a hormonal system level of a user and automatically varying a user experience in the vehicle to promote a healthy hormonal state. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a system for taking an indicator of a hormonal system level of a user and automatically varying a user experience in the vehicle to promote a hormonal state that promotes safety. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a dietary control system wherein at least one of a food or a beverage is made available under control of an automated control system. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an automated restocking system for an in-vehicle dietary system. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a system for optimizing at least one of a vehicle parameter and a user experience parameter to provide a margin of safety. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an expert system for allocating rewards across one or more different types of objectives within a transportation system. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for taking inputs relating to a plurality of self-driving vehicles and determining at least one parameter of a re-charging and/or refueling plan for at least one of the plurality of vehicles based on the inputs, wherein one neural network is used to process inputs relating to charge or fuel states of the plurality of vehicles and another neural network is used to process inputs relating to charging or refueling infrastructure and having a search system that is configured to provide network search results for in-vehicle searchers.

In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan based on inputs relating to a self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an artificial intelligence system that automatically randomizes a parameter of an in-vehicle experience in order to improve a user state that benefits from variation. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a system for taking an indicator of a hormonal system level of a user and automatically varying a user experience in the vehicle to promote a healthy hormonal state. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a system for taking an indicator of a hormonal system level of a user and automatically varying a user experience in the vehicle to promote a hormonal state that promotes safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a dietary control system wherein at least one of a food or a beverage is made available under control of an automated control system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an automated restocking system for an in-vehicle dietary system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a system for optimizing at least one of a vehicle parameter and a user experience parameter to provide a margin of safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an expert system for allocating rewards across one or more different types of objectives within a transportation system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the charge or fuel states of the self-driving vehicles and having a search system that is configured to provide network search results for in-vehicle searchers.

In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan based on inputs relating to a self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an artificial intelligence system that automatically randomizes a parameter of an in-vehicle experience in order to improve a user state that benefits from variation. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a system for taking an indicator of a hormonal system level of a user and automatically varying a user experience in the vehicle to promote a healthy hormonal state. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a system for taking an indicator of a hormonal system level of a user and automatically varying a user experience in the vehicle to promote a hormonal state that promotes safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a dietary control system wherein at least one of a food or a beverage is made available under control of an automated control system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an automated restocking system for an in-vehicle dietary system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a system for optimizing at least one of a vehicle parameter and a user experience parameter to provide a margin of safety. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an expert system for allocating rewards across one or more different types of objectives within a transportation system. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for taking inputs relating to a plurality of self-driving vehicles and determining at least one parameter of a re-charging and/or refueling plan for at least one of the plurality of vehicles based on inputs indicating the availability of charging or refueling from sources within the driving range of the vehicles and having a search system that is configured to provide network search results for in-vehicle searchers.

In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan based on inputs relating to a self-driving vehicle. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an artificial intelligence system that automatically randomizes a parameter of an in-vehicle experience in order to improve a user state that benefits from variation. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a system for taking an indicator of a hormonal system level of a user and automatically varying a user experience in the vehicle to promote a healthy hormonal state. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a system for taking an indicator of a hormonal system level of a user and automatically varying a user experience in the vehicle to promote a hormonal state that promotes safety. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a dietary control system wherein at least one of a food or a beverage is made available under control of an automated control system. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an automated restocking system for an in-vehicle dietary system. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a system for optimizing at least one of a vehicle parameter and a user experience parameter to provide a margin of safety. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an expert system for allocating rewards across one or more different types of objectives within a transportation system. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for taking at least one input relating to a plurality of vehicles from at least one Internet of Things device located in the environment in which the vehicles are operating and determining at least one parameter of a re-charging and/or refueling plan for at least one of the plurality of vehicles and having a search system that is configured to provide network search results for in-vehicle searchers.

In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan based on inputs relating to a self-driving vehicle. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan for a vehicle based on inputs relating to a self-driving vehicle, wherein the inputs include a route plan for the vehicle. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an artificial intelligence system that automatically randomizes a parameter of an in-vehicle experience in order to improve a user state that benefits from variation. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a system for taking an indicator of a hormonal system level of a user and automatically varying a user experience in the vehicle to promote a healthy hormonal state. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a system for taking an indicator of a hormonal system level of a user and automatically varying a user experience in the vehicle to promote a hormonal state that promotes safety. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a dietary control system wherein at least one of a food or a beverage is made available under control of an automated control system. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an automated restocking system for an in-vehicle dietary system. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a system for optimizing at least one of a vehicle parameter and a user experience parameter to provide a margin of safety. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an interface by which a set of expert systems may be configured to provide respective outputs for managing at least one of a set of vehicle parameters, a set of fleet parameters and a set of user experience parameters. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an expert system for allocating rewards across one or more different types of objectives within a transportation system. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cloud-based artificial intelligence system for taking inputs relating to a plurality of self-driving vehicles and determining at least one parameter of a re-charging and/or refueling plan for at least one of the plurality of vehicles based on inputs and having a search system that is configured to provide network search results for in-vehicle searchers.

In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan based on inputs relating to a self-driving vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an artificial intelligence system that automatically randomizes a parameter of an in-vehicle experience in order to improve a user state that benefits from variation. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a system for taking an indicator of a hormonal system level of a user and automatically varying a user experience in the vehicle to promote a healthy hormonal state. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a system for taking an indicator of a hormonal system level of a user and automatically varying a user experience in the vehicle to promote a hormonal state that promotes safety. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a dietary control system wherein at least one of a food or a beverage is made available under control of an automated control system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an automated restocking system for an in-vehicle dietary system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a system for optimizing at least one of a vehicle parameter and a user experience parameter to provide a margin of safety. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an interface by which a set of expert systems may be configured to provide respective outputs for managing at least one of a set of vehicle parameters, a set of fleet parameters and a set of user experience parameters. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an expert system for allocating rewards across one or more different types of objectives within a transportation system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from the self-driving vehicles and a local system positioned on at least one of the self-driving vehicles and having a search system that is configured to provide network search results for in-vehicle searchers.

In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan based on inputs relating to a self-driving vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan for a vehicle based on inputs relating to a self-driving vehicle, wherein the inputs include a route plan for the vehicle. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an artificial intelligence system that automatically randomizes a parameter of an in-vehicle experience in order to improve a user state that benefits from variation. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a system for taking an indicator of a hormonal system level of a user and automatically varying a user experience in the vehicle to promote a healthy hormonal state. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a system for taking an indicator of a hormonal system level of a user and automatically varying a user experience in the vehicle to promote a hormonal state that promotes safety. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a dietary control system wherein at least one of a food or a beverage is made available under control of an automated control system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an automated restocking system for an in-vehicle dietary system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a system for optimizing at least one of a vehicle parameter and a user experience parameter to provide a margin of safety. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an interface by which a set of expert systems may be configured to provide respective outputs for managing at least one of a set of vehicle parameters, a set of fleet parameters and a set of user experience parameters. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an expert system for allocating rewards across one or more different types of objectives within a transportation system. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a distributed artificial intelligence system for taking inputs relating to a plurality of self-driving vehicles and determining at least one parameter of a re-charging and/or refueling plan for at least one of the plurality of vehicles based on inputs, wherein the artificial intelligence system coordinates a cloud-based system remote from charging or refueling infrastructure and a local system positioned with the charging or refueling infrastructure and having a search system that is configured to provide network search results for in-vehicle searchers.

In embodiments, provided herein is a system for transportation having an artificial intelligence system for determining at least one parameter of a charging plan based on inputs relating to a self-driving vehicle. In embodiments, provided herein is a system for transportation having an artificial intelligence system for determining at least one parameter of a charging plan based on inputs relating to a self-driving vehicle and having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for determining at least one parameter of a charging plan based on inputs relating to a self-driving vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for determining at least one parameter of a charging plan based on inputs relating to a self-driving vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for determining at least one parameter of a charging plan based on inputs relating to a self-driving vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for determining at least one parameter of a charging plan based on inputs relating to a self-driving vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for determining at least one parameter of a charging plan based on inputs relating to a self-driving vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for determining at least one parameter of a charging plan based on inputs relating to a self-driving vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan based on inputs relating to a self-driving vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan based on inputs relating to a self-driving vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan based on inputs relating to a self-driving vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan based on inputs relating to a self-driving vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan based on inputs relating to a self-driving vehicle and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan based on inputs relating to a self-driving vehicle and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan based on inputs relating to a self-driving vehicle and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan based on inputs relating to a self-driving vehicle and having a dietary control system wherein at least one of a food or a beverage is made available under control of an automated control system. In embodiments, provided herein is a system for transportation having an artificial intelligence system for determining at least one parameter of a charging plan based on inputs relating to a self-driving vehicle and having an automated restocking system for an in-vehicle dietary system. In embodiments, provided herein is a system for transportation having an artificial intelligence system for determining at least one parameter of a charging plan based on inputs relating to a self-driving vehicle and having a system for optimizing at least one of a vehicle parameter and a user experience parameter to provide a margin of safety. In embodiments, provided herein is a system for transportation having an artificial intelligence system for determining at least one parameter of a charging plan based on inputs relating to a self-driving vehicle and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan based on inputs relating to a self-driving vehicle and having an expert system for allocating rewards across one or more different types of objectives within a transportation system. In embodiments, provided herein is a system for transportation having an artificial intelligence system for determining at least one parameter of a charging plan based on inputs relating to a self-driving vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan based on inputs relating to a self-driving vehicle and having a search system that is configured to provide network search results for in-vehicle searchers.

In embodiments, provided herein is a system for transportation having an artificial intelligence system for determining at least one parameter of a charging plan based on inputs relating to a self-driving vehicle, wherein the inputs include at least one indicator of a charge state of the self-driving vehicle. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a dietary control system wherein at least one of a food or a beverage is made available under control of an automated control system. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an automated restocking system for an in-vehicle dietary system. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a system for optimizing at least one of a vehicle parameter and a user experience parameter to provide a margin of safety. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an expert system for allocating rewards across one or more different types of objectives within a transportation system. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan based on inputs relating to a self-driving vehicle, wherein the inputs include at least one indicator of a charge state of the self-driving vehicle and having a search system that is configured to provide network search results for in-vehicle searchers.

In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an artificial intelligence system that automatically randomizes a parameter of an in-vehicle experience in order to improve a user state that benefits from variation. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a system for taking an indicator of a hormonal system level of a user and automatically varying a user experience in the vehicle to promote a healthy hormonal state. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a system for taking an indicator of a hormonal system level of a user and automatically varying a user experience in the vehicle to promote a hormonal state that promotes safety. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a dietary control system wherein at least one of a food or a beverage is made available under control of an automated control system. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an automated restocking system for an in-vehicle dietary system. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a system for optimizing at least one of a vehicle parameter and a user experience parameter to provide a margin of safety. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an expert system for allocating rewards across one or more different types of objectives within a transportation system. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for determining at least one parameter of a charging plan based on inputs relating to a self-driving vehicle, where distinct parts of the neural net operate on inputs relating to the charging system of the vehicle and other inputs and having a search system that is configured to provide network search results for in-vehicle searchers.

In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an artificial intelligence system that automatically randomizes a parameter of an in-vehicle experience in order to improve a user state that benefits from variation. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a system for taking an indicator of a hormonal system level of a user and automatically varying a user experience in the vehicle to promote a healthy hormonal state. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a system for taking an indicator of a hormonal system level of a user and automatically varying a user experience in the vehicle to promote a hormonal state that promotes safety. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a dietary control system wherein at least one of a food or a beverage is made available under control of an automated control system. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an automated restocking system for an in-vehicle dietary system. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a system for optimizing at least one of a vehicle parameter and a user experience parameter to provide a margin of safety. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an interface by which a set of expert systems may be configured to provide respective outputs for managing at least one of a set of vehicle parameters, a set of fleet parameters and a set of user experience parameters. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an expert system for allocating rewards across one or more different types of objectives within a transportation system. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a hybrid neural network for determining at least one parameter of a charging plan for a vehicle, where parts of the hybrid neural net operate on inputs relating to the charging system of the vehicle and part of the hybrid neural net operate on other data to provide a prediction of the geolocation of a plurality of vehicles within a geographic region of the vehicle and having a search system that is configured to provide network search results for in-vehicle searchers.

In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a dietary control system wherein at least one of a food or a beverage is made available under control of an automated control system. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an automated restocking system for an in-vehicle dietary system. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a system for optimizing at least one of a vehicle parameter and a user experience parameter to provide a margin of safety. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an expert system for allocating rewards across one or more different types of objectives within a transportation system. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan based on inputs relating to a self-driving vehicle, wherein the inputs include inputs relating to charging states of a plurality of vehicles within a geolocation range and having a search system that is configured to provide network search results for in-vehicle searchers.

In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a dietary control system wherein at least one of a food or a beverage is made available under control of an automated control system. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an automated restocking system for an in-vehicle dietary system. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a system for optimizing at least one of a vehicle parameter and a user experience parameter to provide a margin of safety. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an expert system for allocating rewards across one or more different types of objectives within a transportation system. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan based on inputs relating to a plurality of self-driving vehicles, wherein the inputs include inputs relating to charging states of a plurality of vehicles within a geolocation range and the artificial intelligence system optimizes the at least one parameter based on a prediction of geolocations of the plurality of vehicles and having a search system that is configured to provide network search results for in-vehicle searchers.

In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a dietary control system wherein at least one of a food or a beverage is made available under control of an automated control system. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an automated restocking system for an in-vehicle dietary system. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a system for optimizing at least one of a vehicle parameter and a user experience parameter to provide a margin of safety. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an expert system for allocating rewards across one or more different types of objectives within a transportation system. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan for a vehicle based on inputs relating to a self-driving vehicle, wherein the inputs include at least one indicator of a battery state of the vehicle and having a search system that is configured to provide network search results for in-vehicle searchers.

In embodiments, provided herein is a system for transportation having an artificial intelligence system for determining at least one parameter of a charging plan for a vehicle based on inputs relating to a self-driving vehicle, wherein the inputs include a route plan for the vehicle. In embodiments, provided herein is a system for transportation having an artificial intelligence system for determining at least one parameter of a charging plan for a vehicle based on inputs relating to a self-driving vehicle, wherein the inputs include a route plan for the vehicle and having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan for a vehicle based on inputs relating to a self-driving vehicle, wherein the inputs include a route plan for the vehicle and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan for a vehicle based on inputs relating to a self-driving vehicle, wherein the inputs include a route plan for the vehicle and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan for a vehicle based on inputs relating to a self-driving vehicle, wherein the inputs include a route plan for the vehicle and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan for a vehicle based on inputs relating to a self-driving vehicle, wherein the inputs include a route plan for the vehicle and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan for a vehicle based on inputs relating to a self-driving vehicle, wherein the inputs include a route plan for the vehicle and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan for a vehicle based on inputs relating to a self-driving vehicle, wherein the inputs include a route plan for the vehicle and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan for a vehicle based on inputs relating to a self-driving vehicle, wherein the inputs include a route plan for the vehicle and having a dietary control system wherein at least one of a food or a beverage is made available under control of an automated control system. In embodiments, provided herein is a system for transportation having an artificial intelligence system for determining at least one parameter of a charging plan for a vehicle based on inputs relating to a self-driving vehicle, wherein the inputs include a route plan for the vehicle and having an automated restocking system for an in-vehicle dietary system. In embodiments, provided herein is a system for transportation having an artificial intelligence system for determining at least one parameter of a charging plan for a vehicle based on inputs relating to a self-driving vehicle, wherein the inputs include a route plan for the vehicle and having a system for optimizing at least one of a vehicle parameter and a user experience parameter to provide a margin of safety. In embodiments, provided herein is a system for transportation having an artificial intelligence system for determining at least one parameter of a charging plan for a vehicle based on inputs relating to a self-driving vehicle, wherein the inputs include a route plan for the vehicle and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan for a vehicle based on inputs relating to a self-driving vehicle, wherein the inputs include a route plan for the vehicle and having an expert system for allocating rewards across one or more different types of objectives within a transportation system. In embodiments, provided herein is a system for transportation having an artificial intelligence system for determining at least one parameter of a charging plan for a vehicle based on inputs relating to a self-driving vehicle, wherein the inputs include a route plan for the vehicle and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan for a vehicle based on inputs relating to a self-driving vehicle, wherein the inputs include a route plan for the vehicle and having a search system that is configured to provide network search results for in-vehicle searchers.

In embodiments, provided herein is a system for transportation having an artificial intelligence system for determining at least one parameter of a charging plan for a vehicle based on inputs relating to a self-driving vehicle, wherein the inputs include at least one indicator of the value of charging. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having an artificial intelligence system for determining at least one parameter of a charging plan for a vehicle based on inputs relating to a self-driving vehicle, wherein the inputs include at least one indicator of the value of charging and having an artificial intelligence system that automatically randomizes a parameter of an in-vehicle experience in order to improve a user state that benefits from variation. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a system for taking an indicator of a hormonal system level of a user and automatically varying a user experience in the vehicle to promote a healthy hormonal state. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a system for taking an indicator of a hormonal system level of a user and automatically varying a user experience in the vehicle to promote a hormonal state that promotes safety. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a dietary control system wherein at least one of a food or a beverage is made available under control of an automated control system. In embodiments, provided herein is a system for transportation having an artificial intelligence system for determining at least one parameter of a charging plan for a vehicle based on inputs relating to a self-driving vehicle, wherein the inputs include at least one indicator of the value of charging and having an automated restocking system for an in-vehicle dietary system. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a system for optimizing at least one of a vehicle parameter and a user experience parameter to provide a margin of safety. In embodiments, provided herein is a system for transportation having an artificial intelligence system for determining at least one parameter of a charging plan for a vehicle based on inputs relating to a self-driving vehicle, wherein the inputs include at least one indicator of the value of charging and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system for determining at least one parameter of a charging plan for a vehicle based on inputs relating to a self-driving vehicle, wherein the inputs include at least one indicator of the value of charging and having an expert system for allocating rewards across one or more different types of objectives within a transportation system. In embodiments, provided herein is a system for transportation having an artificial intelligence system for determining at least one parameter of a charging plan for a vehicle based on inputs relating to a self-driving vehicle, wherein the inputs include at least one indicator of the value of charging and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system for determining at least one parameter of a charging plan for a vehicle based on inputs relating to a self-driving vehicle, wherein the inputs include at least one indicator of the value of charging and having a search system that is configured to provide network search results for in-vehicle searchers.

In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having an artificial intelligence system that automatically randomizes a parameter of an in-vehicle experience in order to improve a user state that benefits from variation. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a system for taking an indicator of a hormonal system level of a user and automatically varying a user experience in the vehicle to promote a healthy hormonal state. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a system for taking an indicator of a hormonal system level of a user and automatically varying a user experience in the vehicle to promote a hormonal state that promotes safety. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a dietary control system wherein at least one of a food or a beverage is made available under control of an automated control system. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having an automated restocking system for an in-vehicle dietary system. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a system for optimizing at least one of a vehicle parameter and a user experience parameter to provide a margin of safety. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having an interface by which a set of expert systems may be configured to provide respective outputs for managing at least one of a set of vehicle parameters, a set of fleet parameters and a set of user experience parameters. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having an expert system for allocating rewards across one or more different types of objectives within a transportation system. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for facilitating automated negotiation of at least one of a duration, a quantity and a price for charging or refueling a vehicle, wherein the cognitive system takes at least one input providing an indicator of the value of the charging or refueling and having a search system that is configured to provide network search results for in-vehicle searchers.

In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having an artificial intelligence system that automatically randomizes a parameter of an in-vehicle experience in order to improve a user state that benefits from variation. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a system for taking an indicator of a hormonal system level of a user and automatically varying a user experience in the vehicle to promote a healthy hormonal state. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a system for taking an indicator of a hormonal system level of a user and automatically varying a user experience in the vehicle to promote a hormonal state that promotes safety. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a dietary control system wherein at least one of a food or a beverage is made available under control of an automated control system. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having an automated restocking system for an in-vehicle dietary system. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a system for optimizing at least one of a vehicle parameter and a user experience parameter to provide a margin of safety. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having an interface by which a set of expert systems may be configured to provide respective outputs for managing at least one of a set of vehicle parameters, a set of fleet parameters and a set of user experience parameters. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having an expert system for allocating rewards across one or more different types of objectives within a transportation system. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a cognitive system for facilitating automated negotiation of at least one of a duration, a quantity and a price for charging and/or refueling a vehicle, wherein the cognitive system manages a bidding marketplace for charging and/or refueling and having a search system that is configured to provide network search results for in-vehicle searchers.

In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having an artificial intelligence system that automatically randomizes a parameter of an in-vehicle experience in order to improve a user state that benefits from variation. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having a system for taking an indicator of a hormonal system level of a user and automatically varying a user experience in the vehicle to promote a healthy hormonal state. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having a system for taking an indicator of a hormonal system level of a user and automatically varying a user experience in the vehicle to promote a hormonal state that promotes safety. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having a dietary control system wherein at least one of a food or a beverage is made available under control of an automated control system. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having an automated restocking system for an in-vehicle dietary system. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having a system for optimizing at least one of a vehicle parameter and a user experience parameter to provide a margin of safety. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having an interface by which a set of expert systems may be configured to provide respective outputs for managing at least one of a set of vehicle parameters, a set of fleet parameters and a set of user experience parameters. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having an expert system for allocating rewards across one or more different types of objectives within a transportation system. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a robotic process automation system wherein data is captured for each of a set of individuals as the individuals interact with a user interface of a vehicle and an artificial intelligence system is trained using the set of images to interact with the vehicle to automatically undertake actions with the vehicle on behalf of the user and having a search system that is configured to provide network search results for in-vehicle searchers.

In embodiments, provided herein is a system for transportation having an artificial intelligence system that automatically randomizes a parameter of an in-vehicle experience in order to improve a user state that benefits from variation. In embodiments, provided herein is a system for transportation having an artificial intelligence system that automatically randomizes a parameter of an in-vehicle experience in order to improve a user state that benefits from variation and having a system for taking an indicator of a hormonal system level of a user and automatically varying a user experience in the vehicle to promote a healthy hormonal state. In embodiments, provided herein is a system for transportation having an artificial intelligence system that automatically randomizes a parameter of an in-vehicle experience in order to improve a user state that benefits from variation and having a system for taking an indicator of a hormonal system level of a user and automatically varying a user experience in the vehicle to promote a hormonal state that promotes safety. In embodiments, provided herein is a system for transportation having an artificial intelligence system that automatically randomizes a parameter of an in-vehicle experience in order to improve a user state that benefits from variation and having a dietary control system wherein at least one of a food or a beverage is made available under control of an automated control system. In embodiments, provided herein is a system for transportation having an artificial intelligence system that automatically randomizes a parameter of an in-vehicle experience in order to improve a user state that benefits from variation and having an automated restocking system for an in-vehicle dietary system. In embodiments, provided herein is a system for transportation having an artificial intelligence system that automatically randomizes a parameter of an in-vehicle experience in order to improve a user state that benefits from variation and having a system for optimizing at least one of a vehicle parameter and a user experience parameter to provide a margin of safety. In embodiments, provided herein is a system for transportation having an artificial intelligence system that automatically randomizes a parameter of an in-vehicle experience in order to improve a user state that benefits from variation and having an interface by which a set of expert systems may be configured to provide respective outputs for managing at least one of a set of vehicle parameters, a set of fleet parameters and a set of user experience parameters. In embodiments, provided herein is a system for transportation having an artificial intelligence system that automatically randomizes a parameter of an in-vehicle experience in order to improve a user state that benefits from variation and having an expert system for allocating rewards across one or more different types of objectives within a transportation system. In embodiments, provided herein is a system for transportation having an artificial intelligence system that automatically randomizes a parameter of an in-vehicle experience in order to improve a user state that benefits from variation and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an artificial intelligence system that automatically randomizes a parameter of an in-vehicle experience in order to improve a user state that benefits from variation and having a search system that is configured to provide network search results for in-vehicle searchers.

In embodiments, provided herein is a system for transportation having a system for taking an indicator of a hormonal system level of a user and automatically varying a user experience in the vehicle to promote a healthy hormonal state. In embodiments, provided herein is a system for transportation having a system for taking an indicator of a hormonal system level of a user and automatically varying a user experience in the vehicle to promote a healthy hormonal state and having a system for taking an indicator of a hormonal system level of a user and automatically varying a user experience in the vehicle to promote a hormonal state that promotes safety. In embodiments, provided herein is a system for transportation having a system for taking an indicator of a hormonal system level of a user and automatically varying a user experience in the vehicle to promote a healthy hormonal state and having a dietary control system wherein at least one of a food or a beverage is made available under control of an automated control system. In embodiments, provided herein is a system for transportation having a system for taking an indicator of a hormonal system level of a user and automatically varying a user experience in the vehicle to promote a healthy hormonal state and having an automated restocking system for an in-vehicle dietary system. In embodiments, provided herein is a system for transportation having a system for taking an indicator of a hormonal system level of a user and automatically varying a user experience in the vehicle to promote a healthy hormonal state and having a system for optimizing at least one of a vehicle parameter and a user experience parameter to provide a margin of safety. In embodiments, provided herein is a system for transportation having a system for taking an indicator of a hormonal system level of a user and automatically varying a user experience in the vehicle to promote a healthy hormonal state and having an interface by which a set of expert systems may be configured to provide respective outputs for managing at least one of a set of vehicle parameters, a set of fleet parameters and a set of user experience parameters. In embodiments, provided herein is a system for transportation having a system for taking an indicator of a hormonal system level of a user and automatically varying a user experience in the vehicle to promote a healthy hormonal state and having an expert system for allocating rewards across one or more different types of objectives within a transportation system. In embodiments, provided herein is a system for transportation having a system for taking an indicator of a hormonal system level of a user and automatically varying a user experience in the vehicle to promote a healthy hormonal state and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a system for taking an indicator of a hormonal system level of a user and automatically varying a user experience in the vehicle to promote a healthy hormonal state and having a search system that is configured to provide network search results for in-vehicle searchers.

In embodiments, provided herein is a system for transportation having a system for taking an indicator of a hormonal system level of a user and automatically varying a user experience in the vehicle to promote a hormonal state that promotes safety. In embodiments, provided herein is a system for transportation having a system for taking an indicator of a hormonal system level of a user and automatically varying a user experience in the vehicle to promote a hormonal state that promotes safety and having a dietary control system wherein at least one of a food or a beverage is made available under control of an automated control system. In embodiments, provided herein is a system for transportation having a system for taking an indicator of a hormonal system level of a user and automatically varying a user experience in the vehicle to promote a hormonal state that promotes safety and having an automated restocking system for an in-vehicle dietary system. In embodiments, provided herein is a system for transportation having a system for taking an indicator of a hormonal system level of a user and automatically varying a user experience in the vehicle to promote a hormonal state that promotes safety and having a system for optimizing at least one of a vehicle parameter and a user experience parameter to provide a margin of safety. In embodiments, provided herein is a system for transportation having a system for taking an indicator of a hormonal system level of a user and automatically varying a user experience in the vehicle to promote a hormonal state that promotes safety and having an interface by which a set of expert systems may be configured to provide respective outputs for managing at least one of a set of vehicle parameters, a set of fleet parameters and a set of user experience parameters. In embodiments, provided herein is a system for transportation having a system for taking an indicator of a hormonal system level of a user and automatically varying a user experience in the vehicle to promote a hormonal state that promotes safety and having an expert system for allocating rewards across one or more different types of objectives within a transportation system.

In embodiments, provided herein is a system for transportation having a system for taking an indicator of a hormonal system level of a user and automatically varying a user experience in the vehicle to promote a hormonal state that promotes safety and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a system for taking an indicator of a hormonal system level of a user and automatically varying a user experience in the vehicle to promote a hormonal state that promotes safety and having a search system that is configured to provide network search results for in-vehicle searchers.

In embodiments, provided herein is a system for transportation having a dietary control system wherein at least one of a food or a beverage is made available under control of an automated control system. In embodiments, provided herein is a system for transportation having a dietary control system wherein at least one of a food or a beverage is made available under control of an automated control system and having an automated restocking system for an in-vehicle dietary system. In embodiments, provided herein is a system for transportation having a dietary control system wherein at least one of a food or a beverage is made available under control of an automated control system and having a system for optimizing at least one of a vehicle parameter and a user experience parameter to provide a margin of safety. In embodiments, provided herein is a system for transportation having a dietary control system wherein at least one of a food or a beverage is made available under control of an automated control system and having an interface by which a set of expert systems may be configured to provide respective outputs for managing at least one of a set of vehicle parameters, a set of fleet parameters and a set of user experience parameters. In embodiments, provided herein is a system for transportation having a dietary control system wherein at least one of a food or a beverage is made available under control of an automated control system and having an expert system for allocating rewards across one or more different types of objectives within a transportation system. In embodiments, provided herein is a system for transportation having a dietary control system wherein at least one of a food or a beverage is made available under control of an automated control system and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a dietary control system wherein at least one of a food or a beverage is made available under control of an automated control system and having a search system that is configured to provide network search results for in-vehicle searchers.

In embodiments, provided herein is a system for transportation having an automated restocking system for an in-vehicle dietary system. In embodiments, provided herein is a system for transportation having an automated restocking system for an in-vehicle dietary system and having a system for optimizing at least one of a vehicle parameter and a user experience parameter to provide a margin of safety. In embodiments, provided herein is a system for transportation having an automated restocking system for an in-vehicle dietary system and having an interface by which a set of expert systems may be configured to provide respective outputs for managing at least one of a set of vehicle parameters, a set of fleet parameters and a set of user experience parameters. In embodiments, provided herein is a system for transportation having an automated restocking system for an in-vehicle dietary system and having an expert system for allocating rewards across one or more different types of objectives within a transportation system. In embodiments, provided herein is a system for transportation having an automated restocking system for an in-vehicle dietary system and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an automated restocking system for an in-vehicle dietary system and having a search system that is configured to provide network search results for in-vehicle searchers.

In embodiments, provided herein is a system for transportation having a system for optimizing at least one of a vehicle parameter and a user experience parameter to provide a margin of safety. In embodiments, provided herein is a system for transportation having a system for optimizing at least one of a vehicle parameter and a user experience parameter to provide a margin of safety and having an interface by which a set of expert systems may be configured to provide respective outputs for managing at least one of a set of vehicle parameters, a set of fleet parameters and a set of user experience parameters. In embodiments, provided herein is a system for transportation having a system for optimizing at least one of a vehicle parameter and a user experience parameter to provide a margin of safety and having an expert system for allocating rewards across one or more different types of objectives within a transportation system. In embodiments, provided herein is a system for transportation having a system for optimizing at least one of a vehicle parameter and a user experience parameter to provide a margin of safety and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having a system for optimizing at least one of a vehicle parameter and a user experience parameter to provide a margin of safety and having a search system that is configured to provide network search results for in-vehicle searchers.

In embodiments, provided herein is a system for transportation having an interface by which a set of expert systems may be configured to provide respective outputs for managing at least one of a set of vehicle parameters, a set of fleet parameters and a set of user experience parameters. In embodiments, provided herein is a system for transportation having an interface by which a set of expert systems may be configured to provide respective outputs for managing at least one of a set of vehicle parameters, a set of fleet parameters and a set of user experience parameters and having an expert system for allocating rewards across one or more different types of objectives within a transportation system. In embodiments, provided herein is a system for transportation having an interface by which a set of expert systems may be configured to provide respective outputs for managing at least one of a set of vehicle parameters, a set of fleet parameters and a set of user experience parameters and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an interface by which a set of expert systems may be configured to provide respective outputs for managing at least one of a set of vehicle parameters, a set of fleet parameters and a set of user experience parameters and having a search system that is configured to provide network search results for in-vehicle searchers.

In embodiments, provided herein is a system for transportation having an expert system for allocating rewards across one or more different types of objectives within a transportation system. In embodiments, provided herein is a system for transportation having an expert system for allocating rewards across one or more different types of objectives within a transportation system and having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an expert system for allocating rewards across one or more different types of objectives within a transportation system and having a search system that is configured to provide network search results for in-vehicle searchers.

In embodiments, provided herein is a system for transportation having an expert system for configuring a recommendation for a configuration of a vehicle, wherein the recommendation includes at least one parameter of configuration for an expert system that controls a parameter of at least one of a vehicle parameter and a user experience parameter. In embodiments, provided herein is a system for transportation having an expert system for configuring a recommendation for a configuration of a vehicle, wherein the recommendation includes at least one parameter of configuration for an expert system that controls a parameter of at least one of a vehicle parameter and a user experience parameter and having a search system that is configured to provide network search results for in-vehicle searchers.

In embodiments, provided herein is a system for transportation having a search system that is configured to provide network search results for in-vehicle searchers.

Having thus described several aspects and embodiments of the technology of this application, it is to be appreciated that various alterations, modifications, and improvements will readily occur to those skilled in the art. Such alterations, modifications, and improvements are intended to be within the spirit and scope of the technology described in the application. For example, those skilled in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other devices) to perform, or control performance of, the processes or methods.

As used herein, the term system may define any combination of one or more computing devices, processors, modules, software, firmware, or circuits that operate either independently or in a distributed manner to perform one or more functions. A system may include one or more subsystems.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The present disclosure should therefore not be considered limited to the particular embodiments described above. Various modifications, equivalent processes, as well as numerous structures to which the present disclosure may be applicable, will be readily apparent to those skilled in the art to which the present disclosure is directed upon review of the present disclosure.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The terms "a" or "an," as used herein, are defined as one or more than one. The term "another," as used herein, is defined as at least a second or more. The terms "including" and/or "having," as used herein, are defined as comprising (i.e., open transition).

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flowcharts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flowchart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The term "set" should be understood to include a set of a single member or multiple members. The terms "comprising," "having," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 112(f). In particular, any use of "step of" in the claims is not intended to invoke the provision of 35 U.S.C. § 112(f).

Those skilled in the art may appreciate that numerous design configurations may be possible to enjoy the functional benefits of the inventive systems. Thus, given the wide variety of configurations and arrangements of embodiments of the present disclosure, the scope of the disclosure is reflected by the breadth of the claims below rather than narrowed by the embodiments described above.

What is claimed is:

1. A system for transportation to operate a vehicle having a continuously variable powertrain, comprising:
a hybrid neural network for optimizing an operating state of the continuously variable powertrain of the vehicle wherein
a portion of the hybrid neural network is to operate to classify a state of the vehicle based on output from a set of sensors thereby generating a classified state of the vehicle, wherein the set of sensors includes a physiological monitor within the vehicle to monitor a rider, wherein the classified state of the vehicle is a vehicle rider state and wherein the vehicle rider state is indicative of an emotional state of the rider, and
an other portion of the hybrid neural network is to operate to optimize at least one operating parameter of a continuously variable transmission portion of the continuously variable powertrain wherein the at least one operating parameter of the continuously variable transmission portion includes a transmission ratio and the other portion of the hybrid neural network is to operate to optimize the transmission ratio to achieve an optimized combination of vehicle speed, steering, braking, and acceleration for achieving a favorable emotional state of the rider; and
an artificial intelligence system in communication with the set of sensors, the artificial intelligence system operative on at least one processor having access to a non-transitory storage medium that stores computer executable instructions to be executed by the at least one processor, the artificial intelligence system to operate the portion of the hybrid neural network to operate to classify the state of the vehicle and the artificial intelligence system to operate the other portion of the hybrid neural network to optimize the at least one operating parameter of the transmission portion of the continuously variable powertrain based on the classified state of the vehicle.

2. The system for transportation of claim 1 wherein the vehicle comprises a system for automating at least one control parameter of the vehicle.

3. The system for transportation of claim 2 wherein the vehicle is at least a semi-autonomous vehicle.

4. The system for transportation of claim 3 wherein the vehicle is to be automatically routed.

5. The system for transportation of claim 4 wherein the vehicle is a self-driving vehicle.

6. The system for transportation of claim 1 wherein the physiological monitor includes a vision-based sensor that observes and captures images of the rider.

7. The system for transportation of claim 6 wherein captured images of the rider include a face of the rider, and wherein the hybrid neural network is to process feature vectors of a face of the rider in the captured images to determine the emotional state of the rider.

8. The system for transportation of claim 6 wherein the other portion of the hybrid neural network includes a radial basis function neural network to optimize the transmission ratio in response to the indication of change in emotional state of the rider.

9. The system for transportation of claim 1 wherein the portion of the hybrid neural network includes a recurrent neural network to indicate a change in the emotional state of the rider through recognition of patterns of physiological data of the rider captured by the physiological monitor.

10. The system for transportation of claim 1 wherein the physiological monitor includes a galvanic skin response sensor to detect galvanic skin response of the rider wherein the galavanic skin response of the rider is indicative of the emotional state of the rider.

11. The system for transportation of claim 1 wherein the physiological monitor includes electrodes for detecting electrical activity of the brain and recording an electroencephalogram (EEG) of the rider wherein the EEG is indicative of the emotional state of the rider.

12. The system for transportation of claim 1 wherein the favorable emotional state of the driver is associated with lower cortisol levels and wherein the transmission ratio is optimized to achieve a gentle driving motion in the optimized combination of vehicle speed, steering, braking and acceleration.

* * * * *